US012441726B2

(12) United States Patent
Wilson et al.

(10) Patent No.: US 12,441,726 B2
(45) Date of Patent: Oct. 14, 2025

(54) COMPOUNDS AND USES THEREOF

(71) Applicant: Foghorn Therapeutics Inc., Indianapolis, IN (US)

(72) Inventors: Kevin J. Wilson, Roslindale, MA (US); Shawn E. R. Schiller, Haverhill, MA (US); Solymar Negretti, Watertown, MA (US)

(73) Assignee: Foghorn Therapeutics, Inc., Cambridge, MA (US)

( * ) Notice: Subject to any disclaimer, the term of this patent is extended or adjusted under 35 U.S.C. 154(b) by 653 days.

(21) Appl. No.: 17/795,778

(22) PCT Filed: Jan. 29, 2021

(86) PCT No.: PCT/US2021/015943
§ 371 (c)(1),
(2) Date: Jul. 27, 2022

(87) PCT Pub. No.: WO2021/155320
PCT Pub. Date: Aug. 5, 2021

(65) Prior Publication Data

US 2023/0145003 A1 May 11, 2023

Related U.S. Application Data

(60) Provisional application No. 62/967,208, filed on Jan. 29, 2020, provisional application No. 62/967,206, filed on Jan. 29, 2020.

(51) Int. Cl.

| | |
|---|---|
| ***C07D 471/04*** | (2006.01) |
| ***A61P 11/00*** | (2006.01) |
| ***A61P 35/00*** | (2006.01) |
| ***C07D 401/12*** | (2006.01) |
| ***C07D 405/12*** | (2006.01) |
| ***C07D 405/14*** | (2006.01) |
| ***C07D 413/14*** | (2006.01) |
| ***C07D 417/10*** | (2006.01) |
| ***C07D 417/14*** | (2006.01) |
| ***C07D 487/10*** | (2006.01) |
| ***C07D 513/04*** | (2006.01) |
| ***C07D 519/00*** | (2006.01) |

(52) U.S. Cl.
CPC ............ *C07D 471/04* (2013.01); *A61P 11/00* (2018.01); *A61P 35/00* (2018.01); *C07D 401/12* (2013.01); *C07D 405/12* (2013.01); *C07D 405/14* (2013.01); *C07D 413/14* (2013.01); *C07D 417/10* (2013.01); *C07D 417/14* (2013.01); *C07D 487/10* (2013.01); *C07D 513/04* (2013.01); *C07D 519/00* (2013.01); *C07B 2200/05* (2013.01)

(58) Field of Classification Search
CPC .. C07D 471/04; C07D 401/12; C07D 405/12; C07D 405/14; C07D 413/14; C07D 417/10; C07D 417/14; C07D 487/10; C07D 513/04; C07D 519/00; C07D 235/14; C07D 487/04
See application file for complete search history.

(56) References Cited

U.S. PATENT DOCUMENTS

| | | | | |
|---|---|---|---|---|
| 7,169,931 B2 * | 1/2007 | Takemoto | A61P 35/00 548/195 |
| 8,987,307 B2 * | 3/2015 | Bissantz | C07D 213/75 514/339 |
| 2013/0190290 A1 | 7/2013 | Su et al. | |
| 2014/0288123 A1 | 9/2014 | Albrecht et al. | |

FOREIGN PATENT DOCUMENTS

WO 2017087608 A1 5/2017

OTHER PUBLICATIONS

Ates-Alagoz, Zeynep, Tulay Coban, and Erdem Buyukbingol. "Synthesis and Antioxidant Activity of New Tetrahydro-Naphthalene-Indole Derivatives as Retinoid and Melatonin Analogs." *Archiv der Pharmazie: An International Journal Pharmaceutical and Medicinal Chemistry* 339, No. 4 (2006): 193-200.
National Center for Biotechnology Information. "PubChem Compound Summary for CID 145315170" PubChem, https://pubchem.ncbi.nlm.nih.gov/compound/145315170. Accessed Jun. 23, 2022.
PCT International Search Report and the Written Opinion of the International Searching Authority pertaining to international Application No. PCT/2021/015943; Date of Mailing: Apr. 14, 2021; 7 pages.

* cited by examiner

*Primary Examiner* — Laura L Stockton
(74) *Attorney, Agent, or Firm* — Bradley W. Crawford

(57) ABSTRACT

The present disclosure features compounds useful for the treatment of BAF complex-related disorders.

40 Claims, 10 Drawing Sheets

COMPOUNDS AND USES THEREOF

BACKGROUND

The invention relates to compounds useful for modulating BRG1- or BRM-associated factors (BAF) complexes. In particular, the invention relates to compounds useful for treatment of disorders associated with BAF complex function.

Chromatin regulation is essential for gene expression, and ATP-dependent chromatin remodeling is a mechanism by which such gene expression occurs. The human Switch/Sucrose Non-Fermentable (SWI/SNF) chromatin remodeling complex, also known as BAF complex, has two SWI2-like ATPases known as BRG1 (Brahma-related gene-1) and BRM (Brahma). The transcription activator BRG1 is also known as ATP-dependent chromatin remodeler SMARCA4, is encoded by the SMARCA4 gene on chromosome 19. BRG1 is overexpressed in some cancer tumors and is needed for cancer cell proliferation. BRM, also known as probable global transcription activator SNF2L2 and/or ATP-dependent chromatin remodeler SMARCA2, is encoded by the SMARCA2 gene on chromosome 9 and has been shown to be essential for tumor cell growth in cells characterized by loss of BRG1 function mutations. Deactivation of BRG and/or BRM results in downstream effects in cells, including cell cycle arrest and tumor suppression.

SUMMARY

The present invention features compounds useful for modulating a BAF complex. In some embodiments, the compounds are useful for the treatment of disorders associated with an alteration in a BAF complex, e.g., a disorder associated with an alteration in one or both of the BRG1 and BRM proteins. The compounds of the invention, alone or in combination with other pharmaceutically active agents, can be used for treating such disorders.

In an aspect, the invention features a compound having the structure:

Formula I

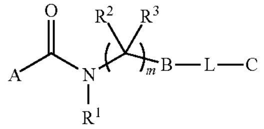

wherein

A is

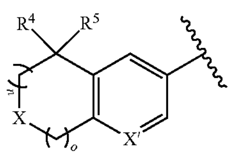

or

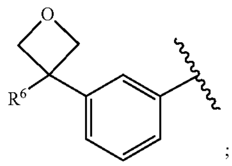

;

m is 0, 1, 2, or 3;

n is 1 or 2;

is 0 or 1;

X is O, $CH_2$, or $NR^7$;

X' is N, CH, or $CR^x$, wherein $R^x$ is a halogen;

B is an optionally substituted 6-membered monocyclic heteroarylene or an optionally substituted 9- or 10-membered bicyclic heteroarylene;

L is a covalent bond, optionally substituted $C_1$-$C_3$ alkylene, $C_2$ alkynylene, optionally substituted $C_2$ alkenylene, optionally substituted $C_2$-$C_3$ heteroalkylene, optionally substituted $C_3$-$C_5$ cycloalkylene, or optionally substituted 4- to 10-membered heterocyclylene;

C is optionally substituted 3- to 10-membered cycloalkyl; optionally substituted 6- to 10-membered aryl; optionally substituted 5- to 10-membered heteroaryl; or optionally substituted 5- to 10-membered heterocyclyl;

$R^1$ and $R^7$ are, independently, hydrogen or optionally substituted $C_1$-$C_6$ alkyl;

each $R^2$ and $R^3$ is independently, hydrogen, optionally substituted $C_1$-$C_6$ alkyl; or optionally substituted $C_1$-$C_6$ heteroalkyl;

$R^4$ is cyano, fluoro, hydroxy, or —$CH_2OH$;

$R^5$ is $C_1$-$C_3$ alkyl optionally substituted with one, two, three, four, five, six, or seven fluoro groups; and $R^6$ is $C_1$-$C_3$ alkyl optionally substituted with one, two, three, four, five, six, or seven fluoro groups, or a pharmaceutically acceptable salt thereof.

In some embodiments, $R^1$ is hydrogen. In some embodiments, m is 1. In some embodiments, $R^3$ is hydrogen. In some embodiments, $R^2$ is hydrogen. In some embodiments, $R^2$ is optionally substituted $C_1$-$C_6$ alkyl (e.g., methyl). In some embodiments, $R^2$ is optionally substituted $C_1$-$C_6$ heteroalkyl (e.g., —$CH_2OCH_3$).

In some embodiments, A is

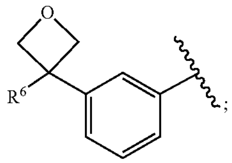

;

In some embodiments, $R^6$ is —$CHF_2$.

In some embodiments, A is

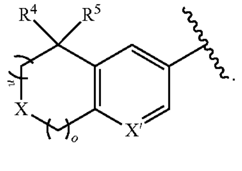

.

In some embodiments, $R^5$ is methyl or —$CHF_2$.

In some embodiments, X is O. In some embodiments, X is $CH_2$. In some embodiments, X is $NR^7$. In some embodiments, X is N. In some embodiments, X is CH. In some embodiments, X is $CR^x$ (e.g., $R^x$ is fluoro). In some embodiments, $R^7$ is hydrogen. In some embodiments, $R^7$ is methyl. In some embodiments, o is 0. In some embodiments, o is 1. In some embodiments, n is 1. In some embodiments, n is 2. In some embodiments, $R^4$ is cyano. In some embodiments, $R^4$ is fluoro. In some embodiments, $R^4$ is hydroxy. In some embodiments, $R^4$ is —$CH_2OH$. In some embodiments, A is

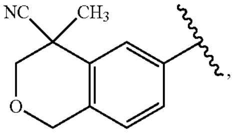, 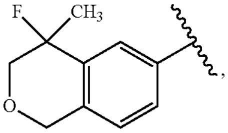, 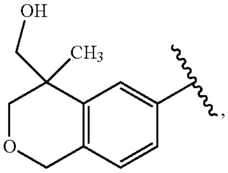, 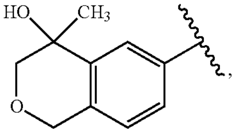, 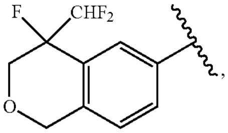, 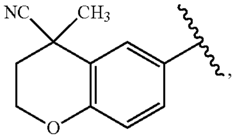, 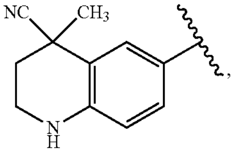, 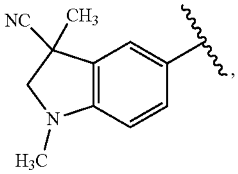, 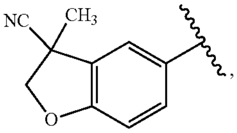, 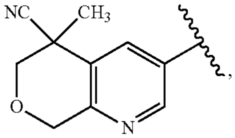, 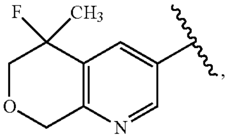, 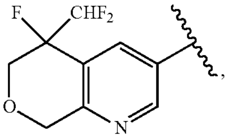, 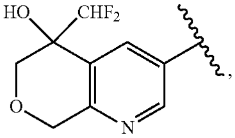, 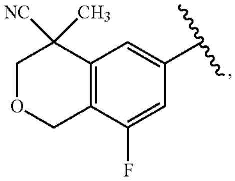, 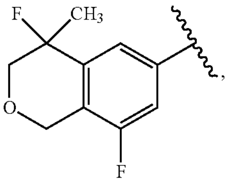, 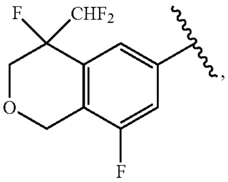, 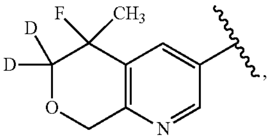, 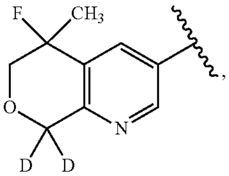, 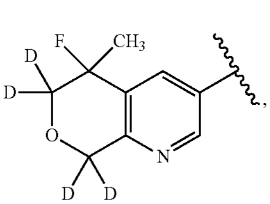, or 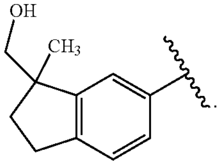.

In some embodiments, C is optionally substituted 3- to 10-membered cycloalkyl (e.g., cyclopropyl).

In some embodiments, C is optionally substituted 6- to 10-membered aryl (e.g., phenyl, 3-difluoromethyl-phenyl, 4-dilfluoromethylphenyl, 2-methoxy-phenyl, 3-methoxy-phenyl, 4-methoxy-phenyl, 3,5-difluorophenyl, 3-difluoromethylphenyl, 2-methoxy-5-methyl-phenyl, 2-methoxy-4-chloro-phenyl, 3-cyano-phenyl, 3-fluoro-5-methoxy-phenyl, 3-fluoro-5-azitidinyl-phenyl, 3-azetidyl-phenyl, 4-azetidyl-2-methoxy-phenyl, 4-morpholin-4-yl-2-methoxy-phenyl, 4-tert-butyl-2-methoxy-phenyl, 4-azetidyl-phenyl, 2-methoxy-4-oxetan-3-yl-phenyl, 2-azetidin-2-one-1-yl-phenyl, 3-(3-difluoromethyloxetan-3-yl)-phenyl, 3-(3-methoxyoxetan-3-yl)-phenyl, 3-(N-methyl-N-acetamido)-phenyl, 3-cyclopropylphenyl, 3-(N-methylazetidin-3-yl)-phenyl, 3-(N-methyl-N'-piperazinyl)-phenyl, 3-fluoro-5-azetidyl-phenyl, 3-methyl ester-phenyl,

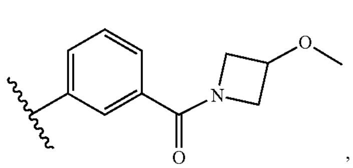,

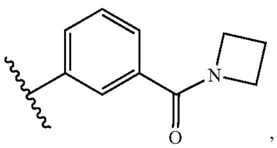, 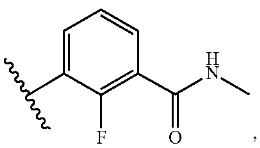,

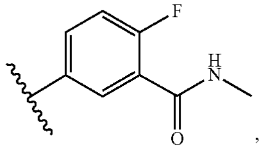, 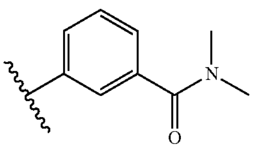,

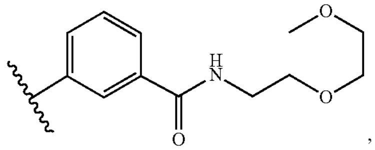,

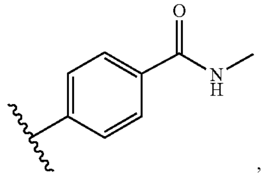, or

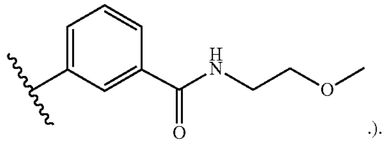.).

In some embodiments, C is optionally substituted 5- to 10-membered heteroaryl (e.g., 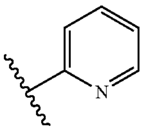, 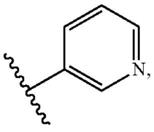, 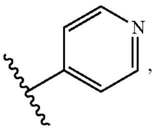, -continued
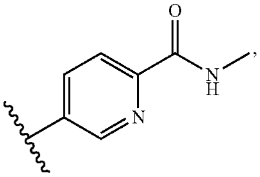
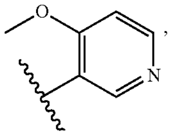
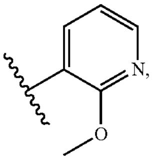
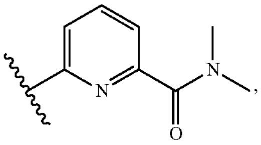
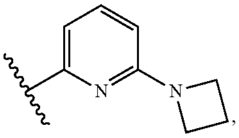
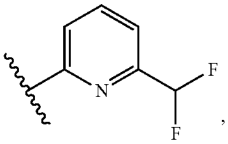
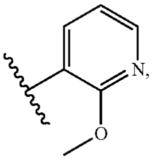
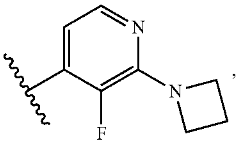
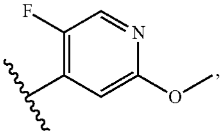
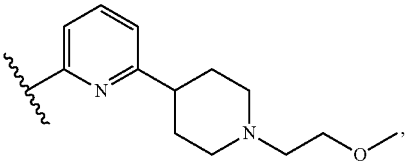
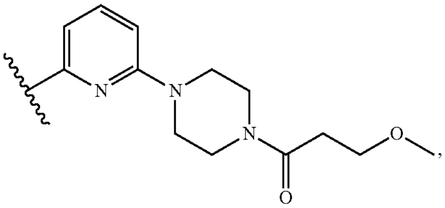
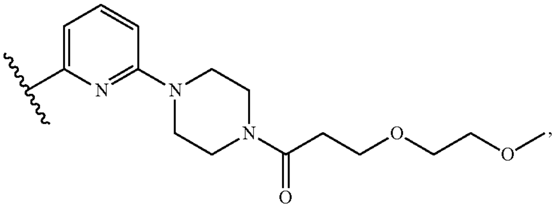
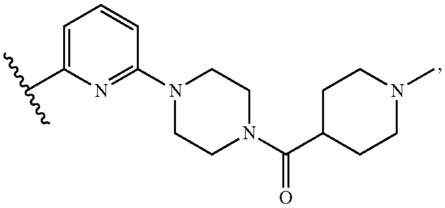
-continued
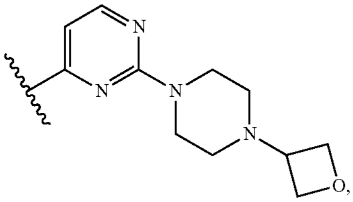
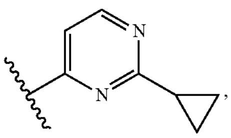
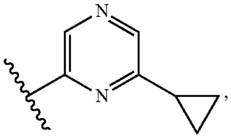
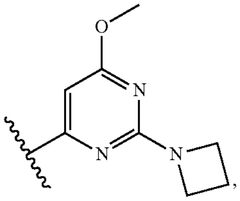
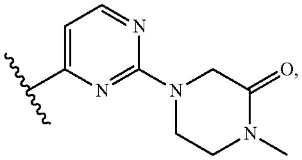
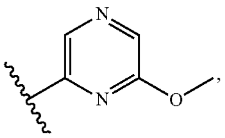
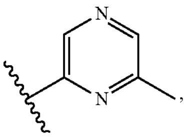
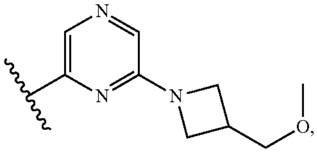
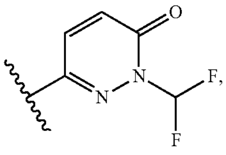
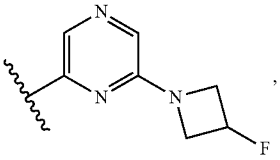
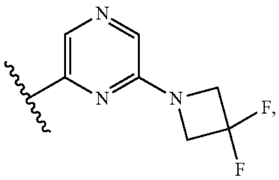
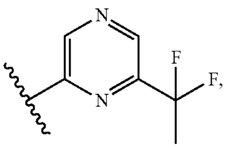
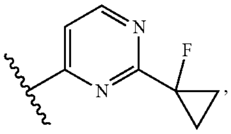
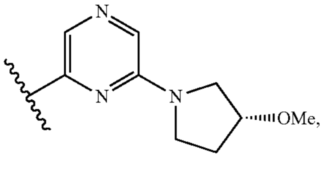

-continued
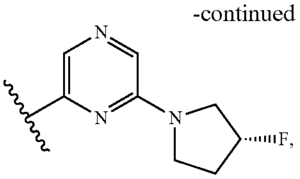
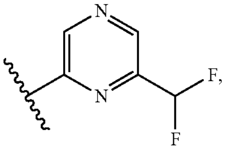
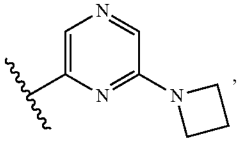
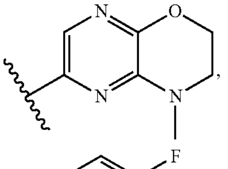
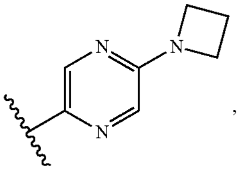
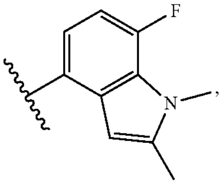
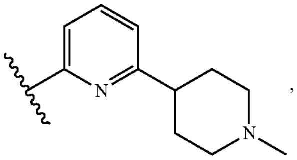
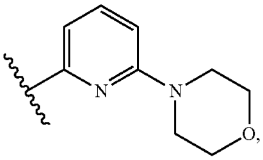
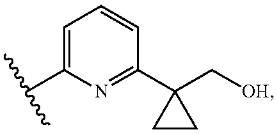
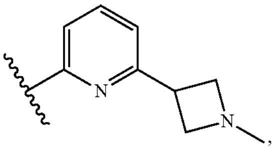
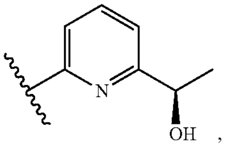
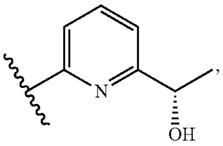
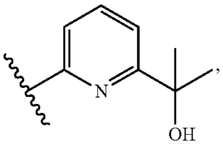
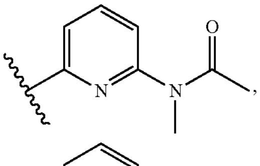
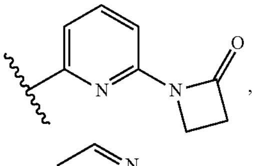
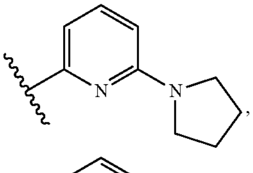
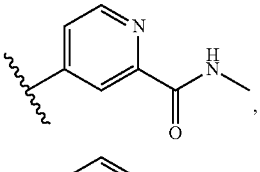
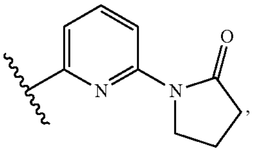
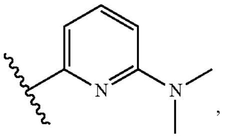
-continued
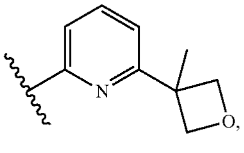
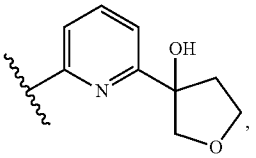
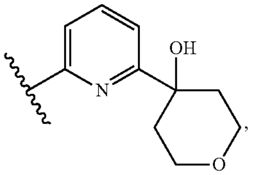
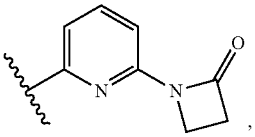
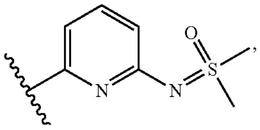
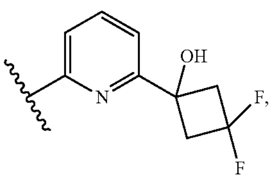
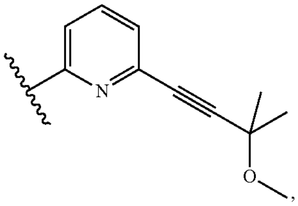
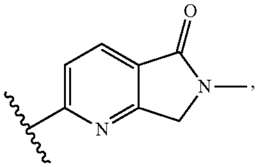
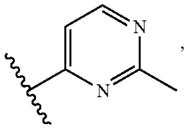
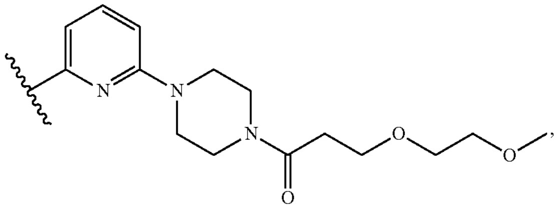
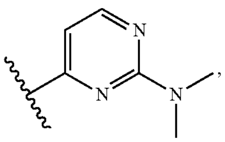
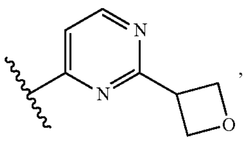
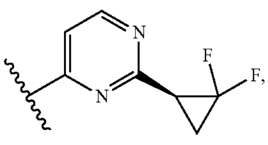
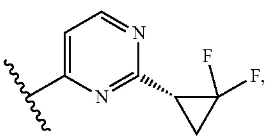
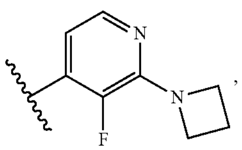

-continued
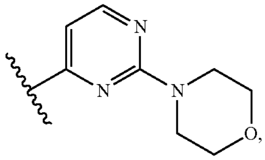,
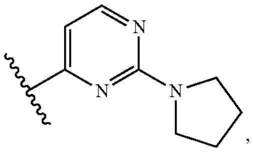,
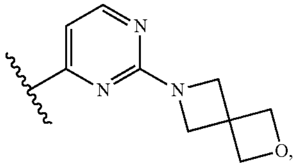,
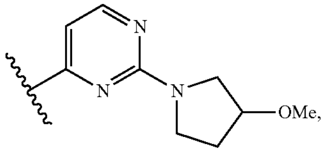,
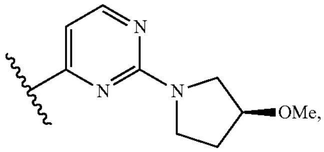,
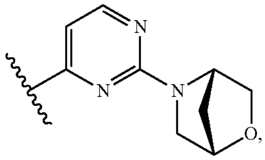,
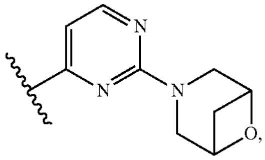,
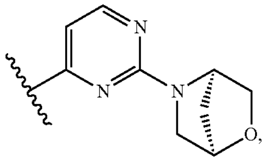,
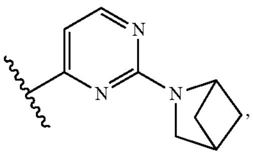,
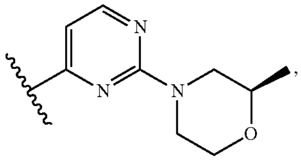,
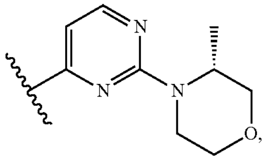,
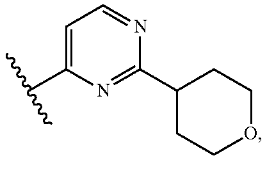,
-continued
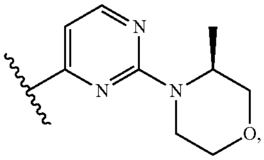,
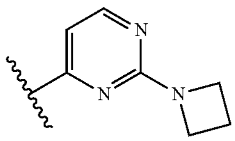,
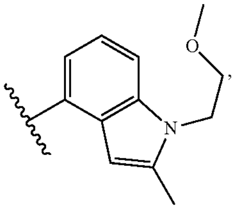,
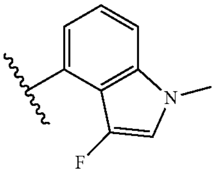,
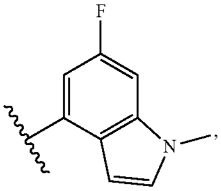,
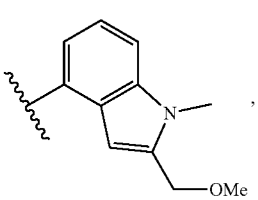,
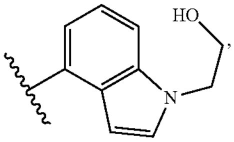,
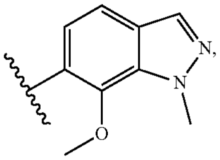,
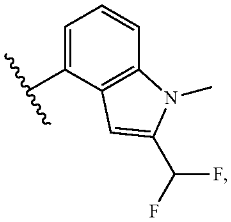,
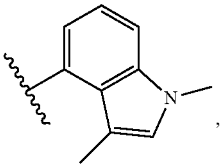,
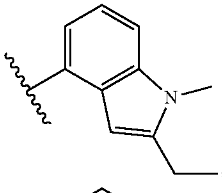,
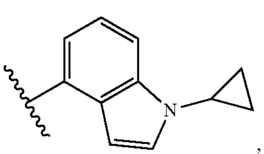,
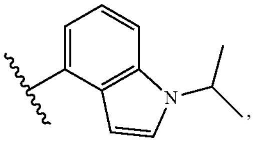,
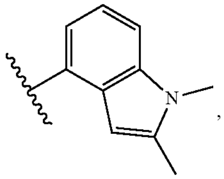,
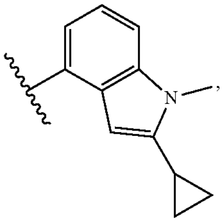,
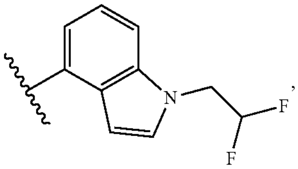,
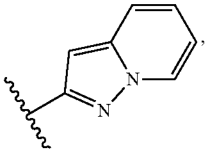,
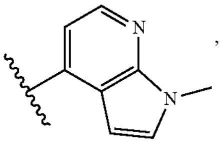, -continued
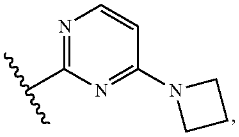, 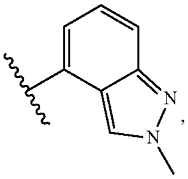,
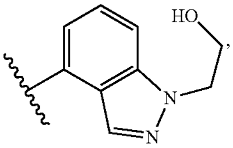, 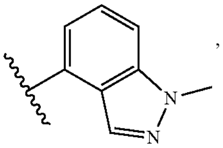,
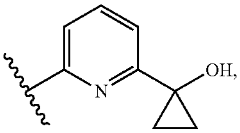 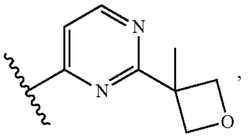,
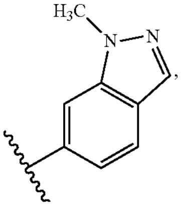, 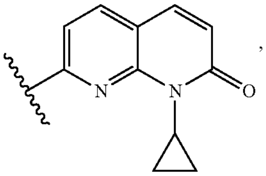,
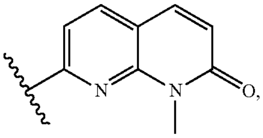
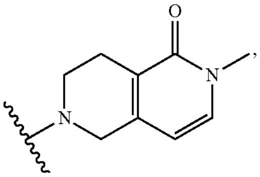, 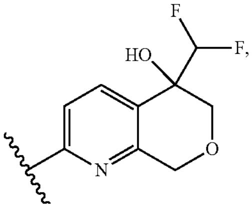
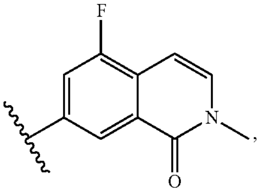,
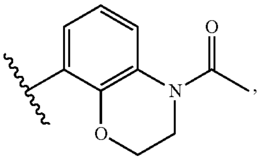,
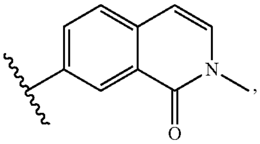,
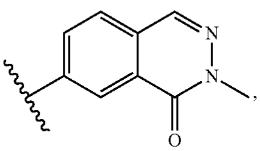, 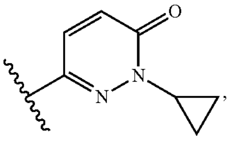,
-continued
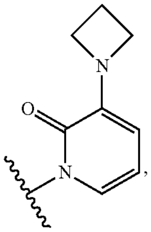, 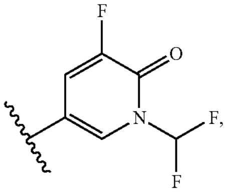
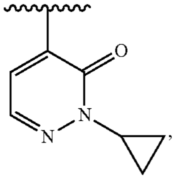, 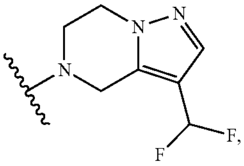
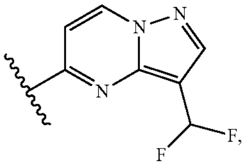 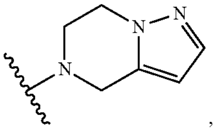,
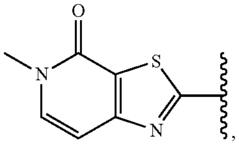, 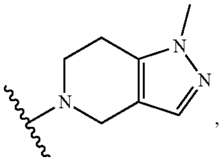,
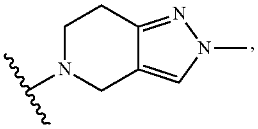, 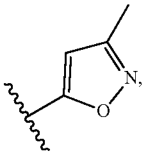
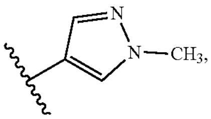 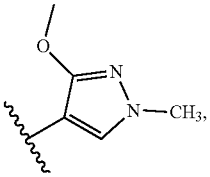
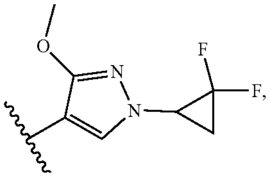 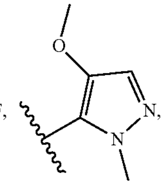
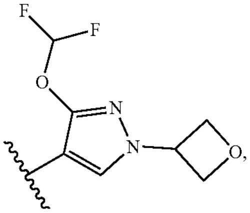 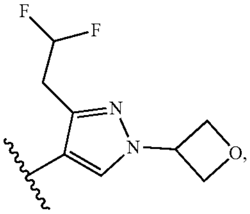
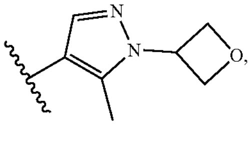 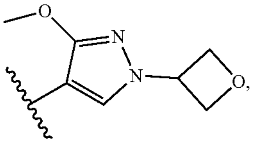

-continued
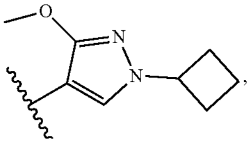, 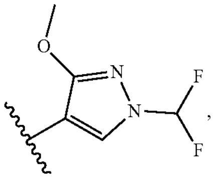,
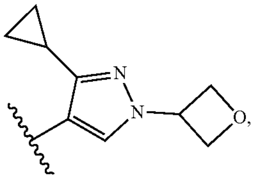
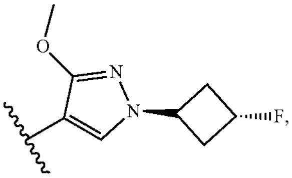
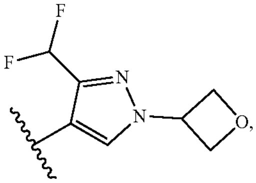 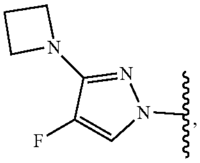
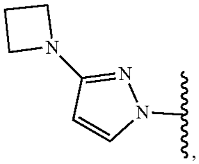, 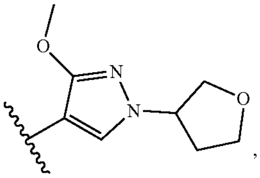,
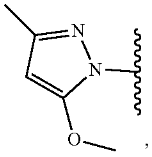, 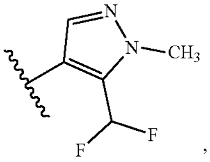,
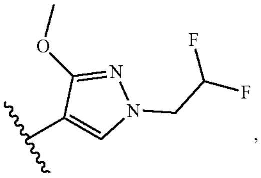,
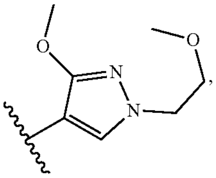 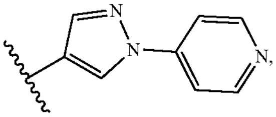
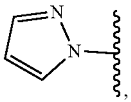, 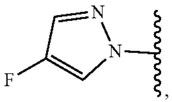, 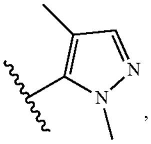,
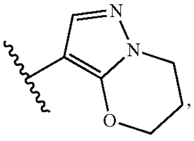, 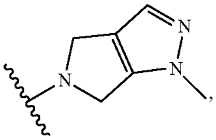
-continued
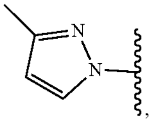, 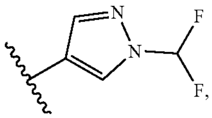
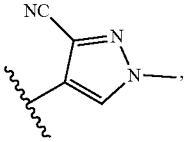 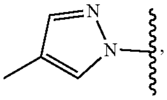, or
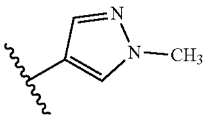).
In some embodiments, C is
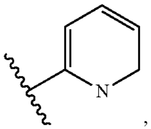, 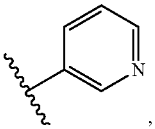,
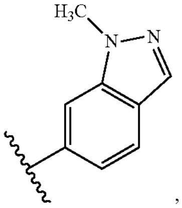, 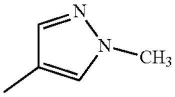, or
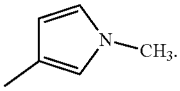
In some embodiments, C is optionally substituted 5- to 10-membered heterocyclyl (e.g.,
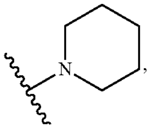, 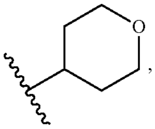,
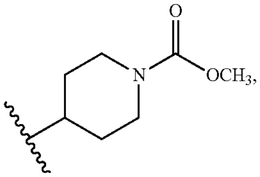 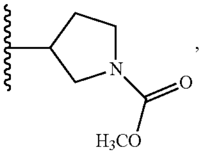,
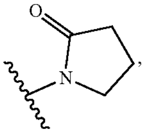, 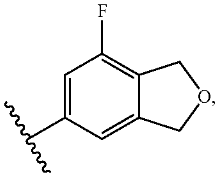
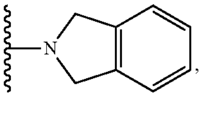, 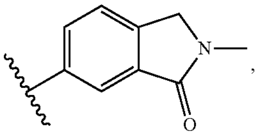, -continued

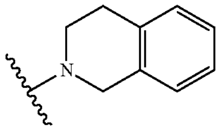, 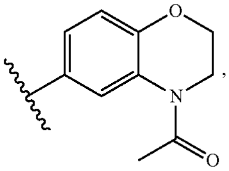,

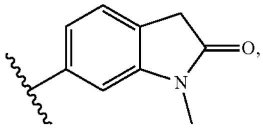, 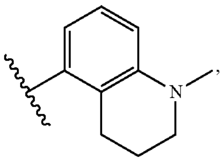,

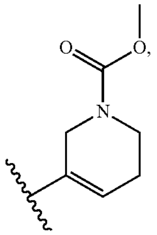, 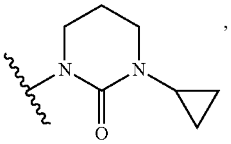,

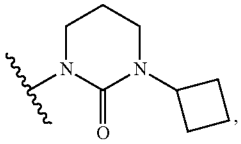, 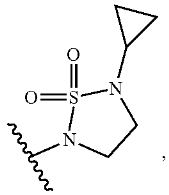,

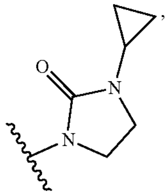, 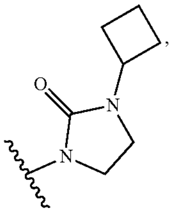,

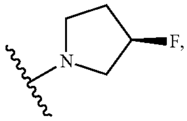, 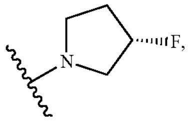,

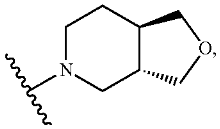, 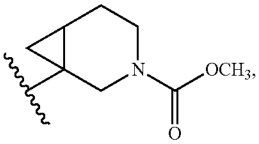,

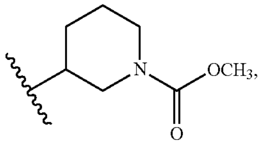, or N-pyrrolidinyl). In some embodiments, C is

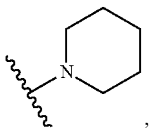, 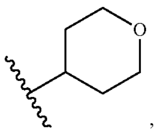, or

-continued

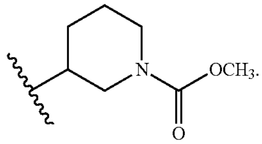.

In some embodiments, B is an optionally substituted 6-membered monocyclic heteroarylene. In some embodiments, B has the structure:

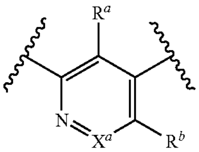

wherein $R^a$ is hydrogen or fluoro;

$R^b$ is hydrogen, fluoro, or $C_1$-$C_3$ alkyl; and $X^a$ is N or CH.

In some embodiments, $R^a$ is hydrogen. In some embodiments, $R^a$ is fluoro. In some embodiments, $R^b$ is hydrogen. In some embodiments, $R^b$ is fluoro. In some embodiments, $C_1$-$C_3$ alkyl (e.g., methyl). In some embodiments, $X^a$ is N. In some embodiments, $X^a$ is CH. In some embodiments, B is

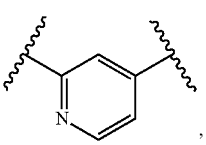 [SMILES: *c1ccnc(*)c1], 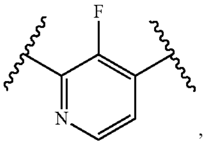,

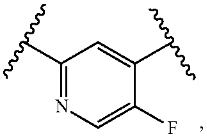, 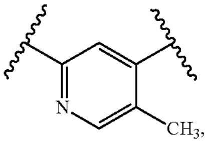, or

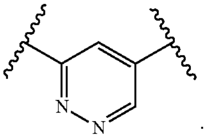.

In some embodiments, B is

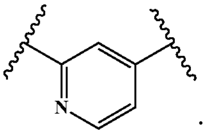.

In some embodiments, B is an optionally substituted 9- or 10-membered bicyclic heteroarylene. In some embodiments, B has the structure:

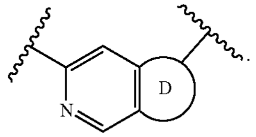.

wherein D is an optionally substituted 5- or 6-membered heteroaryl or optionally substituted 5- or 6-membered heterocyclyl (e.g.,
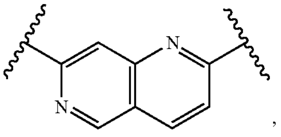,
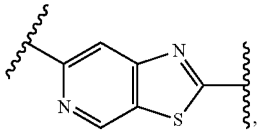, or
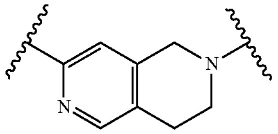).

In some embodiments, L is optionally substituted $C_1$-$C_3$ alkylene, $C_2$ alkynylene, optionally substituted $C_2$ alkenylene, optionally substituted $C_2$-$C_3$ heteroalkylene, optionally substituted $C_3$-$C_5$ cycloalkylene, or optionally substituted 4- to 10-membered heterocyclylene. In some embodiments, L is covalent a bond, e.g., the compound of Formula I is a compound of Formula Ia:

Formula Ia

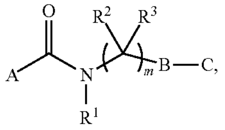

or a pharmaceutically acceptable salt thereof, where all variables are as described herein.

In some embodiments, L is optionally substituted $C_1$-$C_3$ alkylene (e.g., ethylene). In some embodiments, $C_2$ alkynylene. In some embodiments, L is optionally substituted $C_2$ alkenylene (e.g.,
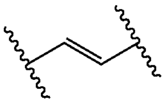,
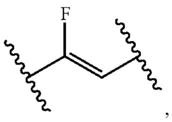,
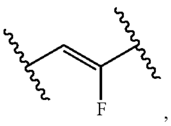, or
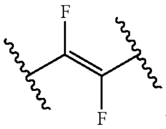).

In some embodiments, L is optionally substituted $C_2$-$C_3$ heteroalkylene (e.g.,
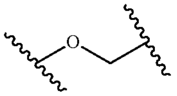 or
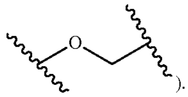).

In some embodiments, L is optionally substituted $C_3$-$C_5$ cycloalkylene (e.g.,
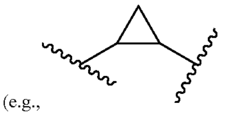 or
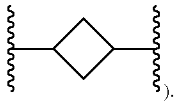).

In some embodiments, L is optionally substituted 4- to 10-membered heterocyclylene (e.g.,
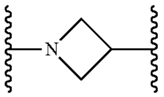,
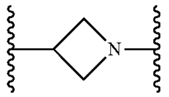,
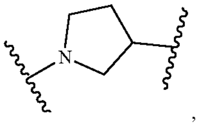,
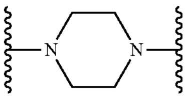,
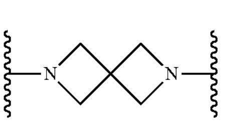,
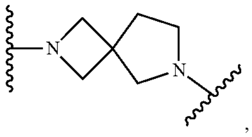, or
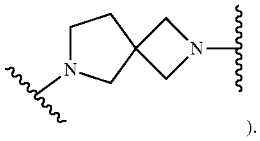).

In some embodiments, the compound is any one of compounds 1-48 in Table 1.

TABLE 1
| Compounds of the invention | |
|---|---|
| # | Compound |
| 1 | 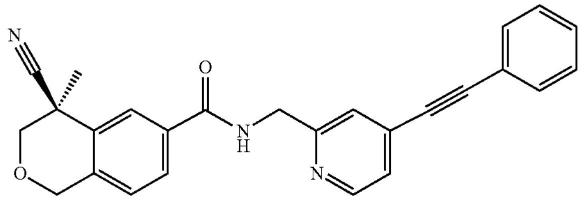 [SMILES: C[C@@]1(C#N)COCc2ccc(C(=O)NCc3cc(C#Cc4ccccc4)ccn3)cc21] |
| 2 | 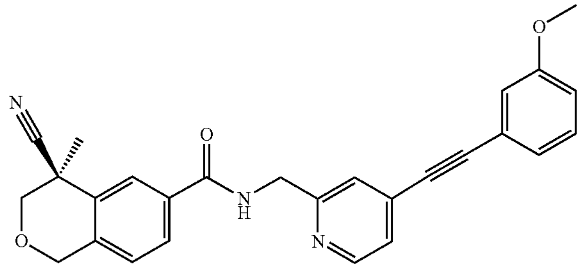 [SMILES: COc1cccc(C#Cc2ccnc(CNC(=O)c3ccc4c(c3)[C@](C)(C#N)COC4)c2)c1] |
| 3 | 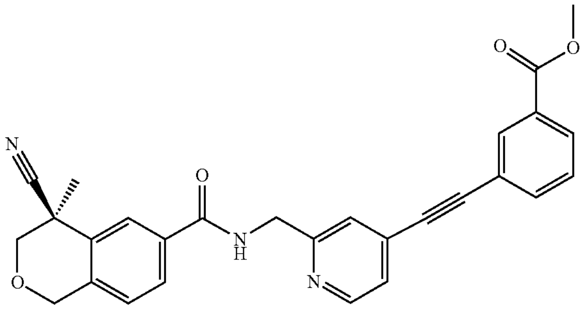 [SMILES: COC(=O)c1cccc(C#Cc2ccnc(CNC(=O)c3ccc4c(c3)[C@](C)(C#N)COC4)c2)c1] |
| 4 | 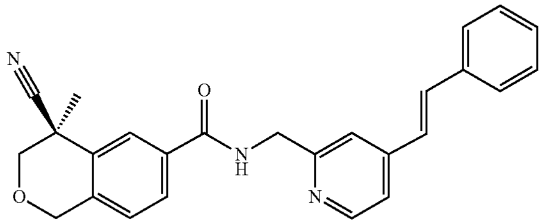 |
| 5 | 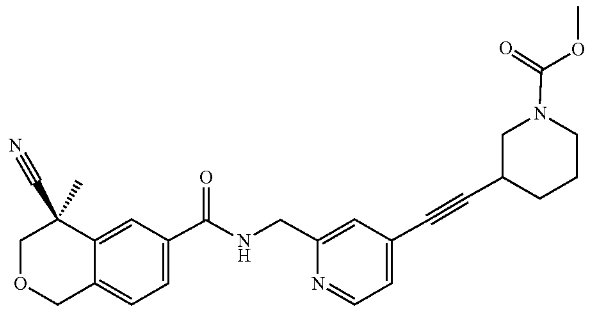 [SMILES: COC(=O)N1CCCC(C#Cc2ccnc(CNC(=O)c3ccc4c(c3)[C@](C)(C#N)COC4)c2)C1] |

TABLE 1-continued
| Compounds of the invention | |
|---|---|
| # | Compound |
| 6 | 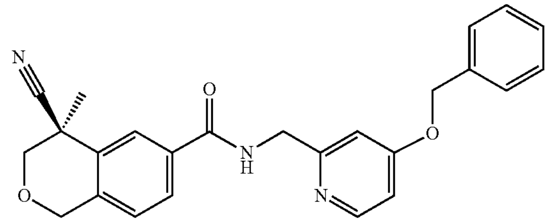 [SMILES: C[C@@]1(C#N)COCc2ccc(C(=O)NCc3cc(OCc4ccccc4)ccn3)cc21] |
| 7 | 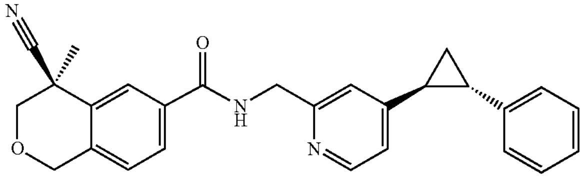 [SMILES: C[C@@]1(C#N)COCc2ccc(C(=O)NCc3cc([C@H]4C[C@@H]4c4ccccc4)ccn3)cc21] |
| 8 | 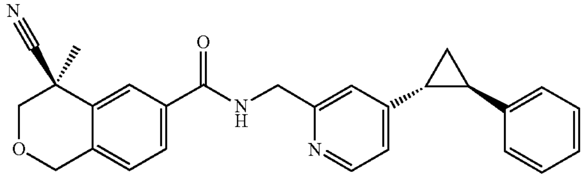 [SMILES: C[C@@]1(C#N)COCc2ccc(C(=O)NCc3cc([C@@H]4C[C@H]4c4ccccc4)ccn3)cc21] |
| 9 | 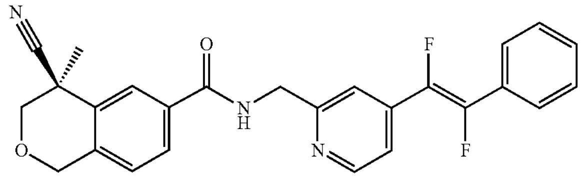 [SMILES: C[C@@]1(C#N)COCc2ccc(C(=O)NCc3cc(/C(F)=C(\F)c4ccccc4)ccn3)cc21] |
| 10 | 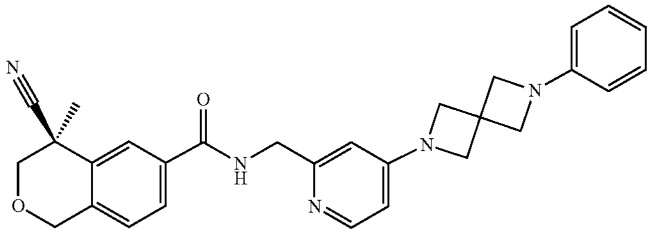 [SMILES: C[C@@]1(C#N)COCc2ccc(C(=O)NCc3cc(N4CC5(CN(c6ccccc6)C5)C4)ccn3)cc21] |
| 11 | 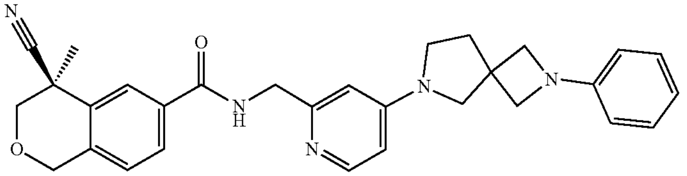 [SMILES: C[C@@]1(C#N)COCc2ccc(C(=O)NCc3cc(N4CCC5(C4)CN(c4ccccc4)C5)ccn3)cc21] |
| 12 | 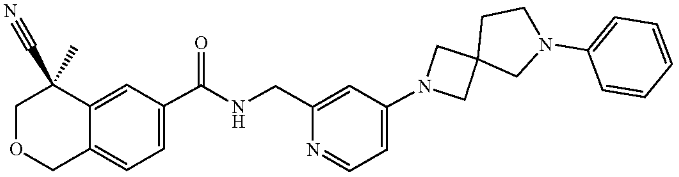 [SMILES: C[C@@]1(C#N)COCc2ccc(C(=O)NCc3cc(N4CC5(CCN(c6ccccc6)C5)C4)ccn3)cc21] |

TABLE 1-continued
| Compounds of the invention | |
|---|---|
| # | Compound |
| 13 | 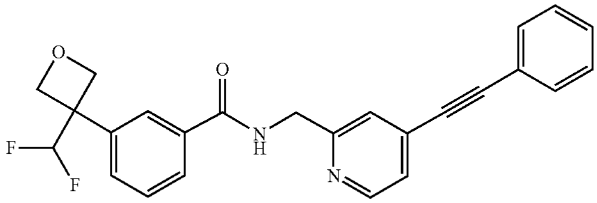 [SMILES: O=C(NCc1cc(C#Cc2ccccc2)ccn1)c1cccc(C2(C(F)F)COC2)c1] |
| 14 | 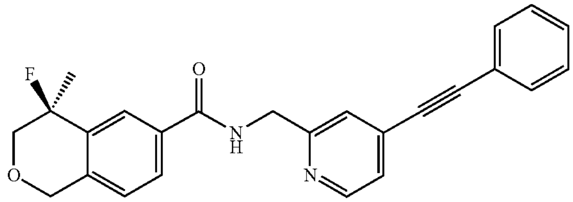 [SMILES: C[C@@]1(F)COCc2ccc(C(=O)NCc3cc(C#Cc4ccccc4)ccn3)cc21] |
| 15 | 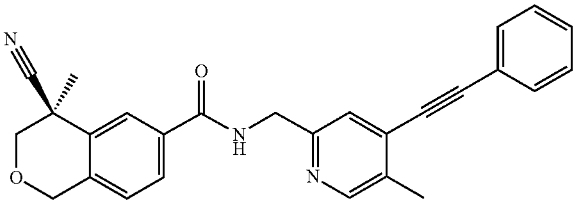 [SMILES: Cc1cnc(CNC(=O)c2ccc3c(c2)[C@](C)(C#N)COC3)cc1C#Cc1ccccc1] |
| 16 | 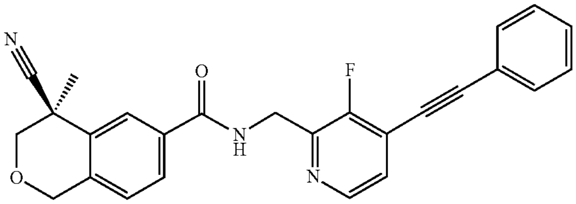 [SMILES: C[C@@]1(C#N)COCc2ccc(C(=O)NCc3nccc(C#Cc4ccccc4)c3F)cc21] |
| 17 | 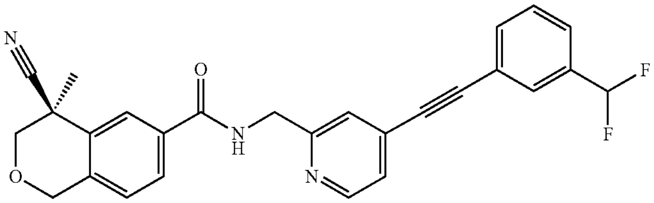 [SMILES: C[C@@]1(C#N)COCc2ccc(C(=O)NCc3cc(C#Cc4cccc(C(F)F)c4)ccn3)cc21] |
| 18 | 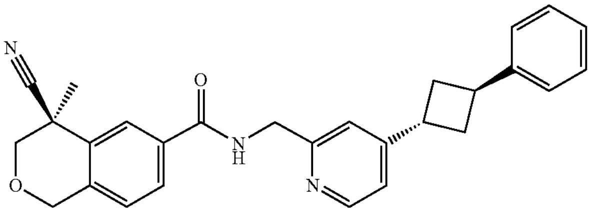 [SMILES: C[C@@]1(C#N)COCc2ccc(C(=O)NCc3cc([C@H]4C[C@H](c5ccccc5)C4)ccn3)cc21] |
| 19 | 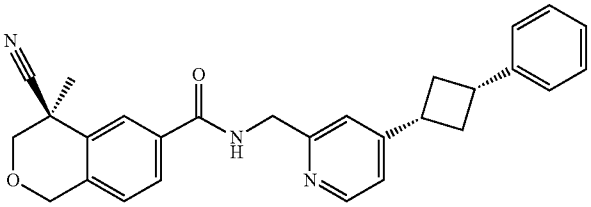 [SMILES: C[C@@]1(C#N)COCc2ccc(C(=O)NCc3cc([C@H]4C[C@@H](c5ccccc5)C4)ccn3)cc21] |

TABLE 1-continued
| Compounds of the invention | |
| --- | --- |
| # | Compound |
| 20 | 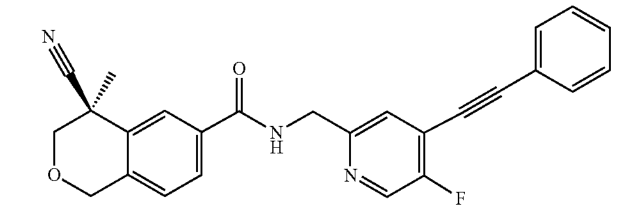 [SMILES: C[C@@]1(C#N)COCc2ccc(C(=O)NCc3cc(C#Cc4ccccc4)c(F)cn3)cc21] |
| 21 | 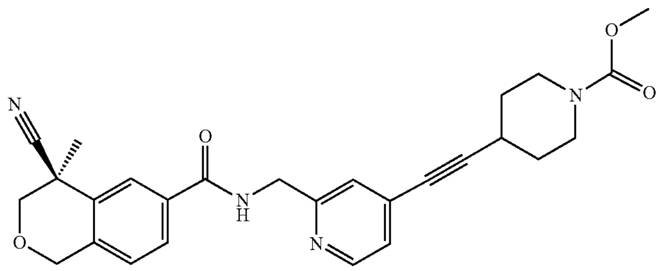 [SMILES: COC(=O)N1CCC(C#Cc2ccnc(CNC(=O)c3ccc4c(c3)[C@](C)(C#N)COC4)c2)CC1] |
| 22 | 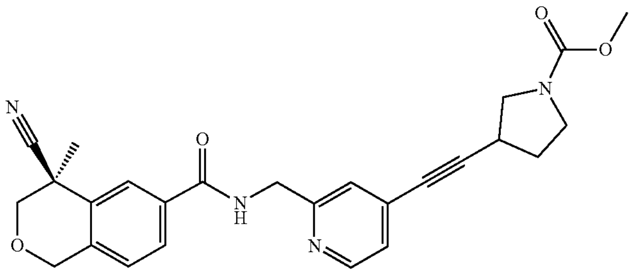 [SMILES: COC(=O)N1CCC(C#Cc2ccnc(CNC(=O)c3ccc4c(c3)[C@](C)(C#N)COC4)c2)C1] |
| 23 | 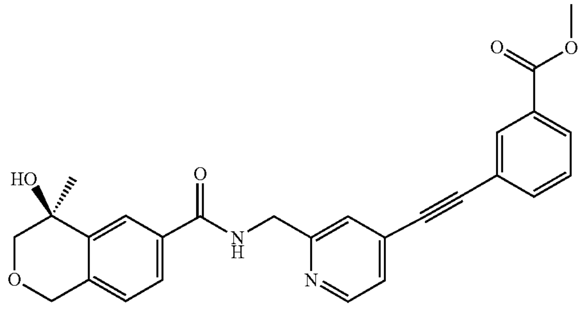 [SMILES: COC(=O)c1cccc(C#Cc2ccnc(CNC(=O)c3ccc4c(c3)[C@](C)(O)COC4)c2)c1] |
| 24 | 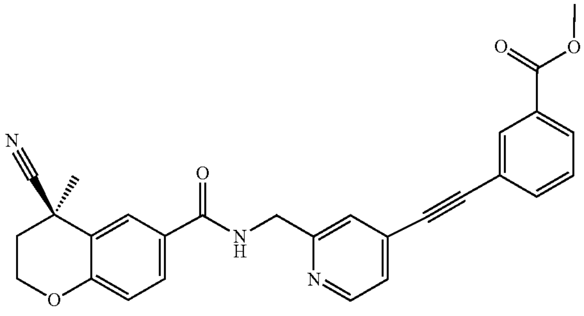 [SMILES: COC(=O)c1cccc(C#Cc2ccnc(CNC(=O)c3ccc4c(c3)[C@](C)(C#N)CCO4)c2)c1] |

TABLE 1-continued
| Compounds of the invention | |
|---|---|
| # | Compound |
| 25 | 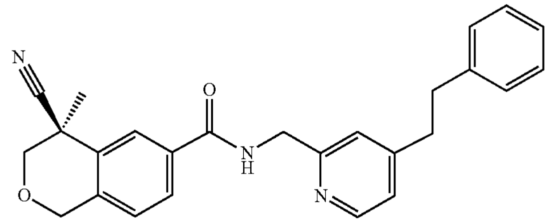 [SMILES: C[C@@]1(C#N)COCc2ccc(C(=O)NCc3cc(CCc4ccccc4)ccn3)cc21] |
| 26 | 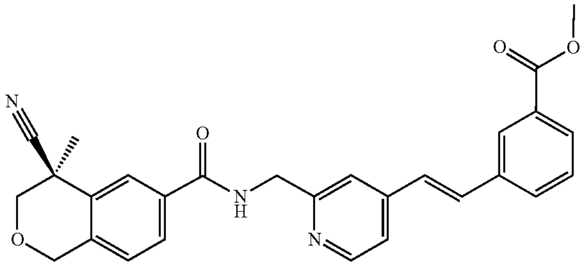 [SMILES: COC(=O)c1cccc(/C=C/c2ccnc(CNC(=O)c3ccc4c(c3)[C@](C)(C#N)COC4)c2)c1] |
| 27 | 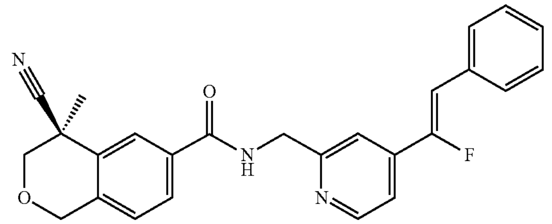 [SMILES: C[C@@]1(C#N)COCc2ccc(C(=O)NCc3cc(/C(F)=C/c4ccccc4)ccn3)cc21] |
| 28 | 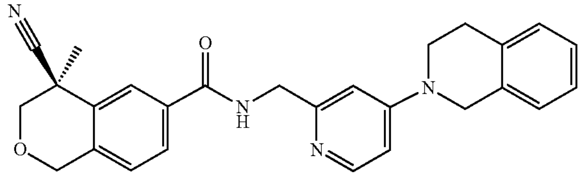 [SMILES: C[C@@]1(C#N)COCc2ccc(C(=O)NCc3cc(N4CCc5ccccc5C4)ccn3)cc21] |
| 29 | 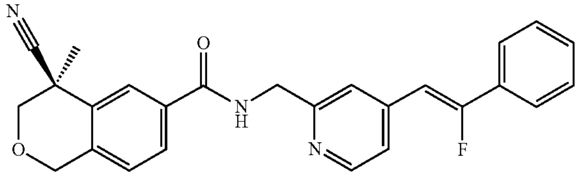 [SMILES: C[C@@]1(C#N)COCc2ccc(C(=O)NCc3cc(/C=C(\F)c4ccccc4)ccn3)cc21] |
| 30 | 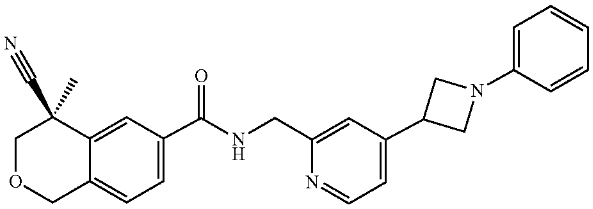 [SMILES: C[C@@]1(C#N)COCc2ccc(C(=O)NCc3cc(C4CN(c5ccccc5)C4)ccn3)cc21] |
| 31 | 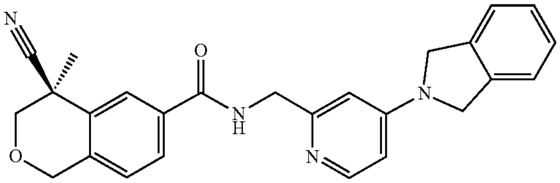 [SMILES: C[C@@]1(C#N)COCc2ccc(C(=O)NCc3cc(N4Cc5ccccc5C4)ccn3)cc21] |

TABLE 1-continued
| Compounds of the invention | |
|---|---|
| # | Compound |
| 32 | 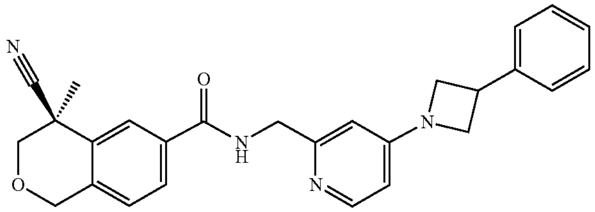 [SMILES: C[C@@]1(C#N)COCc2ccc(C(=O)NCc3cc(N4CC(c5ccccc5)C4)ccn3)cc21] |
| 33 | 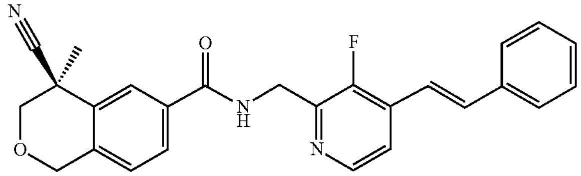 [SMILES: C[C@@]1(C#N)COCc2ccc(C(=O)NCc3nccc(/C=C/c4ccccc4)c3F)cc21] |
| 34 | 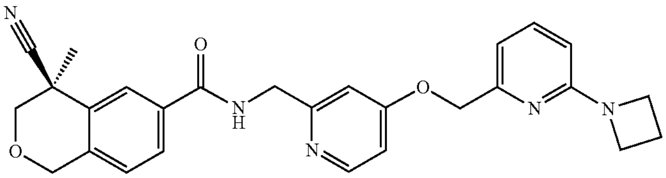 [SMILES: C[C@@]1(C#N)COCc2ccc(C(=O)NCc3cc(OCc4cccc(N5CCC5)n4)ccn3)cc21] |
| 35 | 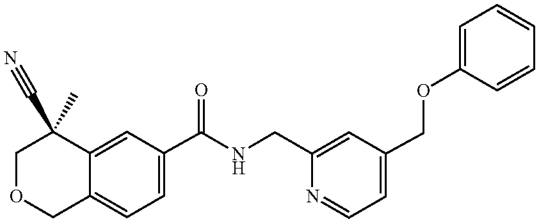 |
| 36 | 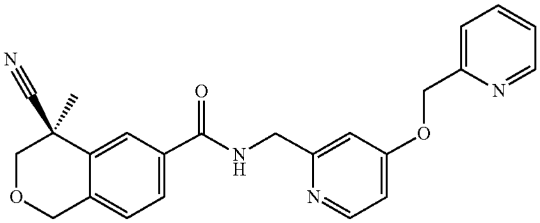 [SMILES: C[C@@]1(C#N)COCc2ccc(C(=O)NCc3cc(OCc4ccccn4)ccn3)cc21] |
| 37 | 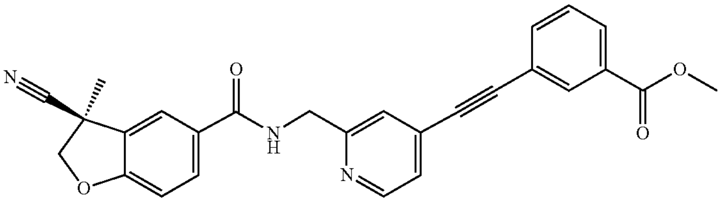 [SMILES: COC(=O)c1cccc(C#Cc2ccnc(CNC(=O)c3ccc4c(c3)[C@](C)(C#N)CO4)c2)c1] |
| 38 | 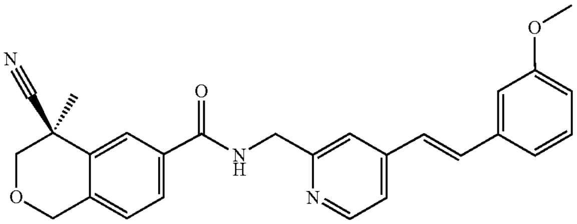 [SMILES: COc1cccc(/C=C/c2ccnc(CNC(=O)c3ccc4c(c3)[C@](C)(C#N)COC4)c2)c1] |

TABLE 1-continued
| Compounds of the invention | |
|---|---|
| # | Compound |
| 39 | 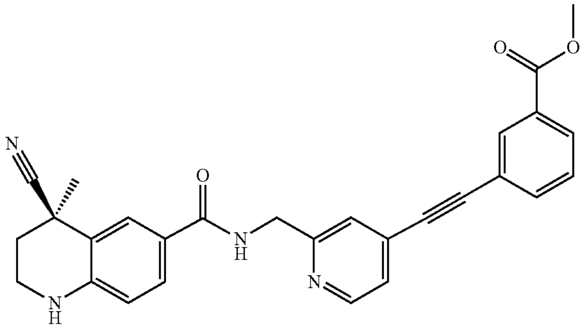 [SMILES: COC(=O)c1cccc(C#Cc2ccnc(CNC(=O)c3ccc4c(c3)[C@](C)(C#N)CCN4)c2)c1] |
| 40 | 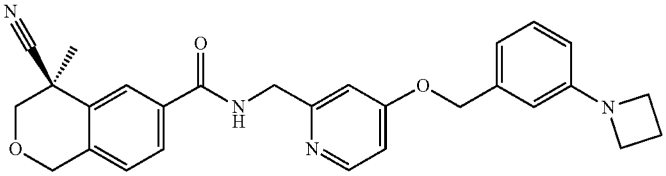 [SMILES: C[C@@]1(C#N)COCc2ccc(C(=O)NCc3cc(OCc4cccc(N5CCC5)c4)ccn3)cc21] |
| 41 | 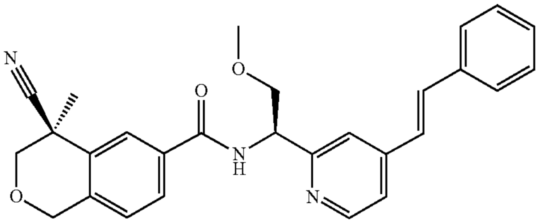 [SMILES: COC[C@H](NC(=O)c1ccc2c(c1)[C@](C)(C#N)COC2)c1cc(/C=C/c2ccccc2)ccn1] |
| 42 | 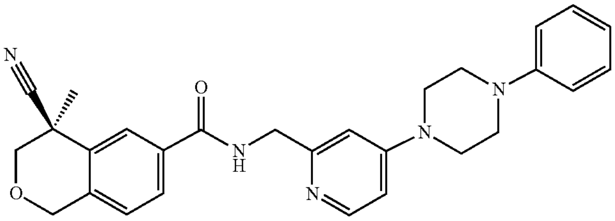 [SMILES: C[C@@]1(C#N)COCc2ccc(C(=O)NCc3cc(N4CCN(c5ccccc5)CC4)ccn3)cc21] |
| 43 | 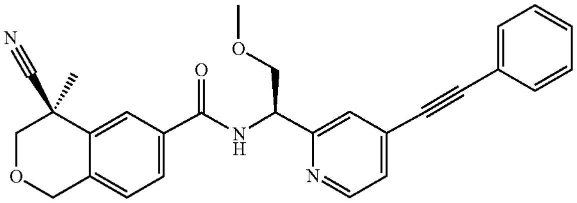 [SMILES: COC[C@H](NC(=O)c1ccc2c(c1)[C@](C)(C#N)COC2)c1cc(C#Cc2ccccc2)ccn1] |
| 44 | 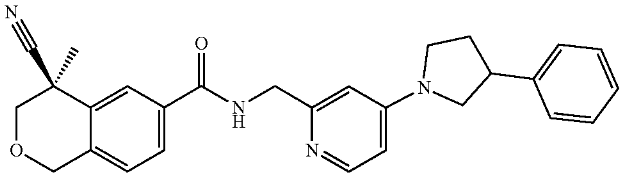 [SMILES: C[C@@]1(C#N)COCc2ccc(C(=O)NCc3cc(N4CCC(c5ccccc5)C4)ccn3)cc21] |

TABLE 1-continued
| Compounds of the invention | |
|---|---|
| # | Compound |
| 45 | 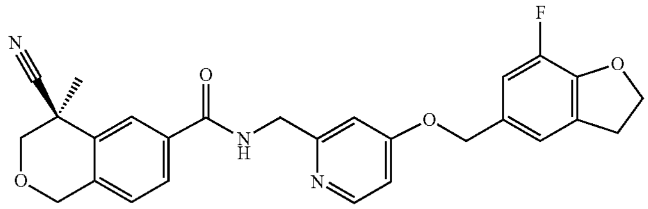 [SMILES: C[C@@]1(C#N)COCc2ccc(C(=O)NCc3cc(OCc4cc(F)c5c(c4)CCO5)ccn3)cc21] |
| 46 | 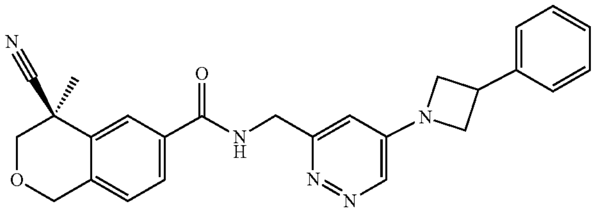 [SMILES: C[C@@]1(C#N)COCc2ccc(C(=O)NCc3cc(N4CC(c5ccccc5)C4)cnn3)cc21] |
| 47 | 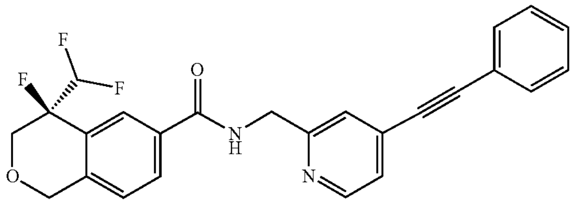 [SMILES: O=C(NCc1cc(C#Cc2ccccc2)ccn1)c1ccc2c(c1)[C@@](F)(C(F)F)COC2] |
| 48 | 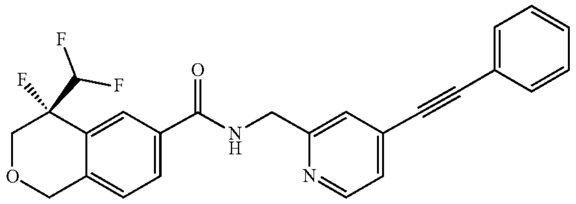 [SMILES: O=C(NCc1cc(C#Cc2ccccc2)ccn1)c1ccc2c(c1)[C@](F)(C(F)F)COC2] |
In some embodiments, the compound is any one of compounds 49-84 in Table 2.
TABLE 2
| Compounds of the invention | |
|---|---|
| # | Compound |
| 49 | 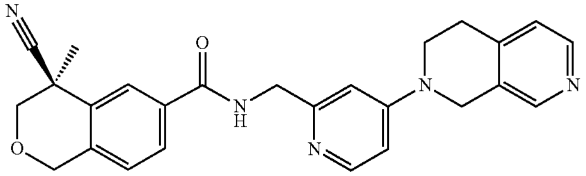 [SMILES: C[C@@]1(C#N)COCc2ccc(C(=O)NCc3cc(N4CCc5ccncc5C4)ccn3)cc21] |
| 50 | 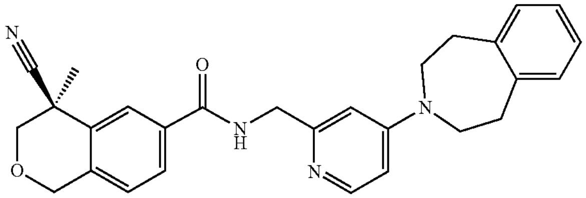 [SMILES: C[C@@]1(C#N)COCc2ccc(C(=O)NCc3cc(N4CCc5ccccc5CC4)ccn3)cc21] |

TABLE 2-continued
| Compounds of the invention | |
|---|---|
| # | Compound |
| 51 | 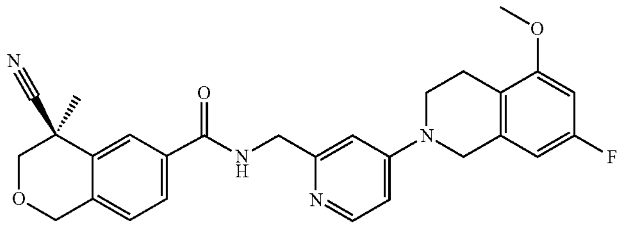 [SMILES: COc1cc(F)cc2c1CCN(c1ccnc(CNC(=O)c3ccc4c(c3)[C@](C)(C#N)COC4)c1)C2] |
| 52 | 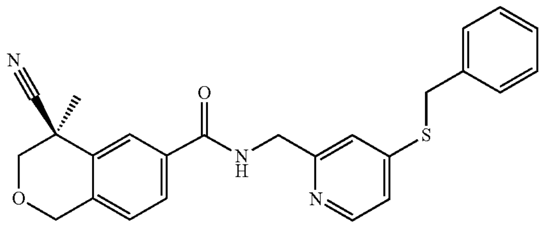 [SMILES: C[C@@]1(C#N)COCc2ccc(C(=O)NCc3cc(SCc4ccccc4)ccn3)cc21] |
| 53 | 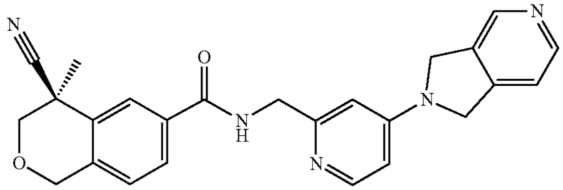 [SMILES: C[C@@]1(C#N)COCc2ccc(C(=O)NCc3cc(N4Cc5ccncc5C4)ccn3)cc21] |
| 54 | 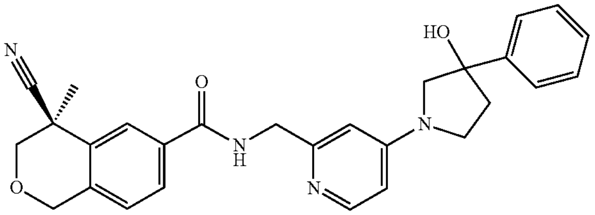 [SMILES: C[C@@]1(C#N)COCc2ccc(C(=O)NCc3cc(N4CCC(O)(c5ccccc5)C4)ccn3)cc21] |
| 55 | 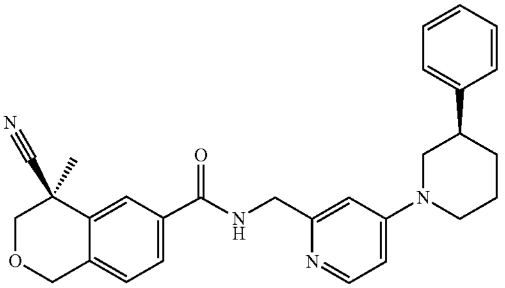 [SMILES: C[C@@]1(C#N)COCc2ccc(C(=O)NCc3cc(N4CCC[C@H](c5ccccc5)C4)ccn3)cc21] |
| 56 | 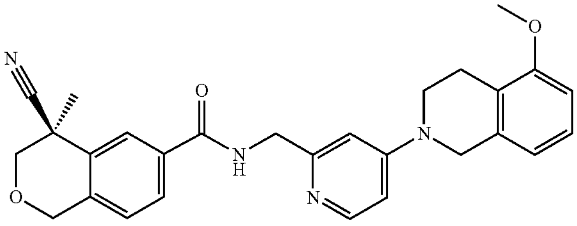 [SMILES: COc1cccc2c1CCN(c1ccnc(CNC(=O)c3ccc4c(c3)[C@](C)(C#N)COC4)c1)C2] |

TABLE 2-continued
| Compounds of the invention | |
|---|---|
| # | Compound |
| 57 | 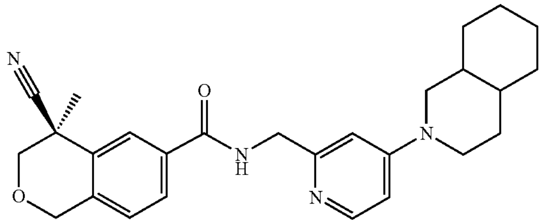 [SMILES: C[C@@]1(C#N)COCc2ccc(C(=O)NCc3cc(N4CCC5CCCCC5C4)ccn3)cc21] |
| 58 | 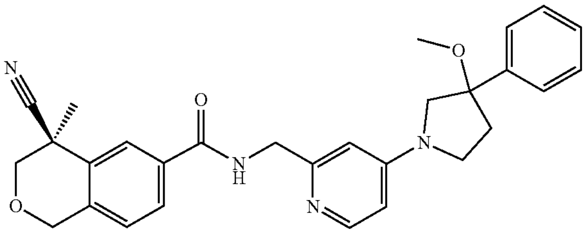 [SMILES: COC1(c2ccccc2)CCN(c2ccnc(CNC(=O)c3ccc4c(c3)[C@](C)(C#N)COC4)c2)C1] |
| 59 | 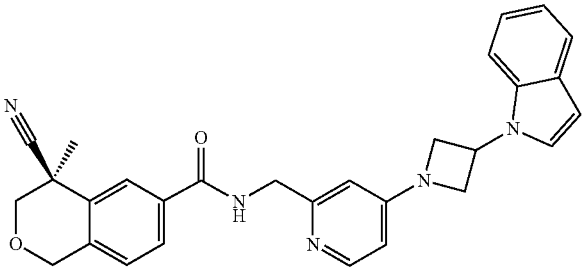 [SMILES: C[C@@]1(C#N)COCc2ccc(C(=O)NCc3cc(N4CC(n5ccc6ccccc65)C4)ccn3)cc21] |
| 60 | 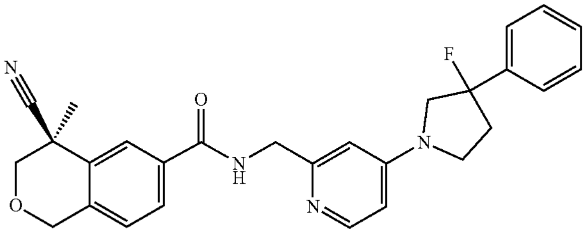 [SMILES: C[C@@]1(C#N)COCc2ccc(C(=O)NCc3cc(N4CCC(F)(c5ccccc5)C4)ccn3)cc21] |
| 61 | 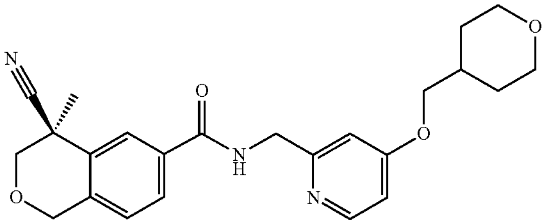 [SMILES: C[C@@]1(C#N)COCc2ccc(C(=O)NCc3cc(OCC4CCOCC4)ccn3)cc21] |
| 62 | 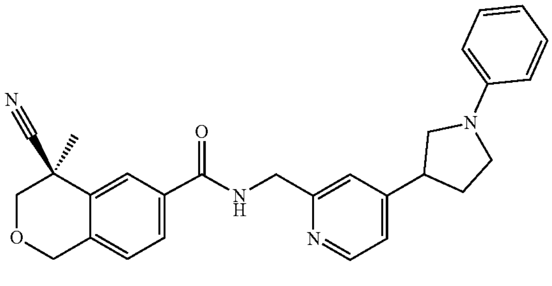 [SMILES: C[C@@]1(C#N)COCc2ccc(C(=O)NCc3cc(C4CCN(c5ccccc5)C4)ccn3)cc21] |

TABLE 2-continued
Compounds of the invention
| # | Compound |
| --- | --- |
| 63 | 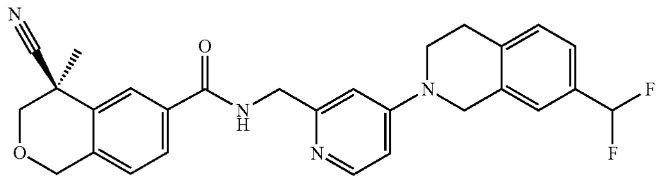 [SMILES: C[C@@]1(C#N)COCc2ccc(C(=O)NCc3cc(N4CCc5ccc(C(F)F)cc5C4)ccn3)cc21] |
| 64 | 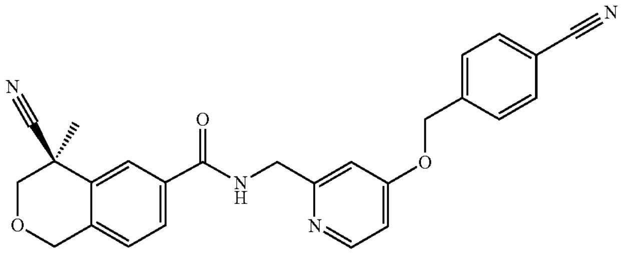 [SMILES: C[C@@]1(C#N)COCc2ccc(C(=O)NCc3cc(OCc4ccc(C#N)cc4)ccn3)cc21] |
| 65 | 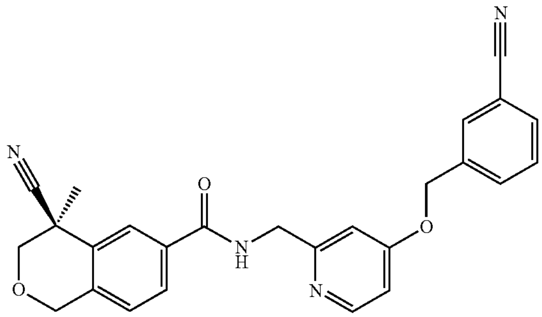 [SMILES: C[C@@]1(C#N)COCc2ccc(C(=O)NCc3cc(OCc4cccc(C#N)c4)ccn3)cc21] |
| 66 | 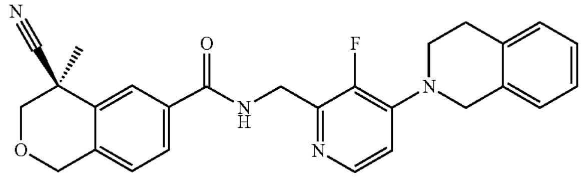 [SMILES: C[C@@]1(C#N)COCc2ccc(C(=O)NCc3nccc(N4CCc5ccccc5C4)c3F)cc21] |
| 67 | 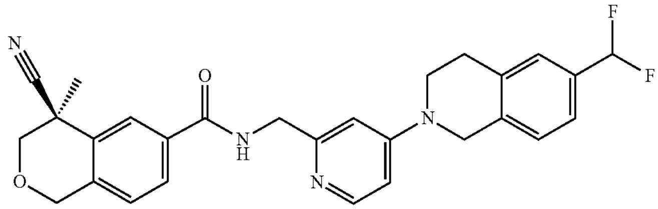 [SMILES: C[C@@]1(C#N)COCc2ccc(C(=O)NCc3cc(N4CCc5cc(C(F)F)ccc5C4)ccn3)cc21] |
| 68 | 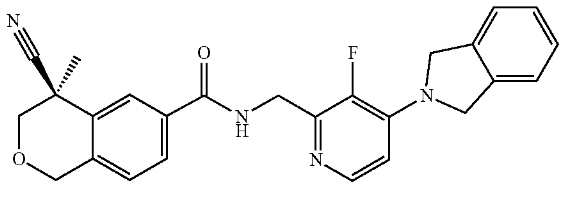 [SMILES: C[C@@]1(C#N)COCc2ccc(C(=O)NCc3nccc(N4Cc5ccccc5C4)c3F)cc21] |

TABLE 2-continued
| Compounds of the invention | |
|---|---|
| # | Compound |
| 69 | 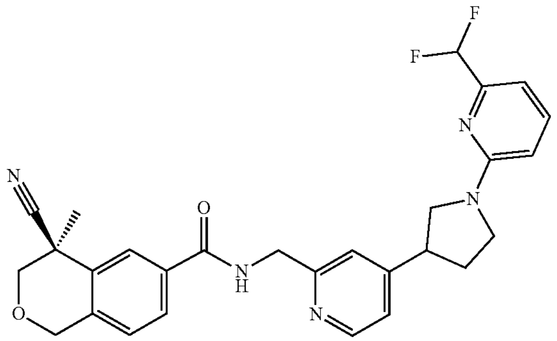 [SMILES: C[C@@]1(C#N)COCc2ccc(C(=O)NCc3cc(C4CCN(c5cccc(C(F)F)n5)C4)ccn3)cc21] |
| 70 | 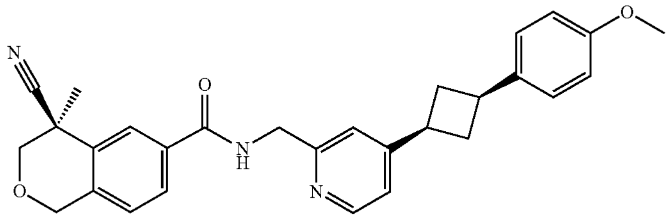 [SMILES: COc1ccc([C@H]2C[C@@H](c3ccnc(CNC(=O)c4ccc5c(c4)[C@](C)(C#N)COC5)c3)C2)cc1] |
| 71 | 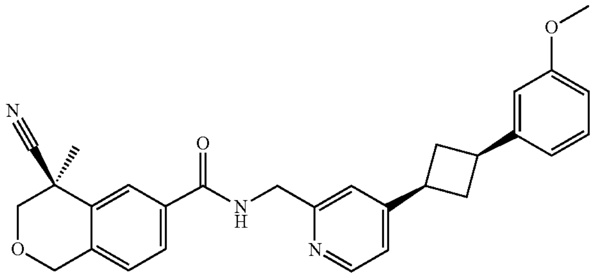 [SMILES: COc1cccc([C@H]2C[C@@H](c3ccnc(CNC(=O)c4ccc5c(c4)[C@](C)(C#N)COC5)c3)C2)c1] |
| 72 | 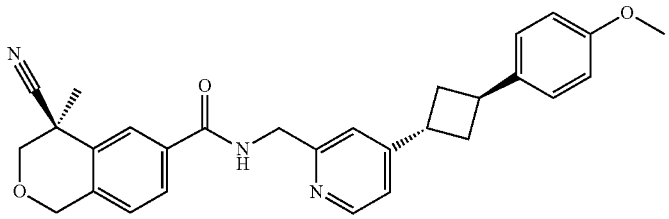 [SMILES: COc1ccc([C@H]2C[C@H](c3ccnc(CNC(=O)c4ccc5c(c4)[C@](C)(C#N)COC5)c3)C2)cc1] |
| 73 | 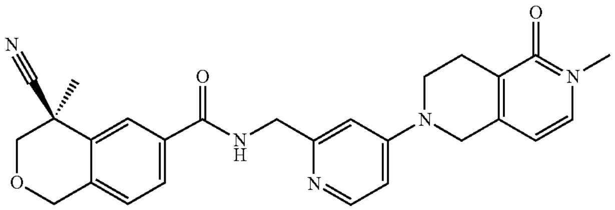 |

TABLE 2-continued
| Compounds of the invention | |
|---|---|
| # | Compound |
| 74 | 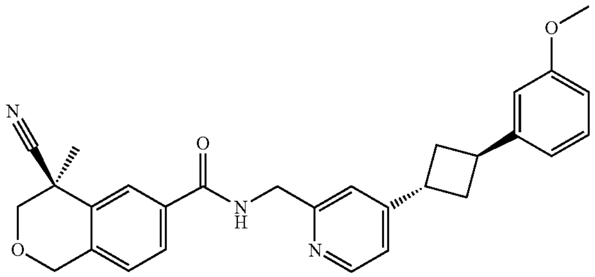 [SMILES: COc1cccc([C@H]2C[C@H](c3ccnc(CNC(=O)c4ccc5c(c4)[C@](C)(C#N)COC5)c3)C2)c1] |
| 75 | 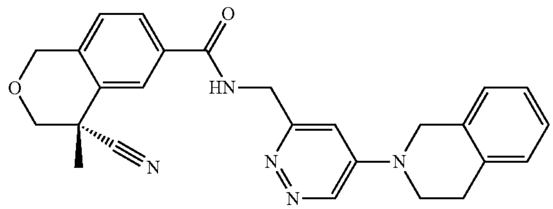 [SMILES: C[C@@]1(C#N)COCc2ccc(C(=O)NCc3cc(N4CCc5ccccc5C4)cnn3)cc21] |
| 76 | 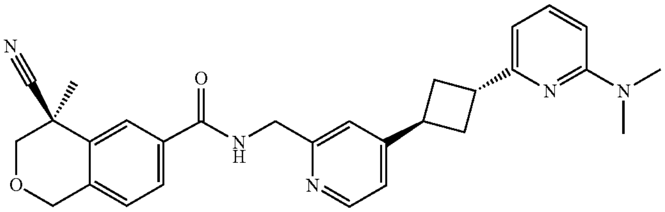 [SMILES: CN(C)c1cccc([C@H]2C[C@H](c3ccnc(CNC(=O)c4ccc5c(c4)[C@](C)(C#N)COC5)c3)C2)n1] |
| 77 | 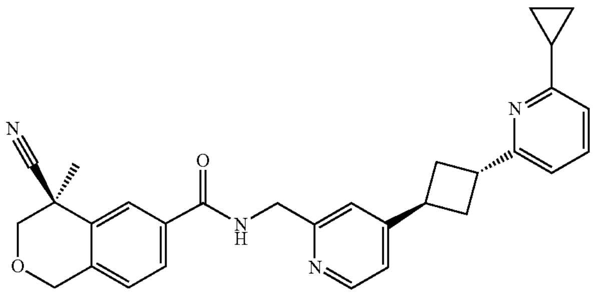 [SMILES: C[C@@]1(C#N)COCc2ccc(C(=O)NCc3cc([C@H]4C[C@H](c5cccc(C6CC6)n5)C4)ccn3)cc21] |
| 78 | 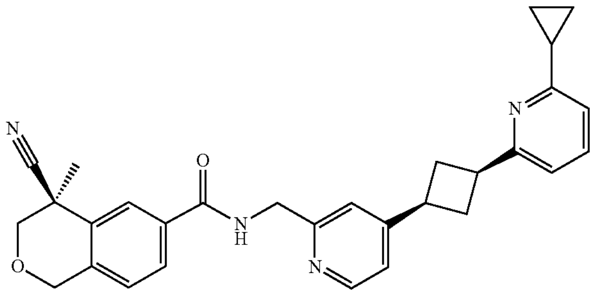 [SMILES: C[C@@]1(C#N)COCc2ccc(C(=O)NCc3cc([C@H]4C[C@@H](c5cccc(C6CC6)n5)C4)ccn3)cc21] |
| 79 | 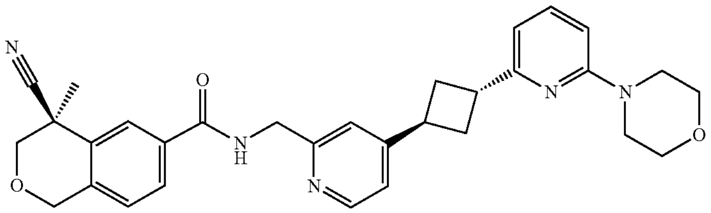 [SMILES: C[C@@]1(C#N)COCc2ccc(C(=O)NCc3cc([C@H]4C[C@H](c5cccc(N6CCOCC6)n5)C4)ccn3)cc21] |

TABLE 2-continued
Compounds of the invention
| # | Compound |
| --- | --- |
| 80 | 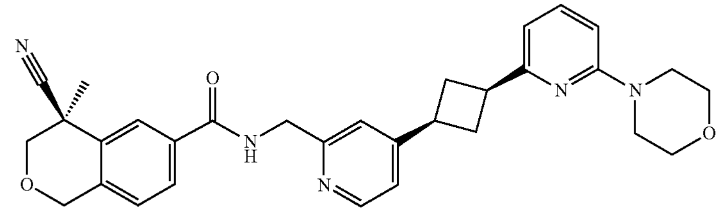 [SMILES: C[C@@]1(C#N)COCc2ccc(C(=O)NCc3cc([C@H]4C[C@@H](c5cccc(N6CCOCC6)n5)C4)ccn3)cc21] |
| 81 | 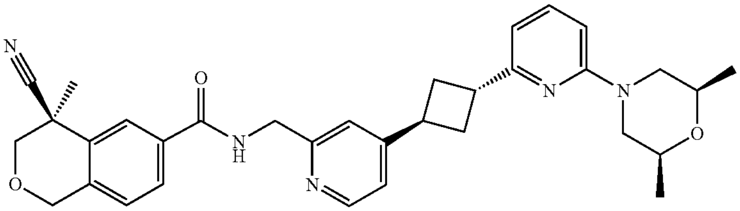 [SMILES: C[C@@H]1CN(c2cccc([C@H]3C[C@H](c4ccnc(CNC(=O)c5ccc6c(c5)[C@](C)(C#N)COC6)c4)C3)n2)C[C@H](C)O1] |
| 82 | 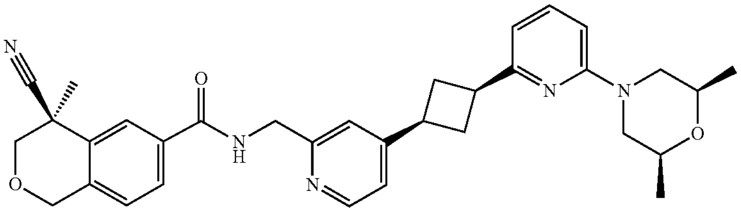 [SMILES: C[C@@H]1CN(c2cccc([C@H]3C[C@@H](c4ccnc(CNC(=O)c5ccc6c(c5)[C@](C)(C#N)COC6)c4)C3)n2)C[C@H](C)O1] |
| 83 | 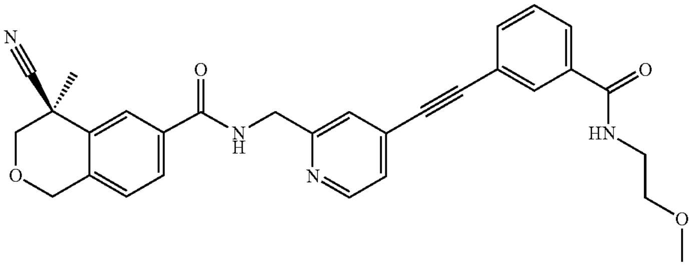 [SMILES: COCCNC(=O)c1cccc(C#Cc2ccnc(CNC(=O)c3ccc4c(c3)[C@](C)(C#N)COC4)c2)c1] |
| 84 | 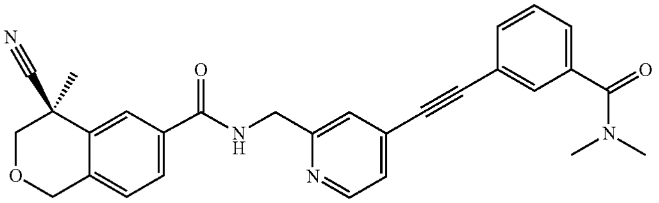 [SMILES: CN(C)C(=O)c1cccc(C#Cc2ccnc(CNC(=O)c3ccc4c(c3)[C@](C)(C#N)COC4)c2)c1] |
In some embodiments, the compound is any one of compounds 85-126 in Table 3.
TABLE 3
Compounds of the invention
| # | Compound |
| --- | --- |
| 85 | 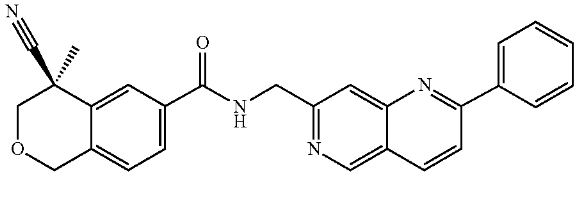 [SMILES: C[C@@]1(C#N)COCc2ccc(C(=O)NCc3cc4nc(-c5ccccc5)ccc4cn3)cc21] |

TABLE 3-continued
| Compounds of the invention | |
|---|---|
| # | Compound |
| 86 | 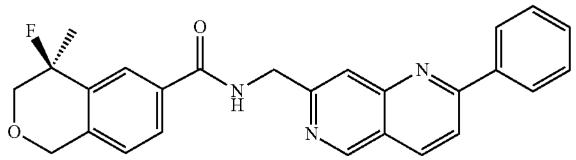 [SMILES: C[C@@]1(F)COCc2ccc(C(=O)NCc3cc4nc(-c5ccccc5)ccc4cn3)cc21] |
| 87 | 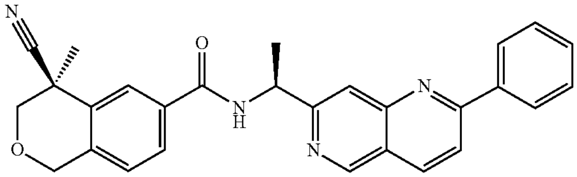 [SMILES: C[C@H](NC(=O)c1ccc2c(c1)[C@](C)(C#N)COC2)c1cc2nc(-c3ccccc3)ccc2cn1] |
| 88 | 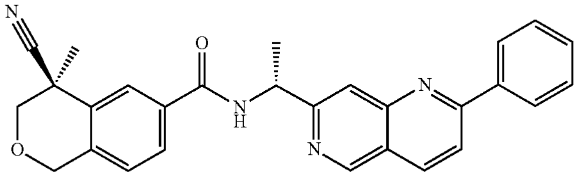 [SMILES: C[C@@H](NC(=O)c1ccc2c(c1)[C@](C)(C#N)COC2)c1cc2nc(-c3ccccc3)ccc2cn1] |
| 89 | 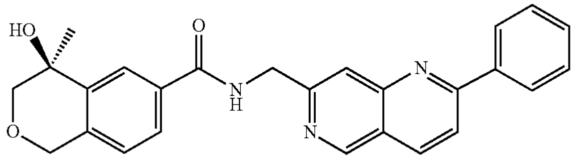 [SMILES: C[C@@]1(O)COCc2ccc(C(=O)NCc3cc4nc(-c5ccccc5)ccc4cn3)cc21] |
| 90 | 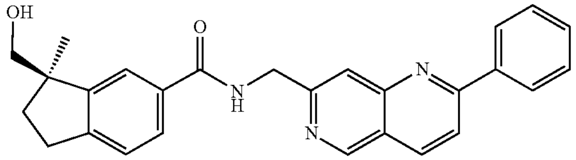 [SMILES: C[C@@]1(CO)CCc2ccc(C(=O)NCc3cc4nc(-c5ccccc5)ccc4cn3)cc21] |
| 91 | 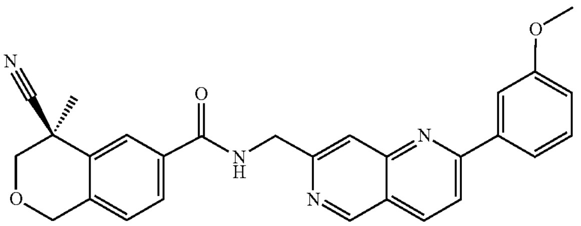 [SMILES: COc1cccc(-c2ccc3cnc(CNC(=O)c4ccc5c(c4)[C@](C)(C#N)COC5)cc3n2)c1] |
| 92 | 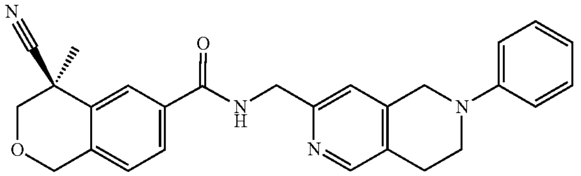 [SMILES: C[C@@]1(C#N)COCc2ccc(C(=O)NCc3cc4c(cn3)CCN(c3ccccc3)C4)cc21] |

TABLE 3-continued
| Compounds of the invention | |
|---|---|
| # | Compound |
| 93 | 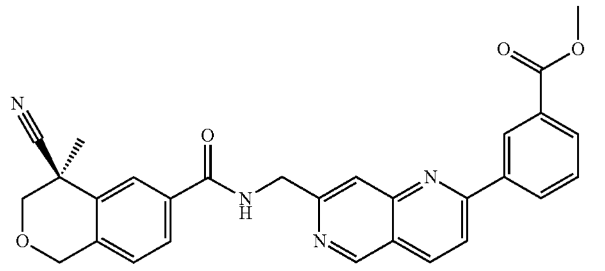 [SMILES: COC(=O)c1cccc(-c2ccc3cnc(CNC(=O)c4ccc5c(c4)[C@](C)(C#N)COC5)cc3n2)c1] |
| 94 | 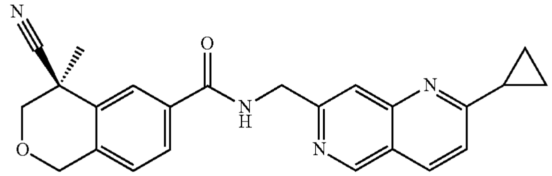 [SMILES: C[C@@]1(C#N)COCc2ccc(C(=O)NCc3cc4nc(C5CC5)ccc4cn3)cc21] |
| 95 | 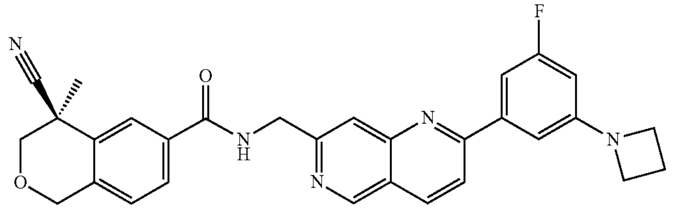 [SMILES: C[C@@]1(C#N)COCc2ccc(C(=O)NCc3cc4nc(-c5cc(F)cc(N6CCC6)c5)ccc4cn3)cc21] |
| 96 | 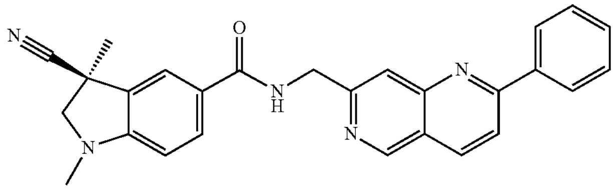 [SMILES: CN1C[C@@](C)(C#N)c2cc(C(=O)NCc3cc4nc(-c5ccccc5)ccc4cn3)ccc21] |
| 97 | 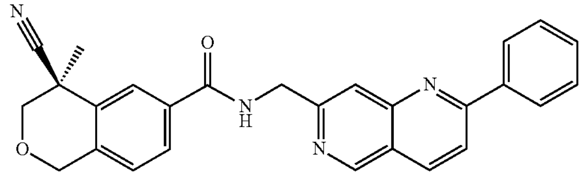 [SMILES: C[C@@]1(C#N)COCc2ccc(C(=O)NCc3cc4nc(-c5ccccc5)ccc4cn3)cc21] |
| 98 | 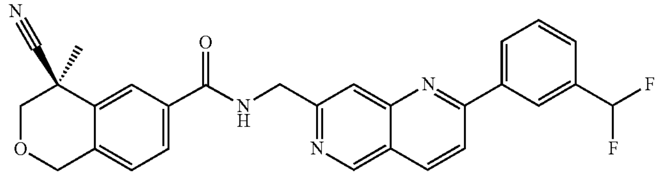 [SMILES: C[C@@]1(C#N)COCc2ccc(C(=O)NCc3cc4nc(-c5cccc(C(F)F)c5)ccc4cn3)cc21] |
| 99 | 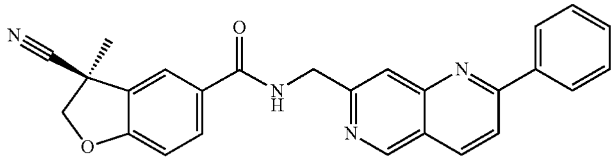 [SMILES: C[C@@]1(C#N)COc2ccc(C(=O)NCc3cc4nc(-c5ccccc5)ccc4cn3)cc21] |

TABLE 3-continued
| Compounds of the invention | |
|---|---|
| # | Compound |
| 100 | 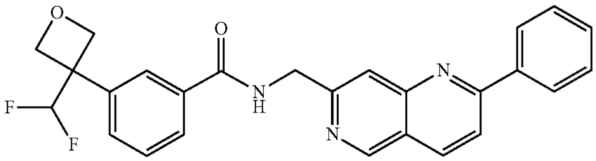 [SMILES: O=C(NCc1cc2nc(-c3ccccc3)ccc2cn1)c1cccc(C2(C(F)F)COC2)c1] |
| 101 | 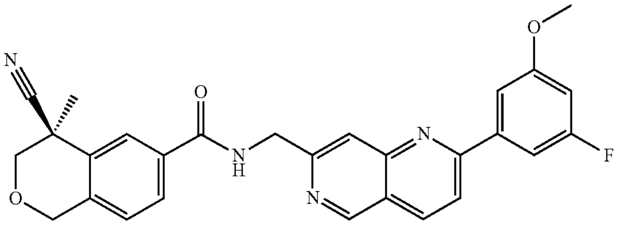 [SMILES: COc1cc(F)cc(-c2ccc3cnc(CNC(=O)c4ccc5c(c4)[C@](C)(C#N)COC5)cc3n2)c1] |
| 102 | 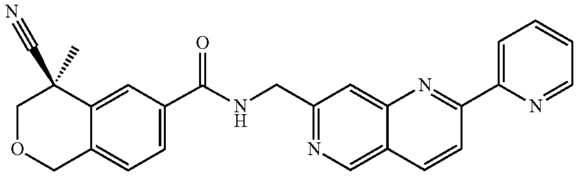 [SMILES: C[C@@]1(C#N)COCc2ccc(C(=O)NCc3cc4nc(-c5ccccn5)ccc4cn3)cc21] |
| 103 | 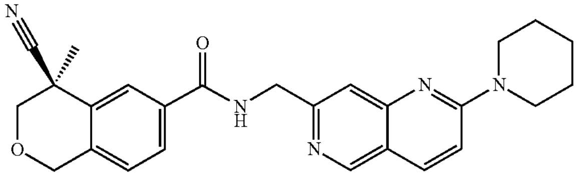 [SMILES: C[C@@]1(C#N)COCc2ccc(C(=O)NCc3cc4nc(N5CCCCC5)ccc4cn3)cc21] |
| 104 | 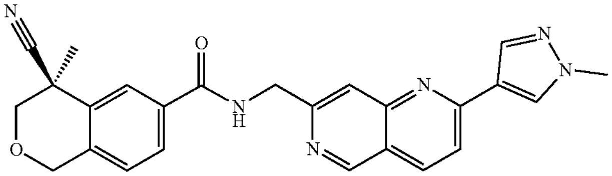 [SMILES: Cn1cc(-c2ccc3cnc(CNC(=O)c4ccc5c(c4)[C@](C)(C#N)COC5)cc3n2)cn1] |
| 105 | 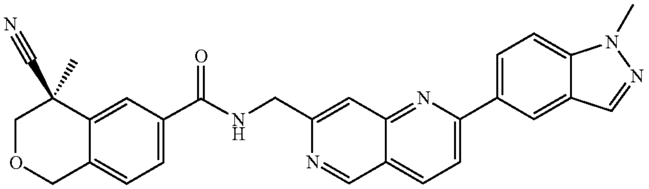 [SMILES: Cn1ncc2cc(-c3ccc4cnc(CNC(=O)c5ccc6c(c5)[C@](C)(C#N)COC6)cc4n3)ccc21] |
| 106 | 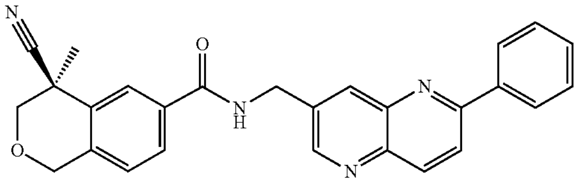 [SMILES: C[C@@]1(C#N)COCc2ccc(C(=O)NCc3cnc4ccc(-c5ccccc5)nc4c3)cc21] |
| 107 | 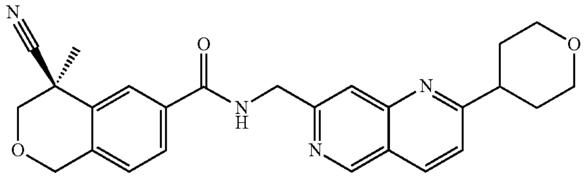 [SMILES: C[C@@]1(C#N)COCc2ccc(C(=O)NCc3cc4nc(C5CCOCC5)ccc4cn3)cc21] |

TABLE 3-continued
| Compounds of the invention | |
|---|---|
| # | Compound |
| 108 | 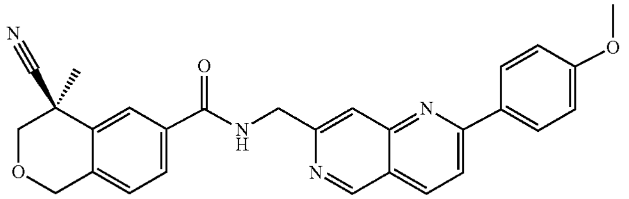 [SMILES: COc1ccc(-c2ccc3cnc(CNC(=O)c4ccc5c(c4)[C@](C)(C#N)COC5)cc3n2)cc1] |
| 109 | 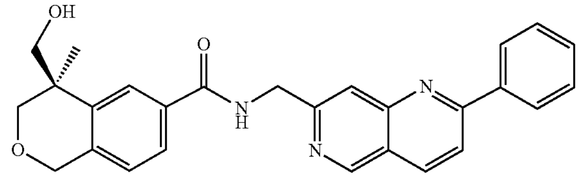 [SMILES: C[C@@]1(CO)COCc2ccc(C(=O)NCc3cc4nc(-c5ccccc5)ccc4cn3)cc21] |
| 110 | 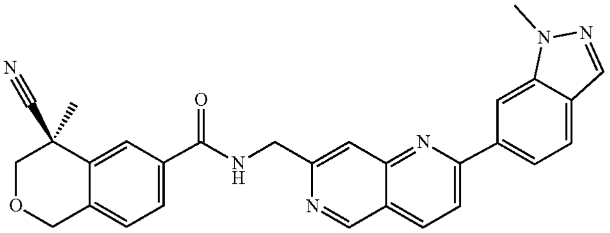 [SMILES: Cn1ncc2ccc(-c3ccc4cnc(CNC(=O)c5ccc6c(c5)[C@](C)(C#N)COC6)cc4n3)cc21] |
| 111 | 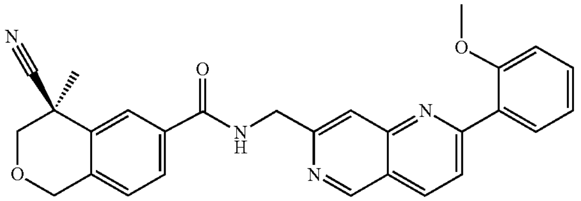 [SMILES: COc1ccccc1-c1ccc2cnc(CNC(=O)c3ccc4c(c3)[C@](C)(C#N)COC4)cc2n1] |
| 112 | 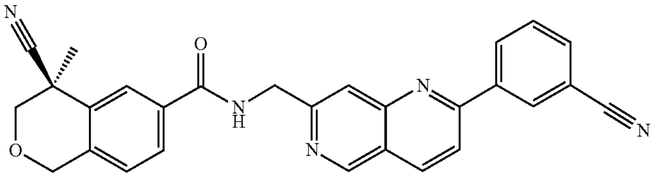 [SMILES: C[C@@]1(C#N)COCc2ccc(C(=O)NCc3cc4nc(-c5cccc(C#N)c5)ccc4cn3)cc21] |
| 113 | 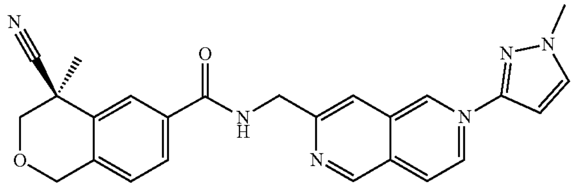 |
| 114 | 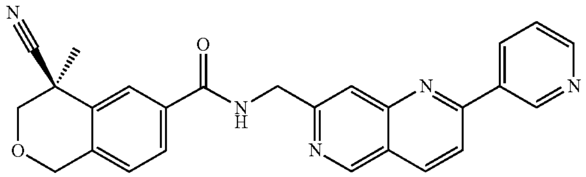 [SMILES: C[C@@]1(C#N)COCc2ccc(C(=O)NCc3cc4nc(-c5cccnc5)ccc4cn3)cc21] |

TABLE 3-continued
| Compounds of the invention | |
|---|---|
| # | Compound |
| 115 | 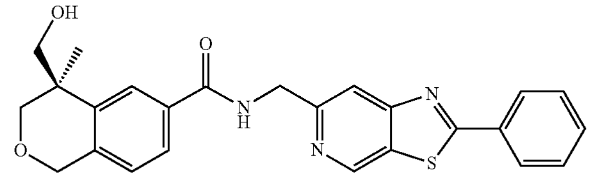 [SMILES: C[C@@]1(CO)COCc2ccc(C(=O)NCc3cc4nc(-c5ccccc5)sc4cn3)cc21] |
| 116 | 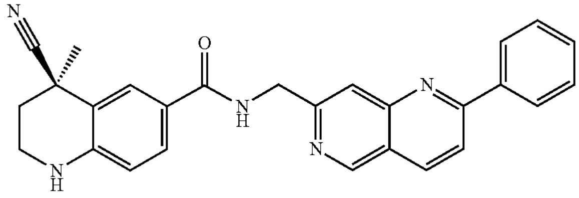 [SMILES: C[C@@]1(C#N)CCNc2ccc(C(=O)NCc3cc4nc(-c5ccccc5)ccc4cn3)cc21] |
| 117 | 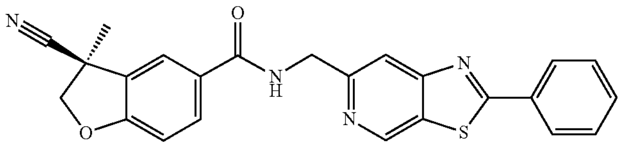 [SMILES: C[C@@]1(C#N)COc2ccc(C(=O)NCc3cc4nc(-c5ccccc5)sc4cn3)cc21] |
| 118 | 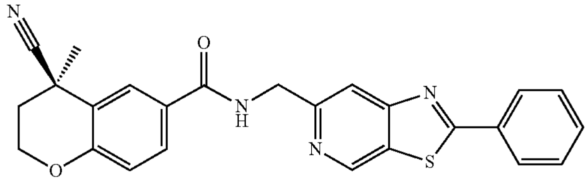 [SMILES: C[C@@]1(C#N)CCOc2ccc(C(=O)NCc3cc4nc(-c5ccccc5)sc4cn3)cc21] |
| 119 | 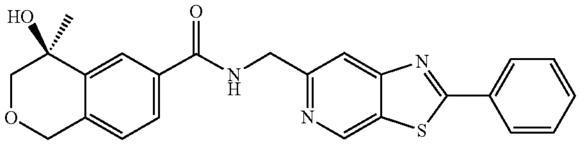 [SMILES: C[C@@]1(O)COCc2ccc(C(=O)NCc3cc4nc(-c5ccccc5)sc4cn3)cc21] |
| 120 | 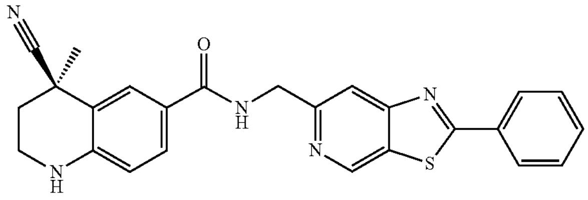 [SMILES: C[C@@]1(C#N)CCNc2ccc(C(=O)NCc3cc4nc(-c5ccccc5)sc4cn3)cc21] |
| 121 | 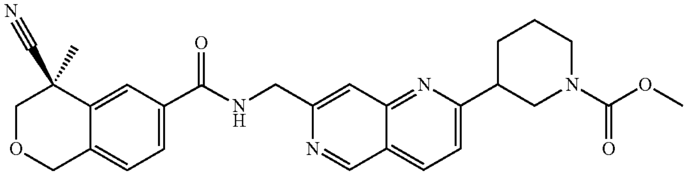 [SMILES: COC(=O)N1CCCC(c2ccc3cnc(CNC(=O)c4ccc5c(c4)[C@](C)(C#N)COC5)cc3n2)C1] |
| 122 | 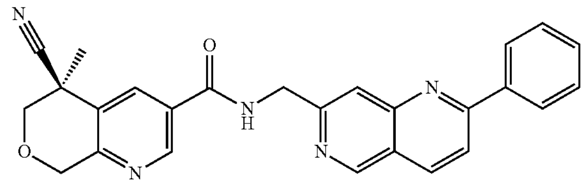 [SMILES: C[C@@]1(C#N)COCc2ncc(C(=O)NCc3cc4nc(-c5ccccc5)ccc4cn3)cc21] |

TABLE 3-continued
| Compounds of the invention | |
|---|---|
| # | Compound |
| 123 | 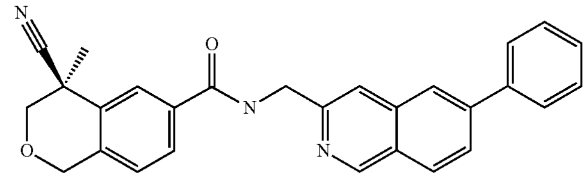 [SMILES: C[C@@]1(C#N)COCc2ccc(C(=O)NCc3cc4cc(-c5ccccc5)ccc4cn3)cc21] |
| 124 | 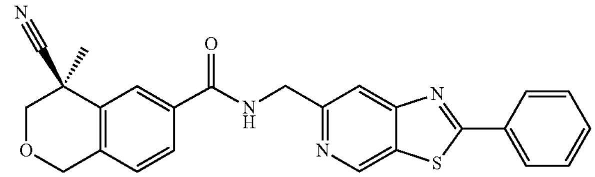 [SMILES: C[C@@]1(C#N)COCc2ccc(C(=O)NCc3cc4nc(-c5ccccc5)sc4cn3)cc21] |
| 125 | 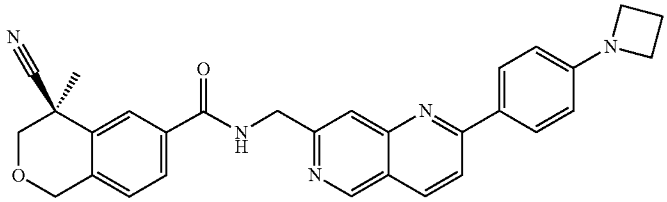 [SMILES: C[C@@]1(C#N)COCc2ccc(C(=O)NCc3cc4nc(-c5ccc(N6CCC6)cc5)ccc4cn3)cc21] |
| 126 | 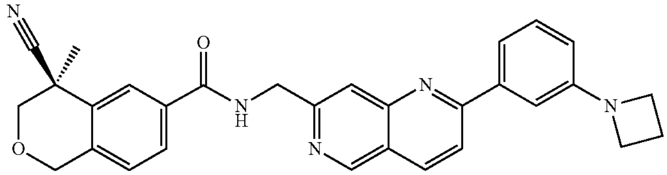 [SMILES: C[C@@]1(C#N)COCc2ccc(C(=O)NCc3cc4nc(-c5cccc(N6CCC6)c5)ccc4cn3)cc21] |
In some embodiments, the compound is any one of compounds 127-525 in Table 3a.
TABLE 3a
| Compounds of the invention | |
|---|---|
| # | Compound |
| 127 | 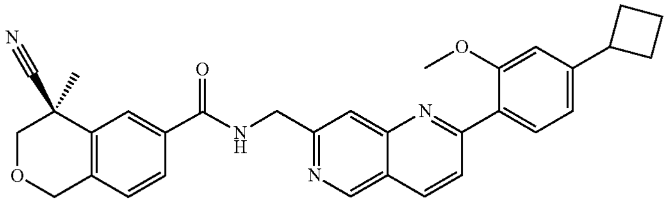 [SMILES: COc1cc(C2CCC2)ccc1-c1ccc2cnc(CNC(=O)c3ccc4c(c3)[C@](C)(C#N)COC4)cc2n1] |
| 128 | 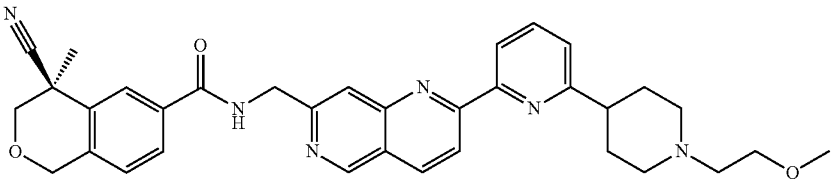 [SMILES: COCCN1CCC(c2cccc(-c3ccc4cnc(CNC(=O)c5ccc6c(c5)[C@](C)(C#N)COC6)cc4n3)n2)CC1] |

TABLE 3a-continued
| Compounds of the invention | |
|---|---|
| # | Compound |
| 129 | 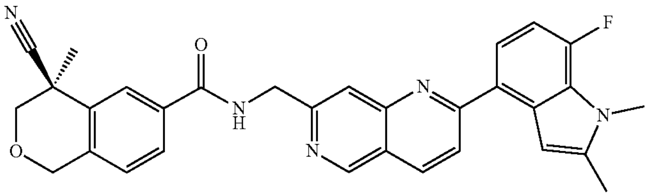 [SMILES: Cc1cc2c(-c3ccc4cnc(CNC(=O)c5ccc6c(c5)[C@](C)(C#N)COC6)cc4n3)ccc(F)c2n1C] |
| 130 | 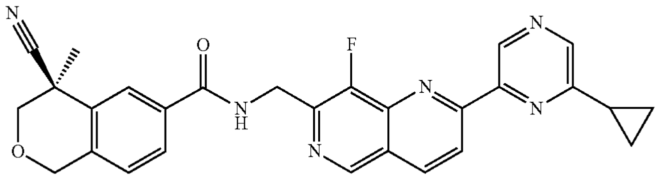 [SMILES: C[C@@]1(C#N)COCc2ccc(C(=O)NCc3ncc4ccc(-c5cncc(C6CC6)n5)nc4c3F)cc21] |
| 131 | 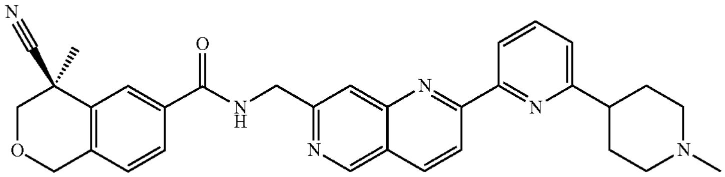 [SMILES: CN1CCC(c2cccc(-c3ccc4cnc(CNC(=O)c5ccc6c(c5)[C@](C)(C#N)COC6)cc4n3)n2)CC1] |
| 132 | 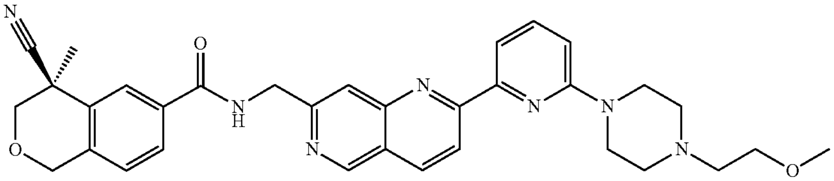 |
| 133 | 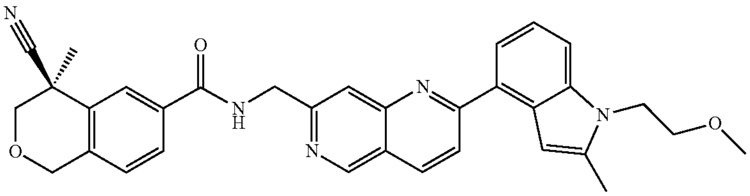 [SMILES: COCCn1c(C)cc2c(-c3ccc4cnc(CNC(=O)c5ccc6c(c5)[C@](C)(C#N)COC6)cc4n3)cccc21] |
| 134 | 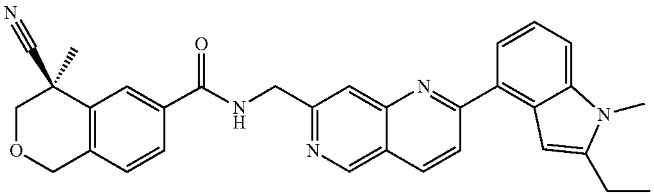 [SMILES: CCc1cc2c(-c3ccc4cnc(CNC(=O)c5ccc6c(c5)[C@](C)(C#N)COC6)cc4n3)cccc2n1C] |
| 135 | 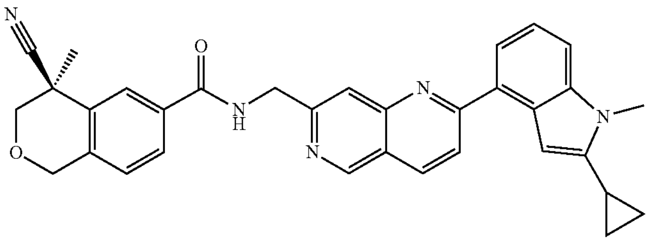 [SMILES: Cn1c(C2CC2)cc2c(-c3ccc4cnc(CNC(=O)c5ccc6c(c5)[C@](C)(C#N)COC6)cc4n3)cccc21] |

TABLE 3a-continued
| Compounds of the invention | |
|---|---|
| # | Compound |
| 136 | 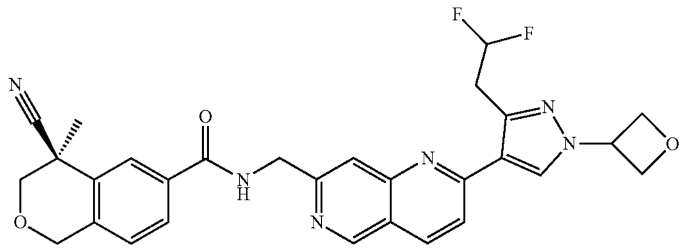 [SMILES: C[C@@]1(C#N)COCc2ccc(C(=O)NCc3cc4nc(-c5cn(C6COC6)nc5CC(F)F)ccc4cn3)cc21] |
| 137 | 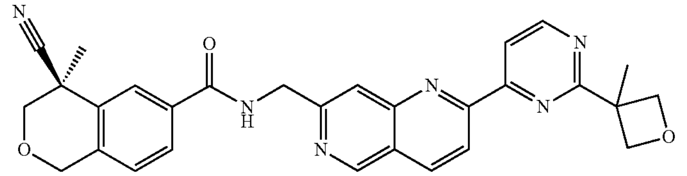 [SMILES: CC1(c2nccc(-c3ccc4cnc(CNC(=O)c5ccc6c(c5)[C@](C)(C#N)COC6)cc4n3)n2)COC1] |
| 138 | 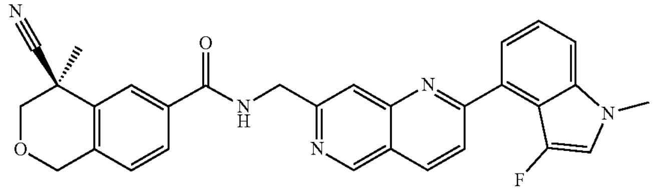 [SMILES: Cn1cc(F)c2c(-c3ccc4cnc(CNC(=O)c5ccc6c(c5)[C@](C)(C#N)COC6)cc4n3)cccc21] |
| 139 | 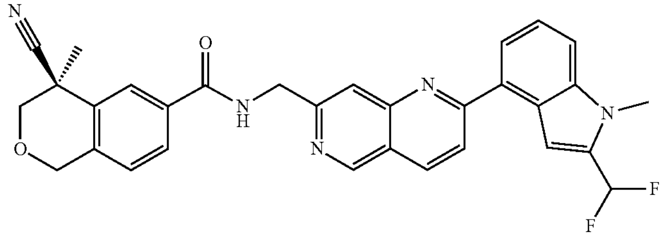 [SMILES: Cn1c(C(F)F)cc2c(-c3ccc4cnc(CNC(=O)c5ccc6c(c5)[C@](C)(C#N)COC6)cc4n3)cccc21] |
| 140 | 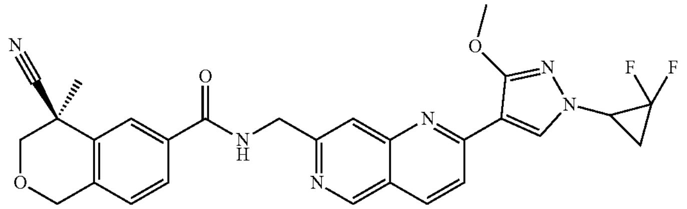 [SMILES: COc1nn(C2CC2(F)F)cc1-c1ccc2cnc(CNC(=O)c3ccc4c(c3)[C@](C)(C#N)COC4)cc2n1] |
| 141 | 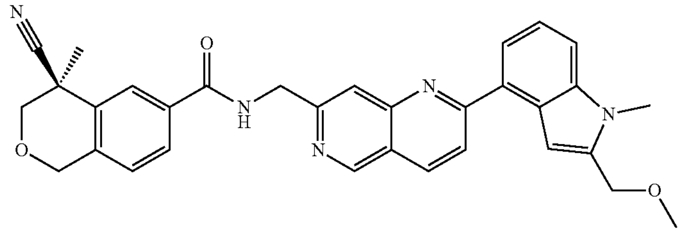 [SMILES: COCc1cc2c(-c3ccc4cnc(CNC(=O)c5ccc6c(c5)[C@](C)(C#N)COC6)cc4n3)cccc2n1C] |

TABLE 3a-continued
| Compounds of the invention | |
|---|---|
| # | Compound |
| 142 | 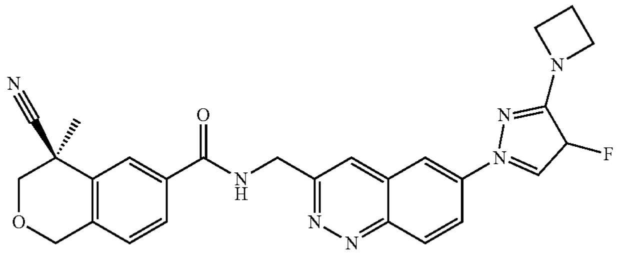 |
| 143 | 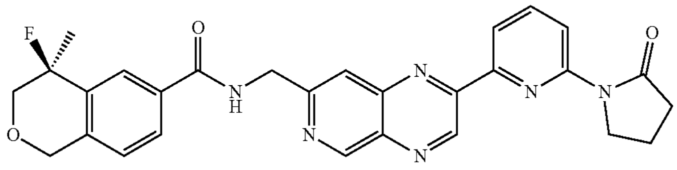 [SMILES: C[C@@]1(F)COCc2ccc(C(=O)NCc3cc4nc(-c5cccc(N6CCCC6=O)n5)cnc4cn3)cc21] |
| 144 | 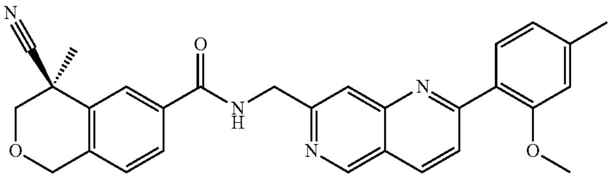 [SMILES: COc1cc(C)ccc1-c1ccc2cnc(CNC(=O)c3ccc4c(c3)[C@](C)(C#N)COC4)cc2n1] |
| 145 | 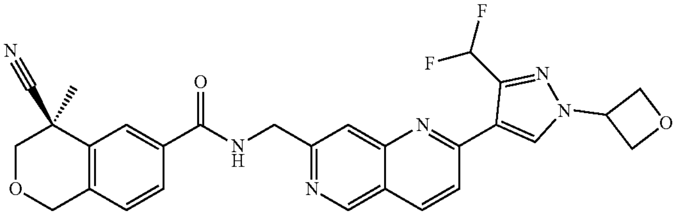 [SMILES: C[C@@]1(C#N)COCc2ccc(C(=O)NCc3cc4nc(-c5cn(C6COC6)nc5C(F)F)ccc4cn3)cc21] |
| 146 | 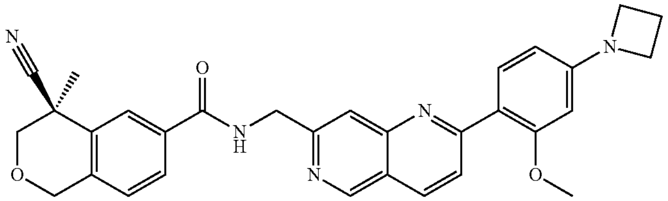 [SMILES: COc1cc(N2CCC2)ccc1-c1ccc2cnc(CNC(=O)c3ccc4c(c3)[C@](C)(C#N)COC4)cc2n1] |
| 147 | 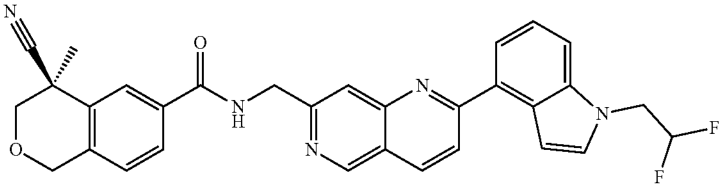 [SMILES: C[C@@]1(C#N)COCc2ccc(C(=O)NCc3cc4nc(-c5cccc6c5ccn6CC(F)F)ccc4cn3)cc21] |
| 148 | 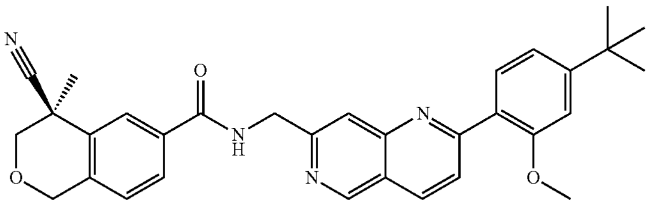 [SMILES: COc1cc(C(C)(C)C)ccc1-c1ccc2cnc(CNC(=O)c3ccc4c(c3)[C@](C)(C#N)COC4)cc2n1] |

TABLE 3a-continued
| Compounds of the invention | |
|---|---|
| # | Compound |
| 149 | 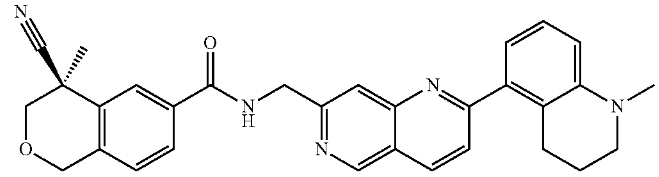 [SMILES: CN1CCCc2c(-c3ccc4cnc(CNC(=O)c5ccc6c(c5)[C@](C)(C#N)COC6)cc4n3)cccc21] |
| 150 | 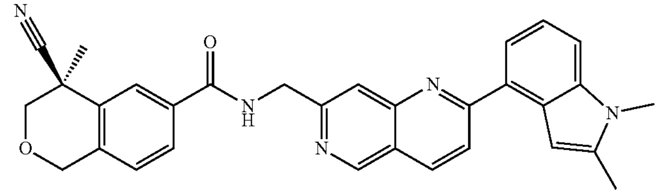 [SMILES: Cc1cc2c(-c3ccc4cnc(CNC(=O)c5ccc6c(c5)[C@](C)(C#N)COC6)cc4n3)cccc2n1C] |
| 151 | 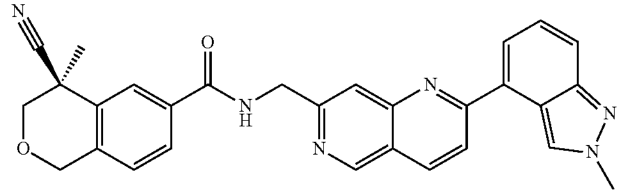 [SMILES: Cn1cc2c(-c3ccc4cnc(CNC(=O)c5ccc6c(c5)[C@](C)(C#N)COC6)cc4n3)cccc2n1] |
| 152 | 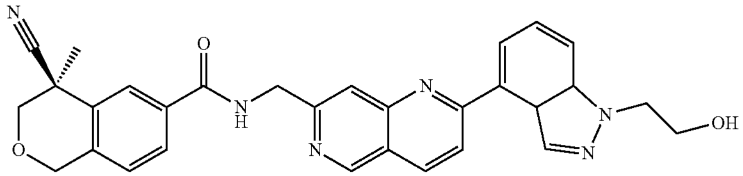 [SMILES: C[C@@]1(C#N)COCc2ccc(C(=O)NCc3cc4nc(C5=CC=CC6C5C=NN6CCO)ccc4cn3)cc21] |
| 153 | 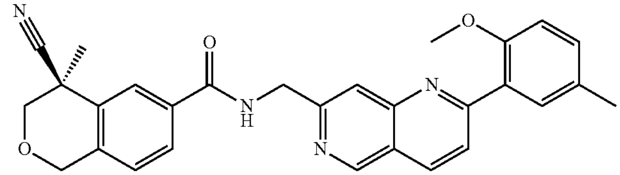 [SMILES: COc1ccc(C)cc1-c1ccc2cnc(CNC(=O)c3ccc4c(c3)[C@](C)(C#N)COC4)cc2n1] |
| 154 | 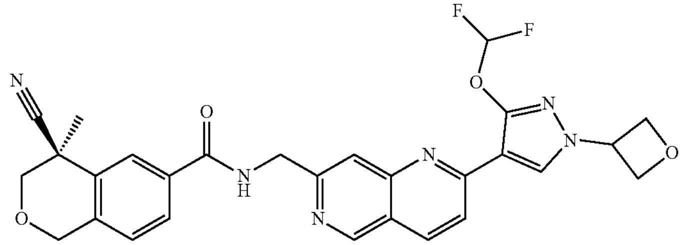 [SMILES: C[C@@]1(C#N)COCc2ccc(C(=O)NCc3cc4nc(-c5cn(C6COC6)nc5OC(F)F)ccc4cn3)cc21] |
| 155 | 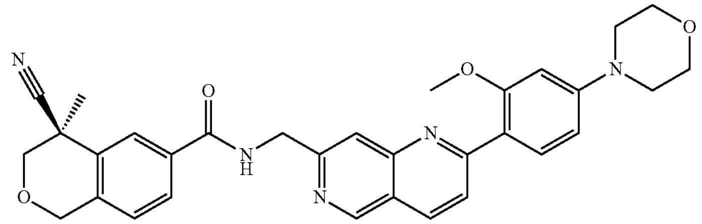 [SMILES: COc1cc(N2CCOCC2)ccc1-c1ccc2cnc(CNC(=O)c3ccc4c(c3)[C@](C)(C#N)COC4)cc2n1] |

TABLE 3a-continued
| Compounds of the invention | |
|---|---|
| # | Compound |
| 156 | 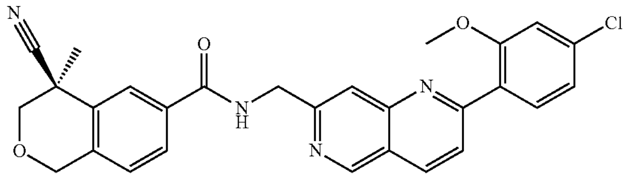 [SMILES: COc1cc(Cl)ccc1-c1ccc2cnc(CNC(=O)c3ccc4c(c3)[C@](C)(C#N)COC4)cc2n1] |
| 157 | 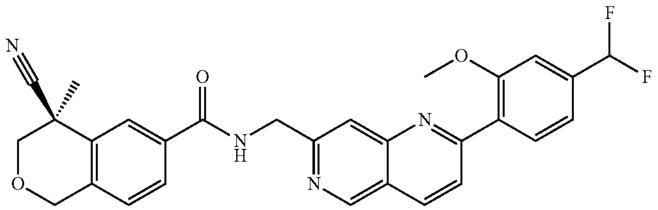 [SMILES: COc1cc(C(F)F)ccc1-c1ccc2cnc(CNC(=O)c3ccc4c(c3)[C@](C)(C#N)COC4)cc2n1] |
| 158 | 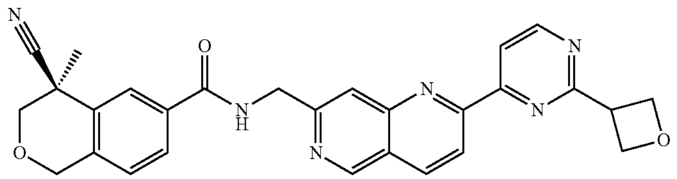 [SMILES: C[C@@]1(C#N)COCc2ccc(C(=O)NCc3cc4nc(-c5ccnc(C6COC6)n5)ccc4cn3)cc21] |
| 159 | 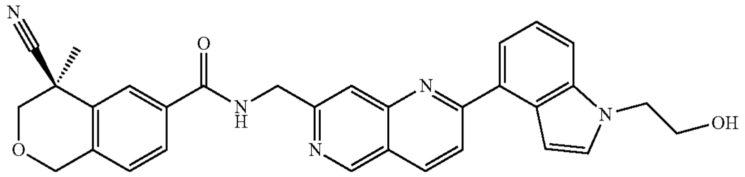 [SMILES: C[C@@]1(C#N)COCc2ccc(C(=O)NCc3cc4nc(-c5cccc6c5ccn6CCO)ccc4cn3)cc21] |
| 160 | 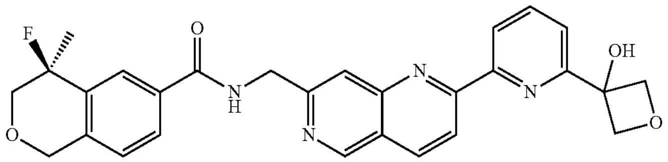 [SMILES: C[C@@]1(F)COCc2ccc(C(=O)NCc3cc4nc(-c5cccc(C6(O)COC6)n5)ccc4cn3)cc21] |
| 161 | 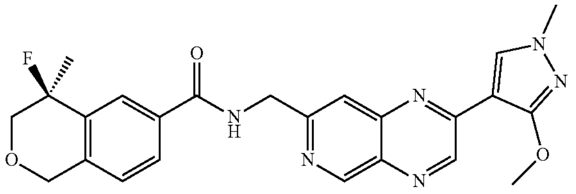 [SMILES: COc1nn(C)cc1-c1cnc2cnc(CNC(=O)c3ccc4c(c3)[C@](C)(F)COC4)cc2n1] |
| 162 | 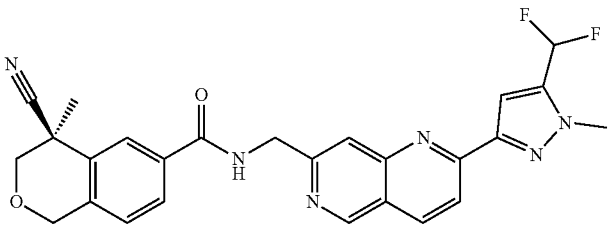 [SMILES: Cn1nc(-c2ccc3cnc(CNC(=O)c4ccc5c(c4)[C@](C)(C#N)COC5)cc3n2)cc1C(F)F] |

TABLE 3a-continued
| Compounds of the invention | |
|---|---|
| # | Compound |
| 163 | 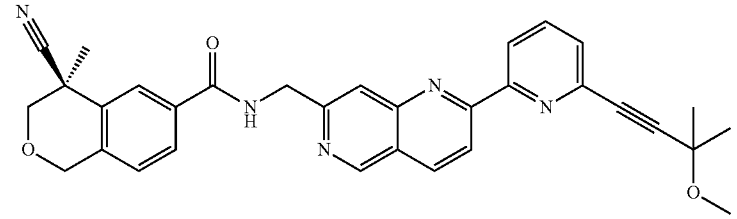 [SMILES: COC(C)(C)C#Cc1cccc(-c2ccc3cnc(CNC(=O)c4ccc5c(c4)[C@](C)(C#N)COC5)cc3n2)n1] |
| 164 | 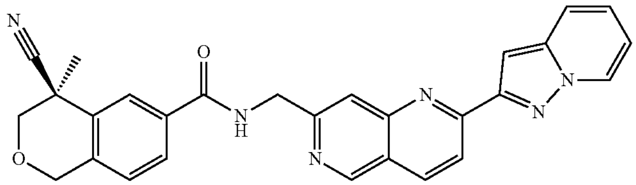 [SMILES: C[C@@]1(C#N)COCc2ccc(C(=O)NCc3cc4nc(-c5cc6ccccn6n5)ccc4cn3)cc21] |
| 165 | 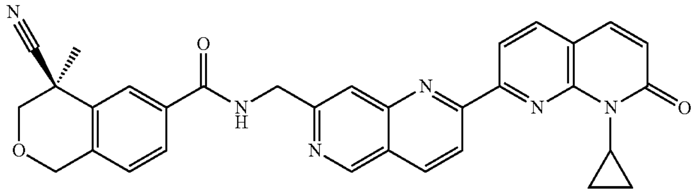 [SMILES: C[C@@]1(C#N)COCc2ccc(C(=O)NCc3cc4nc(-c5ccc6ccc(=O)n(C7CC7)c6n5)ccc4cn3)cc21] |
| 166 | 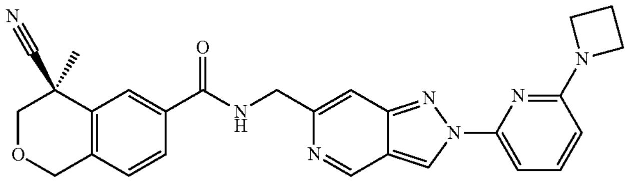 [SMILES: C[C@@]1(C#N)COCc2ccc(C(=O)NCc3cc4nn(-c5cccc(N6CCC6)n5)cc4cn3)cc21] |
| 167 | 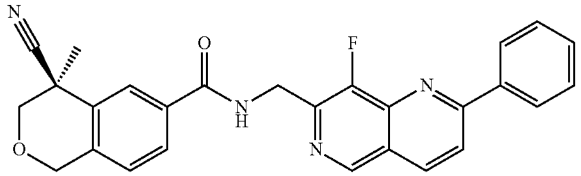 [SMILES: C[C@@]1(C#N)COCc2ccc(C(=O)NCc3ncc4ccc(-c5ccccc5)nc4c3F)cc21] |
| 168 | 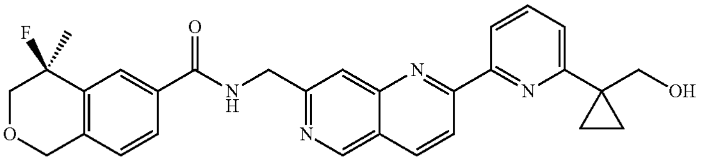 [SMILES: C[C@@]1(F)COCc2ccc(C(=O)NCc3cc4nc(-c5cccc(C6(CO)CC6)n5)ccc4cn3)cc21] |
| 169 | 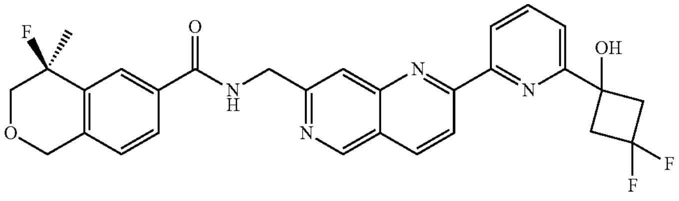 [SMILES: C[C@@]1(F)COCc2ccc(C(=O)NCc3cc4nc(-c5cccc(C6(O)CC(F)(F)C6)n5)ccc4cn3)cc21] |

TABLE 3a-continued
| Compounds of the invention | |
|---|---|
| # | Compound |
| 170 | 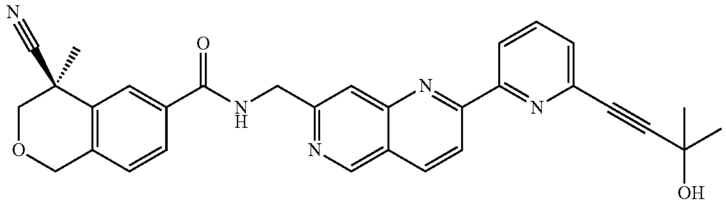 [SMILES: CC(C)(O)C#Cc1cccc(-c2ccc3cnc(CNC(=O)c4ccc5c(c4)[C@](C)(C#N)COC5)cc3n2)n1] |
| 171 | 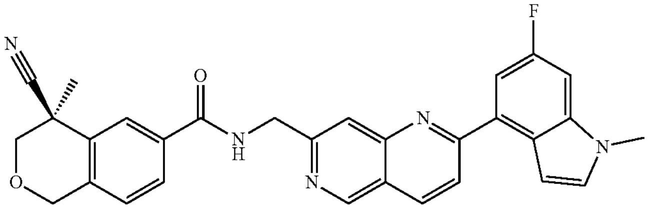 [SMILES: Cn1ccc2c(-c3ccc4cnc(CNC(=O)c5ccc6c(c5)[C@](C)(C#N)COC6)cc4n3)cc(F)cc21] |
| 172 | 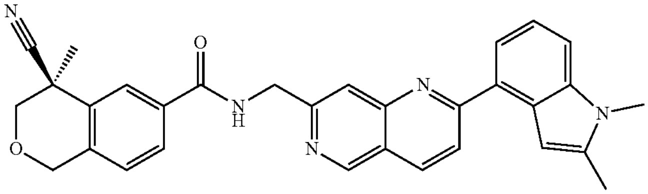 [SMILES: Cc1cc2c(-c3ccc4cnc(CNC(=O)c5ccc6c(c5)[C@](C)(C#N)COC6)cc4n3)cccc2n1C] |
| 173 | 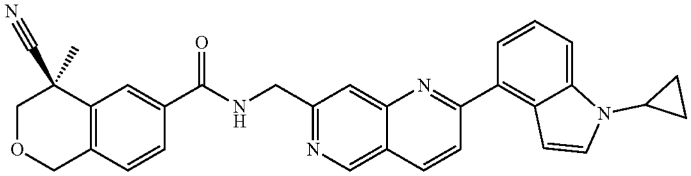 [SMILES: C[C@@]1(C#N)COCc2ccc(C(=O)NCc3cc4nc(-c5cccc6c5ccn6C5CC5)ccc4cn3)cc21] |
| 174 | 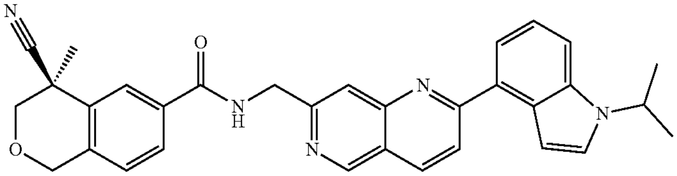 [SMILES: CC(C)n1ccc2c(-c3ccc4cnc(CNC(=O)c5ccc6c(c5)[C@](C)(C#N)COC6)cc4n3)cccc21] |
| 175 | 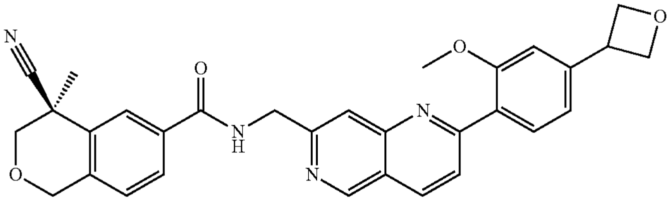 [SMILES: COc1cc(C2COC2)ccc1-c1ccc2cnc(CNC(=O)c3ccc4c(c3)[C@](C)(C#N)COC4)cc2n1] |
| 176 | 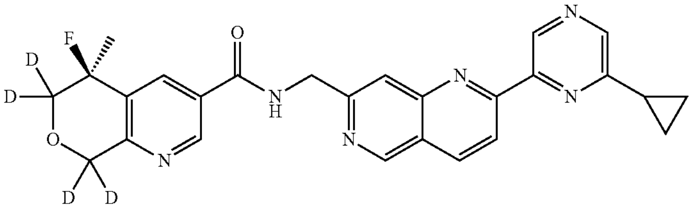 [SMILES: [2H]C1([2H])OC([2H])([2H])[C@@](C)(F)c2cc(C(=O)NCc3cc4nc(-c5cncc(C6CC6)n5)ccc4cn3)cnc21] |

TABLE 3a-continued
| Compounds of the invention | |
|---|---|
| # | Compound |
| 177 | 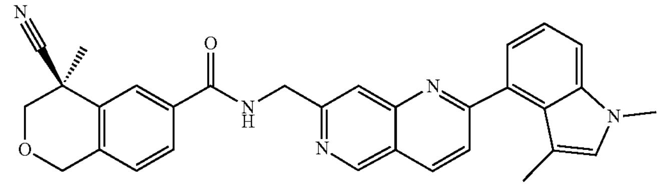 [SMILES: Cc1cn(C)c2cccc(-c3ccc4cnc(CNC(=O)c5ccc6c(c5)[C@](C)(C#N)COC6)cc4n3)c12] |
| 178 | 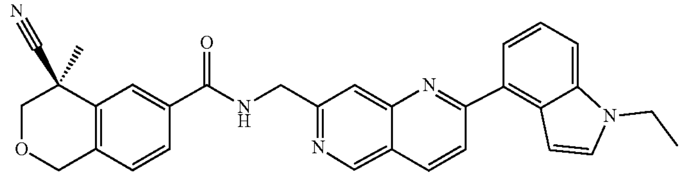 [SMILES: CCn1ccc2c(-c3ccc4cnc(CNC(=O)c5ccc6c(c5)[C@](C)(C#N)COC6)cc4n3)cccc21] |
| 179 | 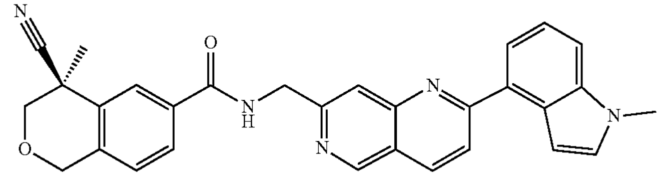 [SMILES: Cn1ccc2c(-c3ccc4cnc(CNC(=O)c5ccc6c(c5)[C@](C)(C#N)COC6)cc4n3)cccc21] |
| 180 | 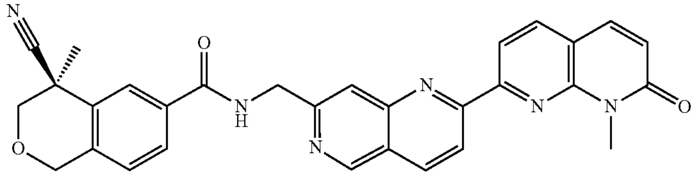 [SMILES: Cn1c(=O)ccc2ccc(-c3ccc4cnc(CNC(=O)c5ccc6c(c5)[C@](C)(C#N)COC6)cc4n3)nc21] |
| 181 | 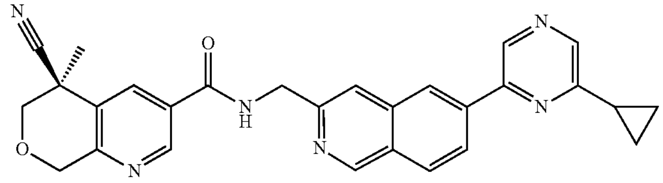 [SMILES: C[C@@]1(C#N)COCc2ncc(C(=O)NCc3cc4cc(-c5cncc(C6CC6)n5)ccc4cn3)cc21] |
| 182 | 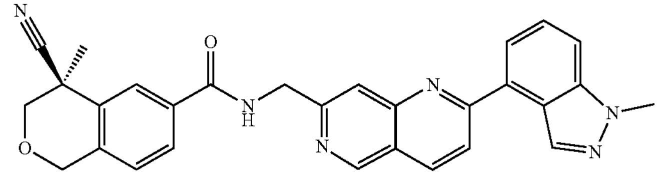 [SMILES: Cn1ncc2c(-c3ccc4cnc(CNC(=O)c5ccc6c(c5)[C@](C)(C#N)COC6)cc4n3)cccc21] |
| 183 | 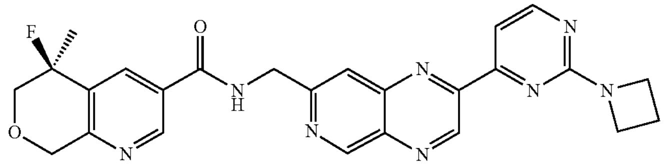 [SMILES: C[C@@]1(F)COCc2ncc(C(=O)NCc3cc4nc(-c5ccnc(N6CCC6)n5)cnc4cn3)cc21] |
| 184 | 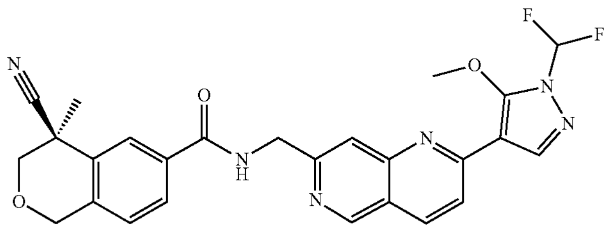 [SMILES: COc1c(-c2ccc3cnc(CNC(=O)c4ccc5c(c4)[C@](C)(C#N)COC5)cc3n2)cnn1C(F)F] |

TABLE 3a-continued
| Compounds of the invention | |
|---|---|
| # | Compound |
| 185 | 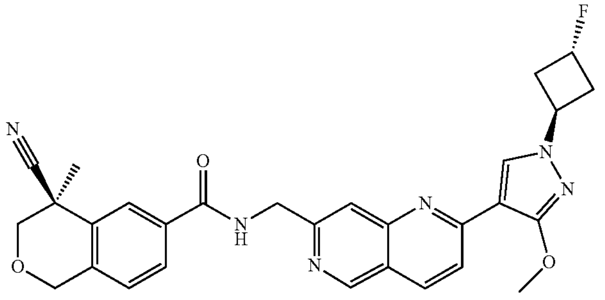 [SMILES: COc1nn([C@H]2C[C@H](F)C2)cc1-c1ccc2cnc(CNC(=O)c3ccc4c(c3)[C@](C)(C#N)COC4)cc2n1] |
| 186 | 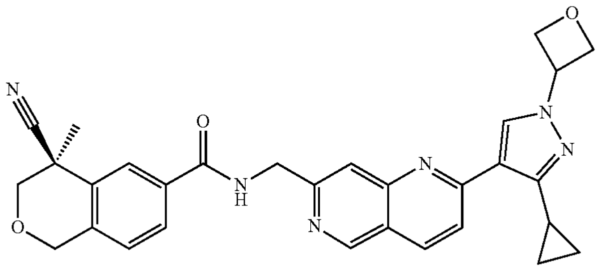 [SMILES: C[C@@]1(C#N)COCc2ccc(C(=O)NCc3cc4nc(-c5cn(C6COC6)nc5C5CC5)ccc4cn3)cc21] |
| 187 | 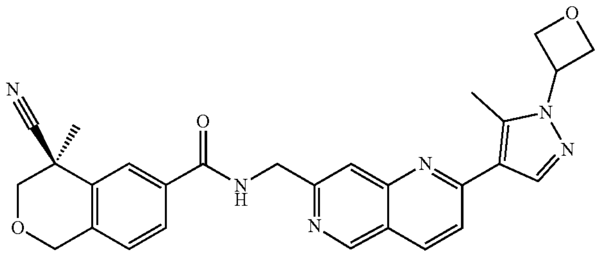 [SMILES: Cc1c(-c2ccc3cnc(CNC(=O)c4ccc5c(c4)[C@](C)(C#N)COC5)cc3n2)cnn1C1COC1] |
| 188 | 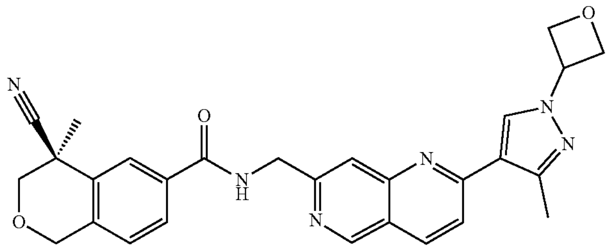 [SMILES: Cc1nn(C2COC2)cc1-c1ccc2cnc(CNC(=O)c3ccc4c(c3)[C@](C)(C#N)COC4)cc2n1] |
| 189 | 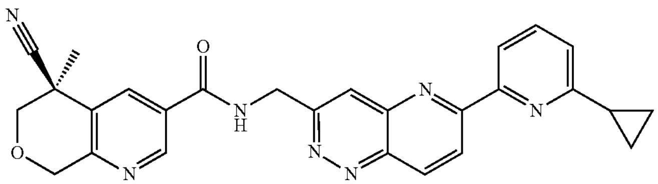 [SMILES: C[C@@]1(C#N)COCc2ncc(C(=O)NCc3cc4nc(-c5cccc(C6CC6)n5)ccc4nn3)cc21] |
| 190 | 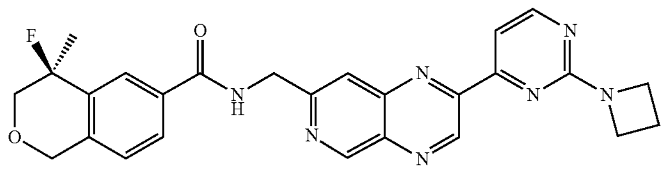 [SMILES: C[C@@]1(F)COCc2ccc(C(=O)NCc3cc4nc(-c5ccnc(N6CCC6)n5)cnc4cn3)cc21] |

TABLE 3a-continued
| Compounds of the invention | |
|---|---|
| # | Compound |
| 191 | 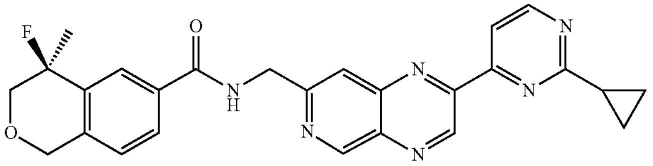 [SMILES: C[C@@]1(F)COCc2ccc(C(=O)NCc3cc4nc(-c5ccnc(C6CC6)n5)cnc4cn3)cc21] |
| 192 | 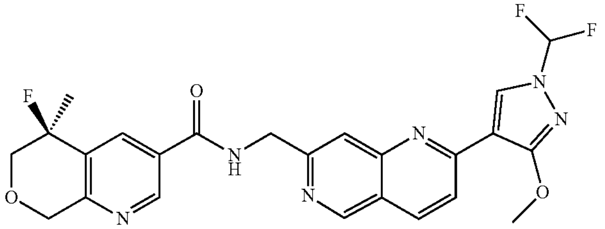 [SMILES: COc1nn(C(F)F)cc1-c1ccc2cnc(CNC(=O)c3cnc4c(c3)[C@](C)(F)COC4)cc2n1] |
| 193 | 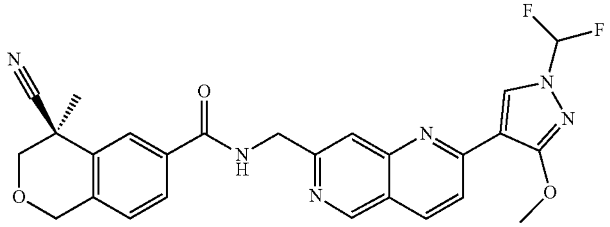 [SMILES: COc1nn(C(F)F)cc1-c1ccc2cnc(CNC(=O)c3ccc4c(c3)[C@](C)(C#N)COC4)cc2n1] |
| 194 | 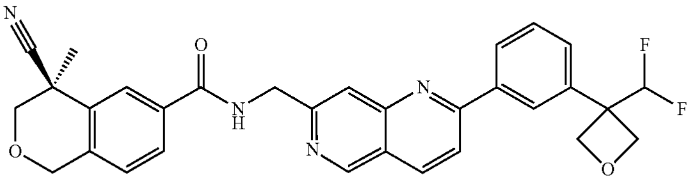 [SMILES: C[C@@]1(C#N)COCc2ccc(C(=O)NCc3cc4nc(-c5cccc(C6(C(F)F)COC6)c5)ccc4cn3)cc21] |
| 195 | 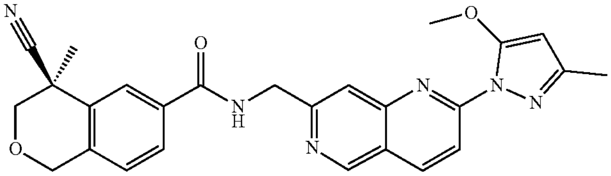 [SMILES: COc1cc(C)nn1-c1ccc2cnc(CNC(=O)c3ccc4c(c3)[C@](C)(C#N)COC4)cc2n1] |
| 196 | 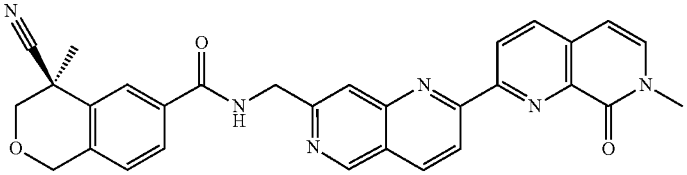 [SMILES: Cn1ccc2ccc(-c3ccc4cnc(CNC(=O)c5ccc6c(c5)[C@](C)(C#N)COC6)cc4n3)nc2c1=O] |
| 197 | 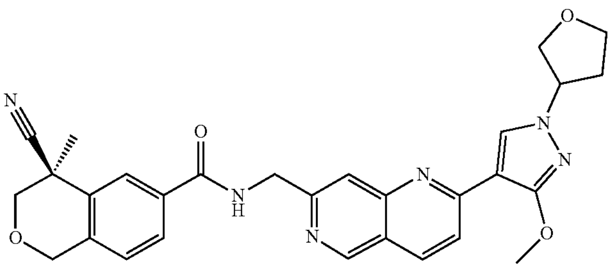 [SMILES: COc1nn(C2CCOC2)cc1-c1ccc2cnc(CNC(=O)c3ccc4c(c3)[C@](C)(C#N)COC4)cc2n1] |

TABLE 3a-continued
| Compounds of the invention | |
|---|---|
| # | Compound |
| 198 | 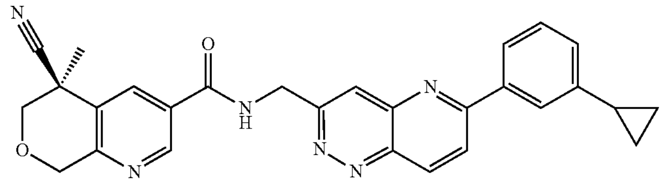 [SMILES: C[C@@]1(C#N)COCc2ncc(C(=O)NCc3cc4nc(-c5cccc(C6CC6)c5)ccc4nn3)cc21] |
| 199 | 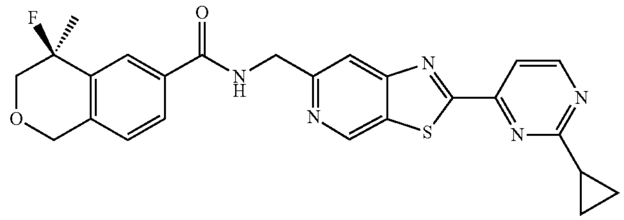 [SMILES: C[C@@]1(F)COCc2ccc(C(=O)NCc3cc4nc(-c5ccnc(C6CC6)n5)sc4cn3)cc21] |
| 200 | 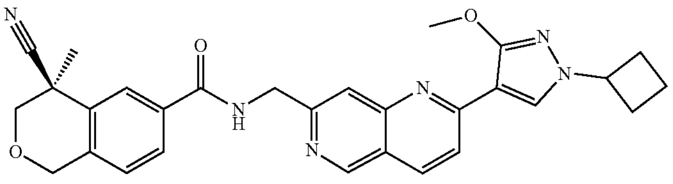 [SMILES: COc1nn(C2CCC2)cc1-c1ccc2cnc(CNC(=O)c3ccc4c(c3)[C@](C)(C#N)COC4)cc2n1] |
| 201 | 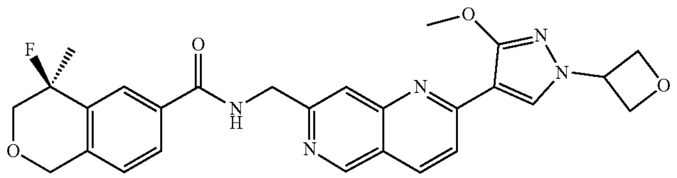 [SMILES: COc1nn(C2COC2)cc1-c1ccc2cnc(CNC(=O)c3ccc4c(c3)[C@](C)(F)COC4)cc2n1] |
| 202 | 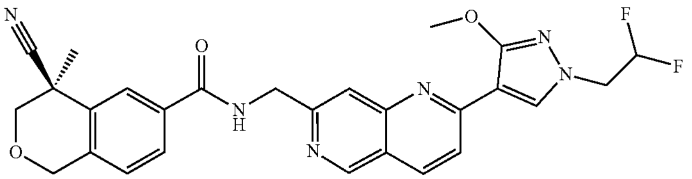 [SMILES: COc1nn(CC(F)F)cc1-c1ccc2cnc(CNC(=O)c3ccc4c(c3)[C@](C)(C#N)COC4)cc2n1] |
| 203 | 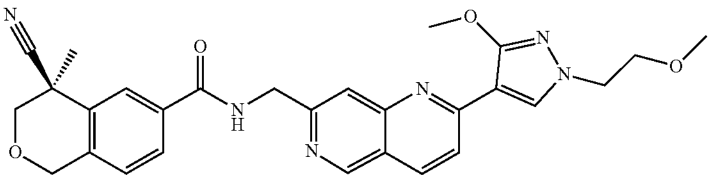 [SMILES: COCCn1cc(-c2ccc3cnc(CNC(=O)c4ccc5c(c4)[C@](C)(C#N)COC5)cc3n2)c(OC)n1] |
| 204 | 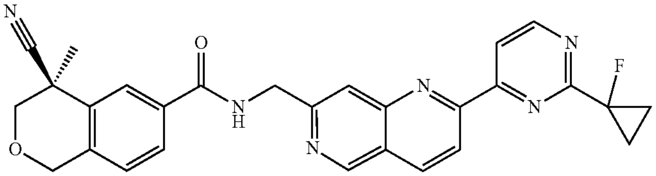 [SMILES: C[C@@]1(C#N)COCc2ccc(C(=O)NCc3cc4nc(-c5ccnc(C6(F)CC6)n5)ccc4cn3)cc21] |
| 205 | 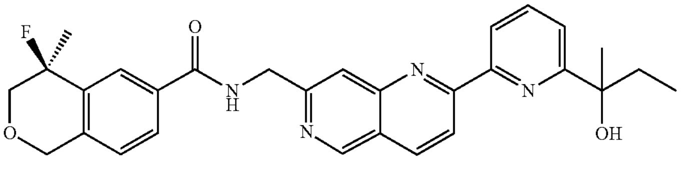 [SMILES: CCC(C)(O)c1cccc(-c2ccc3cnc(CNC(=O)c4ccc5c(c4)[C@](C)(F)COC5)cc3n2)n1] |

TABLE 3a-continued
| Compounds of the invention | |
|---|---|
| # | Compound |
| 206 | 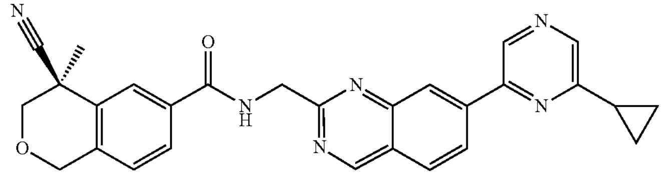 [SMILES: C[C@@]1(C#N)COCc2ccc(C(=O)NCc3ncc4ccc(-c5cncc(C6CC6)n5)cc4n3)cc21] |
| 207 | 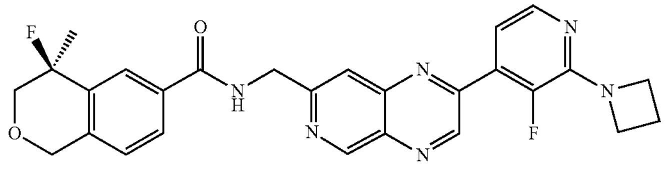 [SMILES: C[C@@]1(F)COCc2ccc(C(=O)NCc3cc4nc(-c5ccnc(N6CCC6)c5F)cnc4cn3)cc21] |
| 208 | 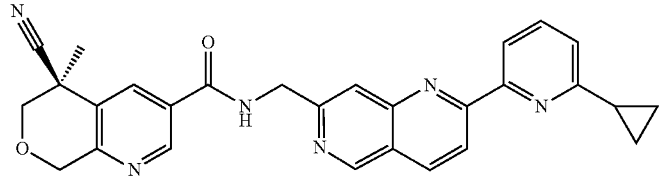 [SMILES: C[C@@]1(C#N)COCc2ncc(C(=O)NCc3cc4nc(-c5cccc(C6CC6)n5)ccc4cn3)cc21] |
| 209 | 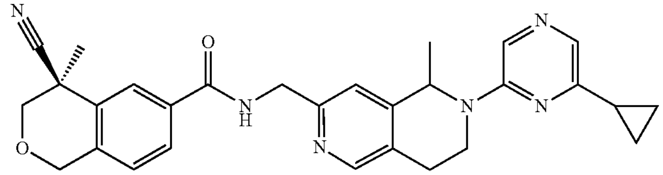 [SMILES: CC1c2cc(CNC(=O)c3ccc4c(c3)[C@](C)(C#N)COC4)ncc2CCN1c1cncc(C2CC2)n1] |
| 210 | 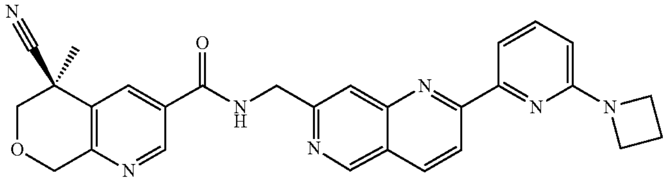 [SMILES: C[C@@]1(C#N)COCc2ncc(C(=O)NCc3cc4nc(-c5cccc(N6CCC6)n5)ccc4cn3)cc21] |
| 211 | 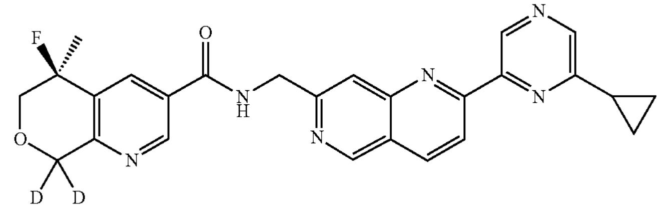 [SMILES: [2H]C1([2H])OC[C@@](C)(F)c2cc(C(=O)NCc3cc4nc(-c5cncc(C6CC6)n5)ccc4cn3)cnc21] |
| 212 | 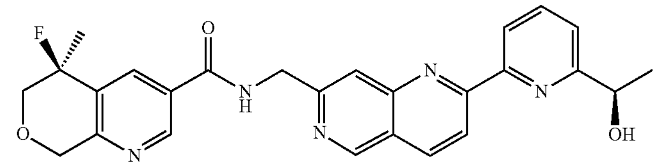 [SMILES: C[C@@H](O)c1cccc(-c2ccc3cnc(CNC(=O)c4cnc5c(c4)[C@](C)(F)COC5)cc3n2)n1] |
| 213 | 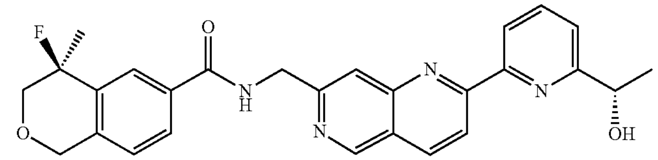 [SMILES: C[C@H](O)c1cccc(-c2ccc3cnc(CNC(=O)c4ccc5c(c4)[C@](C)(F)COC5)cc3n2)n1] |

TABLE 3a-continued
Compounds of the invention
| # | Compound |
|---|---|
| 214 | 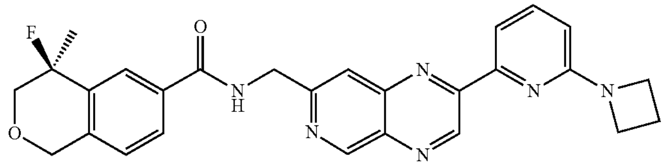 |
| 215 | 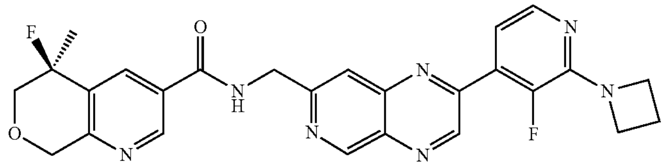 [SMILES: C[C@@]1(F)COCc2ncc(C(=O)NCc3cc4nc(-c5ccnc(N6CCC6)c5F)cnc4cn3)cc21] |
| 216 | 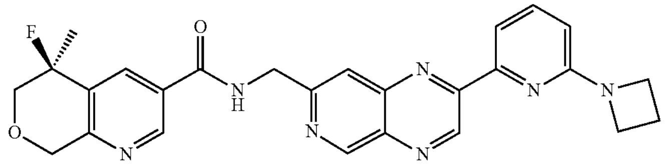 [SMILES: C[C@@]1(F)COCc2ncc(C(=O)NCc3cc4nc(-c5cccc(N6CCC6)n5)cnc4cn3)cc21] |
| 217 | 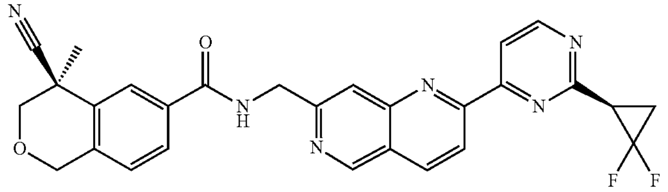 [SMILES: C[C@@]1(C#N)COCc2ccc(C(=O)NCc3cc4nc(-c5ccnc([C@H]6CC6(F)F)n5)ccc4cn3)cc21] |
| 218 | 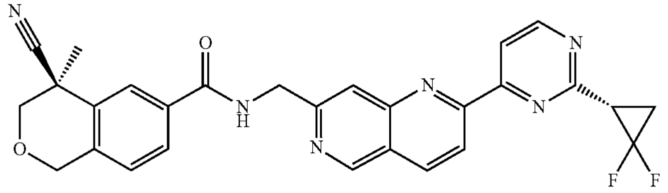 [SMILES: C[C@@]1(C#N)COCc2ccc(C(=O)NCc3cc4nc(-c5ccnc([C@@H]6CC6(F)F)n5)ccc4cn3)cc21] |
| 219 | 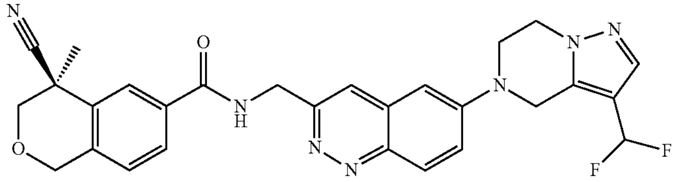 [SMILES: C[C@@]1(C#N)COCc2ccc(C(=O)NCc3cc4cc(N5CCn6ncc(C(F)F)c6C5)ccc4nn3)cc21] |
| 220 | 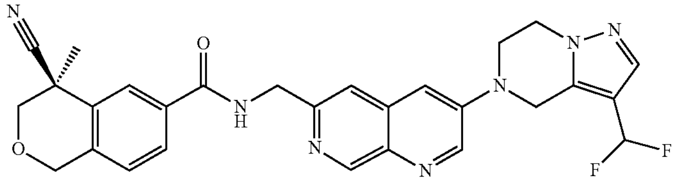 [SMILES: C[C@@]1(C#N)COCc2ccc(C(=O)NCc3cc4cc(N5CCn6ncc(C(F)F)c6C5)cnc4cn3)cc21] |
| 221 | 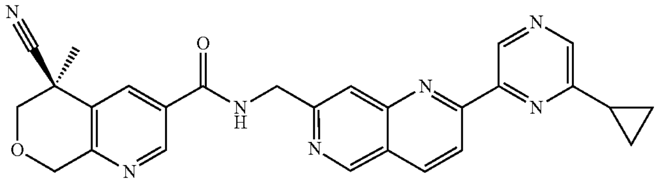 |

TABLE 3a-continued
| Compounds of the invention | |
|---|---|
| # | Compound |
| 222 | 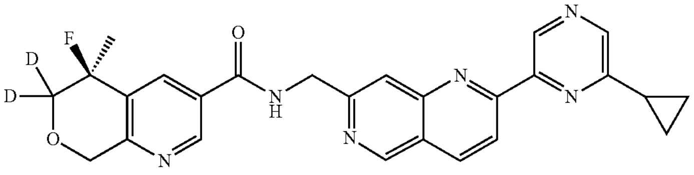 [SMILES: [2H]C1([2H])OCc2ncc(C(=O)NCc3cc4nc(-c5cncc(C6CC6)n5)ccc4cn3)cc2[C@]1(C)F] |
| 223 | 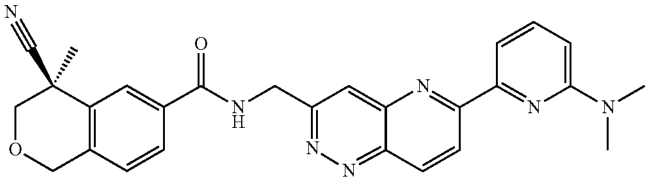 [SMILES: CN(C)c1cccc(-c2ccc3nnc(CNC(=O)c4ccc5c(c4)[C@](C)(C#N)COC5)cc3n2)n1] |
| 224 | 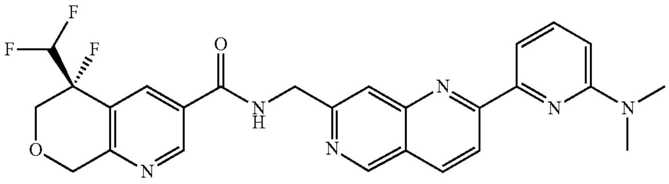 [SMILES: CN(C)c1cccc(-c2ccc3cnc(CNC(=O)c4cnc5c(c4)[C@](F)(C(F)F)COC5)cc3n2)n1] |
| 225 | 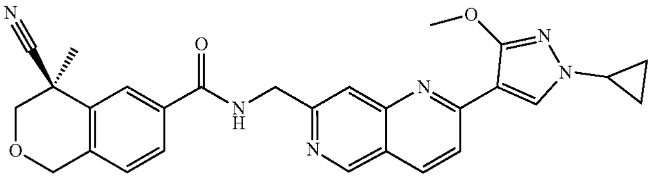 [SMILES: COc1nn(C2CC2)cc1-c1ccc2cnc(CNC(=O)c3ccc4c(c3)[C@](C)(C#N)COC4)cc2n1] |
| 226 | 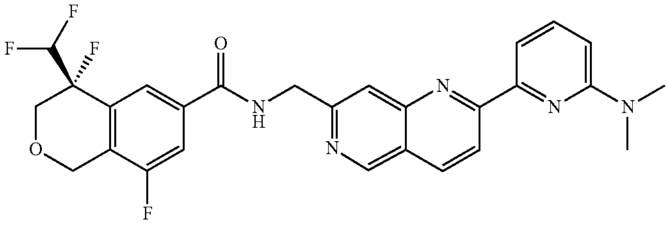 [SMILES: CN(C)c1cccc(-c2ccc3cnc(CNC(=O)c4cc(F)c5c(c4)[C@](F)(C(F)F)COC5)cc3n2)n1] |
| 227 | 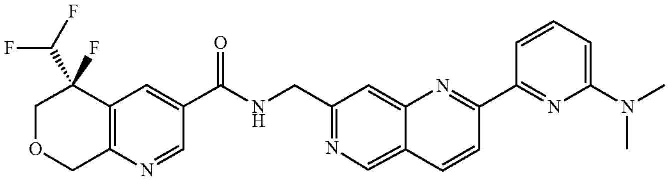 [SMILES: CN(C)c1cccc(-c2ccc3cnc(CNC(=O)c4cnc5c(c4)[C@@](F)(C(F)F)COC5)cc3n2)n1] |
| 228 | 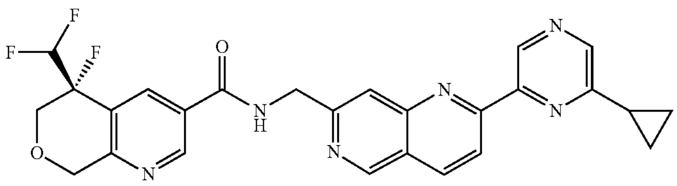 [SMILES: O=C(NCc1cc2nc(-c3cncc(C4CC4)n3)ccc2cn1)c1cnc2c(c1)[C@](F)(C(F)F)COC2] |
| 229 | 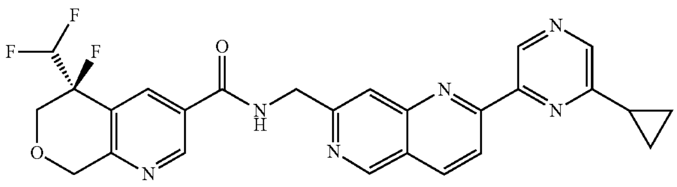 [SMILES: O=C(NCc1cc2nc(-c3cncc(C4CC4)n3)ccc2cn1)c1cnc2c(c1)[C@@](F)(C(F)F)COC2] |

TABLE 3a-continued
| Compounds of the invention | |
|---|---|
| # | Compound |
| 230 | 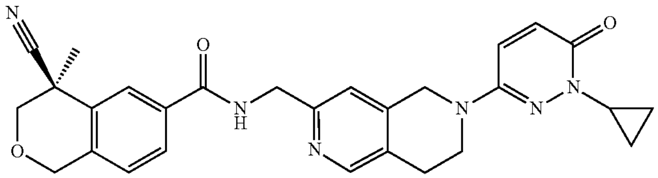 [SMILES: C[C@@]1(C#N)COCc2ccc(C(=O)NCc3cc4c(cn3)CCN(c3ccc(=O)n(C5CC5)n3)C4)cc21] |
| 231 | 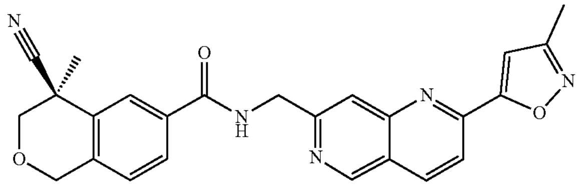 [SMILES: Cc1cc(-c2ccc3cnc(CNC(=O)c4ccc5c(c4)[C@](C)(C#N)COC5)cc3n2)on1] |
| 232 | 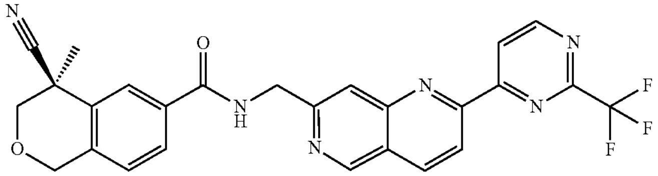 [SMILES: C[C@@]1(C#N)COCc2ccc(C(=O)NCc3cc4nc(-c5ccnc(C(F)(F)F)n5)ccc4cn3)cc21] |
| 233 | 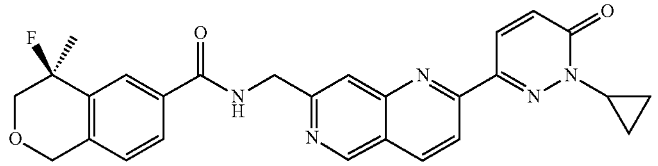 [SMILES: C[C@@]1(F)COCc2ccc(C(=O)NCc3cc4nc(-c5ccc(=O)n(C6CC6)n5)ccc4cn3)cc21] |
| 234 | 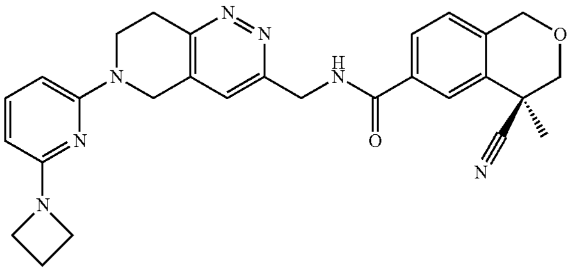 [SMILES: C[C@@]1(C#N)COCc2ccc(C(=O)NCc3cc4c(nn3)CCN(c3cccc(N5CCC5)n3)C4)cc21] |
| 235 | 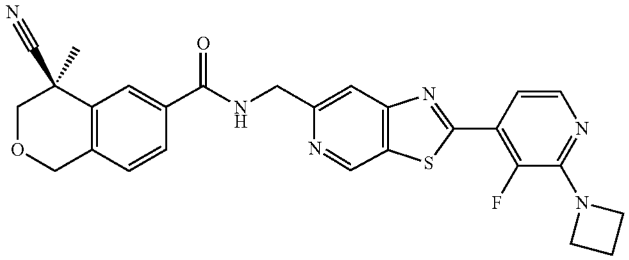 [SMILES: C[C@@]1(C#N)COCc2ccc(C(=O)NCc3cc4nc(-c5ccnc(N6CCC6)c5F)sc4cn3)cc21] |
| 236 | 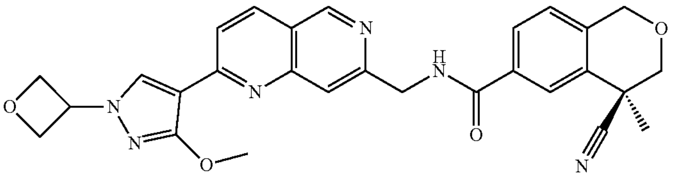 [SMILES: COc1nn(C2COC2)cc1-c1ccc2cnc(CNC(=O)c3ccc4c(c3)[C@](C)(C#N)COC4)cc2n1] |

TABLE 3a-continued
| Compounds of the invention | |
|---|---|
| # | Compound |
| 237 | 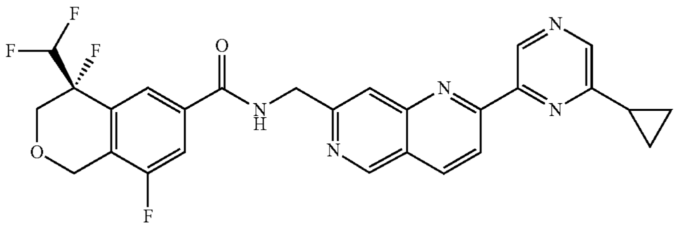 [SMILES: O=C(NCc1cc2nc(-c3cncc(C4CC4)n3)ccc2cn1)c1cc(F)c2c(c1)[C@](F)(C(F)F)COC2] |
| 238 | 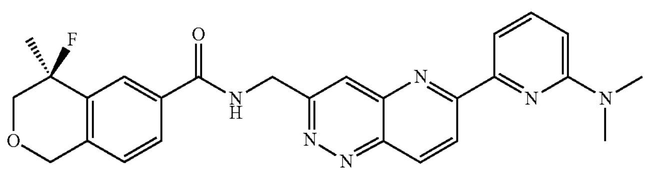 [SMILES: CN(C)c1cccc(-c2ccc3nnc(CNC(=O)c4ccc5c(c4)[C@](C)(F)COC5)cc3n2)n1] |
| 239 | 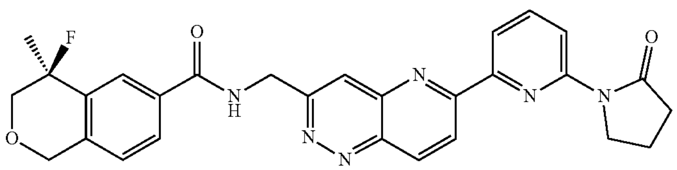 [SMILES: C[C@@]1(F)COCc2ccc(C(=O)NCc3cc4nc(-c5cccc(N6CCCC6=O)n5)ccc4nn3)cc21] |
| 240 | 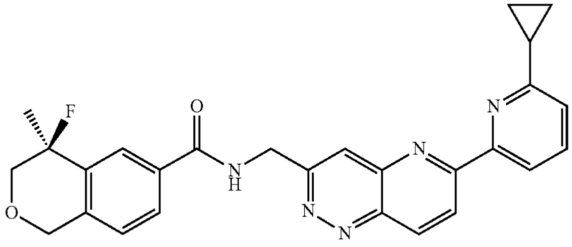 [SMILES: C[C@@]1(F)COCc2ccc(C(=O)NCc3cc4nc(-c5cccc(C6CC6)n5)ccc4nn3)cc21] |
| 241 | 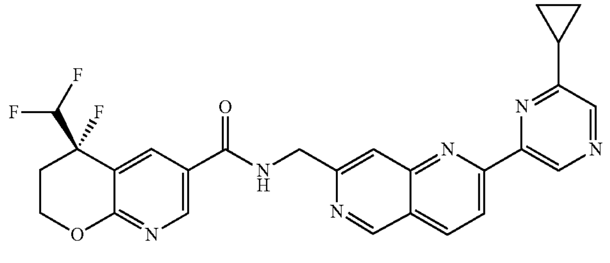 [SMILES: O=C(NCc1cc2nc(-c3cncc(C4CC4)n3)ccc2cn1)c1cnc2c(c1)[C@](F)(C(F)F)CCO2] |
| 242 | 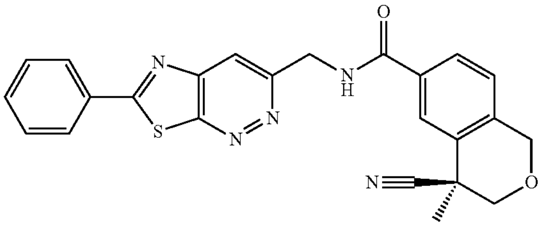 [SMILES: C[C@@]1(C#N)COCc2ccc(C(=O)NCc3cc4nc(-c5ccccc5)sc4nn3)cc21] |

TABLE 3a-continued
| Compounds of the invention | |
|---|---|
| # | Compound |
| 243 | 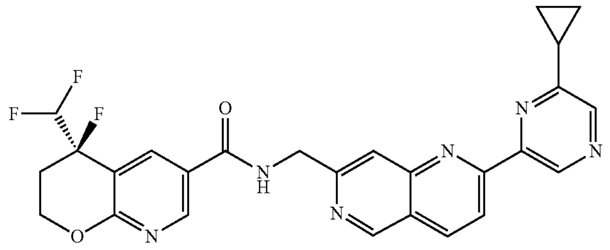 [SMILES: O=C(NCc1cc2nc(-c3cncc(C4CC4)n3)ccc2cn1)c1cnc2c(c1)[C@@](F)(C(F)F)CCO2] |
| 244 | 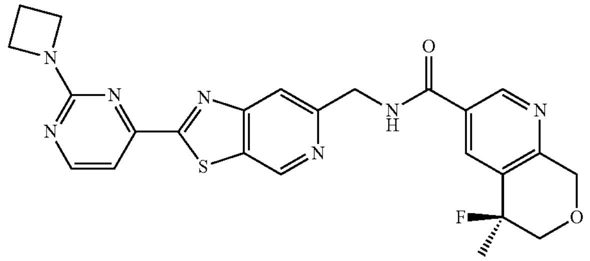 [SMILES: C[C@@]1(F)COCc2ncc(C(=O)NCc3cc4nc(-c5ccnc(N6CCC6)n5)sc4cn3)cc21] |
| 245 | 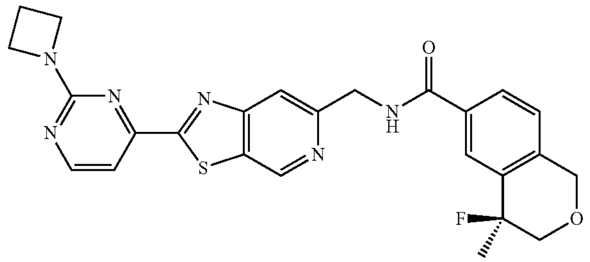 |
| 246 | 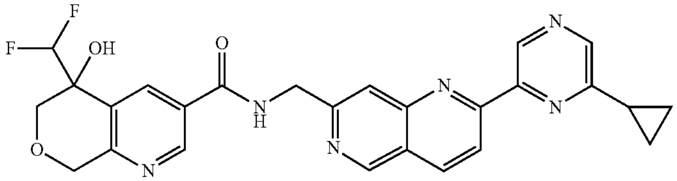 [SMILES: O=C(NCc1cc2nc(-c3cncc(C4CC4)n3)ccc2cn1)c1cnc2c(c1)C(O)(C(F)F)COC2] |
| 247 | 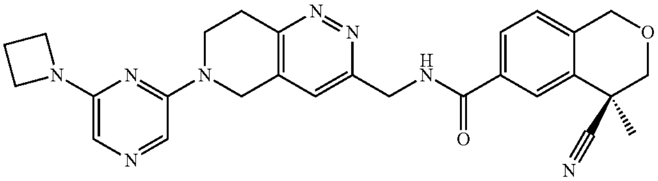 [SMILES: C[C@@]1(C#N)COCc2ccc(C(=O)NCc3cc4c(nn3)CCN(c3cncc(N5CCC5)n3)C4)cc21] |
| 248 | 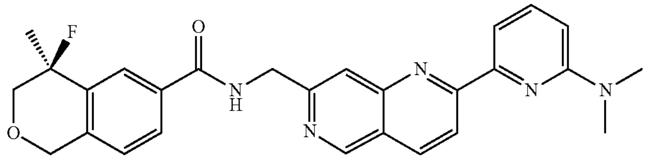 [SMILES: CN(C)c1cccc(-c2ccc3cnc(CNC(=O)c4ccc5c(c4)[C@](C)(F)COC5)cc3n2)n1] |
| 249 | 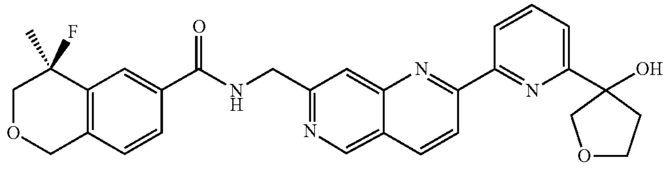 [SMILES: C[C@@]1(F)COCc2ccc(C(=O)NCc3cc4nc(-c5cccc(C6(O)CCOC6)n5)ccc4cn3)cc21] |

TABLE 3a-continued
| Compounds of the invention | |
|---|---|
| # | Compound |
| 250 | 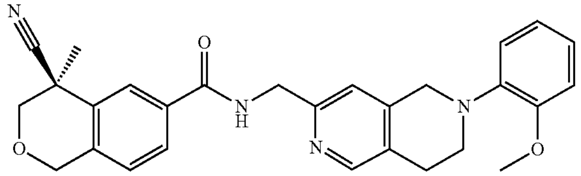 [SMILES: COc1ccccc1N1CCc2cnc(CNC(=O)c3ccc4c(c3)[C@](C)(C#N)COC4)cc2C1] |
| 251 | 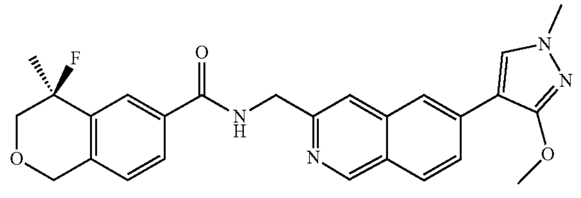 [SMILES: COc1nn(C)cc1-c1ccc2cnc(CNC(=O)c3ccc4c(c3)[C@](C)(F)COC4)cc2c1] |
| 252 | 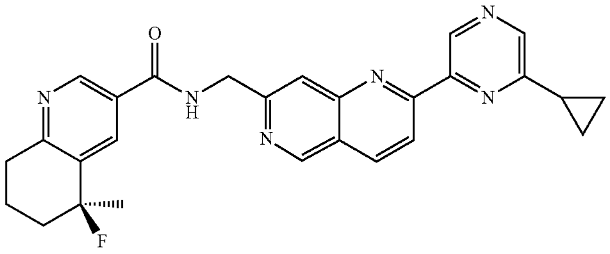 [SMILES: C[C@]1(F)CCCc2ncc(C(=O)NCc3cc4nc(-c5cncc(C6CC6)n5)ccc4cn3)cc21] |
| 253 | 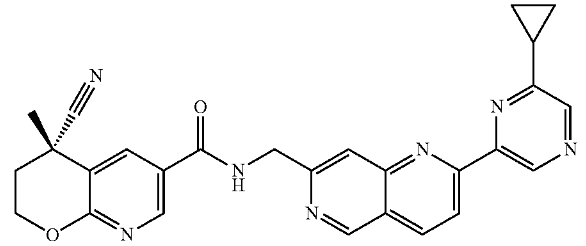 [SMILES: C[C@]1(C#N)CCOc2ncc(C(=O)NCc3cc4nc(-c5cncc(C6CC6)n5)ccc4cn3)cc21] |
| 254 | 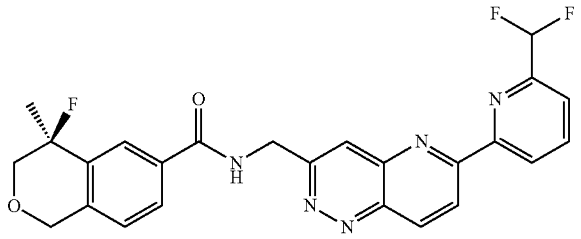 [SMILES: C[C@@]1(F)COCc2ccc(C(=O)NCc3cc4nc(-c5cccc(C(F)F)n5)ccc4nn3)cc21] |
| 255 | 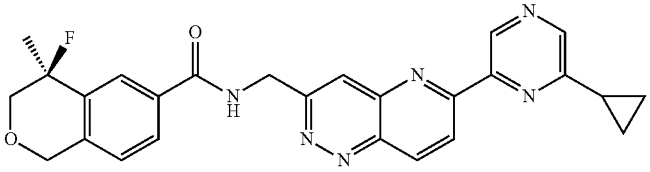 [SMILES: C[C@@]1(F)COCc2ccc(C(=O)NCc3cc4nc(-c5cncc(C6CC6)n5)ccc4nn3)cc21] |
| 256 | 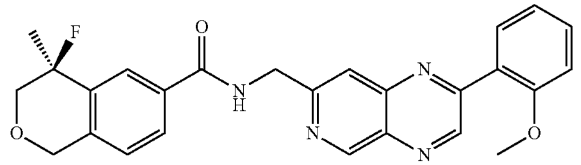 [SMILES: COc1ccccc1-c1cnc2cnc(CNC(=O)c3ccc4c(c3)[C@](C)(F)COC4)cc2n1] |

TABLE 3a-continued
| Compounds of the invention | |
|---|---|
| # | Compound |
| 257 | 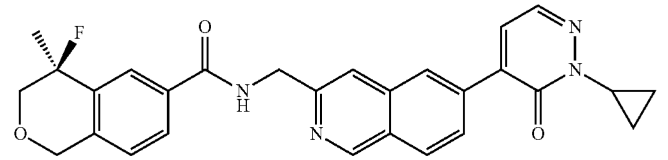 [SMILES: C[C@@]1(F)COCc2ccc(C(=O)NCc3cc4cc(-c5ccnn(C6CC6)c5=O)ccc4cn3)cc21] |
| 258 | 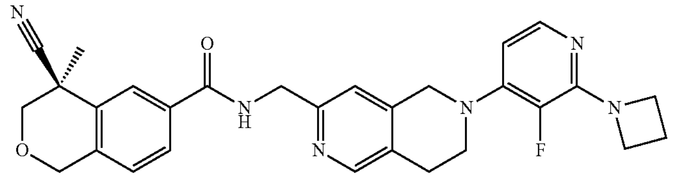 [SMILES: C[C@@]1(C#N)COCc2ccc(C(=O)NCc3cc4c(cn3)CCN(c3ccnc(N5CCC5)c3F)C4)cc21] |
| 259 | 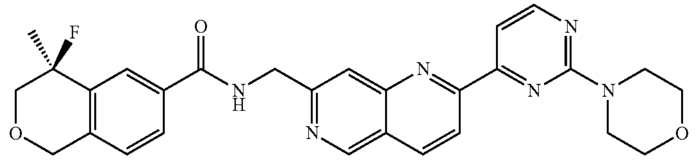 [SMILES: C[C@@]1(F)COCc2ccc(C(=O)NCc3cc4nc(-c5ccnc(N6CCOCC6)n5)ccc4cn3)cc21] |
| 260 | 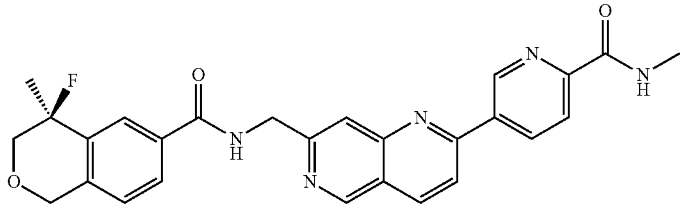 [SMILES: CNC(=O)c1ccc(-c2ccc3cnc(CNC(=O)c4ccc5c(c4)[C@](C)(F)COC5)cc3n2)cn1] |
| 261 | 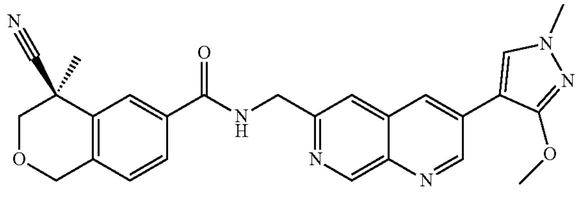 [SMILES: COc1nn(C)cc1-c1cnc2cnc(CNC(=O)c3ccc4c(c3)[C@](C)(C#N)COC4)cc2c1] |
| 262 | 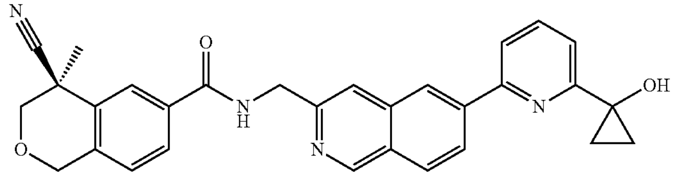 [SMILES: C[C@@]1(C#N)COCc2ccc(C(=O)NCc3cc4cc(-c5cccc(C6(O)CC6)n5)ccc4cn3)cc21] |
| 263 | 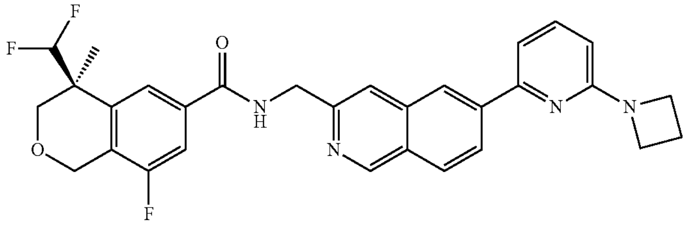 [SMILES: C[C@@]1(C(F)F)COCc2c(F)cc(C(=O)NCc3cc4cc(-c5cccc(N6CCC6)n5)ccc4cn3)cc21] |

TABLE 3a-continued
| Compounds of the invention | |
|---|---|
| # | Compound |
| 264 | 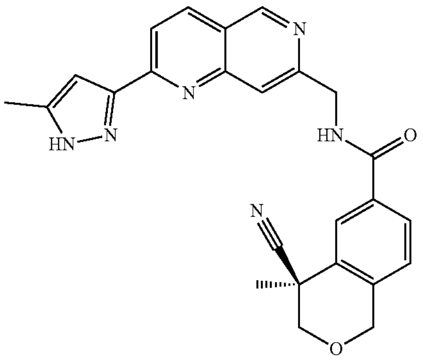 [SMILES: Cc1cc(-c2ccc3cnc(CNC(=O)c4ccc5c(c4)[C@](C)(C#N)COC5)cc3n2)n[nH]1] |
| 265 | 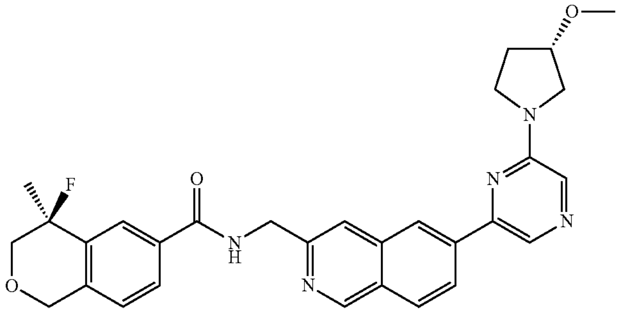 [SMILES: CO[C@H]1CCN(c2cncc(-c3ccc4cnc(CNC(=O)c5ccc6c(c5)[C@](C)(F)COC6)cc4c3)n2)C1] |
| 266 | 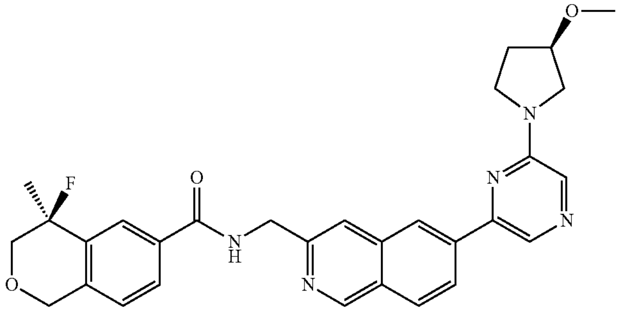 [SMILES: CO[C@@H]1CCN(c2cncc(-c3ccc4cnc(CNC(=O)c5ccc6c(c5)[C@](C)(F)COC6)cc4c3)n2)C1] |
| 267 | 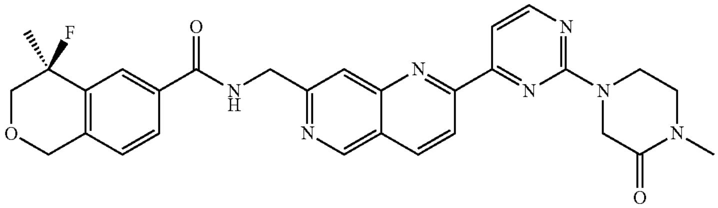 [SMILES: CN1CCN(c2nccc(-c3ccc4cnc(CNC(=O)c5ccc6c(c5)[C@](C)(F)COC6)cc4n3)n2)CC1=O] |
| 268 | 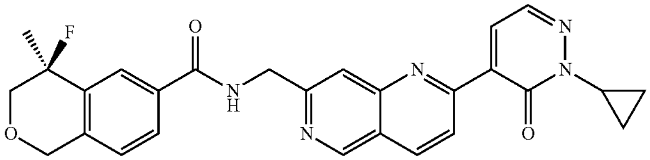 [SMILES: C[C@@]1(F)COCc2ccc(C(=O)NCc3cc4nc(-c5ccnn(C6CC6)c5=O)ccc4cn3)cc21] |

TABLE 3a-continued
| Compounds of the invention | |
|---|---|
| # | Compound |
| 269 | 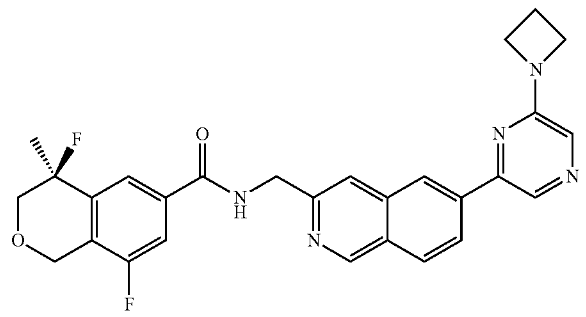 [SMILES: C[C@@]1(F)COCc2c(F)cc(C(=O)NCc3cc4cc(-c5cncc(N6CCC6)n5)ccc4cn3)cc21] |
| 270 | 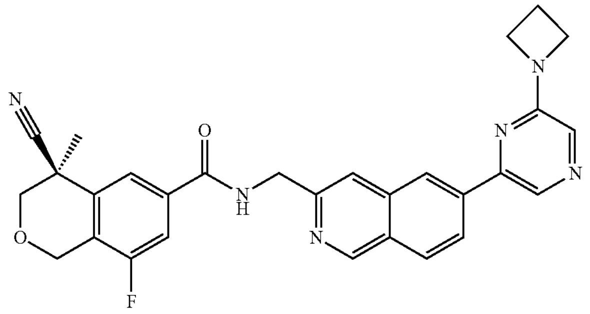 [SMILES: C[C@@]1(C#N)COCc2c(F)cc(C(=O)NCc3cc4cc(-c5cncc(N6CCC6)n5)ccc4cn3)cc21] |
| 271 | 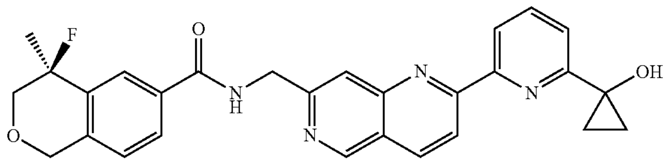 [SMILES: C[C@@]1(F)COCc2ccc(C(=O)NCc3cc4nc(-c5cccc(C6(O)CC6)n5)ccc4cn3)cc21] |
| 272 | 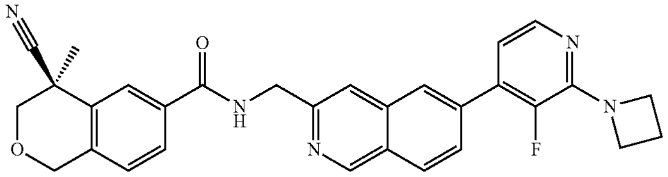 [SMILES: C[C@@]1(C#N)COCc2ccc(C(=O)NCc3cc4cc(-c5ccnc(N6CCC6)c5F)ccc4cn3)cc21] |
| 273 | 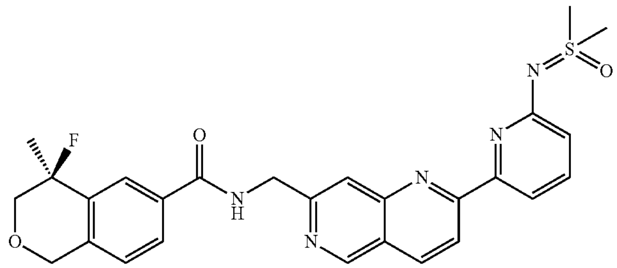 [SMILES: C[C@@]1(F)COCc2ccc(C(=O)NCc3cc4nc(-c5cccc(N=S(C)(C)=O)n5)ccc4cn3)cc21] |
| 274 | 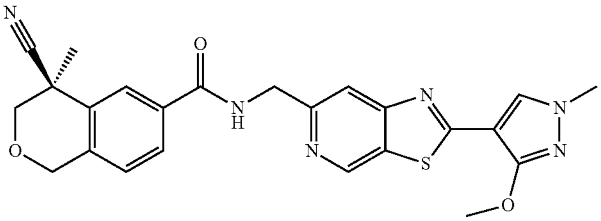 [SMILES: COc1nn(C)cc1-c1nc2cc(CNC(=O)c3ccc4c(c3)[C@](C)(C#N)COC4)ncc2s1] |

TABLE 3a-continued
| Compounds of the invention | |
|---|---|
| # | Compound |
| 275 | 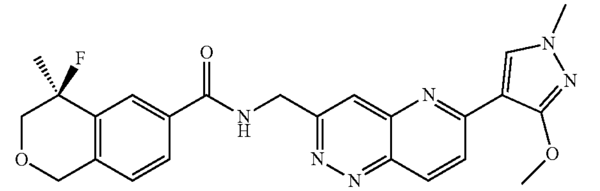 [SMILES: COc1nn(C)cc1-c1ccc2nnc(CNC(=O)c3ccc4c(c3)[C@](C)(F)COC4)cc2n1] |
| 276 | 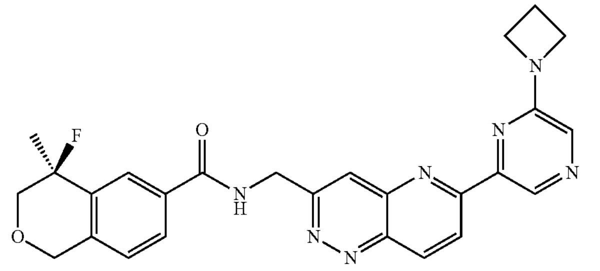 [SMILES: C[C@@]1(F)COCc2ccc(C(=O)NCc3cc4nc(-c5cncc(N6CCC6)n5)ccc4nn3)cc21] |
| 277 | 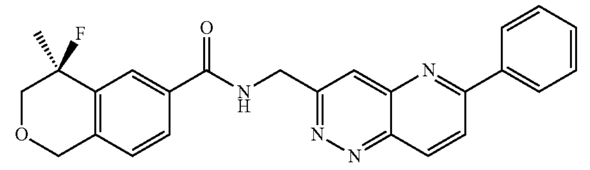 [SMILES: C[C@@]1(F)COCc2ccc(C(=O)NCc3cc4nc(-c5ccccc5)ccc4nn3)cc21] |
| 278 | 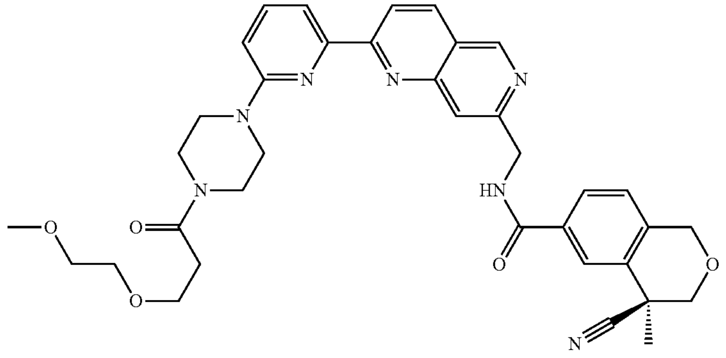 [SMILES: COCCOCCC(=O)N1CCN(c2cccc(-c3ccc4cnc(CNC(=O)c5ccc6c(c5)[C@](C)(C#N)COC6)cc4n3)n2)CC1] |
| 279 | 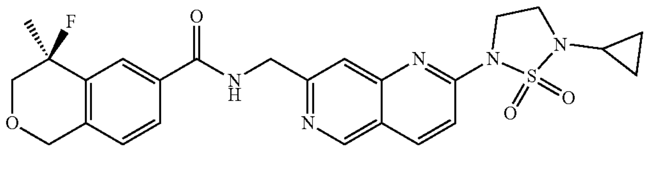 [SMILES: C[C@@]1(F)COCc2ccc(C(=O)NCc3cc4nc(N5CCN(C6CC6)S5(=O)=O)ccc4cn3)cc21] |
| 280 | 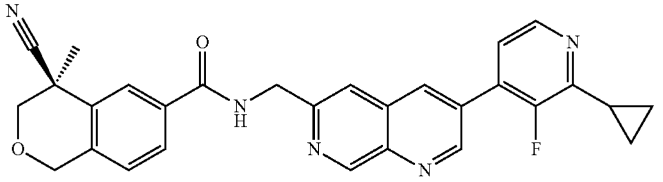 [SMILES: C[C@@]1(C#N)COCc2ccc(C(=O)NCc3cc4cc(-c5ccnc(C6CC6)c5F)cnc4cn3)cc21] |

TABLE 3a-continued
| Compounds of the invention | |
|---|---|
| # | Compound |
| 281 | 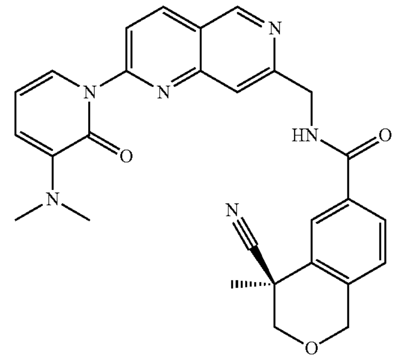 [SMILES: CN(C)c1cccn(-c2ccc3cnc(CNC(=O)c4ccc5c(c4)[C@](C)(C#N)COC5)cc3n2)c1=O] |
| 282 | 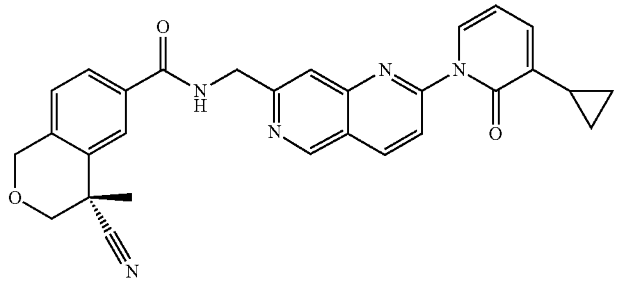 [SMILES: C[C@@]1(C#N)COCc2ccc(C(=O)NCc3cc4nc(-n5cccc(C6CC6)c5=O)ccc4cn3)cc21] |
| 283 | 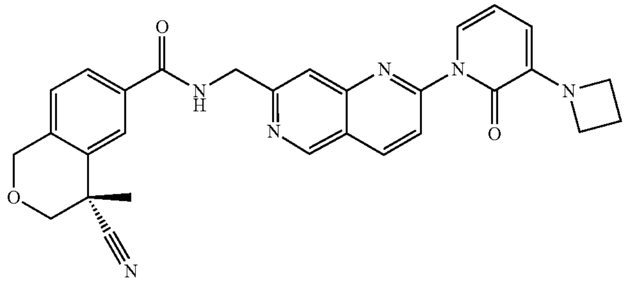 [SMILES: C[C@@]1(C#N)COCc2ccc(C(=O)NCc3cc4nc(-n5cccc(N6CCC6)c5=O)ccc4cn3)cc21] |
| 284 | 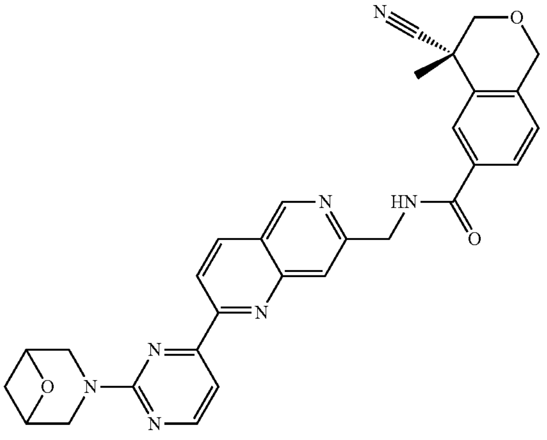 [SMILES: C[C@@]1(C#N)COCc2ccc(C(=O)NCc3cc4nc(-c5ccnc(N6CC7CC(C6)O7)n5)ccc4cn3)cc21] |

TABLE 3a-continued
| Compounds of the invention | |
|---|---|
| # | Compound |
| 285 | 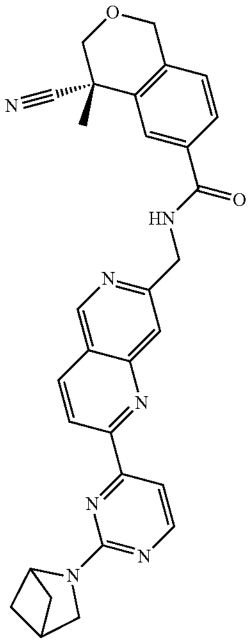 [SMILES: C[C@@]1(C#N)COCc2ccc(C(=O)NCc3cc4nc(-c5ccnc(N6CC7CC6C7)n5)ccc4cn3)cc21] |
| 286 | 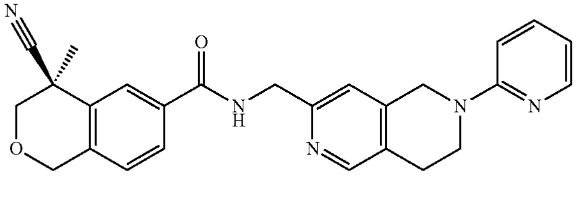 [SMILES: C[C@@]1(C#N)COCc2ccc(C(=O)NCc3cc4c(cn3)CCN(c3ccccn3)C4)cc21] |
| 287 | 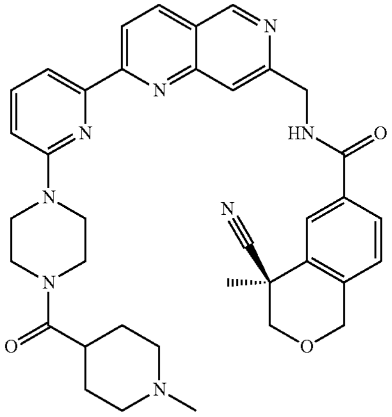 [SMILES: CN1CCC(C(=O)N2CCN(c3cccc(-c4ccc5cnc(CNC(=O)c6ccc7c(c6)[C@](C)(C#N)COC7)cc5n4)n3)CC2)CC1] |

TABLE 3a-continued
| Compounds of the invention | |
|---|---|
| # | Compound |
| 288 | 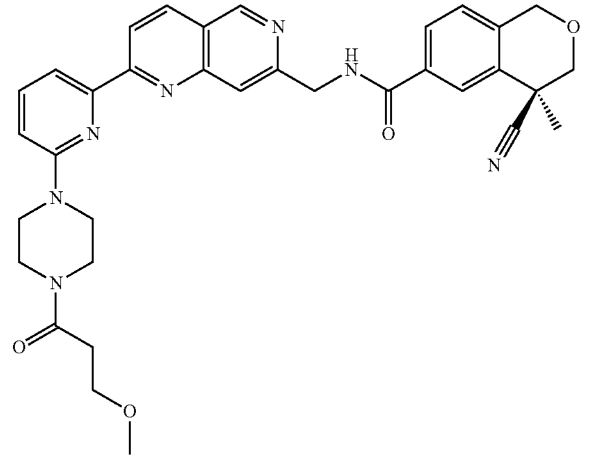 [SMILES: COCCC(=O)N1CCN(c2cccc(-c3ccc4cnc(CNC(=O)c5ccc6c(c5)[C@](C)(C#N)COC6)cc4n3)n2)CC1] |
| 289 | 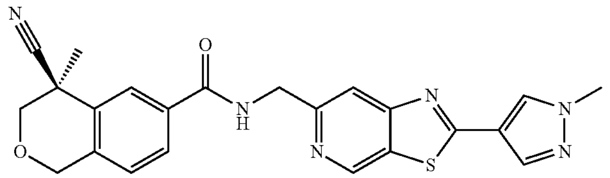 [SMILES: Cn1cc(-c2nc3cc(CNC(=O)c4ccc5c(c4)[C@](C)(C#N)COC5)ncc3s2)cn1] |
| 290 | 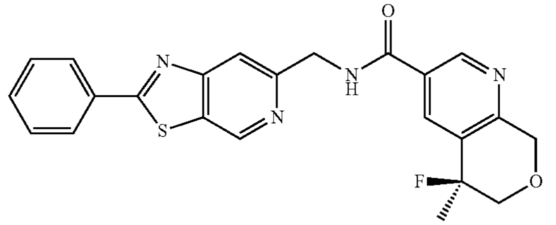 [SMILES: C[C@@]1(F)COCc2ncc(C(=O)NCc3cc4nc(-c5ccccc5)sc4cn3)cc21] |
| 291 | 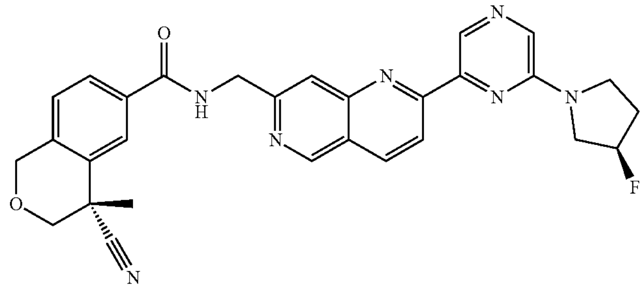 [SMILES: C[C@@]1(C#N)COCc2ccc(C(=O)NCc3cc4nc(-c5cncc(N6CC[C@@H](F)C6)n5)ccc4cn3)cc21] |
| 292 | 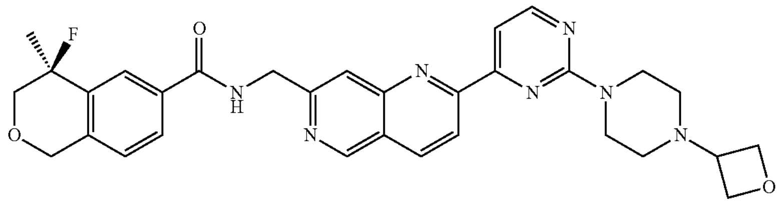 [SMILES: C[C@@]1(F)COCc2ccc(C(=O)NCc3cc4nc(-c5ccnc(N6CCN(C7COC7)CC6)n5)ccc4cn3)cc21] |
| 293 | 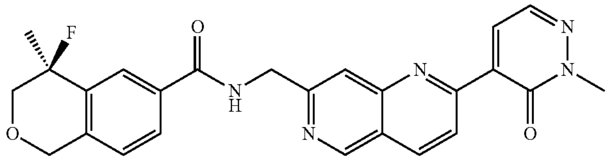 [SMILES: Cn1nccc(-c2ccc3cnc(CNC(=O)c4ccc5c(c4)[C@](C)(F)COC5)cc3n2)c1=O] |

TABLE 3a-continued
| # | Compounds of the invention<br>Compound |
|---|---|
| 294 | 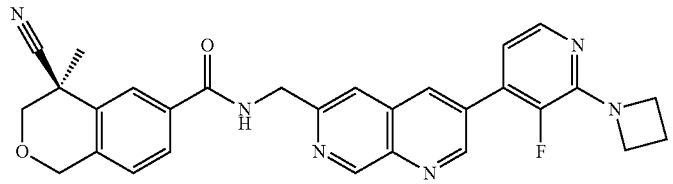 [SMILES: C[C@@]1(C#N)COCc2ccc(C(=O)NCc3cc4cc(-c5ccnc(N6CCC6)c5F)cnc4cn3)cc21] |
| 295 | 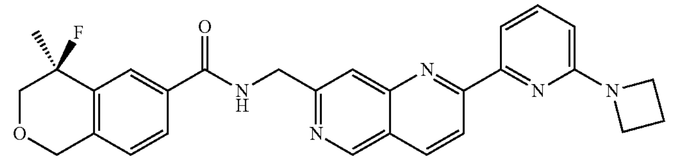 [SMILES: C[C@@]1(F)COCc2ccc(C(=O)NCc3cc4nc(-c5cccc(N6CCC6)n5)ccc4cn3)cc21] |
| 296 | 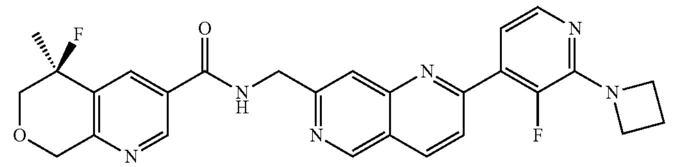 [SMILES: C[C@@]1(F)COCc2ncc(C(=O)NCc3cc4nc(-c5ccnc(N6CCC6)c5F)ccc4cn3)cc21] |
| 297 | 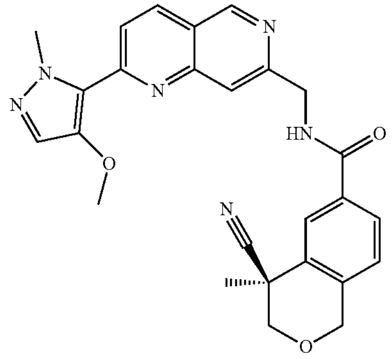 [SMILES: COc1cnn(C)c1-c1ccc2cnc(CNC(=O)c3ccc4c(c3)[C@](C)(C#N)COC4)cc2n1] |
| 298 | 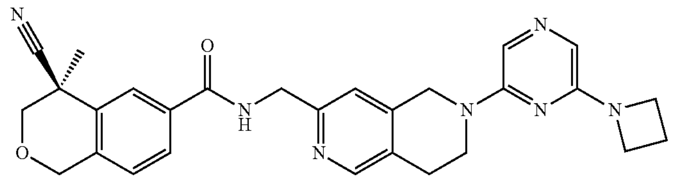 [SMILES: C[C@@]1(C#N)COCc2ccc(C(=O)NCc3cc4c(cn3)CCN(c3cncc(N5CCC5)n3)C4)cc21] |
| 299 | 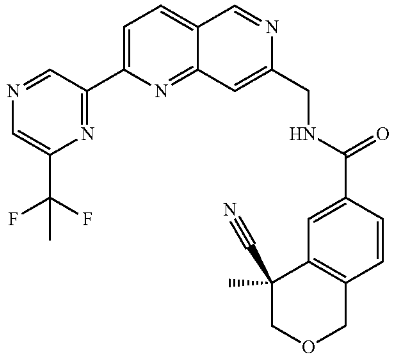 [SMILES: CC(F)(F)c1cncc(-c2ccc3cnc(CNC(=O)c4ccc5c(c4)[C@](C)(C#N)COC5)cc3n2)n1] |

TABLE 3a-continued
| # | Compound |
| --- | --- |
| 300 | 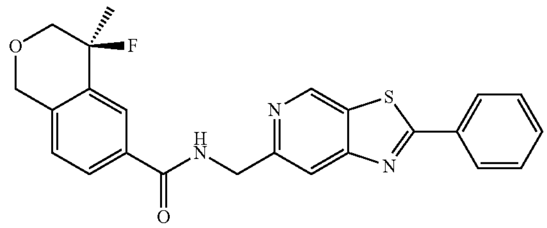 [SMILES: C[C@@]1(F)COCc2ccc(C(=O)NCc3cc4nc(-c5ccccc5)sc4cn3)cc21] |
| 301 | 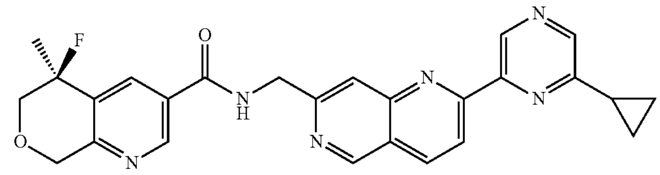 [SMILES: C[C@@]1(F)COCc2ncc(C(=O)NCc3cc4nc(-c5cncc(C6CC6)n5)ccc4cn3)cc21] |
| 302 | 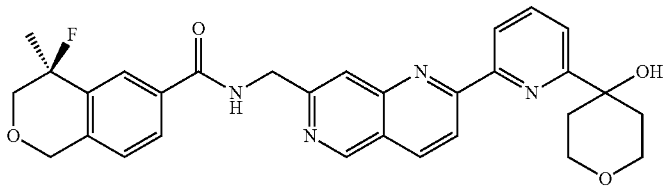 [SMILES: C[C@@]1(F)COCc2ccc(C(=O)NCc3cc4nc(-c5cccc(C6(O)CCOCC6)n5)ccc4cn3)cc21] |
| 303 | 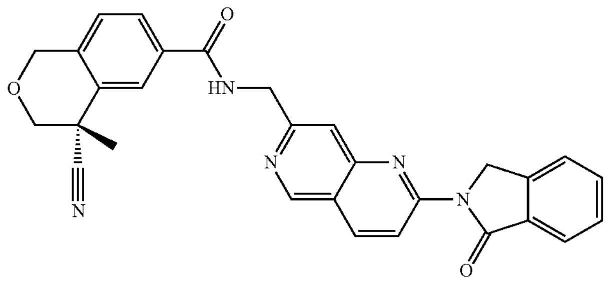 [SMILES: C[C@@]1(C#N)COCc2ccc(C(=O)NCc3cc4nc(N5Cc6ccccc6C5=O)ccc4cn3)cc21] |
| 304 | 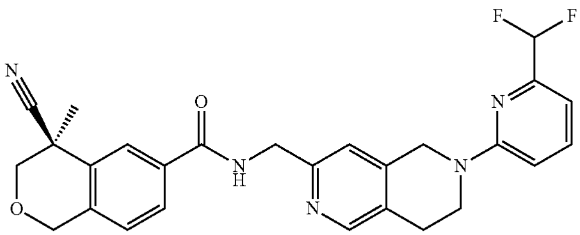 [SMILES: C[C@@]1(C#N)COCc2ccc(C(=O)NCc3cc4c(cn3)CCN(c3cccc(C(F)F)n3)C4)cc21] |
| 305 | 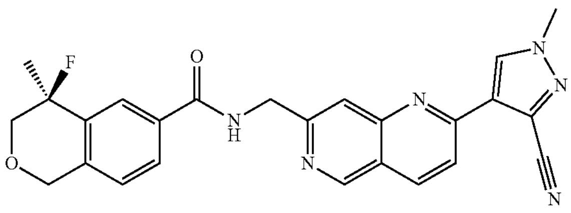 [SMILES: Cn1cc(-c2ccc3cnc(CNC(=O)c4ccc5c(c4)[C@](C)(F)COC5)cc3n2)c(C#N)n1] |
Compounds of the invention TABLE 3a-continued
| Compounds of the invention | |
|---|---|
| # | Compound |
| 306 | 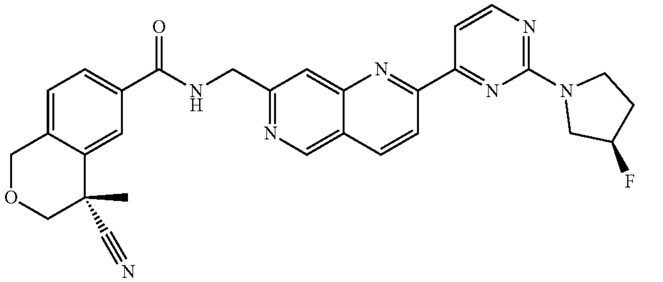 [SMILES: C[C@@]1(C#N)COCc2ccc(C(=O)NCc3cc4nc(-c5ccnc(N6CC[C@@H](F)C6)n5)ccc4cn3)cc21] |
| 307 | 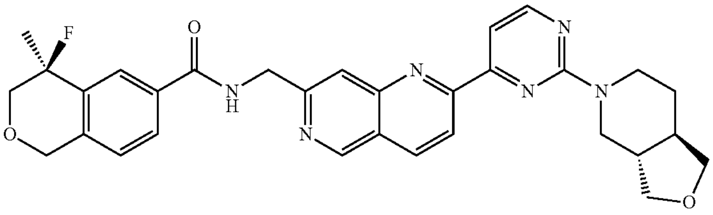 [SMILES: C[C@@]1(F)COCc2ccc(C(=O)NCc3cc4nc(-c5ccnc(N6CC[C@H]7COC[C@@H]7C6)n5)ccc4cn3)cc21] |
| 308 | 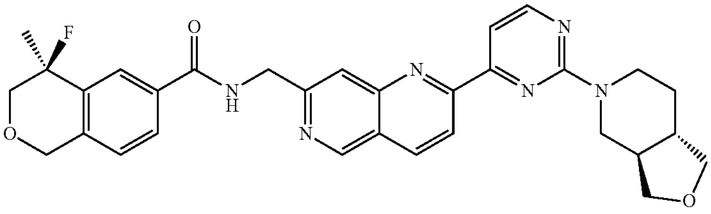 [SMILES: C[C@@]1(F)COCc2ccc(C(=O)NCc3cc4nc(-c5ccnc(N6CC[C@@H]7COC[C@H]7C6)n5)ccc4cn3)cc21] |
| 309 | 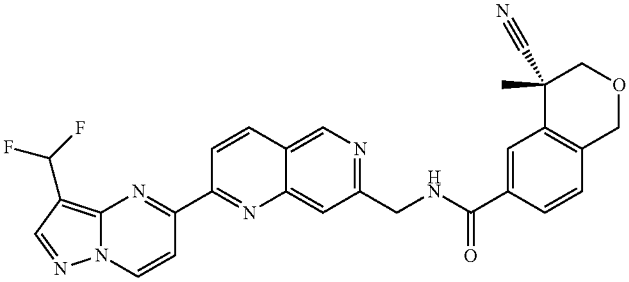 [SMILES: C[C@@]1(C#N)COCc2ccc(C(=O)NCc3cc4nc(-c5ccn6ncc(C(F)F)c6n5)ccc4cn3)cc21] |
| 310 | 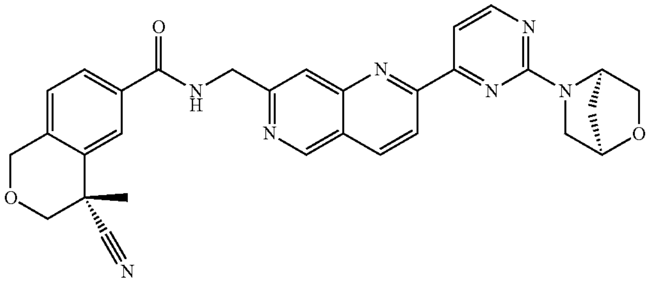 [SMILES: C[C@@]1(C#N)COCc2ccc(C(=O)NCc3cc4nc(-c5ccnc(N6C[C@H]7C[C@@H]6CO7)n5)ccc4cn3)cc21] |

TABLE 3a-continued
| Compounds of the invention | |
|---|---|
| # | Compound |
| 311 | 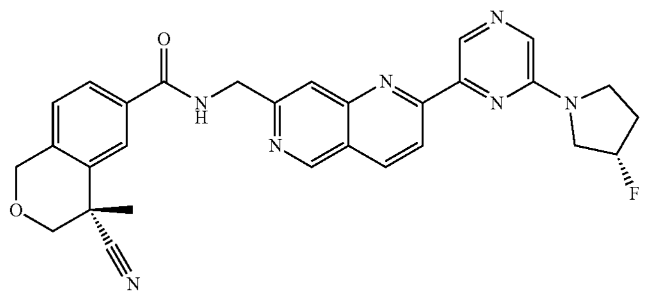 [SMILES: C[C@@]1(C#N)COCc2ccc(C(=O)NCc3cc4nc(-c5cncc(N6CC[C@H](F)C6)n5)ccc4cn3)cc21] |
| 312 | 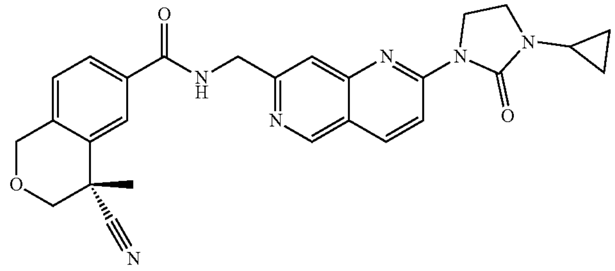 [SMILES: C[C@@]1(C#N)COCc2ccc(C(=O)NCc3cc4nc(N5CCN(C6CC6)C5=O)ccc4cn3)cc21] |
| 313 | 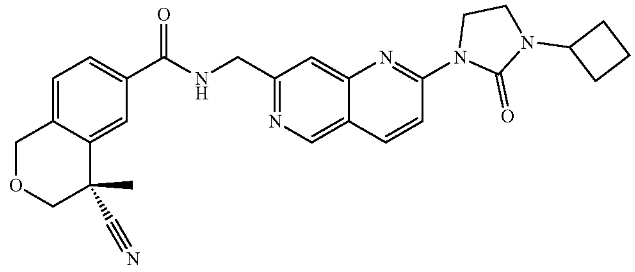 [SMILES: C[C@@]1(C#N)COCc2ccc(C(=O)NCc3cc4nc(N5CCN(C6CCC6)C5=O)ccc4cn3)cc21] |
| 314 | 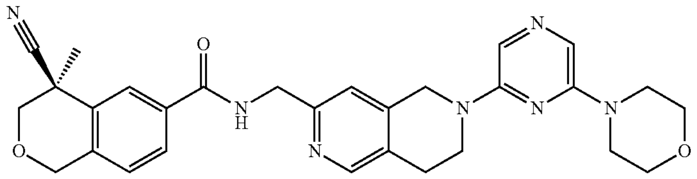 [SMILES: C[C@@]1(C#N)COCc2ccc(C(=O)NCc3cc4c(cn3)CCN(c3cncc(N5CCOCC5)n3)C4)cc21] |
| 315 | 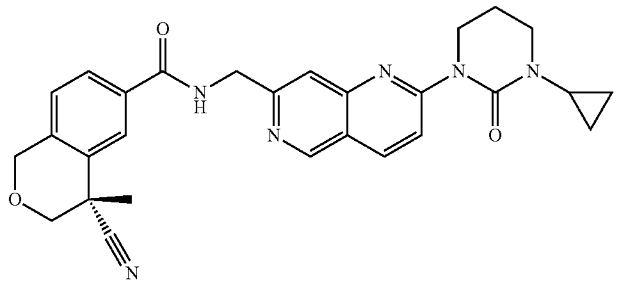 [SMILES: C[C@@]1(C#N)COCc2ccc(C(=O)NCc3cc4nc(N5CCCN(C6CC6)C5=O)ccc4cn3)cc21] |

TABLE 3a-continued
| Compounds of the invention | |
|---|---|
| # | Compound |
| 316 | 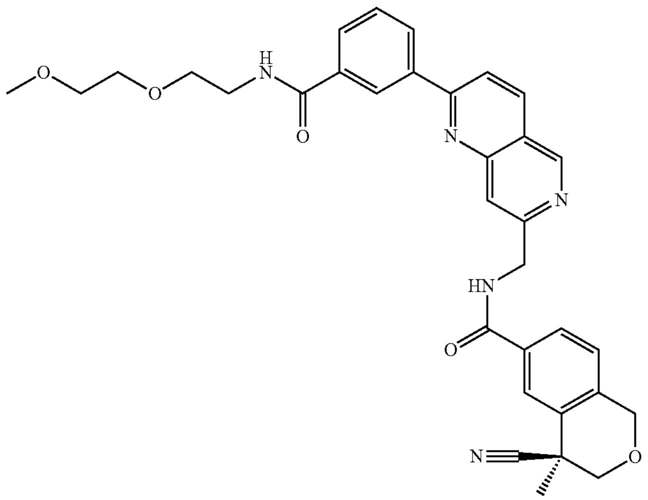 [SMILES: COCCOCCNC(=O)c1cccc(-c2ccc3cnc(CNC(=O)c4ccc5c(c4)[C@](C)(C#N)COC5)cc3n2)c1] |
| 317 | 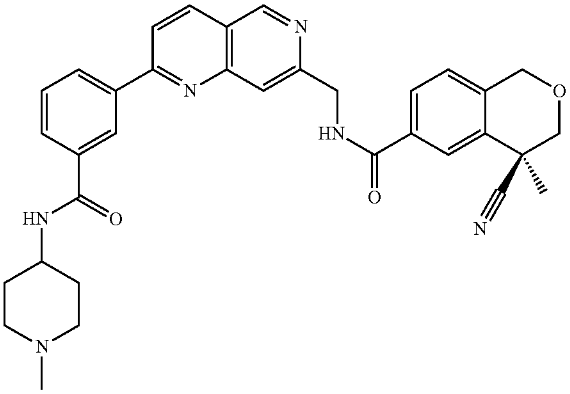 [SMILES: CN1CCC(NC(=O)c2cccc(-c3ccc4cnc(CNC(=O)c5ccc6c(c5)[C@](C)(C#N)COC6)cc4n3)c2)CC1] |
| 318 | 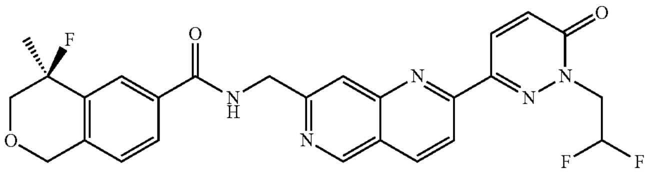 [SMILES: C[C@@]1(F)COCc2ccc(C(=O)NCc3cc4nc(-c5ccc(=O)n(CC(F)F)n5)ccc4cn3)cc21] |
| 319 | 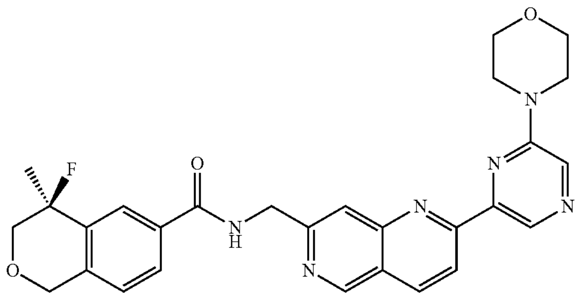 [SMILES: C[C@@]1(F)COCc2ccc(C(=O)NCc3cc4nc(-c5cncc(N6CCOCC6)n5)ccc4cn3)cc21] |

TABLE 3a-continued
| Compounds of the invention | |
|---|---|
| # | Compound |
| 320 | 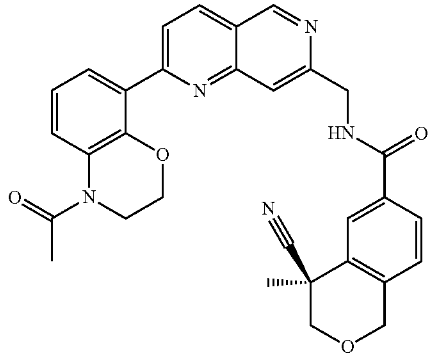 [SMILES: CC(=O)N1CCOc2c(-c3ccc4cnc(CNC(=O)c5ccc6c(c5)[C@](C)(C#N)COC6)cc4n3)cccc21] |
| 321 | 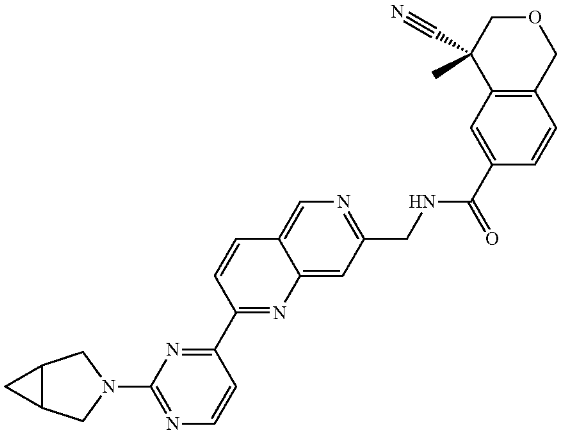 [SMILES: C[C@@]1(C#N)COCc2ccc(C(=O)NCc3cc4nc(-c5ccnc(N6CC7CC7C6)n5)ccc4cn3)cc21] |
| 322 | 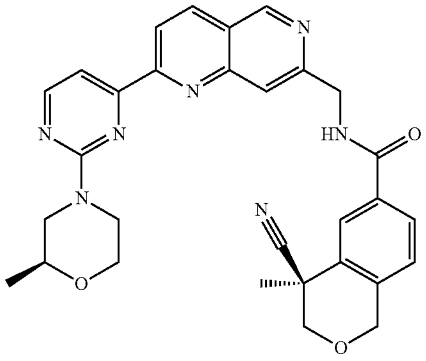 [SMILES: C[C@H]1CN(c2nccc(-c3ccc4cnc(CNC(=O)c5ccc6c(c5)[C@](C)(C#N)COC6)cc4n3)n2)CCO1] |
| 323 | 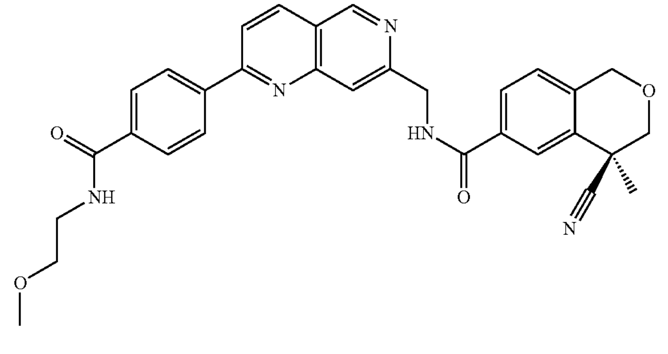 [SMILES: COCCNC(=O)c1ccc(-c2ccc3cnc(CNC(=O)c4ccc5c(c4)[C@](C)(C#N)COC5)cc3n2)cc1] |

TABLE 3a-continued
| # | Compound |
|---|---|
| 324 | 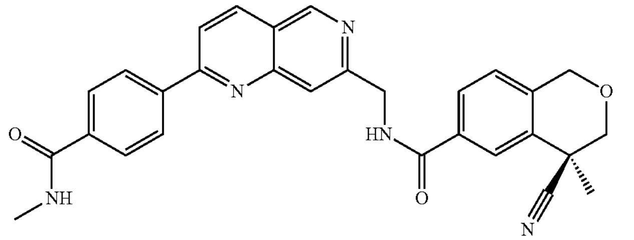 [SMILES: CNC(=O)c1ccc(-c2ccc3cnc(CNC(=O)c4ccc5c(c4)[C@](C)(C#N)COC5)cc3n2)cc1] |
| 325 | 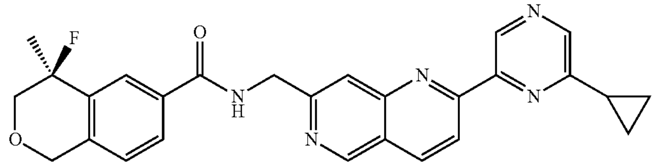 [SMILES: C[C@@]1(F)COCc2ccc(C(=O)NCc3cc4nc(-c5cncc(C6CC6)n5)ccc4cn3)cc21] |
| 326 | 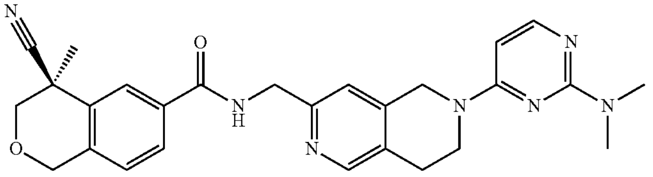 [SMILES: CN(C)c1nccc(N2CCc3cnc(CNC(=O)c4ccc5c(c4)[C@](C)(C#N)COC5)cc3C2)n1] |
| 327 | 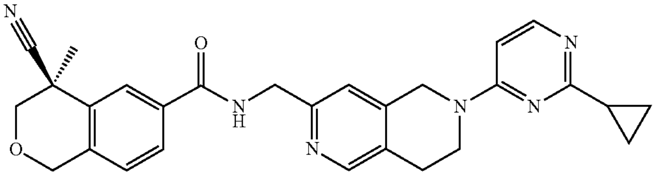 [SMILES: C[C@@]1(C#N)COCc2ccc(C(=O)NCc3cc4c(cn3)CCN(c3ccnc(C5CC5)n3)C4)cc21] |
| 328 | 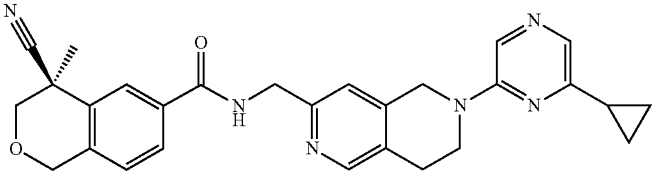 [SMILES: C[C@@]1(C#N)COCc2ccc(C(=O)NCc3cc4c(cn3)CCN(c3cncc(C5CC5)n3)C4)cc21] |
| 329 | 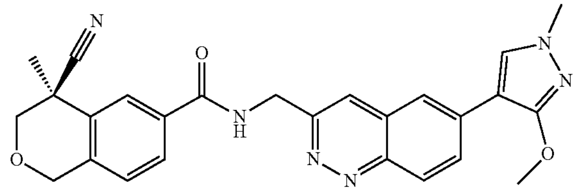 [SMILES: COc1nn(C)cc1-c1ccc2nnc(CNC(=O)c3ccc4c(c3)[C@](C)(C#N)COC4)cc2c1] |
| 330 | 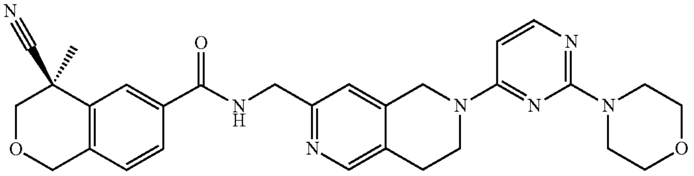 [SMILES: C[C@@]1(C#N)COCc2ccc(C(=O)NCc3cc4c(cn3)CCN(c3ccnc(N5CCOCC5)n3)C4)cc21] |
| 331 | 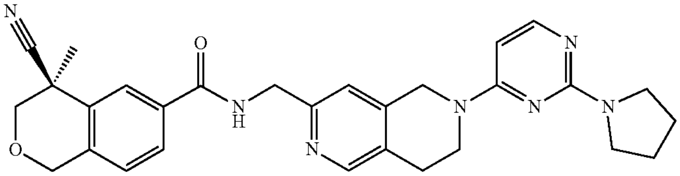 [SMILES: C[C@@]1(C#N)COCc2ccc(C(=O)NCc3cc4c(cn3)CCN(c3ccnc(N5CCCC5)n3)C4)cc21] |

TABLE 3a-continued
| Compounds of the invention | |
|---|---|
| # | Compound |
| 332 | 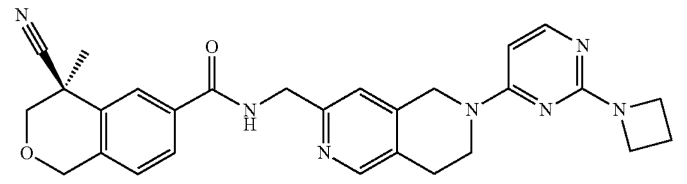 [SMILES: C[C@@]1(C#N)COCc2ccc(C(=O)NCc3cc4c(cn3)CCN(c3ccnc(N5CCC5)n3)C4)cc21] |
| 333 | 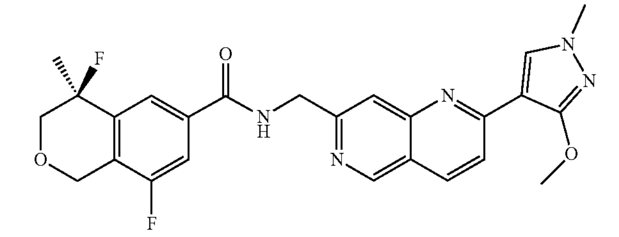 [SMILES: COc1nn(C)cc1-c1ccc2cnc(CNC(=O)c3cc(F)c4c(c3)[C@](C)(F)COC4)cc2n1] |
| 334 | 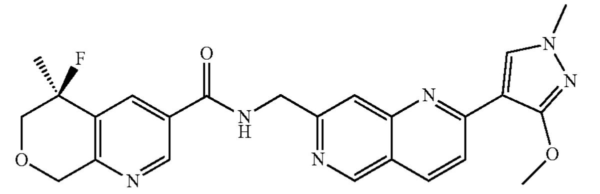 [SMILES: COc1nn(C)cc1-c1ccc2cnc(CNC(=O)c3cnc4c(c3)[C@](C)(F)COC4)cc2n1] |
| 335 | 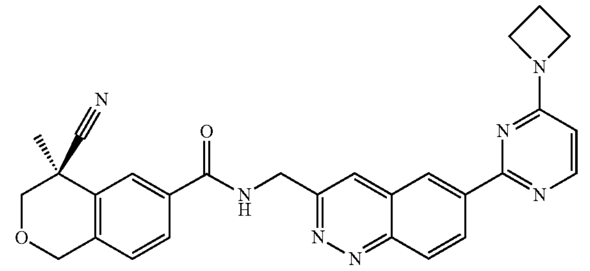 [SMILES: C[C@@]1(C#N)COCc2ccc(C(=O)NCc3cc4cc(-c5nccc(N6CCC6)n5)ccc4nn3)cc21] |
| 336 | 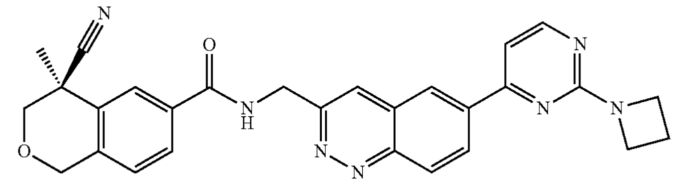 |
| 337 | 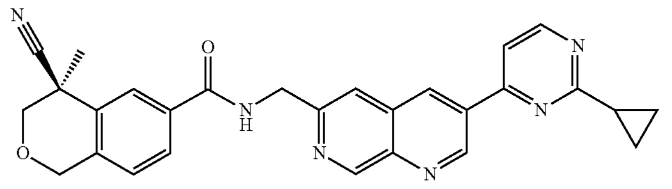 [SMILES: C[C@@]1(C#N)COCc2ccc(C(=O)NCc3cc4cc(-c5ccnc(C6CC6)n5)cnc4cn3)cc21] |
| 338 | 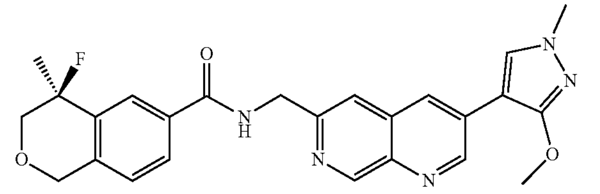 [SMILES: COc1nn(C)cc1-c1cnc2cnc(CNC(=O)c3ccc4c(c3)[C@](C)(F)COC4)cc2c1] |

TABLE 3a-continued
| Compounds of the invention | |
|---|---|
| # | Compound |
| 339 | 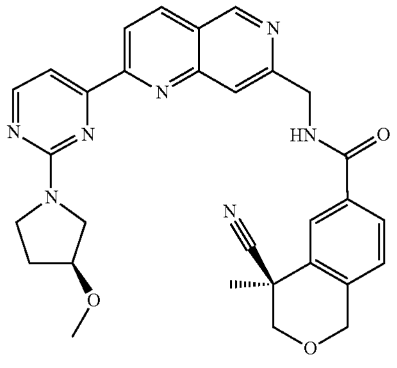 [SMILES: CO[C@H]1CCN(c2nccc(-c3ccc4cnc(CNC(=O)c5ccc6c(c5)[C@](C)(C#N)COC6)cc4n3)n2)C1] |
| 340 | 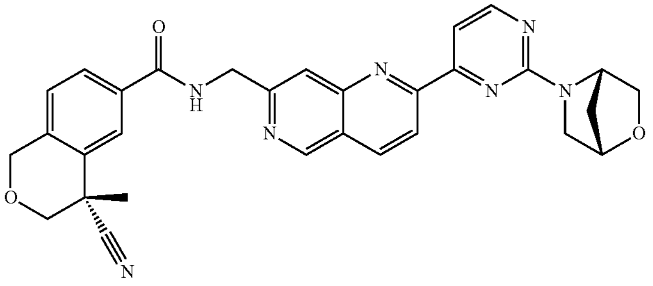 [SMILES: C[C@@]1(C#N)COCc2ccc(C(=O)NCc3cc4nc(-c5ccnc(N6C[C@@H]7C[C@H]6CO7)n5)ccc4cn3)cc21] |
| 341 | 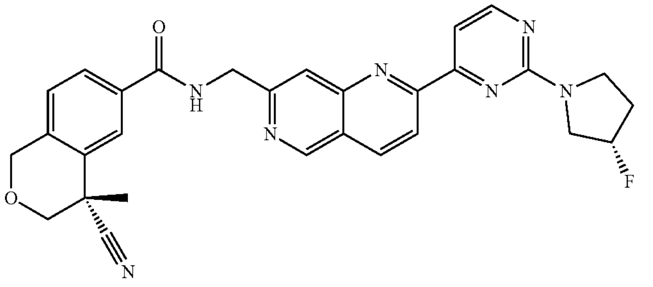 [SMILES: C[C@@]1(C#N)COCc2ccc(C(=O)NCc3cc4nc(-c5ccnc(N6CC[C@H](F)C6)n5)ccc4cn3)cc21] |
| 342 | 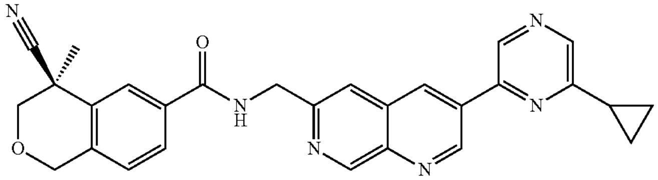 [SMILES: C[C@@]1(C#N)COCc2ccc(C(=O)NCc3cc4cc(-c5cncc(C6CC6)n5)cnc4cn3)cc21] |
| 343 | 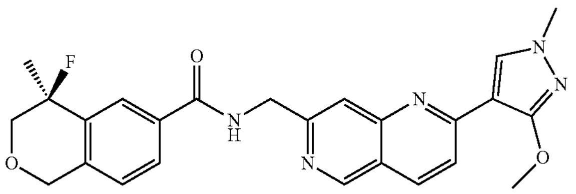 [SMILES: COc1nn(C)cc1-c1ccc2cnc(CNC(=O)c3ccc4c(c3)[C@](C)(F)COC4)cc2n1] |

TABLE 3a-continued
| Compounds of the invention | |
|---|---|
| # | Compound |
| 344 | 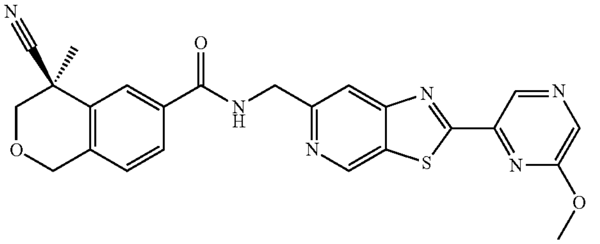 [SMILES: COc1cncc(-c2nc3cc(CNC(=O)c4ccc5c(c4)[C@](C)(C#N)COC5)ncc3s2)n1] |
| 345 | 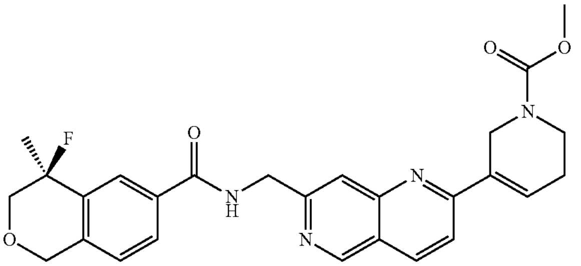 [SMILES: COC(=O)N1CCC=C(c2ccc3cnc(CNC(=O)c4ccc5c(c4)[C@](C)(F)COC5)cc3n2)C1] |
| 346 | 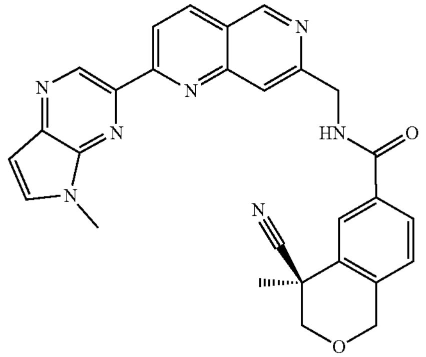 [SMILES: Cn1ccc2ncc(-c3ccc4cnc(CNC(=O)c5ccc6c(c5)[C@](C)(C#N)COC6)cc4n3)nc21] |
| 347 | 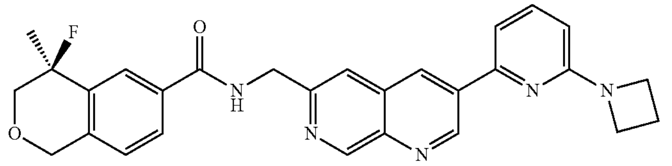 [SMILES: C[C@@]1(F)COCc2ccc(C(=O)NCc3cc4cc(-c5cccc(N6CCC6)n5)cnc4cn3)cc21] |
| 348 | 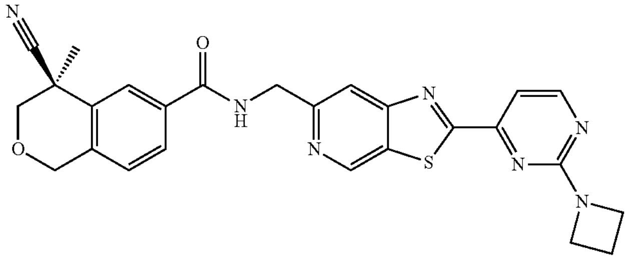 [SMILES: C[C@@]1(C#N)COCc2ccc(C(=O)NCc3cc4nc(-c5ccnc(N6CCC6)n5)sc4cn3)cc21] |
| 349 | 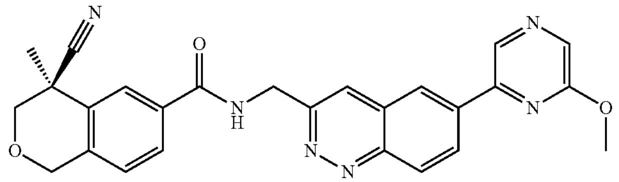 [SMILES: COc1cncc(-c2ccc3nnc(CNC(=O)c4ccc5c(c4)[C@](C)(C#N)COC5)cc3c2)n1] |

TABLE 3a-continued
| Compounds of the invention | |
|---|---|
| # | Compound |
| 350 | 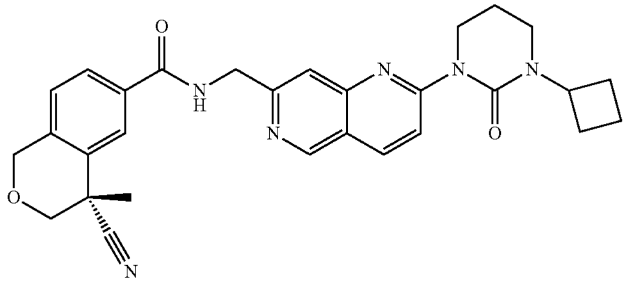 [SMILES: C[C@@]1(C#N)COCc2ccc(C(=O)NCc3cc4nc(N5CCCN(C6CCC6)C5=O)ccc4cn3)cc21] |
| 351 | 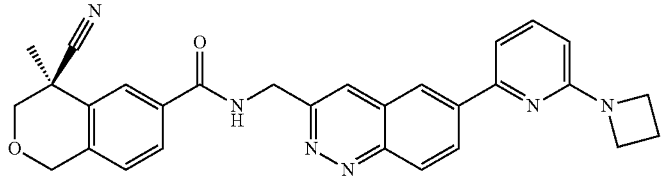 [SMILES: C[C@@]1(C#N)COCc2ccc(C(=O)NCc3cc4cc(-c5cccc(N6CCC6)n5)ccc4nn3)cc21] |
| 352 | 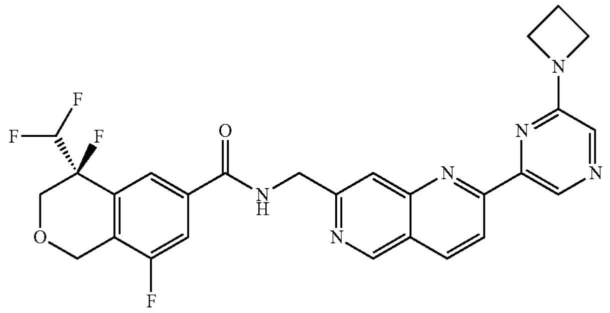 [SMILES: O=C(NCc1cc2nc(-c3cncc(N4CCC4)n3)ccc2cn1)c1cc(F)c2c(c1)[C@@](F)(C(F)F)COC2] |
| 353 | 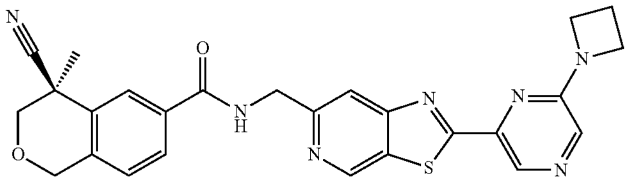 [SMILES: C[C@@]1(C#N)COCc2ccc(C(=O)NCc3cc4nc(-c5cncc(N6CCC6)n5)sc4cn3)cc21] |
| 354 | 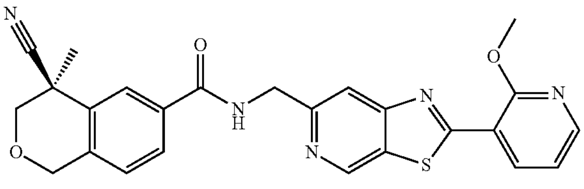 [SMILES: COc1ncccc1-c1nc2cc(CNC(=O)c3ccc4c(c3)[C@](C)(C#N)COC4)ncc2s1] |
| 355 | 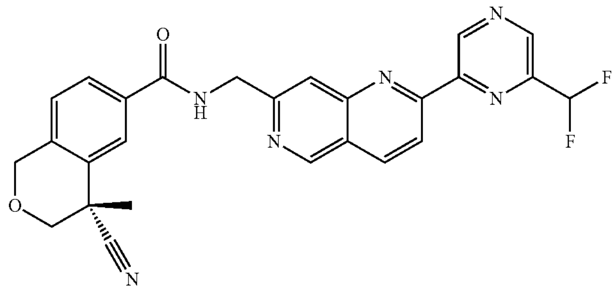 [SMILES: C[C@@]1(C#N)COCc2ccc(C(=O)NCc3cc4nc(-c5cncc(C(F)F)n5)ccc4cn3)cc21] |

TABLE 3a-continued
| Compounds of the invention | |
|---|---|
| # | Compound |
| 356 | 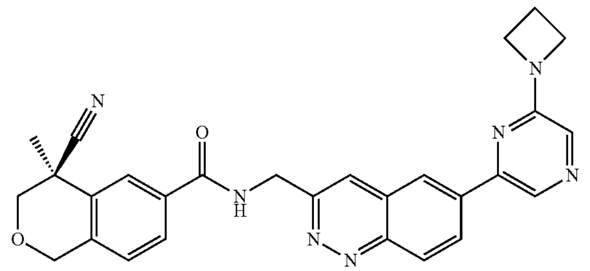 [SMILES: C[C@@]1(C#N)COCc2ccc(C(=O)NCc3cc4cc(-c5cncc(N6CCC6)n5)ccc4nn3)cc21] |
| 357 | 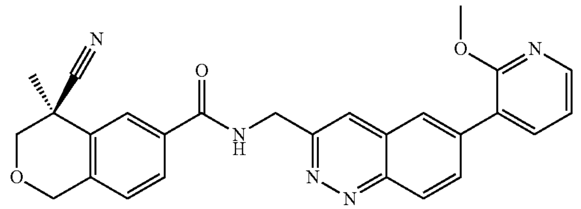 [SMILES: COc1ncccc1-c1ccc2nnc(CNC(=O)c3ccc4c(c3)[C@](C)(C#N)COC4)cc2c1] |
| 358 | 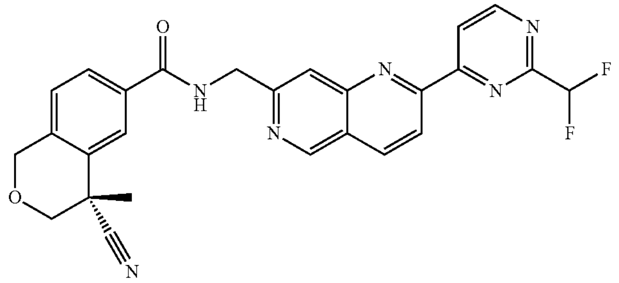 [SMILES: C[C@@]1(C#N)COCc2ccc(C(=O)NCc3cc4nc(-c5ccnc(C(F)F)n5)ccc4cn3)cc21] |
| 359 | 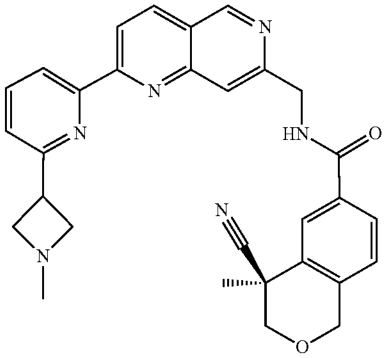 [SMILES: CN1CC(c2cccc(-c3ccc4cnc(CNC(=O)c5ccc6c(c5)[C@](C)(C#N)COC6)cc4n3)n2)C1] |
| 360 | 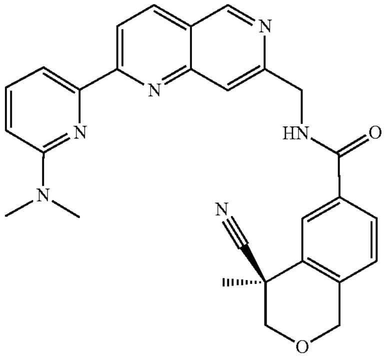 [SMILES: CN(C)c1cccc(-c2ccc3cnc(CNC(=O)c4ccc5c(c4)[C@](C)(C#N)COC5)cc3n2)n1] |

TABLE 3a-continued
| Compounds of the invention | |
|---|---|
| # | Compound |
| 361 | 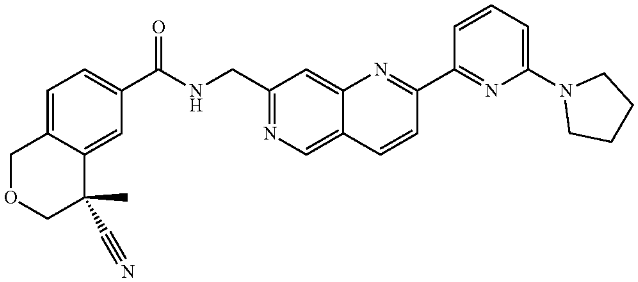 [SMILES: C[C@@]1(C#N)COCc2ccc(C(=O)NCc3cc4nc(-c5cccc(N6CCCC6)n5)ccc4cn3)cc21] |
| 362 | 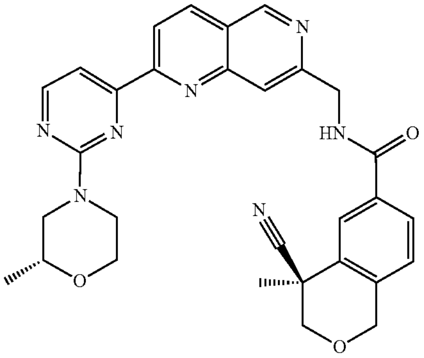 [SMILES: C[C@@H]1CN(c2nccc(-c3ccc4cnc(CNC(=O)c5ccc6c(c5)[C@](C)(C#N)COC6)cc4n3)n2)CCO1] |
| 363 | 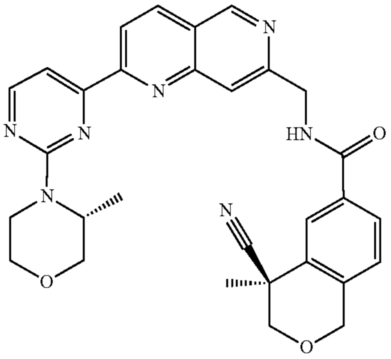 [SMILES: C[C@@H]1COCCN1c1nccc(-c2ccc3cnc(CNC(=O)c4ccc5c(c4)[C@](C)(C#N)COC5)cc3n2)n1] |
| 364 | 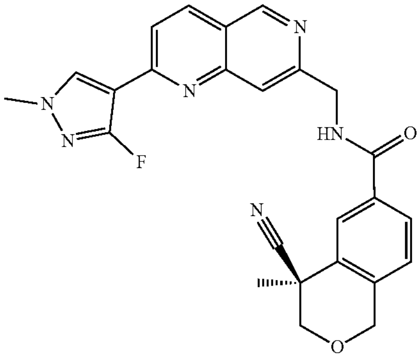 |

TABLE 3a-continued
| Compounds of the invention | |
|---|---|
| # | Compound |
| 365 | 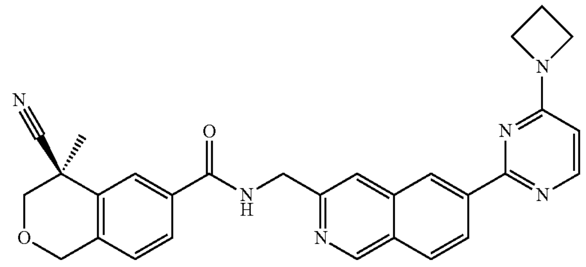 [SMILES: C[C@@]1(C#N)COCc2ccc(C(=O)NCc3cc4cc(-c5nccc(N6CCC6)n5)ccc4cn3)cc21] |
| 366 | 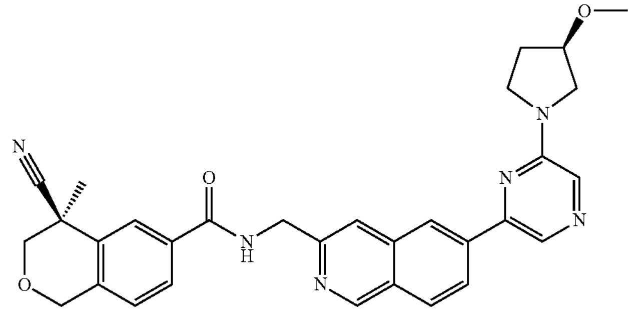 [SMILES: CO[C@@H]1CCN(c2cncc(-c3ccc4cnc(CNC(=O)c5ccc6c(c5)[C@](C)(C#N)COC6)cc4c3)n2)C1] |
| 367 | 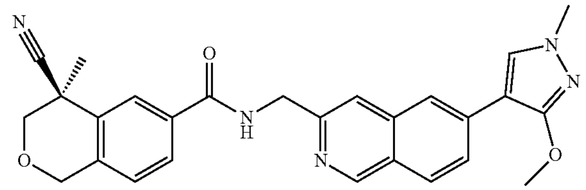 [SMILES: COc1nn(C)cc1-c1ccc2cnc(CNC(=O)c3ccc4c(c3)[C@](C)(C#N)COC4)cc2c1] |
| 368 | 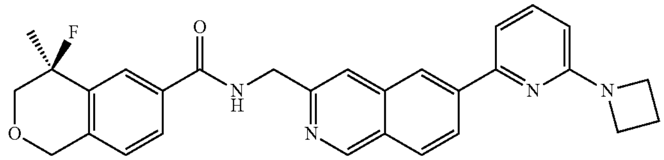 [SMILES: C[C@@]1(F)COCc2ccc(C(=O)NCc3cc4cc(-c5cccc(N6CCC6)n5)ccc4cn3)cc21] |
| 369 | 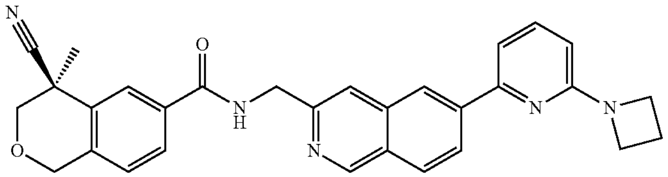 [SMILES: C[C@@]1(C#N)COCc2ccc(C(=O)NCc3cc4cc(-c5cccc(N6CCC6)n5)ccc4cn3)cc21] |
| 370 | 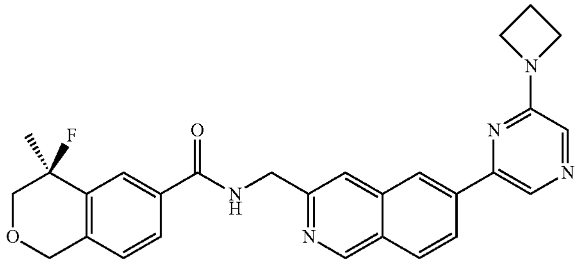 [SMILES: C[C@@]1(F)COCc2ccc(C(=O)NCc3cc4cc(-c5cncc(N6CCC6)n5)ccc4cn3)cc21] |

TABLE 3a-continued
| Compounds of the invention | |
|---|---|
| # | Compound |
| 371 | 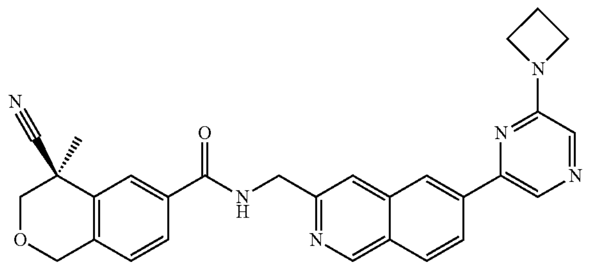 [SMILES: C[C@@]1(C#N)COCc2ccc(C(=O)NCc3cc4cc(-c5cncc(N6CCC6)n5)ccc4cn3)cc21] |
| 372 | 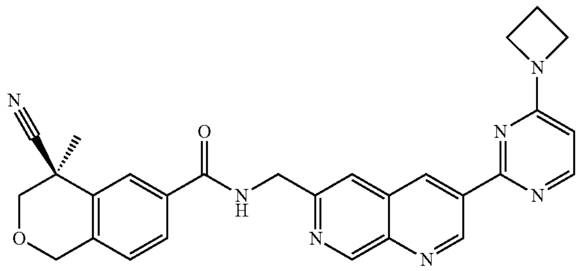 [SMILES: C[C@@]1(C#N)COCc2ccc(C(=O)NCc3cc4cc(-c5nccc(N6CCC6)n5)cnc4cn3)cc21] |
| 373 | 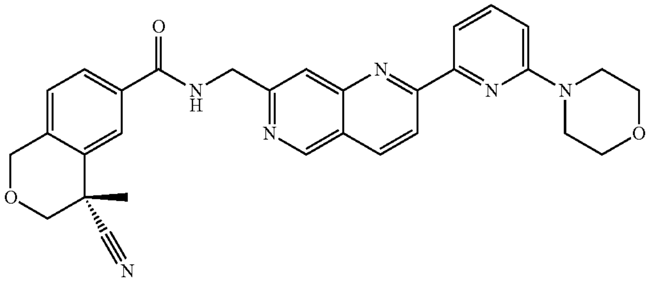 [SMILES: C[C@@]1(C#N)COCc2ccc(C(=O)NCc3cc4nc(-c5cccc(N6CCOCC6)n5)ccc4cn3)cc21] |
| 374 | 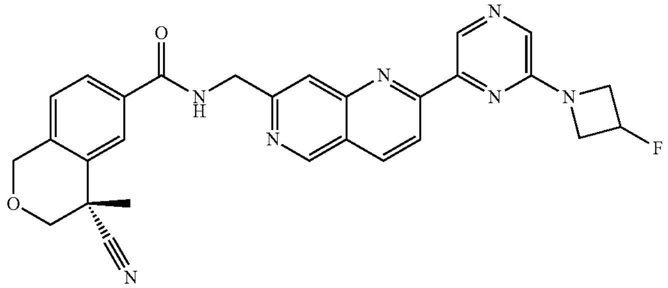 [SMILES: C[C@@]1(C#N)COCc2ccc(C(=O)NCc3cc4nc(-c5cncc(N6CC(F)C6)n5)ccc4cn3)cc21] |
| 375 | 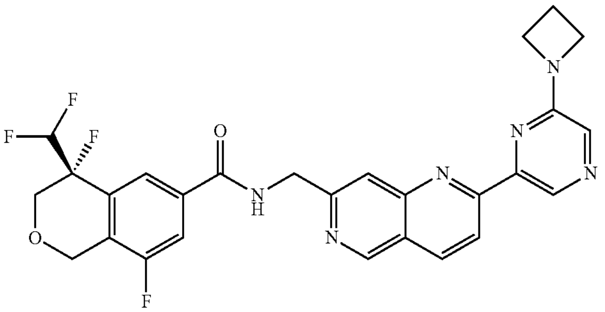 [SMILES: O=C(NCc1cc2nc(-c3cncc(N4CCC4)n3)ccc2cn1)c1cc(F)c2c(c1)[C@](F)(C(F)F)COC2] |

TABLE 3a-continued
| Compounds of the invention | |
|---|---|
| # | Compound |
| 376 | 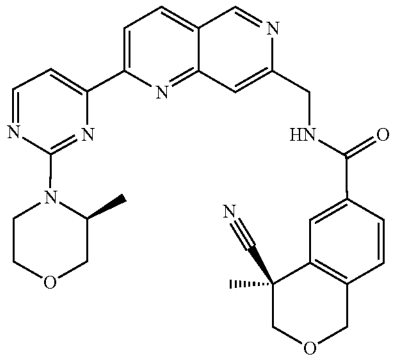 [SMILES: C[C@H]1COCCN1c1nccc(-c2ccc3cnc(CNC(=O)c4ccc5c(c4)[C@](C)(C#N)COC5)cc3n2)n1] |
| 377 | 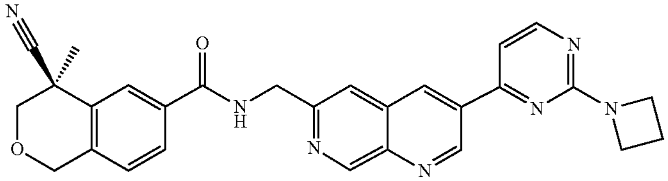 [SMILES: C[C@@]1(C#N)COCc2ccc(C(=O)NCc3cc4cc(-c5ccnc(N6CCC6)n5)cnc4cn3)cc21] |
| 378 | 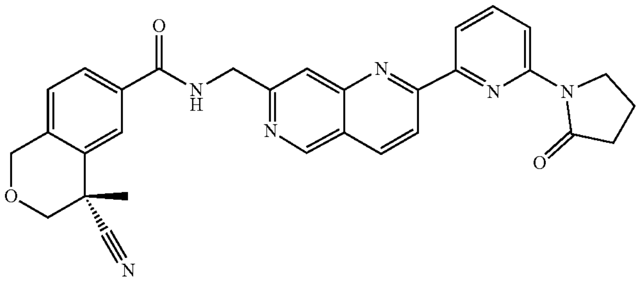 |
| 379 | 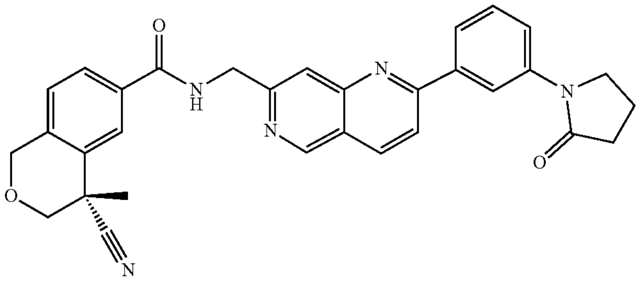 [SMILES: C[C@@]1(C#N)COCc2ccc(C(=O)NCc3cc4nc(-c5cccc(N6CCCC6=O)c5)ccc4cn3)cc21] |
| 380 | 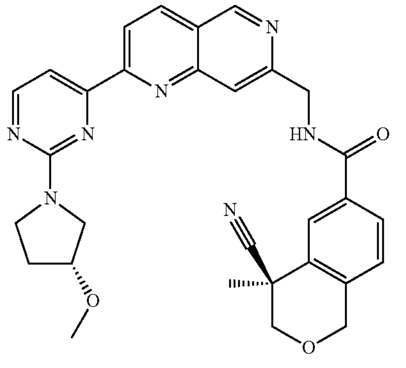 [SMILES: CO[C@@H]1CCN(c2nccc(-c3ccc4cnc(CNC(=O)c5ccc6c(c5)[C@](C)(C#N)COC6)cc4n3)n2)C1] |

TABLE 3a-continued
| Compounds of the invention | |
|---|---|
| # | Compound |
| 381 | 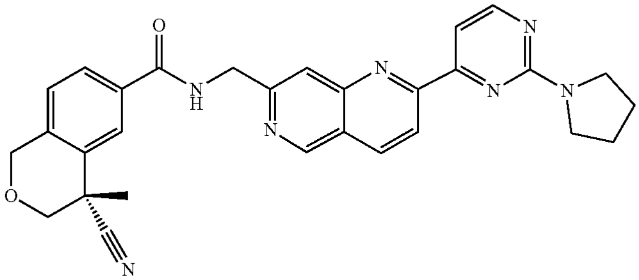 [SMILES: C[C@@]1(C#N)COCc2ccc(C(=O)NCc3cc4nc(-c5ccnc(N6CCCC6)n5)ccc4cn3)cc21] |
| 382 | 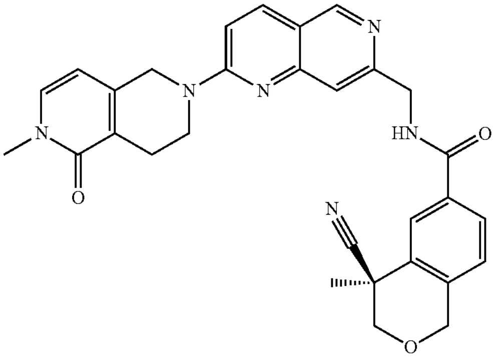 [SMILES: Cn1ccc2c(c1=O)CCN(c1ccc3cnc(CNC(=O)c4ccc5c(c4)[C@](C)(C#N)COC5)cc3n1)C2] |
| 383 | 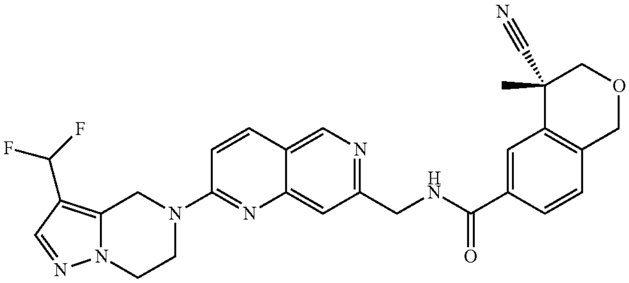 [SMILES: C[C@@]1(C#N)COCc2ccc(C(=O)NCc3cc4nc(N5CCn6ncc(C(F)F)c6C5)ccc4cn3)cc21] |
| 384 | 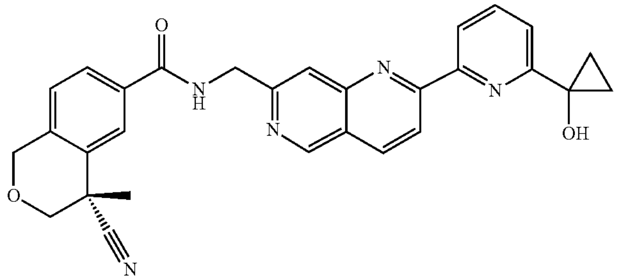 [SMILES: C[C@@]1(C#N)COCc2ccc(C(=O)NCc3cc4nc(-c5cccc(C6(O)CC6)n5)ccc4cn3)cc21] |
| 385 | 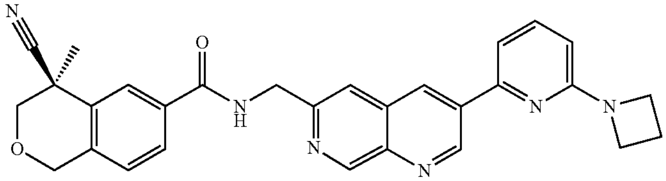 [SMILES: C[C@@]1(C#N)COCc2ccc(C(=O)NCc3cc4cc(-c5cccc(N6CCC6)n5)cnc4cn3)cc21] |

TABLE 3a-continued
| Compounds of the invention | |
|---|---|
| # | Compound |
| 386 | 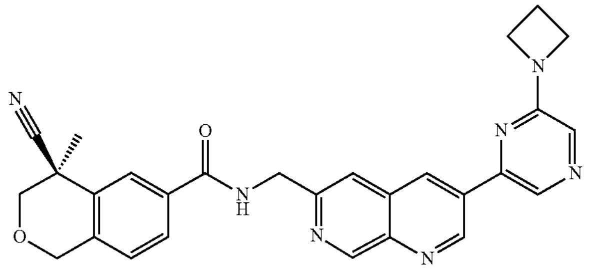 [SMILES: C[C@@]1(C#N)COCc2ccc(C(=O)NCc3cc4cc(-c5cncc(N6CCC6)n5)cnc4cn3)cc21] |
| 387 | 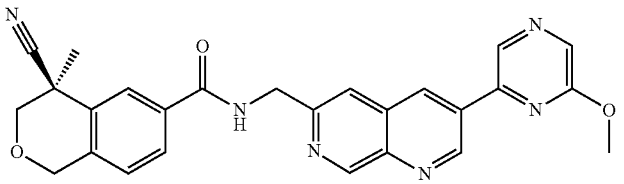 [SMILES: COc1cncc(-c2cnc3cnc(CNC(=O)c4ccc5c(c4)[C@](C)(C#N)COC5)cc3c2)n1] |
| 388 | 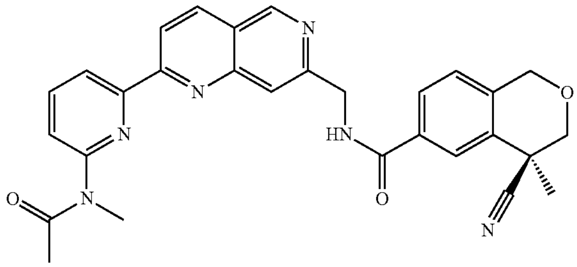 [SMILES: CC(=O)N(C)c1cccc(-c2ccc3cnc(CNC(=O)c4ccc5c(c4)[C@](C)(C#N)COC5)cc3n2)n1] |
| 389 | 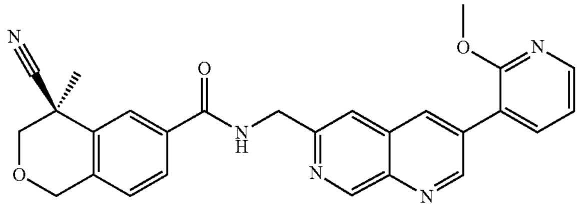 [SMILES: COc1ncccc1-c1cnc2cnc(CNC(=O)c3ccc4c(c3)[C@](C)(C#N)COC4)cc2c1] |
| 390 | 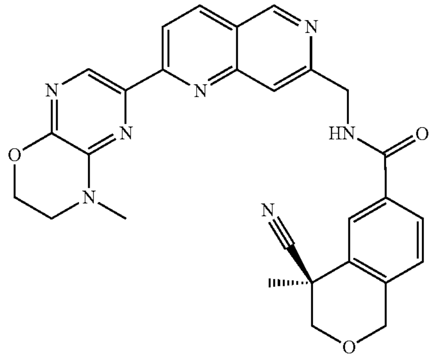 [SMILES: CN1CCOc2ncc(-c3ccc4cnc(CNC(=O)c5ccc6c(c5)[C@](C)(C#N)COC6)cc4n3)nc21] |

TABLE 3a-continued
| Compounds of the invention | |
|---|---|
| # | Compound |
| 391 | 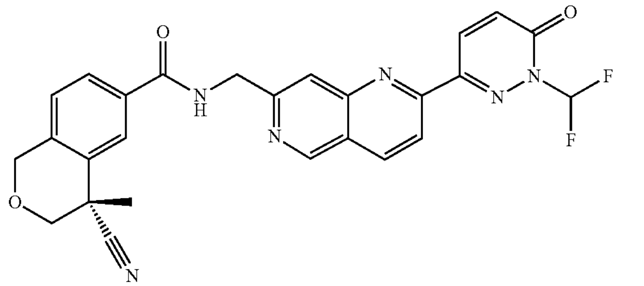 [SMILES: C[C@@]1(C#N)COCc2ccc(C(=O)NCc3cc4nc(-c5ccc(=O)n(C(F)F)n5)ccc4cn3)cc21] |
| 392 | 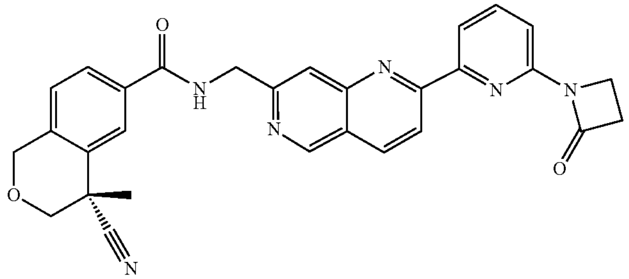 [SMILES: C[C@@]1(C#N)COCc2ccc(C(=O)NCc3cc4nc(-c5cccc(N6CCC6=O)n5)ccc4cn3)cc21] |
| 393 | 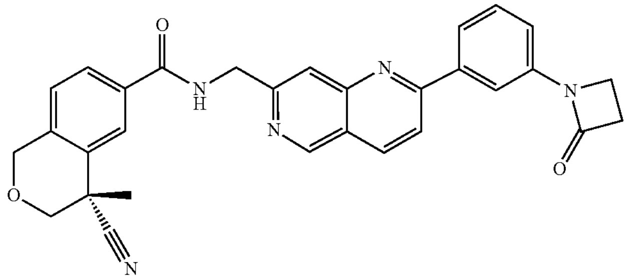 |
| 394 | 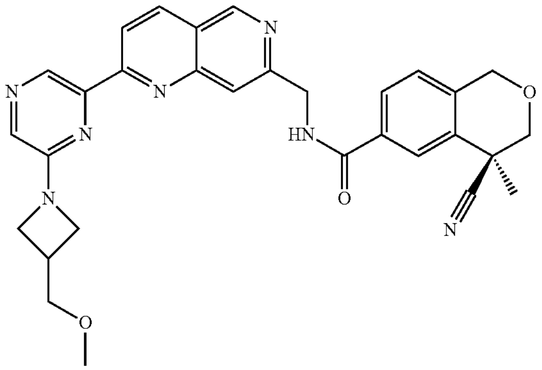 [SMILES: COCC1CN(c2cncc(-c3ccc4cnc(CNC(=O)c5ccc6c(c5)[C@](C)(C#N)COC6)cc4n3)n2)C1] |
| 395 | 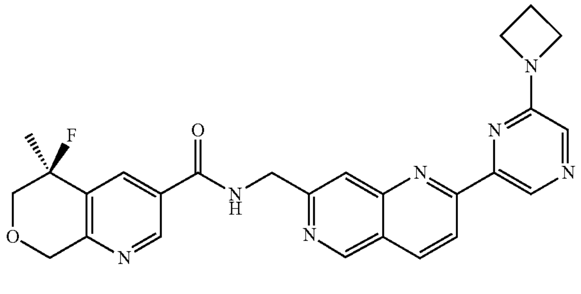 [SMILES: C[C@@]1(F)COCc2ncc(C(=O)NCc3cc4nc(-c5cncc(N6CCC6)n5)ccc4cn3)cc21] |

TABLE 3a-continued
| Compounds of the invention | |
|---|---|
| # | Compound |
| 396 | 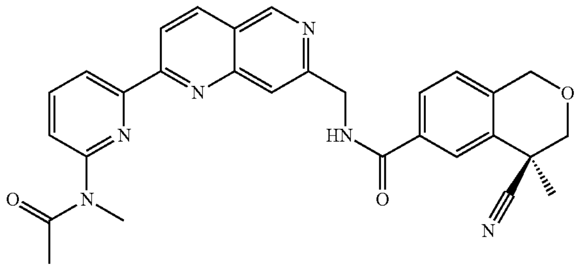 [SMILES: CC(=O)N(C)c1cccc(-c2ccc3cnc(CNC(=O)c4ccc5c(c4)[C@](C)(C#N)COC5)cc3n2)n1] |
| 397 | 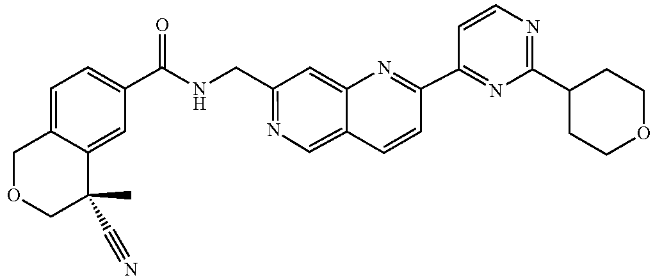 [SMILES: C[C@@]1(C#N)COCc2ccc(C(=O)NCc3cc4nc(-c5ccnc(C6CCOCC6)n5)ccc4cn3)cc21] |
| 398 | 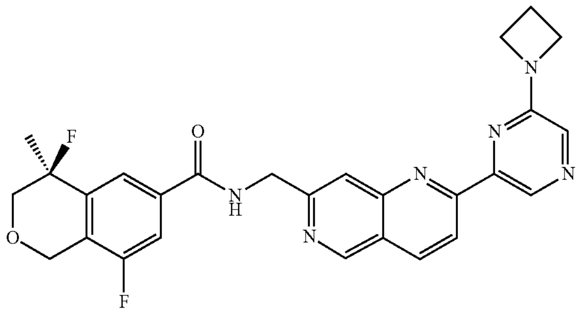 [SMILES: C[C@@]1(F)COCc2c(F)cc(C(=O)NCc3cc4nc(-c5cncc(N6CCC6)n5)ccc4cn3)cc21] |
| 399 | 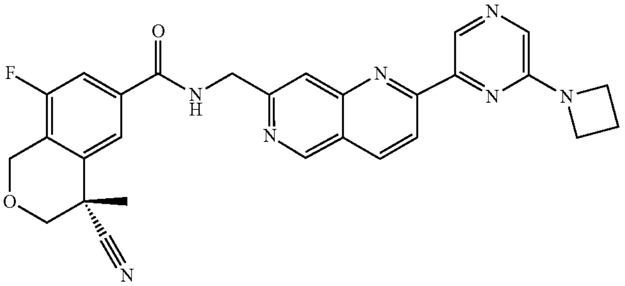 [SMILES: C[C@@]1(C#N)COCc2c(F)cc(C(=O)NCc3cc4nc(-c5cncc(N6CCC6)n5)ccc4cn3)cc21] |
| 400 | 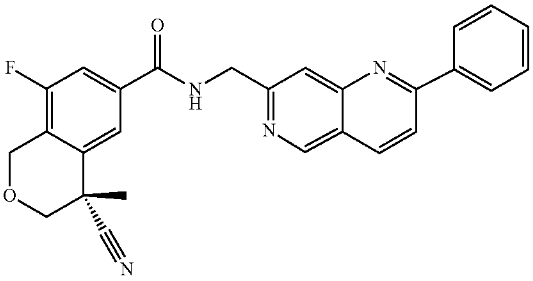 [SMILES: C[C@@]1(C#N)COCc2c(F)cc(C(=O)NCc3cc4nc(-c5ccccc5)ccc4cn3)cc21] |

TABLE 3a-continued
| Compounds of the invention | |
|---|---|
| # | Compound |
| 401 | 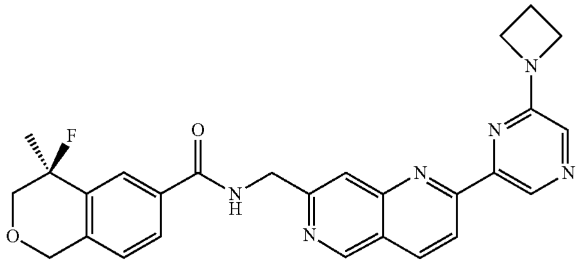 [SMILES: C[C@@]1(F)COCc2ccc(C(=O)NCc3cc4nc(-c5cncc(N6CCC6)n5)ccc4cn3)cc21] |
| 402 | 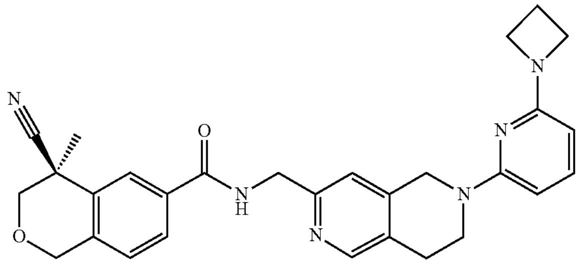 [SMILES: C[C@@]1(C#N)COCc2ccc(C(=O)NCc3cc4c(cn3)CCN(c3cccc(N5CCC5)n3)C4)cc21] |
| 403 | 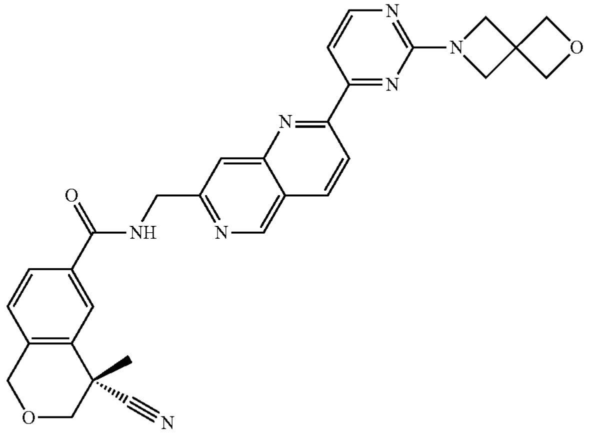 [SMILES: C[C@@]1(C#N)COCc2ccc(C(=O)NCc3cc4nc(-c5ccnc(N6CC7(COC7)C6)n5)ccc4cn3)cc21] |
| 404 | 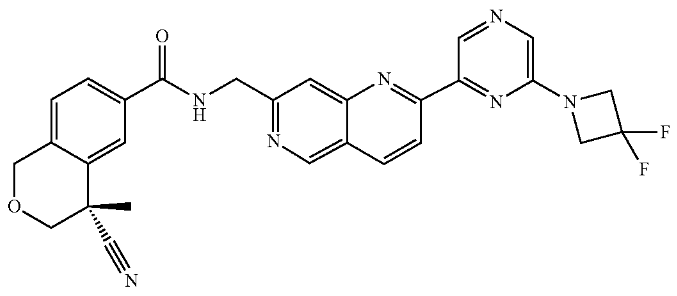 [SMILES: C[C@@]1(C#N)COCc2ccc(C(=O)NCc3cc4nc(-c5cncc(N6CC(F)(F)C6)n5)ccc4cn3)cc21] |

TABLE 3a-continued
| Compounds of the invention | |
|---|---|
| # | Compound |
| 405 | 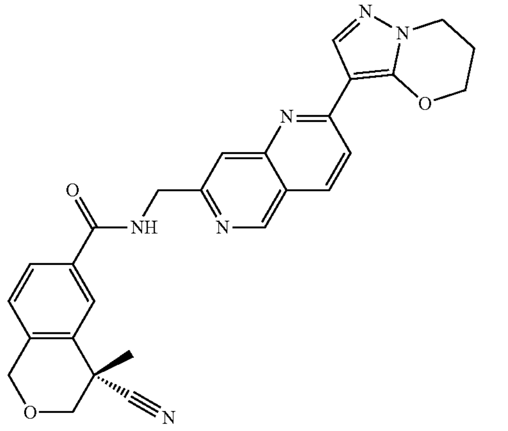 [SMILES: C[C@@]1(C#N)COCc2ccc(C(=O)NCc3cc4nc(-c5cnn6c5OCCC6)ccc4cn3)cc21] |
| 406 | 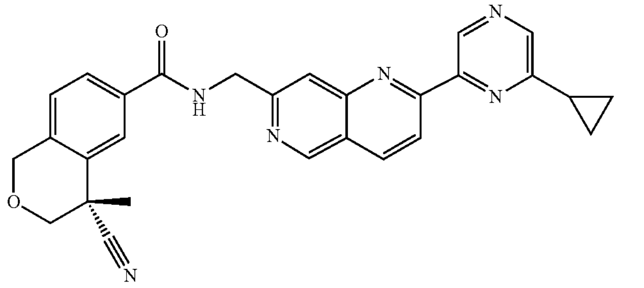 [SMILES: C[C@@]1(C#N)COCc2ccc(C(=O)NCc3cc4nc(-c5cncc(C6CC6)n5)ccc4cn3)cc21] |
| 407 | 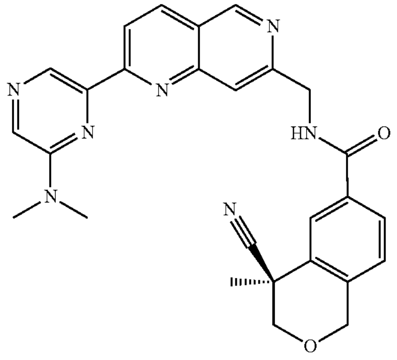 [SMILES: CN(C)c1cncc(-c2ccc3cnc(CNC(=O)c4ccc5c(c4)[C@](C)(C#N)COC5)cc3n2)n1] |
| 408 | 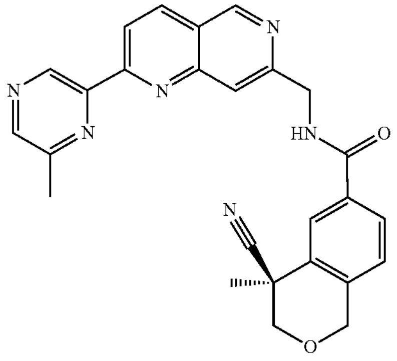 |

TABLE 3a-continued
| Compounds of the invention | |
|---|---|
| # | Compound |
| 409 | 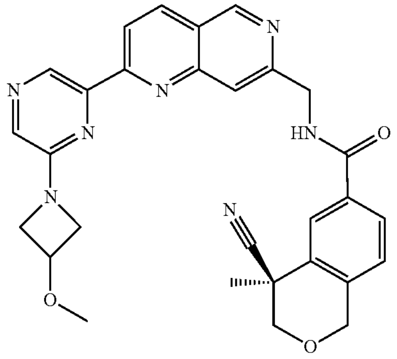 |
| 410 | 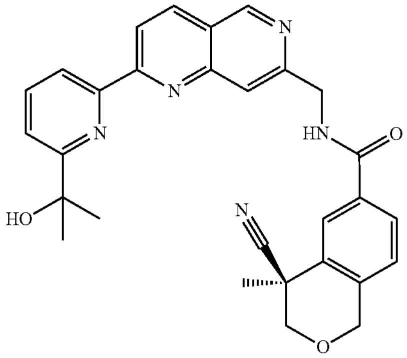 [SMILES: CC(C)(O)c1cccc(-c2ccc3cnc(CNC(=O)c4ccc5c(c4)[C@](C)(C#N)COC5)cc3n2)n1] |
| 411 | 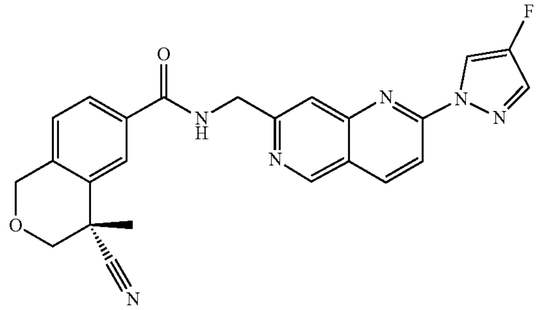 [SMILES: C[C@@]1(C#N)COCc2ccc(C(=O)NCc3cc4nc(-n5cc(F)cn5)ccc4cn3)cc21] |
| 412 | 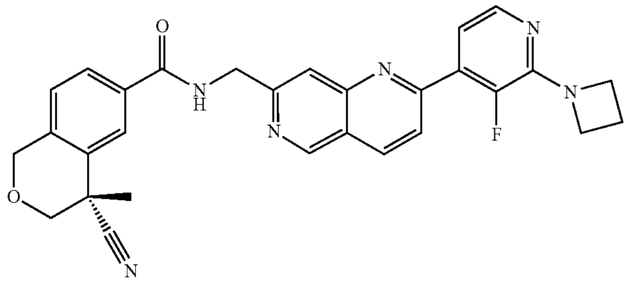 [SMILES: C[C@@]1(C#N)COCc2ccc(C(=O)NCc3cc4nc(-c5ccnc(N6CCC6)c5F)ccc4cn3)cc21] |
| 413 | 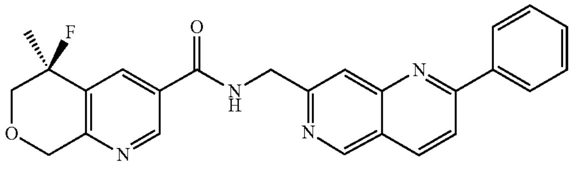 [SMILES: C[C@@]1(F)COCc2ncc(C(=O)NCc3cc4nc(-c5ccccc5)ccc4cn3)cc21] |

TABLE 3a-continued
| Compounds of the invention | |
|---|---|
| # | Compound |
| 414 | 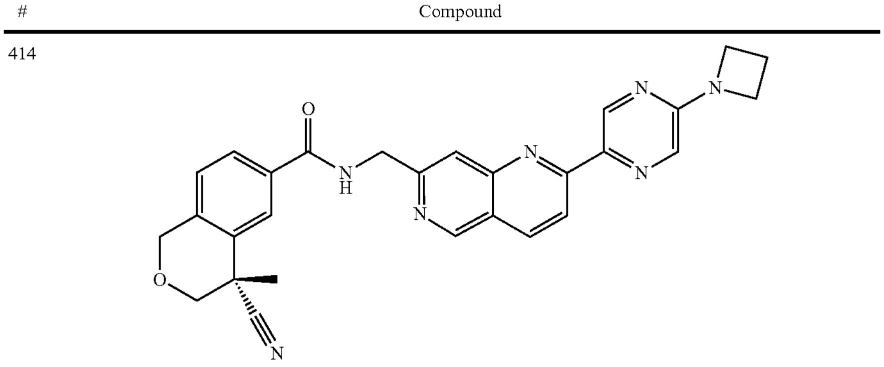 |
| 415 | 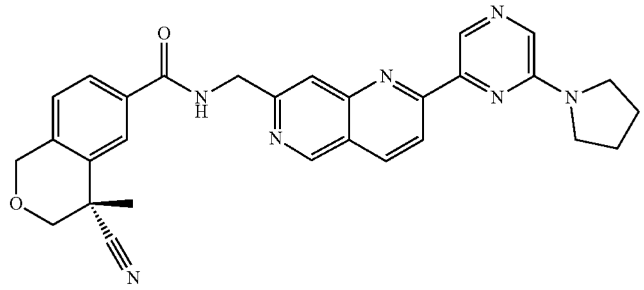 [SMILES: C[C@@]1(C#N)COCc2ccc(C(=O)NCc3cc4nc(-c5cncc(N6CCCC6)n5)ccc4cn3)cc21] |
| 416 | 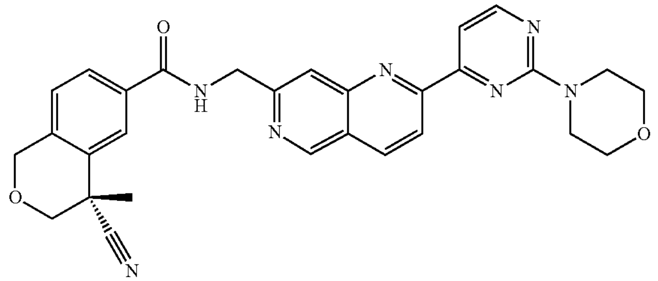 |
| 417 | 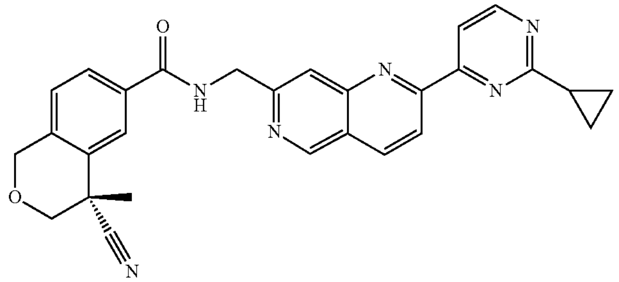 [SMILES: C[C@@]1(C#N)COCc2ccc(C(=O)NCc3cc4nc(-c5ccnc(C6CC6)n5)ccc4cn3)cc21] |
| 418 | 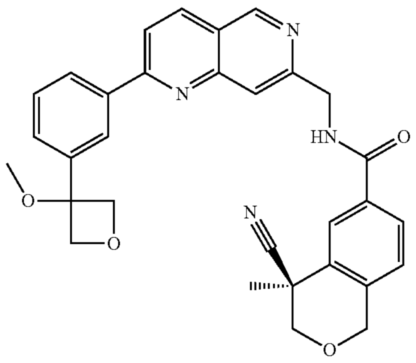 |

TABLE 3a-continued
| Compounds of the invention | |
|---|---|
| # | Compound |
| 419 | 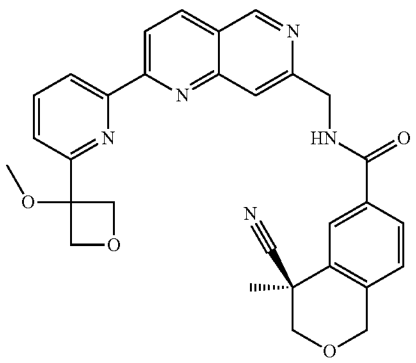 [SMILES: COC1(c2cccc(-c3ccc4cnc(CNC(=O)c5ccc6c(c5)[C@](C)(C#N)COC6)cc4n3)c2)COC1] |
| 420 | 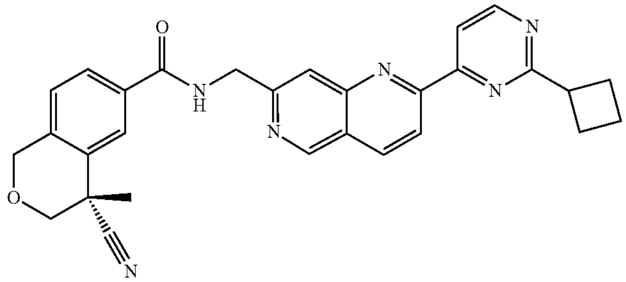 |
| 421 | 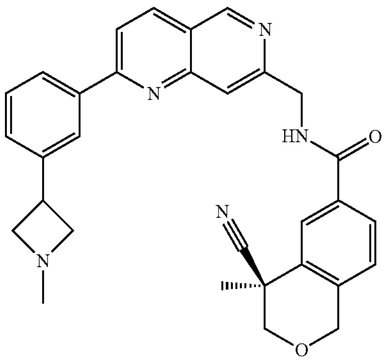 [SMILES: CN1CC(c2cccc(-c3ccc4cnc(CNC(=O)c5ccc6c(c5)[C@](C)(C#N)COC6)cc4n3)c2)C1] |
| 422 | 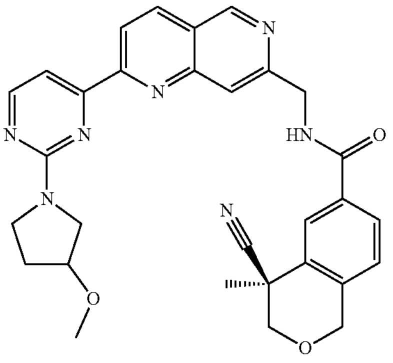 [SMILES: COC1CCN(c2nccc(-c3ccc4cnc(CNC(=O)c5ccc6c(c5)[C@](C)(C#N)COC6)cc4n3)n2)C1] |

TABLE 3a-continued
| Compounds of the invention | |
|---|---|
| # | Compound |
| 423 | 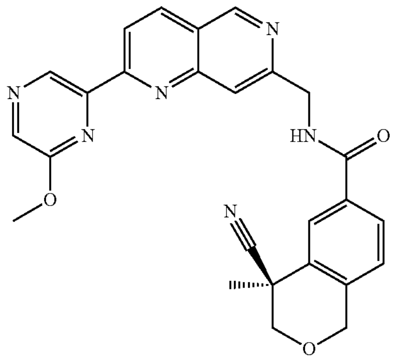 |
| 424 | 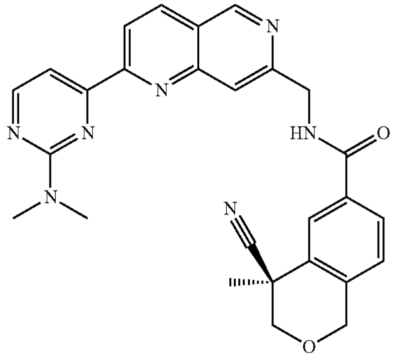 [SMILES: CN(C)c1nccc(-c2ccc3cnc(CNC(=O)c4ccc5c(c4)[C@](C)(C#N)COC5)cc3n2)n1] |
| 425 | 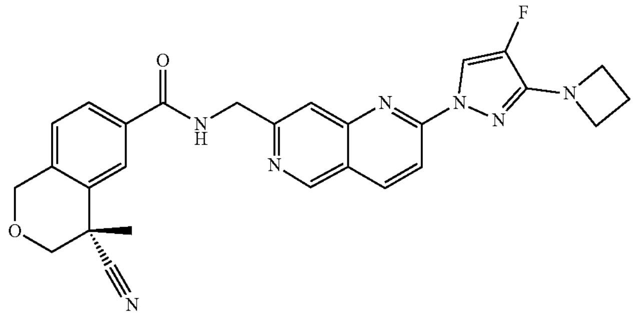 [SMILES: C[C@@]1(C#N)COCc2ccc(C(=O)NCc3cc4nc(-n5cc(F)c(N6CCC6)n5)ccc4cn3)cc21] |
| 426 | 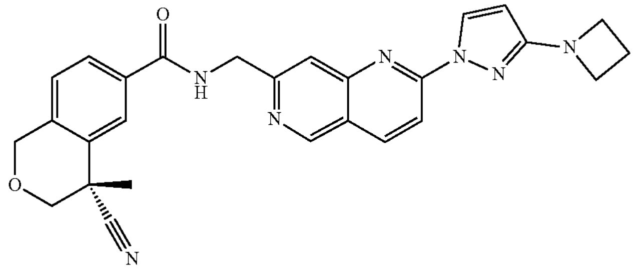 [SMILES: C[C@@]1(C#N)COCc2ccc(C(=O)NCc3cc4nc(-n5ccc(N6CCC6)n5)ccc4cn3)cc21] |

TABLE 3a-continued
| Compounds of the invention | |
|---|---|
| # | Compound |
| 427 | 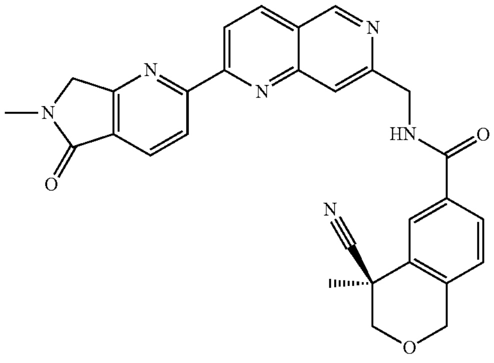 |
| 428 | 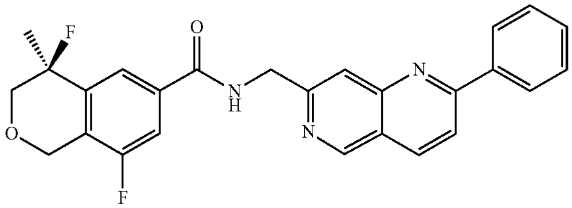 [SMILES: C[C@@]1(F)COCc2c(F)cc(C(=O)NCc3cc4nc(-c5ccccc5)ccc4cn3)cc21] |
| 429 | 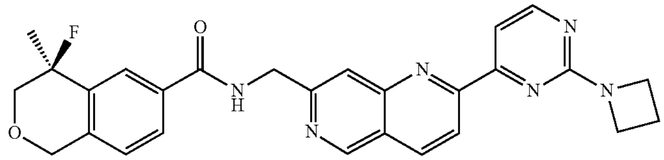 [SMILES: C[C@@]1(F)COCc2ccc(C(=O)NCc3cc4nc(-c5ccnc(N6CCC6)n5)ccc4cn3)cc21] |
| 430 | 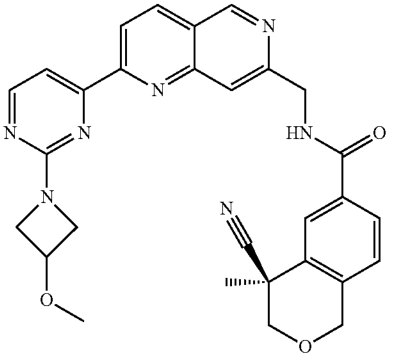 [SMILES: COC1CN(c2nccc(-c3ccc4cnc(CNC(=O)c5ccc6c(c5)[C@](C)(C#N)COC6)cc4n3)n2)C1] |
| 431 | 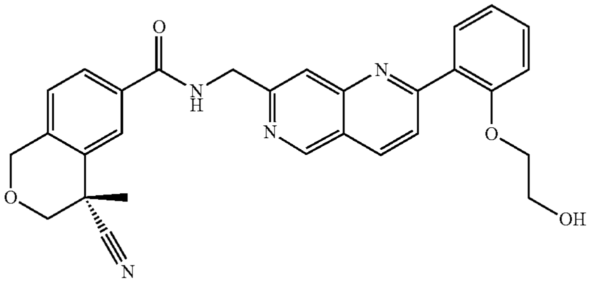 [SMILES: C[C@@]1(C#N)COCc2ccc(C(=O)NCc3cc4nc(-c5ccccc5OCCO)ccc4cn3)cc21] |

TABLE 3a-continued
| Compounds of the invention | |
|---|---|
| # | Compound |
| 432 | 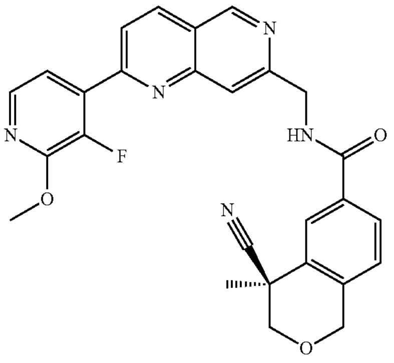 [SMILES: COc1nccc(-c2ccc3cnc(CNC(=O)c4ccc5c(c4)[C@](C)(C#N)COC5)cc3n2)c1F] |
| 433 | 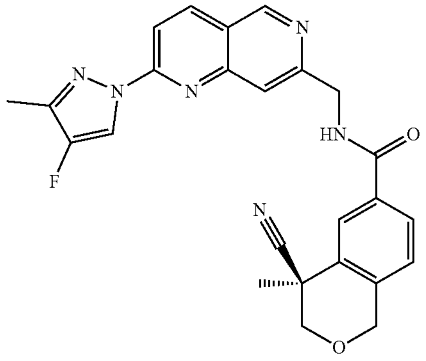 [SMILES: Cc1nn(-c2ccc3cnc(CNC(=O)c4ccc5c(c4)[C@](C)(C#N)COC5)cc3n2)cc1F] |
| 434 | 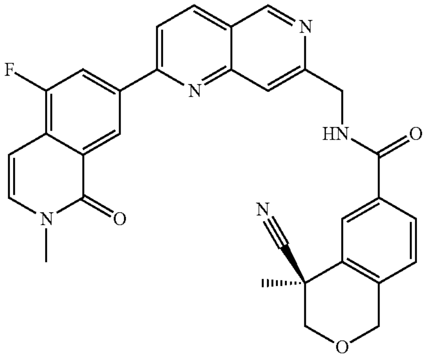 [SMILES: Cn1ccc2c(F)cc(-c3ccc4cnc(CNC(=O)c5ccc6c(c5)[C@](C)(C#N)COC6)cc4n3)cc2c1=O] |
| 435 | 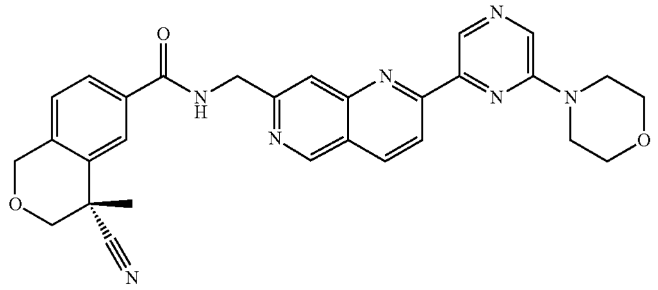 [SMILES: C[C@@]1(C#N)COCc2ccc(C(=O)NCc3cc4nc(-c5cncc(N6CCOCC6)n5)ccc4cn3)cc21] |

TABLE 3a-continued
| Compounds of the invention | |
|---|---|
| # | Compound |
| 436 | 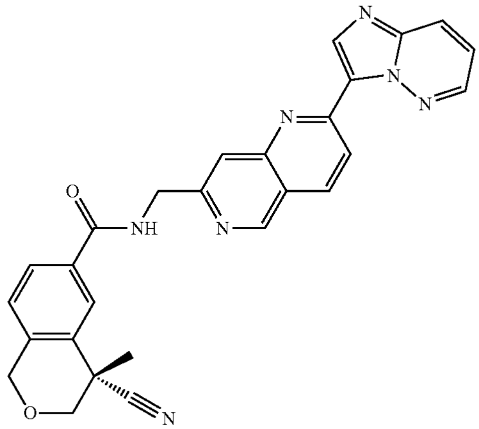 [SMILES: C[C@@]1(C#N)COCc2ccc(C(=O)NCc3cc4nc(-c5cnc6cccnn56)ccc4cn3)cc21] |
| 437 | 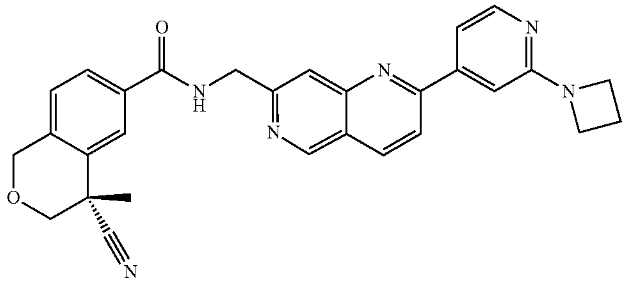 |
| 438 | 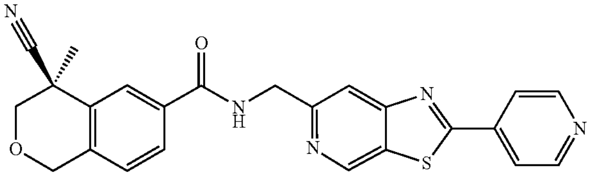 [SMILES: C[C@@]1(C#N)COCc2ccc(C(=O)NCc3cc4nc(-c5ccncc5)sc4cn3)cc21] |
| 439 | 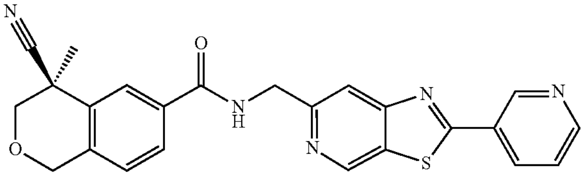 [SMILES: C[C@@]1(C#N)COCc2ccc(C(=O)NCc3cc4nc(-c5cccnc5)sc4cn3)cc21] |
| 440 | 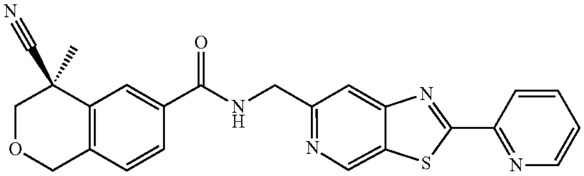 |
| 441 | 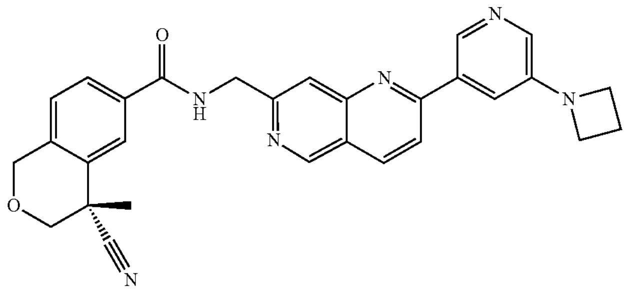 |

TABLE 3a-continued
| Compounds of the invention | |
|---|---|
| # | Compound |
| 442 | 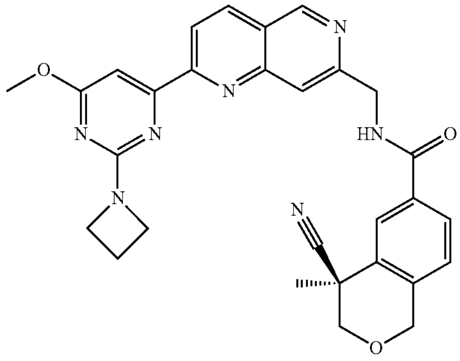 [SMILES: COc1cc(-c2ccc3cnc(CNC(=O)c4ccc5c(c4)[C@](C)(C#N)COC5)cc3n2)nc(N2CCC2)n1] |
| 443 | 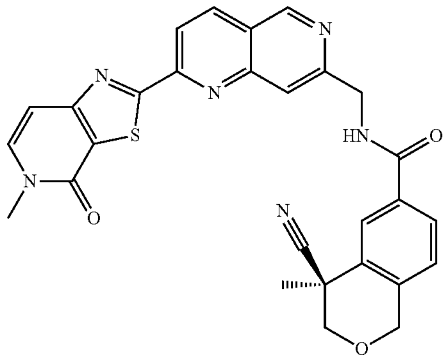 [SMILES: Cn1ccc2nc(-c3ccc4cnc(CNC(=O)c5ccc6c(c5)[C@](C)(C#N)COC6)cc4n3)sc2c1=O] |
| 444 | 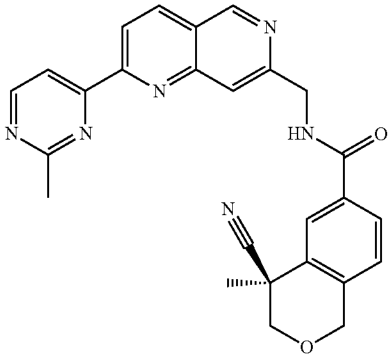 [SMILES: Cc1nccc(-c2ccc3cnc(CNC(=O)c4ccc5c(c4)[C@](C)(C#N)COC5)cc3n2)n1] |
| 445 | 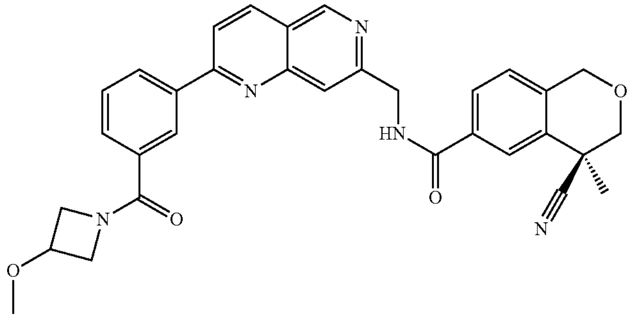 [SMILES: COC1CN(C(=O)c2cccc(-c3ccc4cnc(CNC(=O)c5ccc6c(c5)[C@](C)(C#N)COC6)cc4n3)c2)C1] |

TABLE 3a-continued
| Compounds of the invention | |
|---|---|
| # | Compound |
| 446 | 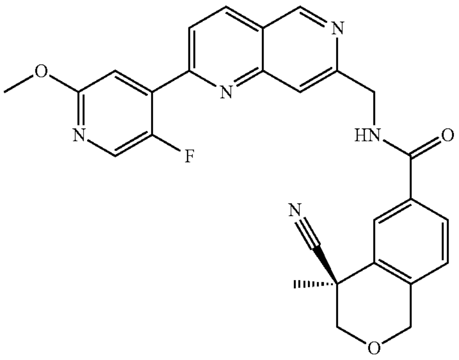 [SMILES: COc1cc(-c2ccc3cnc(CNC(=O)c4ccc5c(c4)[C@](C)(C#N)COC5)cc3n2)c(F)cn1] |
| 447 | 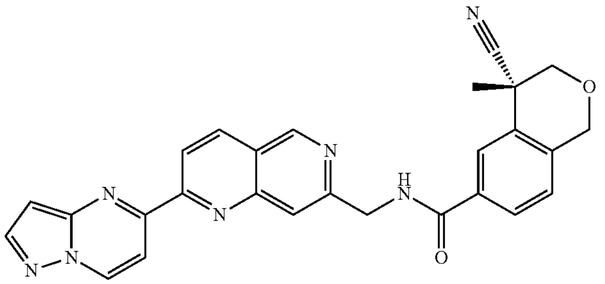 |
| 448 | 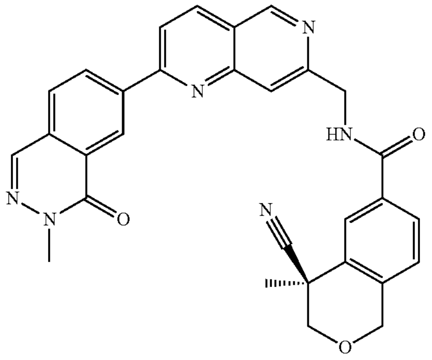 [SMILES: Cn1ncc2ccc(-c3ccc4cnc(CNC(=O)c5ccc6c(c5)[C@](C)(C#N)COC6)cc4n3)cc2c1=O] |
| 449 | 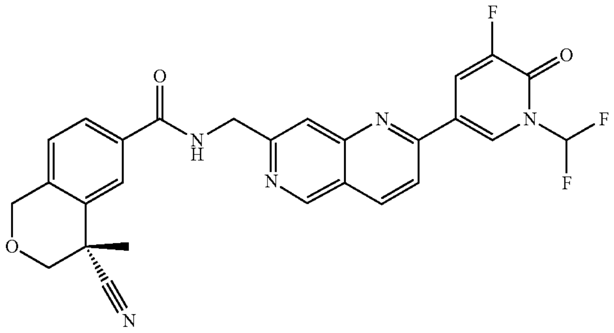 [SMILES: C[C@@]1(C#N)COCc2ccc(C(=O)NCc3cc4nc(-c5cc(F)c(=O)n(C(F)F)c5)ccc4cn3)cc21] |

TABLE 3a-continued
| Compounds of the invention | |
|---|---|
| # | Compound |
| 450 | 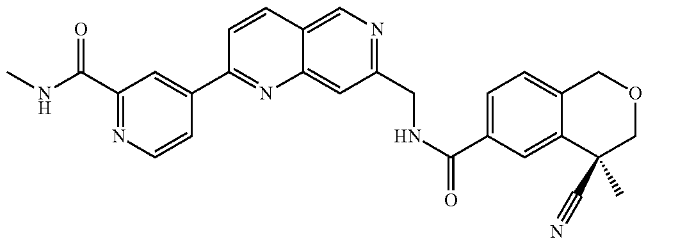 [SMILES: CNC(=O)c1cc(-c2ccc3cnc(CNC(=O)c4ccc5c(c4)[C@](C)(C#N)COC5)cc3n2)ccn1] |
| 451 | 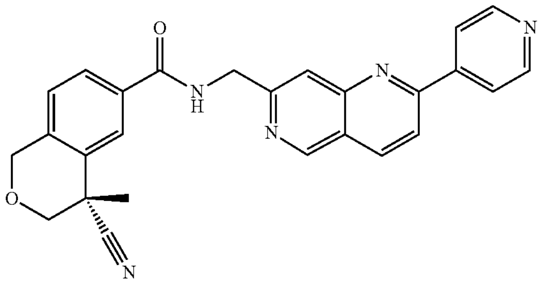 [SMILES: C[C@@]1(C#N)COCc2ccc(C(=O)NCc3cc4nc(-c5ccncc5)ccc4cn3)cc21] |
| 452 | 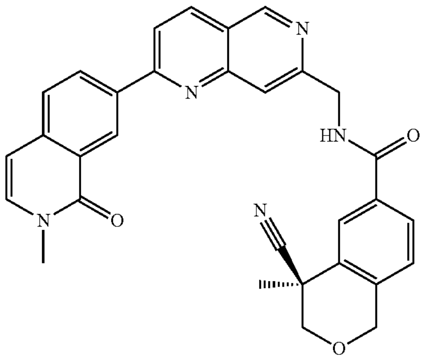 [SMILES: Cn1ccc2ccc(-c3ccc4cnc(CNC(=O)c5ccc6c(c5)[C@](C)(C#N)COC6)cc4n3)cc2c1=O] |
| 453 | 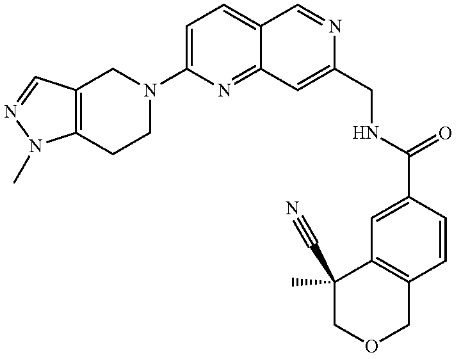 [SMILES: Cn1ncc2c1CCN(c1ccc3cnc(CNC(=O)c4ccc5c(c4)[C@](C)(C#N)COC5)cc3n1)C2] |

TABLE 3a-continued
| Compounds of the invention | |
|---|---|
| # | Compound |
| 454 | 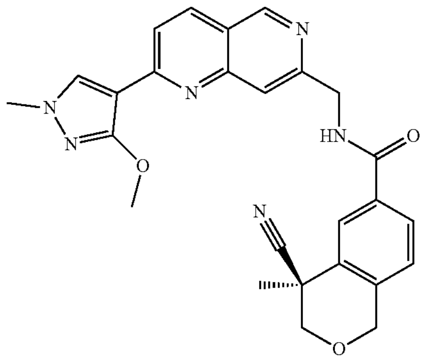 [SMILES: COc1nn(C)cc1-c1ccc2cnc(CNC(=O)c3ccc4c(c3)[C@](C)(C#N)COC4)cc2n1] |
| 455 | 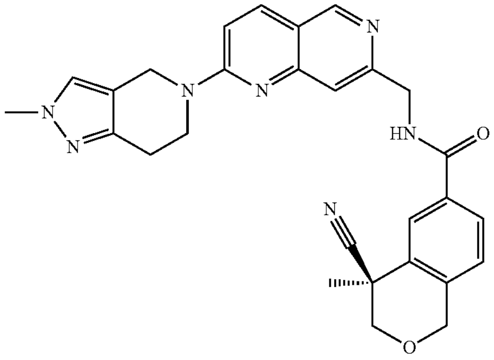 [SMILES: Cn1cc2c(n1)CCN(c1ccc3cnc(CNC(=O)c4ccc5c(c4)[C@](C)(C#N)COC5)cc3n1)C2] |
| 456 | 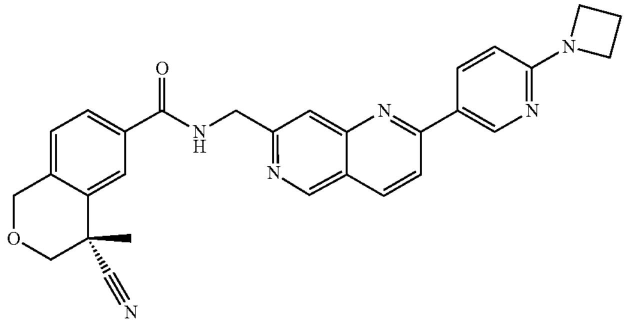 [SMILES: C[C@@]1(C#N)COCc2ccc(C(=O)NCc3cc4nc(-c5ccc(N6CCC6)nc5)ccc4cn3)cc21] |
| 457 | 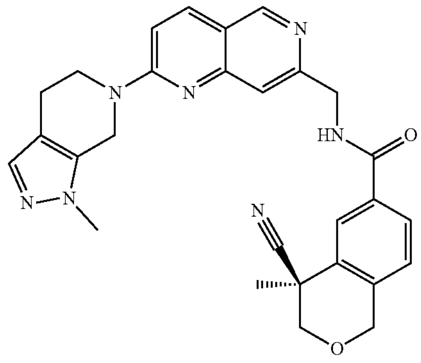 [SMILES: Cn1ncc2c1CN(c1ccc3cnc(CNC(=O)c4ccc5c(c4)[C@](C)(C#N)COC5)cc3n1)CC2] |

TABLE 3a-continued
| Compounds of the invention | |
|---|---|
| # | Compound |
| 458 | 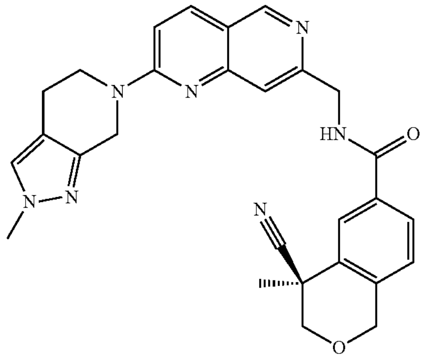 [SMILES: Cn1cc2c(n1)CN(c1ccc3cnc(CNC(=O)c4ccc5c(c4)[C@](C)(C#N)COC5)cc3n1)CC2] |
| 459 | 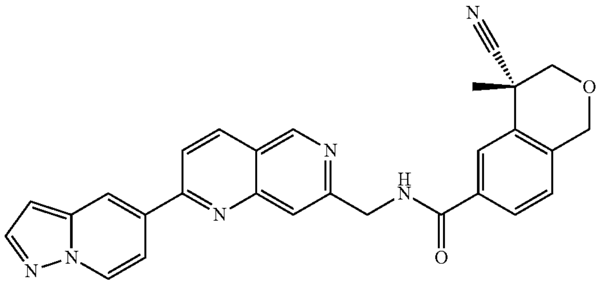 [SMILES: C[C@@]1(C#N)COCc2ccc(C(=O)NCc3cc4nc(-c5ccn6nccc6c5)ccc4cn3)cc21] |
| 460 | 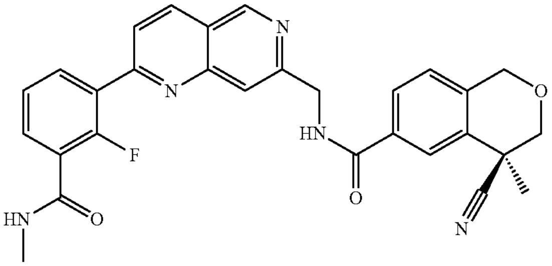 [SMILES: CNC(=O)c1cccc(-c2ccc3cnc(CNC(=O)c4ccc5c(c4)[C@](C)(C#N)COC5)cc3n2)c1F] |
| 461 | 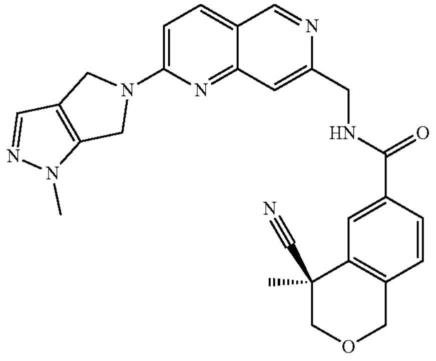 [SMILES: Cn1ncc2c1CN(c1ccc3cnc(CNC(=O)c4ccc5c(c4)[C@](C)(C#N)COC5)cc3n1)C2] |

TABLE 3a-continued
| Compounds of the invention | |
|---|---|
| # | Compound |
| 462 | 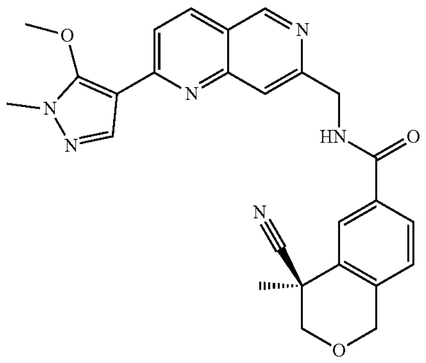 [SMILES: COc1c(-c2ccc3cnc(CNC(=O)c4ccc5c(c4)[C@](C)(C#N)COC5)cc3n2)cnn1C] |
| 463 | 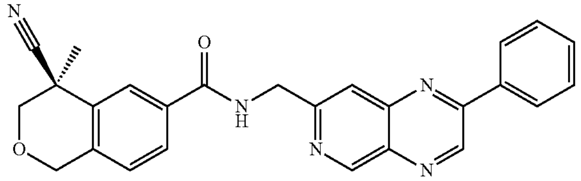 [SMILES: C[C@@]1(C#N)COCc2ccc(C(=O)NCc3cc4nc(-c5ccccc5)cnc4cn3)cc21] |
| 464 | 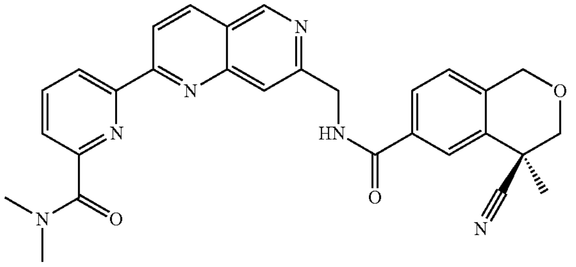 [SMILES: CN(C)C(=O)c1cccc(-c2ccc3cnc(CNC(=O)c4ccc5c(c4)[C@](C)(C#N)COC5)cc3n2)n1] |
| 465 | 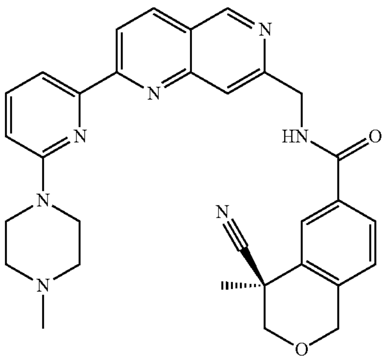 [SMILES: CN1CCN(c2cccc(-c3ccc4cnc(CNC(=O)c5ccc6c(c5)[C@](C)(C#N)COC6)cc4n3)n2)CC1] |
| 466 | 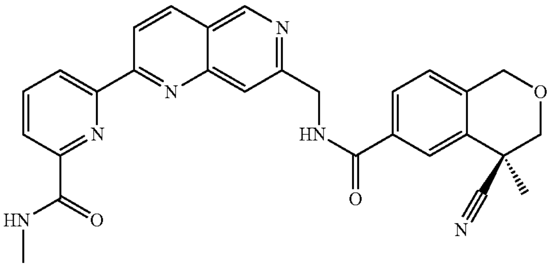 [SMILES: CNC(=O)c1cccc(-c2ccc3cnc(CNC(=O)c4ccc5c(c4)[C@](C)(C#N)COC5)cc3n2)n1] |

TABLE 3a-continued
| Compounds of the invention | |
|---|---|
| # | Compound |
| 467 | 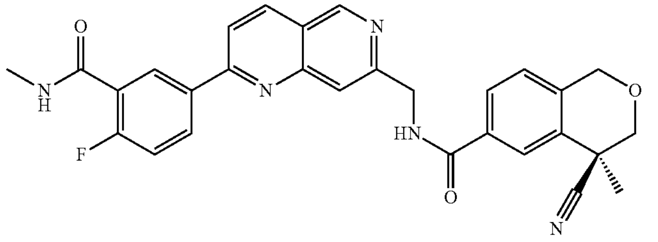 [SMILES: CNC(=O)c1cc(-c2ccc3cnc(CNC(=O)c4ccc5c(c4)[C@](C)(C#N)COC5)cc3n2)ccc1F] |
| 468 | 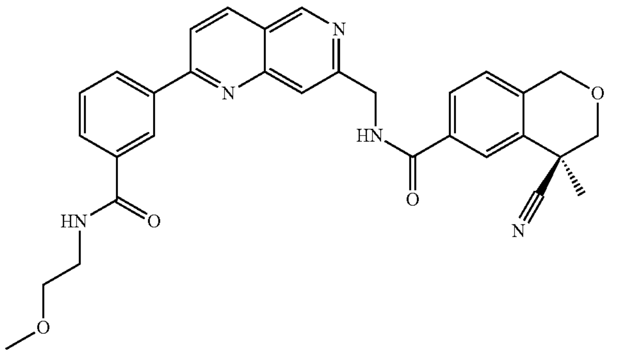 [SMILES: COCCNC(=O)c1cccc(-c2ccc3cnc(CNC(=O)c4ccc5c(c4)[C@](C)(C#N)COC5)cc3n2)c1] |
| 469 | 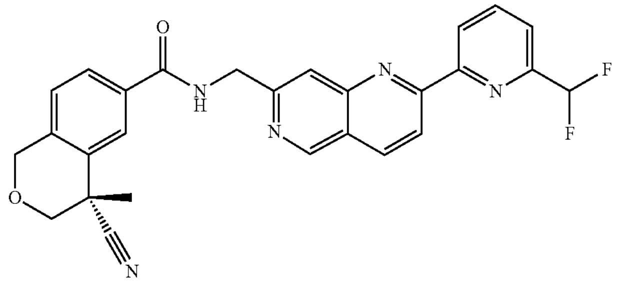 |
| 470 | 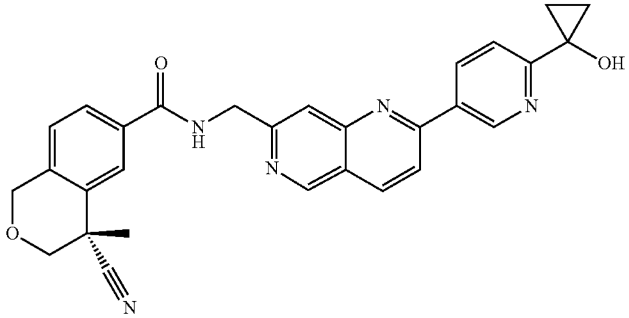 [SMILES: C[C@@]1(C#N)COCc2ccc(C(=O)NCc3cc4nc(-c5ccc(C6(O)CC6)nc5)ccc4cn3)cc21] |
| 471 | 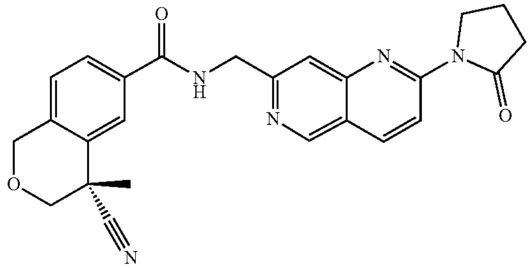 [SMILES: C[C@@]1(C#N)COCc2ccc(C(=O)NCc3cc4nc(N5CCCC5=O)ccc4cn3)cc21] |

TABLE 3a-continued
| Compounds of the invention | |
|---|---|
| # | Compound |
| 472 | 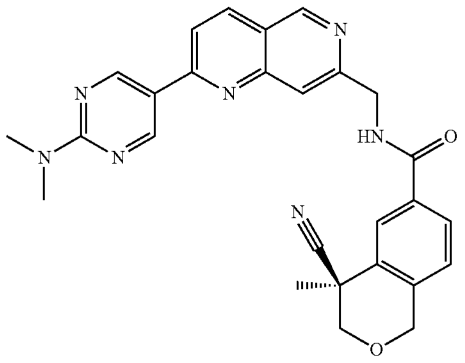 [SMILES: CN(C)c1ncc(-c2ccc3cnc(CNC(=O)c4ccc5c(c4)[C@](C)(C#N)COC5)cc3n2)cn1] |
| 473 | 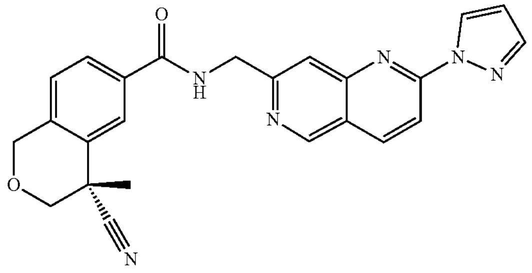 [SMILES: C[C@@]1(C#N)COCc2ccc(C(=O)NCc3cc4nc(-n5cccn5)ccc4cn3)cc21] |
| 474 | 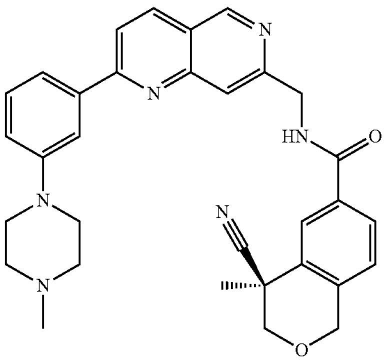 [SMILES: CN1CCN(c2cccc(-c3ccc4cnc(CNC(=O)c5ccc6c(c5)[C@](C)(C#N)COC6)cc4n3)c2)CC1] |
| 475 | 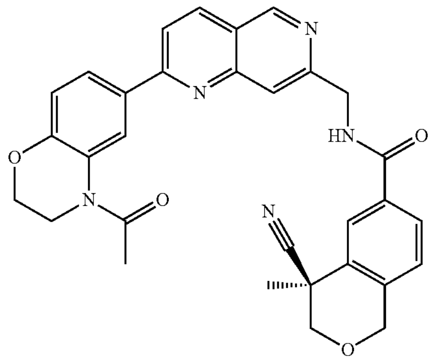 [SMILES: CC(=O)N1CCOc2ccc(-c3ccc4cnc(CNC(=O)c5ccc6c(c5)[C@](C)(C#N)COC6)cc4n3)cc21] |

TABLE 3a-continued
| Compounds of the invention | |
|---|---|
| # | Compound |
| 476 | 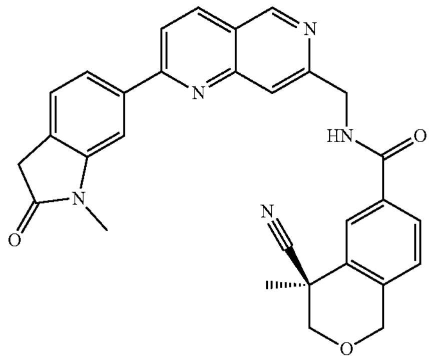 [SMILES: CN1C(=O)Cc2ccc(-c3ccc4cnc(CNC(=O)c5ccc6c(c5)[C@](C)(C#N)COC6)cc4n3)cc21] |
| 477 | 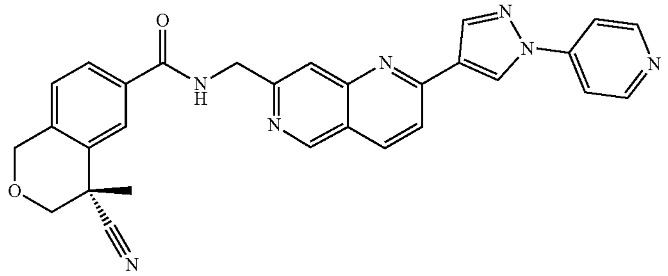 [SMILES: C[C@@]1(C#N)COCc2ccc(C(=O)NCc3cc4nc(-c5cnn(-c6ccncc6)c5)ccc4cn3)cc21] |
| 478 | 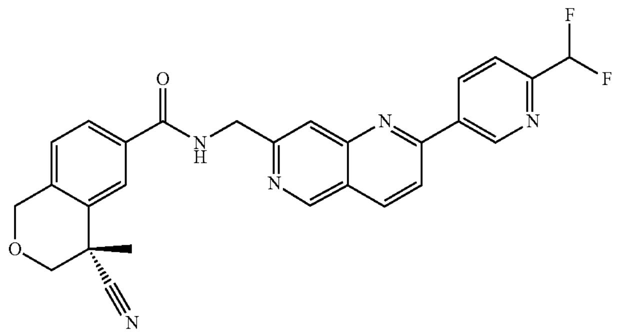 [SMILES: C[C@@]1(C#N)COCc2ccc(C(=O)NCc3cc4nc(-c5ccc(C(F)F)nc5)ccc4cn3)cc21] |
| 479 | 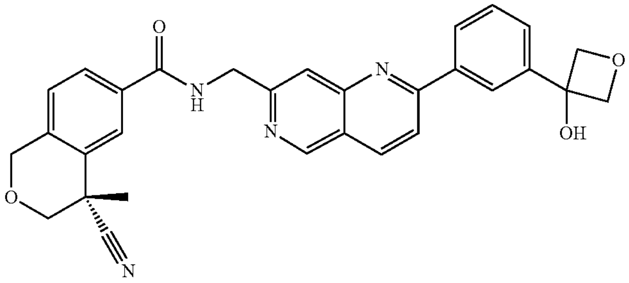 [SMILES: C[C@@]1(C#N)COCc2ccc(C(=O)NCc3cc4nc(-c5cccc(C6(O)COC6)c5)ccc4cn3)cc21] |

TABLE 3a-continued
| Compounds of the invention | |
|---|---|
| # | Compound |
| 480 | 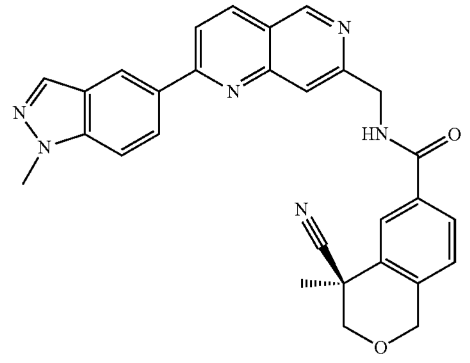 [SMILES: Cn1ncc2cc(-c3ccc4cnc(CNC(=O)c5ccc6c(c5)[C@](C)(C#N)COC6)cc4n3)ccc21] |
| 481 | 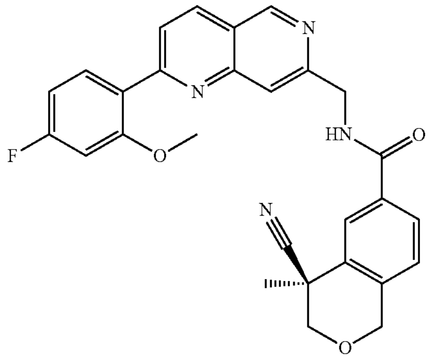 [SMILES: COc1cc(F)ccc1-c1ccc2cnc(CNC(=O)c3ccc4c(c3)[C@](C)(C#N)COC4)cc2n1] |
| 482 | 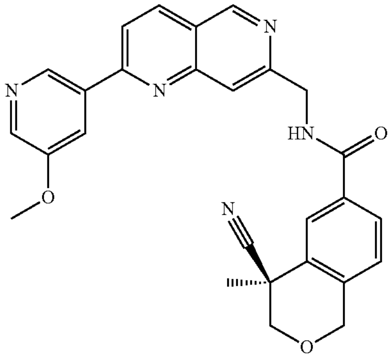 [SMILES: COc1cncc(-c2ccc3cnc(CNC(=O)c4ccc5c(c4)[C@](C)(C#N)COC5)cc3n2)c1] |
| 483 | 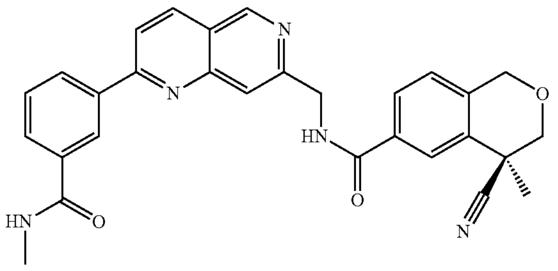 [SMILES: CNC(=O)c1cccc(-c2ccc3cnc(CNC(=O)c4ccc5c(c4)[C@](C)(C#N)COC5)cc3n2)c1] |

TABLE 3a-continued
| Compounds of the invention | |
|---|---|
| # | Compound |
| 484 | 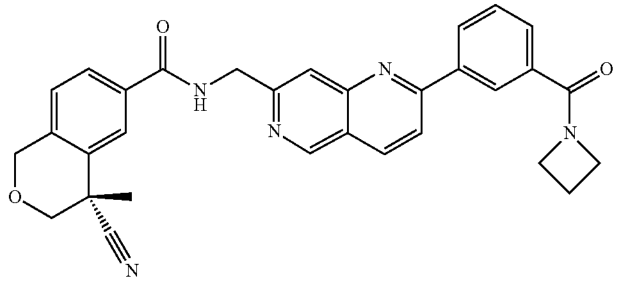 [SMILES: C[C@@]1(C#N)COCc2ccc(C(=O)NCc3cc4nc(-c5cccc(C(=O)N6CCC6)c5)ccc4cn3)cc21] |
| 485 | 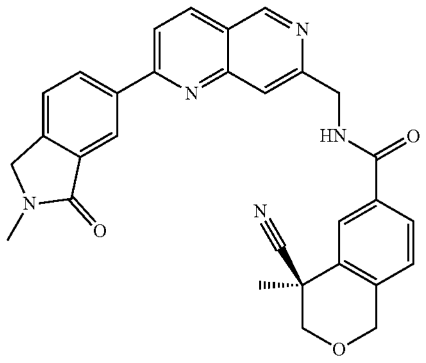 [SMILES: CN1Cc2ccc(-c3ccc4cnc(CNC(=O)c5ccc6c(c5)[C@](C)(C#N)COC6)cc4n3)cc2C1=O] |
| 486 | 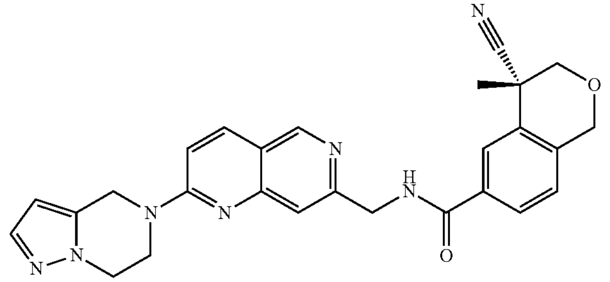 [SMILES: C[C@@]1(C#N)COCc2ccc(C(=O)NCc3cc4nc(N5CCn6nccc6C5)ccc4cn3)cc21] |
| 487 | 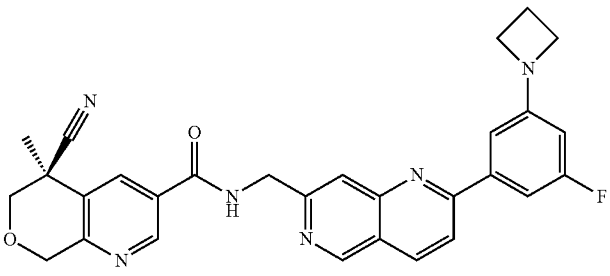 [SMILES: C[C@@]1(C#N)COCc2ncc(C(=O)NCc3cc4nc(-c5cc(F)cc(N6CCC6)c5)ccc4cn3)cc21] |

TABLE 3a-continued
| Compounds of the invention | |
|---|---|
| # | Compound |
| 488 | 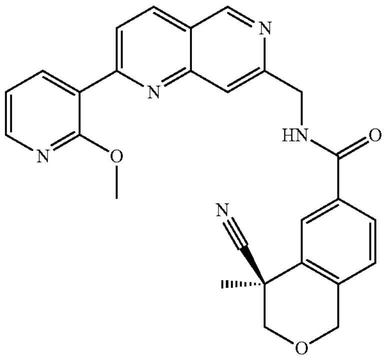 [SMILES: COc1ncccc1-c1ccc2cnc(CNC(=O)c3ccc4c(c3)[C@](C)(C#N)COC4)cc2n1] |
| 489 | 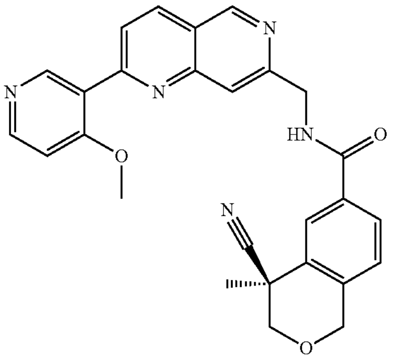 [SMILES: COc1ccncc1-c1ccc2cnc(CNC(=O)c3ccc4c(c3)[C@](C)(C#N)COC4)cc2n1] |
| 490 | 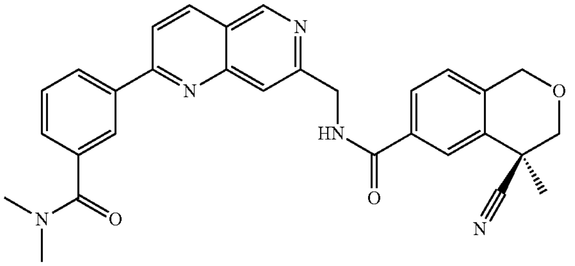 [SMILES: CN(C)C(=O)c1cccc(-c2ccc3cnc(CNC(=O)c4ccc5c(c4)[C@](C)(C#N)COC5)cc3n2)c1] |
| 491 | 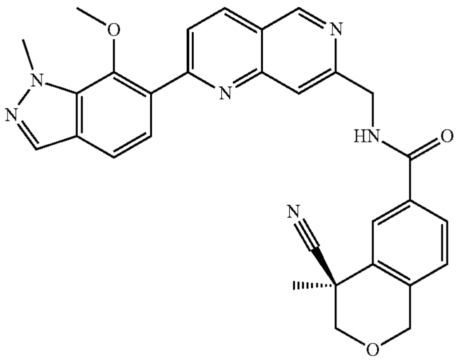 [SMILES: COc1c(-c2ccc3cnc(CNC(=O)c4ccc5c(c4)[C@](C)(C#N)COC5)cc3n2)ccc2cnn(C)c12] |

TABLE 3a-continued
| Compounds of the invention | |
|---|---|
| # | Compound |
| 492 | 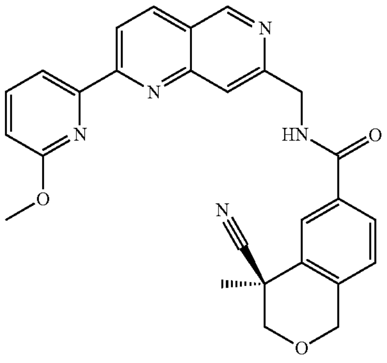 [SMILES: COc1cccc(-c2ccc3cnc(CNC(=O)c4ccc5c(c4)[C@](C)(C#N)COC5)cc3n2)n1] |
| 493 | 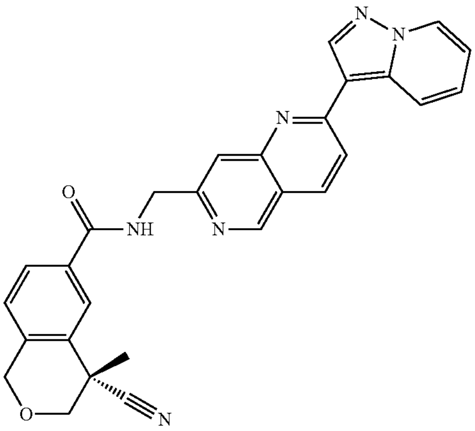 [SMILES: C[C@@]1(C#N)COCc2ccc(C(=O)NCc3cc4nc(-c5cnn6ccccc56)ccc4cn3)cc21] |
| 494 | 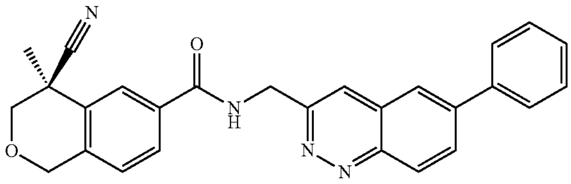 [SMILES: C[C@@]1(C#N)COCc2ccc(C(=O)NCc3cc4cc(-c5ccccc5)ccc4nn3)cc21] |
| 495 | 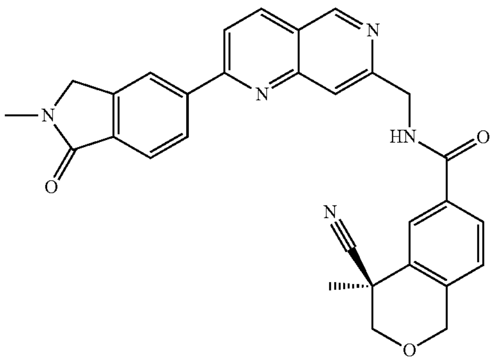 [SMILES: CN1Cc2cc(-c3ccc4cnc(CNC(=O)c5ccc6c(c5)[C@](C)(C#N)COC6)cc4n3)ccc2C1=O] |

TABLE 3a-continued
| Compounds of the invention | |
|---|---|
| # | Compound |
| 496 | 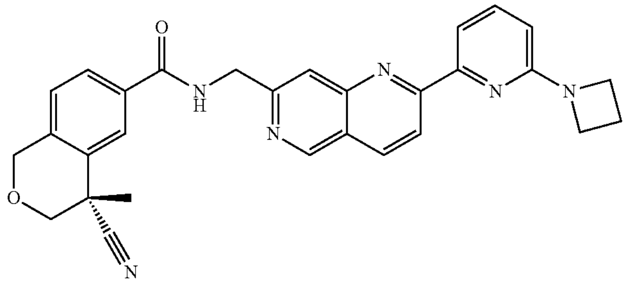 [SMILES: C[C@@]1(C#N)COCc2ccc(C(=O)NCc3cc4nc(-c5cccc(N6CCC6)n5)ccc4cn3)cc21] |
| 497 | 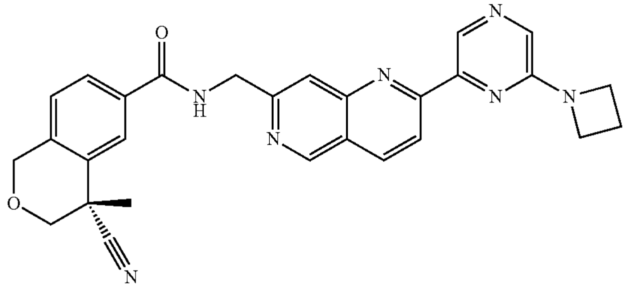 [SMILES: C[C@@]1(C#N)COCc2ccc(C(=O)NCc3cc4nc(-c5cncc(N6CCC6)n5)ccc4cn3)cc21] |
| 498 | 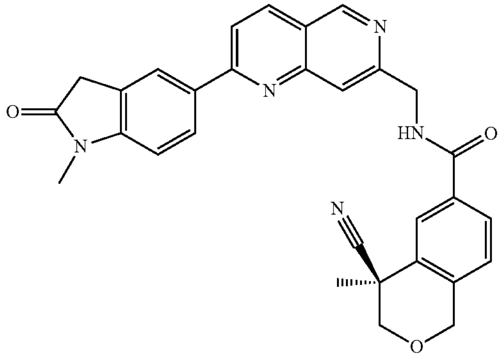 [SMILES: CN1C(=O)Cc2cc(-c3ccc4cnc(CNC(=O)c5ccc6c(c5)[C@](C)(C#N)COC6)cc4n3)ccc21] |
| 499 | 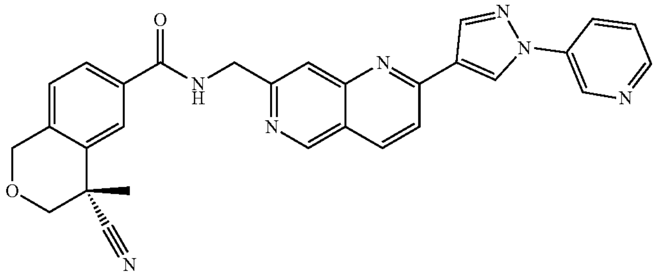 [SMILES: C[C@@]1(C#N)COCc2ccc(C(=O)NCc3cc4nc(-c5cnn(-c6cccnc6)c5)ccc4cn3)cc21] |
| 500 | 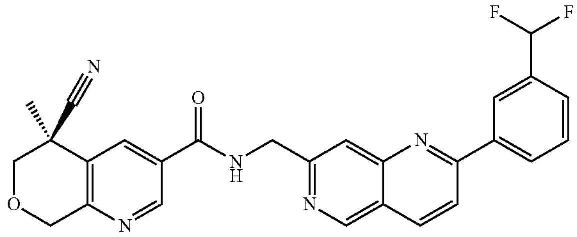 [SMILES: C[C@@]1(C#N)COCc2ncc(C(=O)NCc3cc4nc(-c5cccc(C(F)F)c5)ccc4cn3)cc21] |

TABLE 3a-continued
| Compounds of the invention | |
|---|---|
| # | Compound |
| 501 | 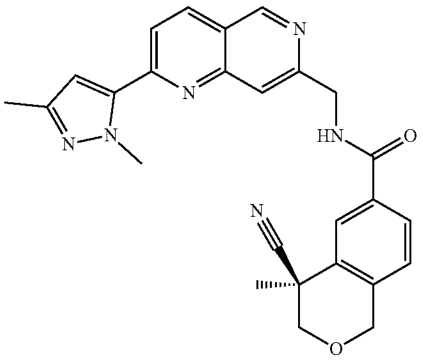 [SMILES: Cc1cc(-c2ccc3cnc(CNC(=O)c4ccc5c(c4)[C@](C)(C#N)COC5)cc3n2)n(C)n1] |
| 502 | 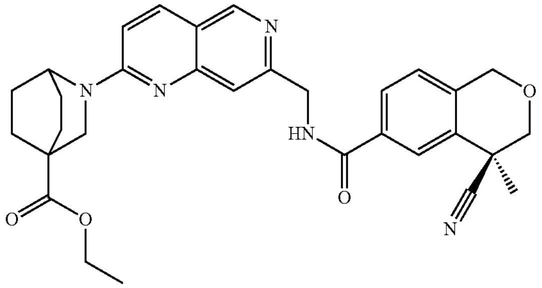 [SMILES: CCOC(=O)C12CCC(CC1)N(c1ccc3cnc(CNC(=O)c4ccc5c(c4)[C@](C)(C#N)COC5)cc3n1)C2] |
| 503 | 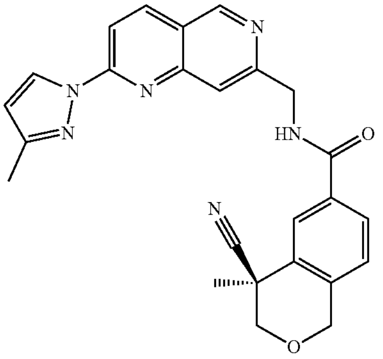 [SMILES: Cc1ccn(-c2ccc3cnc(CNC(=O)c4ccc5c(c4)[C@](C)(C#N)COC5)cc3n2)n1] |
| 504 | 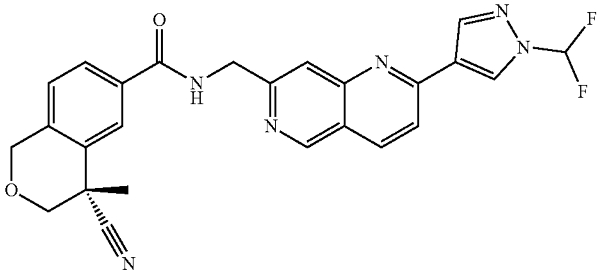 [SMILES: C[C@@]1(C#N)COCc2ccc(C(=O)NCc3cc4nc(-c5cnn(C(F)F)c5)ccc4cn3)cc21] |

TABLE 3a-continued
| Compounds of the invention | |
|---|---|
| # | Compound |
| 505 | 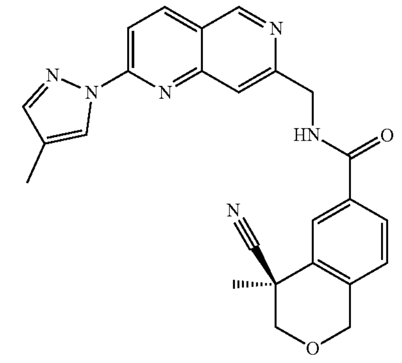 |
| 506 | 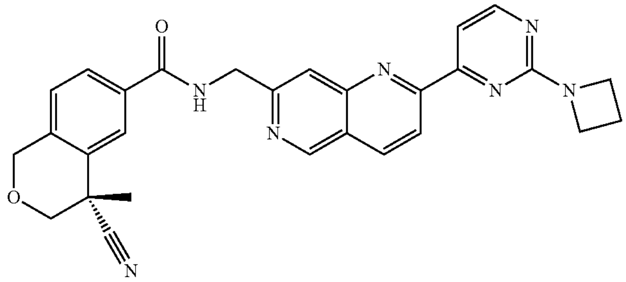 [SMILES: C[C@@]1(C#N)COCc2ccc(C(=O)NCc3cc4nc(-c5ccnc(N6CCC6)n5)ccc4cn3)cc21] |
| 507 | 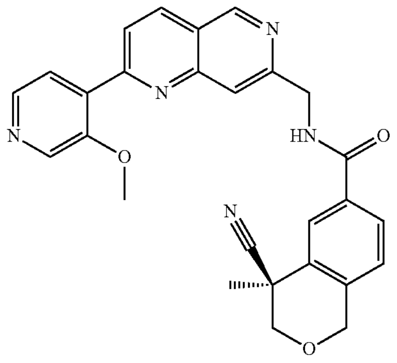 [SMILES: COc1cnccc1-c1ccc2cnc(CNC(=O)c3ccc4c(c3)[C@](C)(C#N)COC4)cc2n1] |
| 508 | 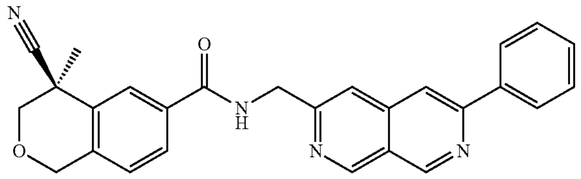 [SMILES: C[C@@]1(C#N)COCc2ccc(C(=O)NCc3cc4cc(-c5ccccc5)ncc4cn3)cc21] |
| 509 | 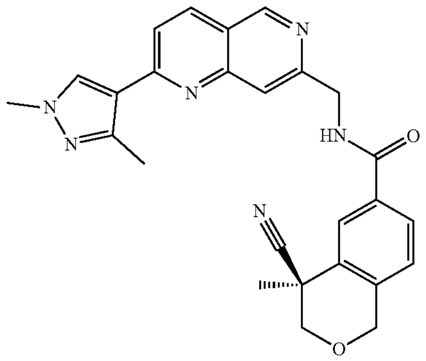 [SMILES: Cc1nn(C)cc1-c1ccc2cnc(CNC(=O)c3ccc4c(c3)[C@](C)(C#N)COC4)cc2n1] |

TABLE 3a-continued
| Compounds of the invention | |
|---|---|
| # | Compound |
| 510 | 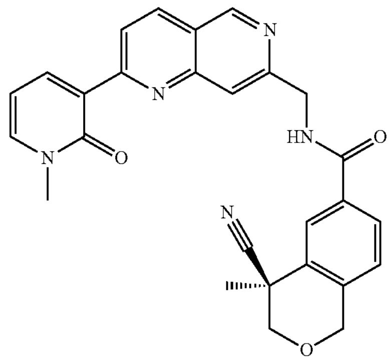 [SMILES: Cn1cccc(-c2ccc3cnc(CNC(=O)c4ccc5c(c4)[C@](C)(C#N)COC5)cc3n2)c1=O] |
| 511 | 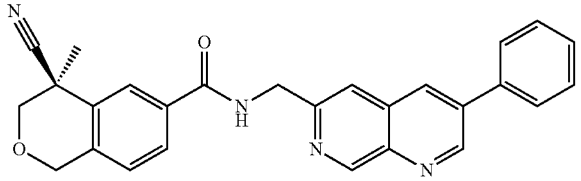 [SMILES: C[C@@]1(C#N)COCc2ccc(C(=O)NCc3cc4cc(-c5ccccc5)cnc4cn3)cc21] |
| 512 | 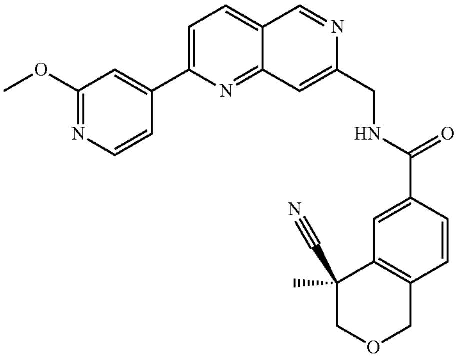 [SMILES: COc1cc(-c2ccc3cnc(CNC(=O)c4ccc5c(c4)[C@](C)(C#N)COC5)cc3n2)ccn1] |
| 513 | 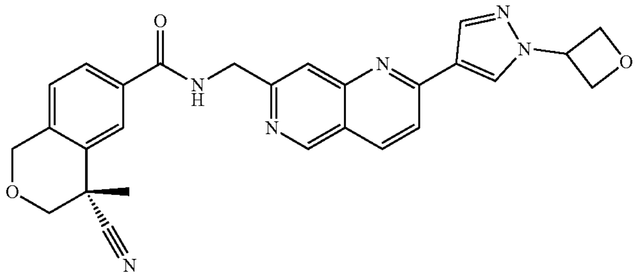 [SMILES: C[C@@]1(C#N)COCc2ccc(C(=O)NCc3cc4nc(-c5cnn(C6COC6)c5)ccc4cn3)cc21] |
| 514 | 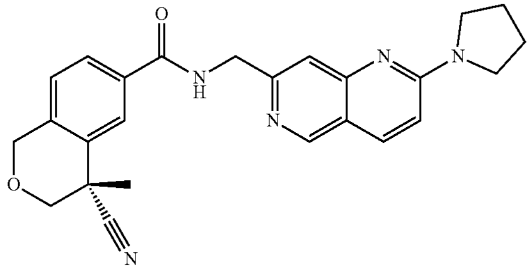 [SMILES: C[C@@]1(C#N)COCc2ccc(C(=O)NCc3cc4nc(N5CCCC5)ccc4cn3)cc21] |

TABLE 3a-continued
| Compounds of the invention | |
|---|---|
| # | Compound |
| 515 | 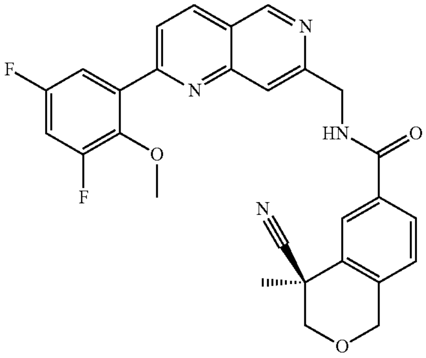 [SMILES: COc1c(F)cc(F)cc1-c1ccc2cnc(CNC(=O)c3ccc4c(c3)[C@](C)(C#N)COC4)cc2n1] |
| 516 | 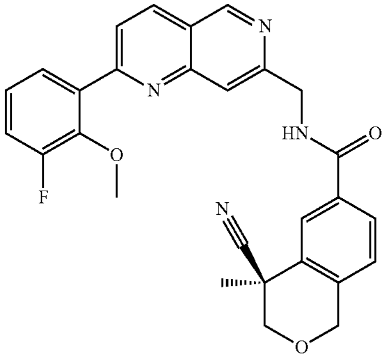 [SMILES: COc1c(F)cccc1-c1ccc2cnc(CNC(=O)c3ccc4c(c3)[C@](C)(C#N)COC4)cc2n1] |
| 517 | 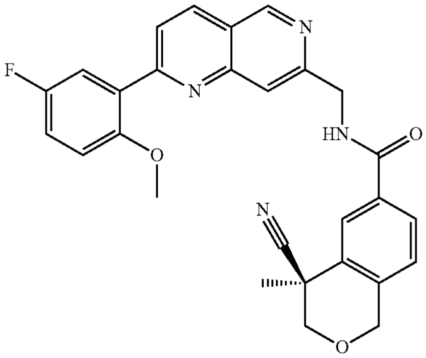 [SMILES: COc1ccc(F)cc1-c1ccc2cnc(CNC(=O)c3ccc4c(c3)[C@](C)(C#N)COC4)cc2n1] |
| 518 | 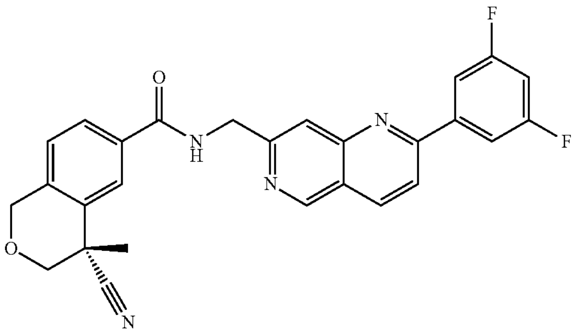 [SMILES: C[C@@]1(C#N)COCc2ccc(C(=O)NCc3cc4nc(-c5cc(F)cc(F)c5)ccc4cn3)cc21] |

TABLE 3a-continued
| # | Compounds of the invention<br>Compound |
|---|---|
| 519 | 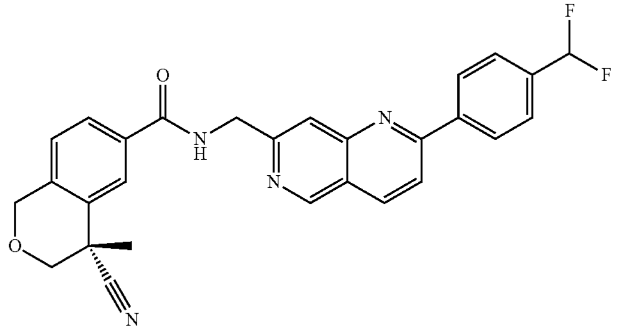 [SMILES: C[C@@]1(C#N)COCc2ccc(C(=O)NCc3cc4nc(-c5ccc(C(F)F)cc5)ccc4cn3)cc21] |
| 520 | 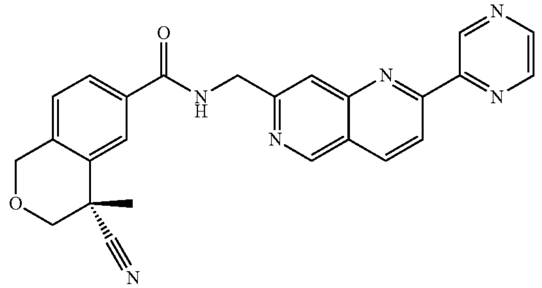 [SMILES: C[C@@]1(C#N)COCc2ccc(C(=O)NCc3cc4nc(-c5cnccn5)ccc4cn3)cc21] |
| 521 | 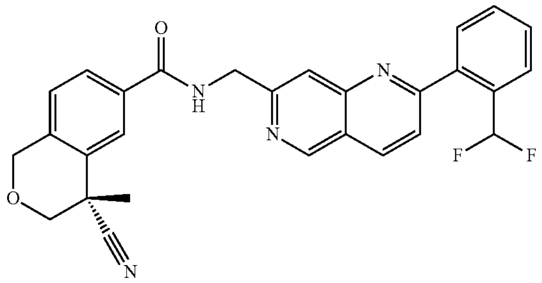 [SMILES: C[C@@]1(C#N)COCc2ccc(C(=O)NCc3cc4nc(-c5ccccc5C(F)F)ccc4cn3)cc21] |
| 522 | 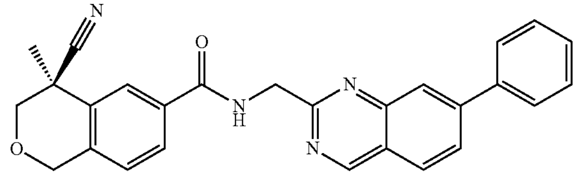 [SMILES: C[C@@]1(C#N)COCc2ccc(C(=O)NCc3ncc4ccc(-c5ccccc5)cc4n3)cc21] |
| 523 | 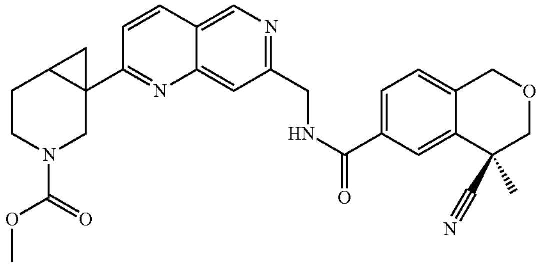 [SMILES: COC(=O)N1CCC2CC2(c2ccc3cnc(CNC(=O)c4ccc5c(c4)[C@](C)(C#N)COC5)cc3n2)C1] |
| 524 | 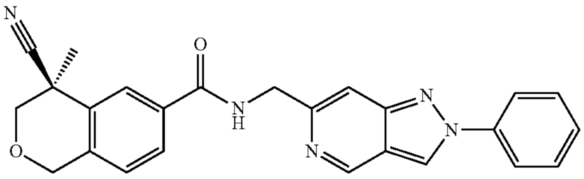 [SMILES: C[C@@]1(C#N)COCc2ccc(C(=O)NCc3cc4nn(-c5ccccc5)cc4cn3)cc21] |

TABLE 3a-continued

| # | Compound |
| --- | --- |
| 525 | 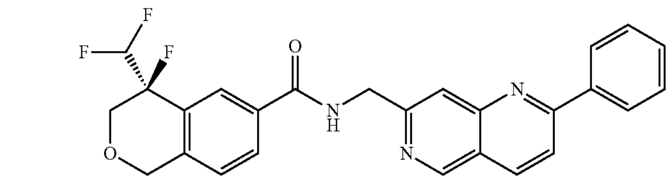 [SMILES: O=C(NCc1cc2nc(-c3ccccc3)ccc2cn1)c1ccc2c(c1)[C@@](F)(C(F)F)COC2] |
| 526 | 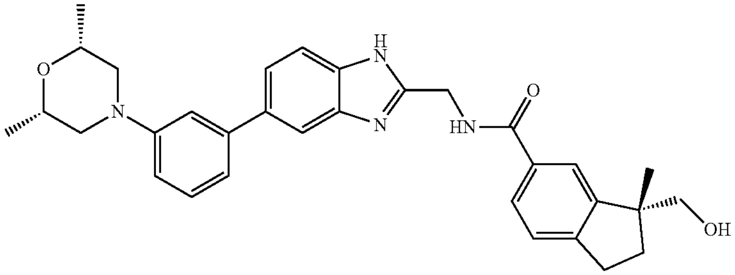 [SMILES: C[C@@H]1CN(c2cccc(-c3ccc4[nH]c(CNC(=O)c5ccc6c(c5)[C@](C)(CO)CC6)nc4c3)c2)C[C@H](C)O1] |

Compounds of the invention

In another aspect, the invention features a pharmaceutical composition including any one of the above compounds and a pharmaceutically acceptable excipient.

In another aspect, the invention features a method of decreasing the activity of a BAF complex in a cell, the method involving contacting the cell with an effective amount of any of the foregoing compounds or a pharmaceutical composition thereof.

In some embodiments, the cell is a cancer cell.

In another aspect, the invention features a method of treating a BAF complex-related disorder in a subject in need thereof, the method involving administering to the subject an effective amount of any of the foregoing compounds or a pharmaceutical composition thereof.

In some embodiments, the BAF complex-related disorder is cancer.

In a further aspect, the invention features a method of inhibiting BRM, the method involving contacting a cell with an effective amount of any of the foregoing compounds or a pharmaceutical composition thereof. In some embodiments, the cell is a cancer cell.

In another aspect, the invention features a method of inhibiting BRG1, the method involving contacting the cell with an effective amount of any of the foregoing compounds or a pharmaceutical composition thereof. In some embodiments, the cell is a cancer cell.

In a further aspect, the invention features a method of inhibiting BRM and BRG1, the method involving contacting the cell with an effective amount of any of the foregoing compounds or a pharmaceutical composition thereof. In some embodiments, the cell is a cancer cell.

In another aspect, the invention features a method of treating a disorder related to a BRG1 loss of function mutation in a subject in need thereof, the method involving administering to the subject an effective amount of any of the foregoing compounds or a pharmaceutical composition thereof.

In some embodiments, the disorder related to a BRG1 loss of function mutation is cancer. In other embodiments, the subject is determined to have a BRG1 loss of function disorder, for example, is determined to have a BRG1 loss of function cancer (for example, the cancer has been determined to include cancer cells with loss of BRG1 function).

In another aspect, the invention features a method of inducing apoptosis in a cell, the method involving contacting the cell with an effective amount of any of the foregoing compounds or a pharmaceutical composition thereof. In some embodiments, the cell is a cancer cell.

In a further aspect, the invention features a method of treating cancer in a subject in need thereof, the method including administering to the subject an effective amount of any of the foregoing compounds or a pharmaceutical composition thereof.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

In some embodiments of any of the foregoing methods, the cancer is non-small cell lung cancer, colorectal cancer, bladder cancer, cancer of unknown primary, glioma, breast cancer, melanoma, non-melanoma skin cancer, endometrial cancer, or penile cancer.

In some embodiments of any of the foregoing methods, the cancer is a drug resistant cancer or has failed to respond to a prior therapy (e.g., vemurafenib, dacarbazine, a CTLA4 inhibitor, a PD1 inhibitor, interferon therapy, a BRAF inhibitor, a MEK inhibitor, radiotherapy, temozolimide, irinotecan, a CAR-T therapy, herceptin, perjeta, tamoxifen, xeloda, docetaxol, platinum agents such as carboplatin, taxanes such as paclitaxel and docetaxel, ALK inhibitors, MET inhibitors, alimta, abraxane, Adriamycin®, gemcitabine, avastin, halaven, neratinib, a PARP inhibitor, ARN810, an mTOR inhibitor, topotecan, gemzar, a VEGFR2 inhibitor, a folate receptor antagonist, demcizumab, fosbretabulin, or a PDL1 inhibitor).

In some embodiments of any of the foregoing methods, the cancer has or has been determined to have BRG1 mutations. In some embodiments of any of the foregoing methods, the BRG1 mutations are homozygous. In some embodiments of any of the foregoing methods, the cancer does not have, or has been determined not to have, an epidermal growth factor receptor (EGFR) mutation. In some embodiments of any of the foregoing methods, the cancer does not have, or has been determined not to have, an anaplastic lymphoma kinase (ALK) driver mutation. In some embodiments of any of the foregoing methods, the cancer has, or has been determined to have, a KRAS mutation. In some embodiments of any of the foregoing methods, the BRG1 mutation is in the ATPase catalytic domain of the protein. In some embodiments of any of the foregoing methods, the BRG1 mutation is a deletion at the C-terminus of BRG1.

In another aspect, the disclosure provides a method treating a disorder related to BAF (e.g., cancer or viral infections) in a subject in need thereof. This method includes contacting a cell with an effective amount of any of the foregoing compounds, or pharmaceutically acceptable salts thereof, or any of the foregoing pharmaceutical compositions. In some embodiments, the disorder is a viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), Togaviridae family (e.g., Rubella virus). In some embodiments, the disorder is Coffin Siris, Neurofibromatosis (e.g., NF-1, NF-2, or Schwannomatosis), or Multiple Meningioma.

In another aspect, the disclosure provides a method for treating a viral infection in a subject in need thereof. This method includes administering to the subject an effective amount of any of the foregoing compounds, or pharmaceutically acceptable salts thereof, or any of the foregoing pharmaceutical compositions. In some embodiments, the viral infection is an infection with a virus of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)), Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), Herpesvitus K*, CMV, varicella-zoster virus), Papillomaviridae family (e.g., Human Papillomavirus (HPV, HPV E1)), Parvoviridae family (e.g., Parvovirus B19), Polyomaviridae family (e.g., JC virus and BK virus), Paramyxoviridae family (e.g., Measles virus), or Togaviridae family (e.g., Rubella virus).

In another aspect, the invention features a method of treating melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of reducing tumor growth of melanoma, prostate cancer, breast cancer, bone cancer, renal cell carcinoma, or a hematologic cancer in a subject in need thereof, the method including administering to the subject an effective amount of any of the foregoing compounds or pharmaceutical compositions thereof.

In another aspect, the invention features a method of suppressing metastatic progression of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of suppressing metastatic colonization of melanoma, prostate cancer, breast cancer, bone cancer, renal cell carcinoma, or a hematologic cancer in a subject, the method including administering an effective amount of any of the foregoing compounds or pharmaceutical compositions thereof.

In another aspect, the invention features a method of reducing the level and/or activity of BRG1 and/or BRM in a melanoma, prostate cancer, breast cancer, bone cancer, renal cell carcinoma, or hematologic cancer cell, the method including contacting the cell with an effective amount of any of the foregoing compounds or pharmaceutical compositions thereof.

In some embodiments of any of the above aspects, the melanoma, prostate cancer, breast cancer, bone cancer, renal cell carcinoma, or hematologic cell is in a subject.

In some embodiments of any of the above aspects, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRG1 by at least 50% (e.g., 55%, 60%, 65%, 70%, 75%, 80%, 85%, 90%, or 95%) as compared to a reference. In some embodiments, the effective amount of the compound that reduces the level and/or activity of BRG1 by at least 90% (e.g., 91%, 92%, 93%, 94%, 95%, 96%, 97%, 98%, or 99%).

In some embodiments, the effective amount of the compound reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRG1 by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments of any of the above aspects, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference. In some embodiments, the effective amount of the compound that reduces the level and/or activity of BRM by at least 50% (e.g., 55%, 60%, 65%, 70%, 75%, 80%, 85%, 90%, or 95%) as compared to a reference. In some embodiments, the effective amount of the compound that reduces the level and/or activity of BRM by at least 90% (e.g., 91%, 92%, 93%, 94%, 95%, 96%, 97%, 98%, or 99%).

In some embodiments, the effective amount of the compound reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 12 hours (e.g., 14 hours, 16 hours, 18 hours, 20 hours, 22 hours, 24 hours, 30 hours, 36 hours, 48 hours, 72 hours, or more). In some embodiments, the effective amount of the compound that reduces the level and/or activity of BRM by at least 5% (e.g., 6%, 7%, 8%, 9%, 10%, 15%, 20%, 25%, 30%, 35%, 40%, 45%, 50%, 55%, 60%, 65%, 70%, 75%, 80%, 85%, 90%, or 95%) as compared to a reference for at least 4 days (e.g., 5 days, 6 days, 7 days, 14 days, 28 days, or more).

In some embodiments, the subject has cancer. In some embodiments, the cancer expresses BRG1 and/or BRM protein and/or the cell or subject has been identified as expressing BRG1 and/or BRM. In some embodiments, the cancer expresses BRG1 protein and/or the cell or subject has been identified as expressing BRG1. In some embodiments, the cancer expresses BRM protein and/or the cell or subject has been identified as expressing BRM. In some embodiments, the cancer is melanoma (e.g., uveal melanoma, mucosal melanoma, or cutaneous melanoma). In some embodiments, the cancer is prostate cancer. In some embodiments, the cancer is a hematologic cancer, e.g., multiple myeloma, large cell lymphoma, acute T-cell leukemia, acute myeloid leukemia, myelodysplastic syndrome, immunoglobulin A lambda myeloma, diffuse mixed histiocytic and lymphocytic lymphoma, B-cell lymphoma, acute lymphoblastic leukemia (e.g., T-cell acute lymphoblastic leukemia or B-cell acute lymphoblastic leukemia), diffuse large cell lymphoma, or non-Hodgkin's lymphoma. In some embodiments, the cancer is breast cancer (e.g., an ER positive breast cancer, an ER negative breast cancer, triple positive breast cancer, or triple negative breast cancer). In some embodiments, the cancer is a bone cancer (e.g., Ewing's sarcoma). In some embodiments, the cancer is a renal cell carcinoma (e.g., a Microphthalmia Transcription Factor (MITF) family translocation renal cell carcinoma (tRCC)). In some embodiments, the cancer is metastatic (e.g., the cancer has spread to the liver). The metastatic cancer can include cells exhibiting migration and/or invasion of migrating cells and/or include cells exhibiting endothelial recruitment and/or angiogenesis. In other embodiments, the migrating cancer is a cell migration cancer. In still other embodiments, the cell migration cancer is a non-metastatic cell migration cancer. The metastatic cancer can be a cancer spread via seeding the surface of the peritoneal, pleural, pericardial, or subarachnoid spaces. Alternatively, the metastatic cancer can be a cancer spread via the lymphatic system, or a cancer spread hematogenously. In some embodiments, the effective amount of a compound of the invention is an amount effective to inhibit metastatic colonization of the cancer to the liver.

In some embodiments the cancer harbors a mutation in GNAQ. In some embodiments the cancer harbors a mutation in GNA11. In some embodiments the cancer harbors a mutation in PLCB4. In some embodiments the cancer harbors a mutation in CYSLTR2. In some embodiments the cancer harbors a mutation in BAP1. In some embodiments the cancer harbors a mutation in SF3B1. In some embodiments the cancer harbors a mutation in EIF1AX. In some embodiments the cancer harbors a TFE3 translocation. In some embodiments the cancer harbors a TFEB translocation. In some embodiments the cancer harbors a MITF translocation. In some embodiments the cancer harbors an EZH2 mutation. In some embodiments the cancer harbors a SUZ12 mutation. In some embodiments the cancer harbors an EED mutation.

In some embodiments of any of the foregoing methods, the method further includes administering to the subject or contacting the cell with an anticancer therapy, e.g., a chemotherapeutic or cytotoxic agent, immunotherapy, surgery, radiotherapy, thermotherapy, or photocoagulation, or a combination thereof. In some embodiments, the anticancer therapy is a chemotherapeutic or cytotoxic agent, e.g., an antimetabolite, antimitotic, antitumor antibiotic, asparagine-specific enzyme, bisphosphonates, antineoplastic, alkylating agent, DNA-Repair enzyme inhibitor, histone deacetylase inhibitor, corticosteroid, demethylating agent, immunomodulatory, janus-associated kinase inhibitor, phosphinositide 3-kinase inhibitor, proteasome inhibitor, or tyrosine kinase inhibitor, or a combination thereof.

In some embodiments of any of the foregoing methods, the compound of the invention is used in combination with another anti-cancer therapy used for the treatment of uveal melanoma such as surgery, a MEK inhibitor, and/or a PKC inhibitor, or a combination thereof. For example, in some embodiments, the method further comprises performing surgery prior to, subsequent to, or at the same time as administration of the compound of the invention. In some embodiments, the method further comprises administration of a MEK inhibitor and/or a PKC inhibitor prior to, subsequent to, or at the same time as administration of the compound of the invention.

In some embodiments, the anticancer therapy and the compound of the invention are administered within 28 days of each other and each in an amount that together are effective to treat the subject.

In some embodiments, the subject or cancer has and/or has been identified as having a BRG1 loss of function mutation. In some embodiments, the subject or cancer has and/or has been identified as having a BRM loss of function mutation.

In some embodiments, the cancer is resistant to one or more chemotherapeutic or cytotoxic agents (e.g., the cancer has been determined to be resistant to chemotherapeutic or cytotoxic agents such as by genetic markers, or is likely to be resistant, to chemotherapeutic or cytotoxic agents such as a cancer that has failed to respond to a chemotherapeutic or cytotoxic agent). In some embodiments, the cancer has failed to respond to one or more chemotherapeutic or cytotoxic agents. In some embodiments, the cancer is resistant or has failed to respond to dacarbazine, temozolomide, cisplatin, treosulfan, fotemustine, IMCgp100, a CTLA-4 inhibitor (e.g., ipilimumab), a PD-1 inhibitor (e.g., Nivolumab or pembrolizumab), a PD-L1 inhibitor (e.g., atezolizumab, avelumab, or durvalumab), a mitogen-activated protein kinase (MEK) inhibitor (e.g., selumetinib, binimetinib, or tametinib), and/or a protein kinase C (PKC) inhibitor (e.g., sotrastaurin or IDE196).

In some embodiments, the cancer is resistant to or failed to respond to a previously administered therapeutic used for the treatment of uveal melanoma such as a MEK inhibitor or PKC inhibitor. For example, in some embodiments, the cancer is resistant to or failed to respond to a mitogen-activated protein kinase (MEK) inhibitor (e.g., selumetinib, binimetinib, or tametinib), and/or a protein kinase C (PKC) inhibitor (e.g., sotrastaurin or IDE196).

Chemical Terms

The terminology employed herein is for the purpose of describing particular embodiments and is not intended to be limiting.

For any of the following chemical definitions, a number following an atomic symbol indicates that total number of atoms of that element that are present in a particular chemical moiety. As will be understood, other atoms, such as H atoms, or substituent groups, as described herein, may be present, as necessary, to satisfy the valences of the atoms. For example, an unsubstituted $C_2$ alkyl group has the formula $—CH_2CH_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

The term "acyl," as used herein, represents a H or an alkyl group that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, 1 to 6 carbon atoms, or 1 to 3 carbon atoms).

An alkylene is a divalent alkyl group. The term "alkenyl," as used herein, alone or in combination with other groups, refers to a straight chain or branched hydrocarbon residue having a carbon-carbon double bond and having 2 to 20 carbon atoms (e.g., 2 to 16 carbon atoms, 2 to 10 carbon atoms, 2 to 6 carbon atoms, or 2 carbon atoms).

The term "alkylsulfinimide," as used herein, refers to a group of formula $—N{=}S(O)R_2$, where each R is independently an alkyl.

The term "alkynyl," as used herein, alone or in combination with other groups, refers to a straight chain or branched hydrocarbon residue having a carbon-carbon triple bond and having 2 to 20 carbon atoms (e.g., 2 to 16 carbon atoms, 2 to 10 carbon atoms, 2 to 6 carbon atoms, or 2 carbon atoms).

The term "amino," as used herein, represents $—N(R^{N1})_2$, wherein each $R^{N1}$ is, independently, H, OH, $NO_2$, $N(R^{N2})_2$, $SO_2OR^{N2}$, $SO_2R^{N2}$, $SOR^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., $—NH_2$) or a substituted amino (i.e., $—N(R^{N1})_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group.

Exemplary unsubstituted arylalkyl groups are from 7 to 30 carbons (e.g., from 7 to 16 or from 7 to 20 carbons, such as $C_1$-$C_6$ alkyl $C_6$-$C_{10}$ aryl, $C_1$-$C_{10}$ alkyl $C_6$-$C_{10}$ aryl, or $C_1$-$C_{20}$ alkyl $C_6$-$C_{10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a $—N_3$ group.

The term "bridged polycycloalkyl," as used herein, refers to a bridged polycyclic group of 5 to 20 carbons, containing from 1 to 3 bridges.

The term "cyano," as used herein, represents a —CN group.

The term "carbocyclyl," as used herein, refers to a non-aromatic $C_3$-$C_{12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, and monovalent mono- or polycarbocyclic radical of 3 to 10, preferably 3 to 6 carbon atoms. This term is further exemplified by radicals such as cyclopropyl, cyclobutyl, cyclopentyl, cyclohexyl, cycloheptyl, norbornyl, and adamantyl.

The term "halo," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group. The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group. The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing 1, 2, or 3 ring atoms selected from nitrogen, oxygen, and sulfur, with the remaining ring atoms being carbon. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl. Heteroarylene is a divalent heteroaryl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_1$-$C_6$ alkyl $C_2$-$C_9$ heteroaryl, $C_1$-$C_{10}$ alkyl $C_2$-$C_9$ heteroaryl, or $C_1$-$C_{20}$ alkyl $C_2$-$C_9$ heteroaryl). In some embodiments, the alkyl and the heteroaryl each can be further substituted with 1, 2, 3, or 4 substituent groups as defined herein for the respective groups.

The term "heterocyclyl," as used herein, refers a mono- or polycyclic radical having 3 to 12 atoms having at least one non-aromatic ring containing 1, 2, 3, or 4 ring atoms selected from N, O and S and no aromatic rings containing any N, O or S ring atoms. Examples of heterocyclyl groups include, but are not limited to, morpholinyl, thiomorpholinyl, piperazinyl, piperidinyl, pyranyl, pyrrolidinyl, tetrahydropyranyl, tetrahydrofuranyl, and 1,3-dioxanyl. Heterocyclylene is a divalent heterocyclyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_1$-$C_6$ alkyl $C_2$-$C_9$ heterocyclyl, $C_1$-$C_{10}$ alkyl $C_2$-$C_9$ heterocyclyl, or $C_1$-$C_{20}$ alkyl $C_2$-$C_9$ heterocyclyl). In some embodiments, the alkyl and the heterocyclyl each can be further substituted with 1, 2, 3, or 4 substituent groups as defined herein for the respective groups.

The term "hydroxyalkyl," as used herein, represents alkyl group substituted with an —OH group.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," 3rd Edition (John Wiley & Sons, New York, 1999). N-protecting groups include, but are not limited to, acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L, or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-20 dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an $—NO_2$ group.

The term "oxo," as used herein, represents an ═O group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: alkyl (e.g., unsubstituted and substituted, where the substituents include any group described herein, e.g., aryl, halo, hydroxy), alkynyl (e.g., unsubstituted and substituted, where the substituents include any group described herein, e.g., aryl, halo, hydroxy, or alkoxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), alkylsulfinimide, azido, cyano, nitro, oxo, or thiol. In some embodiments (e.g., for the compounds of Formula Ia), substituents include, for example: alkyl (e.g., unsubstituted and substituted, where the substituents include any group described herein, e.g., aryl, halo, hydroxy), aryl (e.g., substituted and unsubstituted phenyl), carbocyclyl (e.g., substituted and unsubstituted cycloalkyl), halo (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates, or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99%, or 99.9% by weight relative to the other stereoisomers. When a single enantiomer is named or depicted by structure, the depicted or named enantiomer is at least 60%, 70%, 80%, 90%, 99%, or 99.9% by weight optically pure. When a single diastereomer is named or depicted by structure, the depicted or named diastereomer is at least 60%, 70%, 80%, 90%, 99%, or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99%, or 99.9% by mole fraction pure relative to the other stereoisomers. When a single enantiomer is named or depicted by structure, the depicted or named enantiomer is at least 60%, 70%, 80%, 90%, 99%, or 99.9% by mole fraction pure. When a single diastereomer is named or depicted by structure, the depicted or named diastereomer is at least 60%, 70%, 80%, 90%, 99%, or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound, or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s), or mixtures of diastereomers in which one or more diastereomer is enriched relative to the other diastereomers. The invention embraces all of these forms.

Compounds of the present disclosure also include all of the isotopes of the atoms occurring in the intermediate or final compounds. "Isotopes" refers to atoms having the same atomic number but different mass numbers resulting from a different number of neutrons in the nuclei. For example, isotopes of hydrogen include tritium and deuterium.

Unless otherwise stated, structures depicted herein are also meant to include compounds that differ only in the presence of one or more isotopically enriched atoms. Exemplary isotopes that can be incorporated into compounds of the present invention include isotopes of hydrogen, carbon, nitrogen, oxygen, phosphorus, sulfur, fluorine, chlorine, and iodine, such as $^{2}H$, $^{3}H$, $^{11}C$, $^{13}C$, $^{14}C$, $^{13}N$, $^{15}N$, $^{15}O$, $^{17}O$, $^{18}O$, $^{32}P$, $^{33}P$, $^{35}S$, $^{18}F$, $^{36}Cl$, $^{123}I$ and $^{125}I$. Isotopically-labeled compounds (e.g., those labeled with $^{3}H$ and $^{14}C$) can be useful in compound or substrate tissue distribution assays. Tritiated (i.e., $^{3}H$) and carbon-14 (i.e., $^{14}C$) isotopes can be useful for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements). In some embodiments, one or more hydrogen atoms are replaced by $^{2}H$ or $^{3}H$, or one or more carbon atoms are replaced by $^{13}C$- or $^{14}C$-enriched carbon. Positron emitting isotopes such as 150, $^{13}N$, $^{11}C$, and $^{18}F$ are useful for positron emission tomography (PET) studies to examine substrate receptor occupancy. Preparations of isotopically labelled compounds are known to those of skill in the art. For example, isotopically labeled compounds can generally be prepared by following procedures analogous to those disclosed for compounds of the present invention described herein, by substituting an isotopically labeled reagent for a non-isotopically labeled reagent.

Unless otherwise defined, all technical and scientific terms used herein have the same meaning as commonly understood by one of ordinary skill in the art to which this invention belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Definitions

In this application, unless otherwise clear from context, (i) the term "a" may be understood to mean "at least one"; (ii) the term "or" may be understood to mean "and/or"; and (iii) the terms "comprising" and "including" may be understood to encompass itemized components or steps whether presented by themselves or together with one or more additional components or steps.

As used herein, the terms "about" and "approximately" refer to a value that is within 10% above or below the value being described. For example, the term "about 5 nM" indicates a range of from 4.5 to 5.5 nM.

As used herein, the term "administration" refers to the administration of a composition (e.g., a compound or a preparation that includes a compound as described herein) to a subject or system. Administration to an animal subject (e.g., to a human) may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intratumoral, intravenous, intraventricular, mucosal, nasal, oral, rectal, subcutaneous, sublingual, topical, tracheal (including by intratracheal instillation), transdermal, vaginal, and vitreal.

As used herein, the term "BAF complex" refers to the BRG1- or HBRM-associated factors complex in a human cell.

As used herein, the term "BAF complex-related disorder" refers to a disorder that is caused or affected by the level of activity of a BAF complex.

As used herein, the term "BRG1 loss of function mutation" refers to a mutation in BRG1 that leads to the protein having diminished activity (e.g., at least 1% reduction in BRG1 activity, for example 2%, 5%, 10%, 25%, 50%, or 100% reduction in BRG1 activity). Exemplary BRG1 loss of function mutations include, but are not limited to, a homozygous BRG1 mutation and a deletion at the C-terminus of BRG1.

As used herein, the term "BRG1 loss of function disorder" refers to a disorder (e.g., cancer) that exhibits a reduction in BRG1 activity (e.g., at least 1% reduction in BRG1 activity, for example 2%, 5%, 10%, 25%, 50%, or 100% reduction in BRG1 activity).

The term "cancer" refers to a condition caused by the proliferation of malignant neoplastic cells, such as tumors, neoplasms, carcinomas, sarcomas, leukemias, and lymphomas.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In some embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

By "determining the level" of a protein or RNA is meant the detection of a protein or an RNA, by methods known in the art, either directly or indirectly. "Directly determining" means performing a process (e.g., performing an assay or test on a sample or "analyzing a sample" as that term is defined herein) to obtain the physical entity or value. "Indirectly determining" refers to receiving the physical entity or value from another party or source (e.g., a third party laboratory that directly acquired the physical entity or value). Methods to measure protein level generally include, but are not limited to, western blotting, immunoblotting, enzyme-linked immunosorbent assay (ELISA), radioimmunoassay (RIA), immunoprecipitation, immunofluorescence, surface plasmon resonance, chemiluminescence, fluorescent polarization, phosphorescence, immunohistochemical analysis, matrix-assisted laser desorption/ionization time-of-flight (MALDI-TOF) mass spectrometry, liquid chromatography (LC)-mass spectrometry, microcytometry, microscopy, fluorescence activated cell sorting (FACS), and flow cytometry, as well as assays based on a property of a protein including, but not limited to, enzymatic activity or interaction with other protein partners. Methods to measure RNA levels are known in the art and include, but are not limited to, quantitative polymerase chain reaction (qPCR) and Northern blot analyses.

By a "decreased level" or an "increased level" of a protein or RNA is meant a decrease or increase, respectively, in a protein or RNA level, as compared to a reference (e.g., a decrease or an increase by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 150%, about 200%, about 300%, about 400%, about 500%, or more; a decrease or an increase of more than about 10%, about 15%, about 20%, about 50%, about 75%, about 100%, or about 200%, as compared to a reference; a decrease or an increase by less than about 0.01-fold, about 0.02-fold, about 0.1-fold, about 0.3-fold, about 0.5-fold, about 0.8-fold, or less; or an increase by more than about 1.2-fold, about 1.4-fold, about 1.5-fold, about 1.8-fold, about 2.0-fold, about 3.0-fold, about 3.5-fold, about 4.5-fold, about 5.0-fold, about 10-fold, about 15-fold, about 20-fold, about 30-fold, about 40-fold, about 50-fold, about 100-fold, about 1000-fold, or more). A level of a protein may be expressed in mass/vol (e.g., g/dL, mg/mL, μg/mL, ng/mL) or percentage relative to total protein in a sample.

By "decreasing the activity of a BAF complex" is meant decreasing the level of an activity related to a BAF complex, or a related downstream effect. A non-limiting example of decreasing an activity of a BAF complex is Sox2 activation. The activity level of a BAF complex may be measured using any method known in the art, e.g., the methods described in Kadoch et al. Cell, 2013, 153, 71-85, the methods of which are herein incorporated by reference.

As used herein, the term "inhibiting BRM" refers to blocking or reducing the level or activity of the ATPase catalytic binding domain or the bromodomain of the protein. BRM inhibition may be determined using methods known in the art, e.g., a BRM ATPase assay, a Nano DSF assay, or a BRM Luciferase cell assay.

As used herein, the term "LXS196," also known as IDE196, refers to the PKC inhibitor having the structure:

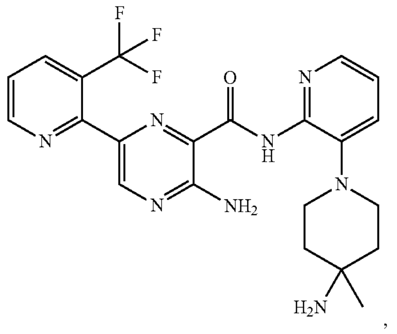 [SMILES: CC1(N)CCN(c2cccnc2NC(=O)c2nc(-c3ncccc3C(F)(F)F)cnc2N)CC1]

or a pharmaceutically acceptable salt thereof.

The term “pharmaceutical composition,” as used herein, represents a composition containing a compound described herein formulated with a pharmaceutically acceptable excipient and appropriate for administration to a mammal, for example a human. Typically, a pharmaceutical composition is manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A “pharmaceutically acceptable excipient,” as used herein, refers to any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration.

As used herein, the term “pharmaceutically acceptable salt” means any pharmaceutically acceptable salt of a compound, for example, any compound of Formula I. Pharmaceutically acceptable salts of any of the compounds described herein may include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

By a “reference” is meant any useful reference used to compare protein or RNA levels. The reference can be any sample, standard, standard curve, or level that is used for comparison purposes. The reference can be a normal reference sample or a reference standard or level. A “reference sample” can be, for example, a control, e.g., a predetermined negative control value such as a “normal control” or a prior sample taken from the same subject; a sample from a normal healthy subject, such as a normal cell or normal tissue; a sample (e.g., a cell or tissue) from a subject not having a disease; a sample from a subject that is diagnosed with a disease, but not yet treated with a compound of the invention; a sample from a subject that has been treated by a compound of the invention; or a sample of a purified protein or RNA (e.g., any described herein) at a known normal concentration. By “reference standard or level” is meant a value or number derived from a reference sample. A “normal control value” is a pre-determined value indicative of non-disease state, e.g., a value expected in a healthy control subject. Typically, a normal control value is expressed as a range (“between X and Y”), a high threshold (“no higher than X”), or a low threshold (“no lower than X”). A subject having a measured value within the normal control value for a particular biomarker is typically referred to as “within normal limits” for that biomarker. A normal reference standard or level can be a value or number derived from a normal subject not having a disease or disorder (e.g., cancer); a subject that has been treated with a compound of the invention. In preferred embodiments, the reference sample, standard, or level is matched to the sample subject sample by at least one of the following criteria: age, weight, sex, disease stage, and overall health. A standard curve of levels of a purified protein or RNA, e.g., any described herein, within the normal reference range can also be used as a reference.

As used herein, the term “subject” refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms “treat,” “treated,” or “treating” mean therapeutic treatment or any measures whose object is to slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total); an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment. Compounds of the invention may also be used to "prophylactically treat" or "prevent" a disorder, for example, in a subject at increased risk of developing the disorder.

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

The details of one or more embodiments of the invention are set forth in the description below. Other features, objects, and advantages of the invention will be apparent from the description and from the claims.

DETAILED DESCRIPTION

Figure 1:
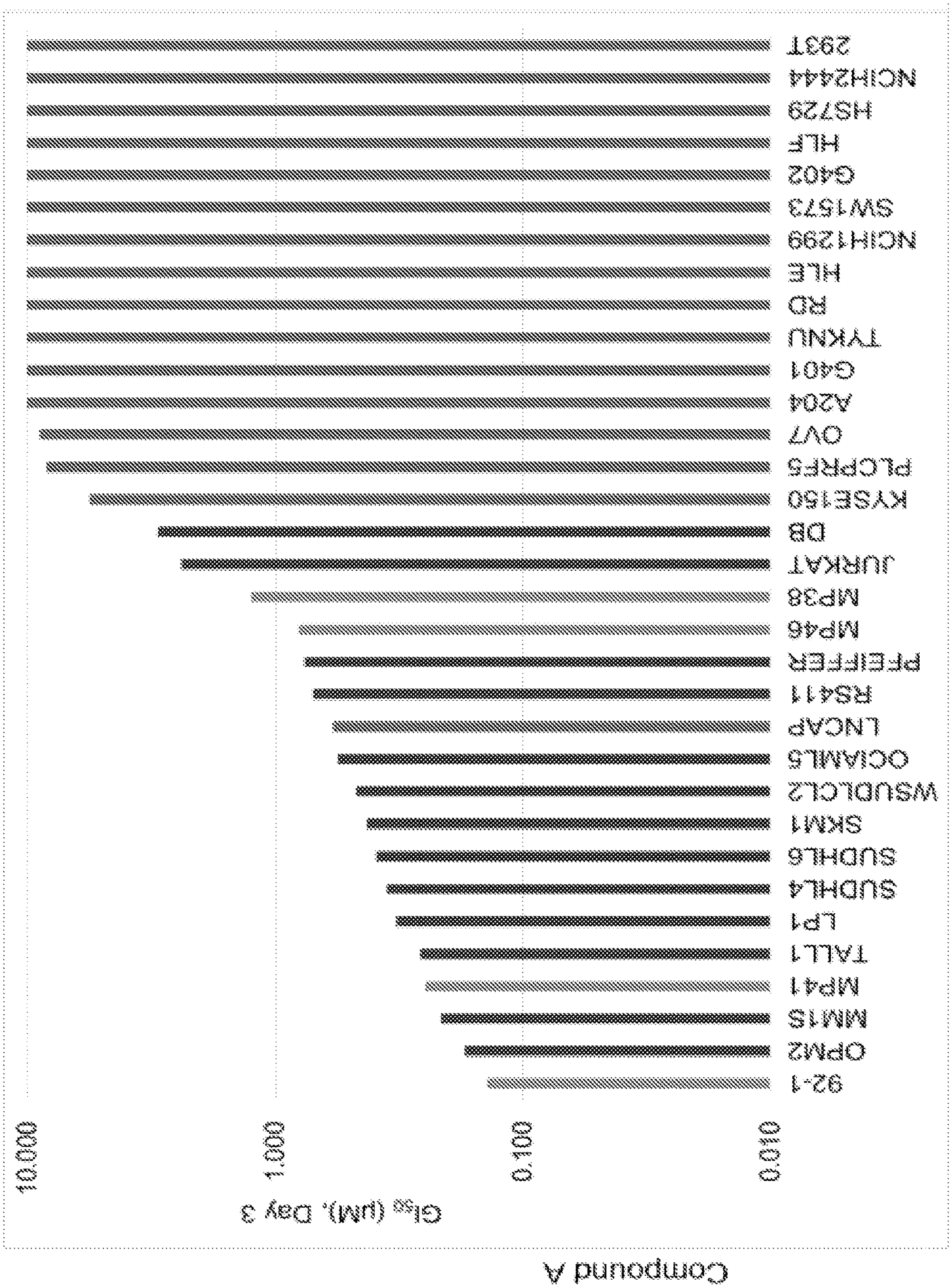
FIG. 1 is a graph illustrating inhibition of cell proliferation of several cancer cell lines by a BRG1/BRM inhibitor (Compound A).

The present disclosure features compounds useful for the inhibition of BRG1 and/or BRM. These compounds may be used to modulate the activity of a BAF complex, for example, for the treatment of a BAF-related disorder, such as cancer. Exemplary compounds described herein include compounds having a structure according to Formula I:

Formula I

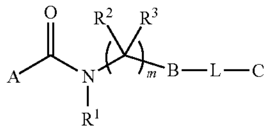

wherein

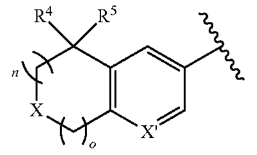

or

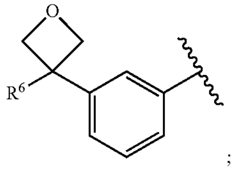

;

A is or m is 0, 1, 2, or 3;

n is 1 or 2;

is 0 or 1;

X is O, $CH_2$, or $NR^7$;

X' is N, CH, or $CR^x$, wherein $R^x$ is a halogen;

B is an optionally substituted 6-membered bicyclic heteroarylene or an optionally substituted 9- or 10-membered bicyclic heteroarylene;

L is a covalent bond, optionally substituted $C_1$-$C_3$ alkylene, $C_2$ alkynylene, optionally substituted $C_2$ alkenylene, optionally substituted $C_2$-$C_3$ heteroalkylene, optionally substituted $C_3$-$C_5$ cycloalkylene, or optionally substituted 4- to 10-membered heterocyclylene;

C is optionally substituted 3- to 10-membered cycloalkyl; optionally substituted 6- to 10-membered aryl; optionally substituted 5- to 10-membered heteroaryl; or optionally substituted 5- to 10-membered heterocyclyl;

$R^1$ and $R^7$ are, independently, hydrogen or optionally substituted $C_1$-$C_6$ alkyl;

each $R^2$ and $R^3$ is independently, hydrogen, optionally substituted $C_1$-$C_6$ alkyl; or optionally substituted $C_1$-$C_6$ heteroalkyl;

$R^4$ is cyano, fluoro, hydroxy, or —$CH_2OH$;

$R^5$ is $C_1$-$C_3$ alkyl optionally substituted with one, two, three, four, five, six, or seven fluoro groups; and $R^6$ is $C_1$-$C_3$ alkyl optionally substituted with one, two, three, four, five, six, or seven fluoro groups, or a pharmaceutically acceptable salt thereof.

Preferably, when B is optionally substituted 6-membered bicyclic heteroarylene, L is a covalent bond, optionally substituted $C_1$-$C_3$ alkylene, $C_2$ alkynylene, optionally substituted $C_2$ alkenylene, optionally substituted $C_2$-$C_3$ heteroalkylene, optionally substituted $C_3$-$C_5$ cycloalkylene, or optionally substituted 4- to 10-membered heterocyclylene. Also preferably, when B is an optionally substituted 9- or 10-membered bicyclic heteroarylene, L is a covalent bond, e.g., the compound of Formula I is a compound of Formula Ia:

Formula Ia

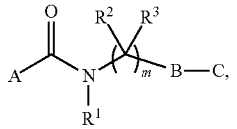

or a pharmaceutically acceptable salt thereof, where all variables are as described herein.

In some embodiments, the compound, or pharmaceutically acceptable salt thereof, has the structure of any one of compounds 1-48 in Table 1, compounds 49-84 in Table 2, or compounds 85-126 in Table 3.

Other embodiments, as well as exemplary methods for the synthesis of production of these compounds, are described herein.

Pharmaceutical Uses

The compounds described herein are useful in the methods of the invention and, while not bound by theory, are believed to exert their ability to modulate the level, status, and/or activity of a BAF complex, i.e., by inhibiting the activity of the BRG1 and/or BRM proteins within the BAF complex in a mammal. BAF complex-related disorders include, but are not limited to, BRG1 loss of function mutation-related disorders.

An aspect of the present invention relates to methods of treating disorders related to BRG1 loss of function mutations such as cancer (e.g., non-small cell lung cancer, colorectal cancer, bladder cancer, cancer of unknown primary, glioma, breast cancer, melanoma, non-melanoma skin cancer, endometrial cancer, or penile cancer) in a subject in need thereof. In some embodiments, the compound is administered in an amount and for a time effective to result in one or more (e.g., two or more, three or more, four or more) of: (a) reduced tumor size, (b) reduced rate of tumor growth, (c) increased tumor cell death (d) reduced tumor progression, (e) reduced number of metastases, (f) reduced rate of metastasis, (g) decreased tumor recurrence (h) increased survival of subject, (i) increased progression free survival of subject.

Treating cancer can result in a reduction in size or volume of a tumor. For example, after treatment, tumor size is reduced by 5% or greater (e.g., 10%, 20%, 30%, 40%, 50%, 60%, 70%, 80%, 90%, or greater) relative to its size prior to treatment. Size of a tumor may be measured by any reproducible means of measurement. For example, the size of a tumor may be measured as a diameter of the tumor.

Treating cancer may further result in a decrease in number of tumors. For example, after treatment, tumor number is reduced by 5% or greater (e.g., 10%, 20%, 30%, 40%, 50%, 60%, 70%, 80%, 90%, or greater) relative to number prior to treatment. Number of tumors may be measured by any reproducible means of measurement, e.g., the number of tumors may be measured by counting tumors visible to the naked eye or at a specified magnification (e.g., 2×, 3×, 4×, 5×, 10×, or 50×).

Treating cancer can result in a decrease in number of metastatic nodules in other tissues or organs distant from the primary tumor site. For example, after treatment, the number of metastatic nodules is reduced by 5% or greater (e.g., 10%, 20%, 30%, 40%, 50%, 60%, 70%, 80%, 90% or greater) relative to number prior to treatment. The number of metastatic nodules may be measured by any reproducible means of measurement. For example, the number of metastatic nodules may be measured by counting metastatic nodules visible to the naked eye or at a specified magnification (e.g., 2×, 10×, or 50×).

Treating cancer can result in an increase in average survival time of a population of subjects treated according to the present invention in comparison to a population of untreated subjects. For example, the average survival time is increased by more than 30 days (more than 60 days, 90 days, or 120 days). An increase in average survival time of a population may be measured by any reproducible means. An increase in average survival time of a population may be measured, for example, by calculating for a population the average length of survival following initiation of treatment with the compound of the invention. An increase in average survival time of a population may also be measured, for example, by calculating for a population the average length of survival following completion of a first round of treatment with a pharmaceutically acceptable salt of the invention.

Treating cancer can also result in a decrease in the mortality rate of a population of treated subjects in comparison to an untreated population. For example, the mortality rate is decreased by more than 2% (e.g., more than 5%, 10%, or 25%). A decrease in the mortality rate of a population of treated subjects may be measured by any reproducible means, for example, by calculating for a population the average number of disease-related deaths per unit time following initiation of treatment with a pharmaceutically acceptable salt of the invention. A decrease in the mortality rate of a population may also be measured, for example, by calculating for a population the average number of disease-related deaths per unit time following completion of a first round of treatment with a pharmaceutically acceptable salt of the invention.

Exemplary cancers that may be treated by the invention include, but are not limited to, non-small cell lung cancer, small-cell lung cancer, colorectal cancer, bladder cancer, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer and penile cancer.

Combination Formulations and Uses Thereof

The compounds of the invention can be combined with one or more therapeutic agents. In particular, the therapeutic agent can be one that treats or prophylactically treats any cancer described herein.

Combination Therapies

A compound of the invention can be used alone or in combination with an additional therapeutic agent, e.g., other agents that treat cancer or symptoms associated therewith, or in combination with other types of treatment to treat cancer. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

In some embodiments, the second therapeutic agent is a chemotherapeutic agent (e.g., a cytotoxic agent or other chemical compound useful in the treatment of cancer). These include alkylating agents, antimetabolites, folic acid analogs, pyrimidine analogs, purine analogs and related inhibitors, vinca alkaloids, epipodopyyllotoxins, antibiotics, L-Asparaginase, topoisomerase inhibitors, interferons, platinum coordination complexes, anthracenedione substituted urea, methyl hydrazine derivatives, adrenocortical suppressant, adrenocorticosteroides, progestins, estrogens, antiestrogen, androgens, antiandrogen, and gonadotropin-releasing hormone analog. Also included is 5-fluorouracil (5-FU), leucovorin (LV), irenotecan, oxaliplatin, capecitabine, paclitaxel and doxetaxel. Non-limiting examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegall (see, e.g., Agnew, Chem. Intl. Ed Engl. 33:183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, Adriamycin® (doxorubicin, including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfomithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., Taxol® paclitaxel (Bristol-Myers Squibb Oncology, Princeton, N.J.), ABraxane®, cremophor-free, albumin-engineered nanoparticle formulation of paclitaxel (American Pharmaceutical Partners, Schaumberg, Ill.), and Taxotere® doxetaxel (Rhone-Poulenc Rorer, Antony, France); chloranbucil; Gemzar® gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; Navelbine® vinorelbine; novantrone; teniposide; edatrexate; daunomycin; aminopterin; xeloda; ibandronate; irinotecan (e.g., CPT-11); topoisomerase inhibitor RFS 2000; difluoromethylornithine (DMFO); retinoids such as retinoic acid; capecitabine; and pharmaceutically acceptable salts, acids or derivatives of any of the above. Two or more chemotherapeutic agents can be used in a cocktail to be administered in combination with the first therapeutic agent described herein. Suitable dosing regimens of combination chemotherapies are known in the art and described in, for example, Saltz et al. (1999) Proc ASCO 18:233a and Douillard et al. (2000) Lancet 355:1041-7.

In some embodiments, the second therapeutic agent is a therapeutic agent which is a biologic such a cytokine (e.g., interferon or an interleukin (e.g., IL-2)) used in cancer treatment. In some embodiments the biologic is an anti-angiogenic agent, such as an anti-VEGF agent, e.g., bevacizumab (Avastin®). In some embodiments the biologic is an immunoglobulin-based biologic, e.g., a monoclonal antibody (e.g., a humanized antibody, a fully human antibody, an Fc fusion protein or a functional fragment thereof) that agonizes a target to stimulate an anti-cancer response or antagonizes an antigen important for cancer. Such agents include Rituxan (Rituximab); Zenapax (Daclizumab); Simulect (Basiliximab); Synagis (Palivizumab); Remicade (Infliximab); Herceptin (Trastuzumab); Mylotarg (Gemtuzumab ozogamicin); Campath (Alemtuzumab); Zevalin (Ibritumomab tiuxetan); Humira (Adalimumab); Xolair (Omalizumab); Bexxar (Tositumomab-I-131); Raptiva (Efalizumab); Erbitux (Cetuximab); Avastin (Bevacizumab); Tysabri (Natalizumab); Actemra (Tocilizumab); Vectibix (Panitumumab); Lucentis (Ranibizumab); Soliris (Eculizumab); Cimzia (Certolizumab pegol); Simponi (Golimumab); Ilaris (Canakinumab); Stelara (Ustekinumab); Arzerra (Ofatumumab); Prolia (Denosumab); Numax (Motavizumab); ABThrax (Raxibacumab); Benlysta (Belimumab); Yervoy (Ipilimumab); Adcetris (Brentuximab Vedotin); Perjeta (Pertuzumab); Kadcyla (Ado-trastuzumab emtansine); and Gazyva (Obinutuzumab). Also included are antibody-drug conjugates.

The second agent may be a therapeutic agent which is a non-drug treatment. For example, the second therapeutic agent is radiation therapy, cryotherapy, hyperthermia and/or surgical excision of tumor tissue.

The second agent may be a checkpoint inhibitor. In one embodiment, the inhibitor of checkpoint is an inhibitory antibody (e.g., a monospecific antibody such as a monoclonal antibody). The antibody may be, e.g., humanized or fully human. In some embodiments, the inhibitor of checkpoint is a fusion protein, e.g., an Fc-receptor fusion protein. In some embodiments, the inhibitor of checkpoint is an agent, such as an antibody, that interacts with a checkpoint protein. In some embodiments, the inhibitor of checkpoint is an agent, such as an antibody, that interacts with the ligand of a checkpoint protein. In some embodiments, the inhibitor of checkpoint is an inhibitor (e.g., an inhibitory antibody or small molecule inhibitor) of CTLA-4 (e.g., an anti-CTLA4 antibody such as ipilimumab/Yervoy or tremelimumab). In some embodiments, the inhibitor of checkpoint is an inhibitor (e.g., an inhibitory antibody or small molecule inhibitor) of PD-1 (e.g., nivolumab/Opdivo®; pembrolizumab/Keytruda®; pidilizumab/CT-011). In some embodiments, the inhibitor of checkpoint is an inhibitor (e.g., an inhibitory antibody or small molecule inhibitor) of PDL1 (e.g., MPDL3280A/RG7446; MEDI4736; MSB0010718C; BMS 936559). In some embodiments, the inhibitor of checkpoint is an inhibitor (e.g., an inhibitory antibody or Fc fusion or small molecule inhibitor) of PDL2 (e.g., a PDL2/lg fusion protein such as AMP 224). In some embodiments, the inhibitor of checkpoint is an inhibitor (e.g., an inhibitory antibody or small molecule inhibitor) of B7-H3 (e.g., MGA271), B7-H4, BTLA, HVEM, TIM3, GAL9, LAG3, VISTA, KIR, 2B4, CD160, CGEN-15049, CHK1, CHK2, A2aR, B-7 family ligands, or a combination thereof.

In any of the combination embodiments described herein, the first and second therapeutic agents are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Pharmaceutical Compositions

The compounds of the invention are preferably formulated into pharmaceutical compositions for administration to a mammal, preferably, a human, in a biologically compatible form suitable for administration in vivo. Accordingly, in an aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard- or soft-shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers. A compound of the invention may also be administered parenterally. Solutions of a compound of the invention can be prepared in water suitably mixed with a surfactant. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999. The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe. Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant. The aerosol dosage forms can also take the form of a pump-atomizer. Compositions suitable for buccal or sublingual administration include tablets, lozenges, and pastilles, where the active ingredient is formulated with a carrier. Compositions for rectal administration are conveniently in the form of suppositories containing a conventional suppository base. A compound described herein may be administered intratumorally, for example, as an intratumoral injection. Intratumoral injection is injection directly into the tumor vasculature and is specifically contemplated for discrete, solid, accessible tumors. Local, regional, or systemic administration also may be appropriate. A compound described herein may advantageously be contacted by administering an injection or multiple injections to the tumor, spaced for example, at approximately, 1 cm intervals. In the case of surgical intervention, the present invention may be used preoperatively, such as to render an inoperable tumor subject to resection. Continuous administration also may be applied where appropriate, for example, by implanting a catheter into a tumor or into tumor vasculature.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg. Dose ranges include, for example, between 10-1000 mg.

Alternatively, the dosage amount can be calculated using the body weight of the patient. For example, the dose of a compound, or pharmaceutical composition thereof, administered to a patient may range from 0.1-100 mg/kg.

EXAMPLES

Definitions Used in the Following Schemes and Elsewhere Herein are

MeCN or ACN acetonitrile
AIBN azobisisobutyronitrile
Boc tert-butoxycarbonyl
n-BuLi n-butyllithium
t-BuOK potassium tert-butoxide
t-BuONa sodium tert-butoxide
t-BuXPhos Pd G3 [(2-Di-tert-butylphosphino-2',4',6'-triisopropyl-1,1'-biphenyl)-2-(2'-amino-1,1'-biphenyl)] palladium(II) methanesulfonate
tBuphos Pd G3 [(2-Di-tert-butylphosphino-2',4',6'-triisopropyl-1,1'-biphenyl)-2-(2'-amino-1,1'-biphenyl)] palladium(II) methanesulfonate
DAST diethylaminosulfur trifluoride
DCE dichloroethane
DCM dichloromethane
DCPP-2HBF$_4$ 1,3-bis(dicyclohexylphosphino)propane bis(tetrafluoroborate)
DEA N,N-diethylamine
DMP Dess-Martin periodinane, 1,1,1-Tris(acetyloxy)-1, 1-dihydro-1,2-
DIAD diisopropyl azodicarboxylate
DIBAL-H diisobutylaluminum hydride
DIEA or DIPEA N,N-diisopropylethylamine
DMA dimethylacetamide
DMAP 4-(dimethylamino)pyridine
DME 1,2-dimethoxyethane
DMF N,N-dimethylformamide
DMSO dimethylsulfoxide
dppf bis(diphenylphosphino)ferrocene
dtbpf 1,1'-bis(di-tert-butylphosphino)ferrocene
EDCI 1-ethyl-(3-dimethylaminopropyl)carbodiimide hydrochloride
ESI electrospray ionization
Et$_3$N or TEA triethylamine
EA ethyl acetate
EtOH ethyl alcohol
FA formic acid
FCC flash column chromatography
g grams
HATU 2-(3H-[1,2,3]triazolo[4,5-b]pyridin-3-yl)-l, 1,3,3-tetramethylisouronium
HCl hydrochloric acid
HOAc acetic acid
HOBt hydroxybenzotriazole
HPLC high performance liquid chromatography
IPA isopropyl alcohol
L liter
LCMS liquid chromatography/mass spectrometry
LiHMDS lithium bis(trimethylsilyl)amide
m-CPBA 3-chloroperoxybenzoic acid
MeCN acetonitrile
MeI methyl iodide
MeOH methyl alcohol
mL milliliter
mmol millimole
mg milligrams
MHz megahertz
MS mass spectrometry
MTBE methyl tert-butyl ether
m/z mass/charge ratio
NBS N-bromosuccinimide
NIS N-iodosuccinimide
nm nanometer
NMR nuclear magnetic resonance
PdCl2(dtbpf) [1,1'-Bis(di-tert-butylphosphino)ferrocene] dichloropalladium(II)
PE petroleum ether
PhMe toluene
ppm parts per million
rt room temperature
RT retention time
SFC supercritical fluid chromatography
SPhos Pd G3 (2-dicyclohexylphosphino-2',6'-dimethoxybiphenyl) [2-(2'-amino-1,1'-biphenyl)]palladium (II) methanesulfonate
TBS tert-butyldimethylsilyl
TBSCl tert-butyldimethylsilyl chloride
TBDMS tert-butyldimethylsilyl chloride
TCCA or TClCA trichloroisocyanuric acid
TFA trifluoroacetic acid
TFAA trifluoroacetic anhydride
THF tetrahydrofuran
TMSCN trimethylsilyl cyanide
TosMIC toluenesulfonylmethyl isocyanide
Ziram zinc dimethyldithiocarbamate

Materials

Unless otherwise noted, all materials were obtained from commercial suppliers and were used without further purification. All reactions involving air- or moisture-sensitive reagents were performed under a nitrogen atmosphere.

Example 1. Preparation of Intermediates

Intermediates 1 and 2: (4S)-4-Cyano-4-methyl-isochromane-6-carboxylic acid and (4R)-4-Cyano-4-methyl-isochromane-6-carboxylic acid

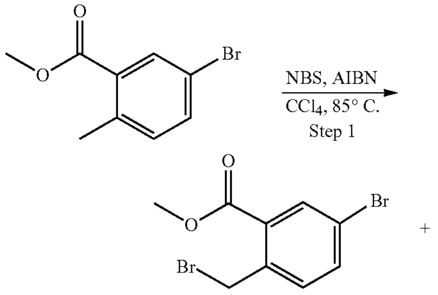

-continued

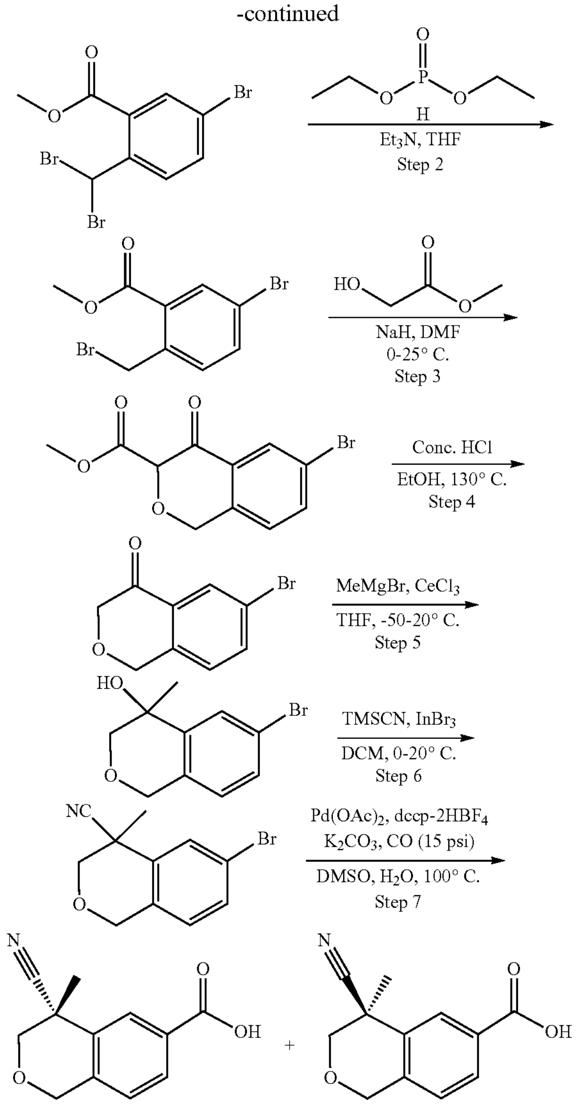

Intermediate 1 + Intermediate 2

Step 1. Methyl 5-bromo-2-(bromomethyl)benzoate and methyl 5-bromo-2-(dibromomethyl)benzoate N-Bromosuccinimide (130.5 g, 733 mmol) and AIBN (11.47 g, 69.8 mmol) was added to a mixture of methyl 5-bromo-2-methyl-benzoate (160 g, 698 mmol) in $CCl_4$ (1.6 L). The mixture was stirred at 80° C. for 8 hrs. The mixture was cooled to 25° C. and filtered. The filtrate was concentrated in vacuo affording a mixture of the title compounds (215 g, crude) as a yellow oil, which was used to next step directly.

Step 2. Methyl 5-bromo-2-(bromomethyl)benzoate

Diisopropylethyl amine (48.6 mL, 279 mmol) and 1-ethoxyphosphonoyloxyethane (36.0 mL, 279 mmol) were added to a mixture of methyl 5-bromo-2-(bromomethyl) benzoate and methyl 5-bromo-2-(dibromomethyl)benzoate (215 g, crude) in THE (1 L) at 0° C. The mixture was stirred at 25° C. for 8 hrs. The mixture was diluted with water (1 L) and extracted with EA (1 L×3). The combined organic phase was washed with brine (1 L), dried over $Na_2SO_4$, filtered, and concentrated in vacuo. The crude product was dissolved with PE:EA=10:1 (1 L). The mixture was filtered through a short silica gel column and washed with PE:EA=10:1 (2 L). The filtrate was concentrated under vacuum affording the title compound (210 g, 682 mmol) as yellow oil.

$^1$H NMR (400 MHz, DMSO-d6) δ=7.99 (d, J=2.0 Hz, 1H), 7.82-7.79 (m, 1H), 7.56 (d, J=8.4 Hz, 1H), 4.97 (s, 2H), 3.88 (s, 3H) ppm.

Step 3. Methyl 6-bromo-4-oxo-isochromane-3-carboxylate

Sodium hydride (39 g, 974 mmol, 60% purity) was added to a mixture of methyl 5-bromo-2-(bromomethyl)benzoate (150 g, 487 mmol) and methyl 2-hydroxyacetate (75 mL, 974 mmol) in DMF (1.5 L) at 0° C. The mixture was stirred at 25° C. for 1 hr. The mixture was poured into saturated $NH_4Cl$ (aq., 6 L), and then extracted with MTBE (3 L×2). The combined organic layers were dried over $Na_2SO_4$, filtered, and concentrated under reduced pressure affording the title compound (140 g, crude) as a brown oil, which was used to next step directly.

Step 4. 6-Bromoisochroman-4-one

A mixture of methyl 6-bromo-4-oxo-isochromane-3-carboxylate (140 g, 487 mmol) in EtOH (500 mL) and HCl (12 M, 1 L) was stirred at 120° C. for 1 hr. The reaction mixture was cooled to 25° C. and filtered. The filter cake was saved. The filtrate was diluted with water (2 L) and extracted with MTBE (1.5 L×2). The combined organic layers were dried over $Na_2SO_4$, filtered, and concentrated under reduced pressure to give brown oil. The brown oil was combined with the filter cake and then triturated with EtOH (200 mL) at 0° C. for 0.5 hrs. The solid was collected by filtration, washed with EtOH (50 mL×2) and dried in vacuo affording the title compound (50 g, 242 mmol) as a yellow solid.

$^1$H NMR (400 MHz, $CDCl_3$) δ=8.17 (d, J=20 Hz, 1H), 7.69-7.67 (m, 1H), 7.13 (d, J=8.4 Hz, 1H), 4.85 (s, 2H), 4.37 (s, 2H) ppm.

Step 5. 6-Bromo-4-methyl-isochroman-4-ol

Methylmagnesium bromide (3 M in THF, 440 mL) was added dropwise to a mixture of 6-bromoisochroman-4-one (100 g, 440 mmol) and $CeCl_3$ (54.3 g, 220 mmol, dried in a muffle furnace at 300° C. for 3 hrs.) in THE (2 L) at −50° C. The mixture was warmed to 20° C. and stirred for 1 hr. The reaction mixture was poured into water (2 L) and then filtered through diatomite. The diatomite was then washed with EA (2 L). The filtrate was separated and the aqueous layer was extracted with EA (1 L×2). The combined organic layers were washed with brine (2 L), dried over $Na_2SO_4$, filtered, and concentrated under reduced pressure to give a residue. The crude residue was purified by FCC (Eluent: PE:EA=50:1 to 3:1) affording the title compound (105 g, 432 mmol) as light yellow oil.

$^1$H NMR (400 MHz, DMSO-d6) δ=7.67 (d, J=2.0 Hz, 1H), 7.38-7.35 (m, 1H), 6.99 (d, J=8.4 Hz, 1H), 5.35 (s, 1H), 4.71-4.58 (m, 2H), 3.68-3.59 (m, 1H), 3.58-3.50 (m, 1H), 1.38 (s, 3H) ppm.

Step 6. 6-Bromo-4-methyl-isochromane-4-carbonitrile

TMSCN (102.9 mL, 823 mmol) was added to a solution of 6-bromo-4-methyl-isochroman-4-ol (100 g, 411 mmol) in DCM (2 L) at 0° C. $InBr_3$ (29.2 g, 82.3 mmol) was then added, and the mixture was warmed and stirred at 25° C. for 1 hr. The mixture was poured into water (2 L) and extracted with DCM (1 L×2). The combined organic layers were washed with brine (1 L), dried over $Na_2SO_4$, filtered, and concentrated under reduced pressure. The crude residue was purified by FCC (Eluent: PE:EA=20:1 to 5:1) affording the title compound (55 g, 218 mmol) as a white solid.

$^1$H NMR (400 MHz, DMSO-d6) δ=7.82 (d, J=2.0 Hz, 1H), 7.55-7.52 (m, 1H), 7.13 (d, J=8.3 Hz, 1H), 4.83-4.68 (m, 2H), 4.17 (d, J=11.5 Hz, 1H), 3.79 (d, J=11.5 Hz, 1H), 1.65 (s, 3H) ppm.

Step 7. (4S)-4-Cyano-4-methyl-isochromane-6-carboxylic acid and (4R)-4-Cyano-4-methyl-isochromane-6-carboxylic acid Palladium acetate (490 mg, 2.18 mmol) and $K_2CO_3$ (9.05 g, 65.4 mmol) were added to a mixture 6-bromo-4-methyl-isochromane-4-carbonitrile (11 g, 43.6 mmol) and DCPP-2HBF$_4$ (2.67 g, 4.36 mmol) in DMSO (110 mL) and $H_2O$ (5.5 mL). The mixture was degassed and purged with CO (g) three times, and then the mixture was stirred at 100° C. for 4 hrs under an atmosphere of CO (15 psi). The aqueous layer was then extracted with EA (1 L×2). The aqueous phase was acidified with HCl (2N) until a pH=3 was achieved. The aqueous layer was then extracted with EA (1 L×3). The combined organic phase was washed with brine (1 L), dried over $Na_2SO_4$, filtered, and concentrated under vacuum. The crude product was triturated with EA (100 mL) at 20° C. for 15 min, then the solid was collected by filtration, washed with EA (50 mL), and dried affording the title compounds (30 g, 138 mmol) as a white solid. The mixture of stereoisomers was purified by SFC separation (column: DAICEL CHIRALPAK AD-H (250 mm×30 mm, 5 μm); mobile phase: [0.1% $NH_3$·$H_2O$ MEOH]; B %: 20%-20%, 3.52 min; 514 minmin). Peak 1 was concentrated under reduced pressure to give an oil. The oil was dissolved in water (200 mL). The mixture was acidified with HCl (2N) to pH=3 and extracted with EA (100 mL×3). The combined organic phase washed with brine (100 mL), dried over $Na_2SO_4$, filtered, and concentrated under vacuum affording Intermediate 1 (4.15 g, 19.1 mmol) as an off-white solid. Peak 2 was concentrated under reduced pressure to give an oil. The oil was dissolved in water (200 mL). The mixture was acidified with HCl (2N) to pH=3 and extracted with EA (100 mL×3). The combined organic phase washed with brine (100 mL), dried over $Na_2SO_4$, filtered, and concentrated under vacuum affording Intermediate 2 (4.1 g, 18.9 mmol) as an off-white solid.

Intermediate 1: Chiral SFC: AD-3_5CM_MEOH(DEA)_5_40_3ML_AT35.M; RT=0.89 min LCMS (ESI) m/z: [M+H]+=218.3.

$^1$HNMR (400 MHz, DMSO-d6) δ=13.17 (br s, 1H), 8.07 (d, J=1.6 Hz, 1H), 7.89-7.87 (m, 1H), 7.29 (d, J=8.0 Hz, 1H), 4.95-4.79 (m, 2H), 4.19 (d, J=11.6 Hz, 1H), 3.88 (d, J=11.6 Hz, 1H), 1.67 (s, 3H) ppm.

Intermediate 2: Chiral SFC: AD-3_5CM_MEOH(DEA)_5_40_3ML_AT35.M; RT=1.03 min LCMS (ESI) m/z: [M+H]+=218.3.

$^1$H NMR (400 MHz, DMSO-d6) δ=13.17 (br s, 1H), 8.07 (d, J=1.6 Hz, 1H), 7.89-7.87 (m, 1H), 7.29 (d, J=8.0 Hz, 1H), 4.95-4.79 (m, 2H), 4.19 (d, J=11.6 Hz, 1H), 3.88 (d, J=11.6 Hz, 1H), 1.67 (s, 3H) ppm.

Intermediates 3 and 4: (4R)-4-Hydroxy-4-methylisochromane-6-carboxylic acid and (4S)-4-Hydroxy-4-methylisochromane-6-carboxylic acid

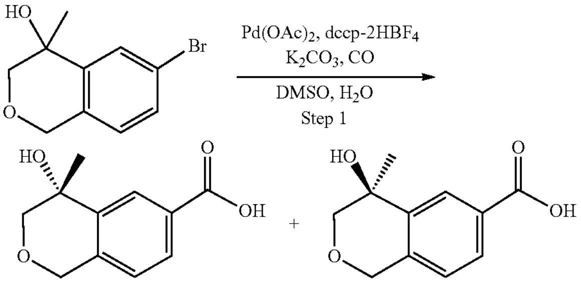

Intermediate 3

Intermediate 4

(4R)-4-Hydroxy-4-methylisochromane-6-carboxylic acid and (4S)-4-Hydroxy-4-methylisochromane-6-carboxylic acid A mixture of 6-bromo-4-methyl-isochroman-4-ol (1.00 g, 4.11 mmol), dccp·2BF$_4$ (252 mg, 0.41 mmol), $K_2CO_3$ (853 mg, 6.17 mmol), Pd(OAC)$_2$ (92.4 mg, 0.41 mmol) and $H_2O$ (1.48 mL, 82.3 mmol) in DMSO (10 mL) was degassed and purged with CO (g) three times. The mixture was stirred at 100° C. for 14 hrs under a CO atmosphere. The reaction mixture was filtered to remove the black solid and then diluted with water (60 mL) and extracted with EA (60 mL×2). The organic layer was discarded and the aqueous phase was adjusted to pH=6 with aqueous HCl. The aqueous solution was then extracted with EA (100 mL×3). The combined organic layer was washed with brine (200 mL×2), dried over anhydrous $Na_2SO_4$, filtered, and concentrated under reduced pressure affording a mixture of the title compounds (550 mg, 2.43 mmol) as a light yellow solid. The stereoisomers were separated by chiral SFC (column: DAICEL CHIRALPAK AD (250 mm*30 mm, 10 m); mobile phase: [0.1% $NH_3$·$H_2O$ IPA]; B %: 40%-40%, 4.0 min; 60 minmin). The desired fractions were collected and concentrated under reduced pressure. The product was diluted with water, adjusted to pH=4 with aq. HCl, then extracted with EA (80 mL×3). The combined organic layers were dried over anhydrous $Na_2SO_4$, filtered, and concentrated under reduced pressure affording Intermediate 3 (260 mg, 1.18 mmol) as a yellow solid and Intermediate 4 (240 mg, 1.04 mmol) as a yellow solid.

Intermediate 3: Chiral SFC: AD-3_5CM_IPA (DEA)_5_40_3ML_AT35.M; RT=1.537 min. LCMS (ESI) m/z: [M−18+H]+=191.1.

$^1$H NMR (400 MHz, DMSO-d6) δ=13.19-12.40 (m, 1H), 8.15 (d, J=1.6 Hz, 1H), 7.75-7.73 (m, 1H), 7.13 (d, J=8.0 Hz, 1H), 5.34 (s, 1H), 4.82-4.68 (m, 2H), 3.71-3.65 (m, 1H), 3.61-3.54 (m, 1H), 1.40 (s, 3H) ppm.

Intermediate 4: Chiral SFC: AD-3_5CM_IPA (DEA)_5_40_3ML_AT35.M; RT=1.926 min. LCMS (ESI) m/z: [M−17+H]+=191.1.

$^1$H NMR (400 MHz, DMSO-d6) δ=12.86 (br s, 1H), 8.15 (d, J=1.6 Hz, 1H), 7.75-7.73 (m, 1H), 7.13 (d, J=8.0 Hz, 1H), 5.34 (s, 1H), 4.84-4.67 (m, 2H), 3.73-3.62 (m, 1H), 3.62-3.53 (m, 1H), 1.40 (s, 3H) ppm.

Intermediates 5 and 6: (S)-4-Cyano-4-methylchroman-6-carboxylic acid and (R)-4-Cyano-4-methylchroman-6-carboxylic acid

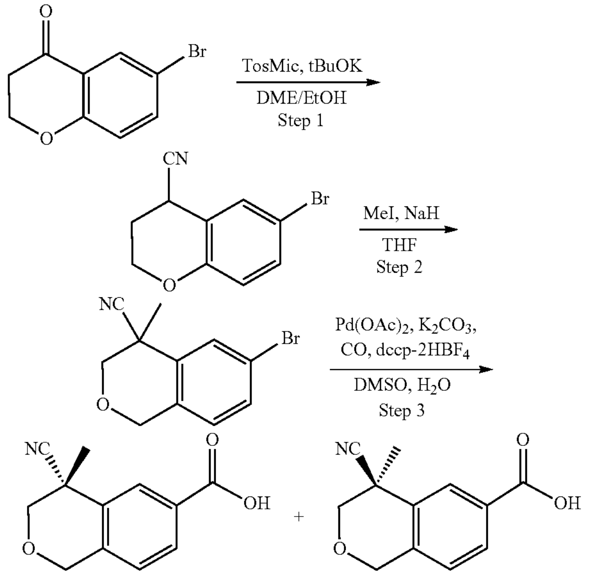

Intermediate 5 Intermediate 6

Step 1. 6-Bromochromane-4-carbonitrile

Potassium tert-butoxide (54.4 g, 484 mmol) was added to a solution of 6-bromochroman-4-one (50 g, 220 mmol) and 1-(isocyanomethylsulfonyl)-4-methyl-benzene (64.5 g, 330 mmol) in DME (2.5 L) and EtOH (100 mL) at 0° C. The reaction mixture was warmed and stirred at 25° C. for 16 hrs. The reaction mixture was poured into water (2 L) and adjusted to pH=6~7 with $NH_4Cl$ (56.9 g). The organic solvents were removed in vacuo. The aqueous phase was extracted with EA (1.5 L×2). The combined organic layers were dried over anhydrous $Na_2SO_4$ and concentrated in vacuum. The residue was purified by FCC (Eluent: PE:EA=20:1). The purified residue was combined with another batch that was run under the same conditions and triturated with MTBE (150 mL). The solid was filtered and concentrated in vacuo affording the title compound (40 g, 151 mmol) as a white solid.

$^1$H NMR (400 MHz, $CDCl_3$) δ=7.43-7.42 (m, 1H), 7.33-7.31 (m, 1H), 6.76 (d, J=8.8 Hz, 1H), 4.36-4.30 (m, 1H), 4.26-4.21 (m, 1H), 4.01-3.98 (m, 1H), 2.35-2.31 (m, 2H) ppm.

Step 2. 6-Bromo-4-methyl-chromane-4-carbonitrile

Sodium hydride (8.40 g, 210 mmol, 60% purity) was added to a solution of 6-bromochromane-4-carbonitrile (25 g, 105 mmol) in THE (250 mL) at 0° C. The reaction mixture was stirred at 0° C. for 0.5 hr, then MeI (32.7 mL, 525 mmol) was added. The reaction mixture was stirred at 25° C. for 2 hrs. The reaction mixture was diluted with saturated $NH_4Cl$ (aq., 800 mL) and extracted with EA (800 mL×3). The combined organic layer was dried over anhydrous $Na_2SO_4$, filtered, and concentrated in vacuo. The crude residue was purified by FCC (Eluent: PE/EA=1:0 to 5:1) affording the title compound (18 g, 69.2 mmol) as a light yellow solid.

$^1$H NMR (400 MHz, DMSO-d6) δ=7.69 (d, J=2.4 Hz, 1H), 7.41-7.38 (m, 1H), 6.83 (d, J=8.8 Hz, 1H), 4.33-4.25 (m, 1H), 4.24-4.15 (m, 1H), 2.41-2.35 (m, 1H), 2.17-2.11 (m, 1H), 1.75 (s, 3H) ppm.

Step 3. (S)-4-Cyano-4-methylchroman-6-carboxylic acid and (R)-4-Cyano-4-methylchroman-6-carboxylic acid A mixture of 6-bromo-4-methyl-chromane-4-carbonitrile (8.5 g, 33.7 mmol), dccp-2HBF$_4$ (2.06 g, 3.37 mmol), $K_2CO_3$ (6.99 g, 50.6 mmol), $Pd(OAc)_2$ (757 mg, 3.37 mmol), and $H_2O$ (1.22 mL, 67.4 mmol) in DMSO (85 mL) was degassed and purged with CO (g) three times. The mixture was then stirred at 100° C. for 14 hrs under a CO (15 psi) atmosphere. The reaction mixture combined with a 2$^{nd}$ batch and filtered to remove the black solid. The filtrate was diluted with water (60 mL) and extracted with EA (60 mL×2). The organic layer was discarded and the pH of aqueous phase was adjusted to pH=4 with aq. HCl resulting in a precipitate. The mixture was filtered and the white solid was washed with water (40 mL×2), filtered, and dried in vacuo affording a mixture of the title compounds (12 g, 51.2 mmol) as a white solid. Intermediates 5 and 6 were separated by chiral SFC (column: DAICEL CHIRALPAK AD-H (250 mm*30 mm, 5 μm); mobile phase: [0.1% $NH_3$—$H_2O$ MEOH]; B %: 30%-30%, 4.7 min; 600 min.). The fraction was concentrated under reduced pressure to get Intermediate 5 (5.3 g, 24.3 mmol) as an off-white solid and Intermediate 6 (5.2 g, 23.6 mmol) as an off-white solid.

Intermediate 5: Chiral SFC: AD-3_5CM_MEOH (DEA) _5_40_3ML_AT35.M, RT=0.958 min LCMS (ESI) m/z: [M+H]+=218.2.

$^1$H NMR (400 MHz, DMSO-d6) δ=8.00 (d, J=2.0 Hz, 1H), 7.79-7.76 (m, 1H), 6.88 (d, J=8.4 Hz, 1H), 4.37-4.22 (m, 2H), 2.45-2.39 (m, 1H), 2.22-1.75 (m, 1H), 1.76 (s, 3H) ppm.

Intermediate 6: Chiral SFC: AD-3_5CM_MEOH (DEA) _5_40_3ML_AT35.M, RT=1.294 LCMS (ESI) m/z: [M+H]+=218.2.

$^1$H NMR (400 MHz, DMSO-d6) δ=8.00 (d, J=2.0 Hz, 1H), 7.79-7.76 (m, 1H), 6.89 (d, J=8.4 Hz, 1H), 4.37-4.23 (m, 2H), 2.50-2.41 (m, 1H), 2.22-2.18 (m, 1H), 1.76 (s, 3H) ppm.

Intermediates 7 and 8: (4R)-4-Fluoro-4-methyl-isochromane-6-carboxylic acid and (4S)-4-Fluoro-4-methyl-isochromane-6-carboxylic acid

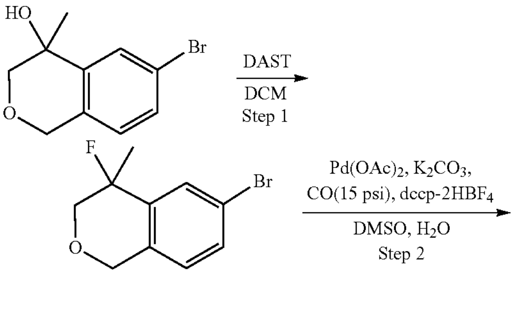

-continued

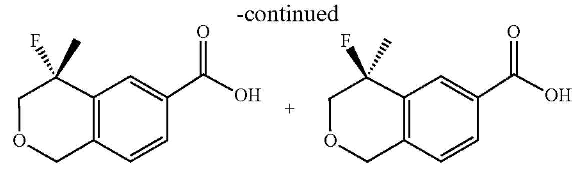

Intermediate 7 Intermediate 8

Step 1. 6-Bromo-4-fluoro-4-methyl-isochromane

DAST (52.2 mL, 395 mmol,) was added dropwise to a mixture of Intermediate 8 (32 g, 132 mmol) in DCM (320 mL) at 0° C. The mixture was warmed and stirred at 25° C. for 20 min. The mixture was poured into ice water (600 mL) and extracted with DCM (250 mL×3). The combined organic layers were dried over anhydrous $Na_2SO_4$, filtered, and concentrated in vacuo. The residue was purified by FCC (Eluent: PE:EA=30:1) affording the title compound (24.5 g, 99.96 mmol) as a yellow oil.

LCMS (ESI) m/z: [M−18+H]+=226.9.

$^1$H NMR (400 MHz, $CDCl_3$) δ=7.72 (s, 1H), 7.45-7.42 (m, 1H), 6.93 (d, J=8.0 Hz, 1H), 4.84-4.74 (m, 1H), 4.73-4.64 (m, 1H), 4.06-4.00 (m, 1H), 3.86-3.78 (m, 1H), 1.76-1.64 (m, 3H) ppm.

Step 2. (4R)-4-Fluoro-4-methyl-isochromane-6-carboxylic acid and (4S)-4-Fluoro-4-methyl-isochromane-6-carboxylic acid Palladium acetate (687 mg, 3.06 mmol), dccp-2HBF$_4$ (1.87 g, 3.06 mmol), $K_2CO_3$ (6.34 g, 45.9 mmol), and $H_2O$ (7.50 mL) were added to a solution of 6-bromo-4-fluoro-4-methyl-isochromane (7.5 g, 30.6 mmol) in DMSO (75 mL) at 25° C. The mixture was purged with CO (g) three times. The mixture was heated and stirred at 100° C. for 4 hrs under an atmosphere of CO (15 psi). The reaction mixture was poured into $H_2O$ (1.2 L) and extracted with EA (400 mL×2). The aqueous phase was acidified with 1N HCl to pH=5 and extracted with EA (300 mL×3). The combined organic layers were washed with brine (300 mL×2), dried over anhydrous $Na_2SO_4$, filtered, and concentrated in vacuo affording a mixture of the title compounds (2.6 g, 12.2 mmol) as a white solid.

$^1$H NMR (400 MHz, DMSO-d6) δ=13.42-12.67 (m, 1H), 8.13 (s, 1H), 7.92-7.88 (m, 1H), 7.29 (d, J=8.0 Hz, 1H), 4.91-4.82 (m, 1H), 4.77-4.68 (m, 1H), 4.10-4.01 (m, 1H), 3.89-3.76 (m, 1H), 1.70-1.58 (m, 3H) ppm.

Intermediates 7 and 8 were separated by SFC (Column: DAICEL CHIRALPAK IG (250 mm*30 mm, 10 m); mobile phase: [0.1% $NH_3$—$H_2O$ MeOH]; B %: 20%-20%, 3.4 min; 2300 minmin) to give two peaks. Peak 1 was concentrated under reduced pressure to remove 95% MeOH and poured into $H_2O$ (500 mL). The mixture was acidified with HCl (1N) to pH=5 and extracted with EA (150 mL×3). The combined organic layers were washed with brine (100 mL), dried over anhydrous $Na_2SO_4$, filtered, and concentrated under reduced pressure to afford Intermediate 7 (1.06 g, 5.04 mmol) as a white solid. Peak 2 was concentrated under reduced pressure and poured into $H_2O$ (500 mL). The mixture was acidified with HCl (1N) to pH=5 and extracted with EA (150 mL×3). The combined organic layers were washed with brine (100 mL), dried over anhydrous $Na_2SO_4$, filtered, and concentrated under reduced pressure to afford Intermediate 8 (1.07 g, 5.09 mmol) as a white solid.

Intermediate 7: Chiral SFC: AD-3_5CM_MEOH (DEA)_5_40_3ML_AT35.M, RT=0.819 min.

$^1$H NMR (400 MHz, DMSO-d6) δ=13.08 (br s, 1H), 8.13 (s, 1H), 7.92-7.88 (m, 1H), 7.29 (d, J=8.0 Hz, 1H), 4.90-4.81 (m, 1H), 4.78-4.68 (m, 1H), 4.05-4.01 (m, 1H), 3.87-3.78 (m, 1H), 1.72-1.58 (m, 3H) ppm.

Intermediate 8: Chiral SFC: AD-3_5CM_MEOH (DEA)_5_40_3ML_AT35.M, RT=0.903 min.

$^1$H NMR (400 MHz, DMSO-d6) δ=13.31-12.88 (m, 1H), 8.13 (s, 1H), 7.92-7.88 (m, 1H), 7.29 (d, J=8.0 Hz, 1H), 4.90-4.81 (m, 1H), 4.78-4.68 (m, 1H), 4.08-4.01 (m, 1H), 3.89-3.77 (m, 1H), 1.72-1.58 (m, 3H) ppm.

Intermediates 9 and 10: (R)-1-(tert-Butoxycarbonyl)-4-cyano-4-methyl-1,2,3,4-tetrahydroquinoline-6-carboxylic acid and (S)-1-(tert-Butoxycarbonyl)-4-cyano-4-methyl-1,2,3,4-tetrahydroquinoline-6-carboxylic acid

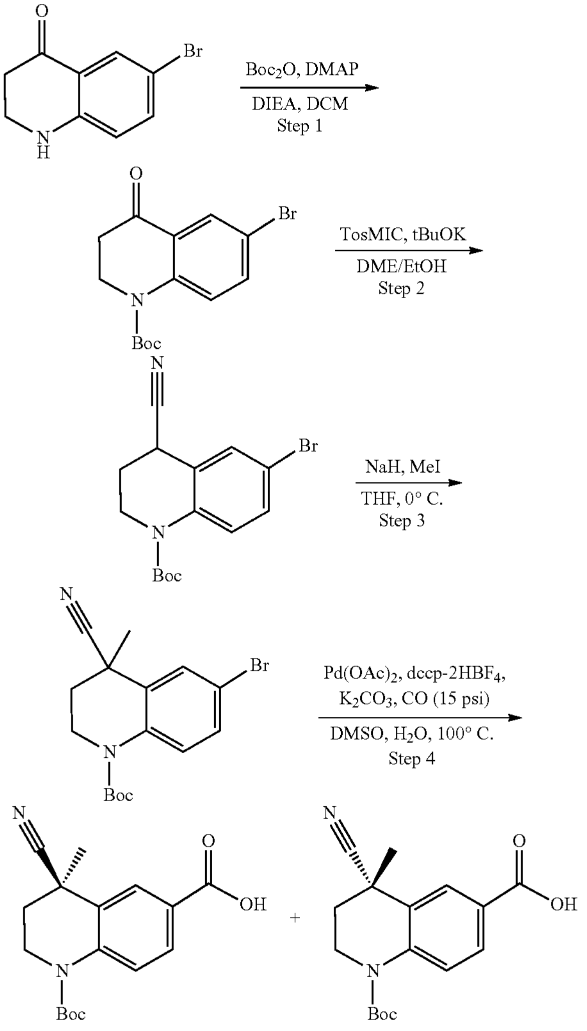

Intermediate 9 Intermediate 10

Step 1. tert-Butyl 6-bromo-4-oxo-3,4-dihydroquinoline-1(2H)-carboxylate

A mixture of 6-bromo-2,3-dihydro-1H-quinolin-4-one (2 g, 8.85 mmol), $Boc_2O$ (3.86 g, 17.7 mmol), DMAP (108 mg, 0.88 mmol), and DIEA (3.1 mL, 17.7 mmol) in DCM (20 mL) was stirred at 60° C. for 12 hrs. The mixture was concentrated under reduced pressure and then poured into water (5 mL). The aqueous solution was then extracted with EA (5 mL×3). The combined organic layers were dried over anhydrous $Na_2SO_4$, filtered, and concentrated under reduced pressure. The residue was purified by FCC (Eluent: 0 to 12% EA in PE) affording the title compound (1.75 g, 5.37 mmol) as a yellow oil.

LCMS (ESI) m/z: [M+H]+=326.0.

$^1$H NMR (400 MHz, DMSO-d6) δ=7.89-7.88 (m, 1H), 7.75 (d, J=1.2 Hz, 2H), 4.11-4.07 (m, 2H), 2.79-2.75 (m, 2H), 1.51 (s, 9H) ppm.

Step 2. tert-Butyl 6-bromo-4-cyano-3,4-dihydroquinoline-1(2H)-carboxylate

Potassium tert-butoxide (1.38 g, 12.26 mmol) was added to a mixture of tert-Butyl 6-bromo-4-oxo-3,4-dihydroquinoline-1(2H)-carboxylate (2 g, 6.13 mmol) and 1-(isocyanomethylsulfonyl)-4-methyl-benzene (1.80 g, 9.20 mmol) in DME (100 mL) and EtOH (4 mL) at 0° C. The mixture was stirred at 25° C. for 12 hrs. The reaction mixture was poured into water (5 mL) and extracted with EA (5 mL×3). The combined organic layers were dried over anhydrous $Na_2SO_4$, filtered, and concentrated under reduced pressure. The residue was purified by FCC (Eluent: 0 to 20% EA in PE) affording the title compound (900 mg, 2.67 mmol) as a yellow oil.

LCMS (ESI) m/z: [M−55]+=281.0.

$^1$H NMR (400 MHz, DMSO-d6) δ=7.67 (d, J=8.8 Hz, 1H), 7.55 (d, J=2.4 Hz, 1H), 7.51-7.47 (m, 1H), 4.48-4.44 (m, 1H), 3.74-3.69 (m, 2H), 2.21-2.15 (m, 2H), 1.48 (s, 9H) ppm.

Step 3. tert-Butyl 6-bromo-4-cyano-4-methyl-3,4-dihydroquinoline-1(2H)-carboxylate Sodium hydride (89 mg, 2.22 mmol, 60% purity) was added slowly to a mixture of tert-butyl 6-bromo-4-cyano-3,4-dihydroquinoline-1(2H)-carboxylate (500 mg, 1.48 mmol) in THE (5 mL) at 0° C. The mixture was stirred at 0° C. for 0.5 hr, then MeI (0.14 mL, 2.22 mmol) was added. The reaction mixture was warmed to 25° C. and stirred for 2 hrs. The reaction mixture was quenched with saturated $NH_4Cl$ (20 mL) and extracted with EA (10 mL×3). The combined organic layers were dried over anhydrous $Na_2SO_4$, filtered, and concentrated under reduced pressure. The resulting oil was purified by FCC (Eluent: 0 to 50% EA in PE) affording the title compound (370 mg, 1.01 mmol) as yellow oil.

LCMS (ESI) m/z: [M−55]+=295.0

$^1$H NMR (400 MHz, CDCl3) δ=7.66 (d, J=8.8 Hz, 1H), 7.56 (d, J=2.0 Hz, 1H), 7.38-7.36 (m, 1H), 3.89-3.80 (m, 2H), 2.40-2.34 (m, 1H), 2.04-2.00 (m, 1H), 1.73 (s, 3H), 1.53 (s, 9H) ppm.

Step 4. (R)-1-(tert-Butoxycarbonyl)-4-cyano-4-methyl-1,2,3,4-tetrahydroquinoline-6-carboxylic acid & (S)-1-(tert-Butoxycarbonyl)-4-cyano-4-methyl-1,2,3,4-tetrahydroquinoline-6-carboxylic acid Palladium acetate (11.8 mg, 0.053 mmol) and dccp·2HBF$_4$ (64.5 mg, 0.11 mmol) were added to a mixture of tert-butyl 6-bromo-4-cyano-4-methyl-3,4-dihydroquinoline-1(2H)-carboxylate (370 mg, 1.05 mmol) and $K_2CO_3$ (218 mg, 1.58 mmol) in DMSO (3 mL) and $H_2O$ (1 mL) at 25° C. The mixture was degassed and purged with CO (g, 15 psi) three times, and then the mixture was warmed stirred at 100° C. under CO (g) for 12 hrs. The reaction mixture was filtered and the filtrate was purified by reversed-phase HPLC affording a mixture of the title compounds (190 mg, 0.60 mmol) as a white solid. The stereoisomers were separated via chiral SFC (DAICEL CHIRALPAK AD (250 mm*30 mm, 10 m); mobile phase: [0.1% $NH_3$—$H_2O$ MEOH]; B %: 20%-20%, 1.75 min; 75 minmin) to afford Intermediate 9 (80 mg, 0.25 mmol) as light yellow solid and Intermediate 10 (90 mg, 0.28 mmol) as light yellow solid.

Intermediate 9: LCMS (ESI) m/a: [M−55]+=261.1

$^1$H NMR (400 MHz, DMSO-d6) δ=7.96 (d, J=1.6 Hz, 1H), 7.80-7.78 (m, 1H), 7.69 (d, J=8.8 Hz, 1H), 3.79-3.74 (m, 2H), 2.36-2.32 (m, 1H), 2.07-2.05 (m, 1H), 1.71 (s, 3H), 1.47 (s, 9H) ppm. Chiral SFC: AD-3_5CM_MEOH(DEA)_5_40_3ML_AT35.M, Rt=0.766 min, ee value=98.82%.

Intermediate 10: LCMS (ESI) m/a: [M−55]+=261.1

$^1$H NMR (400 MHz, DMSO-d6) δ=7.96 (br s, 1H), 7.81-7.78 (m, 1H), 7.71 (br d, J=8.8 Hz, 1H), 3.80-3.74 (m, 2H), 2.36-2.31 (m, 1H), 2.07-2.04 (m, 1H), 1.71 (s, 3H), 1.48 (s, 9H) ppm.

Chiral SFC: AD-3_5CM_MEOH(DEA)_5_40_3ML_AT35.M. Rt=0.916 min, ee value=93.82%.

Intermediate 11: tert-Butyl N-[1-(4-bromo-2-pyridyl)-2-methoxy-ethyl]carbamate

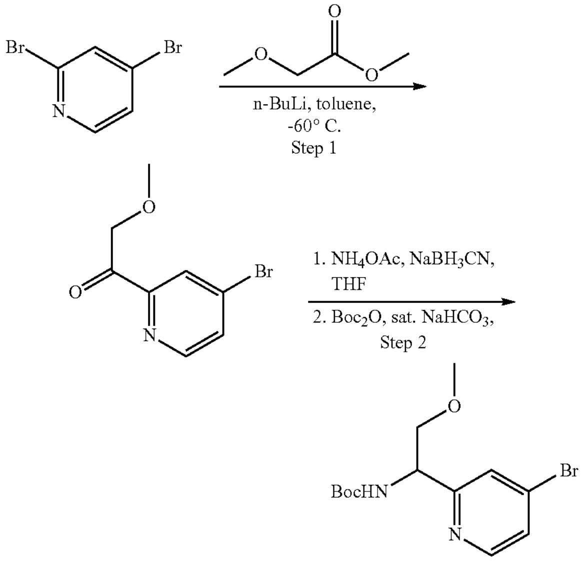

Intermediate 11

Step 1. 1-(4-Bromo-2-pyridyl)-2-methoxy-ethanone n-Butyl lithium (2.5 M, 16.9 mL) was added to a solution of 2,4-dibromopyridine (10.0 g, 42.2 mmol) in toluene (400 mL) at −60° C. The mixture was stirred at −60° C. for 1 hr, and then methyl 2-methoxyacetate (7.53 mL, 76.0 mmol) was added to the mixture and the mixture was stirred at −60° C. for 1 hr. The reaction mixture was quenched by addition water (1 L), and then extracted with EA (1 L×2). The combined organic layers were washed with brine (1 L), dried over anhydrous $Na_2SO_4$, filtered, and concentrated under reduced pressure. The crude product was purified by FCC (Eluent: PE:EA=3:1) affording the title compound (5 g, 21.7 mmol) as a brown solid.

$^1H$ NMR (400 MHz, CDCl3) δ=8.45 (d, J=5.2 Hz, 1H), 8.23 (d, J=2.0 Hz, 1H), 7.68-7.66 (m, 1H), 5.01 (s, 2H), 3.54 (s, 3H) ppm.

Step 2. tert-Butyl N-[1-(4-bromo-2-pyridyl)-2-methoxy-ethyl]carbamate

Ammonium acetate (13.4 g, 174 mmol) and $NaBH_3CN$ (10.93 g, 174 mmol) were added to a solution of 1-(4-bromo-2-pyridyl)-2-methoxy-ethanone (4 g, 17.4 mmol) in THF (120 mL) at 20° C. The mixture was stirred at 20° C. for 2 hr. $Boc_2O$ (22.8 g, 104 mmol) and saturated $NaHCO_3$ (60 mL) were added to the reaction mixture and the mixture was stirred at 20° C. for 2 hrs. The reaction mixture was diluted with water (300 mL) and extracted with EA (300 mL×2). The combined organic layers were washed with brine (300 mL), dried over anhydrous $Na_2SO_4$, filtered, and concentrated under reduced pressure. The crude product was purified by FCC (Eluent: PE:EA=3:1) and concentrated under reduced pressure to give a white solid. The white solid was then re-purified by RPC. The fractions containing the title compound were collected and concentrated to remove the MeCN. The aqueous layer was basified with sodium carbonate (solid) until pH=9.0 was achieved. The aqueous solution was extracted with EA (100 mL×2). The combined organic layers were dried with anhydrous $Na_2SO_4$ and concentrated in vacuo affording the title compound (1.5 g, 4.19 mmol) as brown oil.

LCMS (ESI) m/z: [Br81M+H]+=333.1.

$^1H$ NMR (400 MHz, DMSO-d6) δ=8.41 (d, J=5.2 Hz, 1H), 7.62 (d, J=1.2 Hz, 1H), 7.58-7.56 (m, 1H), 7.37 (br d, J=8.8 Hz, 1H), 4.81-4.76 (m, 1H), 3.56-3.54 (m, 2H), 3.23 (s, 3H), 1.40-1.37 (m, 9H) ppm.

Intermediates 12 and 13: (S)-4-(Difluoromethyl)-4-fluoroisochroman-6-carboxylic acid and (R)-4-(Difluoromethyl)-4-fluoroisochroman-6-carboxylic acid

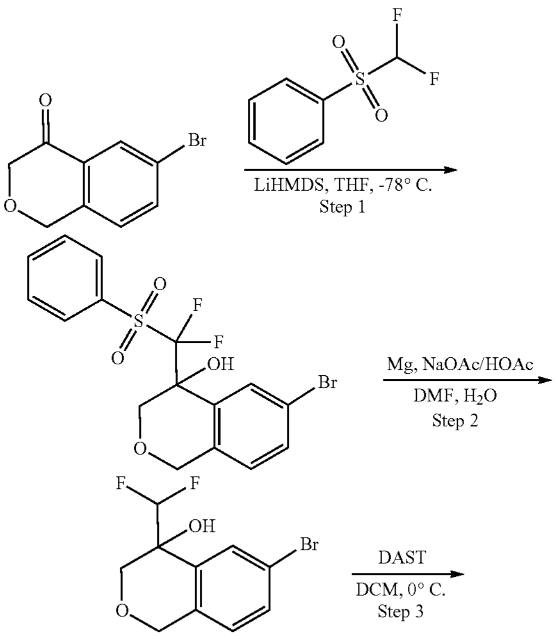

-continued

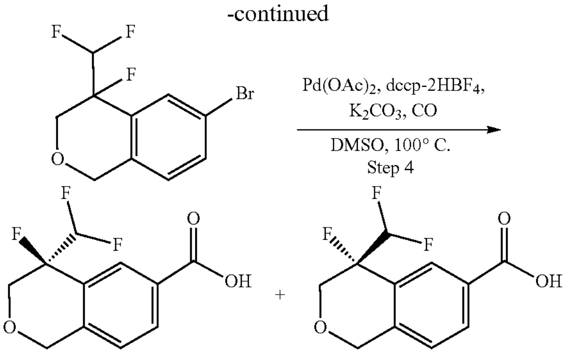

Intermediate 12 Intermediate 13

Step 1. 6-Bromo-4-(difluoro(phenylsulfonyl)methyl)isochroman-4-ol

LiHMDS (1 M, 26.4 mL) was added to a solution of 6-bromoisochroman-4-one (3 g, 13.2 mmol), difluoromethylsulfonylbenzene (2.8 mL, 19.8 mmol) in THE (30 mL) at −78° C. The mixture was stirred at −78° C. for 2 hr. The reaction mixture was poured into saturated aq. $NH_4Cl$ (50 mL) and extracted with EA (50 mL×2). The organic layer was washed with brine (50 mL) and dried over anhydrous $Na_2SO_4$, filtered and concentrated in vacuo. The residue was purified by FCC (Eluent: PE:EA=10:1 to 3:1) affording the title compound (3 g, 6.70 mmol) as yellow solid.

LCMS (ESI) m/z: [M+$H_2O$]+=435.8, 437.8.

$^1H$ NMR (400 MHz, $CDCl_3$) δ=8.04 (d, J=7.6 Hz, 2H), 7.90-7.89 (m, 1H), 7.85-7.76 (m, 1H), 7.71-7.62 (m, 2H), 7.49-7.47 (m, 1H), 6.97 (d, J=8.4 Hz, 1H), 5.00 (d, J=12.4 Hz, 1H), 4.93-4.73 (m, 2H), 3.93-3.88 (m, 1H), 3.83 (s, 1H).

Step 2. 6-Bromo-4-(difluoromethyl)isochroman-4-ol

Magnesium (2.61 g, 107 mmol) was added to a solution of 6-bromo-4-(difluoro(phenylsulfonyl)methyl)isochroman-4-ol (3 g, 7.16 mmol) and NaOAc/HOAc (aq., 8 M, 44.7 mL) in DMF (100 mL). The mixture was stirred at 25° C. for 2 hrs. The reaction mixture was poured into water (50 mL), and then extracted with EA (50 mL×3). The combined organic layer was washed with brine (100 mL), dried over anhydrous $Na_2SO_4$, filtered, and concentrated in vacuo. The residue was purified by FCC (Eluent: PE:EA=10:1 to 3:1) affording the title compound (1.5 g, 5.37 mmol) as colorless oil.

LCMS (ESI) m/z: [79BrM−$H_2O$]+=260.9.

$^1H$ NMR (400 MHz, $CDCl_3$) δ=7.83-7.60 (m, 1H), 7.51-7.33 (m, 1H), 7.11-6.93 (m, 1H), 6.25-5.88 (m, 1H), 4.92-4.70 (m, 2H), 4.26-4.17 (m, 1H), 3.87-3.66 (m, 1H), 2.75-2.58 (m, 1H).

Step 3. 6-Bromo-4-(difluoromethyl)-4-fluoroisochroman

DAST (1.33 mL, 10.0 mmol) was added to a solution of 6-bromo-4-(difluoromethyl)isochroman-4-ol (1.4 g, 5.02 mmol) in DCM (20 mL) at 0° C. The mixture was stirred at 0° C. for 2 hr. The reaction mixture was poured into water (50 mL) and extracted with DCM (20 mL×2). The organic layer was washed with brine (20 mL) and dried over anhydrous $Na_2SO_4$, filtered, and concentrated in vacuo. The residue was purified by FCC (Eluent: PE:EA=10:1 to 5:1) affording the title compound (900 mg, 2.88 mmol) as colorless oil.

$^1$H NMR (400 MHz, $CDCl_3$) δ=7.73-7.51 (m, 1H), 7.48-7.28 (m, 1H), 7.08-6.89 (m, 1H), 6.20-5.80 (m, 1H), 4.82-4.61 (m, 2H), 4.33-4.18 (m, 1H), 4.01-3.82 (m, 1H).

Step 4. (S)-4-(Difluoromethyl)-4-fluoroisochroman-6-carboxylic acid and (R)-4-(Difluoromethyl)-4-fluoroisochroman-6-carboxylic acid Palladium acetate (34.0 mg, 0.15 mmol), $K_2CO_3$ (627 mg, 4.54 mmol) and dccp-·$2HBF_4$ (185 mg, 0.30 mmol) were added to a solution of 6-bromo-4-(difluoromethyl)-4-fluoroisochroman (850 mg, 3.02 mmol), in $H_2O$ (0.11 mL) and DMSO (10 mL). The mixture was stirred at 100° C. for 16 hrs under CO (g, 15 psi). The reaction mixture was poured into water (20 mL) and extracted with EA (20 mL×2). The organic layer was washed with brine (20 mL), dried over anhydrous $Na_2SO_4$, and concentrated in vacuo. The crude product was purified by reverse phase column chromatography affording a mixture of the title compounds (450 mg, 1.64 mmol) as colorless oil. The mixture of stereoisomers was purified by SFC separation (column: DAICEL CHIRALPAK IG (250 mm*30 mm, 10 m); mobile phase: [0.1% $NH_3$—$H_2O$ MEOH]; B %: 20%-20%, 3 min; 36 minmin) to give intermediate 12 (220 mg, 0.89 mmol) as a colorless oil and intermediate 13 (220 mg, 0.89 mmol) as a colorless oil.

Intermediate 12: Chiral SFC: Chiralpak IG-3 50×4.6 mm I.D., RT=0.928 min.

LCMS (ESI) m/z: $[M+H_2O]+$=247.2.

$^1$H NMR (400 MHz, $CDCl_3$) δ=8.36 (s, 1H), 8.14 (d, J=8.0 Hz, 1H), 7.26 (d, J=8.4 Hz, 1H), 6.38-5.96 (m, 1H), 5.01-4.76 (m, 2H), 4.40-4.35 (m, 1H), 4.18-4.01 (m, 1H).

Intermediate 13: Chiral SFC: Chiralpak IG-3 50×4.6 mm I.D., RT=1.115 min.

LCMS (ESI) m/z: $[M+H_2O]+$=247.2.

$^1$H NMR (400 MHz, $CDCl_3$) δ=8.36 (s, 1H), 8.14 (d, J=8.0 Hz, 1H), 7.26 (d, J=8.4 Hz, 1H), 6.38-5.96 (m, 1H), 5.01-4.76 (m, 2H), 4.40-4.35 (m, 1H), 4.18-4.01 (m, 1H).

Intermediates 14 and 15: (R)-3-Cyano-3-methyl-2,3-dihydrobenzofuran-5-carboxylic acid & (S)-3-Cyano-3-methyl-2,3-dihydrobenzofuran-5-carboxylic acid

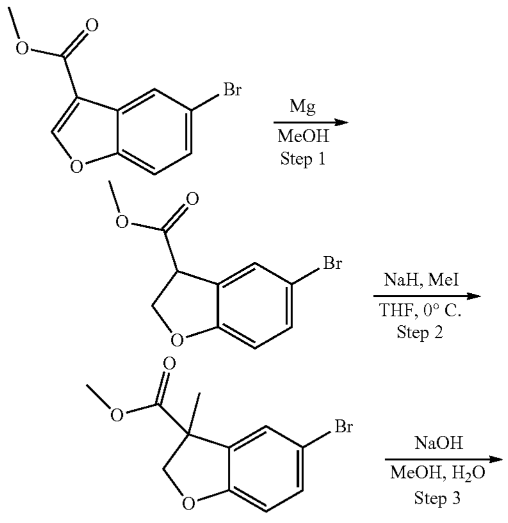

-continued

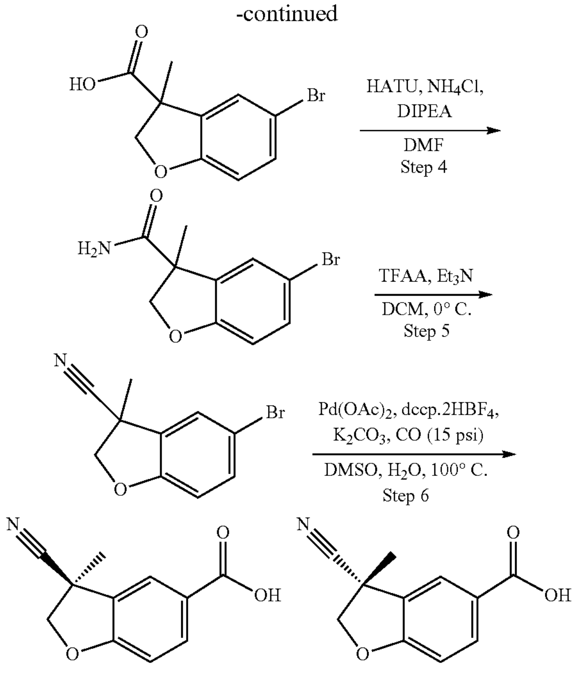

Intermediate 14 Intermediate 15

Step 1. Methyl 5-bromo-2,3-dihydrobenzofuran-3-carboxylate

Magnesium (9.53 g, 392 mmol) was added to a solution of methyl 5-bromobenzofuran-3-carboxylate (10 g, 39.2 mmol) in MeOH (400 mL). The reaction solution was stirred at 25° C. for 6 hrs. 4N HCl (200 mL) was carefully added to the solution. After complete dissolution of the magnesium metal, the solution was concentrated under reduced pressure to remove MeOH. The resulting mixture was partitioned between EA (200 mL×3) and water (100 mL). The organic phase was separated, dried over anhydrous $MgSO_4$, filtered, and concentrated in vacuo. The residue was purified by reversed phase chromatography and concentrated under reduced pressure to remove MeCN. The aqueous layer was then extracted with EA (50 mL×3). The combined organic layers were washed with brine (50 mL×2), dried over anhydrous $Na_2SO_4$, filtered, and concentrated under reduced pressure affording the title compound (6 g, 23.3 mmol) as a red oil.

$^1$H NMR (400 MHz, $CDCl_3$) δ=7.41-7.40 (m, 1H), 7.25-7.16 (m, 1H), 6.62 (d, J=8.8 Hz, 1H), 4.89-4.85 (m, 1H), 4.61-4.60 (m, 1H), 4.28-4.24 (m, 1H), 3.73 (s, 3H) ppm.

Step 2. Methyl 5-bromo-3-methyl-2,3-dihydrobenzofuran-3-carboxylate

Sodium hydride (350 mg, 8.75 mmol, 60% purity) was slowly added to a mixture of methyl 5-bromo-2,3-dihydrobenzofuran-3-carboxylate (1.5 g, 5.83 mmol) in THE (15 mL) at 0° C. The mixture was stirred at 0° C. for 0.5 hr, then MeI (0.54 mL, 8.75 mmol) was added drop-wise at 0° C. The reaction mixture was warmed up to 25° C. and stirred for 2 hrs. The reaction mixture was quenched with saturated aqueous $NH_4Cl$ (30 mL) and extracted with EA (10 mL×3). The combined organic phase was concentrated to afford yellow oil. The oil was purified by FCC (Eluent: 0 to 40% EA/PE) affording the title compound (670 mg, 2.43 mmol) as yellow oil.

LCMS (ESI) m/z: [79BrM+H]+=271.0.

$^1$H NMR (400 MHz, $CDCl_3$) δ=7.43 (d, J=2.0 Hz, 1H), 7.29-7.27 (m, 1H), 6.71 (d, J=8.4 Hz, 1H), 5.08 (d, J=9.2 Hz, 1H), 4.28 (d, J=9.2 Hz, 1H), 3.76 (s, 3H), 1.61 (s, 3H) ppm.

Step 3. 5-Bromo-3-methyl-2,3-dihydrobenzofuran-3-carboxylic acid

A mixture of methyl 5-bromo-3-methyl-2,3-dihydrobenzofuran-3-carboxylate (650 mg, 2.40 mmol) and NaOH (240 mg, 5.99 mmol) in MeOH (5 mL) and $H_2O$ (2 mL) was stirred at 25° C. for 1 hour. The reaction mixture was diluted with water (10 mL). HCl (1 M) was added to adjust pH to 4, and then the solution was extracted with EA (10 mL×3). The combined organic layer was concentrated affording the title compound (600 mg) as a white solid.

$^1$H NMR (400 MHz, DMSO-d6) δ=7.44 (d, J=2.0 Hz, 1H), 7.34-7.31 (m, 1H), 6.80 (d, J=8.4 Hz, 1H), 4.94 (d, J=9.2 Hz, 1H), 4.30 (d, J=9.2 Hz, 1H), 1.53 (s, 3H) ppm.

Step 4. 5-Bromo-3-methyl-2,3-dihydrobenzofuran-3-carboxamide

Ammonium chloride (1.25 g, 23.3 mmol) was added to a mixture of 5-bromo-3-methyl-2,3-dihydrobenzofuran-3-carboxylic acid (600 mg, 2.33 mmol), DIPEA (2.0 mL, 11.7 mmol), and HATU (1.33 g, 3.50 mmol) in DMF (6 mL) at 25° C. The mixture was stirred for 12 hrs. The reaction mixture was diluted with water (20 mL) and extracted with EA (10 mL×3). The combined organic layer was washed with brine (10 mL×3), dried over anhydrous $Na_2SO_4$, filtered, and concentrated in vacuo affording the title compound (580 mg) as a yellow solid.

LCMS (ESI) m/z: [79BrM+H]+=257.0.

$^1$H NMR (400 MHz, DMSO-d6) δ=7.60 (d, J=2.0 Hz, 1H), 7.38-7.24 (m, 3H), 6.76 (d, J=8.4 Hz, 1H), 5.03 (d, J=8.8 Hz, 1H), 4.20 (d, J=9.2 Hz, 1H), 1.52 (s, 3H) ppm.

Step 5. 5-Bromo-3-methyl-2,3-dihydrobenzofuran-3-carbonitrile

Triethylamine (0.95 mL, 6.79 mmol) was added to a mixture of 5-bromo-3-methyl-2,3-dihydrobenzofuran-3-carboxamide (580 mg, 2.26 mmol) in DCM (6 mL) at 0° C. TFAA (0.79 mL, 5.66 mmol) was then added at 0° C. The mixture was stirred for 10 minutes. The reaction mixture was diluted with water (20 mL) and extracted with DCM (10 mL×2). The combined organic phase was concentrated to afford yellow oil. The oil was purified by FCC (Eluent: 0 to 20% EA in PE) affording the title compound (500 mg, 1.89 mmol) as yellow oil.

$^1$H NMR (400 MHz, DMSO-d6) δ=7.80 (d, J=2.0 Hz, 1H), 7.47-7.44 (m, 1H), 6.93 (d, J=8.8 Hz, 1H), 4.96 (d, J=9.4 Hz, 1H), 4.46 (d, J=9.6 Hz, 1H), 1.74 (s, 3H) ppm.

Step 6. (R)-3-Cyano-3-methyl-2,3-dihydrobenzofuran-5-carboxylic acid and (S)-3-Cyano-3-methyl-2,3-dihydrobenzofuran-5-carboxylic acid Palladium acetate (18.9 mg, 0.084 mmol) and dccp·2HBF$_4$ (103 mg, 0.17 mmol) were added to a mixture of 5-bromo-3-methyl-2,3-dihydrobenzofuran-3-carbonitrile (400 mg, 1.68 mmol) and $K_2CO_3$ (348 mg, 2.52 mmol) in DMSO (3.2 mL) and $H_2O$ (0.8 mL) at 25° C. The mixture was degassed and purged with CO (g) three times. The mixture was stirred at 100° C. under a CO atmosphere (15 psi) for 12 hrs. The reaction mixture was filtered and the filtrate was purified by reversed-phase HPLC. The desired fractions were concentrated to remove MeCN and lyophilized affording the mixture of the title compounds (210 mg, 1.02 mmol) as a white solid. The stereoisomers were separated by chiral SFC (DAICEL CHIRALPAK IG (250 mm*30 mm, 10 m); mobile phase: [0.1% $NH_3$—$H_2O$ MEOH]; B %: 20%-20%, 3.9 min).

The eluent was concentrated to afford Intermediate 14 (90 mg, 0.44 mmol) as a red solid and Intermediate 15 (100 mg, 0.49 mol) as a light yellow solid.

Intermediate 14: Chiral SFC: AD-3_5CM_ETOH(DEA)_5_40_3ML_AT35.M, RT=0.924 min.

LCMS (ESI) m/z: [M+H]+=204.1.

$^1$HNMR (400 MHz, DMSO-d6) δ=8.02 (s, 1H), 7.90-7.88 (m, 1H), 6.98 (d, J=8.4 Hz, 1H), 4.99 (d, J=9.6 Hz, 1H), 4.52 (d, J=9.6 Hz, 1H), 1.75 (s, 3H) ppm.

Intermediate 15: Chiral SFC: AD-3_5CM_ETOH(DEA)_5_40_3ML_AT35.M, RT=1.078 min.

LCMS (ESI) m/z: [M+H]+=204.

$^1$H NMR (400 MHz, DMSO-d6) δ=8.02 (d, J=1.6 Hz, 1H), 7.89-7.87 (m, 1H), 6.97 (d, J=8.4 Hz, 1H), 4.99 (d, J=9.6 Hz, 1H), 4.52 (d, J=9.2 Hz, 1H), 1.75 (s, 3H) ppm.

Intermediate 16: 3-[3-(difluoromethyl)oxetan-3-yl]benzoic acid

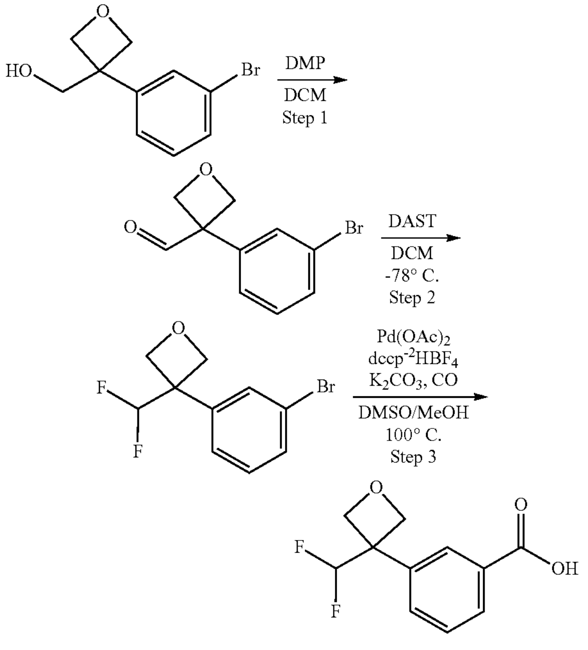

Intermediate 16

Step 1. 3-(3-Bromophenyl)oxetane-3-carbaldehyde

DMP (1.66 mL, 5.35 mmol) was added to a solution of [3-(3-bromophenyl)oxetan-3-yl]methanol (1 g, 4.11 mmol) in DCM (10 mL) at 0° C. The mixture was stirred for 1 hr at 25° C. The mixture was filtered and concentrated. The residue was purified by FCC (Eluent: PE:EA=100:1 to 1:100) affording the title compound (850 mg, 3.53 mmol) as colorless oil.

LCMS (ESI) m/z: [79BrM+H]+=259.0.

$^1$H NMR (400 MHz, $CDCl_3$) δ=9.71 (s, 1H), 7.46-7.40 (m, 1H), 7.24 (t, J=8.0 Hz, 1H), 7.18 (t, J=2.0 Hz, 1H), 6.99-6.92 (m, 1H), 5.08 (d, J=6.4 Hz, 2H), 4.91 (d, J=6.4 Hz, 2H) ppm.

Step 2. 3-(3-Bromophenyl)-3-(difluoromethyl)oxetane

DAST (1.15 mL, 8.71 mmol) was added to a solution of 3-(3-bromophenyl)oxetane-3-carbaldehyde (700 mg, 2.90 mmol) in DCM (7 mL) at −78° C. The mixture was warmed and stirred for 1 hr at 0° C. The mixture was poured into saturated aqueous solution of $NaHCO_3$ (5 mL). The organic layer was collected and concentrated in vacuo. The residue was purified by FCC (Eluent: PE:EA=100:1 to 1:1) affording the title compound (500 mg, 1.90 mmol) as brown oil.

$^1$H NMR (400 MHz, $CDCl_3$) δ=7.59-7.45 (m, 1H), 7.34-7.29 (m, 1H), 7.26 (s, 1H), 7.11-6.94 (m, 1H), 6.43-5.96 (m, 1H), 4.99 (s, 4H) ppm.

Step 3. 3-[3-(Difluoromethyl)oxetan-3-yl]benzoic acid

Palladium acetate (6.40 mg, 0.029 mmol), dccp·2HBF$_4$ (34.9 mg, 0.057 mmol), and $K_2CO_3$ (118 mg, 0.86 mmol was added to a solution of 3-(3-bromophenyl)-3-(difluoromethyl)oxetane (150 mg, 0.57 mmol) in DMSO (5 mL) and $H_2O$ (2.5 mL) at 25° C. The mixture was degassed and purged with CO (g) three times, and then the mixture was stirred at 100° C. for 16 hrs under a CO atmosphere (15 psi). The mixture was extracted with EA (5 ml). The aqueous layer was adjusted pH to 5-6 with aqueous HCl (1 M) and extracted with EA (5 ml×3). The organic layers were combined, dried over anhydrous $Na_2SO_4$, filtered, and concentrated in vacuo affording the title compound (120 mg, 0.53 mmol) as colorless oil.

LCMS (ESI) m/z: [M+H]+=229.1.

Intermediate 17: 4-(3-Oxocyclobutyl)picolinonitrile

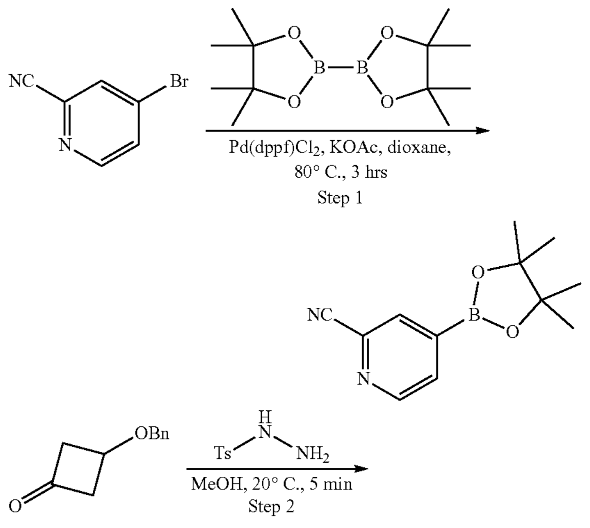

-continued

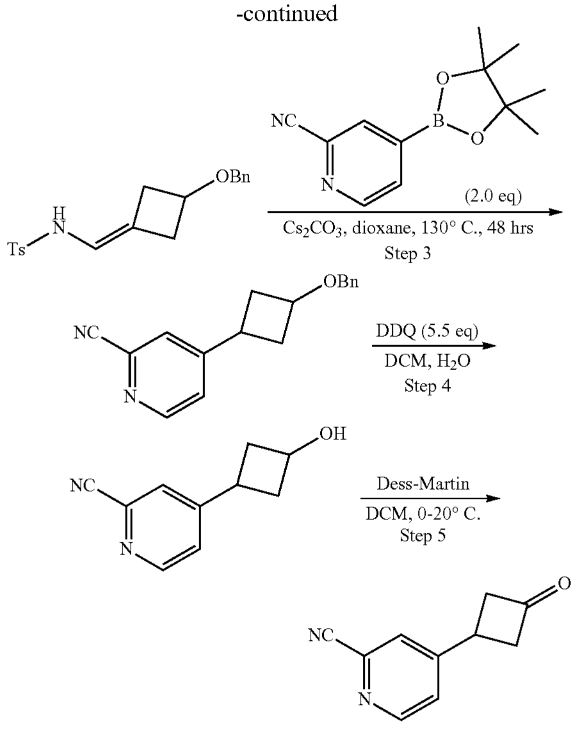

Intermediate 17

Step 1: 4-(4,4,5,5-Tetramethyl-1,3,2-dioxaborolan-2-yl)picolinonitrile

To a solution of 4-bromopyridine-2-carbonitrile (25 g, 136.61 mmol) and 4,4,5,5-tetramethyl-2-(4,4,5,5-tetramethyl-1,3,2-dioxaborolan-2-yl)-1,3,2-dioxaborolane (41.63 g, 163.93 mmol) in dioxane (250 mL) was added KOAc (40.22 g, 409.82 mmol) and Pd(dppf)$Cl_2$·$CH_2C_{12}$ (3 g, 3.67 mmol). The mixture was stirred at 80° C. for 3 hrs. The reaction mixture was poured into water (1000 mL), the solution was extracted with EA (1000 mL*2), the combined organic layer was washed with brine (2000 mL), dried over $Na_2SO_4$, filtered and concentrated. The residue was purified by column chromatography ($SiO_2$, Petroleum ether/Ethyl acetate=10:1-1:1) to give the title compound (24 g, 104.32 mmol, 76.36% yield) as a white solid.

LCMS (ESI) m/z: $[M+H]^+$=231.1

$^1$H NMR (400 MHz, DMSO-d$_6$) δ=8.79 (d, J=4.4 Hz, 1H), 8.04 (s, 1H), 7.87 (d, J=4.8 Hz, 1H), 1.31 (s, 12H) ppm

Step 2: N'-(3-(Benzyloxy)cyclobutylidene)-4-methylbenzenesulfonohydrazide

To a solution of 3-benzyloxycyclobutanone (15 g, 85.13 mmol) in MeOH (150 mL) was added 4-methylbenzenesulfonohydrazide (15.85 g, 85.13 mmol). The mixture was stirred at 20° C. for 5 min. The reaction mixture was filtered, the filter cake was washed MeOH (30 mL) and the filtrate dried in vacuo to give the title compound (23 g, 66.78 mmol, 78.45% yield) as a white solid.

Step 3: 4-(3-(Benzyloxy)cyclobutyl)picolinonitrile

To a solution of N'-(3-(benzyloxy)cyclobutylidene)-4-methylbenzenesulfonohydrazide (23 g, 66.78 mmol) and 4-(4,4,5,5-tetramethyl-1,3,2-dioxaborolan-2-yl)picolinonitrile (23.05 g, 100.17 mmol) in dioxane (450 mL) was added $Cs_2CO_3$ (65.27 g, 200.33 mmol). The mixture was refluxed at 130° C. for 48 hr. The reaction mixture was diluted with water (800 mL) and extracted with EA (300 mL*3). The combined organic layers were washed with dried over $Na_2SO_4$, filtered and concentrated under reduced pressure. The residue was purified by column chromatography ($SiO_2$, DCM/EA=1/0 to 10/1) to give the title compound (3.7 g, 13.29 mmol, 19.90% yield) as yellow oil.

LCMS (ESI) m/z: $[M+H]^+$=265.1

Step 4: 4-(3-Hydroxycyclobutyl)picolinonitrile

To a solution of 4-(3-(benzyloxy)cyclobutyl)picolinonitrile (3.7 g, 14.00 mmol) in DCM (120 mL) and $H_2O$ (12 mL) was added DDQ (17.48 g, 76.99 mmol). The mixture was stirred at 30° C. for 16 hrs under $N_2$. The reaction mixture was poured into sat. $NaSO_3$ solution (500 mL) and extracted with DCM (500 mL*3). The combined organic layer was washed with brine (500 mL), dried over $Na_2SO_4$, filtered and concentrated. The residue was purified by column chromatography ($SiO_2$, Petroleum ether/Ethyl acetate=5:1-0:1) to give the title compound (1.4 g, 8.04 mmol, 57.41% yield) as a yellow oil.

Step 5: 4-(3-Oxocyclobutyl)picolinonitrile

To a solution of 4-(3-hydroxycyclobutyl)picolinonitrile (1.4 g, 5.44 mmol) in DCM (15 mL) was added Dess-Martin (6.92 g, 16.31 mmol). The mixture was stirred at 30° C. for 2 hrs. The reaction mixture was poured into $Na_2SO_3$ solution (100 mL) and extracted with EA (100 mL). The combined organic layer was washed with brine (200 mL), dried over $Na_2SO_4$, filtered and concentrated. The residue was purified by column chromatography ($SiO_2$, Petroleum ether/Ethyl acetate=5:1-0:1) to give the title compound (900 mg, 4.98 mmol, 91.62% yield) as an off-white solid.

LCMS (ESI) m/z: $[M+H]^+$=173.1

Intermediate 18: 2-Methyl-5,6,7,8-tetrahydro-2,6-naphthyridin-1(2H)-one

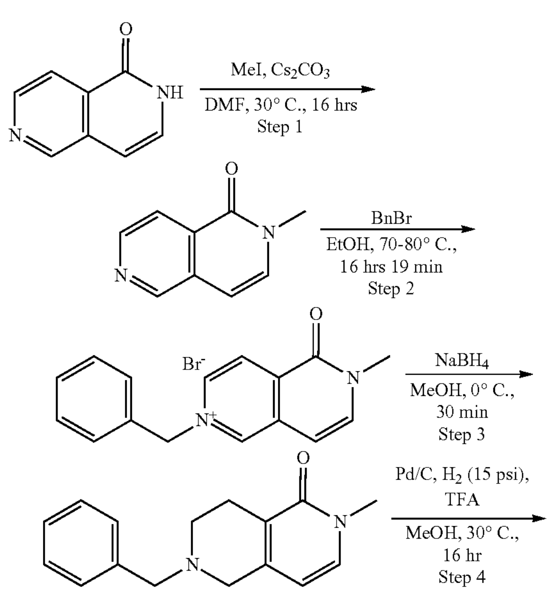

-continued

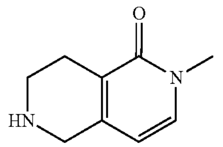

Intermediate 18

Step 1: 2-Methyl-2,6-naphthyridin-1(2H)-one

To a mixture of 2,6-naphthyridin-1(2H)-one (200 mg, 1.37 mmol) in DMF (10 mL) was added $Cs_2CO_3$ (668.82 mg, 2.05 mmol) and MeI (291.36 mg, 2.05 mmol, 127.79 uL) at 30° C. The mixture was stirred at 30° C. for 16 hrs. The mixture was poured into $H_2O$ (10 mL) and extracted with DCM (10 mL*3). The combined organic layers were dried over anhydrous $Na_2SO_4$, filtered and concentrated under reduced pressure. The residue was purified by prep-TLC (DCM/MeOH=20/1, Rf=0.4) to afford the title compound (160 mg, 946.72 umol, 69.18% yield) as a yellow solid.

LCMS (ESI) m/z: $[M+H]^+$=161.1.

$^1H$ NMR (400 MHz, $CDCl_3$) δ=8.98 (s, 1H), 8.69 (d, J=5.2 Hz, 1H), 8.19 (d, J=5.2 Hz, 1H), 7.20 (d, J=7.2 Hz, 1H), 6.58 (d, J=7.2 Hz, 1H), 3.65 (s, 3H) ppm.

Step 2: 2-Benzyl-6-methyl-5-oxo-5,6-dihydro-2,6-naphthyridin-2-ium bromide

A mixture of 2-methyl-2,6-naphthyridin-1(2H)-one (50 mg, 312.16 umol) in EtOH (0.5 mL) was stirred at 70° C. for 10 min. Then benzyl bromide (720.00 mg, 4.21 mmol, 0.5 mL) was added. The mixture was stirred at 80° C. for 16 hrs. The mixture was treated with MTBE (10 mL) and filtered. The filter cake was dried under reduced pressure to afford the title compound (130 mg, crude) as a yellow solid.

$^1H$ NMR (400 MHz, DMSO-d6) δ=9.87 (s, 1H), 8.98-8.97 (m, 1H), 8.68 (d, J=6.4 Hz, 1H), 7.96 (d, J=7.2 Hz, 1H), 7.59-7.42 (m, 5H), 6.96 (d, J=7.6 Hz, 1H), 5.96 (s, 2H), 3.60 (s, 3H) ppm.

Step 3: 6-Benzyl-2-methyl-5,6,7,8-tetrahydro-2,6-naphthyridin-1(2H)-one

To a mixture of 2-benzyl-6-methyl-5-oxo-5,6-dihydro-2,6-naphthyridin-2-ium bromide (70 mg, 211.35 umol) in MeOH (1 mL) was added $NaBH_4$ (39.98 mg, 1.06 mmol) in several portions at 0° C. The mixture was stirred at 0° C. for 30 min. The mixture was poured into 1 M HCl aqueous solution (5 mL) and basified with sat. $NaHCO_3$ to pH=8. The mixture was extracted with EA (10 mL*3). The combined organic layers were dried over anhydrous $Na_2SO_4$, filtered and concentrated under reduced pressure to afford the title compound (35 mg, 137.62 umol, 65.1% yield) as a yellow solid.

LCMS (ESI) m/z: $[M+H]^+$=255.3.

$^1H$ NMR (400 MHz, $CDCl_3$) δ=7.40-7.28 (m, 5H), 7.07 (d, J=7.2 Hz, 1H), 5.84 (d, J=6.8 Hz, 1H), 3.69 (s, 2H), 3.52 (s, 3H), 3.39 (s, 2H), 2.79-2.64 (m, 4H) ppm.

Step 4: 2-Methyl-2,6-naphthyridin-1(2H)-one

To a mixture of 6-benzyl-2-methyl-5,6,7,8-tetrahydro-2,6-naphthyridin-1(2H)-one (35 mg, 137.62 umol) in MeOH (1 mL) was added TFA (31.38 mg, 275.24 umol, 20.38 uL)

and Pd/C (20 mg, 10% purity). The mixture was purged with $H_2$ 3 times and stirred at 30° C. for 16 hrs under $H_2$ (15 psi). The mixture was filtered and the mother liquor was concentrated under reduced pressure to afford the title compound (30 mg, 107.83 umol, 78.4% yield, TFA salt) as a yellow oil.

LCMS (ESI) m/z: $[M+H]^+$=165.1.

Intermediate 19: 7-Fluoro-5-methoxy-1,2,3,4-tetrahydroisoquinoline hydrochloride

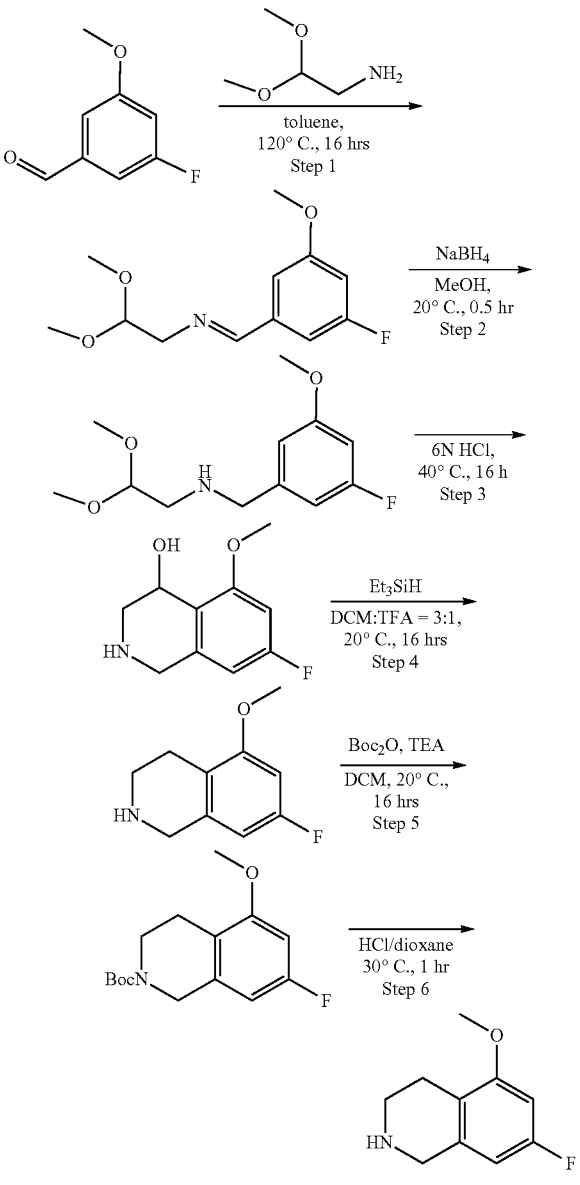

Intermediate 19

Step 1: (E)-N-(2,2-Dimethoxyethyl)-1-(3-fluoro-5-methoxyphenyl)methanimine

To a solution of 3-fluoro-5-methoxy-benzaldehyde (2 g, 12.98 mmol) in toluene (20 mL) was added 2,2-dimethoxy-ethanamine (1.50 g, 14.27 mmol, 1.56 mL). The mixture was stirred at 120° C. for 16 hrs. The reaction mixture was concentrated to give the title compound (3 g, crude) as a yellow oil.

Step 2: N-(3-Fluoro-5-methoxybenzyl)-2,2-dimethoxyethan-1-amine

To a solution of (E)-N-(2,2-dimethoxyethyl)-1-(3-fluoro-5-methoxyphenyl)methanimine (3 g, 12.43 mmol) in MeOH (30 mL) was added $NaBH_4$ (564.53 mg, 14.92 mmol) at 0° C. The mixture was stirred at 30° C. for 30 min. The reaction mixture was poured into water (100 mL) and the mixture was extracted with EA (100 mL*3). The combined organic layer was washed with brine (200 mL), dried over $Na_2SO_4$, filtered and concentrated to give the title compound (2.2 g, 9.04 mmol, 72.73% yield) as a yellow oil.

$^1H$ NMR (400 MHz, DMSO-$d_6$) δ=6.66-6.63 (m, 2H), 6.51-6.48 (m, 1H), 4.49-4.46 (m, 1H), 3.79 (s, 3H), 3.76 (s, 2H), 3.47-3.37 (m, 6H), 2.73 (d, J=5.4 Hz, 2H) ppm.

Step 3: 7-Fluoro-5-methoxy-1,2,3,4-tetrahydroisoquinolin-4-ol

A mixture of N-(3-fluoro-5-methoxybenzyl)-2,2-dimethoxyethan-1-amine (1 g, 4.11 mmol) in HCl (10 mL) was stirred at 40° C. for 12 hrs. The reaction mixture was concentrated to give the title compound (810 mg, crude) as a yellow oil.

Step 4: 7-Fluoro-5-methoxy-1,2,3,4-tetrahydroisoquinoline

To a solution of 7-fluoro-5-methoxy-1,2,3,4-tetrahydroisoquinolin-4-ol (810 mg, 4.11 mmol) in DCM (8 mL) was added $Et_3SiH$ (1.43 g, 12.32 mmol, 1.97 mL) and TFA (5.39 g, 47.27 mmol, 3.5 mL). The mixture was stirred at 30° C. for 16 hrs. The reaction mixture was concentrated to give the title compound (744 mg, crude) as a yellow oil.

LCMS (ESI) m/z: $[M+H]^+$=182.3

Step 5: tert-Butyl 7-fluoro-5-methoxy-3,4-dihydroisoquinoline-2(1H)-carboxylate

To a solution of 7-fluoro-5-methoxy-1,2,3,4-tetrahydroisoquinoline (744 mg, 4.11 mmol) in DCM (10 mL) was added $Et_3N$ (2.08 g, 20.53 mmol, 2.86 mL) and $Boc_2O$ (1.08 g, 4.93 mmol, 1.13 mL). The mixture was stirred at 30° C. for 2 hrs. The reaction mixture was poured into water (20 mL) and extracted with EA (20 mL*3). The combined organic layer was washed with brine (50 mL), dried over $Na_2SO_4$, filtered and concentrated. The residue was purified by column chromatography ($SiO_2$, Petroleum ether/Ethyl acetate=5:1-1:1) to give the title compound (150 mg, 494.22 umol, 12.04% yield) as a white solid.

LCMS (ESI) m/z: $[M+H]^+$=226.2

$^1H$ NMR (400 MHz, DMSO-$d_6$) δ=6.45-6.42 (m, 2H), 4.54-4.51 (m, 2H), 3.80 (s, 3H), 3.63-3.60 (m, 2H), 2.69-2.66 (m, 2H), 1.49 (s, 9H) ppm.

Step 6: 7-Fluoro-5-methoxy-1,2,3,4-tetrahydroisoquinoline hydrochloride

A mixture of tert-butyl 7-fluoro-5-methoxy-3,4-dihydroisoquinoline-2(1H)-carboxylate (150 mg, 533.20 umol) in HCl/dioxane (2 mL) was stirred at 30° C. for 1 hr. The reaction mixture was concentrated and the residue was triturated with MTBE (10 mL) to give the title compound (60 mg, 263.71 umol, 49.46% yield) as a white solid.

LCMS (ESI) m/z: $[M+H]^+$=182.1

$^1$H NMR (400 MHz, DMSO-$d_6$) δ=6.53-6.43 (m, 2H), 4.28 (s, 2H), 3.81 (s, 3H), 3.43 (s, 2H), 3.00 (s, 2H) ppm Intermediate 20: 3-Methoxy-3-phenylpyrrolidine hydrochloride

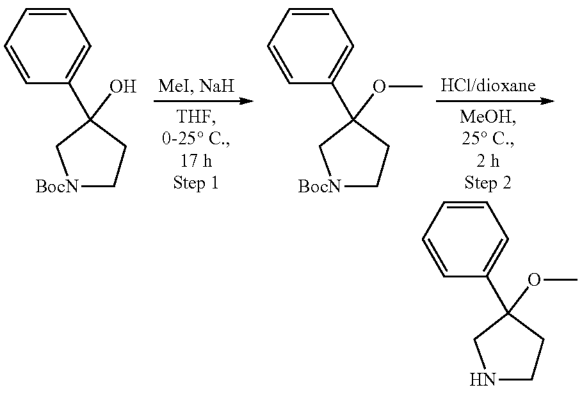

Intermediate 20

Step 1: tert-Butyl 3-methoxy-3-phenylpyrrolidine-1-carboxylate

To a solution of tert-butyl 3-hydroxy-3-phenylpyrrolidine-1-carboxylate (200 mg, 759.50 umol) in DMF (3 mL) was added NaH (42.53 mg, 1.06 mmol, 60% purity) at 0° C. The mixture was stirred at 0° C. for 1 hr. MeI (161.70 mg, 1.14 mmol, 70.92 uL) was added to the mixture and stirring at 25° C. continued for 16 hrs. The mixture was poured into water (50 mL) and extracted with EA (30 mL*3). The combined organic layers were washed with brine (30 mL), dried over $Na_2SO_4$, filtered and concentrated. The residue was purified by flash silica gel chromatography (ISCO®; 12 g SepaFlash® Silica Flash Column, Eluent of 0-60% Ethyl acetate/Petroleum ether gradient @ 60 mL/min) to give the title compound (180 mg, 648.98 umol, 85.45% yield) as a colorless oil.

$^1$HNMR (400 MHz, $CDCl_3$) δ=7.43-7.29 (m, 5H), 3.97-3.78 (m, 1H), 3.64-3.45 (m, 3H), 3.02 (d, J=5.6 Hz, 3H), 2.48-2.36 (m, 1H), 2.24-2.09 (m, 1H), 1.48 (d, J=4.8 Hz, 9H) ppm.

Step 2: 3-Methoxy-3-phenylpyrrolidine hydrochloride

To a solution of tert-butyl 3-methoxy-3-phenylpyrrolidine-1-carboxylate (170 mg, 612.93 umol) in MeOH (2 mL) was added HCl/dioxane (4 M, 2 mL). The mixture was stirred at 25° C. for 2 hrs. The reaction was concentrated under reduced pressure to give the title compound (120 mg, crude, HCl) as a white solid.

$^1$HNMR (400 MHz, DMSO-$d_6$) δ=9.89 (br s, 1H), 9.48 (br s, 1H), 7.47-7.34 (m, 4H), 3.80-3.67 (m, 1H), 3.40-3.14 (m, 3H), 2.92 (s, 3H), 2.63-2.53 (m, 1H), 2.24-2.10 (m, 1H) ppm.

Intermediate 21: 1-(Azetidin-3-yl)-1H-indole

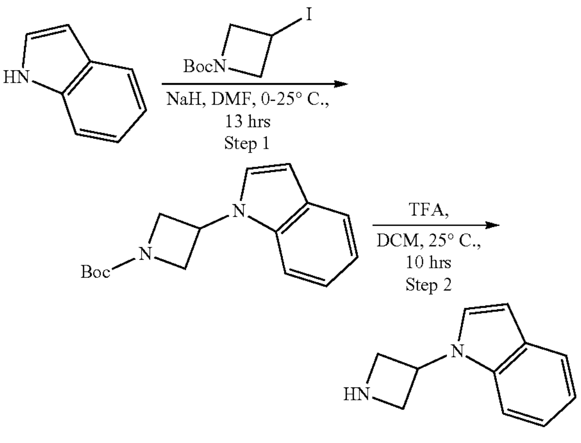

Intermediate 21

Step 1: tert-Butyl 3-(1H-indol-1-yl)azetidine-1-carboxylate

To a solution of indole (500 mg, 4.27 mmol) in DMF (5 mL) was added NaH (256.06 mg, 6.40 mmol, 60% purity) in portions at 0° C. The reaction mixture was stirred at 0° C. for 0.5 hr. tert-Butyl 3-iodoazetidine-1-carboxylate (1.33 g, 4.69 mmol) was then added dropwise. The reaction solution was stirred at 25° C. for 12.5 hrs. The reaction mixture was quenched by saturated aqueous $NH_4Cl$ (10 mL), diluted with $H_2O$ (10 mL) and extracted with EA (10 mL*3). The combined organic layers were washed with brine (10 mL*3), dried over $Na_2SO_4$, filtered and concentrated under reduced pressure. The residue was purified by reversed phase chromatography (FA condition). The fraction was concentrated under reduced pressure to remove MeCN and extracted with EA (25 mL*3). The combined organic layers were washed with brine (20 mL), dried over $Na_2SO_4$, filtered and concentrated under reduced pressure to give the title compound (520 mg, 1.77 mmol, 41.41% yield) as a red oil.

LCMS (ESI) m/z: $[M+H]^+$=273.1

$^1$H NMR (400 MHz, $CDCl_3$-d) δ=7.66 (d, J=7.6 Hz, 1H), 7.39 (d, J=8.4 Hz, 1H), 7.32 (d, J=3.2 Hz, 1H), 7.26-7.22 (m, 1H), 7.19-7.11 (m, 1H), 6.60 (d, J=2.8 Hz, 1H), 5.22-5.18 (m, 1H), 4.52-4.48 (m, 2H), 4.36-4.32 (m, 2H), 1.50 (s, 9H)

Step 2: 1-(Azetidin-3-yl)-1H-indole

To a solution of tert-butyl 3-(1H-indol-1-yl)azetidine-1-carboxylate (220 mg, 807.81 umol) in DCM (3 mL) was added TFA (92.11 mg, 807.81 umol, 59.81 uL). The reaction mixture was stirred at 25° C. for 10 hrs. The reaction mixture was then concentrated under reduced pressure and the residue purified by reversed phase chromatography (FA condition). The fraction was concentrated under reduced pressure to remove MeCN and lyophilized to give the title compound (110 mg, 504.01 umol, 62.39% yield, FA) as a red solid.

LCMS (ESI) m/z: $[M+H]^+$=173.1

Intermediate 22: 7-(Difluoromethyl)-1,2,3,4-tetrahydroisoquinoline hydrochloride

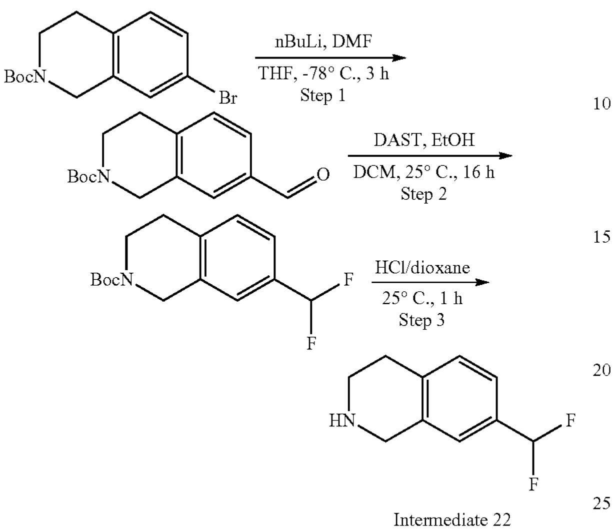

Intermediate 22

Step 1: tert-Butyl 7-formyl-3,4-dihydroisoquinoline-2(1H)-carboxylate

To a solution of tert-butyl 7-bromo-3,4-dihydroisoquinoline-2(1H)-carboxylate (1 g, 3.20 mmol) in THE (40 mL) at −78° C. under $N_2$ was added n-BuLi (2.5 M, 2.56 mL) dropwise. The reaction was stirred at −78° C. for 0.5 hr. DMF (468.25 mg, 6.41 mmol, 492.89 uL) was then added dropwise at −78° C. and stirred at −78° C. for 2.5 hrs. The reaction mixture was quenched with aq. $NH_4Cl$ (60 mL) and extracted with EA (50 mL*3). The combined organic layer was dried over anhydrous $Na_2SO_4$, filtered and concentrated under reduced pressure. The residue purified by flash silica gel chromatography ($SiO_2$, Petroleum ether/Ethyl acetate=1/0~1/1) to give the title compound (280 mg, 1.01 mmol, 31.46% yield) as a colorless oil.

LCMS (ESI) m/z: $[M+H-56]^+$=206.1

$^1H$ NMR (400 MHz, DMSO-$d_6$) δ=9.95 (s, 1H), 7.76-7.68 (m, 2H), 7.39 (d, J=8.0 Hz, 1H), 4.59 (s, 2H), 3.58-3.55 (m, 2H), 2.88-2.85 (m, 2H), 1.46-1.41 (m, 9H) ppm.

Step 2: tert-Butyl 7-(difluoromethyl)-3,4-dihydroisoquinoline-2(1H)-carboxylate To a solution of tert-butyl 7-formyl-3,4-dihydroisoquinoline-2(1H)-carboxylate (150 mg, 574.02 umol) in DCM (1.5 mL) was added DAST (157.29 mg, 975.83 umol, 128.93 uL) and EtOH (5.29 mg, 114.80 umol, 6.71 uL). The mixture was stirred at 25° C. for 14 hrs. Additional DAST (92.53 mg, 574.02 umol, 75.84 uL) was added at 0° C. and the mixture stirred at 25° C. for 2 hrs. The reaction mixture was diluted with $H_2O$ (20 mL) and extracted with EA (20 mL*3). The combined organic layer was dried over anhydrous $Na_2SO_4$, filtered and concentrated under reduced pressure. The residue was purified by flash silica gel chromatography ($SiO_2$, Petroleum ether/Ethyl acetate=1/0 to 1/1) to give the title compound (120 mg, 388.11 umol, 67.61% yield) as a colorless oil.

LCMS (ESI) m/z: $[M+H-56]^+$=228.1

$^1H$ NMR (400 MHz, DMSO-$d_6$) δ=7.40-7.34 (m, 2H), 7.32-7.28 (m, 1H), 7.12-6.82 (m, 1H), 4.54 (s, 2H), 3.57-3.52 (m, 2H), 2.83-2.80 (m, 2H), 1.43 (s, 9H) ppm.

Step 3: 7-(Difluoromethyl)-1,2,3,4-tetrahydroisoquinoline hydrochloride

To a solution of tert-butyl 7-(difluoromethyl)-3,4-dihydroisoquinoline-2(1H)-carboxylate (120 mg, 423.56 umol) in dioxane (1 mL) was added HCl/dioxane (4 M, 756.34 uL). The reaction mixture was stirred at 25° C. for 1 hr. The reaction mixture was concentrated under reduced pressure to give the title compound (90 mg, 378.26 umol, 89.30% yield) as white solid.

LCMS (ESI) m/z: $[M+H]^+$=184.0.

Intermediate 23: 7-Bromo-1,5-naphthyridin-2(1H)-one

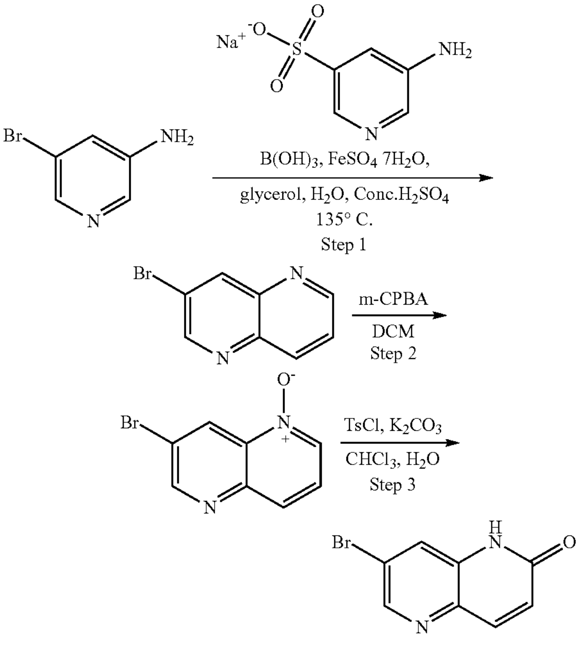

Intermediate 23

Step 1. 3-Bromo-1,5-naphthyridine

Boric acid (5.72 g, 92.5 mmol), $FeSO_4 \cdot 7H_2O$ (2.09 g, 7.51 mmol), and sodium 3-nitrobenzenesulfonate hydrate (28.1 g, 116 mmol) were added to a solution of concentrated $H_2SO_4$ (50 mL) and the mixture was stirred at 30° C. for 0.5 hr. Glycerol (20.3 mL, 272 mmol), 5-bromopyridin-3-amine (10.0 g, 57.8 mmol), and $H_2O$ (50 mL) were added to the reaction solution, and the mixture was stirred at 135° C. for 18 hrs. The mixture was cooled to 30° C., and the pH was adjusted to pH=14 with NaOH. The aqueous layer was extracted with EA (300 mL×3), and the combined organic layer was washed with brine (500 mL), dried over anhydrous $Na_2SO_4$, filtered, and concentrated in vacuo. The residue was purified by FCC (Eluent: PE:EA=10:1 to 2:1) affording the title compound (4.50 g, 19.9 mmol) as a yellow solid.

LCMS (ESI) m/z: [Br79M+H]+=209.0

$^1$H NMR (400 MHz, DMSO-d6) δ=8.98-8.97 (m, 2H), 8.58 (d, J 1.6 Hz, 1H), 8.40-8.37 (m, 1H), 7.67-7.64 (m, 1H).

Step 2. 7-Bromo-1,5-naphthyridine 1-oxide m-CPBA (5.24 g, 25.8 mmol, 85% purity) was added to a solution of 3-bromo-1,5-naphthyridine (4.50 g, 21.5 mmol) in DCM (45.0 mL). The mixture was stirred at 30° C. for 16 hr. The mixture was poured into saturated $Na_2SO_3$ (100 mL) and extracted with DCM (100 mL×3). The combined organic layer was washed with brine (100 mL), dried over anhydrous $Na_2SO_4$, filtered, and concentrated. The crude product was triturated with MTBE (50 mL), and the solid was filtered. The solid was collected and dried in vacuo affording the title compound (3.3 g, 14.66 mmol) as a yellow solid.

$^1$H NMR (400 MHz, DMSO-d6) δ=9.23-9.22 (m, 1H), 9.03 (d, J=2.0 Hz, 1H), 8.55 (d, J=6.4 Hz, 1H), 7.99 (d, J=8.8 Hz, 1H), 7.57-7.53 (m, 1H).

Step 3. 7-Bromo-1,5-naphthyridin-2(1H)-one

Potassium carbonate (6.89 g, 49.86 mmol) in water (25 mL) was added to a solution of 7-bromo-1,5-naphthyridine 1-oxide (3.30 g, 14.7 mmol) and TosCl (3.35 g, 17.6 mmol) in $CHCl_3$ (60 mL). The mixture was stirred at 30° C. for 16 hrs. The reaction mixture was filtered, and the filter cake was dried in vacuo affording the title compound (2.5 g, 10.0 mmol) as a yellow solid.

LCMS (ESI) m/z: [Br79M+H]+=225.1

$^1$H NMR (400 MHz, DMSO-d6) δ=12.21-11.78 (m, 1H), 8.54 (d, J=2.0 Hz, 1H), 7.91 (d, J=10.4 Hz, 1H), 7.85 (d, J=1.6 Hz, 1H), 6.78-6.74 (m, 1H).

Intermediate 24: tert-Butyl N-[1-(2-phenyl-1,6-naphthyridin-7-yl)ethyl]carbamate

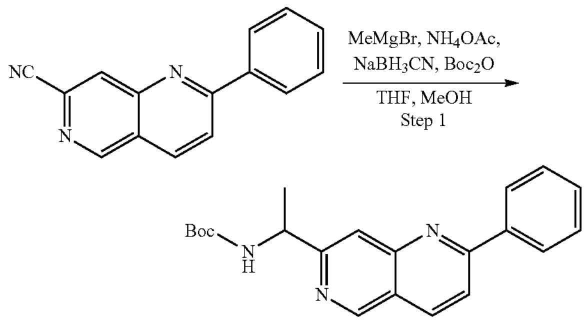

Intermediate 24 tert-Butyl N-[1-(2-phenyl-1,6-naphthyridin-7-yl)ethyl]carbamate

Methylmagnesium bromide (3 M, 1.73 mL) was added to a solution of 2-phenyl-1,6-naphthyridine-7-carbonitrile (300 mg, 1.30 mmol) in THE (6 mL) at 0° C. The mixture was warmed and stirred at 25° C. for 1 hr. The reaction mixture was quenched by addition dry MeOH (3 mL), then $NH_4OAc$ (1 g, 13.0 mmol) and $NaBH_3CN$ (815 mg, 13.0 mmol) were added and the mixture was stirred at 25° C. for 1 hr. $Boc_2O$ (1.70 g, 7.78 mmol) was added and the reaction mixture was stirred at 25° C. for 16 hrs. The reaction mixture was quenched with water (100 mL) and extracted with EA (100 mL×2). The combined organic layers were washed with brine (100 mL), dried over anhydrous $Na_2SO_4$, filtered, and concentrated under in vacuo. The crude product was purified by FCC (Eluent: PE:EA=1:1) affording the title compound (250 mg, 0.68 mmol) as light yellow oil.

LCMS (ESI) m/z: [M+H]+=350.1.

$^1$H NMR (400 MHz, DMSO-d6) δ=9.34 (s, 1H), 8.63 (d, J=8.8 Hz, 1H), 8.33-8.24 (m, 3H), 7.84 (s, 1H), 7.62-7.53 (m, 4H), 4.87 (d, J=7.2 Hz, 1H), 1.47-1.37 (m, 12H) ppm.

Intermediates 25 and 26: (3S)-3-(Hydroxymethyl)-3-methyl-indane-5-carboxylic acid and (3R)-3-(Hydroxymethyl)-3-methyl-indane-5-carboxylic acid

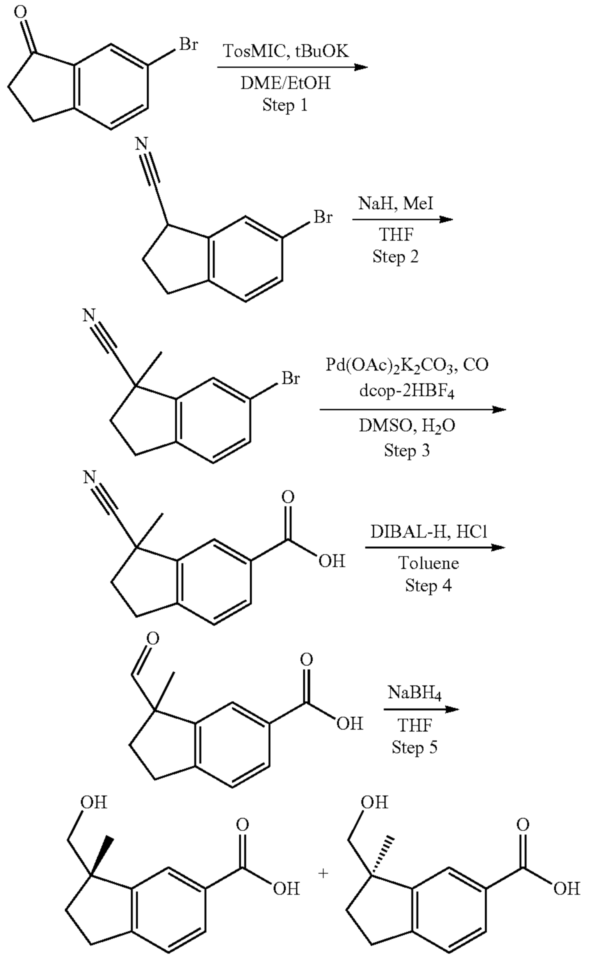

Intermediate 25 Intermediate 26

Step 1. 6-Bromoindane-1-carbonitrile

Potassium tert-butoxide (53.2 g, 474 mmol) was added to a solution of 6-bromoindan-1-one (50 g, 237 mmol) and 1-(isocyanomethylsulfonyl)-4-methyl-benzene (69.4 g, 356 mmol) in DME (2.5 L) and EtOH (100 mL) at 0° C. The reaction mixture was stirred at 25° C. for 16 hrs. The reaction mixture was poured into water (2 L) and extracted with EA (2 L×2). The combined organic layer was concentrated in vacuo. The crude product was diluted with EA (500 mL), washed with brine (500 mL), dried over anhydrous $Na_2SO_4$, and concentrated in vacuo. The residue was purified by FCC (Eluent: PE:EA=20:1). The desired fractions were collected and concentrated in vacuo. The solid was then triturated with MTBE (100 mL) affording the title compound (29 g, 130 mmol) as a white solid.

$^1$H NMR (400 MHz, CHLOROFORM-d) 5=7.58 (s, 1H), 7.42-7.40 (m, 1H), 7.16 (d, J=8.4 Hz, 1H), 4.12-4.08 (m, 1H), 3.10-3.00 (m, 1H), 2.97-2.86 (m, 1H), 2.65-2.55 (m, 1H), 2.43-2.37 (m, 1H) ppm.

Step 2. 6-Bromo-1-methyl-indane-1-carbonitrile

Sodium hydride (10.8 g, 270 mmol, 60% purity) was added to a solution of 6-bromoindane-1-carbonitrile (30 g, 135 mmol) in THE (300 mL) at 0° C. The reaction mixture was warmed and stirred at 10° C. for 0.5 hr. $CH_3I$ (42.1 mL, 675.43 mmol) was added at 0° C. The mixture was warmed and stirred at 25° C. for 2 hrs. The reaction was diluted with $NH_4Cl$ (aq., 800 mL) and extracted with EA (500 mL×3). The combined organic layers were dried over anhydrous $Na_2SO_4$, filtered, and concentrated under reduced pressure. The crude residue was purified by FCC (Eluent: PE:EA=1:0 to 5:1) affording the title compound (27 g, 114 mmol) as a yellow solid.

$^1$H NMR (400 MHz, DMSO-d6) δ=7.70 (d, J=2.0 Hz, 1H), 7.50-7.48 (m, 1H), 7.29 (d, J=8.0 Hz, 1H), 2.97-2.93 (m, 2H), 2.60-2.53 (m, 1H), 2.18 (d, J=12.8 Hz, 1H), 1.64 (s, 3H) ppm.

Step 3. 3-Cyano-3-methyl-indane-5-carboxylic acid

A mixture of 6-bromo-1-methyl-indane-1-carbonitrile (6.5 g, 27.5 mmol), dccp·2HBF$_4$ (1.69 g, 2.75 mmol), potassium carbonate (5.71 g, 41.3 mmol), $Pd(OAc)_2$ (618 mg, 2.75 mmol), and water (0.99 mL) in DMSO (60 mL) was degassed and purged with CO (g) three times. The mixture was stirred at 100° C. for 14 hr under a CO (15 psi) atmosphere. The reaction mixture was filtered to remove the black solid, and then diluted with water (60 mL) and extracted with EA (80 mL×3). The organic layer was discarded and the aqueous phase was adjusted to pH=4 with aq. HCl. The aqueous solution was then extracted with EA (100 mL×3). The combined organic layers were washed with brine (500 mL×2) then dried over anhydrous $Na_2SO_4$, filtered, and concentrated under reduced pressure affording the title compound (4.5 g, 20.7 mmol) as a brown solid.

LCMS (ESI) m/z: [M+H]+=202.1.

$^1$H NMR (400 MHz, DMSO-d6) δ=13.04 (s, 1H), 7.96 (s, 1H), 7.91-7.88 (m, 1H), 7.45 (d, J=8.0 Hz, 1H), 3.07-3.04 (m, 2H), 2.64-2.53 (m, 1H), 2.28-2.19 (m, 1H), 1.65 (s, 3H) ppm.

Step 4. 3-Formyl-3-methyl-indane-5-carboxylic acid

DIBAL-H (1 M, 159.03 mL) was added to a solution of 3-cyano-3-methyl-indane-5-carboxylic acid (16 g, 79.5 mmol) in toluene (160 mL) at −70° C. The mixture was stirred at −70° C. for 2 hrs. The reaction was quenched via the addition of HCl (2 M, 323 mL). The reaction mixture was warmed and stirred at 20° C. for 1 h. The mixture was diluted with water (2 L) and extracted with EA (1.5 L×3). The combined organic layer was dried over anhydrous $Na_2SO_4$, filtered, and concentrated affording the title compound (14 g, 58.2 mmol) as a white solid.

LCMS (ESI) m/z: [M+H]+=205.1.

$^1$H NMR (400 MHz, DMSO-d6) δ=12.91 (br s, 1H), 9.58 (s, 1H), 7.85-7.83 (m, 1H), 7.73 (s, 1H), 7.40 (d, J=8.0 Hz, 1H), 3.06-2.90 (m, 2H), 2.61-2.54 (m, 1H), 1.98-1.87 (m, 1H), 1.39 (s, 3H) ppm.

Step 5. (3S)-3-(Hydroxymethyl)-3-methyl-indane-5-carboxylic acid and (3R)-3-(Hydroxymethyl)-3-methyl-indane-5-carboxylic acid Sodium borohydride (2.49 g, 65.8 mmol) was added to a solution of 3-formyl-3-methyl-indane-5-carboxylic acid (14 g, 58.2 mmol) in THE (150 mL) at 0° C. The mixture was warmed and stirred at 25° C. for 3 hrs. The reaction was diluted with water (200 mL) and extracted with EA (80 mL×2). The organic layer was discarded and the aqueous phase was adjusted to pH=4 with aq. HCl. The aqueous solution was then extracted with EA (300 mL×3). The organic layer was dried over anhydrous $Na_2SO_4$, filtered, and concentrated in vacuo. The residue was washed with DCM (50 mL×3), filtered, and concentrated to get a white solid. The filtrate was concentrated under reduced pressure and the resulting residue was purified by FCC (Eluent: PE:EA=1:0 to 1:5). The desired fractions were collected and concentrated under reduced pressure to get off-white solid. The solid was then washed with MTBE (20 mL×2). This solid was combined with the filtered solid and dried in vacuo affording a mixture of the title compounds (9.5 g, 44.3 mmol) as a white solid. The stereoisomers were separated by chiral SFC (column: DAICEL CHIRALPAK AD-H (250 mm*30 mm, 5 μm); mobile phase: [0.1% $NH_3$—$H_2O$ MEOH]; B %: 40%-40%, 5 min; 540 min) affording the pure title compounds.

Intermediate 25: (4.0 g, 19.40 mmol, white solid)

Chiral SFC: AD-3_5CM_MEOH (DEA)_5_40_3ML_AT35.M, Rt=1.575 min, ee %=100%.

LCMS (ESI) m/z: [M+H]+=207.2.

$^1$H NMR (400 MHz, DMSO-d6) δ=7.74-7.68 (m, 2H), 7.17 (d, J=8.4 Hz, 1H), 3.39-3.31 (m, 2H), 2.87-2.80 (m, 2H), 2.15-2.12 (m, 1H), 1.73-1.65 (m, 1H), 1.20 (s, 3H) ppm.

Intermediate 26: ((4.3 g, 20.44 mmol, light yellow solid)

Chiral SFC: AD-3_5CM_MEOH (DEA)_5_40_3ML_AT35.M, Rt=1.799 min, ee %=97.93%.

LCMS (ESI) m/z: [M+H]+=207.2.

$^1$H NMR (400 MHz, DMSO-d6) δ=7.73-7.64 (m, 2H), 7.16 (d, J=8.4 Hz, 1H), 3.44-3.25 (m, 2H), 2.88-2.78 (m, 2H), 2.15-2.12 (m, 1H), 1.73-1.65 (m, 1H), 1.20 (s, 3H) ppm.

Intermediates 27 and 28: (S)-3-cyano-1,3-dimethyl-indoline-5-carboxylic acid and (R)-3-cyano-1,3-dimethylindoline-5-carboxylic acid

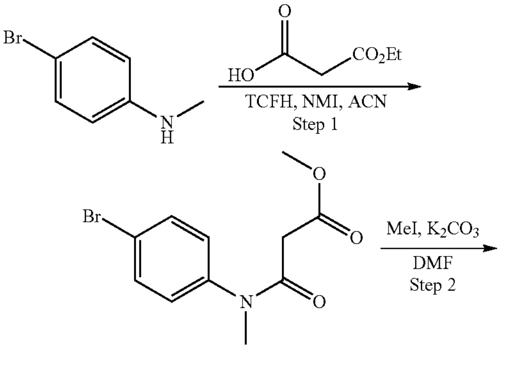

-continued

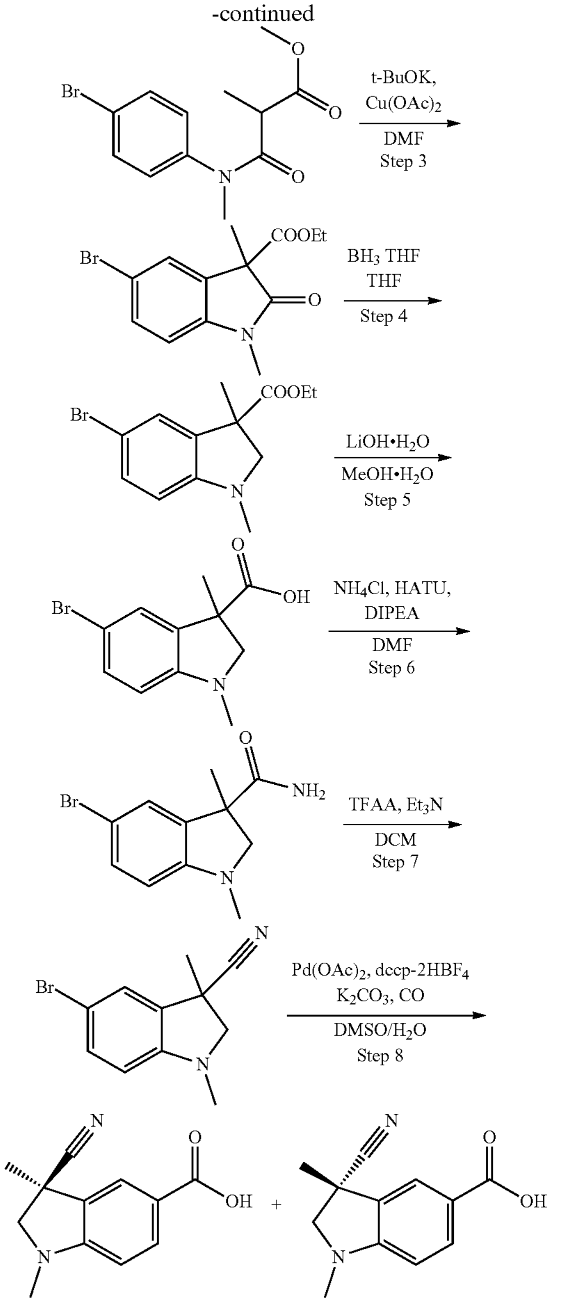

Intermediate 27

Intermediate 28

Step 1. Methyl 3-((4-bromophenyl)(methyl)amino)-3-oxopropanoate

TCFH (22.6 g, 80.6 mmol) and NMI (12.5 mL, 161.2 mmol) were added to a mixture of 4-bromo-N-methyl-aniline (10 g, 53.8 mmol) and 3-ethoxy-3-oxo-propanoic acid (8.52 g, 64.5 mmol) in MeCN (150 mL) at 20° C. The mixture was stirred at 20° C. for 15 hrs. The mixture was concentrated and diluted with water (10 mL). The aqueous solution was then extracted with DCM (15 mL×3). The combined organic phase was dried over anhydrous $Na_2SO_4$, filtered, and concentrated in vacuo. The residue was purified by FCC (Eluent: PE:EA=5:1 to 3:1) affording the title compound (13 g, 43.3 mmol) as a white solid.

LCMS (ESI) m/z: [M+H]+=286.0.

$^1$H NMR (400 MHz, $CDCl_3$) δ=7.56 (d, J=8.4 Hz, 2H), 7.14 (d, J=8.4 Hz, 2H), 4.13 (d, J=7.2 Hz, 2H), 3.29 (s, 3H), 3.21 (s, 2H), 1.29-1.15 (m, 3H) ppm.

Step 2. Methyl 3-((4-bromophenyl)(methyl)amino)-2-methyl-3-oxopropanoate

Potassium carbonate (4.14 g, 30.0 mmol), and MeI (3.7 mL, 59.9 mmol) were added to a mixture of methyl 3-((4-bromophenyl)(methyl)amino)-3-oxopropanoate (6 g, 20.0 mmol) in DMF (60 mL) at 0° C.

The reaction mixture was stirred at 20° C. for 15 hrs. The reaction was diluted with water (100 mL) and extracted with EA (60 mL×3). The combined organic phase was washed with brine (50 mL), dried over anhydrous $Na_2SO_4$, filtered, and concentrated in vacuo. The residue was purified by FCC (Eluent: PE:EA=5:1 to 3:1) affording the title compound (4 g, 12.7 mmol) as a yellow solid.

LCMS (ESI) m/z: [M+H]+=300.0.

$^1$H NMR (400 MHz, $CDCl_3$) δ=7.57 (d, J=8.4 Hz, 2H), 7.18-7.11 (m, 2H), 4.19-4.03 (m, 2H), 3.40-3.28 (m, 1H), 3.28 (s, 3H), 1.31 (d, J=7.2 Hz, 3H), 1.27-1.21 (m, 3H) ppm.

Step 3. Ethyl 5-bromo-1,3-dimethyl-2-oxoindoline-3-carboxylate t-BuOK (2.86 g, 25.5 mmol) and copper(II)acetate monohydrate (5.08 g, 25.5 mmol) were added to a mixture of methyl 3-((4-bromophenyl)(methyl)amino)-2-methyl-3-oxopropanoate (4 g, 12.7 mmol) in DMF (120 mL) at 20° C. The mixture was stirred at 100° C. for 1 hr. The mixture was filtered off, the filtrate was diluted with water (150 mL), and then extracted with EA (50 mL×3). The combined organic phase was washed with brine (50 mL), dried over anhydrous $Na_2SO_4$, filtered, and concentrated in vacuo. The residue was purified by FCC (Eluent: PE:EA=5:1 to 3:1) affording the title compound (2 g, 5.77 mmol) as a yellow solid.

LCMS (ESI) m/z: [M+H]+=312.0.

$^1$H NMR (400 MHz, $CDCl_3$) δ=7.46-7.44 (m, 1H), 7.38 (d, J=2.0 Hz, 1H), 6.75 (d, J=8.4 Hz, 1H), 4.23-4.09 (m, 2H), 3.26-3.19 (m, 3H), 1.66 (s, 3H), 1.21-1.16 (m, 3H) ppm.

Step 4. Ethyl 5-bromo-1,3-dimethylindoline-3-carboxylate $BH_3$·THF (1 M, 9.61 mL) was added to a solution of ethyl 5-bromo-1,3-dimethyl-2-oxoindoline-3-carboxylate (2 g, 6.41 mmol) in THE (20 mL) at 0° C. The mixture was stirred at 60° C. for 2 hrs. The mixture was slowly quenched with MeOH (30 mL) at 0° C. and then concentrated. The crude product was purified by FCC (Eluent: PE:EA=10:1 to 3:1) affording the title compound (300 mg, 0.86 mmol) as colorless oil.

LCMS (ESI) m/z: [M+H]+=298.0.

$^1$H NMR (400 MHz, $CDCl_3$) δ=7.34 (d, J=2.0 Hz, 1H), 7.23-7.20 (m, 1H), 6.35 (d, J=8.4 Hz, 1H), 4.26-4.15 (m, 2H), 3.89 (d, J=9.2 Hz, 1H), 3.19-3.12 (m, 1H), 2.78-2.72 (m, 3H), 1.54 (s, 3H), 1.33-1.25 (m, 3H) ppm.

Step 5. 5-Bromo-1,3-dimethylindoline-3-carboxylic acid

LiOH·$H_2O$ (126.66 mg, 3.02 mmol) was added to a mixture of ethyl 5-bromo-1,3-dimethylindoline-3-carboxylate (300 mg, 1.01 mmol) in MeOH (3 mL) and water (1 mL) at 20° C. The mixture was stirred at 20° C. for 15 hrs. MeOH was removed under vacuum and the solution was diluted with water (1 mL). The pH was adjusted to 3 with 1N HCl and the solution was extracted with EA (5 mL×3). The combined organic phase was washed with brine (10 mL), dried over $Na_2SO_4$, filtered, and concentrated to affording the title compound (220 mg, 0.70 mmol) as a white solid.

LCMS (ESI) m/z: [M+H]+=270.0.

Step 6.
5-Bromo-1,3-dimethylindoline-3-carboxamide

Ammonium chloride (436 mg, 8.14 mmol), HATU (465 mg, 1.22 mmol), and DIPEA (0.56 mL, 4.07 mmol) were added to a mixture of 5-bromo-1,3-dimethylindoline-3-carboxylic acid (220 mg, 0.81 mmol) in DMF (4 mL) at 20° C. The mixture was stirred for 15 hrs. Water (5 mL) was added and the mixture was extracted with EA (5 mL×3). The combined organic layer was washed with brine (10 mL), dried over anhydrous $Na_2SO_4$, filtered, and concentrated in vacuo. The residue was purified by FCC (Eluent: PE:EA=1:1) affording the title compound (210 mg, 0.47 mmol) as colorless oil.

LCMS (ESI) m/z: [M+H]+=269.0.

$^1$H NMR (400 MHz, $CDCl_3$) δ=7.29 (br d, J=2.0 Hz, 1H), 7.22 (d, J=2.0 Hz, 1H), 6.44 (d, J=8.4 Hz, 1H), 3.84 (d, J=9.2 Hz, 1H), 3.10 (d, J=9.2 Hz, 1H), 2.76 (s, 3H), 1.57 (s, 3H) ppm.

Step 7. 5-Bromo-1,3-dimethylindoline-3-carbonitrile

Triethylamine (0.33 mL, 2.34 mmol) was added to a mixture of 5-bromo-1,3-dimethylindoline-3-carboxamide (210 mg, 0.78 mmol) in DCM (3 mL) at 0° C. TFAA (0.27 mL, 1.95 mmol) was added slowly and the resulting mixture was stirred at 20° C. for 4 hrs. The mixture was diluted with water (5 mL) and extracted with DCM (5 mL×3). The combined organic phase was washed with saturated $NaHCO_3$ (aq.), dried over anhydrous $Na_2SO_4$, filtered, and concentrated in vacuo. The residue was purified by FCC (Eluent: PE:EA=10:1 to 5:1) affording the title compound (100 mg, 0.39 mol) as colorless oil.

LCMS (ESI) m/z: [M+H]+=251.1.

$^1$H NMR (400 MHz, $CDCl_3$) δ=7.33 (d, J=2.0 Hz), 7.31-7.28 (m, 1H), 6.42 (d, J=8.4 Hz, 1H), 3.70 (d, J=9.2 Hz, 1H), 3.32 (d, J=9.2 Hz, 1H), 2.77 (s, 3H), 1.68 (s, 3H) ppm.

Step 8. 3-Cyano-1,3-dimethylindoline-5-carboxylic acid

Palladium acetate (2.2 mg, 0.010 mol), dccp·2HBF$_4$ (12.2 mg, 0.020 mmol), and potassium carbonate (41.3 mg, 0.30 mmol) were added to a solution of 5-bromo-1,3-dimethylindoline-3-carbonitrile (50 mg, 0.20 mmol) in DMSO (1 mL) and water (0.007 mL). The mixture was degassed and flushed with CO (g) three times. The mixture was then stirred under a CO atmosphere (15 psi) at 100° C. for 15 hrs. Water (3 mL) was added to the mixture and the mixture was extracted with EA (3 mL×3). The combined organic phase was washed with brine (5 mL), dried over $Na_2SO_4$, filtered, and concentrated in vacuo. The crude product was purified by reversed-phase HPLC. The desired fractions were collected and extracted with DCM (5 mL×3). The combined organic layer was washed with brine (5 mL), dried over $Na_2SO_4$, filtered, and concentrated affording a mixture of the title compounds (40 mg) as a white solid. The stereoisomers were separated by SFC condition (column: DAICEL CHIRALPAK IC (250 mm*30 mm, 5 m); mobile phase: [0.1% $NH_3 \cdot H_2O$ IPA]; B %: 20%-20%, 5 min; 85 minmin) affording intermediate 27 (20 mg, 0.09 mmol) as a white solid and Intermediate 28 (15 mg, 0.07 mmol) as a white solid.

Intermediate 27: Chiral SFC: IC-3-IPA (DEA)-5-40-3 mL-35T.lcm; RT=1.517 min.

LCMS (ESI) m/z: [M+H]+=217.1.

$^1$H NMR (400 MHz, DMSO-d6) δ=12.39 (br s, 1H), 7.85-7.76 (m, 2H), 6.66 (d, J=8.4 Hz, 1H), 3.87 (d, J=10.0 Hz, 1H28 3.44 (d, J=10.0 Hz, 1H), 2.83 (s, 3H), 1.68 (s, 3H) ppm.

Intermediate 28: Chiral SFC: IC-3-IPA (DEA)-5-40-3 mL-35T.lcm; RT=1.608 min.

LCMS (ESI) m/z: [M+H]+=217.1.

$^1$HNMR (400 MHz, DMSO-d6) δ=12.39 (br s, 1H), 7.85-7.76 (m, 2H), 6.66 (d, J=8.4 Hz, 1H), 3.87 (d, J=10.0 Hz, 1H), 3.44 (d, J=10.0 Hz, 1H), 2.83 (s, 3H), 1.68 (s, 3H) ppm.

Intermediates 29 and 30: (R)-5-Cyano-5-methyl-6,8-dihydro-5H-pyrano[3,4-b]pyridine-3-carboxylic acid and (S)-5-Cyano-5-methyl-6,8-dihydro-5H-pyrano[3,4-b]pyridine-3-carboxylic acid

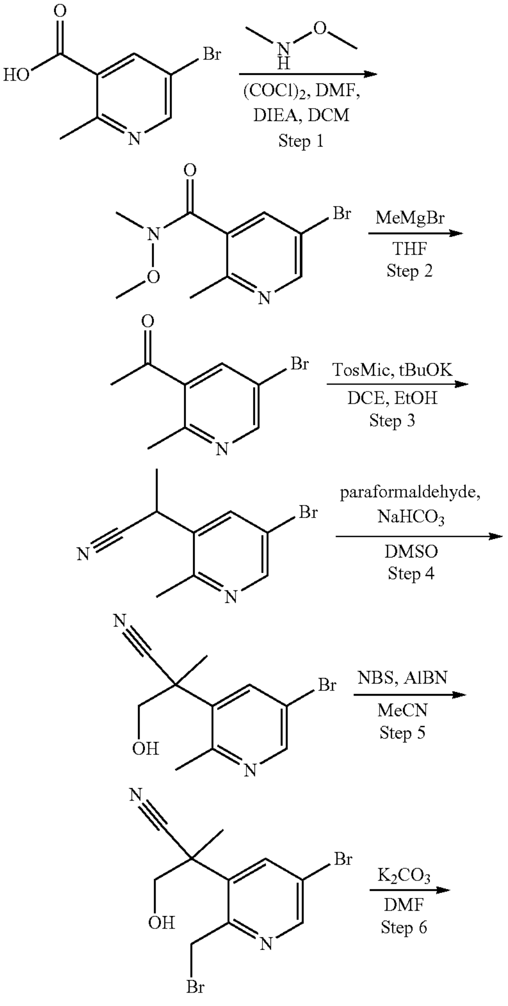

-continued

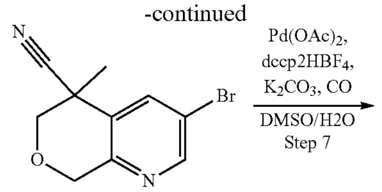

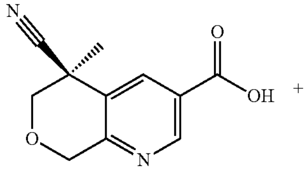
+

Intermediate 29

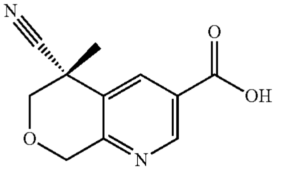

Intermediate 30

Step 1. 5-Bromo-N-methoxy-N,2-dimethylnicotinamide

Oxalyl chloride (12.2 mL, 139 mmol) was added to a solution of 5-bromo-2-methyl-pyridine-3-carboxylic acid (10 g, 46.29 mmol) and DMF (0.036 mL, 0.46 mmol) in DCM (100 mL). The reaction mixture was stirred at 25° C. for 1 hr. The reaction mixture was concentrated in vacuo and the residue was dissolved in DCM (100 mL). The organic solution was added to a solution of N-methoxymethanamine (6.77 g, 69.4 mmol, HCl salt) and DIEA (40.3 mL, 231 mmol) in DCM (50 mL). The reaction mixture was stirred at 25° C. for 14 hrs. The reaction mixture was poured into water (500 mL) and extracted with DCM (500 mL×2). The combined organic layer was dried over anhydrous $Na_2SO_4$, filtered, and concentrated in vacuo. The residue was purified by FCC (Eluent: PE:EA=1:0 to 1:1) affording the title compound (11.5 g, 44.4 mmol) as yellow solid.

LCMS (ESI) m/z: [79BrM+H]+=259.0.

Step 2. 1-(5-Bromo-2-methylpyridin-3-yl)ethenone

Methylmagnesium bromide (3 M, 21.2 mL) was added to a solution of 5-bromo-N-methoxy-N,2-dimethylnicotinamide (11 g, 42.4 mmol) in THE (100 mL) at 0° C. The reaction mixture was stirred at 25° C. for 1 hr. The reaction mixture was poured into saturated aq. $NH_4Cl$ (400 mL) and extracted with EA (400 mL×2). The combined organic layer was dried over anhydrous $Na_2SO_4$, filtered, and concentrated in vacuo. The residue was purified by FCC (Eluent: PE:EA=1:0 to 5:1) affording the title compound (9 g, 41.5 mmol) as yellow oil.

LCMS (ESI) m/z: [79BrM+H]+=214.0.

$^1$H NMR (400 MHz, $CDCl_3$) δ=8.66 (d, J=2.4 Hz, 1H), 8.06 (d, J=2.0 Hz, 1H), 2.70 (s, 3H), 2.60 (s, 3H) ppm.

Step 3. 2-(5-Bromo-2-methylpyridin-3-yl)propanenitrile tBuOK (9.23 g, 82.2 mmol) was added to a solution of 1-(5-bromo-2-methylpyridin-3-yl)ethenone (8 g, 37.4 mmol) and 1-(isocyanomethylsulfonyl)-4-methylbenzene (11.0 g, 56.1 mmol) in DME (400 mL) and EtOH (16 mL) at 0° C. The reaction mixture was stirred at 25° C. for 14 hrs. The reaction mixture was poured into saturated aq. $NH_4Cl$ (400 mL). The mixture was concentrated in vacuo to remove DME and EtOH. The aqueous phase was extracted with EA (400 mL×2). The combined organic layer was dried over anhydrous $Na_2SO_4$, filtered, and concentrated in vacuo. The residue was purified by FCC (Eluent: PE:EA=1:0 to 5:1) affording the title compound (7 g, 31.1 mmol) as colorless oil.

LCMS $(ESI)_3$ m/z: [79BrM+H]+=225.1.

$^1$H NMR (400 MHz, $CDCl_3$) δ=8.55 (d, J=2.4 Hz, 1H), 7.89 (d, J=2.0 Hz, 1H), 4.03-3.98 (m, 1H), 2.57 (s, 3H), 1.66 (d, J=7.2 Hz, 3H) ppm.

Step 4. 2-(5-Bromo-2-methylpyridin-3-yl)-3-hydroxy-2-methylpropanenitrile

Paraformaldehyde (1.12 g, 37.3 mmol) was added to a solution of 2-(5-bromo-2-methylpyridin-3-yl)propanenitrile (7 g, 31.1 mmol) and $NaHCO_3$ (261 mg, 3.11 mmol) in DMSO (60 mL). The reaction mixture was stirred at 25° C. for 14 hrs. The reaction mixture was poured into water (400 mL) and extracted with EA (400 mL×2). The combined organic layer was washed with brine (300 mL), dried over anhydrous $Na_2SO_4$, filtered, and concentrated in vacuo. The residue was purified by FCC (Eluent: PE:EA=1:0 to 1:1) affording the title compound (7.5 g, 29.4 mmol) as white solid.

LCMS (ESI) m/z: [79BrM+H]+=255.1.

$^1$H NMR (400 MHz, $CDCl_3$) δ=8.54 (d, J=2.0 Hz, 1H), 7.79 (d, J=2.0 Hz, 1H), 4.14-4.09 (m, 1H), 3.96-3.92 (m, 1H), 2.80 (s, 3H), 2.69-2.66 (m, 1H), 1.81 (s, 3H) ppm.

Step 5. 2-(5-Bromo-2-(bromomethyl)pyridin-3-yl)-3-hydroxy-2-methylpropanenitrile NBS (1.40 g, 7.84 mmol) and AIBN (64.4 mg, 0.39 mmol) were added to a solution of 2-(5-bromo-2-methylpyridin-3-yl)-3-hydroxy-2-methylpropanenitrile (1 g, 3.92 mmol) in MeCN (10 mL). The reaction mixture was stirred at 80° C. for 4 hrs. The reaction mixture was concentrated. The residue was purified by FCC (Eluent: PE:EA=1:0 to 1:1) affording the title compound (0.25 g, 0.76 mmol) as brown solid.

LCMS (ESI) m/z: [79BrM+H]+=335.0.

$^1$H NMR (400 MHz, $CDCl_3$) δ=8.71 (d, J=2.0 Hz, 1H), 7.89 (d, J=2.0 Hz, 1H), 5.00-4.85 (m, 2H), 4.21-4.06 (m, 2H), 2.24-2.21 (m, 1H), 1.89 (s, 3H) ppm.

Step 6. 3-Bromo-5-methyl-6,8-dihydro-5H-pyrano[3,4-b]pyridine-5-carbonitrile

Potassium carbonate (1.61 g, 11.7 mmol) was added to a solution of 2-(5-bromo-2-(bromomethyl)pyridin-3-yl)-3-hydroxy-2-methylpropanenitrile (1.3 g, 3.89 mmol) in DMF (65 mL). The reaction mixture was stirred at 25° C. for 12 hrs. The reaction mixture was poured into water (300 mL) and extracted with EA (300 mL×2). The combined organic layer was washed with water (300 mL), dried over anhydrous $Na_2SO_4$, filtered, and concentrated in vacuo. The residue was purified by FCC (Eluent: PE:EA=1:0 to 1:1) affording the title compound (350 mg, 1.27 mmol) as white solid.

LCMS (ESI) m/z: [79BrM+H]+=253.0.

$^{1}$HNMR (400 MHz, $CDCl_3$) δ=8.59 (d, J=2.4 Hz, 1H), 7.95 (d, J=2.4 Hz, 1H), 4.85-4.76 (m, 2H), 4.12-3.94 (m, 2H), 1.75 (s, 3H) ppm.

Step 7. (R)-5-Cyano-5-methyl-6,8-dihydro-5H-pyrano[3,4-b]pyridine-3-carboxylic acid and (S)-5-Cyano-5-methyl-6,8-dihydro-5H-pyrano[3,4-b]pyridine-3-carboxylic acid A mixture of 3-bromo-5-methyl-6,8-dihydro-5H-pyrano[3,4-b]pyridine-5-carbonitrile (270 mg, 1.07 mmol), dccp-$2HBF_4$ (65.3 mg, 0.11 mmol), $Pd(OAc)_2$ (23.9 mg, 0.11 mmol), $H_2O$ (0.038 mL), and $K_2CO_3$ (221 mg, 1.60 mmol) in DMSO (3 mL) was degassed and purged with CO (g) three times. The mixture was stirred at 100° C. for 16 hrs under a CO atmosphere (15 psi). The reaction mixture was filtered, poured into water (80 mL), and extracted with EA (30 mL×2). The EA phase was discarded. The aqueous phase was adjusted to pH=5 with aq. HCl (1 M). The aqueous phase was extracted with EA (30 mL×3). The combined organic layers were washed with brine (30 mL), dried over anhydrous $Na_2SO_4$, filtered, and concentrated in vacuo affording a mixture of the title compounds (130 mg, 0.57 mmol) as yellow oil. The stereoisomers were separated by chiral SFC (column: DAICEL CHIRALPAK AD (250 mm*30 mm, 10 m); mobile phase: [0.1% $NH_3{\cdot}H_2O$ MEOH]; B %: 30%-30%, 4.2 min; 55 minmin) affording Intermediate 29 (55 mg, 0.24 mmol) as a yellow solid and Intermediate 30 (50 mg, 0.22 mmol) as a yellow solid.

Intermediate 29: Chiral SFC: AD-3-MeOH(DEA)-5-40-3 mL-35T.lcm; RT=1.055 min.

LCMS (ESI) m/z: [M+H]+=219.0.

$^{1}$H NMR (400 MHz, DMSO-d6) δ=8.99 (d, J=2.0 Hz, 1H), 8.43 (d, J=2.0 Hz, 1H), 4.96-4.75 (m, 2H), 4.26 (d, J=11.8 Hz, 1H), 3.92 (d, J=11.8 Hz, 1H), 1.70 (s, 3H).

Intermediate 30: Chiral SFC: AD-3-MeOH(DEA)-5-40-3 mL-35T.lcm; RT=1.666 min.

LCMS (ESI) m/z: [M+H]+=219.0.

$^{1}$H NMR (400 MHz, DMSO-d6) δ=8.99 (d, J=2.0 Hz, 1H), 8.43 (d, J=2.0 Hz, 1H), 4.96-4.75 (m, 2H), 4.26 (d, J=11.8 Hz, 1H), 3.92 (d, J=11.8 Hz, 1H), 1.70 (s, 3H).

Intermediates 31 and 32: (4S)-4-(hydroxymethyl)-4-methyl-isochromane-6-carboxylic acid and (4R)-4-(hydroxymethyl)-4-methyl-isochromane-6-carboxylic acid

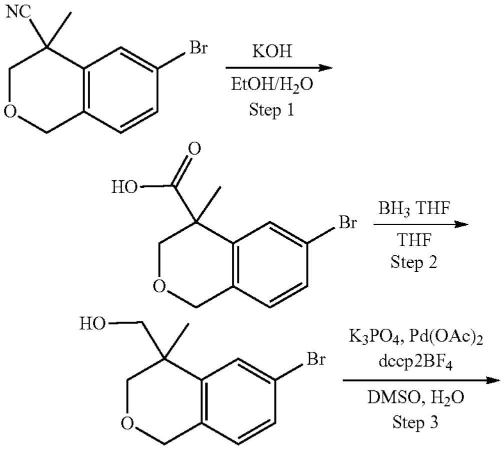

-continued

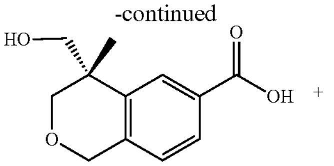

Intermediate 31

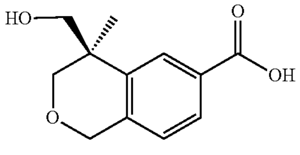

Intermediate 32

Step 1. 6-Bromo-4-methyl-isochromane-4-carboxylic acid

Potassium hydroxide (aq., 9M, 5.29 mL) was added to a solution of 6-bromo-4-methyl-isochromane-4-carbonitrile (1.2 g, 4.76 mmol) in EtOH (12 mL). The mixture was stirred at 90° C. for 5 hrs. The reaction mixture was diluted with $H_2O$ (20 mL) and extracted with EA (30 mL×3). The combined organic layers were discarded and the aqueous phase was adjusted pH=4 with 1N HCl. The aqueous layer was extracted with EA (30 mL×3). The combined organic layers were washed with brine (60 mL), dried over $Na_2SO_4$, filtered, and concentrated in vacuo affording the title compound (800 mg, 2.95 mmol) as yellow oil.

$^{1}$H NMR (400 MHz, DMSO-d6) δ=13.11-12.45 (m, 1H), 7.52 (d, J=2.0 Hz, 1H), 7.40 (d, J=8.4 Hz, 1H), 7.03 (d, J=8.4 Hz, 1H), 4.75-4.62 (m, 2H), 4.16 (d, J=11.2 Hz, 1H), 3.59 (d, J=11.2 Hz, 1H), 1.41 (s, 3H).

Step 2. (6-Bromo-4-methyl-isochroman-4-yl)methanol 6-bromo-4-methyl-isochromane-4-carboxylic acid (800 mg, 2.95 mmol) was dissolved in $BH_3THF$ (1 M, 8.85) at 0° C. and the resulting mixture was stirred at 25° C. for 2 hrs. The reaction mixture was quenched by addition of 1N HCl (25 mL) at 20° C. and stirred for 30 min. Then the mixture was diluted with water (20 mL) and extracted with EA (50 mL×2). The combined organic layers were washed with brine (50 mL), dried over $Na_2SO_4$, filtered, and concentrated in vacuo. The residue was purified by FCC (Eluent: DCM: MeOH=100:1 to 10:1) affording the title compound (400 mg, 1.56 mmol) as colorless oil.

$^{1}$H NMR (400 MHz, $CDCl_3$) δ=7.47 (d, J=2.0, 1H), 7.33 (d, J=8.4 Hz, 1H), 6.89 (d, J=8.4 Hz, 1H), 4.79-4.68 (m, 2H), 4.05 (d, J=11.6 z, 1H), 3.82-3.75 (m, 1H), 3.71-3.63 (m, 1H), 3.53 (d, J=11.6 Hz, 1H), 1.21 (s, 3H).

Step 3. 4-(Hydroxymethyl)-4-methyl-isochromane-6-carboxylic acid

Water (1 mL), $K_2CO_3$ (185 mg, 1.34 mmol), $Pd(OAc)_2$ (20.1 mg, 0.089 mmol), and dccp·$2HBF_4$ (110 mg, 0.18 mmol) were added to a solution of (6-bromo-4-methyl-isochroman-4-yl)methanol (230 mg, 0.89 mmol) in DMSO (5 mL). The reaction mixture was purged with CO (g) three times and the resulting mixture was stirred at 100° C. for 16 hrs under a CO atmosphere (15 psi). The reaction mixture was diluted with $H_2O$ (30 mL) and extracted with EA (50 mL×3). The combined organic layers were discarded and the aqueous layer was adjusted to pH=4 with HCl (1 N). The aqueous layer was extracted with EA (30 mL×3). The combined organic layers were washed with brine (60 mL), dried over $Na_2SO_4$, filtered, and concentrated in vacuo affording a mixture of the title compounds (150 mg, 0.62 mmol) as a yellow solid. The stereoisomers were separated by chiral SFC (column: DAICEL CHIRALPAK IG (250 mm×30 mm, 10 μm); mobile phase: [0.1% $NH_3$—$H_2O$ IPA]; B %: 25%-25%, 6.65 min; 66 min). The mobile phase was concentrated under reduced pressure to remove most of the MeOH. Water (40 mL) was added and each desired compound mixture was lyophilized affording Intermediate 31 (44 mg, 0.20 mmol) as an off-white solid and Intermediate 32 (48 mg, 0.21 mmol) as an off-white solid.

Intermediate 31

$^1$H NMR (400 MHz, DMSO-d6) δ=13.02-12.77 (m, 1H), 7.90 (s, 1H), 7.72 (d, J=1.2 Hz, 1H), 7.14 (d, J=8.0 Hz, 1H), 4.88-4.87 (m, 1H), 4.74 (d, J=4.0 Hz, 2H), 3.90 (d, J=11.2 Hz, 1H), 3.58-3.50 (m, 1H), 3.42-3.35 (m, 2H), 1.14 (s, 3H).

Intermediate 32

$^1$H NMR (400 MHz, DMSO-d6) δ=13.02-12.77 (m, 1H), 7.90 (s, 1H), 7.72 (d, J=1.2 Hz, 1H), 7.14 (d, J=8.0 Hz, 1H), 4.88-4.87 (m, 1H), 4.74 (d, J=4.0 Hz, 2H), 3.90 (d, J=11.2 Hz, 1H), 3.58-3.50 (m, 1H), 3.42-3.35 (m, 2H), 1.14 (s, 3H).

Intermediate 33: 2-Methyl-5,6,7,8-tetrahydro-2,6-naphthyridin-1(2H)-one

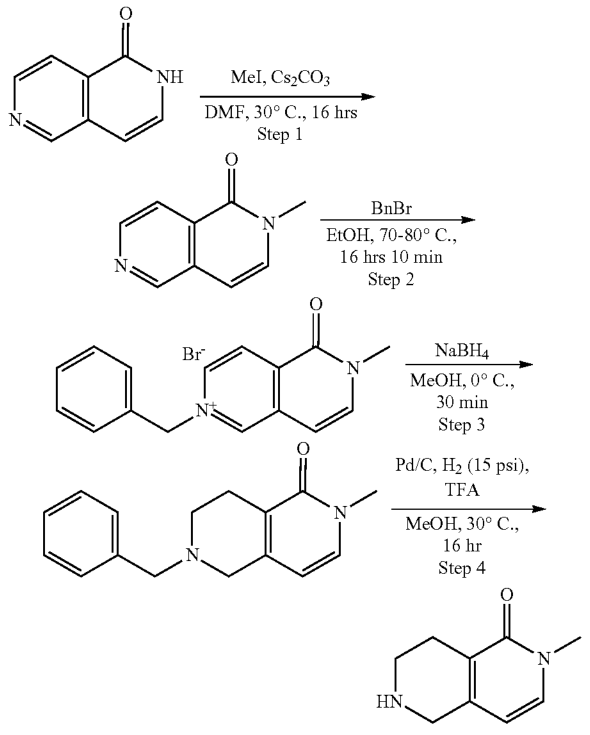

Intermediate 33

Step 1: 2-Methyl-2,6-naphthyridin-1(2H)-one

To a mixture of 2,6-naphthyridin-1(2H)-one (200 mg, 1.37 mmol) in DMF (10 mL) was added $Cs_2CO_3$ (668.82 mg, 2.05 mmol) and MeI (291.36 mg, 2.05 mmol, 127.79 uL) at 30° C. The mixture was stirred at 30° C. for 16 hrs. The mixture was poured into $H_2O$ (10 mL) and extracted with DCM (10 mL*3).

The combined organic layers were dried over anhydrous $Na_2SO_4$, filtered and concentrated under reduced pressure. The residue was purified by prep-TLC (DCM/MeOH=20/1, Rf=0.4) to afford the title compound (160 mg, 946.72 umol, 69.18% yield) as a yellow solid.

LCMS (ESI) m/z: $[M+H]^+$=161.1.

$^1$H NMR (400 MHz, $CDCl_3$) δ=8.98 (s, 1H), 8.69 (d, J=5.2 Hz, 1H), 8.19 (d, J=5.2 Hz, 1H), 7.20 (d, J=7.2 Hz, 1H), 6.58 (d, J=7.2 Hz, 1H), 3.65 (s, 3H) ppm.

Step 2: 2-Benzyl-6-methyl-5-oxo-5,6-dihydro-2,6-naphthyridin-2-ium bromide

A mixture of 2-methyl-2,6-naphthyridin-1(2H)-one (50 mg, 312.16 umol) in EtOH (0.5 mL) was stirred at 70° C. for 10 min. Then benzyl bromide (720.00 mg, 4.21 mmol, 0.5 mL) was added. The mixture was stirred at 80° C. for 16 hrs. The mixture was treated with MTBE (10 mL) and filtered. The filter cake was dried under reduced pressure to afford the title compound (130 mg, crude) as a yellow solid.

$^1$H NMR (400 MHz, DMSO-d6) δ=9.87 (s, 1H), 8.98-8.97 (m, 1H), 8.68 (d, J=6.4 Hz, 1H), 7.96 (d, J=7.2 Hz, 1H), 7.59-7.42 (m, 5H), 6.96 (d, J=7.6 Hz, 1H), 5.96 (s, 2H), 3.60 (s, 3H) ppm.

Step 3: 6-Benzyl-2-methyl-5,6,7,8-tetrahydro-2,6-naphthyridin-1(2H)-one

To a mixture of 2-benzyl-6-methyl-5-oxo-5,6-dihydro-2,6-naphthyridin-2-ium bromide (70 mg, 211.35 umol) in MeOH (1 mL) was added $NaBH_4$ (39.98 mg, 1.06 mmol) in several portions at 0° C. The mixture was stirred at 0° C. for 30 min. The mixture was poured into 1 M HCl aqueous solution (5 mL) and basified with sat. $NaHCO_3$ to pH=8. The mixture was extracted with EA (10 mL*3). The combined organic layers were dried over anhydrous $Na_2SO_4$, filtered and concentrated under reduced pressure to afford the title compound (35 mg, 137.62 umol, 65.1% yield) as a yellow solid.

LCMS (ESI) m/z: $[M+H]^+$=255.3.

$^1$H NMR (400 MHz, $CDCl_3$) δ=7.40-7.28 (m, 5H), 7.07 (d, J=7.2 Hz, 1H), 5.84 (d, J=6.8 Hz, 1H), 3.69 (s, 2H), 3.52 (s, 3H), 3.39 (s, 2H), 2.79-2.64 (m, 4H) ppm.

Step 4: 2-Methyl-2,6-naphthyridin-1(2H)-one

To a mixture of 6-benzyl-2-methyl-5,6,7,8-tetrahydro-2,6-naphthyridin-1(2H)-one (35 mg, 137.62 umol) in MeOH (1 mL) was added TFA (31.38 mg, 275.24 umol, 20.38 uL) and Pd/C (20 mg, 10% purity). The mixture was purged with $H_2$ 3 times and stirred at 30° C. for 16 hrs under $H_2$ (15 psi). The mixture was filtered and the mother liquor was concentrated under reduced pressure to afford the title compound (30 mg, 107.83 umol, 78.4% yield, TFA salt) as a yellow oil.

LCMS (ESI) m/z: $[M+H]^+$=165.1.

Intermediate 34: 1-Bromo-4-cyclobutyl-2-methoxybenzene

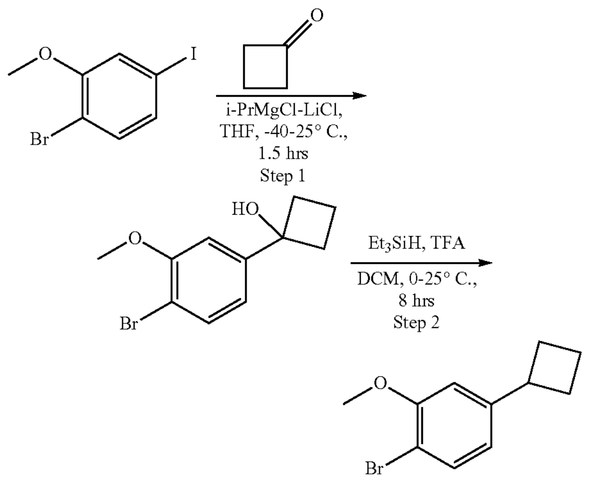

Intermediate 34

Step 1: 1-(4-Bromo-3-methoxyphenyl)cyclobutan-1-ol

To a mixture of 1-bromo-4-iodo-2-methoxy-benzene (2.4 g, 7.67 mmol, 5.41 mL) in THE (25 mL) was added i-PrMgCl—LiCl (1.3 M, 6.19 mL) dropwise at −40° C. The mixture was stirred at −40° C. for 0.5 hr, then cyclobutanone (591.30 mg, 8.44 mmol) was added at −40° C. slowly. The resulting mixture was stirred at 25° C. for 1 hr. The mixture was poured into sat.$NH_4Cl$ (200 mL) and extracted with EA (150 mL*2). The combined organic layers were washed with brine (250 mL), dried over $Na_2SO_4$, filtered and concentrated under reduced pressure. The residue was purified by column chromatography ($SiO_2$, Petroleum ether/Ethyl acetate=20/1 to 1/1) to give the title compound (1.9 g, 6.65 mmol, 86.71% yield) as a colorless oil.

LCMS (ESI) m/z: $[M+H]^+$=211.0.

1H NMR (400 MHz, $CDCl_3$) δ=7.52 (d, J=8.0 Hz, 1H), 7.08 (d, J=2.0 Hz, 1H), 6.98-6.96 (m, 1H), 4.14-4.12 (m, 1H), 3.93 (s, 3H), 2.61-2.48 (m, 2H), 2.43-2.30 (m, 2H), 2.12-1.97 (m, 3H), 1.80-1.68 (m, 1H) ppm Step 2: 1-Bromo-4-cyclobutyl-2-methoxybenzene To a mixture of 1-(4-bromo-3-methoxyphenyl)cyclobutan-1-ol (400 mg, 1.56 mmol) in DCM (20 mL) was added $Et_3SiH$ (1.81 g, 15.56 mmol) and TFA (1.77 g, 15.56 mmol) at 0° C., then the mixture was stirred at 25° C. for 8 hrs. The mixture was diluted with DCM (150 mL), then washed with sat. $NaHCO_3$ (100 mL*2). The organic phase was dried over $Na_2SO_4$, filtered and concentrated under vacuum. The residue was purified by column chromatography ($SiO_2$, Petroleum ether) to give the title compound (150 mg, 622.09 umol, 39.99% yield) as a colorless oil.

$^1$H NMR (400 MHz, $CDCl_3$) δ=7.44 (d, J=8.0 Hz, 1H), 6.78-6.68 (m, 2H), 3.91 (s, 3H), 3.55-3.47 (m, 1H), 2.39-2.32 (m, 2H), 2.15-2.07 (m, 2H), 2.06-1.98 (m, 1H), 1.90-1.85 (m, 1H) ppm Intermediate 35: 4-Bromo-7-fluoro-1,2-dimethyl-1H-indole

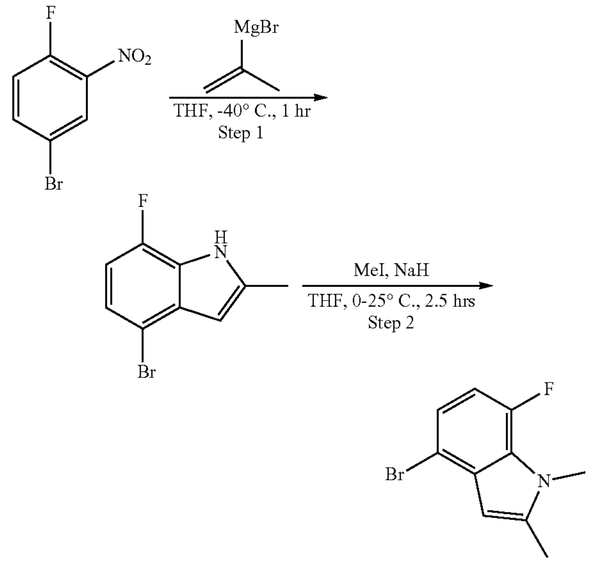

Intermediate 35

Step 1: 4-Bromo-7-fluoro-2-methyl-1H-indole

To a mixture of 4-bromo-1-fluoro-2-nitro-benzene (2 g, 9.09 mmol, 1.12 mL) in THF (20 mL) was added bromo (isopropenyl)magnesium (0.5 M, 72.73 mL) dropwisely at −40° C. under $N_2$. The mixture was stirred at −40° C. for 1 hr. The mixture was poured into sat. $NH_4Cl$ (100 mL) and extracted with ethyl acetate (50 mL*2). The combined organic phase was washed with brine (50 mL*1), dried with anhydrous $Na_2SO_4$, filtered and concentrated under vacuum. The residue was purified by silica gel chromatography (Petroleum ether/Ethyl acetate=20/1) to give the title compound (500 mg, 2.19 mmol, 24.12% yield) as a yellow oil.

Step 2: 4-Bromo-7-fluoro-1,2-dimethyl-1H-indole

To a solution of 4-bromo-7-fluoro-2-methyl-1H-indole (80 mg, 350.78 umol) in THF (1 mL) was added NaH (28.06 mg, 701.57 umol, 60% purity) at 0° C. and stirred at 25° C. for 0.5 hr. MeI (149.37 mg, 1.05 mmol) was then added to the mixture at 0° C. The mixture was stirred at 25° C. for 2 hrs. The reaction mixture was diluted with sat. $NH_4Cl$ (10 mL) and extracted with EA (10 mL*2). The combined organic layers were dried over anhydrous $Na_2SO_4$, filtered and concentrated. The residue was purified by silica gel chromatography (Petroleum ether/Ethyl acetate=3/1) to give the title compound (60 mg, 247.84 umol, 70.65% yield) as a white solid.

$^1$H NMR (400 MHz, $CDCl_3$) δ=7.08-7.06 (m 1H), 6.71-6.66 (m, 1H), 6.30-6.29 (m, 1H), 3.87 (d, J=1.2 Hz, 3H), 2.41 (s, 3H) ppm.

Intermediate 36: 4-Bromo-2-ethyl-1-methyl-1H-indole

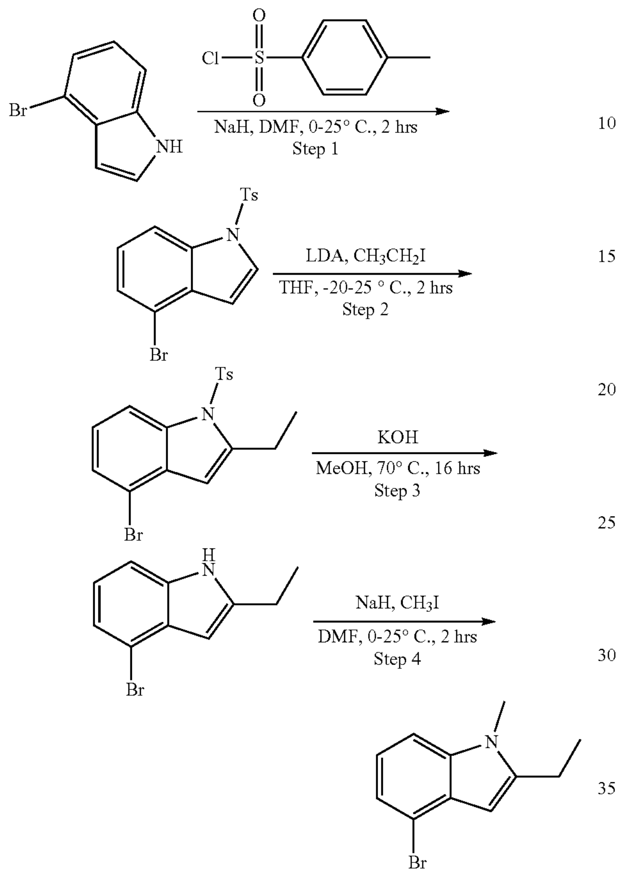

Intermediate 36

Step 1: 4-Bromo-1-tosyl-1H-indole

To a solution of 4-bromo-1H-indole (1 g, 5.10 mmol, 641.03 uL) in DMF (10 mL) was added NaH (244.82 mg, 6.12 mmol, 60% purity) at 0° C. and the mixture was stirred at 0° C. for 1 hr under $N_2$ atmosphere. 4-Methylbenzenesulfonyl chloride (1.16 g, 6.08 mmol) was then added and the mixture was stirred at 25° C. for 1 hr. The reaction mixture was poured into $NH_4Cl$ (30 mL) and extracted with EA (40 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=50/1 to 3/1) to give the title compound (1.6 g, 4.02 mmol, 78.73% yield) as an off-white solid.

$^1$H NMR (400 MHz, DMSO-d6) δ=7.99-7.93 (m, 2H), 7.89 (d, J=8.4 Hz, 2H), 7.49 (d, J=7.6 Hz, 1H), 7.39 (d, J=8.4 Hz, 2H), 7.29-7.27 (m, 1H), 6.77 (d, J=3.6 Hz, 1H), 2.31 (s, 3H) ppm.

Step 2: 4-Bromo-2-ethyl-1-tosyl-1H-indole

To a solution of 4-bromo-1-tosyl-1H-indole (1.2 g, 3.43 mmol) in THE (12 mL) was added LDA (2 M, 2.06 mL) at −20° C. under $N_2$, and the mixture was stirred at −20° C. for 30 min under $N_2$ atmosphere. Iodoethane (801.58 mg, 5.14 mmol) was then added and the mixture was stirred at 25° C. for 2 hrs. The reaction mixture was diluted with $H_2O$ (30 mL) and extracted with EA (40 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=100/1 to 10/1) to give the title compound (220 mg, 581.58 umol, 16.97% yield) as a white solid.

$^1$H NMR (400 MHz, $CDCl_3$) δ=8.15 (d, J=8.4 Hz, 1H), 7.63 (d, J=8.4 Hz, 2H), 7.38 (d, J=7.6 Hz, 1H), 7.22 (d, J=8.4 Hz, 2H), 7.15-7.10 (m, 1H), 6.47 (s, 1H), 3.06-3.01 (m, 2H), 2.36 (s, 3H), 1.39-1.35 (m, 3H) ppm.

Step 3: 4-Bromo-2-ethyl-1H-indole

To a solution of 4-bromo-2-ethyl-1-tosyl-1H-indole (220.00 mg, 581.58 umol) in MeOH (60 mL) was added KOH (1.63 g, 29.08 mmol). The mixture was stirred at 70° C. for 16 hrs. The reaction mixture was treated with 2 N HCl (20 mL) and was extracted with EA (30 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=100/1 to 10/1) to give the title compound (100 mg, 446.24 umol, 76.73% yield) as a colorless oil.

$^1$H NMR (400 MHz, CHLOROFORM-d) 5=8.09-7.95 (m, 1H), 7.24 (d, J=8.0 Hz, 2H), 7.03-6.92 (m, 1H), 6.32 (s, 1H), 2.84-2.79 (m, 2H), 1.40-1.36 (m, 3H) ppm.

Step 4: 4-Bromo-2-ethyl-1-methyl-1H-indole

To a solution of 4-bromo-2-ethyl-1H-indole (150 mg, 669.35 umol) in DMF (2 mL) was added NaH (40.16 mg, 1.00 mmol, 60% purity) at 0° C. under $N_2$. The resulting mixture was stirred at 0° C. for 15 min under $N_2$ atmosphere. Iodomethane (114.01 mg, 803.22 umol) was then added and the resulting mixture was stirred at 25° C. for 2 hrs. The reaction mixture was poured into $NH_4Cl$ (30 mL) and extracted with EA (40 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=100/1 to 10/1) to give the title compound (150 mg, 629.93 umol, 94.11% yield) as colorless oil.

Intermediate 37: 4-Chloro-2-cyclopropyl-1-methyl-1H-indole

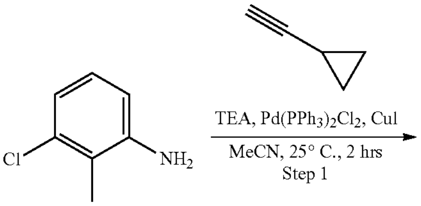

-continued

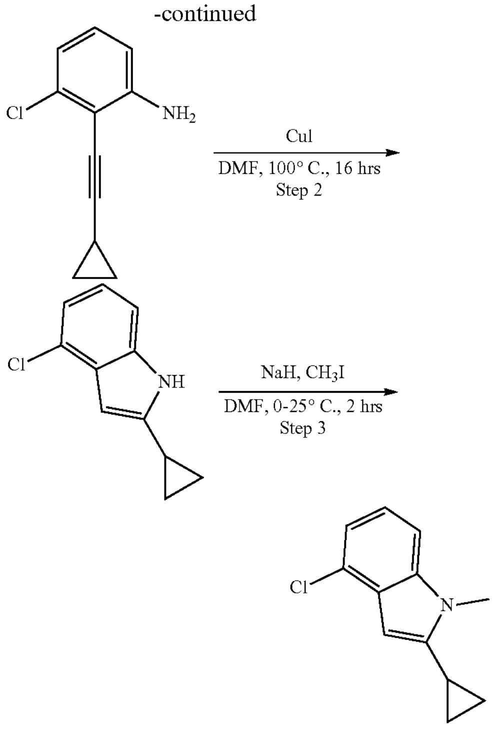

Intermediate 37

Step 1: 3-Chloro-2-(cyclopropylethynyl)aniline

To a mixture of 3-chloro-2-iodo-aniline (2 g, 7.89 mmol) and ethynylcyclopropane (521.57 mg, 7.89 mmol) in MeCN (40 mL) was added TEA (7.98 g, 78.91 mmol), Pd($PPh_3$)$_2C_{12}$ (553.84 mg, 789.06 umol) and CuI (150.28 mg, 789.06 umol). The mixture was degassed and purged with $N_2$ 3 times and the mixture was stirred at 25° C. for 2 hrs under $N_2$ atmosphere. The reaction mixture was diluted with $H_2O$ (20 mL) and extracted with EA (30 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=50/1 to 5/1) to give the title compound (1.3 g, 6.78 mmol, 85.96% yield) as a yellow oil.

$^1$H NMR (400 MHz, DMSO-d6) δ=6.97-6.95 (m, 1H), 6.59 (d, J=8.0 Hz, 2H), 5.50 (s, 2H), 1.63-1.61 (m, 1H), 0.95-0.86 (m, 2H), 0.83-0.76 (m, 2H) ppm.

Step 2: 4-Chloro-2-cyclopropyl-1H-indole

To a solution of 3-chloro-2-(cyclopropylethynyl)aniline (1 g, 5.22 mmol) in DMF (10 mL) was added CuI (2.98 g, 15.65 mmol). The mixture was stirred at 100° C. for 16 hrs. The reaction mixture was diluted with $H_2O$ (20 mL) and extracted with EA (30 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=100/1 to 10/1) to give the title compound (600 mg, 2.71 mmol, 52.01% yield) as a yellow oil.

LCMS (ESI) m/z: [M+H]+=191.9.

$^1$H NMR (400 MHz, CHLOROFORM-d) 5=8.37-7.67 (m, 1H), 7.18 (d, J=7.6 Hz, 1H), 7.11-6.98 (m, 2H), 6.25 (s, 1H), 2.03-1.87 (m, 1H), 1.08-0.95 (m, 2H), 0.89-0.72 (m, 2H) ppm.

Step 3: 4-Chloro-2-cyclopropyl-1-methyl-1H-indole

To a solution of 4-chloro-2-cyclopropyl-1H-indole (180 mg, 939.18 umol) in DMF (2 mL) was added NaH (56.35 mg, 1.41 mmol, 60% purity) at 0° C. under $N_2$ and the mixture was stirred at 0° C. for 15 min under $N_2$ atmosphere. Iodomethane (199.96 mg, 1.41 mmol) was then added and the mixture was stirred at 25° C. for 2 hrs. The reaction mixture was poured into $NH_4Cl$ (30 mL) and extracted with EA (40 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=100/1 to 10/1) to give the title compound (190 mg, 864.18 umol, 92.01% yield) as a colorless oil.

LCMS (ESI) m/z: [M+H]+=206.0.

Intermediate 38: 4-Bromo-3-(difluoromethyl)-1-(oxetan-3-yl)-1H-pyrazole

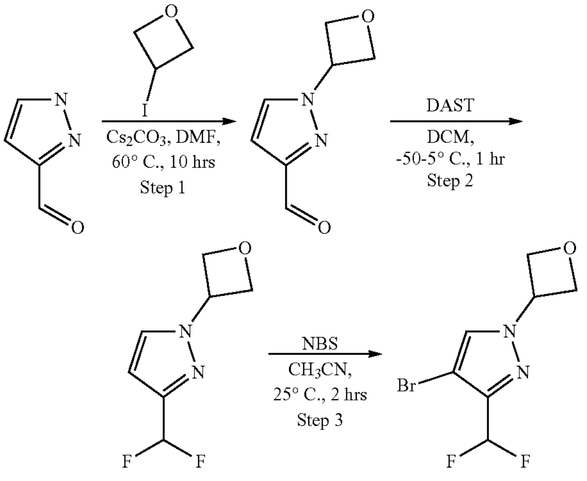

Intermediate 38

Step 1: 1-(Oxetan-3-yl)-1H-pyrazole-3-carbaldehyde

To a mixture of 1H-pyrazole-3-carbaldehyde (10 g, 104.07 mmol) and $Cs_2CO_3$ (67.82 g, 208.14 mmol) in DMF (200 mL) was added 3-iodooxetane (28.72 g, 156.11 mmol), then the mixture was stirred at 60° C. for 10 hrs. The reaction mixture was quenched by the addition of water (1000 mL) and the resulting mixture was extracted with EA (400 mL*3). The combined organic layers were washed with brine (200 mL), dried over $Na_2SO_4$, filtered and concentrated under reduced pressure. The residue was purified by column chromatography ($SiO_2$, Petroleum ether/Ethyl acetate=10/1 to 0/1) to give the title compound (3.1 g, 20.37 mmol, 19.58% yield) as a yellow solid.

$^1$H NMR (400 MHz, $CDCl_3$) δ=10.01 (s, 1H), 7.63-7.62 (m, 1H), 6.86 (d, J=2.4 Hz, 1H), 5.57-5.50 (m, 1H), 5.09 (d, J=6.4 Hz, 4H) ppm.

Step 2: 3-(Difluoromethyl)-1-(oxetan-3-yl)-1H-pyrazole

To a mixture of 1-(oxetan-3-yl)-1H-pyrazole-3-carbaldehyde (600 mg, 3.94 mmol) in DCM (12 mL) was added DAST (1.91 g, 11.83 mmol, 1.56 mL) at −50° C., then the mixture was stirred at 5° C. for 1 hr. The mixture was poured into sat. $NaHCO_3$ (100 mL) and extracted with EA (50 mL*2). The combined organic layers were washed with brine (40 mL), dried over $Na_2SO_4$, filtered and concentrated under vacuum. The residue was purified by reversed phase HPLC (0.1% FA condition). The product fraction was extracted with EA (150 mL*2) and the combined organic layers were washed with brine (150 mL), dried over $Na_2SO_4$, filtered and concentrated under vacuum to give the title compound (170 mg, 898.09 umol, 22.77% yield) as a colorless oil.

LCMS (ESI) m/z: $[M+H]^+$=175.1

Step 3: 4-Bromo-3-(difluoromethyl)-1-(oxetan-3-yl)-1H-pyrazole

To a mixture of 3-(difluoromethyl)-1-(oxetan-3-yl)-1H-pyrazole (170 mg, 976.18 umol) in MeCN (4 mL) was added NBS (191.12 mg, 1.07 mmol) and the mixture was stirred at 25° C. for 2 hrs. The mixture was concentrated under vacuum and the residue was purified by column chromatography ($SiO_2$, Petroleum ether/Ethyl acetate=20/1 to 5/1) to give the title compound (200 mg, 735.05 umol, 75.30% yield) as a colorless oil.

LCMS (ESI) m/z: $[^{81}BrM+H]^+$=255.0

$^1$H NMR (400 MHz, $CDCl_3$) δ=7.68 (s, 1H), 6.84-6.58 (m, 1H), 5.46-5.51 (m, 1H), 5.07-4.99 (m, 4H) ppm Intermediate 39: 4-Bromo-3-(2,2-difluoroethyl)-1-(oxetan-3-yl)-1H-pyrazole

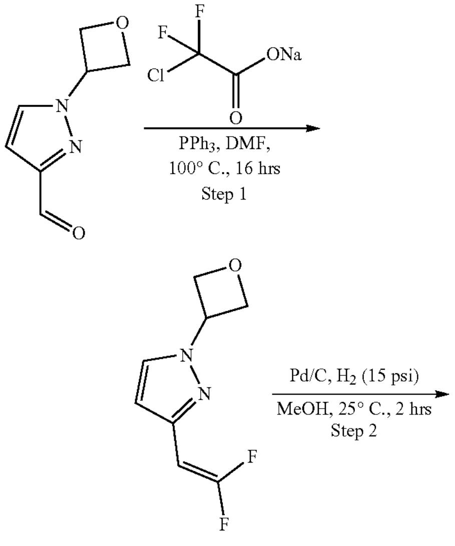

-continued

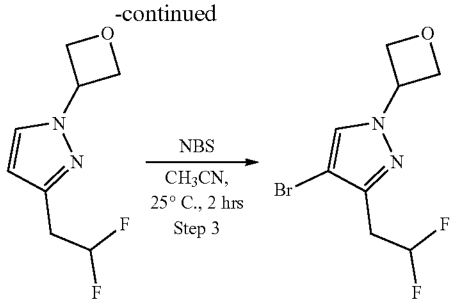

Intermediate 39

Step 1: 3-(2,2-Difluorovinyl)-1-(oxetan-3-yl)-1H-pyrazole

To a mixture of 1-(oxetan-3-yl)-1H-pyrazole-3-carbaldehyde (1 g, 6.57 mmol) and sodium 2-chloro-2,2-difluoroacetate (1.50 g, 9.86 mmol) in DMF (10 mL) was added $PPh_3$ (2.59 g, 9.86 mmol) under $N_2$, then the mixture was stirred at 100° C. for 2 hrs. The reaction mixture was diluted with water (250 mL) and extracted with EA (150 mL*2). The combined organic layers were washed with brine (150 mL*2), dried over $Na_2SO_4$, filtered and concentrated under reduced pressure. The residue was purified by column chromatography ($SiO_2$, Petroleum ether/Ethyl acetate=50/1 to 3/1) to give the title compound (700 mg, 3.12 mmol, 47.49% yield) as a colorless oil.

LCMS (ESI) m/z: $[M+H]^+$=187.1

Step 2: 3-(2,2-Difluoroethyl)-1-(oxetan-3-yl)-1H-pyrazole

A mixture of 3-(2,2-difluorovinyl)-1-(oxetan-3-yl)-1H-pyrazole (250 mg, 1.34 mmol) in MeOH (10 mL) and EA (10 mL) was added Pd/C (100 mg, 1.34 mmol, 10% purity) under $H_2$ (15 psi), then the mixture was stirred at 25° C. for 2 hrs. The mixture was filtered and the filtrate concentrated under vacuum to give the title compound (230 mg, crude) as colorless oil, used directly in the next step.

LCMS (ESI) m/z: $[M+H]^+$=189.1

Step 3: 4-Bromo-3-(2,2-difluoroethyl)-1-(oxetan-3-yl)-1H-pyrazole

A mixture of 3-(2,2-difluoroethyl)-1-(oxetan-3-yl)-1H-pyrazole (210 mg, 1.12 mmol) and NBS (218.49 mg, 1.23 mmol) in MeCN (4 mL) was stirred at 25° C. for 2 hrs. The mixture was concentrated under vacuum and the residue was purified by column chromatography (SiO2, Petroleum ether/Ethyl acetate=20/1 to 3/1) to give the title compound (150 mg, 544.80 umol, 48.82% yield) as a colorless oil.

LCMS (ESI) m/z: $[^{81}BrM+H]^+$=269.0

$^1$H NMR (400 MHz, $CDCl_3$) δ=7.61 (s, 1H), 6.280-5.97 (m, 1H), 5.40-5.36 (m, 1H), 5. 50-4.98 (m, 4H), 3.27-3.17 (m, 2H) ppm Intermediate 40:
4-Bromo-3-fluoro-1-methyl-1H-indole

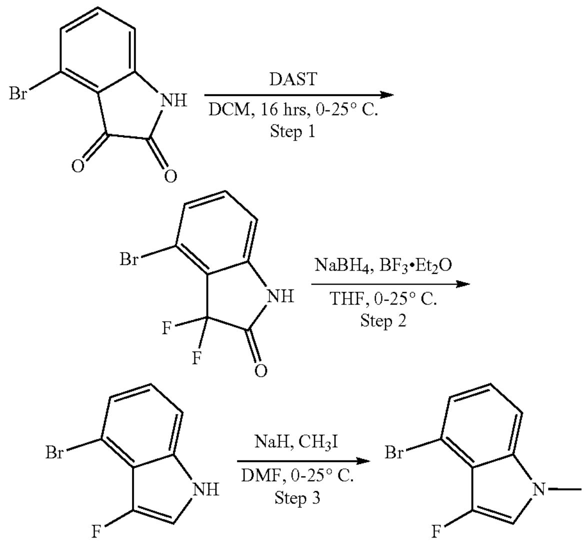

Intermediate 40

Step 1: 4-Bromo-3,3-difluoroindolin-2-one

To a solution of 4-bromoindoline-2,3-dione (1 g, 4.42 mmol) in DCM (10 mL) was added DAST (1.78 g, 11.06 mmol) at 0° C. under $N_2$. The mixture was stirred at 25° C. for 16 hrs. The reaction mixture was poured into sat. $NaHCO_3$ (30 mL) and extracted with DCM (30 mL*3). The combined organic layers were washed with brine (30 mL*2), dried over $Na_2SO_4$, filtered and concentrated under reduced pressure. The residue was purified by column chromatography ($SiO_2$, Petroleum ether/Ethyl acetate=50/1 to 3/1) to give the title compound (1 g, 4.03 mmol, 91.13% yield) as a brown solid.

$^1$H NMR (400 MHz, DMSO-d6) δ=11.41 (d, J=0.8 Hz, 1H), 7.50-7.40 (m, 1H), 7.34 (d, J=8.1 Hz, 1H), 6.99 (d, J=7.6 Hz, 1H) ppm.

Step 2: 4-Bromo-3-fluoro-1H-indole

To a mixture of $NaBH_4$ (91.52 mg, 2.42 mmol) in THE (2 mL) was added $BF_3 \cdot Et_2O$ (343.34 mg, 2.42 mmol) at 0° C. under $N_2$ and the mixture was stirred at 0° C. for 1 hr. This mixture was added to a solution of 4-bromo-3,3-difluoroindolin-2-one (200 mg, 806.37 umol) in THE (2 mL) at 0° C. under $N_2$ and the resulting mixture was stirred at 25° C. for 16 hrs. After 16 hrs, to a solution of $NaBH_4$ (152.54 mg, 4.03 mmol) in THE (2 mL) was added $BF_3$-$Et_2O$ (572.23 mg, 4.03 mmol) at 0° C. and the mixture was stirred at 0° C. for 1 hr. This mixture was then added to the former reaction mixture at 0° C. The resulting mixture was stirred at 25° C. for another 4 hrs. The reaction mixture was quenched by addition of 2N HCl, diluted with $H_2O$ (30 mL) and extracted with EA (40 mL*3). The combined organic layers were washed with brine (30 mL), dried over $Na_2SO_4$, filtered and concentrated under reduced pressure. The residue was purified by column chromatography ($SiO_2$, Petroleum ether/Ethyl acetate=50/1 to 5/1) to give the title compound (100 mg, 420.07 umol, 52.09% yield) as a colorless oil.

$^1$H NMR (400 MHz, DMSO-d6) δ=11.18 (s, 1H), 7.46-7.45 (m, 1H), 7.42-7.35 (m, 1H), 7.22 (d, J=7.6 Hz, 1H), 7.10-7.01 (m, 1H) ppm.

Step 3: 4-Bromo-3-fluoro-1-methyl-1H-indole

To a solution of 4-bromo-3-fluoro-1H-indole (100 mg, 467.22 umol) in DMF (1 mL) was added NaH (28.03 mg, 700.82 umol, 60% purity) at 0° C. under $N_2$, and the mixture was stirred at 0° C. for 15 min. Iodomethane (79.58 mg, 560.66 umol) was then added and the resulting mixture was stirred at 25° C. for 2 hrs. The reaction mixture was poured into $NH_4Cl$ (30 mL) and extracted with EA (40 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=100/1 to 10/1) to give the title compound (60 mg, 263.09 umol, 56.31% yield) as a colorless oil.

$^1$H NMR (400 MHz, DMSO-d6) δ=7.56-7.44 (m, 2H), 7.25 (d, J=7.6 Hz, 1H), 7.16-7.06 (m, 1H), 3.74 (s, 3H) ppm.

Intermediate 41:
4-Bromo-2-(difluoromethyl)-1-methyl-1H-indole

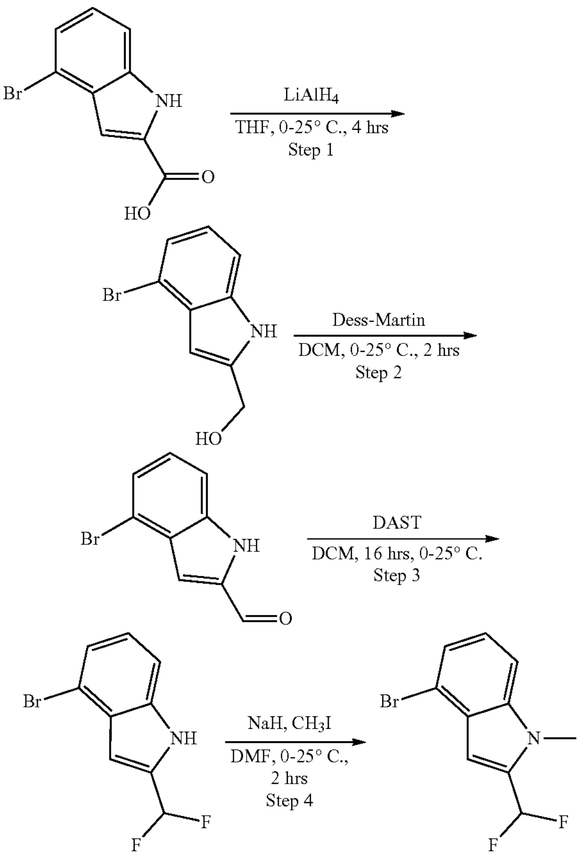

Intermediate 41

Step 1: (4-Bromo-1H-indol-2-yl)methanol

To a solution of 4-bromo-1H-indole-2-carboxylic acid (2 g, 8.33 mmol) in THE (20 mL) was added $LiAlH_4$ (948.65 mg, 24.99 mmol) at 0° C. under $N_2$. The mixture was stirred at 25° C. for 4 hrs. The reaction mixture was quenched by addition of $H_2O$, the mixture was adjusted to pH=2 with HCl (2 N) and extracted with EA (30 mL*3). The combined organic layers were washed with brine (60 mL*2), dried over $Na_2SO_4$, filtered and concentrated under reduced pressure. The residue was purified by column chromatography ($SiO_2$, DCM/MeOH=100:1-10:1) to give the title compound (1 g, 4.24 mmol, 50.86% yield) as a white solid.

LCMS (ESI) m/z: [M+H]+=235.0.

$^1$H NMR (400 MHz, DMSO-d6) δ=11.40 (s, 1H), 7.34 (d, J=8.4 Hz, 1H), 7.16-7.15 (m, 1H), 6.98-6.94 (m, 1H), 6.25 (d, J=1.2 Hz, 1H), 5.34-5.31 (m, 1H), 4.61 (d, J=5.6 Hz, 2H) ppm.

Step 2: 4-Bromo-1H-indole-2-carbaldehyde

To a solution of (4-bromo-1H-indol-2-yl)methanol (300 mg, 1.33 mmol) in DCM (3 mL) was added Dess-Martin (675.42 mg, 1.59 mmol) at 0° C. The mixture was stirred at 25° C. for 2 hrs. The reaction mixture was poured into sat. $NaHCO_3$ (30 mL) and extracted with DCM (30 mL*3). The combined organic layers were washed with brine (30 mL*2), dried over $Na_2SO_4$, filtered and concentrated under reduced pressure to give the title compound (297 mg, crude) as a brown solid, which was used directly in the next step.

Step 3: 4-Bromo-2-(difluoromethyl)-1H-indole

To a solution of 4-bromo-1H-indole-2-carbaldehyde (290 mg, 1.29 mmol) in DCM (3 mL) was added DAST (625.90 mg, 3.88 mmol) at 0° C. The mixture was stirred at 25° C. for 2 hrs. The reaction mixture was poured into sat. $NaHCO_3$ (30 mL) and extracted with DCM (30 mL*3). The combined organic layers were washed with brine (30 mL*2), dried over $Na_2SO_4$, filtered and concentrated under reduced pressure. The residue was purified by column chromatography ($SiO_2$, Petroleum ether/Ethyl acetate=50/1 to 3/1) to give the title compound (110 mg, 408.13 umol, 31.53% yield) as a brown solid.

$^1$H NMR (400 MHz, $CDCl_3$) δ=8.56 (s, 1H), 7.40-7.35 (m, 2H), 7.20-7.12 (m, 1H), 7.05-6.68 (m, 2H) ppm.

Step 4: 4-Bromo-2-(difluoromethyl)-1-methyl-1H-indole

To a solution of 4-bromo-2-(difluoromethyl)-1H-indole (110 mg, 447.06 umol) in DMF (1 mL) was added NaH (26.82 mg, 670.59 umol, 60% purity) at 0° C. The mixture was degassed and purged with $N_2$ for 3 times and stirred at 0° C. for 15 min under $N_2$ atmosphere. Iodomethane (69.80 mg, 491.77 umol) was then added and the resulting mixture was stirred at 25° C. for 2 hrs. The reaction mixture was poured into $NH_4Cl$ (30 mL) and extracted with EA (40 mL*3). The combined organic layers were washed with brine (30 mL*3), dried over $Na_2SO_4$, filtered and concentrated under reduced pressure. The residue was purified by column chromatography ($SiO_2$, Petroleum ether/Ethyl acetate=100/1 to 10/1) to give the title compound (110 mg, 422.95 umol, 94.61% yield) as a colorless oil.

LCMS (ESI) m/z: [M+H]+=261.9.

$^1$H NMR (400 MHz, DMSO-d6) δ=7.63 (d, J=8.4 Hz, 1H), 7.54-7.20 (m, 4H), 6.80 (s, 1H), 3.86 (s, 3H) ppm.

Intermediate 42: 4-Bromo-1-(2,2-difluorocyclopropyl)-3-methoxy-1H-pyrazole

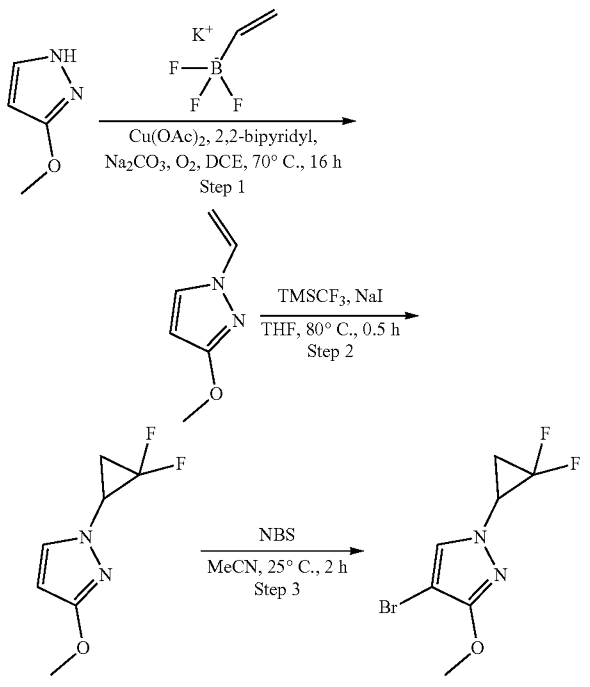

Intermediate 42

Step 1: 3-Methoxy-1-vinyl-1H-pyrazole

A mixture of 3-methoxy-1H-pyrazole (500 mg, 5.10 mmol), potassium trifluoro(vinyl)borate (1.02 g, 7.65 mmol), $Cu(OAc)_2$ (1.02 g, 5.61 mmol), $Na_2CO_3$ (1.19 g, 11.21 mmol) and 2,2'-bipyridyl (875.60 mg, 5.61 mmol) in DCE (10 mL) was degassed and purged with $O_2$ for 3 times. The mixture was stirred at 70° C. for 16 hrs under $O_2$ atmosphere. The mixture was poured into water (100 mL) and extracted with EA (50 mL*3). The combined organic layers were washed with brine (30 mL), dried over $Na_2SO_4$, filtered and concentrated. The residue was purified by flash silica gel chromatography (ISCO®; 25 g SepaFlash® Silica Flash Column, Eluent of 0-20% EA/Petroleum ether gradient @50 mL/min) to give the title compound (400 mg, 3.22 mmol, 63.22% yield) as a yellow oil.

LCMS (ESI) m/z: $[M+H]^+$=125.0

$^1$H NMR (400 MHz, $CDCl_3$-d) δ=7.33 (d, J=2.4 Hz, 1H), 6.94-6.72 (m, 1H), 5.78 (d, J=2.4 Hz, 1H), 5.44-5.32 (m, 1H), 4.67 (d, J=8.8 Hz, 1H), 3.93 (s, 3H) ppm.

Step 2: 1-(2,2-Difluorocyclopropyl)-3-methoxy-1H-pyrazole

To a mixture of 3-methoxy-1-vinyl-1H-pyrazole (400 mg, 3.22 mmol) in THE (5 mL) was added NaI (169.04 mg, 1.13 mmol). $TMSCF_3$ (1.60 g, 11.28 mmol) was then added slowly at 80° C. under $N_2$.

The reaction was stirred at 80° C. for 30 min. The solvent was removed under vacuum and the residue purified by flash silica gel chromatography (ISCO®; 25 g SepaFlash® Silica Flash Column, Eluent of 0-20% EA/Petroleum ether gradient @50 mL/min) to give the title compound (200 mg, 1.15 mmol, 35.64% yield) as a yellow oil.

LCMS (ESI) m/z: $[M+H]^+$=175.0

$^1$HNMR (400 MHz, $CDCl_3$-d) δ=7.32-7.13 (m, 1H), 5.62 (d, J=2.4 Hz, 1H), 3.91-3.83 (m, 1H), 3.81 (s, 3H), 2.08-1.99 (m, 1H), 1.97-1.88 (m, 1H) ppm.

Step 3: 4-Bromo-1-(2,2-difluorocyclopropyl)-3-methoxy-1H-pyrazole

To a mixture of 1-(2,2-difluorocyclopropyl)-3-methoxy-1H-pyrazole (100 mg, 574.22 umol) in MeCN (5 mL) was added NBS (112.42 mg, 631.65 umol). The reaction was stirred at 25° C. for 2 hrs. The solvent was removed under vacuum and the residue purified by flash silica gel chromatography (ISCO®; 20 g SepaFlash® Silica Flash Column, Eluent of 0-20% EA/Petroleum ether gradient @ 50 mL/min) to give the title compound (120 mg, 474.23 umol, 82.59% yield) as a yellow oil.

LCMS (ESI) m/z: $[^{79}BrM+H]^+$=253.0

$^1$H NMR (400 MHz, $CDCl_3$-d) δ=7.34 (s, 1H), 3.95 (s, 3H), 3.94-3.88 (m, 1H), 2.15-1.97 (m, 2H) ppm.

Intermediate 43: 1-(4-Bromo-3-methoxyphenyl)azetidine

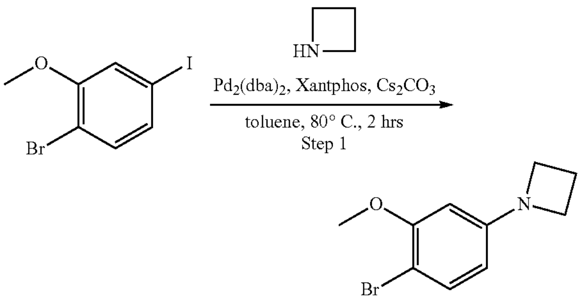

Intermediate 43

Step 1: 1-(4-Bromo-3-methoxyphenyl)azetidine

To a mixture of 1-bromo-4-iodo-2-methoxy-benzene (500 mg, 1.60 mmol) and azetidine (91.35 mg, 1.60 mmol) in toluene (5 mL) was added $Pd_2(dba)_3$ (146.52 mg, 160.00 umol), Xantphos (185.16 mg, 320.00 umol) and $Cs_2CO_3$ (1.56 g, 4.80 mmol) under $N_2$. The mixture was stirred at 80° C. for 16 hrs. The reaction mixture was added slowly into water (50 mL) and extracted with EA (50 mL*2). The combined organic phase was washed with brine (100 mL), dried over anhydrous $Na_2SO_4$, filtered and concentrated under vacuum. The residue was purified by column chromatography ($SiO_2$, PE/EA=10:1-1:1) to give the title compound (150 mg, 619.55 umol, 38.72% yield) as a yellow solid.

LCMS (ESI) m/z=$[M+H]^+$=242.0.

$^1$H NMR (400 MHz, DMSO-$d_6$) δ=7.25 (d, J=8.4 Hz, 1H), 6.06 (d, J=2.4 Hz, 1H), 5.93-5.90 (m, 1H), 3.81-3.78 (m, 7H), 2.32-2.24 (m, 2H) ppm.

Intermediate 44: 1-Bromo-4-(tert-butyl)-2-methoxybenzene

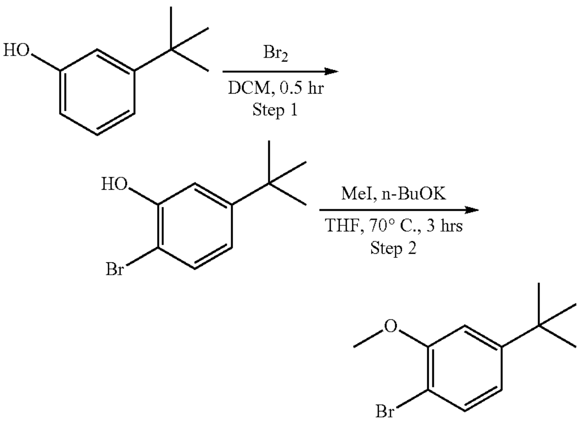

Intermediate 44

Step 1: 2-Bromo-5-(tert-butyl)phenol

To a solution of 3-tert-butylphenol (5 g, 33.29 mmol) in DCM (50 mL) was added a solution of Br2 (5.59 g, 34.95 mmol, 1.80 mL) in DCM (25 mL) over 30 mins at 0° C. The mixture was poured into sat. $Na_2SO_3$ (200 mL) and extracted with DCM (100 mL*2). The combined organic layers were dried over $Na_2SO_4$, filtered and concentrated under vacuum to give the title compound (8 g, crude) as a colorless oil.

$^1$H NMR (400 MHz, DMSO-$d_6$) δ=9.98 (s, 1H), 7.35 (d, J=8.4 Hz, 1H), 6.97 (d, J=2.4 Hz, 1H), 6.77-6.74 (m, 1H), 1.22 (s, 9H) ppm.

Step 2: 1-Bromo-4-(tert-butyl)-2-methoxybenzene

To a solution of 2-bromo-5-(tert-butyl)phenol (1 g, 4.36 mmol) in THE (5 mL) was added t-BuOK (494.66 mg, 4.41 mmol) followed by MeI (631.90 mg, 4.45 mmol). The mixture was stirred at 70° C. for 3 hrs. The mixture was poured into water (100 mL) and extracted with EA (100 mL*2). The combined organic layers were washed with brine (100 mL), dried over $Na_2SO_4$, filtered and concentrated under vacuum. The residue was purified by column chromatography ($SiO_2$, Petroleum ether/Ethyl acetate=1/0 to 10/1) to give the title compound (750 mg, 3.08 mmol, 70.67% yield) as a white solid.

$^1$H NMR (400 MHz, DMSO-$d_6$) δ=7.45 (d, J=8.4 Hz, 1H), 7.07-7.04 (m, 1H), 6.91-6.88 (m, 1H), 3.85 (s, 3H), 1.28 (s, 9H) ppm

Intermediate 45: 4-Bromo-3-(difluoromethoxy)-1-(oxetan-3-yl)-1H-pyrazole

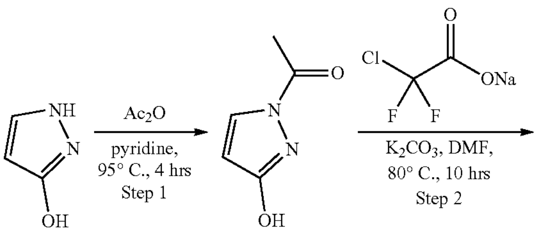

-continued

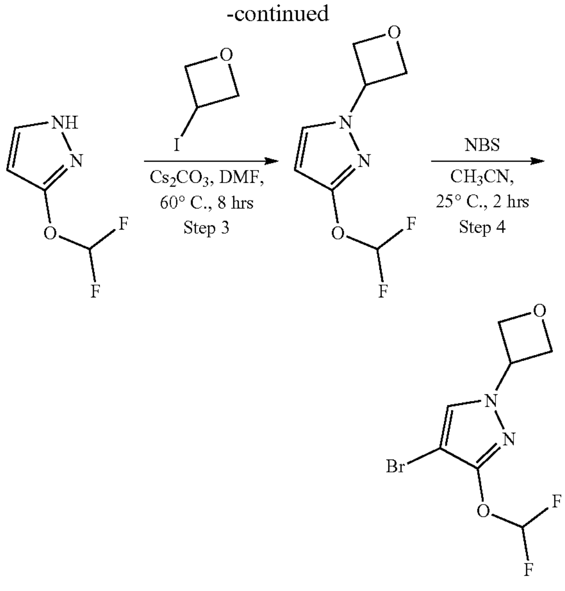

Intermediate 45

Step 1: 1-(3-Hydroxy-1H-pyrazol-1-yl)ethan-1-one

To a solution of 1H-pyrazol-3-ol (3 g, 35.68 mmol) in pyridine (15 mL) was added a solution of $Ac_2O$ (3.82 g, 37.47 mmol, 3.51 mL) in pyridine (6 mL) at 95° C. over 30 min, then the mixture was stirred at 95° C. for 3.5 hrs. The reaction mixture was concentrated under reduced pressure and the residue was triturated in MeOH (20 mL) to give the title compound (3.8 g, 30.13 mmol, 84.45% yield) as a yellow solid.

$^1$H NMR (400 MHz, DMSO-$d_6$) δ=10.97 (s, 1H), 8.12 (d, J=3.6 Hz, 1H), 6.00 (d, J=2.8 Hz, 1H), 2.47 (s, 3H) ppm.

Step 2: 3-(Difluoromethoxy)-1H-pyrazole

To a mixture of 1-(3-hydroxy-1H-pyrazol-1-yl)ethan-1-one (1000 mg, 7.93 mmol) and sodium 2-chloro-2,2-difluoroacetate (1.45 g, 9.52 mmol) in DMF (10 mL) was added $K_2CO_3$ (3.29 g, 23.79 mmol). The mixture was stirred at 80° C. for 10 hrs. The mixture was poured into sat. $NH_4Cl$ (150 mL) and extracted with EA (100 mL*3). The combined organic layers were washed with brine (150 mL*2), dried over $Na_2SO_4$, filtered and concentrated under reduced pressure. The residue was purified by column chromatography ($SiO_2$, Petroleum ether/Ethyl acetate=10/1 to 1/1) to give the title compound (270 mg, 2.01 mmol, 25.39% yield) as a colorless oil.

LCMS (ESI) m/z: $[M+H]^+$=135.1

$^1$H NMR (400 MHz, DMSO-$d_6$) δ=12.49 (s, 1H), 7.69 (s, 1H), 7.41-7.04 (m, 1H), 5.97-5.96 (m, 1H) ppm.

Step 3: 3-(Difluoromethoxy)-1-(oxetan-3-yl)-1H-pyrazole

To a mixture of 3-(difluoromethoxy)-1H-pyrazole (270 mg, 2.01 mmol), 3-iodooxetane (555.70 mg, 3.02 mmol) in DMF (5 mL) was added $Cs_2CO_3$ (1.31 g, 4.03 mmol). The mixture was stirred at 60° C. for 8 hrs. The mixture was poured into water (50 mL) and extracted with EA (50 mL*2). The combined organic layers were washed with brine (100 mL), dried over $Na_2SO_4$, filtered and concentrated under reduced pressure. The residue was purified by column chromatography ($SiO_2$, Petroleum ether/Ethyl acetate=50/1 to 3/1) to give the title compound (270 mg, 1.18 mmol, 58.53% yield) as a colorless oil.

LCMS (ESI) m/z: $[M+H]^+$=427.1

$^1$H NMR (400 MHz, $CDCl_3$) δ=7.41 (d, J=2.4 Hz, 1H), 7.07-6.70 (m, 1H), 5.93 (d, J=2.4 Hz, 1H), 5.34-5.27 (m, 1H), 5.08-4.97 (m, 4H) ppm.

Step 4: 4-Bromo-3-(difluoromethoxy)-1-(oxetan-3-yl)-1H-pyrazole

To a mixture of 3-(difluoromethoxy)-1-(oxetan-3-yl)-1H-pyrazole (270 mg, 1.42 mmol) in MeCN (5 mL) was added NBS (278.00 mg, 1.56 mmol), then the mixture was stirred at 25° C. for 2 hrs. The mixture was concentrated under vacuum and the residue was purified by column chromatography ($SiO_2$, Petroleum ether/Ethyl acetate=10/1 to 1/1) to give the title compound (300 mg, 1.05 mmol, 73.82% yield) as a white solid.

LCMS (ESI) m/z: $[^{79}BrM+H]^+$=269.0

$^1$H NMR (400 MHz, $CDCl_3$) δ=7.49 (s, 1H), 7.16-6.80 (m, 1H), 5.29-5.26 (m, 1H), 5.00 (d, J=6.0 Hz, 4H) ppm.

Intermediate 46: Pyrazolo[1,5-a]pyridin-2-yl trifluoromethanesulfonate

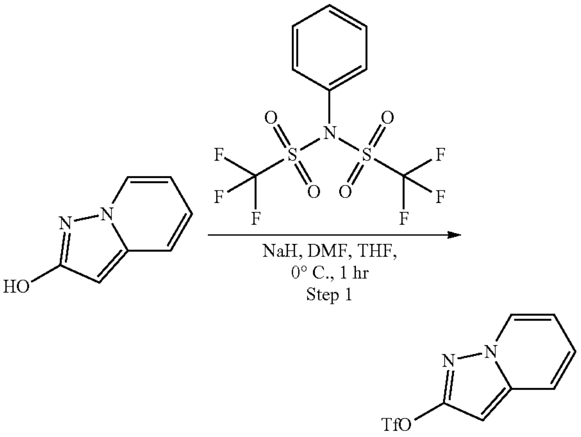

Intermediate 46

Step 1: Pyrazolo[1,5-a]pyridin-2-yl trifluoromethanesulfonate

To a solution of pyrazolo[1,5-a]pyridin-2-ol (200 mg, 1.49 mmol) in DMF (1 mL) and THE (1 mL) was added NaH (65.60 mg, 1.64 mmol, 60% purity) at 0° C. under $N_2$, then 1,1,1-trifluoro-N-phenyl-N-(trifluoromethylsulfonyl) methanesulfonamide (639.21 mg, 1.79 mmol) was added to the reaction mixture at 0° C. The resulting mixture was stirred at 0° C. for 1 hr under $N_2$. The reaction mixture was quenched by addition of water (20 mL) and then extracted with EA (20 mL*3). The combined organic layers were washed with brine (50 mL), dried over $Na_2SO_4$, filtered and concentrated under reduced pressure. The residue was purified by column chromatography ($SiO_2$, PE/EA=5:1) to give the title compound (300 mg, 1.06 mmol, 71.05% yield) as a light yellow oil.

LCMS (ESI) m/z: $[M+H]^+$=267.1

Intermediate 47: 3-(4-Bromo-3-methoxyphenyl)oxetane

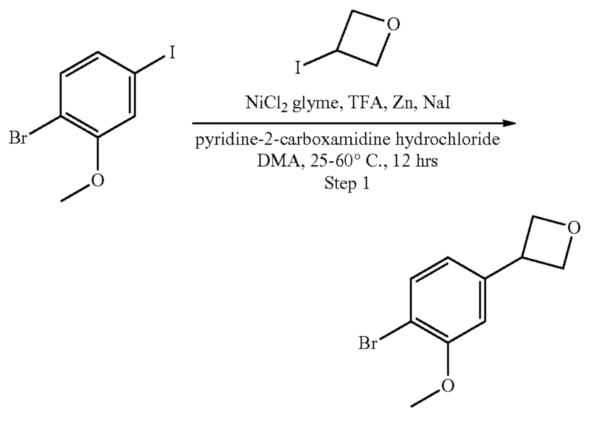

Intermediate 47

Step 1: 3-(4-Bromo-3-methoxyphenyl)oxetane

To a mixture of 1-bromo-4-iodo-2-methoxy-benzene (500 mg, 1.60 mmol) and 3-iodooxetane (352.75 mg, 1.92 mmol) in DMA (4 mL) was added nickel(II) chloride ethylene glycol dimethyl ether complex (35.11 mg, 159.78 umol), pyridine-2-carboxamidine hydrochloride (25.18 mg, 159.78 umol), TFA (18.22 mg, 159.78 umol, 11.83 uL), Zn (208.96 mg, 3.20 mmol) and NaI (119.75 mg, 798.90 umol) in one portion at 25° C. under $N_2$. The mixture was stirred at 60° C. for 12 hrs. The solids were removed by filtration and the filtrate concentrated under vacuum. The residue was purified by reversed phase column (0.1% FA). The product fraction was concentrated to remove MeCN and the aqueous phase was extracted with ethyl acetate (20 mL*2). The combined organic phase was washed with brine (20 mL), dried with anhydrous $Na_2SO_4$, filtered and concentrated under vacuum to give the title compound (200 mg, 668.21 umol, 41.82% yield) as yellow oil.

LCMS (ESI) m/z: $[M+H]^+$=242.8, 244.9.

Intermediate 48: 1-(8-Bromo-2,3-dihydro-4H-benzo[b][1,4]oxazin-4-yl)ethan-1-one

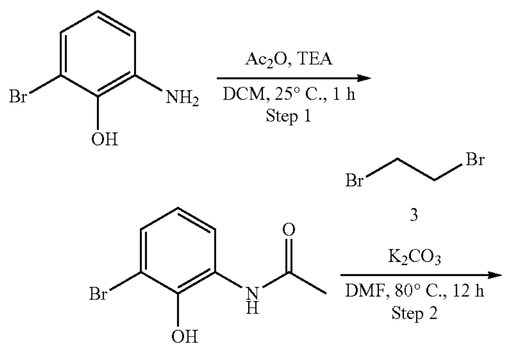

-continued

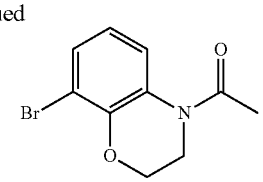

Intermediate 48

Step 1: N-(3-Bromo-2-hydroxyphenyl)acetamide

To a solution of 2-amino-6-bromo-phenol (1 g, 5.32 mmol) in DCM (10 mL) was added $Ac_2O$ (651.56 mg, 6.38 mmol, 597.76 uL) and TEA (1.61 g, 15.96 mmol, 2.22 mL) at 0° C. under $N_2$. The mixture was heated to 25° C. and stirred for 1 hr. Water was added (10 mL) and the mixture extracted by dichloromethane (50 mL*3). The combined organic phase was washed with brine (50 mL*2), dried over anhydrous sodium sulfate, filtered and concentrated under reduced pressure. The residue was purified by column chromatography ($SiO_2$, Petroleum ether/Ethyl acetate=100/1 to 3/1) to give the title compound (300 mg, 1.11 mmol, 20.84% yield) as a light brown solid.

LCMS (ESI) m/z: $[^{79}BrM+H]^+$=229.9.

$^1$HNMR (400 MHz, $CDCl_3$) δ=7.96 (br s, 1H), 7.90 (s, 1H), 7.59-7.53 (m, 1H), 7.32-7.28 (m, 1H), 6.80-6.72 (m, 1H), 2.24 (s, 3H).

Step 2: 1-(8-Bromo-2,3-dihydro-4H-benzo[b][1,4]oxazin-4-yl)ethan-1-one

To a solution of N-(3-bromo-2-hydroxyphenyl)acetamide (100 mg, 434.67 umol) in DMF (2 mL) was added $K_2CO_3$ (180.22 mg, 1.30 mmol) and 1,2-dibromoethane (163.32 mg, 869.35 umol, 65.59 uL) under $N_2$. The mixture was heated to 80° C. and stirred for 12 hrs. The mixture was poured into water (5 mL) and extracted with ethyl acetate (10 mL*3). The combined organic phase was washed with brine (10 mL*2), dried over anhydrous sodium sulfate, filtered and concentrated under reduced pressure. The residue was purified by prep-TLC ($SiO_2$, PE/EA=1:1) to give the title compound (100 mg, 351.43 umol, 26.95% yield) as a white solid.

LCMS (ESI) m/z: $[^{79}BrM+H]^+$=255.9

$^1$HNMR (400 MHz, DMSO-$d_6$) δ=7.77-7.67 (m, 1H), 7.33 (d, J=7.9 Hz, 1H), 6.82 (t, J=8.0 Hz, 1H), 4.40-4.33 (m, 2H), 3.89 (t, J=4.5 Hz, 2H), 3.09 (s, 1H), 2.25 (s, 3H)

Intermediate 49: 7-Bromo-5-fluoro-2-methylisoquinolin-1(2H)-one

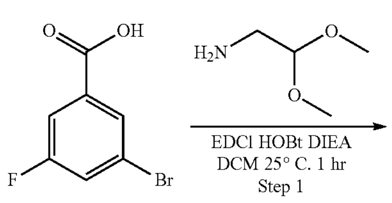

-continued

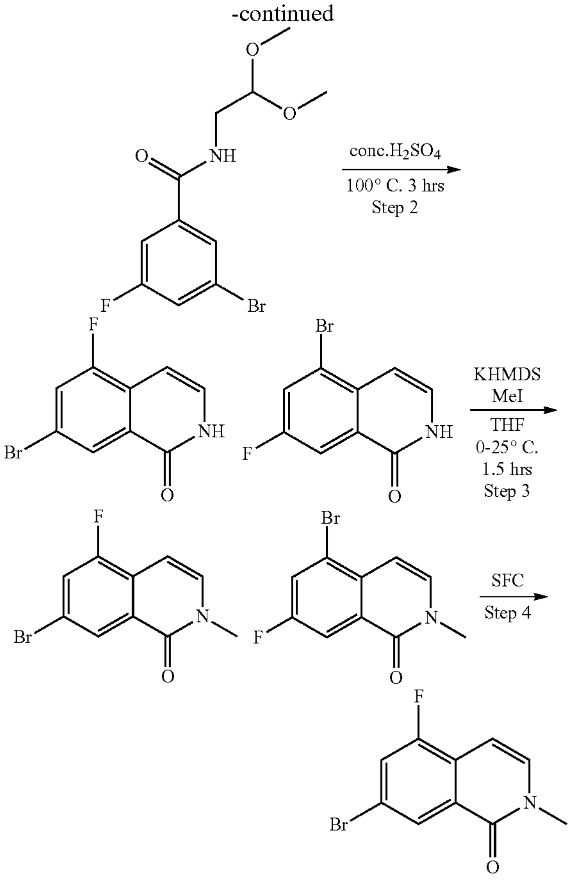

Intermediate 49

Step 1: 3-Bromo-N-(2,2-dimethoxyethyl)-5-fluorobenzamide

To a solution of 3-bromo-5-fluoro-benzoic acid (5 g, 22.83 mmol), 2,2-dimethoxyethanamine (2.40 g, 22.83 mmol, 2.49 mL) in DCM (50 mL) was added EDCI (8.75 g, 45.66 mmol), HOBt (6.17 g, 45.66 mmol) and DIEA (7.38 g, 57.08 mmol). The mixture was stirred at 25° C. for 1 hr. The mixture was poured into water (100 mL) and extracted with DCM (30 mL*3). The combined organic layer was dried over $Na_2SO_4$, filtered and concentrated under vacuum. The residue was purified by column chromatography ($SiO_2$, Petroleum ether/Ethyl acetate=10:1) to give the title compound (6.1 g, 19.93 mmol, 87.28% yield) as a white solid.

LCMS (ESI) m/z: $[M+H-OMe]^+$=275.9.

$^1$H NMR (400 MHz, MeOD-d4) δ=7.84 (s, 1H), 7.58-7.53 (m, 2H), 4.57-4.53 (m, 1H), 3.48 (d, J=5.6 Hz, 2H), 3.40 (s, 6H) ppm.

Step 2: 7-Bromo-5-fluoroisoquinolin-1(2H)-one and 5-bromo-7-fluoroisoquinolin-1(2H)-one A solution of 3-bromo-N-(2,2-dimethoxyethyl)-5-fluorobenzamide (5.6 g, 18.29 mmol) in $H_2SO_4$ (34 mL) was stirred at 100° C. for 3 hrs. The mixture poured into water and the resulting solid was collected by filtration and dried to give a mixture of the title compounds (3.5 g, 14.46 mmol, 79.05% yield) as a white solid.

Step 3: 7-Bromo-5-fluoro-2-methylisoquinolin-1(2H)-one and 5-bromo-7-fluoro-2-methylisoquinolin-1(2H)-one To a solution of 7-bromo-5-fluoroisoquinolin-1(2H)-one and 5-bromo-7-fluoroisoquinolin-1(2H)-one (1.5 g, 6.20 mmol) in THE (15 mL) was added KHMDS (1 M, 7.44 mL) at 0° C. The mixture was stirred for 0.5 hr and then iodomethane (3.52 g, 24.79 mmol) was added. The mixture was stirred for 1 hr at 25° C. before pouring into water (5 mL) and extracting with EA (10 mL*3). The organic layer was concentrated, and the residue was purified by column chromatography ($SiO_2$, Petroleum ether/Ethyl acetate=1:1, Rf=0.3) to give a mixture of the title compounds (750 mg, 2.93 mmol, 47.26% yield) as a yellow solid.

LCMS (ESI) m/z: $[M+H]^+$=256.1.

Step 4: 7-Bromo-5-fluoro-2-methylisoquinolin-1(2H)-one

The mixture of 7-bromo-5-fluoro-2-methylisoquinolin-1(2H)-one and 5-bromo-7-fluoro-2-methylisoquinolin-1(2H)-one (750 mg, 2.93 mmol) was purified by SFC separation: {method column: DAICEL CHIRALPAK AD (250 mm*30 mm, 10 um); mobile phase: [0.1% $NH_3H_2O$ MEOH]; B %: 40%-40%, 4.25; 105 min.} to give the title compound (270 mg, 1.05 mmol, 35.95% yield) as a white solid.

LCMS (ESI) m/z: $[M+H]^+$=256.2.

$^1$H NMR (400 MHz, MeOD-d4) δ=8.22 (s, 1H), 7.67-7.63 (m, 1H), 7.47 (d, J=7.6 Hz, 1H), 6.72 (d, J=7.6 Hz, 1H), 3.61 (s, 3H) ppm.

Intermediate 50: 6-Bromo-7-methoxy-1-methyl-1H-indazole

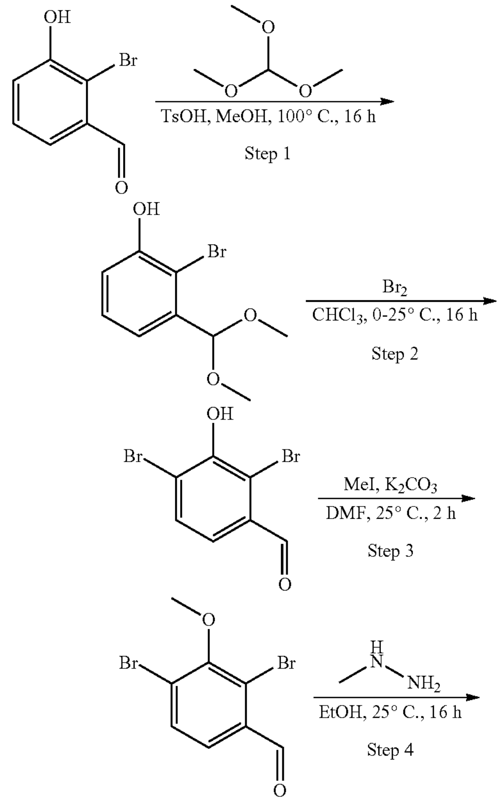

-continued

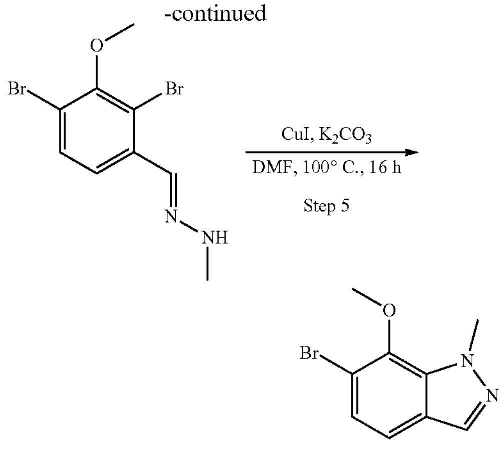

Intermediate 50

Step 1: 2-Bromo-3-(dimethoxymethyl)phenol

To a solution of 2-bromo-3-hydroxybenzaldehyde (2 g, 9.95 mmol) and trimethoxymethane (5.28 g, 49.75 mmol, 5.45 mL) in MeOH (30 mL) was added TsOH (171.33 mg, 994.94 umol). The mixture was stirred at 100° C. for 16 hrs. The solvent was removed under vacuum and the residue was purified by flash silica gel chromatography (ISCO®; 40 g SepaFlash® Silica Flash Column, Eluent of 0-60% EA/Petroleum ether gradient @100 mL/min) to give the title compound (1.6 g, 6.48 mmol, 65.08% yield) as a yellow oil.

LCMS (ESI) m/z: $[M+H]^+$=214.9

$^1$H NMR (400 MHz, $CDCl_3$-d) δ=7.29-7.24 (m, 1H), 7.23-7.18 (m, 1H), 7.07-7.02 (m, 1H), 5.79 (s, 1H), 5.53 (s, 1H), 3.40 (s, 6H) ppm.

Step 2: 2,4-Dibromo-3-hydroxybenzaldehyde

To a solution of 2-bromo-3-(dimethoxymethyl)phenol (1.4 g, 5.67 mmol) in $CHCl_3$ (7 mL) was added a solution of $Br_2$ (1.18 g, 7.37 mmol, 379.72 uL) in $CHCl_3$ (7 mL) at 0° C. The reaction was stirred at 25° C. for 16 hrs. The reaction was quenched by aq. $Na_2S_2O_3$ (80 mL) and extracted with EA (50 mL*3). The combined organic layers were washed with brine (50 mL), dried over $Na_2SO_4$, filtered and concentrated. The residue was purified by flash silica gel chromatography (ISCO®; 25 g SepaFlash® Silica Flash Column, Eluent of 0-60% EA/Petroleum ether gradient @ 100 mL/min) to give the title compound (1.3 g, 4.64 mmol, 81.97% yield) as a white solid.

LCMS (ESI) m/z: $[Br\ M+H]^+$=280.8.

$^1$H NMR (400 MHz, DMSO-$d_6$) δ=10.44 (s, 1H), 10.17 (d, J=0.8 Hz, 1H), 7.83-7.65 (m, 1H), 7.27 (d, J=8.4 Hz, 1H) ppm.

Step 3: 2,4-Dibromo-3-methoxybenzaldehyde

To a solution of 2,4-dibromo-3-hydroxybenzaldehyde (1.3 g, 4.64 mmol) and $K_2CO_3$ (1.28 g, 9.29 mmol) in DMF (15 mL) was added MeI (988.80 mg, 6.97 mmol, 433.69 uL). The mixture was stirred at 25° C. for 2 hrs, then poured into water (60 mL) and extracted with EA (30 mL*3). The combined organic layers were washed with brine (30 mL), dried over $Na_2SO_4$, filtered and concentrated under vacuum. The residue was purified by flash silica gel chromatography (ISCO®; 12 g SepaFlash® Silica Flash Column, Eluent of 0-60% EA/Petroleum ether gradient @ 60 mL/min) to give the title compound (1.2 g, crude) as a white solid.

$^1$H NMR (400 MHz, DMSO-$d_6$) δ=10.17 (s, 1H), 7.89-7.82 (m, 1H), 7.53 (d, J=8.4 Hz, 1H), 3.85 (s, 3H) ppm.

Step 4: (E)-1-(2,4-Dibromo-3-methoxybenzylidene)-2-methylhydrazine

To a solution of 2,4-dibromo-3-methoxybenzaldehyde (500 mg, 1.70 mmol) and methylhydrazine (391.84 mg, 3.40 mmol, 447.82 uL) in EtOH (5 mL) was stirred at 25° C. for 16 hrs. The mixture was poured into water (80 mL) and extracted with EA (30 mL*3). The combined organic layer were washed with brine (30 mL), dried over $Na_2SO_4$, filtered and concentrated under vacuum. The residue was purified by flash silica gel chromatography (ISCO®; 12 g SepaFlash® Silica Flash Column, Eluent of 0-50% EA/Petroleum ether gradient @ 60 mL/min) to give the title compound (250 mg, 776.41 umol, 45.64% yield) as a yellow oil.

LCMS (ESI) m/z: $[Br\ M+H]^+$=322.8.

$^1$H NMR (400 MHz, $CDCl_3$-d) δ=7.72 (s, 1H), 7.58-7.51 (m, 1H), 7.48-7.41 (m, 1H), 5.90 (br s, 1H), 3.90 (s, 3H), 3.02 (s, 3H) ppm.

Step 5: 6-Bromo-7-methoxy-1-methyl-1H-indazole

To a solution of (E)-1-(2,4-dibromo-3-methoxybenzylidene)-2-methylhydrazine (230 mg, 714.29 umol) in DMF (4 mL) was added $K_2CO_3$ (296.16 mg, 2.14 mmol) and CuI (13.60 mg, 71.43 umol). The mixture was stirred at 100° C. for 16 hrs. Water (40 mL) was added and the products extracted into EA (20 mL*3). The combined organic layers were washed with brine (20 mL), dried over $Na_2SO_4$, filtered and concentrated under vacuum. The residue was purified by flash silica gel chromatography (ISCO®; 12 g SepaFlash® Silica Flash Column, Eluent of 0-60% Ethylacetate/Petroleum ethergradient @ 40 mL/min) to give the title compound (120 mg, 497.75 umol, 69.68% yield) as a yellow oil.

LCMS (ESI) m/z: $[Br\ M+H]^+$=242.9.

$^1$H NMR (400 MHz, $CDCl_3$-d) δ=7.98 (s, 1H), 7.41-7.35 (m, 1H), 7.30 (d, J=10.0 Hz, 1H), 4.33 (s, 3H), 4.05 (s, 3H) ppm.

Intermediate 51: 2-(3-Methyloxetan-3-yl)pyrimidin-4-yl trifluoromethanesulfonate

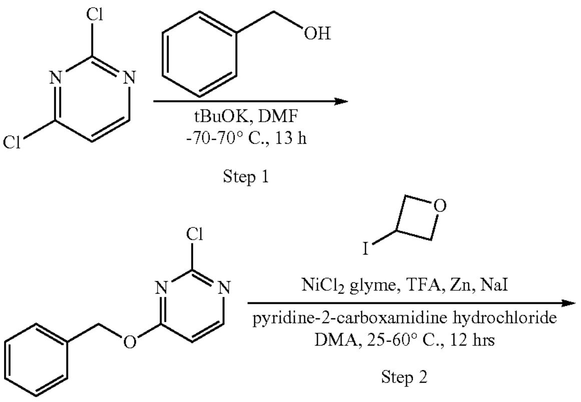

-continued

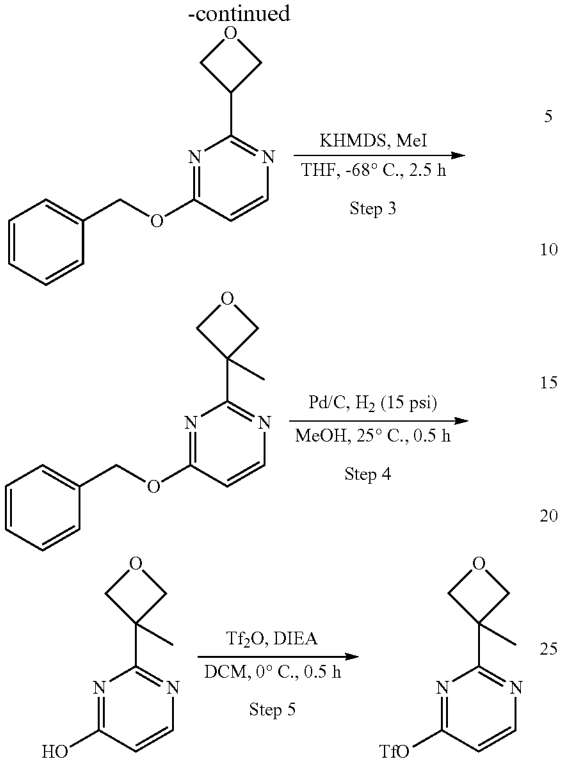

Intermediate 51

Step 1: 4-(Benzyloxy)-2-chloropyrimidine

A mixture of phenylmethanol (29.03 g, 268.50 mmol, 27.92 mL) and t-BuOK (15.06 g, 134.25 mmol) in THE (80 mL) was heated to 70° C. and stirred for 0.5 hr. The reaction mixture was cooled to 0° C. and slowly added dropwise to the solution of 2,4-dichloropyrimidine (20 g, 134.25 mmol) in DMF (100 mL), maintaining the temperature below −70° C. After stirring for 0.5 hr, the reaction was allowed to warm to 25° C. and stirred for 12 hrs. The reaction mixture was added dropwise to cold water (150 mL) and white solid was formed. The solid was collected by filtration and dried to give the title compound (22 g, 84.75 mmol, 63.13% yield) as a white solid.

LCMS (ESI) m/z: $[M+H]^+$=221.1

$^1$H NMR (400 MHz, DMSO-$d_6$) δ=8.49 (d, J=5.6 Hz, 1H), 7.50-7.46 (m, 2H), 7.42-7.35 (m, 3H), 7.06 (d, J=5.6 Hz, 1H), 5.41 (s, 2H) ppm.

Step 2: 4-(Benzyloxy)-2-(oxetan-3-yl)pyrimidine

To a mixture of 4-(benzyloxy)-2-chloropyrimidine (20 g, 90.64 mmol) and 3-iodooxetane (20.01 g, 108.77 mmol) in DMA (400 mL) was added nickel(II) chloride ethylene glycol dimethyl ether complex (1.99 g, 9.06 mmol), pyridine-2-carboxamidine hydrochloride (1.43 g, 9.06 mmol), TFA (1.03 g, 9.06 mmol, 671.08 uL), Zn (11.85 g, 181.28 mmol) and NaI (6.79 g, 45.32 mmol) in one portion at 25° C. The mixture was stirred at 60° C. for 12 hours under $N_2$. The reaction mixture was filtered, poured into $H_2O$ (800 mL) and extracted with EA (800 mL*3). The combined organic layer was washed with water (800 mL) and brine (800 mL), dried over $Na_2SO_4$, filtered and concentrated. The residue was purified by flash silica gel chromatography (Eluent of 0-20% EA/Petroleum ether gradient) to give the title compound (1 g, 2.48 mmol, 2.73% yield) as a yellow oil.

LCMS (ESI) m/z: [M+H]+=243.1.

$^1$H NMR (400 MHz, DMSO-$d_6$) δ=8.61-8.47 (m, 1H), 7.49-7.31 (m, 5H), 7.14-6.84 (m, 1H), 5.49-5.38 (m, 2H), 4.96-4.66 (m, 4H), 4.37 (d, J=8.8 Hz, 1H) ppm.

Step 3: 4-(Benzyloxy)-2-(3-methyloxetan-3-yl)pyrimidine

To a solution of 4-(benzyloxy)-2-(oxetan-3-yl)pyrimidine (1 g, 4.13 mmol) in THE (4 mL) was added KHMDS (1 M, 6.19 mL) at −68° C. The mixture was stirred at −68° C. for 0.5 hr. Iodomethane (2.93 g, 20.64 mmol, 1.28 mL) was then added at −68° C. The mixture was stirred at 25° C. for 2 hrs. The reaction mixture was quenched with aq. $NH_4Cl$ (40 mL) at 0° C. and extracted with EA (40 mL*3). The combined layers were dried over anhydrous $Na_2SO_4$, filtered and concentrated under reduced pressure. The residue was purified by flash silica gel chromatography ($SiO_2$, Petroleum ether/Ethyl acetate=1/0 to 1/1) to give the title compound (220 mg, 858.37 umol, 20.80% yield) as a yellow oil.

LCMS (ESI) m/z: $[M+H]^+$=257.0

$^1$H NMR (400 MHz, DMSO-$d_6$) δ=8.53 (d, J=5.6 Hz, 1H), 7.50-7.44 (m, 2H), 7.43-7.32 (m, 3H), 6.86 (d, J=6.0 Hz, 1H), 5.43 (s, 2H), 4.96 (d, J=5.6 Hz, 2H), 4.48 (d, J=5.6 Hz, 2H), 1.66 (s, 3H) ppm.

Step 4: 2-(3-Methyloxetan-3-yl)pyrimidin-4-ol

To a solution of 4-(benzyloxy)-2-(3-methyloxetan-3-yl)pyrimidine (200 mg, 780.34 umol) in MeOH (15 mL) was added Pd/C (40 mg, 10% purity). The mixture was degassed and purged with $H_2$ balloon 3 times. The mixture was stirred at 25° C. for 0.5 hr under $H_2$ atmosphere (15 psi). The reaction was filtered to remove Pd/C and concentrated under reduced pressure to give the title compound (110 mg, 661.95 umol, 84.83% yield) as a white solid.

LCMS (ESI) m/z: $[M+H]^+$=167.0.

$^1$H NMR (400 MHz, DMSO-$d_6$) δ=7.89 (d, J=6.8 Hz, 1H), 6.19 (d, J=6.8 Hz, 1H), 4.89 (d, J=6.0 Hz, 2H), 4.38 (d, J=6.0 Hz, 2H), 1.61 (s, 3H) ppm.

Step 5: 2-(3-Methyloxetan-3-yl)pyrimidin-4-yl trifluoromethanesulfonate

To a solution of 2-(3-methyloxetan-3-yl)pyrimidin-4-ol (50 mg, 300.88 umol) and DIEA (116.66 mg, 902.65 umol, 157.22 uL) in DCM (1 mL) was added $Tf_2O$ (101.87 mg, 361.06 umol, 59.57 uL) at 0° C. The mixture was stirred at 0° C. for 0.5 hr. The reaction mixture was quenched with aq. $NaHCO_3$ (20 mL) and extracted with DCM (20 mL*3). The combined organic layer was dried over anhydrous $Na_2SO_4$, filtered and concentrated under reduced pressure to give the title compound (88 mg, 295.07 umol, 98.07% yield) as a yellow oil.

LCMS (ESI) m/z: $[M+H]^+$=299.0.

Intermediate 52: 4-Chloro-2-(1-fluorocyclopropyl)pyrimidine

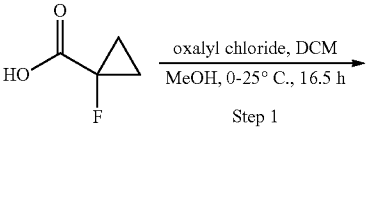

-continued

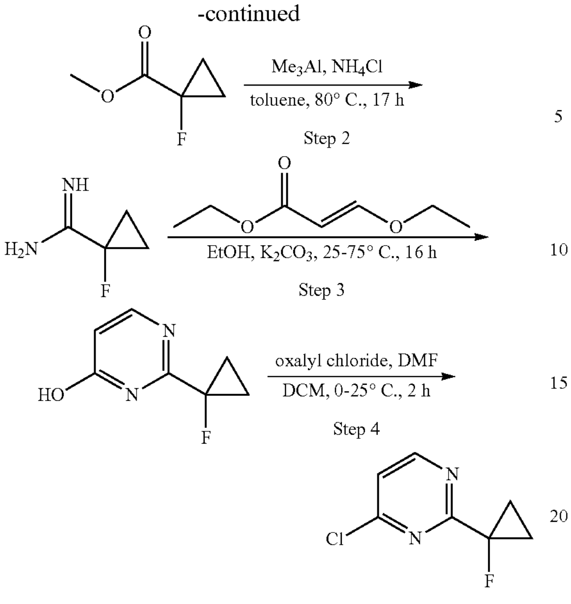

Intermediate 52

Step 1: Methyl 1-fluorocyclopropane-1-carboxylate

To a mixture of 1-fluorocyclopropanecarboxylic acid (4 g, 38.43 mmol) in DCM (20 mL) was added oxalyl dichloride (7.32 g, 57.65 mmol, 5.05 mL) at 0° C. The reaction was stirred at 25° C. for 16 hrs. The mixture was concentrated and then dissolved in DCM (20 mL). MeOH (3.69 g, 115.30 mmol, 4.67 mL) was then added at 0° C. and the mixture was stirred at 25° C. for 30 mins. The reaction was quenched with the addition of aq. $NaHCO_3$ (50 mL) and the products were extracted with DCM (30 mL*3). The combined organic layers were concentrated at 25° C. to give the title product (2 g, crude) as a yellow oil.

$^1$H NMR (400 MHz, $CDCl_3$-d) δ=3.76 (s, 3H), 1.39-1.29 (m, 4H) ppm.

Step 2: 1-Fluorocyclopropane-1-carboximidamide

To a mixture of $NH_4Cl$ (4.53 g, 84.67 mmol) in toluene (30 mL) was added $AlMe_3$ (2 M, 42.33 mL) at 0° C. The mixture was stirred at 25° C. for 1 hr. Methyl 1-fluorocyclopropane-1-carboxylate (2 g, 16.93 mmol) was added into the mixture at 0° C. The reaction was stirred at 80° C. for 16 hrs. The reaction mixture was cooled to 0° C., MeOH (50 mL) was added and the mixture stirred for 10 min. The mixture was filtered and the filtrate was concentrated under vacuum to give the title product (2.1 g, crude) as a white solid.

Step 3: 2-(1-Fluorocyclopropyl)pyrimidin-4-ol

To a mixture of 1-fluorocyclopropane-1-carboximidamide (2.02 g, 19.77 mmol) and $K_2CO_3$ (5.46 g, 39.54 mmol) in EtOH (30 mL) was added ethyl (E)-3-ethoxyprop-2-enoate (0.95 g, 6.59 mmol, 951.90 uL) at 25° C. The reaction was stirred at 75° C. for 16 hrs. The reaction mixture was filtered and the filtrate was concentrated under vacuum. The residue was purified by flash silica gel chromatography (ISCO®; 40 g SepaFlash® Silica Flash Column, Eluent of 0-20% DCM/MeOH gradient @ 100 mL/min) to give the title compound (140 mg, 908.26 umol, 13.78% yield) as a yellow solid.

LCMS (ESI) m/z: $[M+H]^+$=155.1

$^1$H NMR (400 MHz, $CDCl_3$-d) δ=11.80-10.90 (m, 1H), 7.85 (d, J=6.8 Hz, 1H), 6.33 (d, J=6.8 Hz, 1H), 1.68-1.52 (m, 4H) ppm.

Step 4: 4-Chloro-2-(1-fluorocyclopropyl)pyrimidine

To a mixture of 2-(1-fluorocyclopropyl)pyrimidin-4-ol (70 mg, 454.13 umol) and DMF (3.32 mg, 45.41 umol, 3.49 uL) in DCM (1 mL) was added oxalyl chloride (63.41 mg, 499.54 umol, 43.73 uL) at 0° C. The reaction was stirred at 25° C. for 2 hrs. The mixture was poured into aq. $NaHCO_3$ (30 mL) and extracted with EA (20 mL*3). The combined organic layers were washed with brine (20 mL), dried over $Na_2SO_4$, filtered and concentrated under vacuum. The residue was purified by flash silica gel chromatography (ISCO®; 4 g SepaFlash® Silica Flash Column, Eluent of 0-50% PE/EA gradient @ 36 mL/min) to give the title compound (35 mg, 202.80 umol, 44.66% yield) as a yellow oil.

$^1$H NMR (400 MHz, $CDCl_3$-d) δ=8.58 (d, J=5.6 Hz, 1H), 7.22 (d, J=5.2 Hz, 1H), 1.68-1.61 (m, 2H), 1.58-1.52 (m, 2H) ppm.

Intermediate 53: 3-(Dimethylamino)pyridin-2(1H)-one

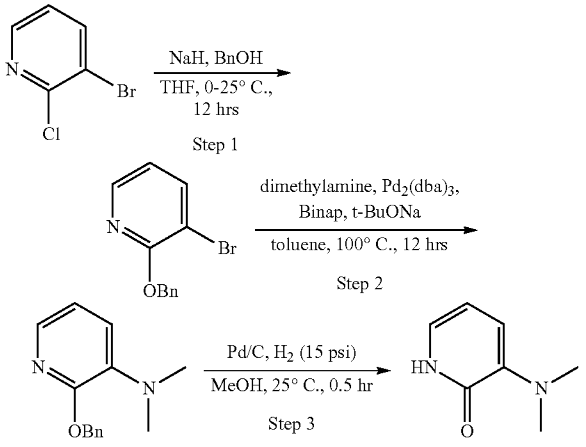

Intermediate 53

Step 1: 2-(Benzyloxy)-3-bromopyridine

To a mixture of phenylmethanol (3.37 g, 31.18 mmol, 3.24 mL) in THE (50 mL) was added NaH (1.25 g, 31.18 mmol, 60% purity) in portions at 0° C. under $N_2$. The mixture was stirred at 0° C. for 30 min, then to the mixture was added 3-bromo-2-chloro-pyridine (5 g, 25.98 mmol) at 0° C. The mixture was stirred at 25° C. for 11.5 hrs. The mixture was poured into water (300 mL) and the products extracted with ethyl acetate (100 mL*2). The combined organic phase was washed with brine (100 mL*1), dried over anhydrous $Na_2SO_4$, filtered and concentrated under vacuum. The residue was purified by silica gel chromatography (Petroleum ether/Ethyl acetate=20/1) to give the title compound (5.2 g, 19.69 mmol, 75.78% yield) as a light yellow oil.

Step 2:
2-(Benzyloxy)-N,N-dimethylpyridin-3-amine

To a mixture of 2-(benzyloxy)-3-bromopyridine (500 mg, 1.89 mmol) and dimethylamine hydrochloride (255.62 mg, 5.67 mmol, 287.22 uL) in toluene (10 mL) was added $Pd_2(dba)_3$ (86.54 mg, 94.50 umol), BINAP (117.68 mg, 189.00 umol) and t-BuONa (908.15 mg, 9.45 mmol) in one portion at 25° C. under $N_2$. The mixture was stirred at 100° C. for 12 hrs. The mixture was poured into water (20 mL) and the products extracted with ethyl acetate (10 mL*2). The combined organic phase was washed with brine (10 mL*1), dried with anhydrous $Na_2SO_4$, filtered and concentrated under vacuum. The residue was purified by silica gel chromatography (Petroleum ether/Ethyl acetate=15/1) to give the title compound (200 mg, 876.08 umol, 46.35% yield) as a yellow oil.

Step 3: 3-(Dimethylamino)pyridin-2(1H)-one

To a solution of 2-(benzyloxy)-N,N-dimethylpyridin-3-amine (100 mg, 438.04 umol) and MeOH (2 mL) was added Pd/C (10 mg, 438.04 umol, 10% purity). The mixture was degassed and purged with $H_2$ 3 times, and then the mixture was stirred at 25° C. for 0.5 hr under $H_2$ (15 psi). The mixture was filtered and the filtrate was concentrated to give the title compound (50 mg, 361.88 umol, 82.61% yield) as a white solid.

LCMS (ESI) m/z: $[M+H]^+$=139.0

Intermediate 54: 1-Cyclopropylimidazolidin-2-one

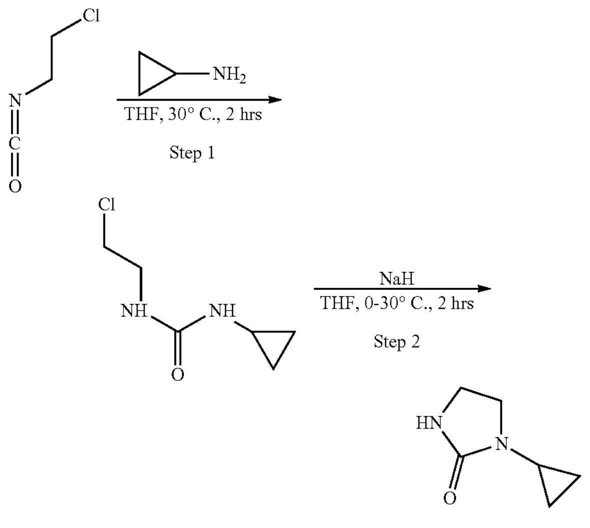

Intermediate 54

Step 1: 1-(2-Chloroethyl)-3-cyclopropylurea

To a mixture of cyclopropanamine (541.06 mg, 9.48 mmol) in THF (10 mL) was added dropwise 1-chloro-2-isocyanato-ethane (1 g, 9.48 mmol), then the mixture was stirred at 30° C. for 2 hrs. The reaction was concentrated under vacuum to give the title compound (1.52 g, 9.35 mmol, 98.63% yield) as white solid, which was used directly in the next step.

$^1$HNMR (400 MHz, $CDCl_3$) δ=6.30 (s, 1H), 6.13 (s, 1H), 3.61-3.53 (m, 2H), 3.33-3.28 (m, 2H), 2.43-2.35 (m, 1H), 0.61-0.53 (m, 2H), 0.37-0.29 (m, 2H) ppm.

Step 2: 1-Cyclopropylimidazolidin-2-one

To a mixture of 1-(2-chloroethyl)-3-cyclopropylurea (1.5 g, 9.22 mmol) in THF (50 mL) was added portionwise NaH (442.76 mg, 11.07 mmol, 60% purity) at 0° C., and then the mixture was stirred at 30° C. for 2 hrs. The reaction was quenched by adding sat. $NH_4Cl$ (30 mL) and the products were extracted with DCM (30 mL*5). The combined organic layers were dried over $Na_2SO_4$, filtered and concentrated under vacuum. The residue was triturated with PE (10 mL) at 20 and the solid was collected by filtered and dried to give the title compound (0.8 g, 6.34 mmol, 68.75% yield) as a gray solid.

LCMS (ESI) m/z: $[M+H]^+$=127.1.

$^1$H NMR (400 MHz, DMSO-$d_6$) δ=6.28 (s, 1H), 3.30-3.23 (m, 2H), 3.20-3.12 (m, 2H), 2.36-2.27 (m, 1H), 0.58-0.51 (m, 4H) ppm.

Intermediate 55:
2-Cyclopropyl-1,2,5-thiadiazolidine 1,1-dioxide

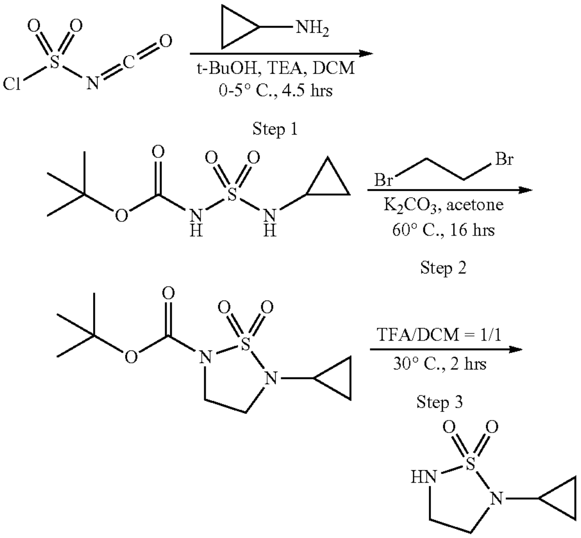

Intermediate 55

Step 1: tert-Butyl
(N-cyclopropylsulfamoyl)carbamate

To a solution of sulfurisocyanatidic chloride (5 g, 35.33 mmol, 3.07 mL) in DCM (60 mL) was added 2-methylpropan-2-ol (2.62 g, 35.33 mmol, 3.38 mL) at 0° C. After stirring for 90 min, the resulting solution and TEA (10.91 g, 107.77 mmol) in DCM (60 mL) were added dropwise to a solution of cyclopropanamine (2.02 g, 35.33 mmol, 2.45 mL) in DCM (75 mL) and TEA (6.54 g, 64.66 mmol). The reaction mixture was stirred at 5° C. for 3 hrs then poured into water 200 mL and extracted with DCM (200 mL*3). The combined organic layer was washed with brine (500 mL), dried over $Na_2SO_4$, filtered and concentrated. The residue was triturated with PE (100 mL), and the solid was filtered and dried under vacuum to give the title compound (2.5 g, 10.58 mmol, 29.95% yield) as a white solid.

$^1$H NMR (400 MHz, $CDCl_3$) δ=7.17 (br s, 1H), 5.47 (s, 1H), 2.46-2.43 (m, 1H), 1.52 (s, 9H), 0.79-0.72 (m, 4H) ppm Step 2: tert-Butyl 5-cyclopropyl-1,2,5-thiadiazolidine-2-carboxylate 1,1-dioxide To a solution of tert-butyl (N-cyclopropylsulfamoyl)carbamate (200 mg, 846.42 umol) and 1,2-dibromoethane (182.20 mg, 969.84 umol) in acetone (3 mL) was added $K_2CO_3$ (346.34 mg, 2.51 mmol). The resulting mixture was stirred at 60° C. for 16 hrs. The reaction mixture was poured into water (20 mL) and the products were extracted with EA (20 mL*3). The combined organic layer was washed with brine (50 mL), dried over $Na_2SO_4$, filtered and concentrated to give the title compound (120 mg, 457.45 umol, 54.04% yield) as a white solid.

$^1$H NMR (400 MHz, $CDCl_3$) δ=3.77-3.73 (m, 2H), 3.41-3.38 (m, 2H), 2.37-2.34 (m, 1H), 1.54 (s, 9H), 0.89-0.84 (m, 2H), 0.77-0.77 (m, 2H) ppm.

Step 3: 2-Cyclopropyl-1,2,5-thiadiazolidine 1,1-dioxide

To a solution of tert-butyl 5-cyclopropyl-1,2,5-thiadiazolidine-2-carboxylate 1,1-dioxide (120 mg, 457.45 umol) in DCM (1.5 mL) was added TFA (1.5 mL). The mixture was stirred at 30° C. for 2 hrs then concentrated under vacuum to give the title compound (74 mg, 456.20 umol, 99.73% yield) as a yellow solid $^1$H NMR (400 MHz, $CDCl_3$) δ=3.52-3.45 (m, 4H), 2.35-2.28 (m, 1H), 0.82-0.79 (m, 2H), 0.74-0.72 (m, 2H) ppm.

Intermediate 56: 3-(Difluoromethyl)-4,5,6,7-tetrahydropyrazolo[1,5-a]pyrazine hydrochloride

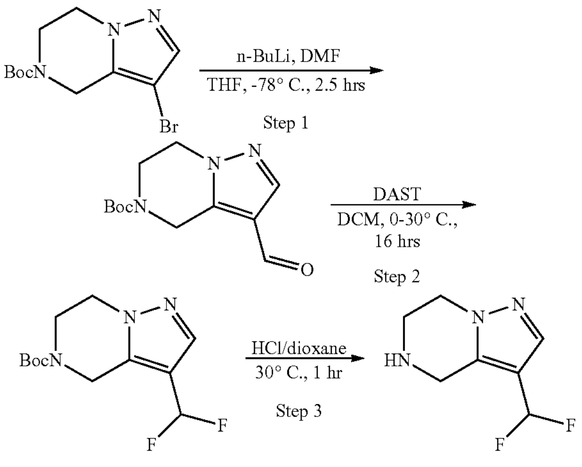

Intermediate 56

Step 1: tert-Butyl 3-formyl-6,7-dihydropyrazolo[1,5-a]pyrazine-5(4H)-carboxylate To a solution of tert-butyl 3-bromo-6,7-dihydro-4H-pyrazolo[1,5-a]pyrazine-5-carboxylate (3000 mg, 9.93 mmol) in THE (30 mL) was added n-BuLi (2.5 M, 8.34 mL) under $N_2$ at −78° C. and stirred at −78° C. for 0.5 hr. DMF (798.27 mg, 10.92 mmol, 840.28 uL) was then added and the resulting mixture was stirred at −78° C. for another 2 hrs. The reaction mixture was quenched with water (200 mL) and the products were extracted with EA (200 mL*2). The combined organic layers were washed with brine (200 mL), dried over $Na_2SO_4$, filtered and concentrated under reduced pressure. The residue was purified by column chromatography ($SiO_2$, PE/EA=1:1) to give the title compound (400 mg, 1.45 mmol, 14.59% yield) as a light yellow oil.

LCMS (ESI) m/z: $[M+H]^+$=252.2.

$^1$H NMR (400 MHz, CDCl3) δ=9.88 (s, 1H), 7.95 (s, 1H), 4.92 (s, 2H), 4.23 (t, J=5.2 Hz, 2H), 3.93 (t, J=5.2 Hz, 2H), 1.51 (s, 9H) ppm Step 2: tert-Butyl 3-(difluoromethyl)-6,7-dihydropyrazolo[1,5-a]pyrazine-5(4H)-carboxylate To a solution of tert-butyl 3-formyl-6,7-dihydropyrazolo[1,5-a]pyrazine-5(4H)-carboxylate (400 mg, 1.59 mmol) in DCM (8 mL) was added DAST (1.28 g, 7.96 mmol, 1.05 mL) at 0° C., and the mixture was stirred at 30° C. for 4 hrs. Additional DAST (2.57 g, 15.92 mmol, 2.10 mL) was added to the mixture and stirring continued at 30° C. for 12 hr. The mixture was quenched with sat. $NaHCO_3$ (200 mL) and extracted with EA (200 mL*2). The combined organic layers were washed with brine 200 (mL), dried over $Na_2SO_4$, filtered and concentrated under reduced pressure. The residue was purified by column chromatography ($SiO_2$, PE/EA=2:1) to give the title compound (250 mg, 850.78 umol, 53.45% yield) as a light yellow oil.

LCMS (ESI) m/z: $[M+H]^+$=274.0.

$^1$H NMR (400 MHz, CHLOROFORM-d) 5=7.60 (s, 1H), 6.88-6.51 (m, 1H), 4.76 (br s, 2H), 4.21 (br t, J=5.2 Hz, 2H), 3.91 (br t, J=5.2 Hz, 2H), 1.51 (s, 9H) ppm.

Step 3: 3-(Difluoromethyl)-4,5,6,7-tetrahydropyrazolo[1,5-a]pyrazine hydrochloride A solution of tert-butyl 3-(difluoromethyl)-6,7-dihydropyrazolo[1,5-a]pyrazine-5(4H)-carboxylate (100 mg, 365.93 umol) in 4M HCl/dioxane (2 mL) was stirred at 30° C. for 1 hr. The reaction mixture was concentrated under reduced pressure to give the title compound (120 mg, crude) as a white solid.

Intermediates 57 and 58: (R)-5-Fluoro-5-methyl-5,8-dihydro-6H-pyrano[3,4-b]pyridine-3-carboxylic acid and (S)-5-fluoro-5-methyl-5,8-dihydro-6H-pyrano[3,4-b]pyridine-3-carboxylic acid

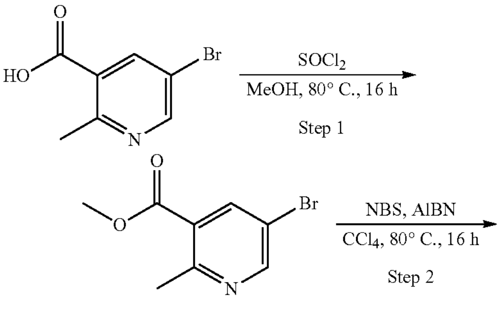

-continued

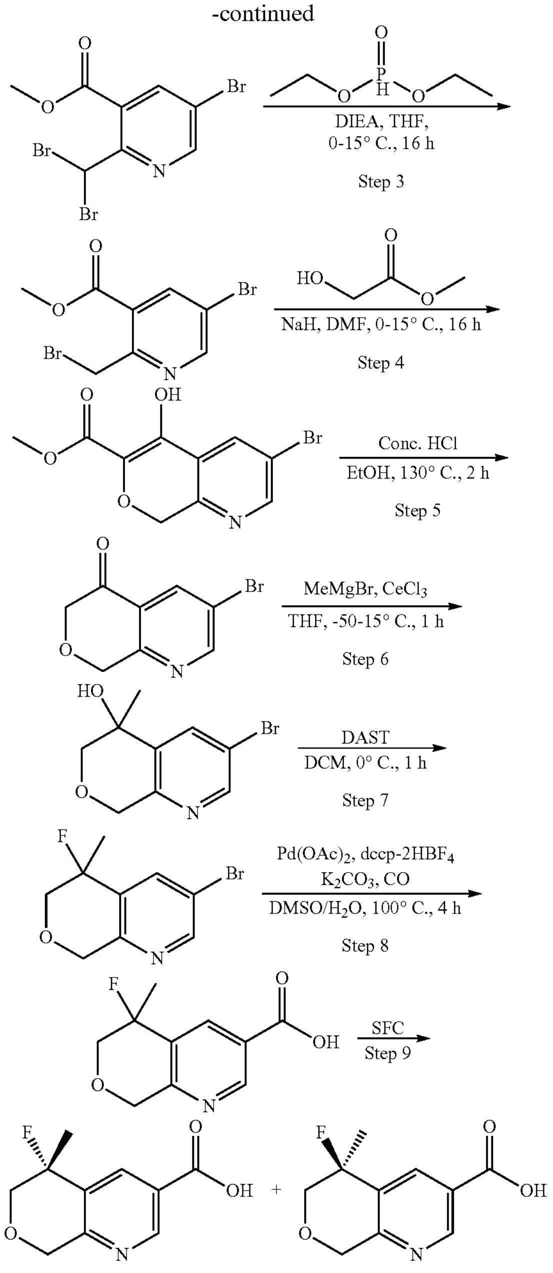

Intermediate 57 Intermediate 58

Step 1: Methyl 5-bromo-2-methylnicotinate

To a solution of 5-bromo-2-methylnicotinic acid (10 g, 46.29 mmol, 1 eq) in MeOH (100 mL) was added $SOCl_2$ (8.26 g, 69.43 mmol, 5.04 mL). The mixture was stirred at 80° C. for 16 hrs. Room temperature was attained and the solvent removed under vacuum. The residue was taken up in aq.$NaHCO_3$ (200 mL) and extracted with EA (100 mL*3). The combined organic layers were washed with brine (100 mL), dried over $Na_2SO_4$, filtered and concentrated to give the title compound (8.8 g, 38.25 mmol, 82.63% yield) as a brown solid.

LCMS (ESI) m/z: [Br M+H]$^+$=229.9

$^1$H NMR (400 MHz, $CDCl_3$-d) δ=8.66 (d, J=2.4 Hz, 1H), 8.32 (d, J=2.4 Hz, 1H), 3.93 (s, 3H), 2.78 (s, 3H) ppm.

Step 2: Methyl 5-bromo-2-(dibromomethyl)nicotinate

To a solution of methyl 5-bromo-2-methylnicotinate (5.6 g, 24.34 mmol) in $CCl_4$ (60 mL) was added NBS (4.77 g, 26.78 mmol) and AIBN (399.71 mg, 2.43 mmol). The mixture was stirred at 80° C. for 16 hrs. The reaction mixture was filtered and concentrated under reduced pressure to give the title compound (10 g, crude) as yellow oil.

Step 3: Methyl 5-bromo-2-(bromomethyl)nicotinate

To a solution of methyl 5-bromo-2-(dibromomethyl)nicotinate (11 g, 28.36 mmol) and DIEA (1.47 g, 11.34 mmol, 1.98 mL) in THE (100 mL) was added diethyl phosphonate (1.57 g, 11.34 mmol, 1.46 mL) at 0° C. The mixture was stirred at 15° C. for 16 hrs. The mixture was filtered, poured into water (300 mL) and extracted with EA (150 mL*3). The combined organic layers were washed with brine (100 mL), dried over $Na_2SO_4$, filtered and concentrated. The residue was purified by flash silica gel chromatography (ISCO®; 120 g SepaFlash® Silica Flash Column, Eluent of 0-50% EA/Petroleum ether gradient @ 120 mL/min) to give the title compound (7.4 g, 23.95 mmol, 84.46% yield) as a yellow oil.

LCMS (ESI) m/z: [Br M+H]$^+$=309.7

Step 4: Methyl 3-bromo-5-hydroxy-8H-pyrano[3,4-b]pyridine-6-carboxylate

To a solution of methyl 5-bromo-2-(bromomethyl)nicotinate (9.9 g, 32.04 mmol) and methyl 2-hydroxyacetate (5.77 g, 64.09 mmol, 4.93 mL) in DMF (100 mL) was added NaH (2.56 g, 64.09 mmol, 60% purity) at 0° C. The mixture was stirred at 15° C. for 16 hrs. The mixture was poured into aq. $NaHCO_3$ (600 mL) and extracted with EA (200 mL*3). The combined organic layers were washed with brine (200 mL), dried over $Na_2SO_4$, filtered and concentrated to give the title compound (7.6 g, crude) as a white solid.

Step 5: 3-Bromo-6H-pyrano[3,4-b]pyridin-5(8H)-one

To a solution of methyl 3-bromo-5-hydroxy-8H-pyrano[3,4-b]pyridine-6-carboxylate (7.6 g, 26.57 mmol) in EtOH (80 mL) was added HCl (12 M, 152.00 mL). The mixture was stirred at 130° C. for 2 hrs.

The mixture was adjusted to PH=8 with aq. $NaHCO_3$ and the products were extracted with EA (300 mL*3). The combined organic layers were washed with brine (300 mL), dried over $Na_2SO_4$, filtered and concentrated. The residue was purified by flash silica gel chromatography (ISCO®; 80 g SepaFlash® Silica Flash Column, Eluent of 0-60% EA/Petroleum ether gradient @60 mL/min) to give the title compound (3.3 g, 14.47 mmol, 54.47% yield) as a yellow solid.

Step 6: 3-Bromo-5-methyl-5,8-dihydro-6H-pyrano[3,4-b]pyridin-5-ol

To a solution of 3-bromo-6H-pyrano[3,4-b]pyridin-5(8H)-one (3.3 g, 14.47 mmol) and $CeCl_3$ (1.78 g, 7.24 mmol) in THE (60 mL) was added MeMgBr (3 M, 14.47 mL) at −50° C. under $N_2$. The mixture was stirred at 15° C. for 1 hr. Water (150 mL) was added, the mixture was filtered and the products were extracted with EA (80 mL*3). The combined organic layers were washed with brine (80 mL), dried over $Na_2SO_4$, filtered and concentrated. The residue was purified by flash silica gel chromatography (ISCO®; 40 g SepaFlash® Silica Flash Column, Eluent of 0-60% EA/Petroleum ether gradient @80 mL/min) to give the title compound (2.9 g, 11.88 mmol, 82.10% yield) as a white solid.

Step 7: 3-Bromo-5-fluoro-5-methyl-5,8-dihydro-6H-pyrano[3,4-b]pyridine

To a solution of 3-bromo-5-methyl-5,8-dihydro-6H-pyrano[3,4-b]pyridin-5-ol (2.9 g, 11.88 mmol in DCM (30 mL) was added DAST (2.11 g, 13.07 mmol, 1.73 mL) at 0° C. The reaction was stirred at 0° C. for 1 hr. The mixture was poured into aq. $NaHCO_3$ (100 mL) and extracted with DCM (50 mL*3). The combined organic layers were washed with brine (50 mL), dried over $Na_2SO_4$, filtered and concentrated. The residue was purified by flash silica gel chromatography (ISCO®; 40 g SepaFlash® Silica Flash Column, Eluent of 0-60% EA/Petroleum ether gradient @100 mL/min) to give the title compound (2.4 g, 9.75 mmol, 82.09% yield) as a yellow oil.

Step 8: 5-Fluoro-5-methyl-5,8-dihydro-6H-pyrano[3,4-b]pyridine-3-carboxylic acid A mixture of 3-bromo-5-fluoro-5-methyl-5,8-dihydro-6H-pyrano[3,4-b]pyridine (2.4 g, 9.75 mmol), 1,3-bis(dicyclohexylphosphino)propane bis(tetrafluoroborate) (597.14 mg, 975.31 umol), $Pd(OAc)_2$ (218.97 mg, 975.31 umol), $H_2O$ (351.50 mg, 19.51 mmol, 351.50 uL) and $K_2CO_3$ (2.02 g, 14.63 mmol) in DMSO (40 mL) was degassed and purged with CO 3 times. The mixture was stirred at 100° C. for 4 hrs under CO atmosphere (15 Psi). The mixture was filtered, poured into water (100 mL) and extracted with EA (60 mL*2). The EA layer was discarded. The aqueous phase was adjusted to PH=5 by aq. HCl (1 M) and extracted with EA (60 mL*5). The combined organic layers were washed with brined (60 mL*2), dried over $Na_2SO_4$, filtered and concentrated under vacuum to give the title compound (1.6 g, 7.27 mmol, 74.57% yield) as a yellow solid.

LCMS (ESI) m/z: $[M+H]^+$=212.0

$^1$H NMR (400 MHz, DMSO-$d_6$) δ=14.29-12.75 (m, 1H), 9.01 (s, 1H), 8.45 (s, 1H), 4.93-4.69 (m, 2H), 4.24-4.03 (m, 1H), 3.97-3.79 (m, 1H), 1.76-1.57 (m, 3H) ppm.

Step 9: (R)-5-Fluoro-5-methyl-5,8-dihydro-6H-pyrano[3,4-b]pyridine-3-carboxylic acid and (S)-5-fluoro-5-methyl-5,8-dihydro-6H-pyrano[3,4-b]pyridine-3-carboxylic acid 5-Fluoro-5-methyl-5,8-dihydro-6H-pyrano[3,4-b]pyridine-3-carboxylic acid (1.6 g, 7.58 mmol) was separated by SFC (column: DAICEL CHIRALPAK IG (250 mm*30 mm, 10 um); mobile phase: [0.1% $NH_3H_2O$ MeOH]; B %: 30%-30%, 4 min; 150 minmin) and SFC (column: DAICEL CHIRALPAK IG (250 mm*30 mm, 10 um); mobile phase: [0.1% $NH_3H_2O$ EtOH]; B %: 20%-20%, 3.8 min; 80 minmin). The product fractions were concentrated under vacuum, adjusted to PH=5 by aq. HCl (1 M) and extracted with EA (50 mL*6). The combined organic layers were dried over $Na_2SO_4$, filtered and concentrated to give Intermediate 50 (610 mg, 2.88 mmol, 37.96% yield) as a white solid and Intermediate 51 (400 mg, 1.83 mmol, 62.21% yield) as a white solid. Stereochemistry was assigned arbitrarily.

(R)-5-Fluoro-5-methyl-5,8-dihydro-6H-pyrano[3,4-b]pyridine-3-carboxylic acid LCMS (ESI) m/z: $[M+H]^+$=212.0

$^1$H NMR (400 MHz, DMSO-$d_6$) δ=14.20-12.71 (m, 1H), 9.01 (s, 1H), 8.45 (s, 1H), 4.87-4.71 (m, 2H), 4.16-4.05 (m, 1H), 3.97-3.82 (m, 1H), 1.75-1.63 (m, 3H) ppm.

Chiral SFC: IG-3_5CM_MEOH(DEA)_5_40_3ML_T35.M; Rt=1.251 mins, ee %=100%.

(S)-5-Fluoro-5-methyl-5,8-dihydro-6H-pyrano[3,4-b]pyridine-3-carboxylic acid

LCMS (ESI) m/z: $[M+H]^+$=212.0

$^1$H NMR (400 MHz, DMSO-$d_6$) δ=13.97-13.03 (m, 1H), 9.04-8.98 (m, 1H), 8.51-8.38 (m, 1H), 4.87-4.71 (m, 2H), 4.16-4.04 (m, 1H), 3.98-3.81 (m, 1H), 1.74-1.61 (m, 3H) ppm.

Chiral SFC: IG-3_5CM_MEOH(DEA)_5_40_3ML_T35.M, Rt=1.597 mins, ee %=100%.

Intermediates 59 and 60: (R)-4-Cyano-8-fluoro-4-methylisochromane-6-carboxylic acid and (S)-4-cyano-8-fluoro-4-methylisochromane-6-carboxylic acid

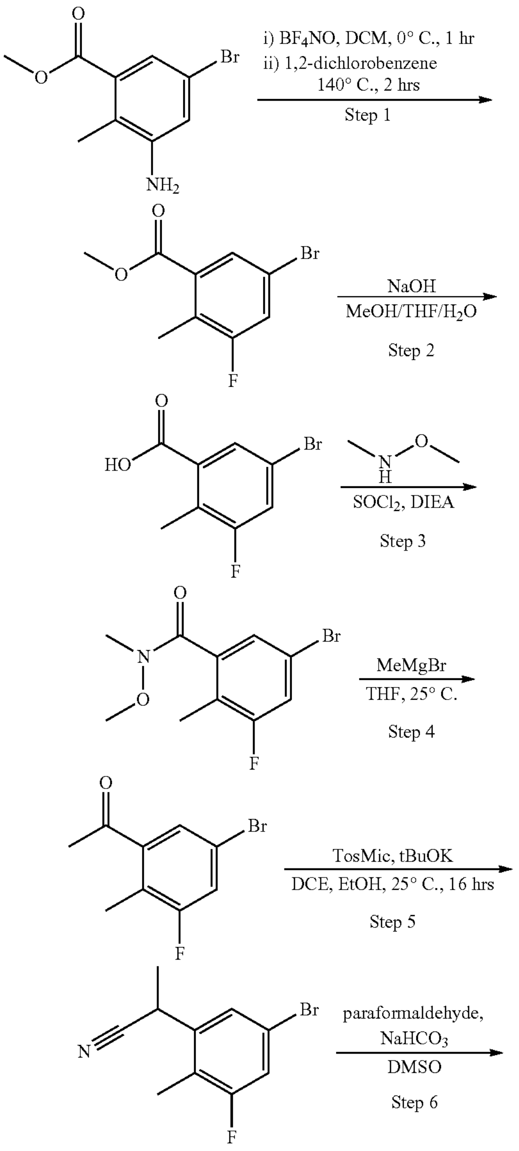

-continued

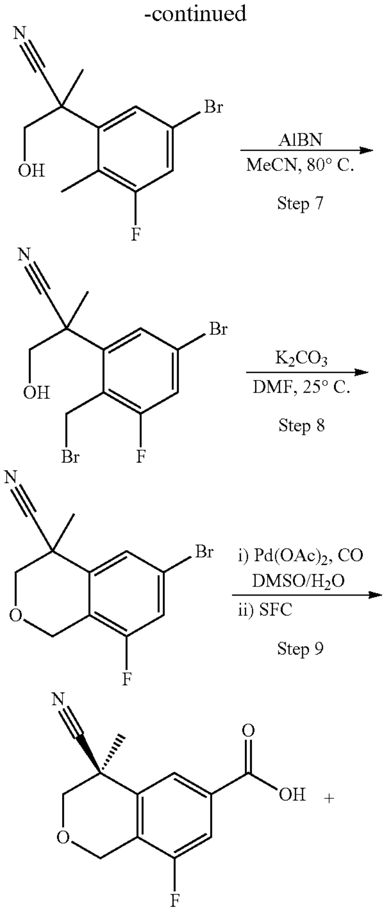

Intermediate 59

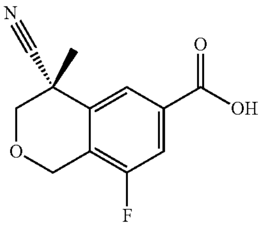

Intermediate 60

Step 1: Methyl 5-bromo-3-fluoro-2-methylbenzoate

To a mixture of methyl 3-amino-5-bromo-2-methyl-benzoate (50 g, 204.85 mmol) in DCM (500 mL) was added nitrosonium tetrafluoroborate (31.11 g, 266.30 mmol) portionwise at 0° C. under $N_2$. The mixture was stirred at 0° C. for 1 hr. o-Xylene (869.90 g, 8.19 mol, 990.78 mL) was then added and the mixture slowly heated to 130° C. before stirring at 130° C. for 2 hrs. The reaction mixture was poured into water (200 mL) and extracted with EA (100 mL*3). The combined organic layers were washed with brine (200 mL), dried over anhydrous $Na_2SO_4$, filtered and concentrated under reduced pressure. The residue was purified by column chromatography ($SiO_2$, PE/EA=50/1 to 10/1) to give the title compound (49 g, 198.33 mmol, 96.82% yield) as a yellow oil.

$^1$H NMR (400 MHz, CHLOROFORM-d) 5=7.75 (s, 1H), 7.29-7.26 (m, 1H), 3.83 (s, 3H), 2.37 (d, J=2.4 Hz, 3H) ppm.

Step 2: 5-Bromo-3-fluoro-2-methylbenzoic acid

To a mixture of methyl 5-bromo-3-fluoro-2-methylbenzoate (10 g, 40.48 mmol) in MeOH (10 mL), THF (10 mL) and $H_2O$ (5 mL) was added $LiOH{\cdot}H_2O$ (5.10 g, 121.43 mmol). The mixture was stirred at 25° C. for 1 hr. The mixture was poured into water (80 mL) and adjusted to pH=4 by 1N HCl. The mixture was then extracted with EA (30.0 mL*3). The combined organics were washed with brine (80 mL), dried over $Na_2SO_4$, filtered and concentrated to give the title compound (8.5 g, 36.48 mmol, 90.12% yield) as a white solid.

$^1$H NMR (400 MHz, DMSO-$d_6$) δ=13.54-13.49 (m, 1H), 7.76-7.73 (m, 2H), 2.36 (d, J=2.4 Hz, 3H) ppm.

Step 3:
5-Bromo-3-fluoro-N-methoxy-N,2-dimethylbenzamide

To a mixture of 5-bromo-3-fluoro-2-methylbenzoic acid (14.7 g, 63.08 mmol) and DMF (46.11 mg, 630.81 umol) in DCM (150 mL) was added $(COCl)_2$ (24.02 g, 189.24 mmol). The mixture was stirred at 25° C. for 1 hr and then concentrated under vacuum. The residue was dissolved in DCM (150 mL) and the resulting solution was added to a mixture of N-methoxymethanamine (9.23 g, 94.62 mmol, 1.5 eq) and DIEA (32.61 g, 252.32 mmol, 43.95 mL) in DCM (50 mL). The reaction was stirred at 25° C. for 16 hrs. The reaction mixture was poured into water (400 mL) and extracted with DCM (300 mL*2). The combined organic layer was washed with brine (400 mL), dried over anhydrous $Na_2SO_4$, filtered and concentrated under vacuum. The residue was purified by column chromatography ($SiO_2$, PE:EtOAc=100:1-8:1) to give the title compound (11.5 g, 41.65 mmol, 66.03% yield) as a white solid.

$^1$H NMR (400 MHz, DMSO-$d_6$) δ=7.58-7.55 (m, 1H), 7.40 (s, 1H), 3.43 (br s, 3H), 3.29 (br d, J=8.8 Hz, 3H), 2.09 (d, J=2.0 Hz, 3H) ppm.

Step 4:
1-(5-Bromo-3-fluoro-2-methylphenyl)ethan-1-one

To a solution of 5-bromo-3-fluoro-N-methoxy-N,2-dimethylbenzamide (11 g, 39.84 mmol) in THE (100 mL) was added MeMgBr (3 M, 19.92 mL) at 0° C. The reaction mixture was stirred at 25° C. for 1 hr. The reaction mixture was poured into sat. $NH_4Cl$ (300 mL) and extracted with EA (80 mL*3). The combined organic layer was washed with brine (200 mL), dried over anhydrous $Na_2SO_4$, filtered and concentrated under vacuum. The residue was purified by column chromatography ($SiO_2$, PE:EtOAc=100:1-5:1) to give the title compound (9.1 g, 39.38 mmol, 98.85% yield) as a white solid.

$^1$H NMR (400 MHz, DMSO-$d_6$) δ=7.81 (s, 1H), 7.71-7.68 (m, 1H), 2.57 (s, 3H), 2.23 (d, J=2.0 Hz, 3H) ppm.

Step 5:
2-(5-Bromo-3-fluoro-2-methylphenyl)propanenitrile

To a mixture of 1-(5-bromo-3-fluoro-2-methylphenyl) ethan-1-one (10 g, 43.28 mmol) and p-toluenesulfonylmethyl isocyanide (12.67 g, 64.92 mmol) in DME (500 mL) and EtOH (15.95 g, 346.23 mmol) was added t-BuOK (10.68 g, 95.21 mmol) at 0° C. The resulting mixture was stirred at 25° C. for 12 hrs. The reaction mixture was poured into sat. $NH_4Cl$ (400 mL) and extracted with EtOAc (200 mL*2). The combined organic phase was washed with brine (300 mL), dried over anhydrous $Na_2SO_4$, filtered and concentrated under vacuum. The residue was purified by column chromatography ($SiO_2$, PE:EtOAc=30:1-5:1) to give the title compound (7.7 g, 31.81 mmol, 73.49% yield) as a white solid.

$^1H$ NMR (400 MHz, DMSO-$d_6$) δ=7.54-7.51 (m, 1H), 7.45 (s, 1H), 4.53-4.47 (m, 1H), 2.20 (d, J=2.4 Hz, 3H), 1.54 (d, J=7.2 Hz, 3H) ppm.

Step 6: 2-(5-Bromo-3-fluoro-2-methylphenyl)-3-hydroxy-2-methylpropanenitrile

To a mixture of 2-(5-bromo-3-fluoro-2-methylphenyl) propanenitrile (7.7 g, 31.81 mmol) and $NaHCO_3$ (267.20 mg, 3.18 mmol) in DMSO (60 mL) was added paraformaldehyde (1.15 g, 38.17 mmol). The mixture was stirred at 25° C. for 16 hrs. Water (400 mL) was added and the mixture was extracted with EtOAc (200 mL*2). The combined organic phase was washed with brine (400 mL*2), dried over anhydrous $Na_2SO_4$, filtered and concentrated under vacuum. The residue was purified by column chromatography ($SiO_2$, PE; EtOAc=10:1-3:1) to give the title compound (8.0 g, 29.40 mmol, 92.43% yield) as a white solid.

$^1H$ NMR (400 MHz, DMSO-$d_6$) δ=7.58-7.56 (m, 1H), 7.36 (s, 1H), 5.84-5.81 m, 1H), 3.95-3.91 (m, 1H), 3.69-3.66 (m, 1H), 2.40 (d, J=4.0 Hz, 3H), 1.70 (s, 3H) ppm.

Step 7: 2-(5-Bromo-2-(bromomethyl)-3-fluorophenyl)-3-hydroxy-2-methylpropanenitrile To a mixture of 2-(5-bromo-3-fluoro-2-methylphenyl)-3-hydroxy-2-methylpropanenitrile (8 g, 29.40 mmol) in MeCN (80 mL) was added NBS (10.99 g, 61.74 mmol) and AIBN (1.45 g, 8.82 mmol). The mixture was stirred at 80° C. for 2 hrs. The solvent was removed under reduced pressure and the residue purified by column chromatography ($SiO_2$, PE:EtOAc=10:1-3:1) to give the title compound (8.5 g, 24.22 mmol, 82.37% yield) as a colorless oil.

$^1H$ NMR (400 MHz, DMSO-$d_6$) δ=7.74-7.71 (m, 1H), 7.44 (s, 1H), 5.93 (br s, 1H), 4.97-4.86 (m, 2H), 3.95-3.91 (m, 1H), 3.77-3.73 (m, 1H), 1.76 (s, 3H) ppm.

Step 8: 6-Bromo-8-fluoro-4-methylisochromane-4-carbonitrile

To a mixture of 2-(5-bromo-2-(bromomethyl)-3-fluorophenyl)-3-hydroxy-2-methylpropanenitrile (6.3 g, 17.95 mmol) in DMF (320 mL) was added $K_2CO_3$ (7.44 g, 53.84 mmol). The mixture was stirred at 25° C. for 16 hrs. Water (3000 mL) was added and the mixture was extracted with EtOAc (500 mL*2). The combined organic phase was washed with brine (1000 mL*2), dried over anhydrous $Na_2SO_4$, filtered and concentrated under vacuum. The residue was purified by column chromatography ($SiO_2$, PE; EtOAc=10:1-3:1) to give the title compound (2.5 g, 9.26 mmol, 51.57% yield) as a white solid.

$^1H$ NMR (400 MHz, DMSO-$d_6$) δ=7.75 (s, 1H), 7.61-7.59 (m, 1H), 4.87-4.71 (m, 2H), 4.20 (d, J=11.2 Hz, 1H), 3.81 (d, J=11.6 Hz, 1H), 1.67 (s, 3H) ppm.

Step 9: (R)-4-Cyano-8-fluoro-4-methylisochromane-6-carboxylic acid and (S)-4-cyano-8-fluoro-4-methylisochromane-6-carboxylic acid A mixture of 6-bromo-8-fluoro-4-methylisochromane-4-carbonitrile (2.1 g, 7.77 mmol), $K_2CO_3$ (1.61 g, 11.66 mmol), $Pd(OAc)_2$ (174.55 mg, 777.50 umol) and 1,3-bis (dicyclohexylphosphino)propane bis(tetrafluoroborate) (952.06 mg, 1.55 mmol) in DMSO (40 mL) and $H_2O$ (4 mL) was degassed and purged with CO 3 times. The mixture was stirred under CO (15 psi) atmosphere at 100° C. for 4 hrs. The mixture was poured into water (300 mL) and extracted with EA (50.0 mL*2). The combined organics were discarded, the aqueous was adjusted to pH=5 by aq. HCl (1 M), and the products were extracted with EA (50.0 mL*3). The combined organics were washed with brine (100.0 mL*2), dried over $Na_2SO_4$, filtered and evaporated to dryness to give racemic 4-cyano-8-fluoro-4-methylisochromane-6-carboxylic acid. The racemate was separated by SFC (column: DAICEL CHIRALPAK IC (250 mm*30 mm, 5 um); mobile phase: [0.1% $NH_3H_2O$ EtOH]; B %: 20%-20%, 3.1 min; 600 minmin). The eluent of peak 1 (Rt=1.120 min) was concentrated under vacuum. The residue was diluted with $H_2O$ (50 mL) and adjusted to pH=5 with 1N HCl, then the mixture was extracted with EA (50 mL*2). The combined organic layers were dried over anhydrous $Na_2SO_4$, filtered and concentrated to give the title compound (570 mg, 2.30 mmol, 29.58% yield) as a yellow solid. The eluent of peak 2 (Rt=1.258 min) was concentrated under vacuum. The residue was diluted with $H_2O$ (50 mL) and adjusted to pH=5 with 1N HCl, then the mixture was extracted with EA (50 mL*2). The combined organic layers were dried over anhydrous $Na_2SO_4$, filtered and concentrated to give a yellow solid. This product was further purified by SFC separation (column: DAICEL CHIRALPAK IC (250 mm*30 mm, 5 um); mobile phase: [0.1% $NH_3H_2O$ EtOH]; B %: 20%-20%, 3.2 min; 73 min) to give the title compound (590 mg, 2.48 mmol, 31.84% yield) as a yellow solid. Stereochemistry was assigned arbitrarily.

(R)-4-Cyano-8-fluoro-4-methylisochromane-6-carboxylic acid $^1H$ NMR (400 MHz, DMSO-$d_6$) δ=13.84-13.85 (m, 1H), 7.95 (s, 1H), 7.66-7.64 (m, 1H), 4.97-4.84 (m, 2H), 4.21 (d, J=11.6 Hz, 1H), 3.90 (d, J=11.6 Hz, 1H), 1.69 (s, 3H) ppm.

Chiral SFC: IC-3-EtOH(DEA)-5-40-3 mL-35T.lcm, Rt=1.120 min, ee %=95.99%.

(S)-4-Cyano-8-fluoro-4-methylisochromane-6-carboxylic acid $^1H$ NMR (400 MHz, DMSO-$d_6$) δ=13.58-13.50 (m, 1H), 7.96 (s, 1H), 7.67-7.64 (m, 1H), 4.97-4.84 (m, 2H), 4.21 (d, J=11.6 Hz, 1H), 3.90 (d, J=11.6 Hz, 1H), 1.69 (s, 3H) ppm.

Chiral SFC: IC-3-EtOH(DEA)-5-40-3 mL-35T.lcm, Rt=1.159 min, ee %=99.13%.

Intermediate 61: 3-Bromo-6H-pyrano[3,4-b]pyridin-5(8H)-one-6,6-$d_2$

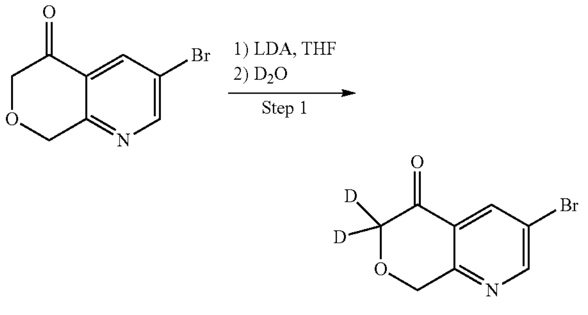

Intermediate 61

Step 1: 3-Bromo-6H-pyrano[3,4-b]pyridin-5(8H)-one-6,6-$d_2$

To a solution of 3-bromo-6H-pyrano[3,4-b]pyridin-5(8H)-one (3.00 g, 13.155 mmol, 1.00 equiv) in THE (250.00 mL) was added NaHDMS (52 mL, 1 M, 52.620 mmol, 4.00 equiv) under nitrogen at 0° C. The resulting mixture was stirred at 0° C. for 2 hours. $D_2O$ (100.00 mL) was then added to the reaction mixture and stirring at room temperature continued for 16 hours. The aqueous layer was extracted with EtOAc (50 mL×3). The organic layer was dried over $Na_2SO_4$, filtered and evaporated to afford crude product. The crude product was purified by flash silica chromatography, elution gradient 0 to 50% EtOAc in petroleum ether. Pure fractions were evaporated to dryness to afford the title compound (1.1 g, 36.35%) as a yellow solid.

LCMS (ESI) m/z: $[M+H]^+$=230.

Intermediate 62:_3-Chloro-6H-pyrano[3,4-b]pyridin-5(8H)-one-8,8-$d_2$

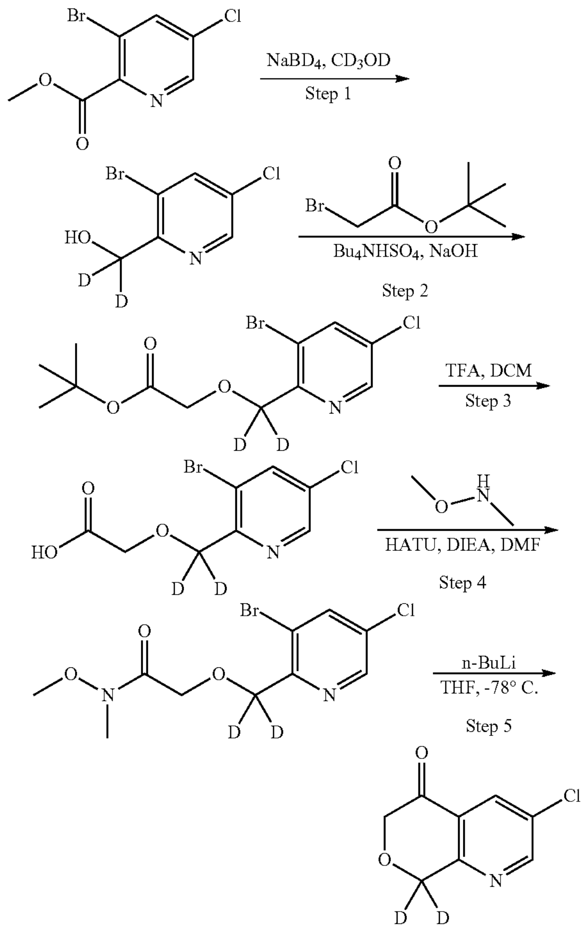

Intermediate 62

Step 1: (3-Bromo-5-chloropyridin-2-yl)methan-$d_2$-ol

To a stirred solution of methyl 3-bromo-5-chloropyridine-2-carboxylate (1.00 g, 3.992 mmol, 1.00 equiv) in $CD_3OD$ (10.00 mL) was added $NaBD_4$ (670.71 mg, 15.969 mmol, 4.00 equiv) at 0° C. under $N_2$ atmosphere. The resulting mixture was stirred for 2 h at room temperature under $N_2$ atmosphere. The reaction was quenched with water at room temperature. The aqueous mixture was extracted with EtOAc (3×100 mL). The combined organic extracts were concentrated under vacuum. The residue was purified by silica gel column chromatography, eluting with PE/EtOAc (12:1) to give the title compound (644 mg, 71.86%) as a light yellow solid.

(LCMS (ESI) m/z $[M+H]^+$=224.

Step 2: tert-Butyl 2-((3-bromo-5-chloropyridin-2-yl)methoxy-$d_2$)acetate

To a stirred solution of (3-bromo-5-chloropyridin-2-yl)methan-$d_2$-ol (5.10 g, 22.719 mmol, 1.00 equiv) and tert-butyl 2-bromoacetate (8.86 g, 45.438 mmol, 2.00 equiv) in toluene (30.00 mL) were added $Bu_4NHSO_4$ (0.77 g, 2.272 mmol, 0.10 equiv) and 10 M NaOH (30 mL) at 0° C. The resulting mixture was stirred overnight at room temperature. The reaction was quenched by the addition of sat. $NH_4Cl$ (10 mL) at room temperature. The aqueous layer was extracted with EtOAc (3×10 mL). The combined organic extracts were concentrated under vacuum. The residue was purified by silica gel column chromatography, eluting with PE/EtOAc (12:1) to give the title compound (6.5 g, crude) as a light yellow oil.

(LCMS (ESI) m/z $[M+H]^+$=338.

Step 3: 2-((3-Bromo-5-chloropyridin-2-yl)methoxy-$d_2$)acetic acid

To a stirred solution of tert-butyl 2-((3-bromo-5-chloropyridin-2-yl)methoxy-$d_2$)acetate (6.50 g, 19.196 mmol, 1.00 equiv) in DCM (40.00 mL) was added TFA (10.00 mL) at room temperature. The resulting mixture was stirred for 1 h at room temperature. The resulting mixture was concentrated under reduced pressure to give the title compound (6.4 g, crude) as a white solid.

(LCMS (ESI) m/z $[M+H]^+$=282.

Step 4: 2-((3-Bromo-5-chloropyridin-2-yl)methoxy-$d_2$)-N-methoxy-N-methylacetamide To a stirred solution of 2-((3-bromo-5-chloropyridin-2-yl)methoxy-$d_2$)acetic acid (6.40 g, 22.654 mmol, 1.00 equiv) and N,O-dimethylhydroxylamine (1.66 g, 27.185 mmol, 1.20 equiv) in DMF (60.00 mL) were added HATU (10.34 g, 27.185 mmol, 1.20 equiv) and DIEA (8.78 g, 67.962 mmol, 3.00 equiv) at room temperature. The resulting mixture was stirred for 2 h at room temperature. Water was added and the aqueous mixture was extracted with EtOAc. The combined organic extracts were concentrated under reduced pressure. The residue was purified by prep-HPLC to give the title compound (4.45 g, 60.33%) as a light yellow oil.

(LCMS (ESI) m/z $[M+H]^+$=325.

Step 5: 3-Chloro-6H-pyrano[3,4-b]pyridin-5(8H)-one-8,8-$d_2$

To a stirred solution of 2-((3-bromo-5-chloropyridin-2-yl)methoxy-$d_2$)-N-methoxy-N-methylacetamide (3 g, 9.214 mmol, 1.00 equiv) in THE (40.00 mL) was added nBuLi (4.42 mL, 11.057 mmol, 1.20 equiv) at −78° C. under nitrogen atmosphere. The resulting mixture was stirred for 2 h at −78° C. under nitrogen atmosphere. The reaction was quenched by the addition of sat. $NH_4Cl$ (10 mL) at room temperature. The aqueous mixture was extracted with EtOAc (3×10 mL). The combined organic extracts were concentrated under reduced pressure. The residue was purified by prep-HPLC to give the title compound (380 mg, 22.22%) as a light yellow oil.

(LCMS (ESI) m/z $[M+H]^+$=187.

Intermediate 63: Ethyl 2-azabicyclo[2.2.2]octane-4-carboxylate

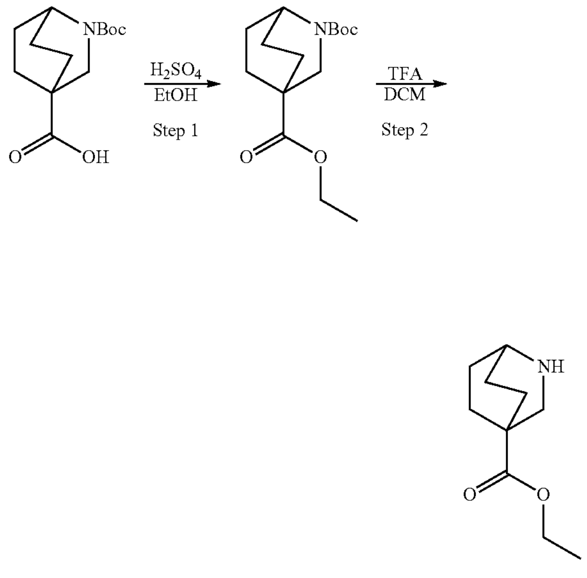

Intermediate 63

Step 1. 2-tert-Butyl 4-ethyl 2-azabicyclo[2.2.2]octane-2,4-dicarboxylate

2-[(tert-Butoxy)carbonyl]-2-azabicyclo[2.2.2]octane-4-carboxylic acid (0.2 g, 0.783 mmol) was dissolved in EtOH (2.6 mL). Catalytic sulfuric acid (0.26 mL) was added and the reaction mixture stirred overnight. The excess solvent was then removed under vacuum. The crude residue was dissolved in EtOAc, the organic layer washed with saturated $NaHCO_3$, dried over $Na_2SO_4$, filtered, and concentrated under reduced pressure to give the title compound as a yellow oil (0.14 g).

LCMS (ESI) m/z: [M+H-Boc]+=184.2.

Step 2. Ethyl 2-azabicyclo[2.2.2]octane-4-carboxylate

2-Azabicyclo[2.2.2]octane-2,4-dicarboxylate (0.065 g, 0.24 mmol) was dissolved in DCM in (1.2 mL) and cooled to 0° C. Trifluoroacetic acid (0.19 mL, 2.4 mmol) was added dropwise and the reaction mixture stirred for 1 h at 0° C. The solvent was then removed under vacuum. The crude residue was dissolved in DCM, the organic layer washed with saturated $NaHCO_3$, dried over $Na_2SO_4$, filtered, and concentrated under reduced pressure to give the title compound as a yellow oil (0.04 g).

LCMS (ESI) m/z: [M+H]+=184.2.

Intermediate 64: 2-Chloro-8-fluoro-1,6-naphthyridine-7-carbonitrile

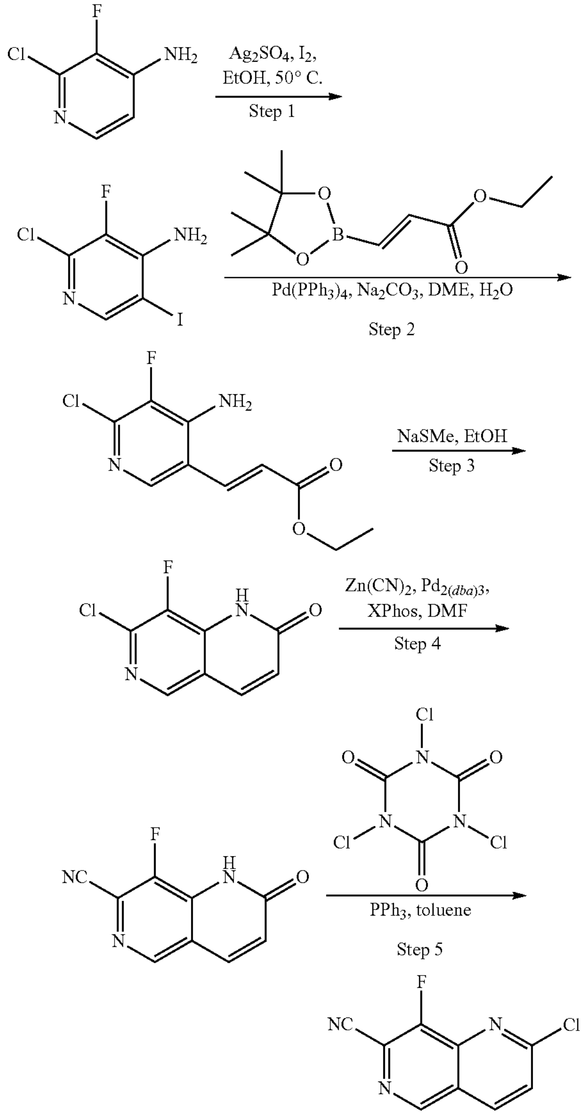

Intermediate 64

Step 1: 2-Chloro-3-fluoro-5-iodopyridin-4-amine

To a stirred solution of 2-chloro-3-fluoropyridin-4-amine (6.00 g, 40.942 mmol, 1.00 equiv) and $Ag_2SO_4$ (12.77 g, 40.956 mmol, 1.00 equiv) in ethanol (150 mL) was added 12 (10.39 g, 40.942 mmol, 1 equiv). The resulting mixture was stirred at 55° C. for 2 h. The solid was filtered out and the filtrate was concentrated under reduced pressure. The residue was dissolved in DCM (300 mL), washed with water (50 mL×2) and saturated brine (30 mL×1), dried over anhydrous $Na_2SO_4$. After filtration, the filtrate was concentrated under reduced pressure to give the title compound (8.8 g, 78.89%) as a light yellow solid.

LCMS (ESI) m/z: $[M+H]^+$=273.

Step 2: Ethyl (E)-3-(4-amino-6-chloro-5-fluoropyridin-3-yl)acrylate

To a stirred solution of 2-chloro-3-fluoro-5-iodopyridin-4-amine (6.00 g, 22.022 mmol, 1.00 equiv) and ethyl (2E)-3-(4,4,5,5-tetramethyl-1,3,2-dioxaborolan-2-yl)prop-2-enoate (6.47 g, 28.629 mmol, 1.3 equiv) in DME (90 mL) and $H_2O$ (30 mL) were added $Pd(PPh_3)_4$ (2.54 g, 2.202 mmol, 0.1 equiv) and $Na_2CO_3$ (4.67 g, 44.045 mmol, 2 equiv). The resulting mixture was stirred at 100° C. for 3 h under nitrogen atmosphere. The reaction mixture was concentrated under reduced pressure. The residue was purified by silica gel column chromatography, eluting with PE/EtOAc (5:1) to give the title compound (5.0 g, 92.80%) as a light yellow oil.

LCMS (ESI) m/z: $[M+H]^+$=245.

Step 3: 7-Chloro-8-fluoro-1,6-naphthyridin-2(1H)-one

A solution of ethyl (E)-3-(4-amino-6-chloro-5-fluoropyridin-3-yl)acrylate (5.00 g, 20.437 mmol, 1.00 equiv) and NaSMe (17.88 g, 51.093 mmol, 2.5 equiv, 20% in $H_2O$) in ethanol (60 mL) was stirred for 4 h at 60° C. The mixture was acidified to pH 7 with 1 N. HCl. The resulting mixture was extracted with EtOAc (200 mL×2). The combined organic layers were washed with water (100 mL) and dried over anhydrous $Na_2SO_4$. After filtration, the filtrate was concentrated under reduced pressure. The residue was purified by silica gel column chromatography, eluting with PE/EtOAc (5:1) to give the title compound (2.23 g, 54.95%) as a light yellow solid.

LCMS (ESI) m/z: $[M+H]^+$=199.

Step 4: 8-Fluoro-2-oxo-1,2-dihydro-1,6-naphthyridine-7-carbonitrile

To a stirred solution of 7-chloro-8-fluoro-1,6-naphthyridin-2(1H)-one (1.00 g, 5.036 mmol, 1.00 equiv) and $Zn(CN)_2$ (1.18 g, 10.072 mmol, 2 equiv) in DMF (5 mL) were added $Pd_2(dba)_3$ (0.92 g, 1.007 mmol, 0.2 equiv) and XPhos (0.96 g, 2.014 mmol, 0.4 equiv). The resulting mixture was stirred at 100° C. for 4 h under nitrogen atmosphere. The reaction mixture was concentrated under reduced pressure. The residue was purified by prep-HPLC to give the title compound (561 mg, 58.90%) as a light yellow solid.

LCMS (ESI) m/z: $[M+H]^+$=190.

Step 5: 2-Chloro-8-fluoro-1,6-naphthyridine-7-carbonitrile

A solution of trichloroisocyanuric acid (568.01 mg, 2.444 mmol, 0.67 equiv) and $PPh_3$ (1913.59 mg, 7.296 mmol, 2 equiv) in toluene (1 mL) was stirred overnight at room temperature under nitrogen atmosphere. To the above mixture was added 8-fluoro-2-oxo-1,2-dihydro-1,6-naphthyridine-7-carbonitrile (690.00 mg, 3.648 mmol, 1.00 equiv) at room temperature. The resulting mixture was stirred for an additional 4 h at 110° C. under nitrogen atmosphere. The mixture was concentrated under reduced pressure. The residue was purified by silica gel column chromatography, eluting with PE/EtOAc (1:1) to give the title compound (346 mg, 45.69%) as a white solid.

LCMS (ESI) m/z: $[M+H]^+$=208.

Intermediate 65: tert-Butyl ((6-bromoisoquinolin-3-yl)methyl)carbamate

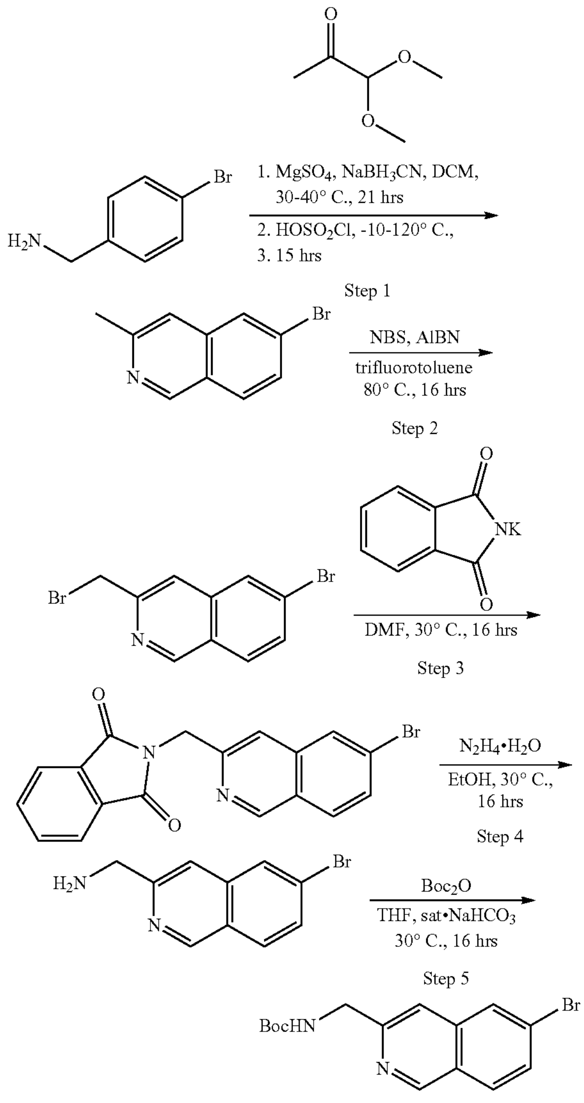

Intermediate 65

Step 1: 6-Bromo-3-methylisoquinoline

To a solution of (4-bromophenyl)methanamine (30 g, 161.25 mmol) in DCM (500 mL) was added 1,1-dimethoxypropan-2-one (20.95 g, 177.37 mmol) and $MgSO_4$ (60.00 g, 498.47 mmol). The resulting mixture was stirred at 40° C. for 16 hrs. $NaBH_3CN$ (12.16 g, 193.50 mmol) was then added and the mixture stirred at 30° C. for 5 hrs before filtering. The filtrate was concentrated to give a yellow oil. Chlorosulfonic acid (157.50 g, 1.35 mol) was cooled to −10° C. and the above crude product was added dropwise for 3 hrs under $N_2$. The reaction mixture was heated to 120° C. for 10 mins. The reaction mixture was cooled to 25° C. and poured into ice water (2 L). The solution was neutralized with 2 M NaOH and extracted with EA (1000 mL*3). The combined organic layer was washed with brine (2000 mL), dried over $Na_2SO_4$, filtered and concentrated. The residue was purified by column chromatography ($SiO_2$, Petroleum ether/Ethyl acetate=10:1-5:1) to give the title compound (8.5 g, 38.27 mmol, 23.74% yield) as a yellow solid.

$^1H$ NMR (400 MHz, DMSO-$d_6$) δ=9.06 (s, 1H), 7.8 (d, J=1.2 Hz, 1H), 7.71 (d, J=8.4 Hz, 1H), 7.52-7.50 (m, 1H), 7.30 (s, 1H), 2.62 (s, 3H) ppm.

Step 2: 6-Bromo-3-(bromomethyl)isoquinoline

To a solution of 6-bromo-3-methylisoquinoline (8.3 g, 37.37 mmol) in trifluoromethylbenzene (200 mL) was added NBS (7.97 g, 44.77 mmol) and AIBN (919.64 mg, 5.60 mmol). The mixture was stirred at 80° C. for 16 hrs. The reaction mixture was concentrated and the residue was purified by column chromatography ($SiO_2$, Petroleum ether/Ethyl acetate=40:1-20:1) to give the title compound (3 g, 9.22 mmol, 24.68% yield) as a yellow solid.

LCMS (ESI) m/z: $[^{79}BrM+H]^+$=301.9

$^1H$ NMR (400 MHz, DMSO-$d_6$) δ=9.22 (s, 1H), 8.02-8.00 (m, 2H), 7.86 (d, J=8.8 Hz, 1H), 7.72-7.68 (m, 2H), 4.72 (s, 2H) ppm.

Step 3: 2-((6-Bromoisoquinolin-3-yl)methyl)isoindoline-1,3-dione

A mixture of 6-bromo-3-(bromomethyl)isoquinoline (3 g, 9.97 mmol) and (1,3-dioxoisoindolin-2-yl)potassium (2.03 g, 10.96 mmol) in DMF (65 mL) was stirred at 30° C. for 16 hrs. The reaction mixture was poured into $NaHCO_3$ solution (200 mL) and the products were extracted with DCM (200 mL*3). The combined organic layer was washed with brine (500 mL), dried over $Na_2SO_4$, filtered and concentrated to give the title compound (3.6 g, 9.80 mmol, 98.36% yield) as a yellow solid.

$^1H$ NMR (400 MHz, DMSO-$d_6$) δ=9.15 (s, 1H), 7.95-7.89 (m, 3H), 7.76-7.74 (m, 3H), 7.65 (s, 1H), 7.54 (s, 1H), 5.30 (s, 2H) ppm.

Step 4: (6-Bromoisoquinolin-3-yl)methanamine

To a solution of 2-((6-bromoisoquinolin-3-yl)methyl)isoindoline-1,3-dione (3.6 g, 9.80 mmol) in EtOH (60 mL) was added $NH_2NH_2{\cdot}H_2O$ (1.72 g, 34.31 mmol). The mixture was stirred at 30° C. for 16 hrs. The reaction mixture was concentrated under vacuum to give the title compound (2.32 g, 9.79 mmol, 100.00% yield) as a yellow solid.

$^1H$ NMR (400 MHz, DMSO-$d_6$) δ=9.25-9.23 (m, 1H), 8.22-8.20 (m, 1H), 8.05 (d, J=8.8 Hz, 1H), 7.78-7.71 (m, 2H), 3.95 (s, 2H) ppm.

Step 5: tert-Butyl ((6-bromoisoquinolin-3-yl)methyl)carbamate

To a solution of (6-bromoisoquinolin-3-yl)methanamine (2.32 g, 9.79 mmol) in THE (25 mL) was added $NaHCO_3$ (1.64 g, 19.57 mmol) and $Boc_2O$ (2.56 g, 11.74 mmol). The mixture was stirred at 30° C. for 2 hrs. The reaction mixture was poured into water (100 mL) and the products were extracted with EA (50 mL*3). The combined organic layer was washed with brine (100 mL), dried over $Na_2SO_4$, filtered and concentrated. The residue was purified by column chromatography ($SiO_2$, Petroleum ether/Ethyl acetate=20:1-2:1) to give the title compound (2.2 g, 6.25 mmol, 63.87% yield) as a yellow solid.

LCMS (ESI) m/z: $[^{79}BrM+H]^+$=339.1

$^1H$ NMR (400 MHz, DMSO-$d_6$) δ=9.17 (s, 1H), 7.97-7.95 (m, 1H), 7.83 (d, J=8.8 Hz, 1H), 7.67-7.64 (m, 1H), 7.53 (s, 1H), 4.58 (br d, J=6.0 Hz, 2H), 1.48 (s, 9H) ppm.

Intermediate 66: 2-((6-Bromocinnolin-3-yl)methyl)isoindoline-1,3-dione

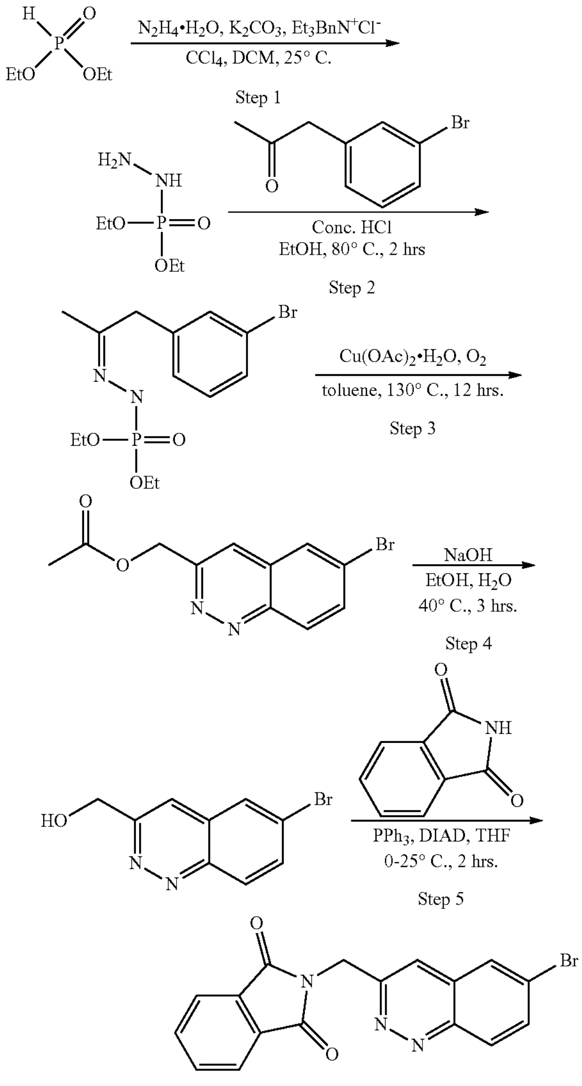

Intermediate 66

Step 1: Diethyl hydrazineylphosphonate

Hydrazine hydrate (21.32 g, 362.05 mmol, 20.70 mL) was added dropwise with efficient stirring to a mixture of $CCl_4$ (180 mL), DCM (300 mL), anhydrous $K_2CO_3$ (75.06 g, 543.08 mmol) and benzyl(triethyl)ammonium chloride (824.66 mg, 3.62 mmol) at 25° C. Stirring was continued for 15 min at 25° C. and a solution of diethyl phosphonate (50 g, 362.05 mmol, 46.73 mL) in DCM (60 mL) was then added at 25° C. with occasional external cooling. After the addition had been completed, stirring was continued for 4 hrs at 25° C. Potassium carbonate was then filtered off and the filter cake washed with DCM. The filtrate was concentrated under reduced pressure to provide the title compound (56 g, 333.07 mmol, 92.00% yield) as a light yellow oil that was used directly in the next step.

Step 2: Diethyl (Z)-(2-(1-(3-bromophenyl)propan-2-ylidene)hydrazineyl)phosphonate A mixture of 1-(3-bromophenyl)propan-2-one (20.9 g, 98.09 mmol), diethyl hydrazineylphosphonate (17.32 g, 102.99 mmol) and HCl (0.6 mL) in EtOH (400 mL) was stirred at 80° C. for 2 hrs. The reaction mixture was concentrated to afford a yellow oil. The oil was dissolved in water (100 mL) and sat. $NaHCO_3$ was added to adjust pH to 9. The products were extracted with DCM (50 mL*3). The combined organic phase was dried over anhydrous $Na_2SO_4$ and concentrated to afford a brown residue. The residue was purified by column chromatography ($SiO_2$, Dichloromethane/Methanol=1/0 to 10/1) to give the title compound (26.65 g, 66.04 mmol, 67.33% yield) as a light yellow solid.

LCMS (ESI) m/z: [M+H]+=362.9/364.9

Step 3: (6-Bromocinnolin-3-yl)methyl acetate

To a solution of diethyl (Z)-(2-(1-(3-bromophenyl)propan-2-ylidene)hydrazineyl)phosphonate (3.65 g, 10.05 mmol) in toluene (92 mL) was added $Cu(OAc)_2 \cdot H_2O$ (2.01 g, 10.05 mmol, 2.01 mL) at 25° C. The mixture was stirred at 130° C. for 12 hrs under $O_2$ (15 psi). The mixture was diluted with $H_2O$ (500 mL) and extracted with EA (500 mL*2). The combined organic layers were dried over anhydrous $Na_2SO_4$, filtered and concentrated. The residue was purified by column chromatography ($SiO_2$, DCM/EA=1/0 to 0/1) to give the title compound (1 g, 3.56 mmol, 17.70% yield) as a brown solid.

$^1$H NMR (400 MHz, $CDCl_3$) δ=8.45 (d, J=9.2 Hz, 1H), 8.05 (d, J=1.6 Hz, 1H), 7.94-7.91 (m, 1H), 7.83 (s, 1H), 5.70 (s, 2H), 2.20 (s, 3H) ppm.

Step 4: (6-Bromocinnolin-3-yl)methanol

To a solution of (6-bromocinnolin-3-yl)methyl acetate (1 g, 3.56 mmol) in MeOH/THE/$H_2O$=2/2/1 (10 mL) was added NaOH (213.44 mg, 5.34 mmol). The mixture was stirred at 40° C. for 3 hrs. The reaction mixture was diluted with $H_2O$ (30 mL) and extracted with DCM (30 mL*2). The combined organic layers were dried over anhydrous $Na_2SO_4$, filtered and concentrated. The residue was triturated with MTBE (20 mL) and the yellow solid was collected by filtration to give the title compound (580 mg, 2.43 mmol, 68.20% yield) as a yellow solid.

LCMS (ESI) m/z: [M+H]+=238.8/240.8.

$^1$H NMR (400 MHz, DMSO-d6) δ=8.47 (d, J=1.6 Hz, 1H), 8.41 (d, J=9.2 Hz, 1H), 8.16 (s, 1H), 8.03-8.01 (m, 1H), 5.82-5.79 (m, 1H), 5.07 (d, J=5.6 Hz, 2H) ppm.

Step 5: 2-((6-Bromocinnolin-3-yl)methyl)isoindoline-1,3-dione

To a solution of (6-bromocinnolin-3-yl)methanol (580 mg, 2.43 mmol), isoindoline-1,3-dione (392.65 mg, 2.67 mmol) and $PPh_3$ (954.51 mg, 3.64 mmol) in THF (20 mL) was added a solution of DEAD (633.79 mg, 3.64 mmol, 661.58 uL) in THE (10 mL) at 0° C. The mixture was stirred at 25° C. for 2 hrs under $N_2$. The reaction mixture was diluted with $H_2O$ (100 mL) and extracted with DCM (100 mL*2). The combined organic layers were dried over anhydrous $Na_2SO_4$, filtered and concentrated. The residue was triturated with MeOH (20 mL) and the off-white solid collected by filtration to give the title compound (550 mg, 1.49 mmol, 61.57% yield).

LCMS (ESI) m/z: [M+H]+=369.9.

$^1$H NMR (400 MHz, DMSO-d6) δ=8.39-8.37 (m, 2H), 8.21 (s, 1H), 8.04-8.02 (m, 1H), 7.96-7.93 (m, 2H), 7.90-7.89 (m, 2H), 5.34 (s, 2H) ppm.

Intermediate 67: tert-Butyl ((3-bromo-1,7-naphthyridin-6-yl)methyl)carbamate

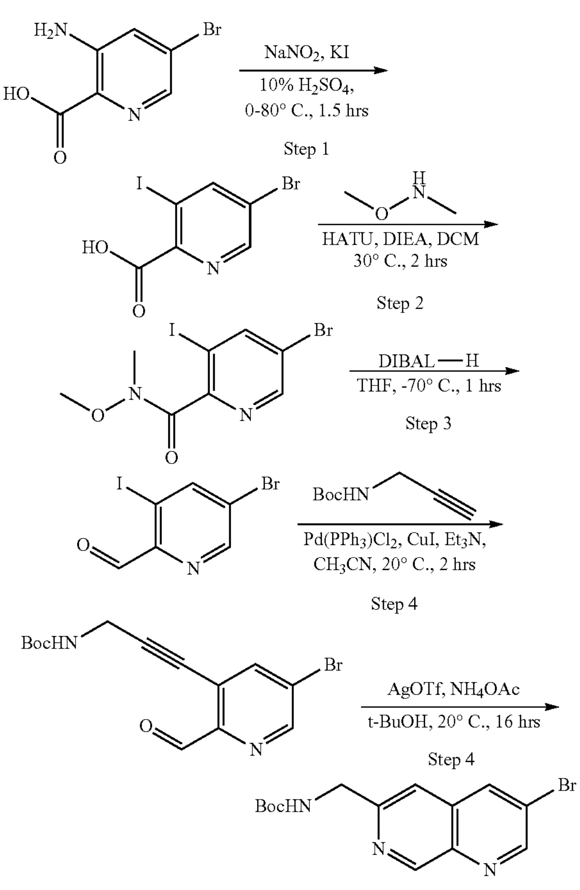

Intermediate 67

Step 1: 5-Bromo-3-iodopicolinic acid

To a solution of 3-amino-5-bromo-pyridine-2-carboxylic acid (4 g, 18.43 mmol) in 10% $H_2SO_4$ (30 mL) was added $NaNO_2$ (1.91 g, 27.65 mmol) at 0° C. The mixture was stirred at 0° C. for 30 min. KI (9.18 g, 55.29 mmol) was added and the reaction was stirred at 0° C. for 30 min and then heated to 80° C. for 1 hr. The reaction mixture was cooled to 20° C. and slowly poured into ice water (80 mL). The resulting yellow solid was collected by filtration and dried to give the title compound (4.5 g, 13.72 mmol, 74.46% yield).

LCMS (ESI) m/z: [$^{79}$BrM+H]$^+$=327.8.

$^1$HNMR (400 MHz, DMSO-$d_6$) δ=8.73 (d, J=2.0 Hz, 1H), 8.70 (d, J=2.0 Hz, 1H) ppm.

Step 2: 5-Bromo-3-iodo-N-methoxy-N-methylpicolinamide

To a solution of 5-bromo-3-iodopicolinic acid (2 g, 6.10 mmol) in DCM (15 mL) was added HATU (3.48 g, 9.15 mmol), DIPEA (3.94 g, 30.50 mmol) and N,O-dimethylhydroxylamine (713.95 mg, 7.32 mmol). The mixture was stirred at 30° C. for 2 hrs. Water (30 mL) was added and the products extracted with ethyl acetate (30 mL*3). The combined organic phase was washed with brine (30 mL), dried over $Na_2SO_4$, filtered and concentrated under reduced pressure. The residue was purified by column chromatography ($SiO_2$, Petroleum ether/Ethyl acetate=1/1) to give the title compound (2.2 g, 5.93 mmol, 97.23% yield) as a yellow oil.

LCMS (ESI) m/z: $[^{81}BrM+H]^+$=372.8.

Step 3: 5-Bromo-3-iodopicolinaldehyde

To a solution of 5-bromo-3-iodo-N-methoxy-N-methylpicolinamide (1 g, 2.70 mmol) in THE (10 mL) was added drop wise DIBAL-H (1 M, 5.39 mL, 5.39 mmol) at −70° C. under $N_2$. The mixture was stirred at −70° C. for 1 hr. The reaction was quenched by adding water (50 mL) and the products were extracted with ethyl acetate (50 mL*3). The combined organic layers were washed with brine (30 mL), dried over $Na_2SO_4$, concentrated under vacuum. The residue was purified by column chromatography ($SiO_2$, Petroleum ether/Ethyl acetate=3/1) to give the title compound (0.6 g, 1.92 mmol, 71.36% yield) as a yellow oil.

LCMS (ESI) m/z: $[^{79}BrM+H]^+$=311.8.

$^1$HNMR (400 MHz, $CDCl_3$) δ=9.98 (s, 1H), 8.83 (d, J=2.0 Hz, 1H), 8.53 (d, J=2.0 Hz, 1H) ppm.

Step 4: tert-Butyl (3-(5-bromo-2-formylpyridin-3-yl)prop-2-yn-1-yl)carbamate

5-Bromo-3-iodopicolinaldehyde (150 mg, 480.92 umol), tert-butyl N-prop-2-ynylcarbamate (74.64 mg, 480.92 umol), $Et_3N$ (486.64 mg, 4.81 mmol, 669.39 uL), CuI (9.16 mg, 48.09 umol) and $Pd(PPh_3)_2Cl_2$ (33.76 mg, 48.09 umol) in $CH_3CN$ (6 mL) was de-gassed and purged with $N_2$ before stirring at 20° C. for 2 hrs under $N_2$. The reaction was quenched by adding water (30 mL) and the products were extracted with ethyl acetate (30 mL*3). The combined organic phase was washed with brine (30 mL), dried over $Na_2SO_4$, filtered and concentrated to give the title compound (0.2 g, crude) as a yellow oil that was used in the next step without further purification.

LCMS (ESI) m/z: $[^{79}BrM+H]^+$=339.0.

Step 5: tert-Butyl ((3-bromo-1,7-naphthyridin-6-yl)methyl)carbamate

To a solution of tert-butyl (3-(5-bromo-2-formylpyridin-3-yl)prop-2-yn-1-yl)carbamate (0.2 g, 589.65 umol) in tBuOH (5 mL) was added $NH_4OAc$ (68.18 mg, 884.48 umol) and AgOTf (30.30 mg, 117.93 umol). The mixture was stirred at 20° C. for 16 hrs. The reaction mixture was quenched by adding water (30 mL) and the products were extracted with ethyl acetate (30 mL*3). The combined organic phase was washed with brine (30 mL), dried over $Na_2SO_4$, filtered and concentrated. The residue was purified by column chromatography ($SiO_2$, Petroleum ether/Ethyl acetate=1/1) to give the title compound (110 mg, 315.49 umol, 53.51% yield) as a yellow oil.

LCMS (ESI) m/z: $[^{79}BrM+H]^+$=338.1.

Intermediate 68: 2-((2-Chlorothiazolo[5,4-c]pyridin-6-yl)methyl)isoindoline-1,3-dione

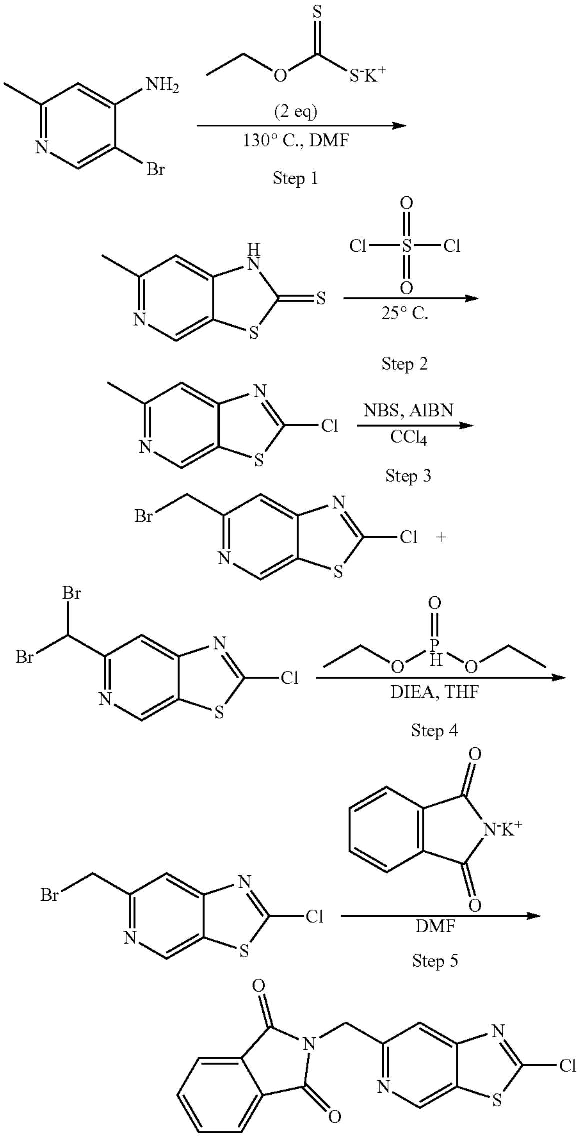

Intermediate 68

Step 1: 6-Methylthiazolo[5,4-c]pyridine-2(1H)-thione

A solution of 5-bromo-2-methylpyridin-4-amine (7.50 g, 40.098 mmol, 1.00 equiv) and potassium ethyl xanthate (25.71 g, 160.393 mmol, 4 equiv) in DMF (75 mL) was stirred for 15 h at 130° C. The resulting mixture was diluted with water (200 mL) and extracted with EtOAc (300 mL). The organic layer was discarded, and the aqueous layer was concentrated under reduced pressure. The residue was slurried with EtOAc (500 mL) and stirred at 25° C. for 1 h. The solid was removed by filtration and the filtrate was concentrated under reduced pressure to give the title compound (3.5 g, 47.89%) as a light yellow solid.

LCMS (ESI) m/z: $[M+H]^+$=183.

Step 2: 2-Chloro-6-methylthiazolo[5,4-c]pyridine

A solution of 6-methylthiazolo[5,4-c]pyridine-2(1H)-thione (2.10 g, 11.522 mmol, 1.00 equiv) in sulfonyl chloride (20.00 mL) was stirred at room temperature for 2 hours. The mixture was poured into ice-water (200 mL). The aqueous mixture was basified to pH 9 with $Na_2CO_3$. And extracted with EtOAc (200 mL×3). The combined organic layers were washed with water (50 mL×1), dried over anhydrous $Na_2SO_4$, filtered and concentrated under reduced pressure to give the title compound (0.726 g, 34.13%) as a light yellow solid.

LCMS (ESI) m/z: $[M+H]^+$=185.

Step 3: 6-(Bromomethyl)-2-chlorothiazolo[5,4-c]pyridine and 2-chloro-6-(dibromomethyl)thiazolo[5,4-c]pyridine To a stirred solution of 2-chloro-6-methylthiazolo[5,4-c]pyridine (1.83 g, 9.911 mmol, 1.00 equiv) and NBS (1.76 g, 9.911 mmol, 1 equiv) in $CCl_4$ (30 mL) was added AIBN (0.16 g, 0.991 mmol, 0.1 equiv). The resulting mixture was stirred at 80° C. for 15 hours under nitrogen atmosphere. The reaction mixture was poured into water (30 mL) and extracted with DCM (60 mL). The combined organic layers were washed with brine (30 mL×1), dried over anhydrous $Na_2SO_4$, filtered and concentrated under reduced pressure. The residue was purified by silica gel column chromatography, eluting with PE/EtOAc (10:1) to give a mixture of the title compounds (1.57 g, 60.11%) as a light yellow solid.

LCMS (ESI) m/z: $[M+H]^+$=265.

Step 4: 6-(Bromomethyl)-2-chlorothiazolo[5,4-c]pyridine

To a stirred solution of a mixture of 6-(bromomethyl)-2-chlorothiazolo[5,4-c]pyridine and 2-chloro-6-(dibromomethyl)thiazolo[5,4-c]pyridine (1.87 g, 5.461 mmol, 1.00 equiv) and diethyl phosphonate (4.53 g, 32.766 mmol, 6 equiv) in THE (25 mL) was added DIEA (4.23 g, 32.766 mmol, 6 equiv). The mixture was stirred at room temperature for 15 hours. The mixture was concentrated under vacuum and the residue was purified by silica gel column chromatography, eluting with PE/EtOAc (12:1) to give the title compound (1.42 g, 98.67%) as a light yellow solid.

LCMS (ESI) m/z: $[M+H]^+$=265.

Step 5: 2-((2-Chlorothiazolo[5,4-c]pyridin-6-yl)methyl)isoindoline-1,3-dione

A solution of 6-(bromomethyl)-2-chlorothiazolo[5,4-c]pyridine (100.00 mg, 0.379 mmol, 1.00 equiv) and potassium phthalimide (84.34 mg, 0.455 mmol, 1.2 equiv) in DMF (1 mL) was stirred for 1 hour at room temperature. The mixture was poured into water (2 mL) and stirred for 10 min. The resulting mixture was filtered, the filter cake was washed with water (5 mL×2). The solid was dried under vacuum to give the title compound (114 mg, 91.11%) as a white solid.

LCMS (ESI) m/z: $[M+H]^+$=330.

Intermediate 69: tert-Butyl ((6-chloropyrido[3,2-c]pyridazin-3-yl)methyl)carbamate

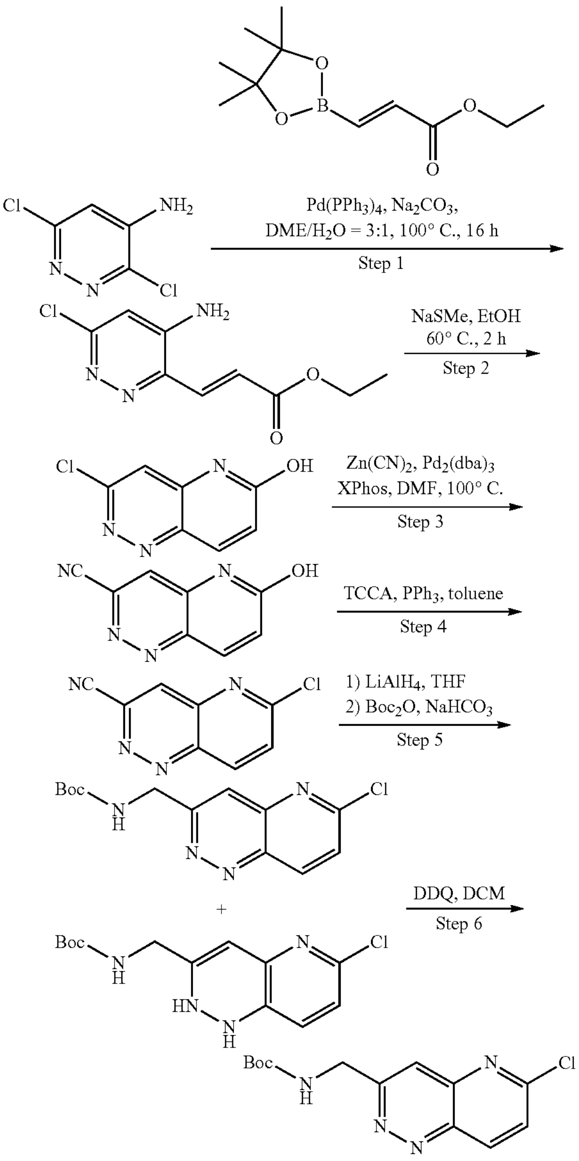

Intermediate 69

Step 1: Ethyl (E)-3-(4-amino-6-chloropyridazin-3-yl)acrylate

To a stirred solution of 3,6-dichloropyridazin-4-amine (24.00 g, 146.350 mmol, 1.00 equiv), ethyl (2E)-3-(4,4,5,5-tetramethyl-1,3,2-dioxaborolan-2-yl)prop-2-enoate (39.70 g, 175.620 mmol, 1.20 equiv) in DME (270.00 mL) and $H_2O$ (90.00 mL) was added $Pd(PPh_3)_4$ (16.91 g, 14.635 mmol, 0.10 equiv) and $Na_2CO_3$ (31.02 g, 292.701 mmol, 2.00 equiv). The mixture was stirred at 100° C. for overnight. The resulting mixture was concentrated under reduced pressure. The residue was diluted with water (300 mL) and extracted with EtOAc (300 mL×5). The combined organic layers were washed with brine (80 mL), dried over anhydrous $Na_2SO_4$, filtered and evaporated. The crude product was purified by silica gel column chromatography, elution gradient 0 to 100% EtOAc in petroleum ether to give a mixture of 3,6-dichloropyridazin-4-amine and the title compound (15 g, crude) as a yellow solid. The mixture was re-crystallized from EtOAc (260 mL) to give the title compound (10 g, 30.02%) as a yellow solid.

LCMS (ESI) m/z: $[M+H]^+$=228.

Step 2: 3-Chloropyrido[3,2-c]pyridazin-6-ol

To a stirred solution of ethyl (E)-3-(4-amino-6-chloro-pyridazin-3-yl)acrylate (11.80 g, 51.834 mmol, 1.00 equiv) in EtOH (150 mL) was added NaSMe (9.08 g, 129.548 mmol, 2.50 equiv) dropwise at room temperature. The resulting mixture was stirred for 2 h at 60° C. The mixture was diluted with water (100 mL) and neutralized to pH 7 with 1M HCl (aq.). The resulting mixture was filtered and the filter cake was washed with tert-butyl methyl ether (10 mL×3). The filter cake was dried under vacuum to give the title compound (6.3 g, 63.59%) as a grey solid.

LCMS (ESI) m/z: $[M+H]^+$=182.

Step 3: 6-Hydroxypyrido[3,2-c]pyridazine-3-carbonitrile

To a stirred solution of 3-chloropyrido[3,2-c]pyridazin-6-ol (3500.00 mg, 19.275 mmol, 1.00 equiv) in DMF (40 mL) was added $Zn(CN)_2$ (4527.53 mg, 38.551 mmol, 2 equiv), $Pd_2(dba)_3$ (3530.15 mg, 3.855 mmol, 0.2 equiv) and XPhos (3675.53 mg, 7.710 mmol, 0.40 equiv). The mixture was stirred at 100° C. overnight under nitrogen atmosphere. The resulting mixture was concentrated under reduced pressure. The crude product was purified by prep-HPLC to give the title compound (900 mg, 31.64%) as a yellow solid.

LCMS (ESI) m/z: $[M+H]^+$=173.

Step 4: 6-Chloropyrido[3,2-c]pyridazine-3-carbonitrile

To a stirred solution of $PPh_3$ (3047.23 mg, 11.618 mmol, 2 equiv) in 1,4-dioxane (100 mL) was added trichloroisocyanuric acid (904.51 mg, 3.892 mmol, 0.67 equiv) in portions. The resulting mixture was stirred for 23 h at room temperature. To the above mixture was added 6-hydroxypyrido[3,2-c]pyridazine-3-carbonitrile (1000.00 mg, 5.809 mmol, 1.00 equiv) in portions. The resulting mixture was stirred for additional 4 h at 108° C. The resulting mixture was concentrated under reduced pressure. The residue was purified by silica gel column chromatography, elution gradient 0 to 100% PE in EtOAc to give the title compound (581 mg, 52.48%) as a yellow solid.

LCMS (ESI) m/z: $[M+H]^+$=191.

Step 5: tert-Butyl ((6-chloropyrido[3,2-c]pyridazin-3-yl)methyl)carbamate and tert-butyl ((6-chloro-1,2-dihydropyrido[3,2-c]pyridazin-3-yl)methyl)carbamate To a stirred solution of 6-chloropyrido[3,2-c]pyridazine-3-carbonitrile (300.00 mg, 1.574 mmol, 1.00 equiv) in THE (8 mL) was added a 2.5 M solution of $LiAlH_4$ (1.9 mL, 4.722 mmol, 3.00 equiv) in THE dropwise at 0° C. The resulting mixture was stirred for 30 min at 0° C. The reaction was quenched by the addition of sat. $NaHCO_3$ (aq.) (10 mL) at 0° C. To the above mixture was added $Boc_2O$ (1030.60 mg, 4.722 mmol, 3.00 equiv) dropwise at 0° C. The resulting mixture was stirred for additional 1 h at room temperature. The mixture was concentrated under reduced pressure to give a mixture of the title compounds (231 mg, crude) that was used directly without further purification.

LCMS (ESI) m/z: $[M+H]^+$=295.

Step 6: tert-Butyl ((6-chloropyrido[3,2-c]pyridazin-3-yl)methyl)carbamate

To a stirred solution of the mixture of tert-butyl ((6-chloropyrido[3,2-c]pyridazin-3-yl)methyl)carbamate and tert-butyl ((6-chloro-1,2-dihydropyrido[3,2-c]pyridazin-3-yl)methyl)carbamate (231 mg, crude) in DCM (8 mL) was added DDQ (714.64 mg, 3.148 mmol, 2.00 equiv) in portions. The resulting mixture was stirred for 2 h at room temperature. The resulting mixture was filtered and the filter cake was washed with DCM (5 mL×3). The filtrate was concentrated under reduced pressure. The residue was purified by prep-HPLC to give the title compound (112 mg, 24.14%) as a brown solid.

LCMS (ESI) m/z: $[M+H]^+$=295.

Intermediate 70: tert-Butyl ((5-methyl-5,6,7,8-tetrahydro-2,6-naphthyridin-3-yl)methyl)carbamate

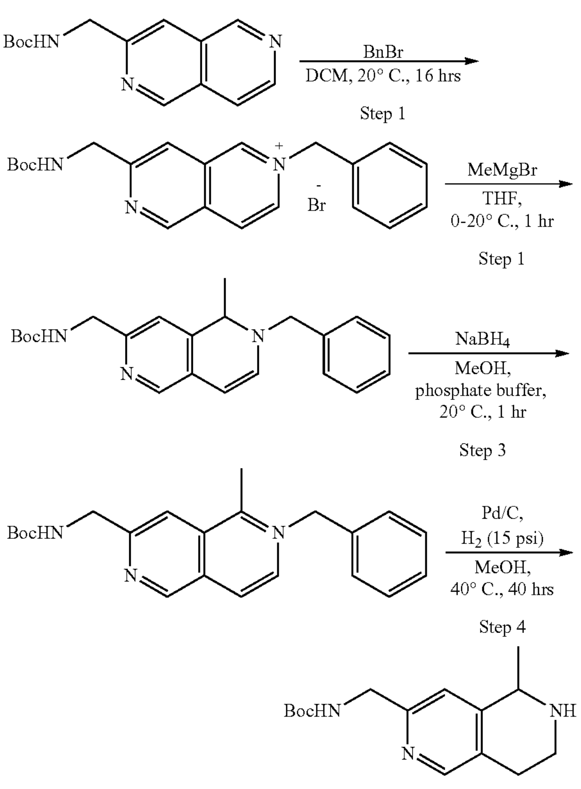

Intermediate 70

Step 1: 2-Benzyl-7-(((tert-butoxycarbonyl)amino)methyl)-2,6-naphthyridin-2-ium bromide To a solution of tert-butyl ((2,6-naphthyridin-3-yl)methyl)carbamate (3.6 g, 13.88 mmol) in DCM (10 mL) was added (bromomethyl)benzene (3.56 g, 20.83 mmol). The mixture was stirred at 30° C. for 16 hrs. The reaction mixture was concentrated and the residue was triturated in MTBE (50 mL) to give the title compound (4.5 g, crude) as a gray solid.

LCMS (ESI) m/z: $[M]^+$=350.3.

Step 2: tert-Butyl ((6-benzyl-5-methyl-5,6-dihydro-2,6-naphthyridin-3-yl)methyl)carbamate 2-Benzyl-7-(((tert-butoxycarbonyl)amino)methyl)-2,6-naphthyridin-2-ium bromide (2.0 g, 4.65 mmol) was added portionwise to a solution of MeMgBr (3 M, 9.30 mL) in THE (50 mL) at 0° C. under $N_2$. The mixture was stirred at 20° C. for 1 hr. The reaction was quenched by adding sat. $NH_4Cl$ (50 mL) and the products were extracted with ethyl acetate (50 mL*3). The combined organic layers were washed with brine (30 mL), dried over $Na_2SO_4$, filtered and concentrated to give the title compound (2 g, crude) as a yellow oil.

LCMS (ESI) m/z: $[M+H]^+$=366.3.

Step 3: tert-Butyl ((6-benzyl-5-methyl-5,6,7,8-tetrahydro-2,6-naphthyridin-3-yl)methyl)carbamate To a solution of tert-butyl ((6-benzyl-5-methyl-5,6-dihydro-2,6-naphthyridin-3-yl)methyl)carbamate (2 g, 5.47 mmol) in MeOH (20 mL) and phosphate buffer pH 7.0 (20 mL) was added $NaBH_4$ (828.09 mg, 21.89 mmol) at 0° C. The mixture was stirred at 20° C. for 1 hr. The reaction was quenched by adding 0.5N HCl (50 mL) and the products were extracted with ethyl acetate (50 mL*3). The combined organic layers were washed with brine (30 mL), dried over $Na_2SO_4$, filtered and concentrated. The residue was purified by column chromatography ($SiO_2$, Petroleum ether/Ethyl acetate=10/1 to 0/1) to give the title compound (1.3 g, crude) as a yellow oil.

LCMS (ESI) m/z: $[M+H]^+$=368.2.

Step 4: tert-Butyl ((5-methyl-5,6,7,8-tetrahydro-2,6-naphthyridin-3-yl)methyl)carbamate A mixture of tert-butyl ((6-benzyl-5-methyl-5,6,7,8-tetrahydro-2,6-naphthyridin-3-yl)methyl)carbamate (0.5 g, 1.36 mmol) and Pd/C (666.67 mg, 634.92 umol, 10% purity) in MeOH (15 mL) was degassed and purged with $H_2$ 3 times. The mixture was stirred at 40° C. for 40 hrs under $H_2$ atmosphere (15 psi). The reaction mixture was filtered and the filtrate was concentrated under vacuum to give the title compound (0.35 g, crude) as a yellow oil.

LCMS (ESI) m/z: $[M+H]^+$=278.3.

$^1$H NMR (400 MHz, DMSO-$d_6$) δ=8.10 (s, 1H), 7.40-7.22 (m, 1H), 7.01 (s, 1H), 4.18-4.12 (m, 2H), 3.93-3.82 (m, 1H), 3.20-3.15 (m, 1H), 3.13-3.04 (m, 1H), 2.82-2.74 (m, 1H), 2.70-2.65 (m, 1H), 2.59 (br s, 1H), 1.44-1.38 (m, 9H), 1.32-1.29 (m, 3H) ppm.

Intermediate 71: 2-((5,6,7,8-tetrahydropyrido[4,3-c]pyridazin-3-yl)methyl)isoindoline-1,3-dione hydrochloride

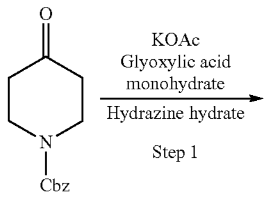

-continued

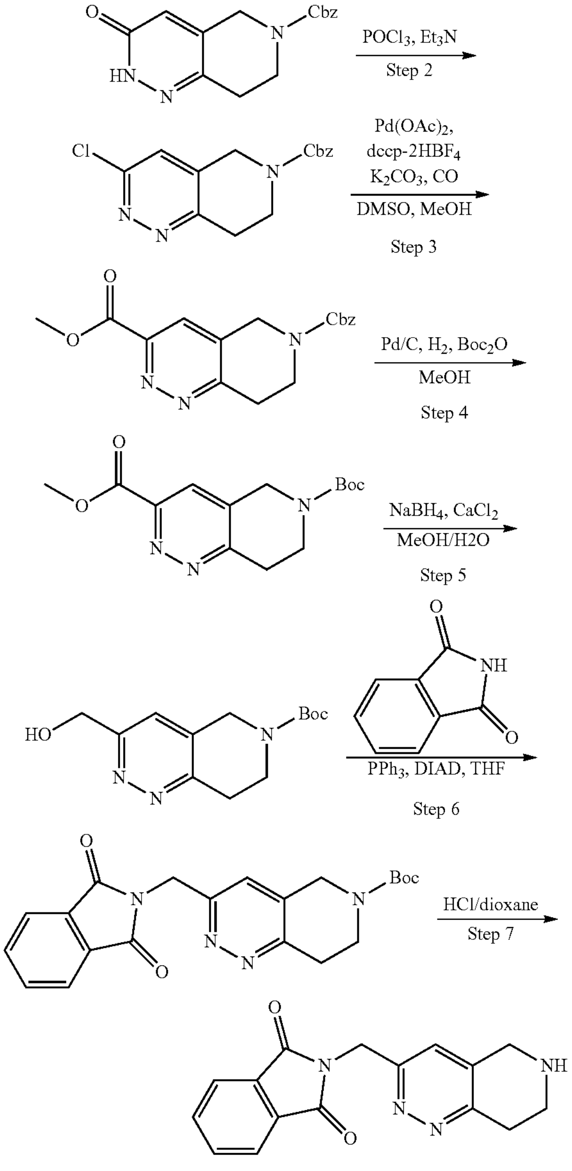

Intermediate 71

Step 1: Benzyl 3-oxo-3,5,7,8-tetrahydropyrido[4,3-c]pyridazine-6(2H)-carboxylate A mixture of benzyl 4-oxopiperidine-1-carboxylate (25 g, 107.18 mmol), KOAc (0.4 g, 4.08 mmol) and glyoxylic acid monohydrate (10 g, 135.07 mmol) was stirred at 90° C. for 12 hours. $N_2H_4 \cdot H_2O$ (5.67 g, 96.19 mmol, 5.5 mL) was then added dropwise to the mixture at 90° C. before stirring at 90° C. for an additional 0.5 hr. The mixture was diluted with MeOH (100 mL), cooled to 25° C. and filtered. The solid was washed with MeOH and dried to give the title compound (10 g, 35.05 mmol, 32.70% yield) as a white solid.

LCMS (ESI) m/z: $[M+H]^+$=286.0.

$^1$H NMR (400 MHz, DMSO-d6) δ=7.48-7.25 (m, 5H), 6.80 (s, 1H), 5.13 (s, 2H), 4.54 (br s, 2H), 3.67 (br s, 2H), 2.75-2.72 (m, 2H).

Step 2: Benzyl 3-chloro-7,8-dihydropyrido[4,3-c]pyridazine-6(5H)-carboxylate

To a mixture of benzyl 3-oxo-3,5,7,8-tetrahydropyrido[4,3-c]pyridazine-6(2H)-carboxylate (9 g, 31.55 mmol) in $POCl_3$ (38.61 g, 251.81 mmol, 23.40 mL) was added $Et_3N$ (65.43 mg, 646.61 umol) in one portion at 25° C. under $N_2$. The mixture was stirred at 80° C. 3 hours. The mixture was poured into water (2000 mL, 25° C.) and stirred for 5 min. Sat. $NaHCO_3$ was added to the mixture to adjust pH=7. The aqueous phase was extracted with EA (1000 mL*2). The combined organic phase was washed with brine (1000 mL), dried with anhydrous $Na_2SO_4$, filtered and concentrated under vacuum. The residue was purified by silica gel chromatography (Petroleum ether/Ethyl acetate=3/1) to give the title compound (7.7 g, 25.35 mmol, 80.36% yield) as a yellow oil.

LCMS (ESI) m/z: $[M+H]^+$=304.0.

$^1$H NMR (400 MHz, MeOD) δ=7.75-7.63 (m, 1H), 7.46-7.28 (m, 5H), 5.23-5.15 (m, 2H), 4.82-4.74 (m, 2H), 4.63-4.57 (m, 1H), 3.96-3.84 (m, 2H), 3.24-3.12 (m, 2H).

Step 3: 6-Benzyl 3-methyl 7,8-dihydropyrido[4,3-c]pyridazine-3,6(5H)-dicarboxylate To a solution of benzyl 3-chloro-7,8-dihydropyrido[4,3-c]pyridazine-6(5H)-carboxylate (7.5 g, 24.69 mmol) in DMSO (225 mL) was added $Pd(OAc)_2$ (277.18 mg, 1.23 mmol), $K_2CO_3$ (5.12 g, 37.04 mmol), 1,3-bis(dicyclohexylphosphino)propane bis(tetrafluoroborate) (1.51 g, 2.47 mmol) and MeOH (11.88 g, 370.69 mmol, 15.00 mL) under $N_2$ at 25° C. The suspension was degassed under vacuum and purged with CO several times. The mixture was stirred under CO (15 psi) at 100° C. for 1.5 hours. The combined mixture was poured into water (1500 mL) and extracted with ethyl acetate (500 mL*2). The combined organic phase was washed with brine (500 mL*2), dried with anhydrous $Na_2SO_4$, filtered and concentrated under vacuum. The residue was purified by silica gel chromatography (Petroleum ether/Ethyl acetate=1/2) to give the title compound (3.3 g, 9.92 mmol, 40.16% yield) as a yellow oil.

LCMS (ESI) m/z: $[M+H]^+$=327.9.

$^1$H NMR (400 MHz, DMSO-d6) δ=8.21-8.12 (m, 1H), 7.43-7.28 (m, 5H), 5.17-5.10 (m, 2H), 4.89-4.68 (m, 2H), 3.99-3.90 (m, 3H), 3.86-3.75 (m, 2H), 3.26-3.13 (m, 2H).

Step 4: 6-(tert-Butyl) 3-methyl 7,8-dihydropyrido[4,3-c]pyridazine-3,6(5H)-dicarboxylate To a solution of 6-benzyl 3-methyl 7,8-dihydropyrido[4,3-c]pyridazine-3,6(5H)-dicarboxylate (3.2 g, 9.78 mmol) in MeOH (65 mL) was added $Boc_2O$ (3.20 g, 14.66 mmol, 3.37 mL) and Pd/C (300 mg, 10% purity) under $N_2$. The suspension was degassed and purged with $H_2$ several times. The mixture was stirred under $H_2$ (15 psi) at 25° C. for 2 hours. The reaction mixture was filtered and the filtrate was concentrated to give the title compound (2.9 g, crude) as a light yellow oil, which was used directly in the next step.

LCMS (ESI) m/z: $[M+H]^+$=294.0.

$^1$H NMR (400 MHz, $CDCl_3$) δ=7.89-7.84 (m, 1H), 4.66-4.60 (m, 2H), 3.79-3.72 (m, 2H), 3.32-3.21 (m, 2H), 1.44-1.42 (m, 9H).

Step 5: tert-Butyl 3-(hydroxymethyl)-7,8-dihydropyrido[4,3-c]pyridazine-6(5H)-carboxylate To a mixture of 6-(tert-butyl) 3-methyl 7,8-dihydropyrido[4,3-c]pyridazine-3,6(5H)-dicarboxylate (2.8 g, 9.55 mmol) and $CaCl_2$ (4.24 g, 38.18 mmol) in MeOH (28 mL)/THF (14 mL) was added $NaBH_4$ (722.29 mg, 19.09 mmol) in one portion at 0° C. under $N_2$. The mixture was stirred at 25° C. for 1 hour. The mixture was poured into sat. $NH_4Cl$ (100 mL) and extracted with ethyl acetate (100 mL*2). The combined organic phase was washed with brine (100 mL*1), dried with anhydrous $Na_2SO_4$, filtered and concentrated under vacuum. The residue was purified by reverse phase column (FA). The eluent was concentrated to remove MeCN and the aqueous phase was extracted with ethyl acetate (50 mL*2). The combined organic phase was washed with brine (50 mL*1), dried with anhydrous $Na_2SO_4$, filtered and concentrated to give the title compound (1.3 g, 4.90 mmol, 51.33% yield) as a light yellow oil.

LCMS (ESI) m/z: $[M+H]^+$=266.0.

$^1$H NMR (400 MHz, MeOD) δ=7.68-7.60 (m, 1H), 4.85-4.84 (m, 2H), 4.75-4.66 (m, 2H), 3.85-3.77 (m, 2H), 3.21-3.08 (m, 2H), 2.03-1.99 (m, 2H), 1.51-1.49 (m, 9H).

Step 6: tert-butyl 3-((1,3-dioxoisoindolin-2-yl)methyl)-7,8-dihydropyrido[4,3-c]pyridazine-6(5H)-carboxylate To a mixture of tert-butyl 3-(hydroxymethyl)-7,8-dihydropyrido[4,3-c]pyridazine-6(5H)-carboxylate (1.15 g, 4.33 mmol), $PPh_3$ (1.71 g, 6.50 mmol) and isoindoline-1,3-dione (701.53 mg, 4.77 mmol) in THE (12 mL) was added DEAD (1.13 g, 6.50 mmol, 1.18 mL) dropwise at 0° C. under $N_2$. The mixture was stirred at 25° C. for 2 hours. The combined mixture was poured into water (50 mL) and extracted with ethyl acetate (30 mL*2). The combined organic phase was washed with brine (30 mL*1), dried with anhydrous $Na_2SO_4$, filtered and concentrated under vacuum. The residue was purified by silica gel chromatography (Petroleum ether/Ethyl acetate=1/1) to give the title compound (1.2 g, 3.04 mmol, 70.19% yield) as a yellow oil.

LCMS (ESI) m/z: $[M+H]^+$=395.0.

$^1$H NMR (400 MHz, $CDCl_3$) δ=7.85-7.75 (m, 2H), 7.71-7.65 (m, 2H), 7.13-7.08 (m, 1H), 5.14-5.08 (m, 2H), 4.56-4.48 (m, 2H), 3.75-3.64 (m, 2H), 3.17-3.07 (m, 2H), 1.43-1.39 (m, 9H).

Step 7: 2-((5,6,7,8-Tetrahydropyrido[4,3-c]pyridazin-3-yl)methyl)isoindoline-1,3-dione hydrochloride To a mixture of tert-butyl 3-((1,3-dioxoisoindolin-2-yl)methyl)-7,8-dihydropyrido[4,3-c]pyridazine-6(5H)-carboxylate (950 mg, 2.41 mmol) in dioxane (5 mL) was added HCl/dioxane (4 M, 5 mL) in one portion at 25° C. under $N_2$. The mixture was stirred at 25° C. for 30 min. The mixture was filtered and the solid was washed with MTBE (5 mL) to give the title compound (360 mg, 1.09 mmol, 45.19% yield) as a yellow solid.

LCMS (ESI) m/z: $[M+H]^+$=294.9.

$^1$H NMR (400 MHz, MeOD) δ=8.11-8.04 (m, 1H), 7.96-7.81 (m, 4H), 5.25 (s, 2H), 4.62 (s, 2H), 3.77-3.68 (m, 2H), 3.57-3.49 (m, 2H).

Intermediate 72: 2-Bromo-6-(1-((tert-butyldimethylsilyl)oxy)cyclopropyl)pyridine

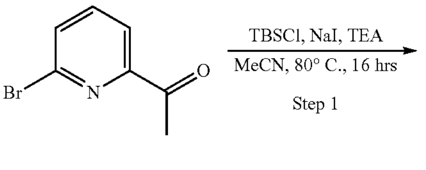

-continued

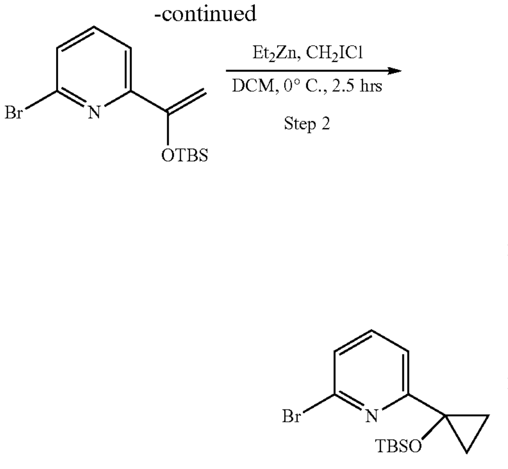

Intermediate 72

Step 1: 2-Bromo-6-(1-((tert-butyldimethylsilyl)oxy) vinyl)pyridine

To a solution of 1-(6-bromo-2-pyridyl)ethanone (5 g, 25.00 mmol), TBSCl (15.07 g, 99.98 mmol, 12.25 mL) and NaI (14.99 g, 99.98 mmol) in MeCN (100 mL) was added TEA (11.38 g, 112.48 mmol, 15.66 mL). The mixture was stirred at 80° C. for 16 hrs. The reaction mixture was poured into water (500 mL) and extracted with EA (500 mL*3). The combined organic layer was washed with brine (800 mL), dried over $Na_2SO_4$, filtered and concentrated. The residue was purified by flash silica gel chromatography (ISCO®; 40 g SepaFlash® Silica Flash Column, Eluent of 0-10% Ethyl acetate/Petroleum ether gradient) to give the title compound (7.5 g, 23.79 mmol, 95.16% yield) as a yellow oil.

LCMS (ESI) m/z: [81 BrM+H]+=316.1.

1H NMR (400 MHz, $CDCl_3$) δ=7.53 (s, 2H), 7.37-7.35 (m, 1H), 5.69 (d, J=1.2 Hz, 1H), 4.60 (d, J=1.2 Hz, 1H), 1.01 (s, 9H), 0.25 (s, 6H) ppm.

Step 2: 2-Bromo-6-(1-((tert-butyldimethylsilyl)oxy) cyclopropyl)pyridine

To a solution of diethylzinc (1 M, 38.18 mL) in DCM (180 mL) at 0° C. was added a solution of chloro(iodo) methane (13.47 g, 76.36 mmol, 5.54 mL) in DCM (60 mL) dropwise. The reaction mixture was stirred at 0° C. for 30 minutes. Then to the mixture was added a solution of 2-bromo-6-(1-((tert-butyldimethylsilyl)oxy)vinyl)pyridine (4 g, 12.73 mmol) in DCM (180 mL). The reaction mixture was stirred at 0° C. for 2 hrs. The reaction mixture was poured into aq. $NH_4Cl$ (200 mL) and extracted with DCM (100 mL*3). The combined organic layer was washed with brine (400 mL), dried over $Na_2SO_4$, filtered and concentrated. The residue was purified by flash silica gel chromatography (ISCO®; 120 g SepaFlash® Silica Flash Column, Eluent of 0-10% Ethyl acetate/Petroleum ether gradient) to give the title compound (700 mg, 2.13 mmol, 16.75% yield) as a colorless solid.

LCMS (ESI) m/z: [79BrM+H]+=328.1.

1H NMR (400 MHz, $CDCl_3$) δ=7.60-7.58 (m, 1H), 7.49-7.45 (m, 1H), 7.23-7.21 (m, 1H), 1.45-1.39 (m, 2H), 1.27-1.23 (m, 2H), 0.95 (s, 9H), 0.10 (s, 6H) ppm.

Intermediate 73: 6-Phenyl-2,7-naphthyridine-3-carbonitrile

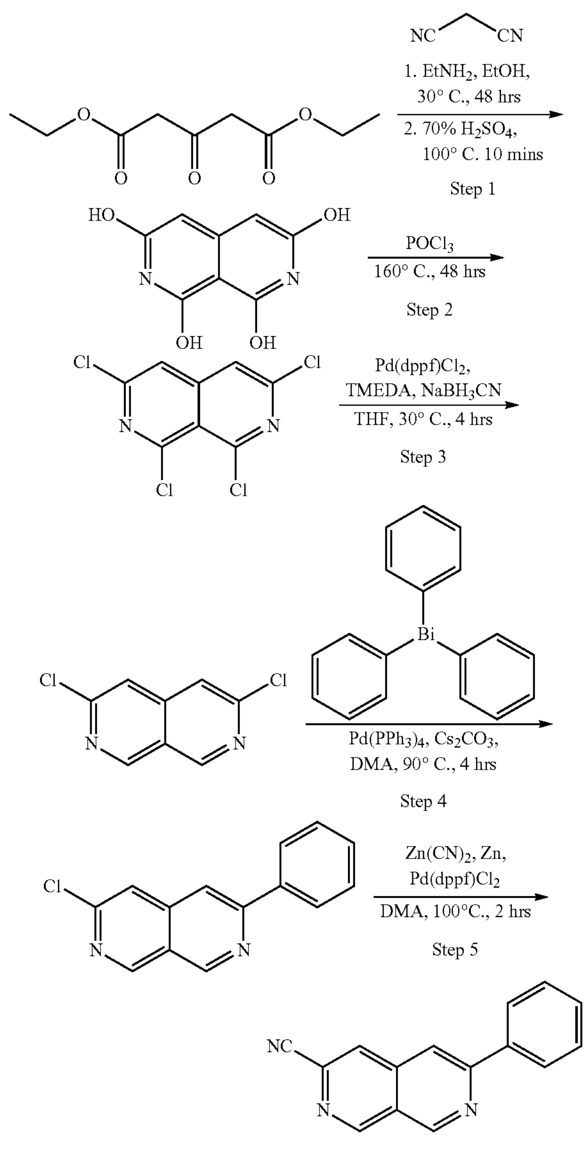

Intermediate 73

Step 1: 2,7-Naphthyridine-1,3,6,8-tetraol

To a solution of propanedinitrile (5.39 g, 81.60 mmol, 5.13 mL) in EtOH (70 mL) was added diethyl 3-oxopentanedioate (15 g, 74.18 mmol, 13.51 mL) and ethylamine (167.21 mg, 3.71 mmol, 242.68 uL). The mixture was stirred at 30° C. for 48 hrs. The reaction mixture was concentrated under reduced pressure. The residue was added to $H_2SO_4$ (70%, 20 mL) and stirred at 100° C. for 10 mins. The mixture was cooled to 20° C. and quenched by pouring slowly into ice water (180 mL), generating a yellow solid. The solid was collected and dried to give the title compound (14 g, 72.11 mmol, 97.21% yield).

LCMS (ESI) m/z: [M+H]+=195.0.

1 HNMR (400 MHz, DMSO-d6) δ=11.38 (s, 2H), 5.79 (s, 2H) ppm.

Step 2: 1,3,6,8-Tetrachloro-2,7-naphthyridine

A mixture of 2,7-naphthyridine-1,3,6,8-tetraol (5 g, 25.75 mmol) and $POCl_3$ (49.50 g, 322.83 mmol, 30.00 mL) was stirred at 160° C. for 48 hrs. The reaction mixture was quenched by addition of sat. $NaHCO_3$ (1000 mL) and extracted with ethyl acetate (300 mL*3). The combined organic phase was washed with brine (100 mL*3), dried over $Na_2SO_4$, filtered and concentrated under reduced pressure. The residue was purified by column chromatography ($SiO_2$, Petroleum ether/Ethyl acetate=10/1) to give the title compound (1.6 g, 5.97 mmol, 23.19% yield) as a yellow solid.

LCMS (ESI) m/z: [M+H]+=268.9.

1HNMR (400 MHz, $CDCl_3$) δ=7.58 (s, 2H) ppm.

Step 3: 3,6-Dichloro-2,7-naphthyridine

A mixture of 1,3,6,8-tetrachloro-2,7-naphthyridine (1 g, 3.73 mmol), $NaBH_3CN$ (1.17 g, 18.66 mmol), Pd(dppf)$Cl_2$ (273.10 mg, 373.24 umol) and TMEDA (1.08 g, 9.33 mmol, 1.41 mL) in THE (10 mL) was degassed and purged with $N_2$ 3 times. The mixture was stirred at 30° C. for 4 hrs under $N_2$ atmosphere. The reaction mixture was quenched by addition of water (30 mL), and extracted with ethyl acetate (30 mL*3). The combined organic phase was washed with brine (10 mL*3), dried over $Na_2SO_4$, filtered and concentrated under reduced pressure. The residue was purified by column chromatography ($SiO_2$, Petroleum ether/Ethyl acetate=5/1) to give the title compound (0.6 g, 2.83 mmol, 75.92% yield) as a yellow solid.

LCMS (ESI) m/z: [M+H]+=199.0.

1HNMR (400 MHz, $CDCl_3$) δ=9.30-9.20 (m, 2H), 7.68 (m, 2H) ppm.

Step 4: 3-Chloro-6-phenyl-2,7-naphthyridine

A mixture of 3,6-dichloro-2,7-naphthyridine (150 mg, 753.63 umol), triphenylbismuth (109.50 mg, 248.70 umol), $Cs_2CO_3$ (982.19 mg, 3.01 mmol) and $Pd(PPh_3)_4$ (87.09 mg, 75.36 umol) in DMA (5 mL) was degassed and purged with $N_2$ 3 times. The mixture was stirred at 90° C. for 4 hrs under $N_2$ atmosphere. The reaction was quenched by adding water (15 mL) and the mixture was extracted with ethyl acetate (20 mL*3). The combined organic layers were washed with brine (10 mL*3), dried over $Na_2SO_4$, filtered and concentrated under vacuum. The residue was purified by column chromatography ($SiO_2$, Petroleum ether/Ethyl acetate=1/1) to give the title compound (160 mg, 664.76 umol, 88.21% yield) as a yellow solid.

LCMS (ESI) m/z: [M+H]+=241.1.

Step 5: 6-Phenyl-2,7-naphthyridine-3-carbonitrile

A mixture of 3-chloro-6-phenyl-2,7-naphthyridine (50 mg, 207.74 umol), Pd(dppf)$Cl_2$ (15.20 mg, 20.77 umol), Zn (2.72 mg, 41.55 umol) and $Zn(CN)_2$ (48.79 mg, 415.48 umol, 26.37 uL) in DMA (3 mL) was degassed and purged with $N_2$ for 3 times. The mixture was stirred at 100° C. for 2 hrs under $N_2$ atmosphere. The reaction mixture was quenched by addition of water (10 mL), and extracted with ethyl acetate (10 mL*3). The combined organic phase was washed with brine (10 mL), dried over $Na_2SO_4$, filtered and concentrated under reduced pressure. The residue was purified by prep-TLC ($SiO_2$, Petroleum ether/Ethyl acetate=1/1) to give the title compound (35 mg, 148.32 umol, 71.40% yield) as a yellow oil.

LCMS (ESI) m/z: [M+H]+=232.1.

1HNMR (400 MHz, CDC13) δ=9.61 (s, 1H), 9.46 (s, 1H), 8.22-8.17 (m, 3H), 8.12 (s, 1H), 7.60-7.49 (m, 3H) ppm.

Example 2. Methyl (R)-3-((2-((4-cyano-4-methylchromane-6-carboxamido)methyl)pyridin-4-yl)ethynyl)benzoate

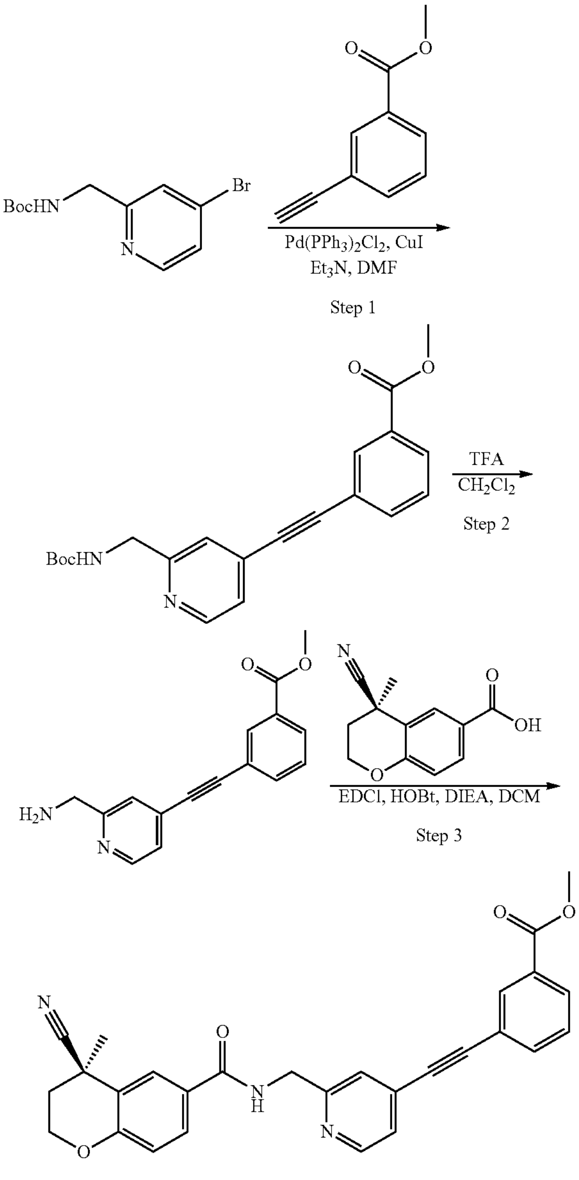

Step 1. Methyl 3-[2-[2-[(tert-butoxycarbonylamino)methyl]-4-pyridyl]ethynyl]benzoate $Pd(PPh_3)_2Cl_2$ (73.3 mg, 0.10 mmol) and methyl 3-ethynylbenzoate (669 mg, 4.18 mmol) were added to a solution of tert-butyl N-[(4-bromo-2-pyridyl)methyl]carbamate (300 mg, 1.04 mmol), CuI (19.9 mg, 0.10 mmol), and $Et_3N$ (0.44 mL, 3.13 mmol) in DMF (3 mL). The mixture was stirred at 100° C. for 1 hr. The mixture was filtered. The filtered liquid was diluted with water (20 mL) and extracted with EA (20 mL×2). The combined organic layer was dried with anhydrous $Na_2SO_4$ and concentrated to afford a residue. The residue was purified by column chromatography ($SiO_2$, Petroleum ether/Ethyl acetate=1/0 to 0/1). The eluent was concentrated to give the title compound (300 mg, 0.54 mmol) as colorless oil.

LCMS (ESI) m/z: [M+H]+=367.1.

Step 2. Methyl 3-[2-[2-(aminomethyl)-4-pyridyl] ethynyl]benzoate

TFA (0.24 mL, 3.28 mmol) was added to a solution of methyl 3-[2-[2-[(tert-butoxycarbonylamino)methyl]-4-pyridyl]ethynyl]benzoate (120 mg, 0.33 mmol) in DCM (1 mL). The mixture was stirred at 25° C. for 1 hr. The mixture was diluted with water (3 mL) and extracted with DCM (3 mL×2). The combined organic layer was discarded. The aqueous layer was adjusted to pH=10 with saturated $NaHCO_3$ solution and extracted with DCM (3 mL×2). The combined organic layer was dried with anhydrous $Na_2SO_4$ and concentrated affording the title compound (40 mg, 0.14 mmol) as a white solid which was used into the next step without further purification.

LCMS (ESI) m/z: [M+H]+=267.1.

Step 3. Methyl 3-[2-[2-[[[(4R)-4-cyano-4-methyl-chromane-6-carbonyl]amino]methyl]-4-pyridyl]ethynyl]benzoate HOBt (30.4 mg, 0.23 mmol), EDCI (43.2 mg, 0.23 mmol), and DIPEA (0.078 mL, 0.45 mmol) were added to a solution of methyl 3-[2-[2-(aminomethyl)-4-pyridyl]ethynyl]benzoate (40 mg, 0.15 mmol) and (4R)-4-cyano-4-methyl-chromane-6-carboxylic acid (35.9 mg, 0.17 mmol) in DCM (0.5 mL). The mixture was stirred at 25° C. for 1 hr. The reaction mixture was diluted with water (10 mL) and extracted with DCM (10 mL×2). The combined organic layers were dried with anhydrous $Na_2SO_4$ and concentrated to afford a residue. The residue was purified by prep-HPLC (FA condition) (column: 3_Phenomenex Luna C18 75*30 mm*3 um; mobile phase: [water (0.225% FA)-ACN]; B %: 45%-75%, 7 min). The eluent was lyophilized to afford the title compound (23.5 mg, 0.051 mmol) as a white solid.

LCMS (ESI) m/z: [M+H]+=466.2.

$^1$H NMR (400 MHz, DMSO-d6) δ=9.15-9.12 (m, 1H), 8.60-8.58 (m, 1H), 8.12 (d, J=2.0 Hz, 2H), 8.03-8.01 (m, 1H), 7.89-7.86 (m, 2H), 7.63-7.59 (m, 1H), 7.47-7.44 (m, 2H), 6.95 (d, J=8.4 Hz, 1H), 4.60 (d, J=4.4 Hz, 2H), 4.35-4.33 (m, 2H), 3.87 (s, 3H), 2.47-2.41 (m, 1H), 2.23-2.21 (m, 1H), 1.79 (s, 3H) ppm.

The following examples in Table 4 were prepared using standard chemical manipulations and procedures similar to those used for the preparation of Example 2.

TABLE 4

Compounds of the Invention

| # | LCMS (m/z) | 1H NMR |
|---|---|---|
| 1 | 408.1 | 1H NMR (400 MHz, DMSO-d6) δ = 9.28-9.24 (m, 1H), 8.59-8.57 (m, 1H), 8.15 (d, J = 1.6 Hz, 1H), 7.91-7.88 (m, 1H), 7.65-7.56 (m, 2H), 7.52-7.40 (m, 5H), 7.28 (d, J = 8.0 Hz, 1H), 4.95-4.77 (m, 2H), 4.61 (d, J = 4.4 Hz, 2H), 4.21 (d, J = 11.6 Hz, 1H), 3.86 (d, J = 11.6 Hz, 1H), 1.69 (s, 3H) ppm. |
| 2 | 438.0 | 1H NMR (400 MHz, DMSO-d6) δ = 9.33-9.21 (m, 1H), 8.58 (d, J = 4.8 Hz, 1H), 8.15 (d, J = 1.6 Hz, 1H), 7.95-7.85 (m, 1H), 7.47-7.40 (m, 2H), 7.38-7.32 (m, 1H), 7.28 (d, J = 8.0 Hz, 1H), 7.20-7.13 (m, 2H), 7.07-7.01 (m, 1H), 4.93-4.79 (m, 2H), 4.66-4.57 (m, 2H), 4.21 (d, J = 11.2 Hz, 1H), 3.86 (d, J = 11.6 Hz, 1H), 3.78 (s, 3H), 1.69 (s, 3H) ppm. |
| 3 | 466.1 | 1H NMR (400 MHz, DMSO-d6) δ = 9.35-9.21 (m, 1H), 8.60 (d, J = 4.4 Hz, 1H), 8.21-8.10 (m, 2H), 8.06-7.98 (m, 1H), 7.95-7.81 (m, 2H), 7.66-7.58 (m, 1H), 7.52-7.45 (m, 2H), 7.29 (d, J = 8.0 Hz, 1H), 4.95-4.78 (m, 2H), 4.62 (d, J = 5.6 Hz, 2H), 4.21 (d, J = 11.6 Hz, 1H), 3.90-3.82 (m, 4H), 1.69 (s, 3H). ppm. |
| 5 | 473.2 | 1H NMR (400 MHz, DMSO-d6) δ = 9.25-9.23 (m, 1H), 8.51-8.49 (m, 1H), 8.14-8.13 (m, 1H), 7.90-7.88 (m, 1H), 7.32-7.20 (m, 3H), 4.94-4.77 (m, 2H), 4.58-4.56 (m, 2H), 4.22-4.20 (m, 1H), 3.88-3.84 (m, 1H), 3.75-3.62 (m, 1H), 3.54 (s, 3H), 3.48-3.41 (m, 1H), 3.29 (s, 2H), 2.84-2.74 (m, 1H), 1.98-1.85 (m, 1H), 1.68 (s, 3H), 1.67-1.56 (m, 2H), 1.48-1.34 (m, 1H) ppm |
| 13 | 412.9 | 1H NMR (400 MHz, DMSO-d6) δ = 9.22-9.19 (m, 1H), 8.58 (d, J = 4.8 Hz, 1H), 7.93 (m, 1H), 7.77 (s, 1H), 7.61-7.59 (m, 2H), 7.55-7.54 (m, 1H), 7.48-7.42 (m, 6H), 6.67-6.39 (m, 1H), 4.95-4.90 (m, 4H), 4.61 (m, 2H) ppm. |
| 14 | 401.2 | 1H NMR (400 MHz, DMSO-d6) δ = 9.26-9.24 (m, 1H), 8.58 (d, J = 4.8 Hz, 1H), 8.22 (s, 1H), 7.93 (m, 1H), 7.60-7.59 (m, 2H), 7.45-7.42 (m, 5H), 7.29 (m, 1H), 4.86-4.82 (m, 1H), 4.74-4.73 (m, 1H), 4.62-4.59 (m, 2H), 4.06-4.03 (m, 1H), 3.87-3.76 (m, 1H), 1.70-1.65 (m, 3H) ppm. |
| 15 | 422.3 | 1H NMR (400 MHz, MeOD-d4) δ = 9.24 (m, 1H), 8.50 (s, 1H), 8.14 (d, J = 1.2 Hz, 1H), 7.89 (m, 1H), 7.64-7.57 (m, 2H), 7.53-7.43 (m, 3H), 7.39 (s, 1H), 7.28 (d, J = 8.0 Hz, 1H), 4.92-4.79 (m, 2H), 4.57 (m, 2H), 4.21 (d, J = 11.6 Hz, 1H), 3.85 (d, J = 11.6 Hz, 1H), 2.43 (s, 3H), 1.77-1.61 (m, 3H) ppm. |
| 16 | 426.3 | 1H NMR (400 MHz, MeOD-d4) δ = 8.41-8.25 (m, 1H), 8.16-8.03 (m, 1H), 7.92-7.79 (m, 1H), 7.65-7.55 (m, 2H), 7.54-7.37 (m, 4H), 7.31-7.18 (m, 1H), 4.96-4.89 (m, 2H), 4.84-4.77 (m, 2H), 4.29-4.12 (m, 1H), 4.03-3.83 (m, 1H), 1.75 (s, 3H) ppm. |
| 17 | 458.1 | 1H NMR (400 MHz, DMSO-d6) δ = 9.29-9.27 (m, 1H), 8.60 (d, J = 4.8 Hz, 1H), 8.15 (d, J = 1.2 Hz, 1H), 7.91-7.89 (m, 1H), 7.80-7.78 (m, 2H), 7.65-7.64 (m, 1H), 7.63-7.56 (m, 1H), 7.47-7.45 (m, 2H), 7.29 (d, J = 8.0 Hz, 1H), 7.27-6.91 (m, 1H), 4.91-4.84 (m, 2H), 4.62 (m, 2H), 4.22 (d, J = 11.2 Hz, 1H), 3.87 (d, J = 11.2 Hz, 1H), 1.68 (s, 3H) ppm. |

TABLE 4-continued

| Compounds of the Invention | | |
|---|---|---|
| # | LCMS (m/z) | 1H NMR |
| 20 | 426.3 | 1H NMR (400 MHz, MeOD-d4) δ = 8.48 (d, J = 1.2 Hz, 1H), 8.12 (d, J = 1.6 Hz, 1H), 7.87 (m, 1H), 7.61-7.53 (m, 3H), 7.49-7.38 (m, 3H), 7.26 (d, J = 8.0 Hz, 1H), 4.90 (d, J = 3.6 Hz, 2H), 4.69 (s, 2H), 4.19 (d, J = 11.6 Hz, 1H), 3.92 (d, J = 11.6 Hz, 1H), 1.75 (s, 3H) ppm. |
| 21 | 473.3 | 1H NMR (400 MHz, MeOD-d4) δ = 8.45 (d, J = 5.6 Hz, 1H), 8.11 (d, J = 1.6 Hz, 1H), 7.90-7.83 (m, 1H), 7.37 (s, 1H), 7.30-7.23 (m, 2H), 4.90 (d, J = 3.6 Hz, 2H), 4.67 (s, 2H), 4.20 (d, J = 11.2 Hz, 1H), 3.92 (d, J = 11.6 Hz, 1H), 3.83-3.76 (m, 2H), 3.68 (s, 3H), 3.30-3.19 (m, 2H), 2.96-2.84 (m, 1H), 1.96-1.83 (m, 2H), 1.75 (s, 3H), 1.69-1.58 (m, 2H) ppm. |
| 22 | 459.2 | 1H NMR (400 MHz, DMSO-d6) δ = 9.23-9.20 (m, 1H), 8.50 (d, J = 5.2 Hz, 1H), 8.13 (d, J = 1.6 Hz, 1H), 7.89-7.87 (m, 1H), .32-7.24 (m, 3H), 4.95-4.78 (m, 2H), 4.57 (d, J = 4.8 Hz, 2H), 4.21 (d, J = 11.2 Hz, 1H), 3.86 (d, J = 11.6 Hz, 1H), 3.66-3.60 (m, 1H), 3.58 (s, 3H), 3.45-3.40 (m, 1H), 3.35 (s, 1H), 3.30-3.25 (m, 2H), 2.22-2.17 (m, 1H), 2.06-1.86 (m, 1H), 1.68 s, 3H) ppm. |
| 23 | 457.2 | 1H NMR (400 MHz, MeOD-d4) δ = 8.57 (d, J = 5.2 Hz, 1H), 8.19 (d, J = 1.6 Hz, 2H), 8.08-8.05 (m, 1H), 7.83-7.74 (m, 2H), 7.62-7.59 (m, 1H), 7.57-7.50 (m, 2H), 7.17 (d, J = 8.0 Hz, 1H), 4.82 (d, J = 3.2 Hz, 2H), 4.74 (s, 2H), 3.93 (s, 3H), 3.81-3.72 (m, 2H), 1.55 (s, 3H) ppm. |
| 37 | 452.2 | 1H NMR (400 MHz, DMSO-d6) δ = 9.11-9.08 (m, 1H), 8.59 (d, J = 4.8 Hz, 1H), 8.12 (d, J = 2.0 Hz, 2H), 8.03-8.01 (m, 1H), 7.95-9.92 (m, 1H), 7.89-7.87 (m, 1H), 7.63-7.59 (m, 1H), 7.48-7.46 (m, 2H), 7.05 (d, J = 8.8 Hz, 1H), 5.01 (d, J = 9.6 Hz, 1H), 4.60 (d, J = 6.0 Hz, 2H), 4.55 (d, J = 9.6 Hz, 1H), 3.87 (s, 3H), 1.76 (s, 3H) ppm |
| 39 | 465.3 | 1H NMR (400 MHz, DMSO + D2O) δ = 8.89-8.88 (m, 1H), 8.52 (d, J = 5.2 Hz, 1H), 8.06 (s, 1H), 7.99 (d, J = 8.4 Hz, 1H), 7.82-7.80 (m, 2H), 7.58-7.55 (m, 2H), 7.423(d, J = 5.2 Hz, 1H), 7.36 (s, 1H), 6.57 (d, J = 8.8 Hz, 1H), 4.51 (brs, 2H), 3.82 (s, 3H), 3.31-3.28 (m, 2H), 2.18-2.12 (m, 1H), 1.95-1.90 (m, 1H), 1.66 (s, 3H) ppm |
| 43 | 452.2 | 1H NMR (400 MHz, DMSO-d6) δ = 9.00 (d, J = 8.0 Hz, 1H), 8.62 (d, J = 5.2 Hz, 1H), 8.17 (d, J = 1.6 Hz, 1H), 7.93-7.91 (m, 1H), 7.63-7.60 (m, 3H), 7.49-7.44 (m, 4H), 7.28 (d, J = 8.0 Hz, 1H), 5.44-5.38 (m, 1H), 4.92-4.81 (m, 2H), 4.22 (d, J = 11.6 Hz, 1H), 3.88-3.81 (m, 3H), 3.31 (s, 3H), 1.70 (s, 3H) ppm |
| 47 | 437.2 | 1H NMR (400 MHz, MeOD-d4) δ = 8.52 (d, J = 5.2 Hz, 1H), 8.21 (s, 1H), 8.02-7.94 (m, 1H), 7.60-7.48 (m, 3H), 7.45-7.33 (m, 5H), 6.54-6.21 (m, 1H), 4.84-4.78 (m, 2H), 4.71 (s, 2H), 4.34-4.26 (m, 1H), 4.15-4.04 (m, 1H) ppm |
| 48 | 437.2 | 1H NMR (400 MHz, MeOD-d4) δ = 8.52 (d, J = 5.2 Hz, 1H), 8.21 (s, 1H), 7.98 (d, J = 8.4 Hz, 1H), 7.59-7.47 (m, 3H), 7.45-7.33 (m, 5H), 6.54-6.21 (m, 1H), 4.80 (s, 2H), 4.71 (s, 2H), 4.34-4.27 (m, 1H), 4.14-4.04 (m, 1H) ppm |

Example 3. (4R)-4-Cyano-4-methyl-N-[[4-(2-phenyl-2,7-diazaspiro[3.4]octan-7-yl)-2-pyridyl]methyl]isochromane-6-carboxamide

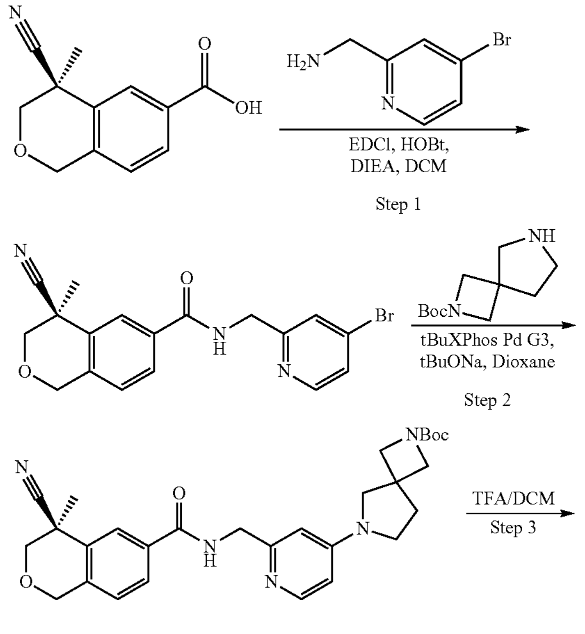

-continued

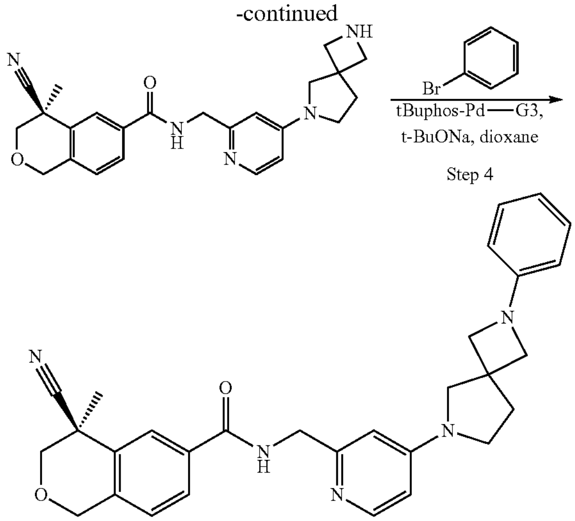

Step 1. (4R)—N-[(4-Bromo-2-pyridyl)methyl]-4-cyano-4-methyl-isochromane-6-carboxamide EDCI (1.54 g, 8.02 mmol), HOBt (1.08 g, 8.02 mmol), DIEA (4.66 mL, 26.7 mmol), and (4-bromo-2-pyridyl)methanamine (1 g, 5.35 mmol, HCl) were added to a solution of (4R)-4-cyano-4-methyl-isochromane-6-carboxylic acid (1.28 g, 5.88 mmol) in DCM (10 mL). The reaction mixture was stirred at 25° C. for 2 hrs. The mixture was diluted with $H_2O$ (40 mL), and then extracted with DCM (40 mL×2). The combined organic layer was dried over anhydrous $Na_2SO_4$, filtered, and concentrated under reduced pressure to afford a residue. The residue was purified by flash silica gel chromatography $SiO_2$, Petroleum ether/Ethyl Acetate=1/0 to 1/10) affording the title compound (1.2 g, 3.10 mmol) as white a solid.

LCMS (ESI) m/z: [81 BrM+H]+=388.0.

$^1$HNMR (400 MHz, $CDCl_3$) δ=8.39 (d, J=5.6 Hz, 1H), 8.01 (d, J=1.6 Hz, 1H), 7.78-7.76 (m, 1H), 7.56-7.49 (m, 2H), 7.42-7.40 (m, 1H), 7.13 (d, J=8.0 Hz, 1H), 4.87 (s, 2H), 4.74 (d, J=5.2 Hz, 2H), 4.14-4.11 (m, 1H), 3.94 (d, J=11.2 Hz, 1H), 1.76 (s, 3H) ppm.

Step 2. tert-Butyl 7-[2-[[[(4R)-4-cyano-4-methyl-isochromane-6-carbonyl]amino]methyl]-4-pyridyl]-2,7-diazaspiro[3.4]octane-2-carboxylate

[2-(2-aminophenyl)phenyl]-methylsulfonyloxy-palladium; ditert-butyl-[2-(2,4,6-triisopropylphenyl)phenyl] phosphane (41.1 mg, 51.8 μmol) and tBuONa (149.3 mg, 1.55 mmol) were added to a solution of (4R)—N-[(4-bromo-2-pyridyl)methyl]-4-cyano-4-methyl-isochromane-6-carboxamide (200 mg, 0.52 mmol) and tert-butyl 2,7-diazaspiro [3.4]octane-2-carboxylate (220 mg, 1.04 mmol) in dioxane (4 mL). The mixture was stirred at 70° C. for 2 hrs. The reaction mixture was poured into water (80 mL) and extracted with EA (30 mL×3). The combined organic layer was washed with brine (30 mL), dried over anhydrous $Na_2SO_4$, filtered, and concentrated. The crude product was purified by reversed-phase HPLC (0.1% FA condition). The fractions containing product were combined and extracted with EA (20 mL×3). The combined organic layers were dried over anhydrous $Na_2SO_4$, filtered, and concentrated affording the title compound (80 mg, 0.11 mmol) as yellow oil.

LCMS (ESI) m/z: [M+H]+=518.2.

Step 3. (4R)-4-Cyano-N-[[4-(2,6-diazaspiro[3.4]octan-6-yl)-2-pyridyl]methyl]-4-methyl-isochromane-6-carboxamide TFA (0.5 mL) was added to a solution of tert-Butyl 7-[2-[[[(4R)-4-cyano-4-methyl-isochromane-6-carbonyl]amino]methyl]-4-pyridyl]-2,7-diazaspiro[3.4]octane-2-carboxylate (80 mg, 0.11 mmol) in DCM (1 mL). The mixture was stirred at 25° C. for 1 hr. The reaction mixture was concentrated in vacuo. The crude residue was triturated with a mixture of PE (2 mL) and MTBE (1 mL). The residue was filtered and dried in vacuo affording the title compound (70 mg, TFA) as a yellow oil which was used directly for next step.

LCMS (ESI) m/z: [M+H]+=418.2.

Step 4. (4R)-4-Cyano-4-methyl-N-[[4-(2-phenyl-2,7-diazaspiro[3.4]octan-7-yl)-2-pyridyl]methyl]isochromane-6-carboxamide A mixture of (4R)-4-cyano-N-[[4-(2,6-diazaspiro[3.4]octan-6-yl)-2-pyridyl]methyl]-4-methyl-isochromane-6-carboxamide (65 mg, 0.12 mmol, TFA), bromobenzene (57.6 mg, 0.37 mmol, 39 μL), [2-(2-aminophenyl)phenyl]-methylsulfonyloxy-palladium; ditert-butyl-[2-(2,4,6-triisopropylphenyl)phenyl]phosphane (9.7 mg, 12 μmol), and t-BuONa (58.8 mg, 0.61 mmol) in dioxane (1.5 mL) was degassed and purged with $N_2$ three times. The reaction mixture was then stirred at 70° C. for 3 hrs. The reaction mixture was then poured into water (80 mL) and extracted with EA (30 mL×3). The combined organic layers were washed with brine (30 mL), dried over $Na_2SO_4$, filtered, and concentrated. The residue was purified by prep-HPLC (column: Waters Xbridge C18 150*50 mm*10 um; mobile phase: [water (10 mM NH4HCO3)-ACN]; B %: 46%-66%, 10 min) and the fraction was lyophilized to give the title compound (3.62 mg, 7.13 μmol, 5.83% yield) as a white solid.

LCMS (ESI) m/z: [M+H]+=494.2.

$^1$HNMR (400 MHz, DMSO-d6) δ=9.17-9.07 (m, 1H), 8.12 (d, J=1.6 Hz, 1H), 8.07 (d, J=6.0 Hz, 1H), 7.91-7.83 (m, 1H), 7.26 (d, J=8.0 Hz, 1H), 7.20-7.12 (m, 2H), 6.72-6.64 (m, 1H), 6.52-6.39 (m, 4H), 4.92-4.78 (m, 2H), 4.52-4.42 (m, 2H), 4.20 (d, J=11.6 Hz, 1H), 3.85 (d, J=11.6 Hz, 1H), 3.77 (s, 4H), 3.54 (s, 2H), 3.40-3.35 (m, 2H), 2.27-2.18 (m, 2H), 1.67 (s, 3H) ppm.

The following examples in Table 5 were prepared using standard chemical manipulations and procedures similar to those used for the preparation of Example 3.

TABLE 5

Compounds of the Invention

| # | LCMS (m/z) | 1H NMR |
|---|---|---|
| 10 | 480.2 | 1H NMR (400 MHz, DMSO-d6) δ = 9.16-9.06 (m, 1H), 8.13-8.05 (m, 2H), 7.89-7.83 (m, 1H), 7.26 (d, J = 8.0 Hz, 1H), 7.20-7.12 (m, 2H), 6.71-6.64 (m, 1H), 6.42 (d, J = 7.8 Hz, 2H), 6.36-6.27 (m, 2H), 4.92-4.77 (m, 2H), 4.51-4.37 (m, 2H), 4.20 (d, J = 11.6 Hz, 1H), 4.09 (s, 4H), 3.96 (s, 4H), 3.84 (d, J = 11.6 Hz, 1H), 1.67 (s, 3H) ppm. |
| 12 | 494.3 | 1H NMR (400 MHz, MeOD-d4) δ = 9.11-9.08 (m, 1H), 8.12 (d, J = 1.6 Hz, 1H), 8.08 (d, J = 5.6 Hz, 1H), 7.87-7.85 (m, 1H), 7.26 (d, J = 8.0 Hz, 1H), 7.16-7.12 (m, 2H), 6.60-6.57 (m, 1H), 6.51 (d, J = 8.0 Hz, 2H), 6.32 (d, J = 2.0 Hz, 1H), 6.29-6.27 (m, 1H), 4.93-4.77 (m, 2H), 4.52-4.35 (m, 2H), 4.20 (d, J = 11.2 Hz, 1H), 3.94-3.81 (m, 4H), 3.45 (s, 2H), 3.30-3.27 (m, 2H), 2.23-2.20 (m, 2H), 1.67 (s, 3H) ppm. |
| 28 | 439.3 | 1H NMR (400 MHz, MeOD-d4) δ = 8.14-8.09 (m, 2H), 7.86-7.84 (m, 1H), 7.26 (d, J = 8.0 Hz, 1H), 7.23-7.16 (m, 4H), 6.88 (d, J = 2.4 Hz, 1H), 6.80-6.77 (m, 1H), 4.89 (d, J = 3.2 Hz, 2H), 4.60 (d, J = 2.4 Hz, 2H), 4.53 (s, 2H), 4.19 (d, J = 11.2 Hz, 1H), 3.92 (d, J = 11.2 Hz, 1H), 3.65-3.62 (m, 2H), 2.97-2.94 (m, 2H), 1.75 (s, 3H) ppm. |
| 31 | 425.2 | 1H NMR (400 MHz, DMSO-d6) δ = 9.16 (t, J = 5.6 Hz, 1H), 8.18-8.14 (m, 3H), 7.89-7.88 (m, 1H), 7.40-7.38 (m, 2H), 7.32-7.30 (m, 3H), 6.60 (d, J = 2.4 Hz, 1H), 6.54-6.53 (m, 1H), 4.91-4.84 (m, 2H), 4.67-4.64 (m, 4H), 4.53-4.48 (m, 2H), 4.22 (d, J = 11.2 Hz, 1H), 3.87 (d, J = 11.6 Hz, 1H), 1.69 (s, 3H) ppm |

TABLE 5-continued

Compounds of the Invention

| # | LCMS (m/z) | 1H NMR |
|---|---|---|
| 33 | 439.4 | 1H NMR (400 MHz, MeOD) δ = 8.11 (d, J = 1.6 Hz, 1H), 8.05 (d, J = 6.0 Hz, 1H), 7.87-7.84 (m, 1H), 7.42-7.32 (m, 4H), 7.30-7.22 (m, 2H), 6.59-6.43 (m, 2H), 4.67-4.55 (m, 4H), 4.54-4.49 (m, 2H), 4.18 (d, J = 11.6 Hz, 1H), 4.15-4.04 (m, 3H), 3.92 (d, J = 11.2 Hz, 1H), 1.74 (s, 3H) ppm |
| 42 | 468.4 | 1H NMR (400 MHz, DMSO-d6) δ = 9.12-9.08 (m, 1H), 8.18-8.12 (m, 2H), 7.89-7.86 (m, 1H), 7.30-7.19 (m, 3H), 6.97 (d, J = 8.0 Hz, 2H), 6.86 (d, J = 2.4 Hz, 1H), 6.83-6.77 (m, 2H), 4.95-4.79 (m, 2H), 4.57-4.40 (m, 2H), 4.21 (d, J = 11.6 Hz, 1H), 3.86 (d, J = 11.6 Hz, 1H), 3.47-3.43 (m, 4H), 3.26-3.23 (m, 4H), 1.69 (s, 3H) ppm |
| 44 | 453.3 | 1H NMR (400 MHz, DMSO-d6) δ = 9.10-9.07 (m, 1H), 8.12 (d, J = 1.2 Hz, 1H), 8.06 (d, J = 6.0 Hz, 1H), 7.87-7.84 (m, 1H), 7.33-7.31 (m, 4H), 7.26-7.22 (m, 2H), 6.50 (s, 1H), 6.46-6.44 (m, 1H), 4.90-4.83 (m, 2H), 4.46-4.44 (m, 2H), 4.20 (d, J = 11.6 Hz, 1H), 3.85 (d, J = 11.6 Hz, 1H), 3.74-3.72 (m, 1H), 3.53-3.46 (m, 4H), 2.38-2.34 (m, 1H), 2.10-2.08 (m, 1H), 1.66 (s, 3H) ppm |
| 46 | 440.2 | 1H NMR (400 MHz, MeOD) δ = 8.37 (d, J = 2.8 Hz, 1H), 8.10 (d, J = 1.6 Hz, 1H), 7.85-7.83 (m, 1H), 7.38-7.32 (m, 4H), 7.25-7.23 (m, 2H), 6.59 (d, J = 2.8 Hz, 1H), 4.87 (br s, 2H), 4.70 (s, 2H), 4.50-7.49 (m, 2H), 4.18 (d, J = 11.6 Hz, 1H), 4.15-4.06(m, 3H), 3.91 (d, J = 11.2 Hz, 1H), 1.72 (s, 3H) ppm |

Example 4. (4R)-4-Cyano-4-methyl-N-[[4-(1-phenylazetidin-3-yl)-2-pyridyl]methyl]isochromane-6-carboxamide

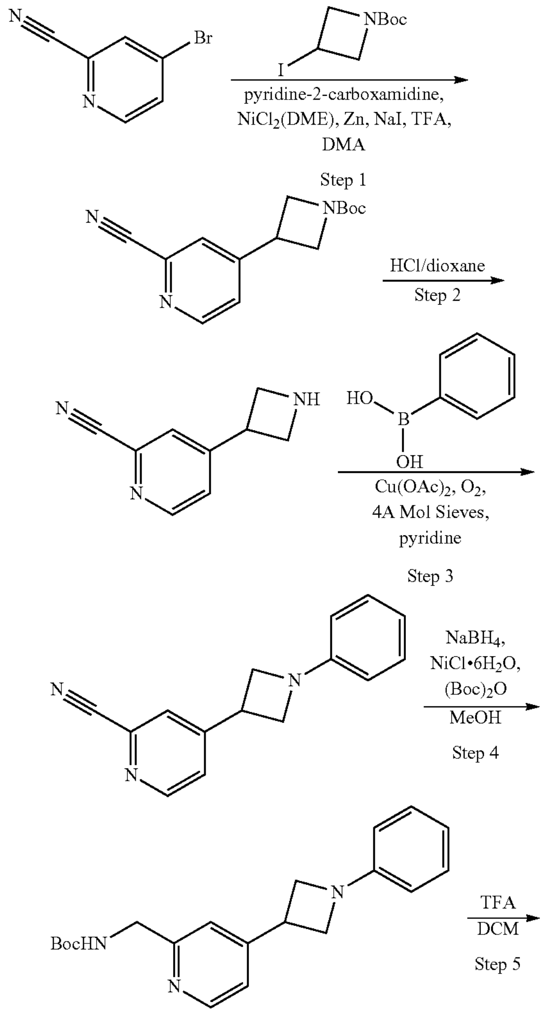

-continued

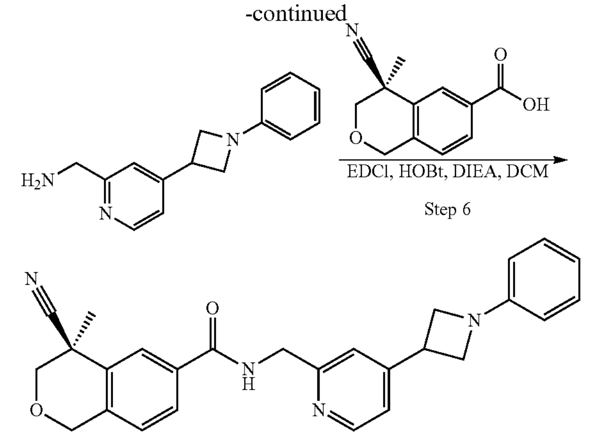

Step 1. tert-Butyl 3-(2-cyano-4-pyridyl)azetidine-1-carboxylate

A mixture of 4-bromopyridine-2-carbonitrile (4 g, 21.9 mmol), tert-butyl 3-iodoazetidine-1-carboxylate (7.43 g, 26.2 mmol), dichloronickel; 1,2-dimethoxyethane (480 mg, 2.19 mmol), pyridine-2-carboxamidine hydrochloride (344 mg, 2.19 mmol), NaI (1.64 g, 10.9 mmol), Zn (2.86 g, 43.7 mmol), and TFA (249 mg, 2.19 mmol, 162 μL) in DMA (80 mL) was degassed and purged with $N_2$ three times. The reaction mixture was stirred at 60° C. for 4 hrs. The mixture was filtered. The filtrate was diluted with water (500 mL) and extracted with EA (500 mL×2). The combined organic layers were dried with anhydrous $Na_2SO_4$ and concentrated to afford a crude residue. The residue was purified by column chromatography (SiO2, Petroleum ether/EA=1/0 to 0/1). The eluent was concentrated affording the title compound (3.8 g, 14.6 mmol) as yellow oil.

LCMS (ESI) m/z: [M+H]+=260.0.

$^1$H NMR (400 MHz, DMSO-d6) δ=8.70-7.68 (m, 1H), 8.08-8.07 (m, 1H), 7.72-7.70 (m, 1H), 4.24-4.23 (m, 2H), 3.93-3.90 (m, 3H), 1.40 (s, 9H) ppm.

Step 2. 4-(Azetidin-3-yl)pyridine-2-carbonitrile

A mixture of tert-butyl 3-(2-cyano-4-pyridyl)azetidine-1-carboxylate (2.0 g, 7.71 mmol) in HCl/dioxane (4N, 20 mL)

was stirred at 25° C. for 0.5 hrs. The mixture was concentrated affording the title compound (1.6 g, crude, HCl) as a white solid which was used into the next step without further purification.

LCMS (ESI) m/z: [M+H]+=160.0.

Step 3. 4-(1-Phenylazetidin-3-yl)pyridine-2-carbonitrile

To a solution of phenylboronic acid (3.0 g, 24.5 mmol) and 4-(azetidin-3-yl)pyridine-2-carbonitrile (1.6 g, 8.18 mmol, HCl) in pyridine (16 mL) was added copper (II) acetate (1.71 g, 9.40 mmol) and 4 A molecular sieves (1.6 g). The mixture was stirred at 80° C. for 12 hrs under oxygen atmosphere. The reaction mixture was diluted with water (100 mL) and extracted with EA (100 mL×2), the combined organic layer was dried with anhydrous $Na_2SO_4$ and concentrated to afford a residue. The residue was purified by column chromatography ($SiO_2$, Petroleum ether/Ethyl acetate=1/0 to 0/1). The eluent was concentrated affording the title compound (120 mg, 0.45 mmol) as a white solid.

LCMS (ESI) m/z: [M+H]+=236.0.

$^1$H NMR (400 MHz, DMSO-d6) δ=8.71 (d, J=4.8 Hz, 1H), 8.12-8.11 (m, 1H), 7.78-7.77 (m, 1H), 7.21-7.17 (m, 2H), 6.74-6.70 (m, 1H), 6.50 (d, J=7.6 Hz, 2H), 4.22-4.19 (m, 2H), 4.04-4.01 (m, 1H), 3.87-3.84 (m, 2H) ppm.

Step 4. tert-Butyl N-[[4-(1-phenylazetidin-3-yl)-2-pyridyl]methyl]carbamate

To a solution of 4-(1-phenylazetidin-3-yl)pyridine-2-carbonitrile (100 mg, 0.43 mmol) and $NiCl_2·6H_2O$ (253 mg, 1.06 mmol) in MeOH (2 mL) was added $NaBH_4$ (161 mg, 4.25 mmol) at 0° C. The mixture was stirred at 25° C. for 1 hr. $Boc_2O$ (1.39 g, 6.38 mmol) was added. Then the mixture was stirred at 25° C. for 2 hrs. THE (2 mL) and $NaHCO_3$ (2 mL) was added to the mixture. Then the mixture was stirred at 25° C. for 12 hrs. The mixture was diluted with saturated $NH_4Cl$ solution (30 mL) and extracted with EA (30 mL×2). The combined organic layers were dried with anhydrous $Na_2SO_4$ and concentrated to afford a residue. The residue was purified by flash silica gel chromatography (ISCO®; 12 g SepaFlash® Silica Flash Column, Eluent of 0-100% Ethylacetate/Petroleum ether gradient @40 mL/min). The eluent was concentrated affording the title compound (50 mg, 0.12 mmol) as a white solid.

LCMS (ESI) m/z: [M+H]+=340.3.

Step 5. [4-(1-Phenylazetidin-3-yl)-2-pyridyl]methanamine

TFA (168 mg, 1.47 mmol, 109 μL) was added to a solution of tert-Butyl N-[[4-(1-phenylazetidin-3-yl)-2-pyridyl]methyl]carbamate (50 mg, 0.15 mmol) in DCM (1 mL). The mixture was stirred at 25° C. for 1 hr. The reaction mixture was dried by $N_2$ airflow. The crude product was triturated with PE/MTBE=1:1 (3 mL) affording the title compound (30 mg, 0.085 mmol, TFA) as a yellow solid which was used into the next step without further purification.

LCMS (ESI) m/z: [M+H]+=240.0.

Step 6. (4R)-4-Cyano-4-methyl-N-[[4-(1-phenylazetidin-3-yl)-2-pyridyl]methyl]isochromane-6-carboxamide HOBt (17.2 mg, 0.13 mmol), EDCI (24.4 mg, 0.13 mmol), and DIPEA (32.9 mg, 0.25 mmol, 44 L) were added to a solution of [4-(1-phenylazetidin-3-yl)-2-pyridyl]methanamine (30 mg, 0.085 mmol, TFA salt) and (4R)-4-cyano-4-methylisochromane-6-carboxylic acid (20.3 mg, 0.093 mmol) in DCM (0.5 mL). The mixture was stirred at 25° C. for 1 hr. The reaction mixture was diluted with water (10 mL) and extracted with DCM (10 mL×2). The combined organic layers were dried with anhydrous $Na_2SO_4$ and concentrated to afford a crude residue. The residue was purified by prep-HPLC (neutral condition) (column: Waters Xbridge C18 150*50 mm*10 m; mobile phase: [water (10 mM $NH_4HCO_3$)-ACN]; B %: 36%-66%, 10 min) affording the title compound (12.8 mg, 0.030 mmol) as a yellow gum.

LCMS (ESI) m/z: [M+H]+=439.3.

$^1$HNMR (400 MHz, $CD_3OD$) δ=8.46 (d, J=5.2 Hz, 1H), 8.08 (d, J=1.6 Hz, 1H), 7.82-7.80 (m, 1H), 7.51 (s, 1H), 7.38-7.37 (m, 1H), 7.21-7.17 (m, 3H), 6.75-6.70 (m, 1H), 6.52-6.50 (m, 2H), 4.88 (s, 2H), 4.70 (s, 2H), 4.26-4.24 (m, 2H), 4.18 (d, J=11.2 Hz, 1H), 3.91-3.83 (m, 4H), 1.71 (s, 3H) ppm.

The following examples in Table 6 were prepared using standard chemical manipulations and procedures similar to those used for the preparation of Example 4.

TABLE 6

Compounds of the Invention

| # | LCMS (m/z) | 1H NMR |
|---|---|---|
| 18 | 438.3 | 1H NMR (400 MHz, DMSO-d6) δ = 9.23 (br s, 1H), 8.48 (d, J = 5.2 Hz, 1H), 8.16 (s, 1H), 7.90 (m, 1H), 7.39-7.24 (m, 7H), 7.23-7.21 (m, 1H), 4.86 (d, J = 12.0 Hz, 2H), 4.69-4.54 (m, 2H), 4.22 (d, J = 11.6 Hz, 1H), 3.86 (d, J = 11.6 Hz, 1H), 3.63-3.61 (m, 2H), 2.59-2.53 (m, 4H), 1.68 (s, 3H) ppm. |
| 19 | 438.3 | 1H NMR (400 MHz, DMSO-d6) δ = 9.23-9.20 (m, 1H), 8.44 (d, J = 5.2 Hz, 1H), 8.14 (d, J = 1.2 Hz, 1H), 7.91-7.89 (m, 1H), 7.31-7.24 (m, 6H), 7.23-7.17 (m, 2H), 4.93-4.79 (m, 2H), 4.59 (br d, J = 4.4 Hz, 2H), 4.22 (d, J = 11.6 Hz, 1H), 3.86 (d, J = 11.6 Hz, 1H), 3.57-3.45 (m, 2H), 2.77-2.67 (m, 2H), 2.20-2.08 (m, 2H), 1.67 (s, 3H) ppm. |

Example 5. (R,E)-4-Cyano-N-((4-(1,2-difluoro-2-phenylvinyl)pyridin-2-yl)methyl)-4-methylisochromane-6-carboxamide

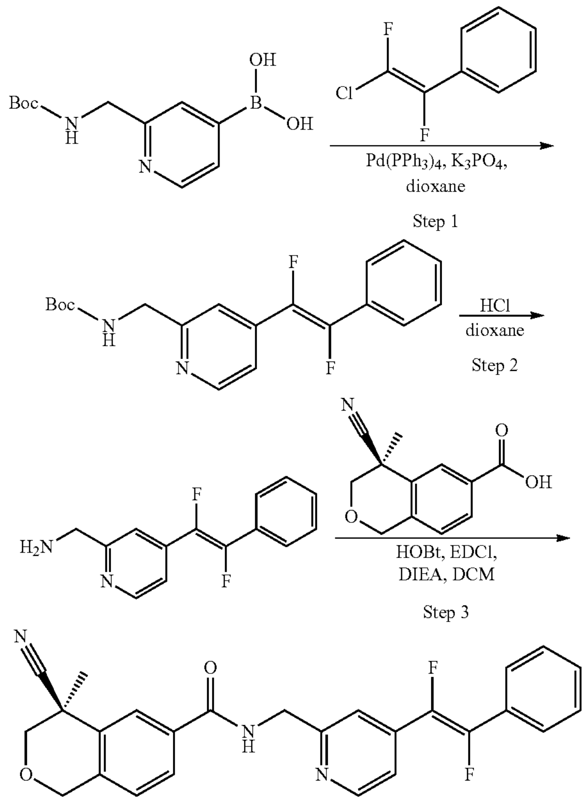

Step 1. tert-Butyl N-[[4-[(E)-1,2-difluoro-2-phenyl-vinyl]-2-pyridyl]methyl]carbamate $Pd(PPh_3)_4$ (53 mg, 0.046 mmol) and $K_3PO_4$ (292 mg, 1.37 mmol) were added to a mixture of (Z)-(2-chloro-1,2-difluorovinyl)benzene (80 mg, 0.46 mmol) and (2-(((tert-butoxycarbonyl)amino)methyl) pyridin-4-yl)boronic acid (173 mg, 0.69 mmol) in dioxane (3 mL) at 25° C. under $N_2$. The mixture was stirred at 100° C. for 2 hrs. The reaction mixture was poured into water (30 mL) and extracted with EA (30 mL×2). The combined organic phase was washed with brine (20 mL), dried with anhydrous $Na_2SO_4$, filtered, and concentrated in vacuum. The residue was purified by prep-TLC (Petroleum ether/EA=3/1) affording the title compound (60 mg, 0.14 mmol) as a light yellow solid.

LCMS (ESI) m/z: [M+H]+=347.2.

Step 2. [4-[(E)-1,2-difluoro-2-phenyl-vinyl]-2-pyridyl]methanamine

4N HCl/dioxane (0.22 mL) was added to a mixture of tert-butyl N-[[4-[(E)-1,2-difluoro-2-phenyl-vinyl]-2-pyridyl]methyl]carbamate (60 mg, 0.17 mmol) in dioxane (1 mL) at 25° C. The mixture was stirred for 30 minutes. The mixture was concentrated under reduced pressure affording the title compound (40 mg, 0.14 mmol, HCl salt) as a light yellow solid.

LCMS (ESI) m/z: [M+H]+=247.2.

Step 3. (4R)-4-Cyano-N-[[4-[(E)-1,2-difluoro-2-phenyl-vinyl]-2-pyridyl]methyl]-4-methyl-isochromane-carboxamide HOBt (28.7 mg, 0.21 mmol), EDCI (40.7 mg, 0.21 mmol), and DIEA (0.12 mL, 0.71 mmol) were added to a mixture of [4-[(E)-1,2-difluoro-2-phenyl-vinyl]-2-pyridyl] methanamine (40 mg, 0.14 mmol, HCl salt) and (4R)-4-cyano-4-methyl-isochromane-6-carboxylic acid (36.9 mg, 0.17 mmol) in DCM (2 mL) at 25° C. The mixture was stirred for 2 hrs. The mixture was poured into water (20 mL) and extracted with DCM (10 mL×2). The combined organic phase was washed with brine (10 mL), dried over anhydrous $Na_2SO_4$, filtered, and concentrated in vacuum. The residue was purified by reverse phase column chromatography. The eluent was lyophilized affording the title compound (22.3 mg, 0.050 mmol, FA salt) as a white solid.

LCMS (ESI) m/z: [M+H]+=446.3.

$^1H$ NMR (400 MHz, $CD_3OD$) δ=8.68-8.56 (m, 1H), 8.17-8.08 (m, 1H), 7.90-7.84 (m, 1H), 7.82-7.73 (m, 3H), 7.68-7.60 (m, 1H), 7.56-7.42 (m, 3H), 7.33-7.19 (m, 1H), 4.92-4.88 (m, 2H), 4.76 (s, 2H), 4.20-3.90 (m, 2H), 1.75 (s, 3H) ppm.

The following examples in Table 7 were prepared using standard chemical manipulations and procedures similar to those used for the preparation of Example 5.

TABLE 7

| Compounds of the Invention | | |
|---|---|---|
| # | LCMS (m/z) | 1H NMR |
| 27 | 428.1 | 1H NMR (400 MHz, DMSO-d6) δ = 9.28 (m, 1H), 8.62 (d, J = 5.2 Hz, 1H), 8.16 (d, J = 1.2 Hz, 1H), 7.91 (m, 1H), 7.70 (d, J = 7.5 Hz, 2H), 7.66-7.60 (m, 2H), 7.48-7.41 (m, 2H), 7.40-7.33 (m, 1H), 7.29 (d, J = 8.0 Hz, 1H), 7.19-6.99 (m, 1H), 4.95-4.79 (m, 2H), 4.65 (m, 2H), 4.22 (d, J = 11.6 Hz, 1H), 3.86 (d, J = 11.6 Hz, 1H), 1.69 (s, 3H) ppm. |
| 29 | 428.3 | 1H NMR (400 MHz, MeOD-d4) δ = 8.48 (d, J = 5.2 Hz, 1H), 8.14 (d, J = 1.6 Hz, 1H), 7.89-7.87 (m, 1H), 7.75-7.73 (m, 2H), 7.67 (s, 1H), 7.56-7.55 (m, 1H), 7.45-7.44 (m, 3H), 7.27 (d, J = 8.0 Hz, 1H), 6.66-6.55 (m, 1H), 4.90 (d, J = 4.0 Hz, 2H), 4.73 (s, 2H), 4.20 (d, J = 11.6 Hz, 1H), 3.92 (d, J = 11.2 Hz, 1H), 1.76 (s, 3H) ppm. |

Example 6. (4R)—N-[(4-Benzyloxy-2-pyridyl)methyl]-4-cyano-4-methyl-isochromane-6-carboxamide

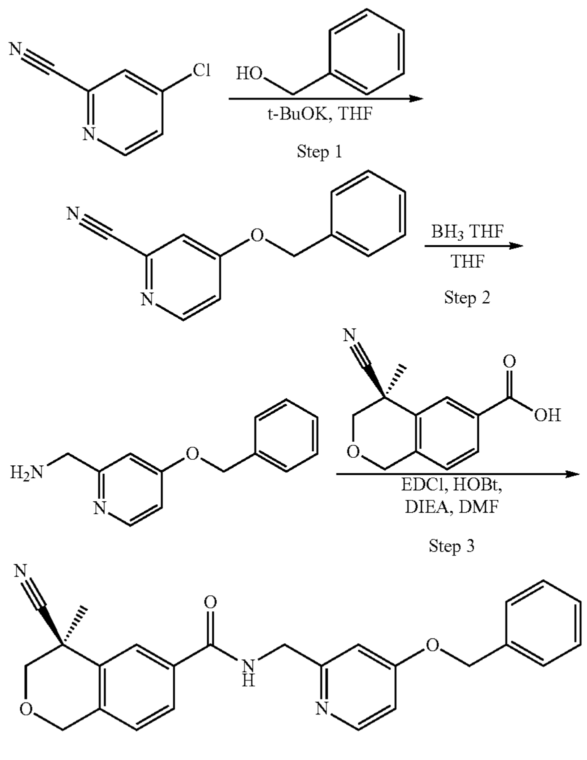

Step 1. 4-Benzyloxypyridine-2-carbonitrile t-BuOK (2.43 g, 21.65 mmol) was added to a solution of 4-chloropyridine-2-carbonitrile (1 g, 7.2 mmol) and phenylmethanol (0.90 mL, 8.7 mmol) in THE (10 mL) at 0° C. The mixture was warmed to 25° C. and stirred for 1 hr. The reaction mixture was poured into saturated $NH_4Cl$ (aq., 20 mL) and extracted with EA (7 mL×2). The organic layer was washed with brine (10 mL), dried over anhydrous $Na_2SO_4$, filtered, and concentrated. The crude product was purified by column chromatography ($SiO_2$, Petroleum ether/EA=10/1 to 1/1) affording the title compound (1.1 g, 4.24 mmol) as a yellow solid.

$^1H$ NMR (400 MHz, DMSO-d6) δ=8.63 (d, J=5.2 Hz, 1H), 8.45 (d, J=5.6 Hz, 1H), 8.04 (d, J=2.0 Hz, 1H), 7.78-7.76 (m, 1H), 7.64 (d, J=2.8 Hz, 1H), 7.45-7.39 (m, 2H), 7.23-7.21 (m, 1H), 5.29 (s, 2H) ppm.

Step 2. (4-Benzyloxy-2-pyridyl)methanamine $BH_3$-THE (1 M, 4.76 mL) was added dropwise to a solution of 4-benzyloxypyridine-2-carbonitrile (200 mg, 0.95 mmol) in THE (2 mL) at 0° C. The reaction mixture was warmed 25° C. and stirred for 4 hrs. The reaction mixture was cooled to 0° C. and 2N HCl (5 mL) was added. The reaction mixture was heated to reflux for 30 minutes and then cooled to 25° C. 2N NaOH was added until pH=12 was achieved. The reaction mixture was then extracted with EA (5 mL×2). The combined organic layers were dried over anhydrous $Na_2SO_4$, filtered, and concentrated affording the title compound (170 mg, 0.56 mmol) as yellow oil.

LCMS (ESI) m/z: [M+H]+=215.1.

$^1H$ NMR (400 MHz, DMSO-d6) δ=8.48-8.43 (m, 1H), 8.30 (d, J=5.6 Hz, 2H), 7.64 (d, J=2.8 Hz, 1H), 7.44-7.39 (m, 5H), 7.25-7.21 (m, 1H), 5.19 (s, 2H), 4.50 (d, J=2.8 Hz, 2H) ppm.

Step 3. (4R)—N-[(4-Benzyloxy-2-pyridyl)methyl]-4-cyano-4-methyl-isochromane-6-carboxamide DIEA (0.41 mL, 2.3 mmol) was added to a solution of (4-benzyloxy-2-pyridyl)methanamine (100 mg, 0.47 mmol), (4R)-4-cyano-4-methyl-isochromane-6-carboxylic acid (101 mg, 0.47 mmol), EDCI (179 mg, 0.93 mmol), and HOBt (126 mg, 0.93 mmol) in DMF (2 mL). The mixture was stirred at 2500 for 1 hr. The reaction mixture was filtered and the filtrate was purified by prep-HPLC (column: Phenomenex Synergi 018 150*25*7-m; mobile phase: [water (0.225% FA)-ACN]; B %: 20%-50%, 9 μm) affording the title compound (51.8 mg, 0.11 mmol, FA salt) as a yellow gum.

LCMS (ESI) m/z: [M+H]+=414.2.

$^1H$ NMR (400 MHz, DMSO-d6) δ=9.21-9.18 (i, 1H), 8.40-8.30 (m, 1H), 8.14 (d, J=1.6 Hz, 1H), 7.89-7.88 (m, 1H), 7.48-7.39 (m, 2H), 7.38-7.32 (m, 3H), 7.28 (d, J=8.0 Hz, 1H), 6.99-6.91 (m, 2H), 5.17 (s, 2H), 4.95-4.80 (m, 2H), 4.58-4.49 (m, 2H), 4.22 (d, J=11.6 Hz, 1H), 3.86 (d, J=11.6 Hz, 1H), 1.69 (s, 3H) ppm.

The following examples in Table 8 were prepared using standard chemical manipulations and procedures similar to those used for the preparation of Example 6.

TABLE 8

Compounds of the Invention

| # | LCMS (m/z) | 1H NMR |
|---|---|---|
| 34 | 470.3 | 1H NMR (400 MHz, MeOD) δ = 8.31 (d, J = 6.0 Hz, 1H), 8.10 (d, J = 1.6 Hz, 1H), 7.86-7.81 (m, 1H), 7.50-7.40 (m, 1H), 7.27 (d, J = 8.2 Hz, 1H), 7.01 (d, J = 2.4 Hz, 1H), 6.97-6.93 (m, 1H), 6.69 (d, J = 7.2 Hz, 1H), 6.26 (d, J = 8.4 Hz, 1H), 5.09 (s, 2H), 4.90 (d, J = 4.0 Hz, 2H), 4.64 (s, 2H), 4.20 (d, J = 11.6 Hz, 1H), 4.00-3.95 (m, 4H), 3.91 (d, J = 11.6 Hz, 1H), 2.40-2.33 (m, 2H), 1.75 (s, 3H) ppm |
| 36 | 415.2 | 1H NMR (400 MHz, DMSO-d6) δ = 9.19-9.16 (m, 1H), 8.51-8.50 (m, 1H), 8.38-8.37 (m, 1H), 8.35-8.33 (m, 1H), 8.12 (d, J = 1.2 Hz, 1H), 7.90-7.88 (m, 1H), 7.81-7.77 (m, 1H), 7.48 (d, J = 8.0 Hz, 1H), 7.33-7.30 (m, 1H), 7.28 (d, J = 8.0 Hz, 1H), 6.96 (d, J = 2.8 Hz, 2H), 5.23 (s, 2H), 4.91-4.80 (m, 2H), 4.53-4.50 (m, 2H), 4.24-4.14 (m, 1H), 3.85 (d, J = 11.6 Hz, 1H), 1.68 (s, 3H) ppm |
| 40 | 469.1 | 1H NMR (400 MHz, MeOD) δ = 8.30 (d, J = 5.6 Hz, 1H), 8.11 (d, J = 1.6 Hz, 1H), 7.89-7.79 (m, 1H), 7.27 (d, J = 8.0 Hz, 1H), 7.15-7.06 (m, 1H), 7.02 (d, J = 2.4 Hz, 1H), 6.98-6.93 (m, 1H), 6.72 (d, J = 7.6 Hz, 1H), 6.48 (s, 1H), 6.43-6.34 (m, 1H), 5.13 (s, 2H), 4.93 (br d, J = 9.6 Hz, 2H), 4.64 (s, 2H), 4.20 (d, J = 11.6 Hz, 1H), 3.92 (d, J = 11.2 Hz, 1H), 3.85-3.76 (m, 4H), 2.40-2.26 (m, 2H), 1.75 (s, 3H) ppm |

TABLE 8-continued

| Compounds of the Invention | | |
|---|---|---|
| # | LCMS (m/z) | 1H NMR |
| 45 | 474.2 | 1H NMR (400 MHz, MeOD) δ = 8.30 (d, J = 6.0 Hz, 1H), 8.11 (d, J = 1.6 Hz, 1H), 7.88-7.80 (m, 1H), 7.26 (d, J = 8.0 Hz, 1H), 7.06 (s, 1H), 7.01-6.91 (m, 3H), 5.09 (s, 2H), 4.90 (br d, J = 3.6 Hz, 2H), 4.65-4.57 (m, 4H), 4.19 (d, J = 11.6 Hz, 1H), 3.92 (d, J = 11.2 Hz, 1H), 3.23-3.14 (m, 2H), 1.75 (s, 3H) ppm |
| 61 | 422.2 | 1H NMR (400 MHz, DMSO-d6) δ = 9.21-9.18 (m, 1H), 8.33 (d, J = 5.6 Hz, 1H), 8.14 (s, 1H), 7.90-7.88 (m, 1H), 7.28 (d, J = 8.0 Hz, 1H), 6.95-6.82 (m, 2H), 4.97-4.78 (m, 2H), 4.60-4.47 (m, 2H), 4.22 (d, J = 11.6 Hz, 1H), 3.97-3.78 (m, 5H), 3.31-3.25 (m, 2H), 2.06-1.92 (m, 1H), 1.74-1.57 (m, 5H), 1.34-1.28 (m, 2H) ppm |

Example 7. (4R)-4-Cyano-4-methyl-N-[[4-[(1S,2S)-2-phenylcyclopropyl]-2-pyridyl]methyl]isochromane-6-carboxamide and (4R)-4-Cyano-4-methyl-N-[[4-[(1R,2R)-2-phenylcyclopropyl]-2-pyridyl]methyl]isochromane-6-carboxamide

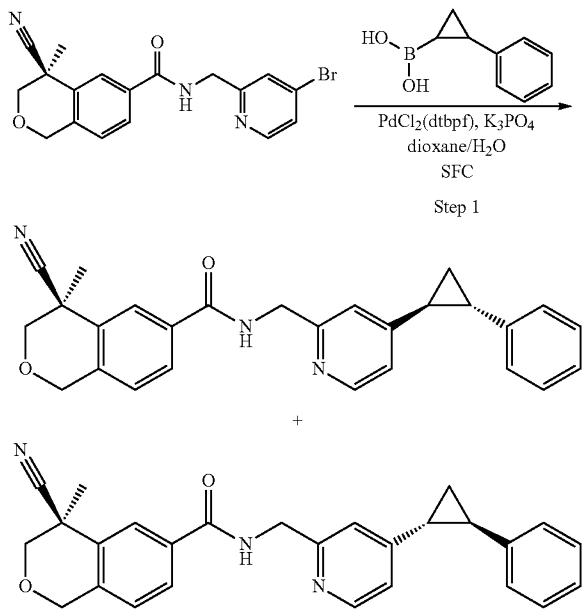

Step 1. (4R)-4-Cyano-4-methyl-N-[[4-[(1S,2S)-2-phenylcyclopropyl]-2-pyridyl]methyl]isochromane-6-carboxamide and (4R)-4-cyano-4-methyl-N-[[4-[(1R,2R)-2-phenylcyclopropyl]-2-pyridyl]methyl]isochromane-6-carboxamide $PdCl_2$ (dtbpf) (33.7 mg, 0.052 mmol) and $K_3PO_4$ (165 mg, 0.78 mmol) were added to a solution of (4R)—N-[(4-bromo-2-pyridyl)methyl]-4-cyano-4-methyl-isochromane-6-carboxamide (100 mg, 0.26 mmol), and (2-phenylcyclopropyl) boronic acid (83.9 mg, 0.52 mmol) in dioxane (1 mL) and $H_2O$ (0.1 mL). The mixture was stirred at 80° C. for 12 hrs. The reaction mixture was washed with water (50 mL) and extracted with EA (50 mL×2). The combined organic phase was washed with brine (20 mL), dried with anhydrous $Na_2SO_4$, filtered, and concentrated in vacuo. The residue was purified by prep-HPLC (column: Phenomenex luna C18 150*25 mm*10 μm; mobile phase: [water (0.1% TFA)-ACN]; B %: 32%-52%, 10 min) affording a mixture of the title compounds (60 mg, 132.24 μmol, 51.08% yield) as a brown solid. The mixture was separated by chiral SFC (column: DAICEL CHIRALCEL OJ-H (250 mm×30 mm, 5 μm); mobile phase: [0.1% $NH_3 \cdot H_2O$ MeOH]; B %: 40%-40%, 3.9 min; 70 min), the solution was concentrated under reduced pressure affording the title compounds. $1^{st}$ eluting compound (12.9 mg, 0.029 mmol, off-white solid):

LCMS (ESI) m/z: [M+H]+=424.1.

$^1$H NMR (400 MHz, DMSO-d6) δ=9.18-9.14 (m, 1H), 8.37 (d, J=5.2 Hz, 1H), 8.13 (d, J=1.2 Hz, 1H), 7.90-7.86 (m, 1H), 7.29-7.25 (m, 3H), 7.19-7.15 (m, 4H), 7.07-7.04 (m, 1H), 4.91-4.79 (m, 2H), 4.57-4.53 (m, 2H), 4.21 (d, J=11.2 Hz, 1H), 3.85 (d, J=11.6 Hz, 1H), 2.29-2.21 (m, 2H), 1.68 (s, 3H), 1.57-1.52 (m, 2H) ppm.

$2^{nd}$ eluting compound (11.3 mg, 0.027 mmol, yellow solid):

LCMS (ESI) m/z: [M+H]+=424.1.

$^1$H NMR (400 MHz, DMSO-d6) δ=9.25-9.21 (m, 1H), 8.43 (d, J=5.2 Hz, 1H), 8.13 (d, J=1.6 Hz, 1H), 7.90-7.87 (m, 1H), 7.30-7.25 (m, 3H), 7.20-7.16 (m, 4H), 7.07-7.03 (m, 1H), 4.91-4.79 (m, 2H), 4.60 (d, J=5.2 Hz, 2H), 4.21 (d, J=11.6 Hz, 1H), 3.85 (d, J=11.2 Hz, 1H), 2.36-2.30 (m, 2H), 1.67 (s, 3H), 1.64-1.59 (m, 2H) ppm.

The following examples in Table 9 were prepared using standard chemical manipulations and procedures similar to those used for the preparation of Examples 7.

TABLE 9

| Compounds of the Invention | | |
|---|---|---|
| # | LCMS (m/z) | 1H NMR |
| 4 | 410.2 | 1H NMR (400 MHz, DMSO-d6) δ = 9.36 (m, 1H), 8.65 (d, J = 5.6 Hz, 1H), 8.15 (d, J = 1.6 Hz, 1H), 7.91 (m, 1H), 7.88-7.88 (m, 1H), 7.88-7.79 (m, 2H), 7.77 (s, 3H), 7.50-7.35 (m, 4H), 7.30 (d, J = 8.0 Hz, 1H), 4.94-4.80 (m, 2H), 4.72 (d, J = 5.6 Hz, 2H), 4.22 (d, J = 11.6 Hz, 1H), 3.88-3.85 (m, 1H), 1.69 (s, 3H) ppm. |

TABLE 9-continued

Compounds of the Invention

| # | LCMS (m/z) | 1H NMR |
|---|---|---|
| 38 | 440.3 | 1H NMR (400 MHz, DMSO-d6) δ = 9.26-9.23 (m, 1H), 8.51 (d, J = 5.2 Hz, 1H), 8.17 (d, J = 1.6 Hz, 1H), 7.93-7.92 (m, 1H), 7.55-7.44 (m, 3H), 7.37-7.27 (m, 3H), 7.26-7.21 (m, 2H), 6.91-6.89 (m, 1H), 4.99-4.77 (m, 2H), 4.62-4.60 (m, 2H), 4.23 (d, J = 11.2 Hz) ppm |

Example 8. (4R)-4-Cyano-4-methyl-N-[[4-(2-phenylethyl)-2-pyridyl]methyl]isochromane-6-carboxamide

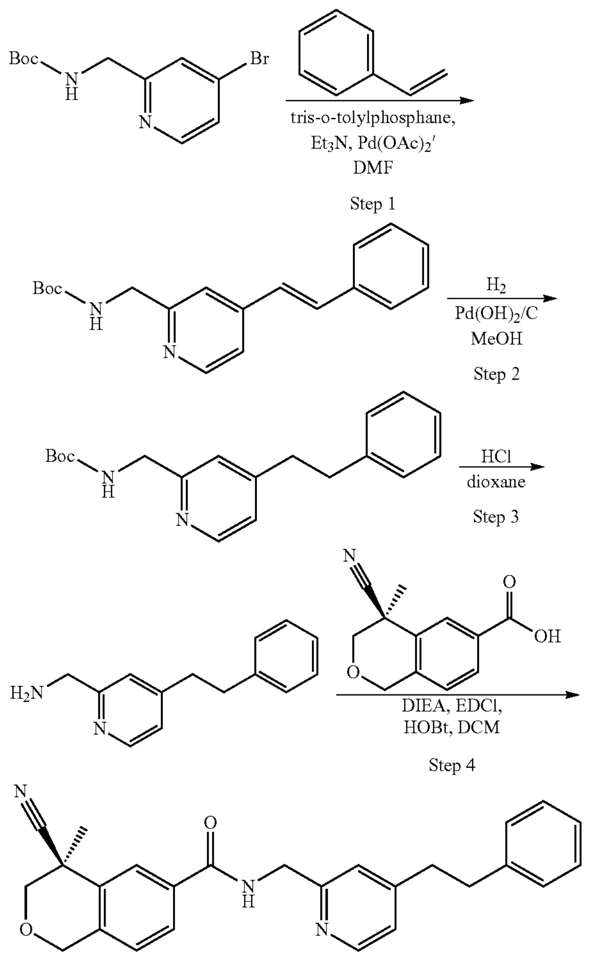

Step 1. tert-butyl N-[[4-[(E)-styryl]-2-pyridyl]methyl]carbamate $Pd(OAc)_2$ (7.8 mg, 0.0325 mmol) was added to a solution of tert-butyl ((4-bromopyridin-2-yl)methyl)carbamate (200 mg, 0.70 mmol), styrene (363 mg, 3.48 mmol), $Et_3N$ (0.14 mL, 1.04 mmol), and tris-o-tolylphosphane (21.2 mg, 0.070 mmol) in DMF (2 mL). The mixture was stirred at 100° C. for 2 hrs.

The reaction mixture was diluted with $H_2O$ (10 mL) and extracted with DCM (10 mL×2), the combined organic layers were dried over anhydrous $Na_2SO_4$, filtered, and concentrated in vacuo. The crude residue was purified by column chromatography ($SiO_2$, Petroleum ether/EA=1/0 to 0/1) affording the title compound (200 mg, 0.64 mmol) as a yellow solid.

LCMS (ESI) m/z: [M+H]+=311.4

$^1$H NMR (400 MHz, $CDCl_3$) δ=8.51 (d, J=5.2 Hz, 1H), 7.55 (d, J=7.2 Hz, 2H), 7.42-7.40 (m, 2H), 7.38-7.28 (m, 4H), 7.04 (d, J=16.4 Hz, 1H), 4.47 (d, J=5.6 Hz, 2H), 1.49 (s, 9H) ppm.

Step 2. tert-Butyl N-[[4-(2-phenylethyl)-2-pyridyl]methyl]carbamate $Pd(OH)_2$/C (30 mg) was added to a mixture of tert-butyl N-[[4-[(E)-styryl]-2-pyridyl]methyl]carbamate (100 mg, 0.32 mmol) in MeOH (2 mL). The mixture was degassed and purged with $H_2$ three times, and then the mixture was stirred at 25° C. for 12 hrs under a $H_2$ atmosphere (15 psi). The reaction mixture was filtered. The filtrate was concentrated affording the title compound (90 mg, 0.29 mmol) as a yellow oil.

LCMS (ESI) m/z: [M+H]+=313.0.

$^1$H NMR (400 MHz, $CDCl_3$) δ=8.41 (d, J=4.8 Hz, 1H), 7.31-7.27 (m, 2H), 7.21-7.18 (m, 1H), 7.16-7.14 (m, 2H), 7.06 (s, 1H), 6.98-6.97 (m, 1H), 4.41 (br d, J=5.2 Hz, 2H), 2.92 (s, 4H), 1.47 (s, 9H) ppm.

Step 3. [4-(2-Phenylethyl)-2-pyridyl]methanamine

A solution of tert-butyl N-[[4-(2-phenylethyl)-2-pyridyl]methyl]carbamate (90 mg, 0.29 mmol) in 4N HCl/dioxane (5.0 mL) was stirred at 25° C. for 1 hr. The reaction mixture was concentrated affording the title compound (70 mg, 0.28 mmol, HCl salt) as a white solid.

LCMS (ESI) m/z: [M+H]+=213.3.

Step 4. (4R)-4-cyano-4-methyl-N-[[4-(2-phenylethyl)-2-pyridyl]methyl]isochromane-6-carboxamide DIEA (0.14 mL, 0.80 mmol), EDCI (46.2 mg, 0.24 mmol), and HOBt (32.6 mg, 0.24 mmol) were added to a solution of [4-(2-Phenylethyl)-2-pyridyl]methanamine (40 mg, 0.16 mmol, HCl salt) and (4R)-4-cyano-4-methylisochromane-6-carboxylic acid (38.4 mg, 0.18 mmol) in DCM (0.5 mL). The mixture was stirred at 30° C. for 12 hrs. The reaction mixture was diluted with $H_2O$ (3 mL) and extracted with DCM (3 mL×2). The combined organic layers were dried over anhydrous $Na_2SO_4$, filtered, and concentrated under reduced pressure. The crude residue was purified by column chromatography ($SiO_2$, Petroleum ether/EA=1/0 to 0/1) affording the title compound (23.5 mg, 0.054 mmol) as a yellow solid.

LCMS (ESI) m/z: [M+H]+=412.3.

$^1$H NMR (400 MHz, $CD_3OD$) δ=8.34 (d, J=4.8 Hz, 1H), 8.10 (d, J=0.8 Hz, 1H), 7.85-7.83 (m, 1H), 7.27 (d, J=8.0 Hz, 1H), 7.20-7.16 (m, 3H), 7.14-7.12 (m, 3H), 7.10-7.07 (m, 1H), 4.90 (d, J=3.2 Hz, 2H), 4.64 (s, 2H), 4.20 (d, J=11.6 Hz, 1H), 3.92 (d, J=11.2 Hz, 1H), 2.95-2.92 (m, 4H), 1.74 (s, 3H) ppm.

Example 9. Methyl 3-[(E)-2-[2-[[[(4R)-4-cyano-4-methyl-isochromane-6-carbonyl]amino]methyl]-4-pyridyl]vinyl]benzoate

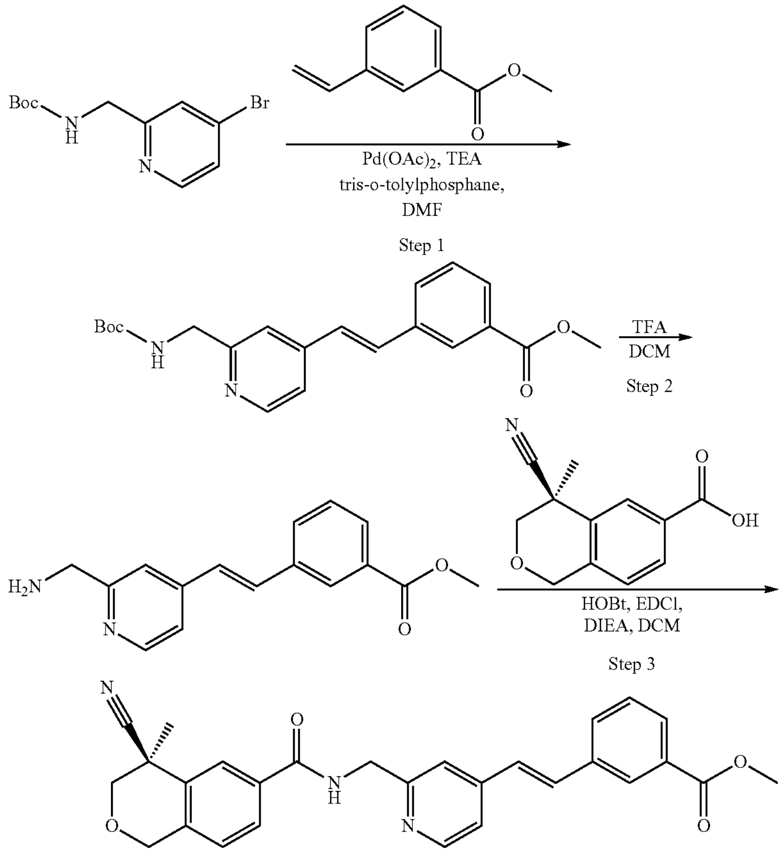

Step 1. Methyl 3-[(E)-2-[2-[(tert-butoxycarbonylamino)methyl]-4-pyridyl]vinyl]benzoate $Pd(OAc)_2$ (15.6 mg, 0.070 mmol), tris-o-tolylphosphane (42.4 mg, 0.14 mmol) and $Et_3N$ (0.19 mL, 1.39 mmol) were added to a mixture of tert-butyl N-[(4-bromo-2-pyridyl)methyl]carbamate (200 mg, 0.70 mmol) and methyl 3-vinylbenzoate (226 mg, 1.39 mmol) in DMF (2 mL). The reaction mixture was stirred at 100° C. for 1 hr. The reaction mixture was poured into water (30 mL) and extracted with EA (20 mL×2). The combined organic phase was washed with brine (20 mL), dried with anhydrous $Na_2SO_4$, filtered, and concentrated in vacuo. The crude residue was purified by silica gel chromatography (Petroleum ether/EA=10/1 to 3/1) affording the title compound (200 mg, 0.54 mmol) as light yellow oil LCMS (ESI) m/z: [M+H]+=369.2.

$^1$H NMR (400 MHz, $CDCl_3$) δ=8.52 (d, J=5.2 Hz, 1H), 8.24 (s, 1H), 8.00 (d, J=7.6 Hz, 1H), 7.71 (d, J=7.6 Hz, 1H), 7.48-7.46 (m, 1H), 7.39-7.28 (m, 3H), 7.10 (d, J=16.4 Hz, 1H), 4.48 (d, J=5.6 Hz, 2H), 4.12 (s, 3H), 1.55 (s, 9H) ppm.

Step 2. Methyl 3-[(E)-2-[2-(aminomethyl)-4-pyridyl]vinyl]benzoate

TFA (0.50 mL, 6.75 mmol) was added to a mixture of Methyl 3-[(E)-2-[2-[(tert-butoxycarbonylamino)methyl]-4-pyridyl]vinyl]benzoate (100 mg, 0.27 mmol) in DCM (1 mL). The reaction mixture was stirred at 25° C. for 1 hrs. The mixture was poured into saturated $NaHCO_3$ (30 mL) and extracted with DCM (20 mL×2). The combined organic phase was washed with brine (20 mL×2), dried over anhydrous $Na_2SO_4$, filtered, and concentrated in vacuo affording the title compound (60 mg, 0.22 mmol) as yellow oil.

LCMS (ESI) m/z: [M+H]+=269.1.

Step 3. Methyl 3-[(E)-2-[2-[[[(4R)-4-cyano-4-methyl-isochromane-6-carbonyl]amino]methyl]-4-pyridyl]vinyl]benzoate HOBt (22.7 mg, 0.17 mmol), EDCI (32.1 mg, 0.17 mmol, and DIEA (0.058 mL, 0.33 mmol) were added to a mixture of Methyl 3-[(E)-2-[2-(aminomethyl)-4-pyridyl]vinyl]benzoate (30 mg, 0.11 mmol) and (4R)-4-cyano-4-methyl-isochromane-6-carboxylic acid (29.1 mg, 0.13 mmol) in DCM (1 mL). The mixture was stirred at 25° C. for 12 hrs. The mixture was poured into water (20 mL) and extracted with DCM (20 mL×2). The combined organic phase was washed with brine (20 mL), dried with anhydrous $Na_2SO_4$, filtered, and concentrated in vacuo. The crude residue was purified by prep-TLC (DCM/MeOH=10/1) affording the title compound (25.2 mg, 0.052 mmol) as a blue solid.

LCMS (ESI) m/z: [M+H]+=468.3.

$^1$H NMR (400 MHz, $CD_3OD$) δ=8.52-8.46 (m, 1H), 8.30-8.24 (m, 1H), 8.18-8.14 (m, 1H), 8.01-7.95 (m, 1H), 7.93-7.85 (m, 2H), 7.64-7.60 (m, 1H), 7.59-7.49 (m, 3H), 7.34-7.26 (m, 2H), 4.94-4.91 (m, 2H), 4.74 (s, 2H), 4.25-3.90 (m, 5H), 1.77 (s, 3H) ppm.

The following examples in Table 10 were prepared using standard chemical manipulations and procedures similar to those used for the preparation of Example 9.

-continued

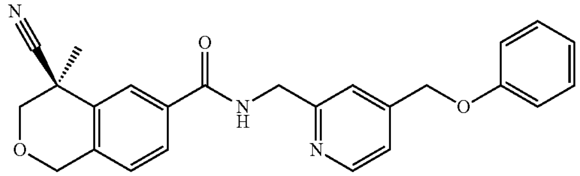

TABLE 10

Compounds of the Invention

| # | LCMS (m/z) | 1H NMR |
|---|---|---|
| 33 | 428.2 | 1H NMR (400 MHz, DMSO-d6) δ = 9.16-9.13 (m, 1H), 8.35 (d, J = 5.0 Hz, 1H), 8.14 (d, J = 1.4 Hz, 1H), 7.88-7.85 (dm, 1H), 7.76-7.70 (m, 2H), 7.67-7.56 (m, 1H), 7.51-7.17 (m, 5H), 4.94-4.79 (m, 2H), 4.78-4.62 (m, 2H), 4.27-4.16 (m, 1H), 3.93-3.80 (m, 1H), 1.68(s, 3H)ppm |
| 41 | 454.2 | 1H NMR (400 MHz, DMSO-d6) δ = 8.97 (d, J = 8.0, 1H), 8.53 (d, J = 5.2, 1H), 8.18 (d, J = 1.2, 1H), 7.93-7.90 (m, 1H), 7.67-7.61 (m, 3H), 7.55-7.49 (m, 2H), 7.42-7.38 (m, 2H), 7.35-7.31 (m, 1H), 7.29-7.25 (m, 2H), 5.43-5.38 (m, 1H), 4.91-4.80 (m, 2H), 4.21 (d, J = 11.6, 1H), 3.87-3.81 (m, 3H), 3.30 (s, 3H), 1.69 (s, 3H) ppm |

Example 10. (4R)-4-Cyano-4-methyl-N-[[4-(phenoxymethyl)-2-pyridyl]methyl]isochromane-6-carboxamide

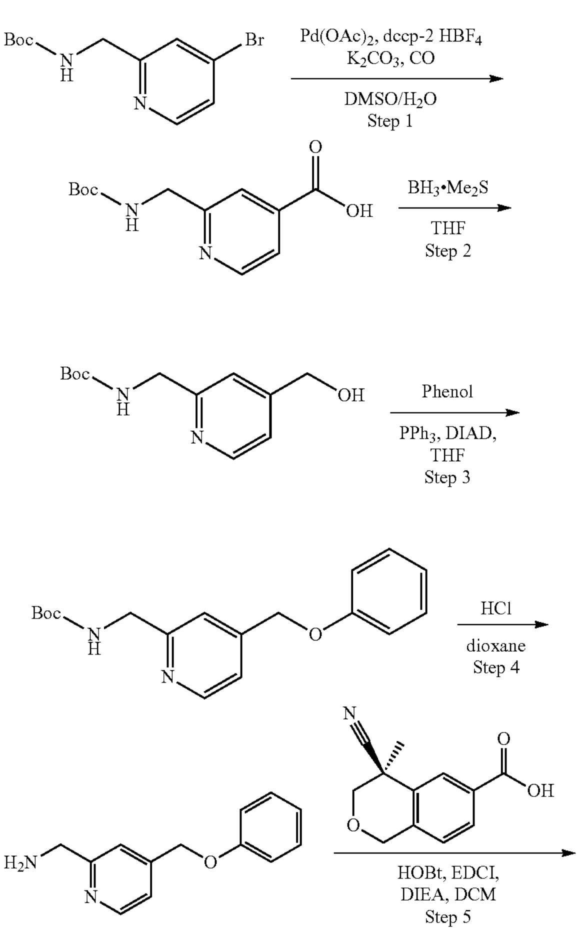

Step 1. 2-[(tert-Butoxycarbonylamino)methyl]pyridine-4-carboxylic acid $Pd(OAc)_2$ (62.6 mg, 0.28 mmol), DCPP (171 mg, 0.28 mmol), $H_2O$ (2 mL), and $K_2CO_3$ (578 mg, 4.18 mmol) were added to a solution of 2 tert-butyl N-[(4-bromo-2-pyridyl) methyl]carbamate (800 mg, 2.79 mmol) in DMSO (8 mL). The reaction mixture was purged with CO(g) three times. The resulting mixture was stirred at 100° C. for 16 hr under a CO atmosphere (15 psi). The reaction mixture was diluted with $H_2O$ (30 mL) and extracted with EA (30 mL×3). The combined organic layers were discarded, and the aqueous layers were combined and 1N HCl was added until a pH=4 was achieved. The reaction mixture was extracted with EA (30 mL×3). The combined organic layers were washed with brine (60 mL), dried over anhydrous $Na_2SO_4$, filtered, and concentrated under reduced pressure affording the title compound (436 mg, 1.68 mmol) as a yellow solid.

LCMS (ESI) m/z: [M+H]+=253.2.

$^1$H NMR (400 MHz, DMSO-d6) δ=13.63-13.56 (m, 1H), 8.67-8.66 (m, 1H), 7.71 (s, 1H), 7.68-7.66 (m, 1H), 7.55-7.53 (m, 1H), 4.29 (br d, J=5.6 Hz, 2H), 1.40 (s, 9H) ppm.

Step 2. tert-Butyl N-[[4-(hydroxymethyl)-2-pyridyl]methyl]carbamate $BH_3 \cdot Me_2S$ (10 M, 0.18 mL) was added dropwise to a solution of 2-[(tert-Butoxycarbonylamino)methyl]pyridine-4-carboxylic acid (150 mg, 0.59 mmol) in THF (2 mL) at 0° C. The mixture was warmed to 25° C. and stirred for 12 hrs. MeOH (5 mL) was added to the reaction mixture at 0° C. and then warmed and stirred at 70° C. for 1 hr. The mixture was then diluted with $H_2O$ (40 mL) and extracted with EA (40 mL×2). The combined organic layers were dried over anhydrous $Na_2SO_4$, filtered, and concentrated in vacuo. The crude residue was purified by column chromatography ($SiO_2$, Petroleum ether/EA=1/0 to 0/1) affording the title compound (100 mg, 0.42 mmol) as yellow oil.

LCMS (ESI) m/z: [M+H]+=239.2.

$^1$H NMR (400 MHz, $CDCl_3$) δ=8.50 (d, J=5.2 Hz, 1H), 7.29-7.27 (m, 1H), 7.19 (d, J=4.8 Hz, 1H), 5.56 (br s, 1H), 4.74 (s, 2H), 4.44 (br d, J=5.6 Hz, 2H), 1.46 (s, 9H) ppm.

Step 3. tert-Butyl N-[[4-(phenoxymethyl)-2-pyridyl]methyl]carbamate

DIAD (0.098 mL, 0.50 mmol) was added to a solution of tert-Butyl N-[[4-(hydroxymethyl)-2-pyridyl]methyl]carbamate (80 mg, 0.34 mmol), $PPh_3$ (132 mg, 0.50 mmol), and phenol (0.060 mL, 0.67 mmol) in THE (1 mL) at 0° C. The mixture was warmed and stirred at 25° C. for 16 hr. The mixture was diluted with $H_2O$ (10 mL) and extracted with EA (10 mL×2). The combined organic layers were dried over anhydrous $Na_2SO_4$, filtered, and concentrated in vacuo. The crude residue was purified by column chromatography ($SiO_2$, Petroleum ether/EA=1/0 to 1/1) affording the title compound (75 mg, 0.24 mmol) as a yellow solid.

LCMS (ESI) m/z: [M+H]+=315.2.

$^1$H NMR (400 MHz, $CDCl_3$) δ=8.54 (d, J=5.2 Hz, 1H), 7.34-7.29 (m, 3H), 7.25 (br s, 1H), 7.00-6.94 (m, 3H), 5.54 (br s, 1H), 5.09 (s, 2H), 4.47 (br d, J=4.8 Hz, 2H), 1.47 (s, 9H) ppm.

Step 4. [4-(Phenoxymethyl)-2-pyridyl]methanamine

A solution of tert-butyl N-[[4-(phenoxymethyl)-2-pyridyl]methyl]carbamate (40 mg, 0.13 mmol) in HCl/dioxane (4N, 1 mL) was stirred at 25° C. for 1 hr. The reaction mixture was concentrated affording the title compound (30 mg, 0.12 mmol, HCl salt) as a white solid.

LCMS (ESI) m/z: [M+H]+=215.3.

Step 5. (4R)-4-Cyano-4-methyl-N-[[4-(phenoxymethyl)-2-pyridyl]methyl]isochromane-6-carboxamide DIEA (0.10 mL, 0.60 mmol), EDCI (34.4 mg, 0.18 mmol), and HOBt (24.2 mg, 0.18 mmol) were added to a solution of (4R)-4-cyano-4-methyl-isochromane-6-carboxylic acid (26 mg, 0.12 mmol) and [4-(phenoxymethyl)-2-pyridyl]methanamine (30 mg, 0.12 mmol, HCl salt) in DCM (0.5 mL). The mixture was stirred at 30° C. for 12 hrs. The reaction mixture was diluted with $H_2O$ (3 mL) and extracted with DCM (3 mL×2). The combined organic layers were dried over anhydrous $Na_2SO_4$, filtered, and concentrated under reduced pressure. The crude residue was purified by column chromatography ($SiO_2$, Petroleum ether/EA=1/0 to 0/1) affording the title compound (18.8 mg, 0.045 mmol) as a white solid.

LCMS (ESI) m/z: [M+H]+=414.4.

$^1$H NMR (400 MHz, $CD_3OD$) δ=8.49 (d, J=5.12 Hz, 1H), 8.10 (d, J=1.6 Hz, 1H), 7.84-7.82 (m, 1H), 7.51-7.40 (m, 1H), 7.26-7.21 (m, 3H), 6.95-6.91 (m, 3H) 5.17 (s, 2H), 4.90 (d, J=4.0 Hz, 2H), 4.71 (s, 2H), 4.20 (d, J=11.6 Hz, 1H), 3.92 (d, J=11.6 Hz, 1H), 1.74 (s, 3H) ppm.

Examples 11 and 12: (R)-4-Cyano-4-methyl-N-((4-((1r,3R)-3-(6-morpholinopyridin-2-yl)cyclobutyl)pyridin-2-yl)methyl)isochromane-6-carboxamide and (R)-4-cyano-4-methyl-N-((4-((1s,3S)-3-(6-morpholinopyridin-2-yl)cyclobutyl)pyridin-2-yl)methyl)isochromane-6-carboxamide

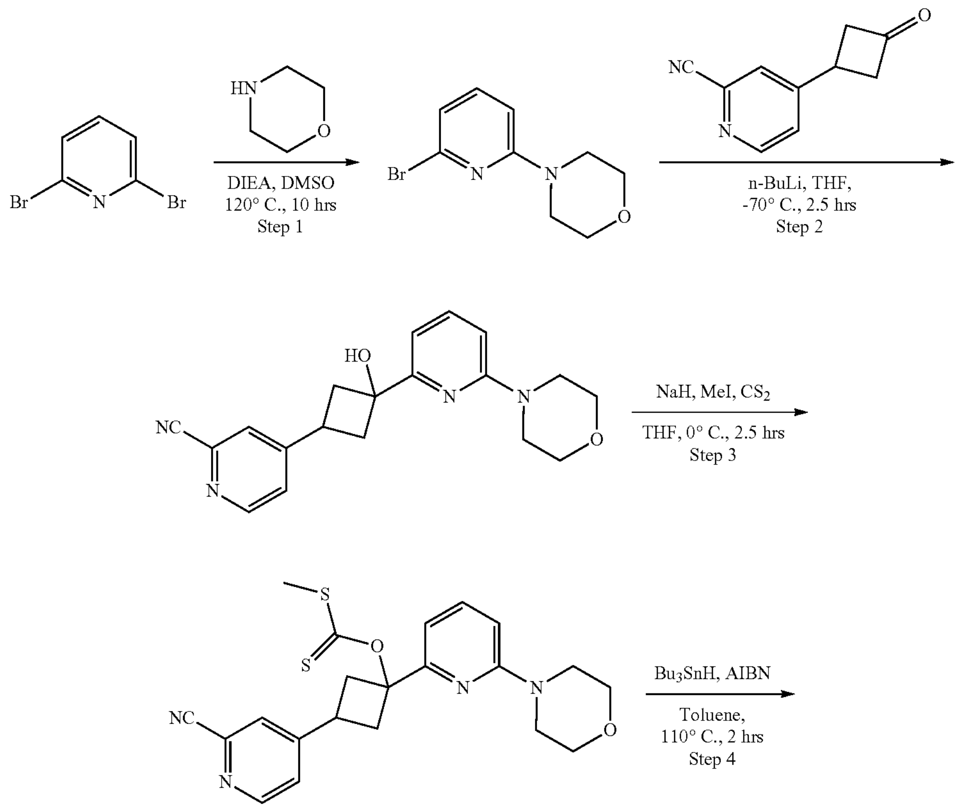

-continued

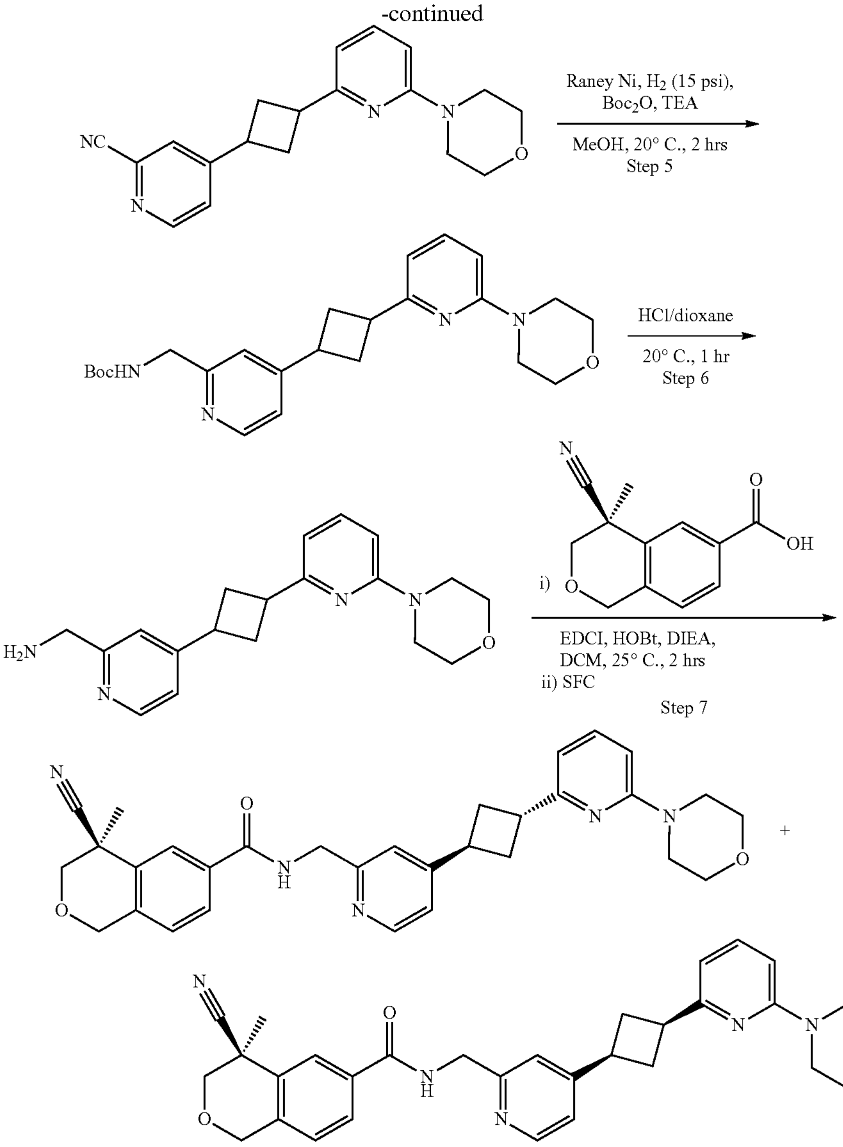

Step 1: 4-(6-Bromopyridin-2-yl)morpholine

To a mixture of 2,6-dibromopyridine (2 g, 8.44 mmol) and morpholine (2.94 g, 33.77 mmol, 2.97 mL) in DMSO (20 mL) was added DIEA (3.27 g, 25.33 mmol). The mixture was stirred at 120° C. for 10 hrs. The mixture was poured into water (150 mL), then extracted with EA (100 mL*3). The combined organic layers were washed with brine (250 mL), dried over $Na_2SO_4$, filtered and concentrated under reduced pressure. The residue was purified by column chromatography ($SiO_2$, DCM/Ethyl acetate=50/1 to 1/1) to give the title compound (1.6 g, 6.58 mmol, 77.96% yield) as a white solid.

$^1$H NMR (400 MHz, $CDCl_3$) δ=7.34-7.30 (m, 1H), 6.80 (d, J=7.6 Hz, 1H), 6.52 (d, J=8.4 Hz, 1H), 3.87-3.75 (m, 4H), 3.52-3.49 (m, 4H) ppm.

Step 2: 4-(3-Hydroxy-3-(6-morpholinopyridin-2-yl)cyclobutyl)picolinonitrile

To a mixture of 4-(6-bromopyridin-2-yl)morpholine (1.41 g, 5.81 mmol) in THF (10 mL) was added n-BuLi (2.5 M, 2.32 mL) at −70° C. under $N_2$. The mixture was stirred at −70° C. for 0.5 hr, then the resulting solution was added to a solution of 4-(3-oxocyclobutyl)picolinonitrile (500 mg, 2.90 mmol) in THF (10 mL) at −70° C. under $N_2$. The mixture was stirred at −70° C. for 2 hrs. The mixture was poured into sat. $NH_4Cl$ (100 mL), and extracted with EA (100 mL*2). The combined organic layers were washed with brine (150 mL), dried over $Na_2SO_4$, filtered and concentrated under reduced pressure. The residue was purified by column chromatography ($SiO_2$, Petroleum ether/Ethyl acetate=20/1 to 0/1) to give the title compound (430 mg, 1.25 mmol, 43.14% yield) as a white solid.

LCMS (ESI) m/z: $[M+H]^+$=337.1

$^1$H NMR (400 MHz, DMSO-$d_6$) δ=8.68 (d, J=5.2 Hz, 1H), 8.08-8.07 (m, 1H), 7.73-7.71 (m, 1H), 7.58-7.54 (m, 1H), 6.94 (d, J=7.2 Hz, 1H), 6.72 (d, J=8.4 Hz, 1H), 5.84 (s, 1H), 5.75 (s, 1H), 3.74-3.72 (m, 4H), 3.49-3.47 (m, 4H), 2.95-2.90 (m, 2H), 2.42-2.37 (m, 2H) ppm.

Step 3: O-(3-(2-Cyanopyridin-4-yl)-1-(6-morpholinopyridin-2-yl)cyclobutyl)S-methyl carbonodithioate To a mixture of NaH (59.45 mg, 1.49 mmol, 60% purity) in THE (2 mL) was added 4-(3-hydroxy-3-(6-morpholinopyridin-2-yl)cyclobutyl)picolinonitrile (200 mg, 594.55 umol) in THE (2 mL) at 0° C. under $N_2$. The mixture was stirred at 10° C. for 0.5 hr, then $CS_2$ (242.19 mg, 3.18 mmol, 192.22 uL) was added drop wise at 0° C. The resulting mixture was stirred at 10° C. for 1 hr, then MeI (219.41 mg, 1.55 mmol, 96.23 uL) was added to the mixture drop wise at 0° C. The resulting mixture was stirred at 10° C. for 1 hr. The reaction mixture was diluted with $H_2O$ (40 mL) and extracted with EA (30 mL*3). The combined organic layers were dried over anhydrous $Na_2SO_4$, filtered and concentrated. The residue was purified by column chromatography ($SiO_2$, Petroleum ether/Ethyl acetate=10:1-1:1) to give the title compound (250 mg, 533.34 umol, 89.70% yield) as a yellow oil.

LCMS (ESI) m/z: $[M+H]^+$=427.1

Step 4: 4-(3-(6-Morpholinopyridin-2-yl)cyclobutyl)picolinonitrile

To a mixture of O-(3-(2-cyanopyridin-4-yl)-1-(6-morpholinopyridin-2-yl)cyclobutyl)S-methyl carbonodithioate (125 mg, 293.05 umol) in toluene (3 mL) was added $Bu_3SnH$ (255.88 mg, 879.14 umol, 232.62 uL) and AIBN (9.62 mg, 58.61 umol). The mixture was stirred at 110° C. for 2 hrs. The mixture was poured into sat. KF solution (50 mL) and stirred for 15 min. The mixture was extracted with EA (50 mL*2). The combined organic layers was washed with brine (100 mL), dried over $Na_2SO_4$, filtered and concentrated. The residue was purified by column chromatography ($SiO_2$, Petroleum ether/Ethyl acetate=10/1 to 0/1) to give the title compound (80 mg, 187.27 umol, 63.91% yield) as a yellow oil.

LCMS (ESI) m/z: $[M+H]^+$=321.2

Step 5: tert-Butyl ((4-(3-(6-morpholinopyridin-2-yl)cyclobutyl)pyridin-2-yl)methyl)carbamate To a mixture of 4-(3-(6-morpholinopyridin-2-yl)cyclobutyl)picolinonitrile (80 mg, 249.70 umol) in MeOH (2 mL) and EA (2 mL) was added TEA (75.80 mg, 749.09 umol), $(Boc)_{2}O$ (108.99 mg, 499.40 umol) and Raney-Ni (50 mg, 583.60 umol). The mixture was stirred at 25° C. for 2 hrs. The mixture was diluted with EA then filtered carefully with EA (15 mL*3). The filtrate was washed with brine (50 mL), dried over $Na_2SO_4$, filtered and concentrated under vacuum. The residue was purified by column chromatography ($SiO_2$, Petroleum ether/Ethyl acetate=10/1 to 0/1) to give the title compound (90 mg, 188.68 umol, 75.56% yield) as a white solid.

LCMS (ESI) m/z: $[M+H]^+$=425.3.

Step 6: (4-(3-(6-Morpholinopyridin-2-yl)cyclobutyl)pyridin-2-yl)methanamine hydrochloride A mixture of tert-butyl ((4-(3-(6-morpholinopyridin-2-yl)cyclobutyl)pyridin-2-yl)methyl)carbamate (90 mg, 212.00 umol) in HCl/dioxane (4 M, 4 mL) was stirred at 25° C. for 1 hr. The mixture was concentrated under vacuum to give the title compound (76 mg, crude, HCl salt) as a white solid, used directly in the next step.

LCMS (ESI) m/z: $[M+H]^+$=325.2

Step 7: (R)-4-Cyano-4-methyl-N-((4-((1r,3R)-3-(6-morpholinopyridin-2-yl)cyclobutyl)pyridin-2-yl)methyl)isochromane-6-carboxamide and (R)-4-cyano-4-methyl-N-((4-((1s,3S)-3-(6-morpholinopyridin-2-yl)cyclobutyl)pyridin-2-yl)methyl)isochromane-6-carboxamide To a mixture of (4-(3-(6-morpholinopyridin-2-yl)cyclobutyl)pyridin-2-yl)methanamine hydrochloride (76 mg, 210.60 umol), (4R)-4-cyano-4-methyl-isochromane-6-carboxylic acid (54.89 mg, 252.72 umol) and DIEA (81.65 mg, 631.79 umol, 110.05 uL) in DCM (3 mL) was added EDCI (60.56 mg, 315.89 umol) and HOBt (42.68 mg, 315.89 umol). The mixture was stirred at 25° C. for 2 hrs. The mixture concentrated under vacuum to remove DCM. The residue was purified by prep-TLC (DCM:MeOH=10:1) to give crude racemic product (34 mg). The racemic product was further separated by SFC (column: DAICEL CHIRALPAK AD (250 mm*30 mm, 10 um); mobile phase: [0.1% $NH_3H_2O$ IPA]; B %: 50%-50%, 4.5 min; 25 minmin) to give peak 1 (Rf=0.743 min) and peak 2 (Rf=1.102 min). The fraction of peak 1 (Rf=0.743 min) was concentrated under vacuum to give a residue, then purified by reversed phase HPLC (0.1% FA condition) and lyophilized to give (R)-4-cyano-4-methyl-N-((4-((1r,3R)-3-(6-morpholinopyridin-2-yl)cyclobutyl)pyridin-2-yl)methyl)isochromane-6-carboxamide (3.10 mg, 5.92 umol, 2.81% yield) as an off-white solid. The fraction of peak 2 (Rf=1.102 mins) was concentrated under vacuum to give a residue, then purified by reversed phase HPLC (0.1% FA condition) and lyophilized to give (R)-4-cyano-4-methyl-N-((4-((1 s,3S)-3-(6-morpholinopyridin-2-yl)cyclobutyl)pyridin-2-yl)methyl)isochromane-6-carboxamide (7.55 mg, 14.42 umol, 6.85% yield) as an off-white solid.

(R)-4-Cyano-4-methyl-N-((4-((1r,3R)-3-(6-morpholinopyridin-2-yl)cyclobutyl)pyridin-2-yl)methyl)isochromane-6-carboxamide LCMS (ESI) m/z: $[M+H]^+$=524.2

$^1H$ NMR (400 MHz, MeOD) δ=8.43 (d, J=4.8 Hz, 1H), 8.12 (d, J=1.6 Hz, 1H), 7.88-7.85 (m, 1H), 7.49-7.45 (m, 1H), 7.39 (s, 1H), 7.32-7.30 (m, 1H), 7.26 (d, J=8.0 Hz, 1H), 6.62-6.58 (m, 2H), 4.90 (s, 2H), 4.70 (s, 2H), 4.19 (d, J=11.2 Hz, 1H), 3.91 (d, J=11.2 Hz, 1H), 3.92-3.78 (m, 5H), 3.55-3.51 (m, 5H), 2.79-2.72 (m, 2H), 2.56-2.49 (m, 2H), 1.74 (s, 3H) ppm.

Chiral SFC: AD-3_5CM_IPA(DEA)_40_3ML_T35.M, Rt=0.743 min, ee %=100%.

(R)-4-Cyano-4-methyl-N-((4-((1s,3S)-3-(6-morpholinopyridin-2-yl)cyclobutyl)pyridin-2-yl)methyl)isochromane-6-carboxamide LCMS (ESI) m/z: $[M+H]^+$=524.2

$^1H$ NMR (400 MHz, MeOD) δ=8.40 (d, J=4.8 Hz, 1H), 8.10 (d, J=1.2 Hz, 1H), 7.86-7.83 (m, 1H), 7.44-7.41 (m, 1H), 7.36 (s, 1H), 7.27-7.24 (m, 2H), 6.58-6.53 (m, 2H), 4.90 (s, 1H), 4.66 (m, 2H), 4.18 (d, J=11.2 Hz, 1H), 3.91 (d, J=11.2 Hz, 1H), 3.76-3.73 (m, 4H), 3.56-3.42 (m, 6H), 2.72-2.64 (m, 2H), 2.50-2.42 (m, 2H), 1.72 (s, 3H) ppm.

Chiral SFC: AD-3_5CM_IPA(DEA)_40_3ML_T35.M, Rt=1.100 mins, ee %=100%.

The following examples in Table 11 were prepared using standard chemical manipulations and procedures similar to those used for the preparation of Examples 11 and 12.

TABLE 11

| Compounds of the Invention | | |
|---|---|---|
| # | LCMS (m/z) | 1H NMR |
| 76 | 482.4 | 1H NMR (400 MHz, DMSO-d6) δ = 8.48-8.39 (m, 1H), 8.27-8.19 (m, 1H), 8.12 (d, J = 1.6 Hz, 1H), 7.87-7.85 (m, 1H), 7.52-7.49 (m, 1H), 7.42 (s, 1H), 7.33-7.32 (m, 1H), 7.27 (d, J = 8.0 Hz, 1H), 6.60-6.56 (m, 2H), 4.93 (br s, 2H), 4.71 (s, 2H), 4.20-4.17 (m, 1H), 3.91 (d, J = 11.6 Hz, 1H), 3.84-3.80 (m, 1H), 3.65-3.59 (m, 1H), 3.13 (s, 6H), 2.77-2.75 (m, 2H), 2.60-2.55 (m, 2H), 1.74 (s, 3H) ppm |
| 77 | 479.3 | 1H NMR (400 MHz, DMSO-d6) δ = 8.44 (d, J = 5.2 Hz, 1H), 8.12 (d, J = 1.6 Hz, 1H), 7.87-7.85 (m, 1H), 7.55-7.51 (m, 1H), 7.41 (s, 1H), 7.32 (d, J = 5.4 Hz, 1H), 7.26 (d, J = 8.0 Hz, 1H), 7.05-6.97 (m, 2H), 4.89 (s, 2H), 4.71 (s, 2H), 4.19 (d, J = 11.6 Hz, 1H), 3.91 (d, J = 11.6 Hz, 1H), 3.79-3.75 (m, 1H), 3.66-3.64 (m, 1H), 2.74-2.72 (m, 2H), 2.58-2.55 (m, 2H), 2.06-2.01 (m, 1H), 1.74 (s, 3H), 1.00-0.95 (m, 4H) ppm |
| 78 | 479.3 | 1H NMR (400 MHz, DMSO-d6) δ = 8.42 (d, J = 4.8 Hz, 1H), 8.12 (d, J = 2.0 Hz, 1H), 7.87-7.85 (m, 1H), 7.55-7.50 (m, 1H), 7.38 (s, 1H), 7.31-7.30 (m, 1H), 7.26 (d, J = 8.4 Hz, 1H), 6.99-6.95 (m, 2H), 4.90 (br s, 2H), 4.70 (s, 2H), 4.19 (d, J = 11.6 Hz, 1H), 3.91 (d, J = 11.6 Hz, 1H), 3.62-3.55 (m, 2H), 2.75-2.70 (m, 2H), 2.47-2.42 (m, 2H), 2.05-2.02 (m, 1H), 1.73 (s, 3H), 0.95-0.93 (m, 4H) ppm |
| 81 | 552.3 | 1H NMR (400 MHz, DMSO-d6) δ = 9.22-9.20 (m, 1H), 8.52-8.43 (m, 1H), 8.39 (s, 1H), 8.14 (d, J = 1.6 Hz, 1H), 7.89-7.87 (m, 1H), 7.48-7.44 (m, 1H), 7.28-7.26 (m, 3H), 6.66-6.57 (m, 2H), 4.91-4.79 (m, 2H), 4.64-4.55 (m, 2H), 4.22-4.16 (m, 3H), 3.85 (d, J = 11.2 Hz, 1H), 3.68-3.48 (m, 5H), 2.68-2.62 (m, 2H), 2.46-2.34 (m, 4H), 1.68 (s, 3H), 1.14 (d, J = 6.4 Hz, 6H) ppm |
| 82 | 552.3 | 1H NMR (400 MHz, DMSO-d6) δ = 9.20-9.17 (m, 1H), 8.44 (d, J = 4.8 Hz, 1H), 8.36 (s, 1H), 8.13 (d, J = 1.6 Hz, 1H), 7.89-7.87 (m, 1H), 7.45-7.41 (m, 1H), 7.28-7.24 (m, 3H), 6.65 (d, J = 8.4 Hz, 1H), 6.55 (d, J = 7.2 Hz, 1H), 4.91-4.80 (m, 2H), 4.61-4.56 (m, 2H), 4.23-4.14 (m, 3H), 3.86 (d, J = 11.6 Hz, 1H), 3.64-3.58 (m, 2H), 3.47 (br d, J = 7.6 Hz, 2H), 2.64-2.59 (m, 2H), 2.39-2.31 (m, 4H), 1.68 (s, 3H), 1.15 (d, J = 6.0 Hz, 6H) ppm |

Examples 13 and 14: (R)-4-Cyano-N-((4-((1r,3R)-3-(3-methoxyphenyl)cyclobutyl)pyridin-2-yl)methyl)-4-methylisochromane-6-carboxamide and (R)-4-cyano-N-((4-((1s,3S)-3-(3-methoxyphenyl)cyclobutyl)pyridin-2-yl)methyl)-4-methylisochromane-6-carboxamide

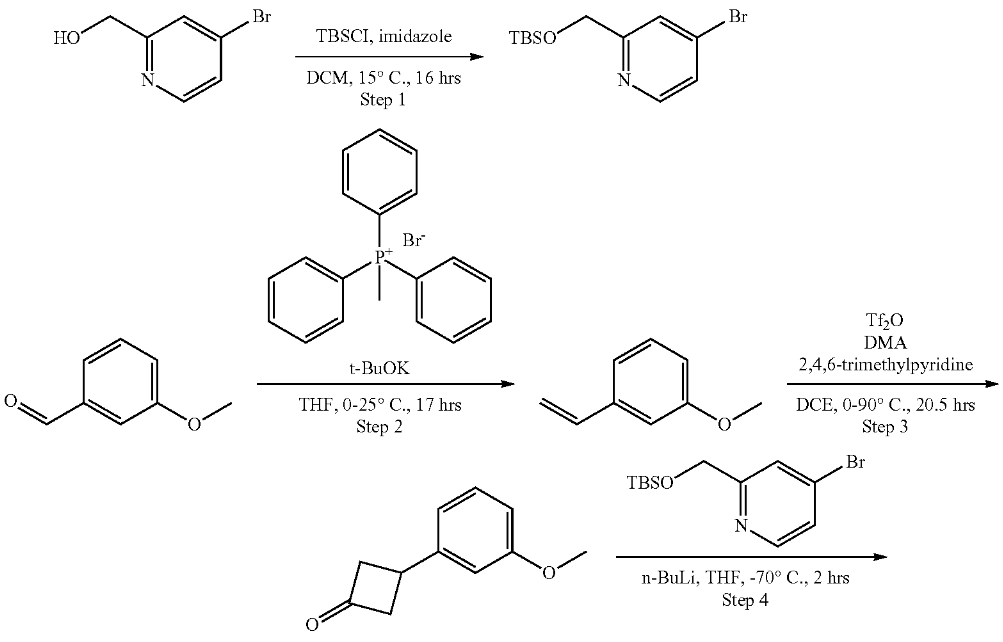

-continued
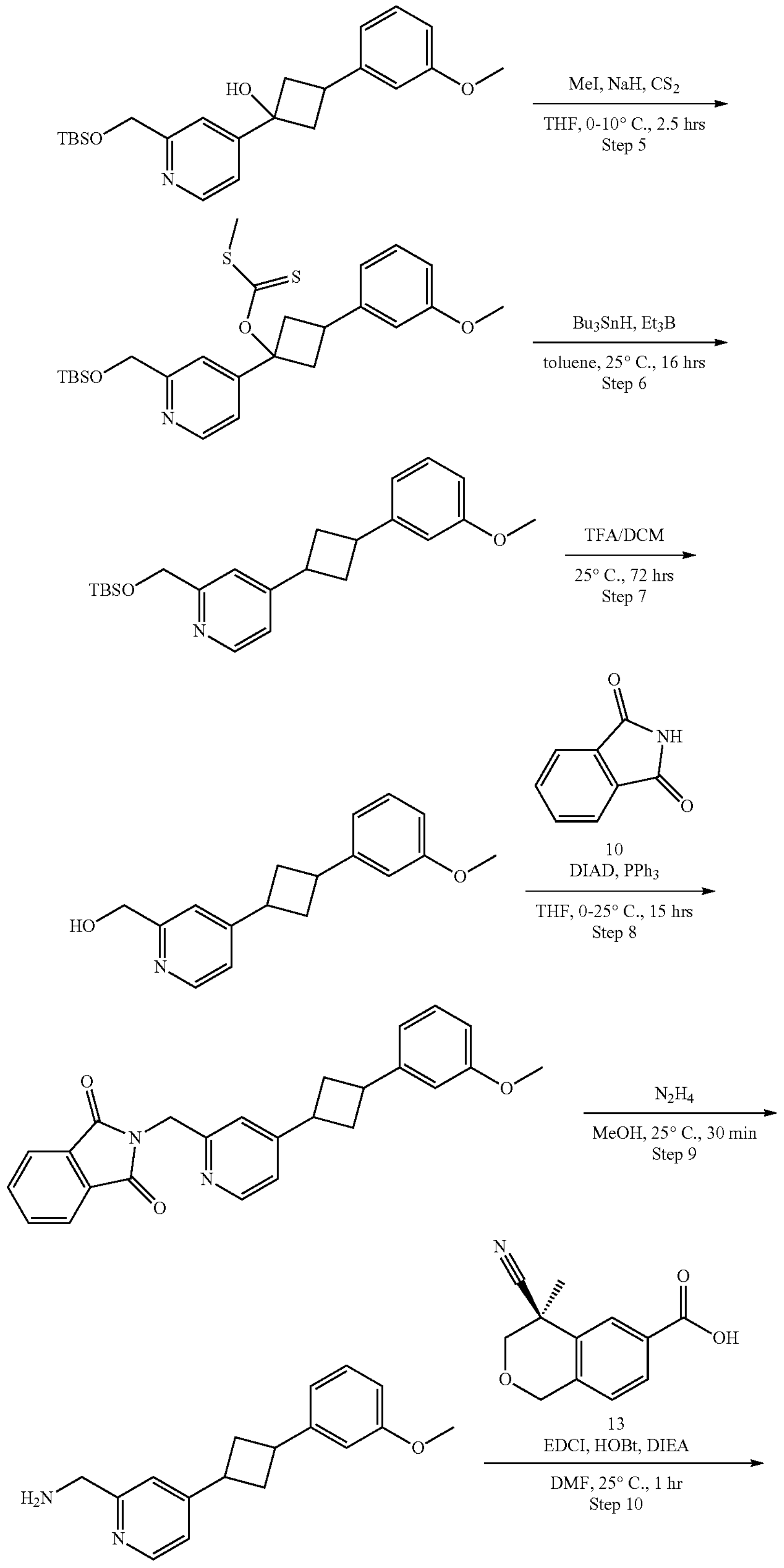

-continued

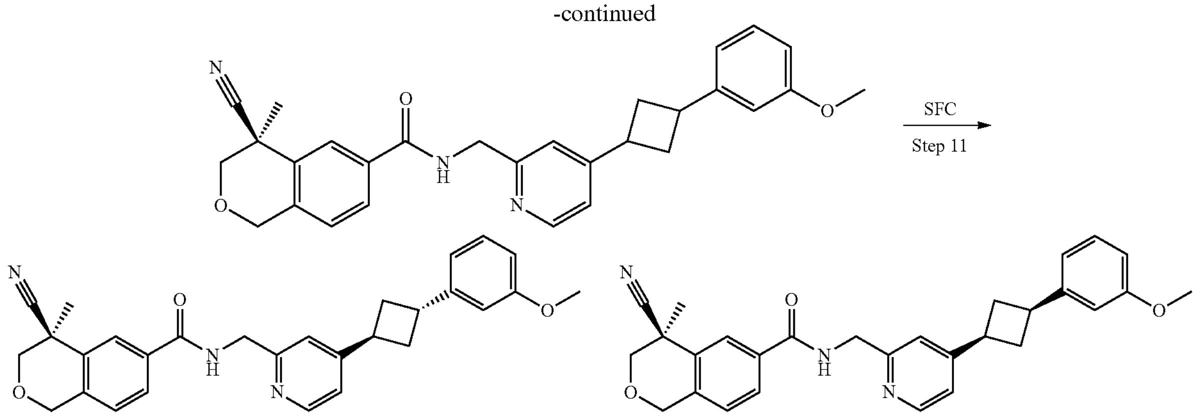

Step 1: 4-Bromo-2-(((tert-butyldimethylsilyl)oxy)methyl)pyridine

To a mixture of (4-bromo-2-pyridyl)methanol (3 g, 15.96 mmol) and imidazole (1.63 g, 23.93 mmol) in DCM (75 mL) was added TBSCl (2.89 g, 19.15 mmol, 2.35 mL) at 15° C. The mixture was stirred at 15° C. for 16 hrs. The mixture was filtered and the mother liquor was concentrated under reduced pressure. The residue was purified by silica gel chromatography (PE/EA=20/1-5/1) and to afford the title compound (5.4 g, crude) as a yellow oil.

LCMS (ESI) m/z: $[^{79}BrM+H]^+$=302.2.

$^1$H NMR (400 MHz, $CDCl_3$) δ=8.32 (d, J=5.2 Hz, 1H), 7.69 (d, J=0.8 Hz, 1H), 7.35-7.27 (m, 1H), 4.82 (s, 2H), 0.98 (s, 9H), 0.14 (s, 6H) ppm.

Step 2: 1-Methoxy-3-vinylbenzene

To a mixture of methyltriphenylphosphonium bromide (25.19 g, 70.51 mmol) in THF (100 mL) was added t-BuOK (8.57 g, 76.39 mmol) in several portions at 0° C. under $N_2$. The mixture was stirred at 0° C. for 1 hr under $N_2$. Then 3-methoxybenzaldehyde (8 g, 58.76 mmol, 7.14 mL) was added dropwise at 0° C. under $N_2$. The mixture was stirred at 25° C. for 16 hr. The mixture was diluted with PE (100 mL) and filtered. The mother liquor was concentrated under reduced pressure and the residue was purified by silica gel chromatography (PE–PE/EA=100/1) to afford the title compound (4 g, 29.81 mmol, 50.7% yield) as a yellow oil.

$^1$H NMR (400 MHz, $CDCl_3$) δ=7.27-7.22 (m, 1H), 7.02 (d, J=7.6 Hz, 1H), 6.98-6.94 (m, 1H), 6.84-6.81 (m, 1H), 6.73-6.66 (m, 1H), 5.78-5.73 (m, 1H), 5.26 (d, J=10.8 Hz, 1H), 3.83 (s, 3H) ppm.

Step 3: 3-(3-Methoxyphenyl)cyclobutan-1-one

Trifluoromethanesulfonic anhydride (14.72 g, 52.17 mmol, 8.61 mL) was added dropwise at 0° C. under $N_2$ to a mixture of DMA (3.90 g, 44.72 mmol, 4.16 mL) and DCE (50 mL). The mixture was stirred at 0° C. for 30 min. A mixture of 1-methoxy-3-vinylbenzene (5 g, 37.26 mmol, 5.17 mL) and 2,4,6-trimethylpyridine (6.32 g, 52.17 mmol, 6.89 mL) in DCE (25 mL) was then added dropwise under $N_2$. The mixture was stirred at 90° C. for 16 hrs. Then the mixture was concentrated to afford a residue which was dissolved in $CCl_4$ (50 mL) and $H_2O$ (50 mL). The mixture was stirred at 90° C. for 4 hrs. The reaction mixture was diluted with $H_2O$ (100 mL) and extracted with DCM (100 mL*2). The combined organic layers were dried over anhydrous $Na_2SO_4$, filtered and concentrated under reduced pressure. The residue was purified by silica gel chromatography (PE–PE/EA=20/1) to afford the title compound (3.2 g, 18.16 mmol, 48.7% yield) as a yellow oil.

$^1$H NMR (400 MHz, $CDCl_3$) δ=7.32-7.28 (m, 1H), 6.91 (d, J=7.6 Hz, 1H), 6.88-6.78 (m, 2H), 3.83 (s, 3H), 3.71-3.65 (m, 1H), 3.56-3.44 (m, 2H), 3.33-3.22 (m, 2H) ppm.

Step 4: 1-(2-(((tert-Butyldimethylsilyl)oxy)methyl)pyridin-4-yl)-3-(3-methoxyphenyl)cyclobutan-1-ol To a mixture of 4-bromo-2-(((tert-butyldimethylsilyl)oxy)methyl)pyridine (3.29 g, 10.90 mmol) in THF (30 mL) was added n-BuLi (2.5 M, 5.45 mL) dropwise at −70° C. The mixture was stirred at −70° C. for 1 hr. A solution of 3-(3-methoxyphenyl)cyclobutan-1-one (1.6 g, 9.08 mmol) in THF (10 mL) was then added dropwise at −70° C. The mixture was stirred at −70° C. for 1 hr. The reaction mixture was added dropwise to $H_2O$ (150 mL) and extracted with EA (100 mL*2). The combined organic layers were dried over anhydrous $Na_2SO_4$, filtered and concentrated under reduced pressure. The residue was purified by silica gel chromatography (PE/EA=10/1-2/1) to afford the title compound (1.6 g, 4.00 mmol, 44.1% yield) as a yellow solid.

LCMS (ESI) m/z: $[M+H]^+$=400.1.

$^1$H NMR (400 MHz, $CDCl_3$) δ=8.56 (d, J=5.2 Hz, 1H), 7.79 (d, J=1.2 Hz, 1H), 7.43-7.40 (m, 1H), 7.30-7.27 (m, 1H), 6.90 (d, J=7.6 Hz, 1H), 6.86-6.83 (m, 1H), 6.80-6.77 (m, 1H), 4.90 (s, 2H), 3.83 (s, 3H), 3.27-3.16 (m, 1H), 3.06-2.94 (m, 2H), 2.66-2.55 (m, 2H), 2.19 (s, 1H), 0.99 (s, 9H), 0.16 (s, 6H) ppm.

Step 5: O-(1-(2-(((tert-Butyldimethylsilyl)oxy)methyl)pyridin-4-yl)-3-(3-methoxyphenyl)cyclobutyl)S-methyl carbonodithioate To a mixture of NaH (250.23 mg, 6.26 mmol, 60% purity) in THF (8 mL) was added a solution of 1-(2-(((tert-Butyldimethylsilyl)oxy)methyl)pyridin-4-yl)-3-(3-methoxyphenyl)cyclobutan-1-ol (1 g, 2.50 mmol) in THF (12 mL) dropwise at 0° C. under $N_2$. The mixture was stirred at 10° C. for 30 min under $N_2$. Then $CS_2$ (1.02 g, 13.39 mmol, 809.05 uL) was added dropwise to the mixture at 0° C. The mixture was stirred at 10° C. for 1 hr. Then MeI (923.53 mg, 6.51 mmol, 405.06 uL) was added to the mixture dropwise at 0° C. The mixture was stirred at 10° C. for 1 hr. The reaction mixture was quenched with MeOH (2 mL), diluted with $H_2O$ (40 mL) and extracted with EA (30 mL*3). The combined organic layers were dried over anhydrous $Na_2SO_4$, filtered and concentrated. The residue was purified by silica gel chromatography (PE/EA=10/1-3/1) to afford the title compound (1.08 g, 2.21 mmol, 88.1% yield) as a yellow solid.

LCMS (ESI) m/z: $[M+H]^+$=490.5.

$^1H$ NMR (400 MHz, $CDCl_3$) δ=8.52 (d, J=5.2 Hz, 1H), 7.65 (d, J=0.8 Hz, 1H), 7.26-7.23 (m, 2H), 6.87 (d, J=7.6 Hz, 1H), 6.82-6.78 (m, 2H), 4.88 (s, 2H), 3.83 (s, 3H), 3.44-3.34 (m, 1H), 3.23-3.18 (m, 2H), 2.93-2.86 (m, 2H), 2.50 (s, 3H), 0.99 (s, 9H), 0.14 (s, 6H) ppm.

Step 6: 2-(((tert-Butyldimethylsilyl)oxy)methyl)-4-(3-(3-methoxyphenyl)cyclobutyl)pyridine To a mixture of O-(1-(2-(((tert-butyldimethylsilyl)oxy)methyl)pyridin-4-yl)-3-(3-methoxyphenyl)cyclobutyl)S-methyl carbonodithioate (1.08 g, 2.21 mmol) in toluene (11 mL) was added $Bu_3SnH$ (1.93 g, 6.62 mmol, 1.75 mL) and triethylborane (1 M, 6.62 mL) at 25° C. The mixture was stirred at 25° C. for 16 hrs. The mixture was poured into saturated KF aqueous solution (30 mL) and stirred at 15° C. for 30 min. The mixture was then extracted with EA (30 mL*3). The combined organic layers were washed with brine (30 mL), dried over anhydrous $Na_2SO_4$, filtered and concentrated under reduced pressure. The residue was purified by silica gel chromatography (PE/EA=20/1-5/1) to afford the title compound (740 mg, 1.88 mmol, 85.0% yield) as a yellow oil.

LCMS (ESI) m/z: $[M+H]^+$=384.2.

Step 7: (4-(3-(3-Methoxyphenyl)cyclobutyl)pyridin-2-yl)methanol

A mixture of 2-(((tert-butyldimethylsilyl)oxy)methyl)-4-(3-(3-methoxyphenyl)cyclobutyl)pyridine (740 mg, 1.93 mmol) in DCM (4 mL) and TFA (12.32 g, 108.05 mmol, 8 mL) was stirred at 25° C. for 72 hrs. The mixture was poured into $H_2O$ (50 mL) and the pH adjusted to 9 with $NaHCO_3$. The mixture was extracted with DCM (30 mL*2). The combined organic layers were dried over anhydrous $Na_2SO_4$, filtered and concentrated under reduced pressure. The residue was purified by silica gel chromatography (PE/EA=5/1–EA) to afford the title compound (470 mg, 1.75 mmol, 90.5% yield) as a yellow oil.

LCMS (ESI) m/z: $[M+H]^+$=270.0.

Step 8: 2-((4-(3-(3-Methoxyphenyl)cyclobutyl)pyridin-2-yl)methyl)isoindoline-1,3-dione To a mixture of (4-(3-(3-methoxyphenyl)cyclobutyl)pyridin-2-yl)methanol (200 mg, 742.56 umol), isoindoline-1,3-dione (163.88 mg, 1.11 mmol) and $PPh_3$ (292.15 mg, 1.11 mmol) in THE (4 mL) was added DIAD (225.23 mg, 1.11 mmol, 216.57 uL) dropwise at 0° C. under $N_2$. The mixture was stirred at 25° C. for 15 hrs. The mixture was poured into water (30 mL) and extracted with ethyl acetate (20 mL*3). The combined organic phase was washed with brine (20 mL), dried with anhydrous $Na_2SO_4$, filtered and concentrated. The residue was purified by silica gel chromatography (PE/EA=10/1-1/1) to afford the title compound (245 mg, 582.96 umol, 78.5% yield) as a yellow oil.

LCMS (ESI) m/z: $[M+H]^+$=399.3.

$^1H$ NMR (400 MHz, $CDCl_3$) δ=8.50-8.39 (m, 1H), 7.94-7.86 (m, 2H), 7.80-7.69 (m, 2H), 7.26-6.70 (m, 6H), 5.04-4.98 (m, 2H), 3.87-3.77 (m, 3H), 3.69-3.41 (m, 2H), 2.86-2.15 (m, 4H) ppm.

Step 9: (4-(3-(3-Methoxyphenyl)cyclobutyl)pyridin-2-yl)methanamine

To a mixture of 2-((4-(3-(3-methoxyphenyl)cyclobutyl)pyridin-2-yl)methyl)isoindoline-1,3-dione (245 mg, 614.88 umol) in MeOH (3 mL) was added $NH_2NH_2 \cdot H_2O$ (307.81 mg, 6.15 mmol, 298.84 uL). The mixture was stirred at 25° C. for 30 min. The mixture was poured into $H_2O$ (20 mL) and extracted with EA (20 mL*3). The combined organic layers were dried over anhydrous $Na_2SO_4$, filtered and concentrated under reduced pressure to afford the title compound (170 mg, crude) as a yellow oil.

LCMS (ESI) m/z: $[M+H]^+$=269.2.

Step 10: (R)-4-Cyano-N-((4-(3-(3-methoxyphenyl)cyclobutyl)pyridin-2-yl)methyl)-4-methylisochromane-6-carboxamide To a mixture of (4-(3-(3-methoxyphenyl)cyclobutyl)pyridin-2-yl)methanamine (80 mg, 298.12 umol) (4R)-4-cyano-4-methyl-isochromane-6-carboxylic acid (64.76 mg, 298.12 umol), EDCI (85.72 mg, 447.17 umol) and HOBt (60.42 mg, 447.17 umol) in DMF (1.5 mL) was added DIEA (115.59 mg, 894.35 umol, 155.78 uL). The mixture was stirred at 25° C. for 1 hr. The mixture was poured into $H_2O$ (15 mL) and extracted with EA (10 mL*2). The combined organic layer was washed with brine (10 mL), dried over anhydrous $Na_2SO_4$, filtered and concentrated under reduced pressure. The residue was purified by silica gel chromatography (PE/EA=5/1–EA) to afford the title compound (85 mg, 175.04 umol, 58.7% yield) as a yellow solid.

LCMS (ESI) m/z: $[M+H]^+$=468.4.

Step 11: (R)-4-Cyano-N-((4-((1r,3R)-3-(3-methoxyphenyl)cyclobutyl)pyridin-2-yl)methyl)-4-methylisochromane-6-carboxamide and (R)-4-cyano-N-((4-((1s,3S)-3-(3-methoxyphenyl)cyclobutyl)pyridin-2-yl)methyl)-4-methylisochromane-6-carboxamide (R)-4-Cyano-N-((4-(3-(3-methoxyphenyl)cyclobutyl)pyridin-2-yl)methyl)-4-methylisochromane-6-carboxamide (85 mg, 181.80 umol) was separated by SFC (column: DAICEL CHIRALCEL OD (250 mm*30 mm, 10 um); mobile phase: [0.1% $NH_3H_2O$IPA]; B %: 50%-50%, 5.0 min; 30 min). The mobile phase (Peak 1, Rt=0.487 min) was concentrated under reduced pressure to afford a yellow solid. The yellow solid was purified by reverse phase column (0.1% FA condition). The eluent was concentrated under reduced pressure to remove MeCN and lyophilized to afford (R)-4-cyano-N-((4-((1s,3S)-3-(3-methoxyphenyl)cyclobutyl)pyridin-2-yl)methyl)-4-methylisochromane-6-carboxamide (34.42 mg, 73.62 umol, 40.5% yield, 100% purity) as a white solid. The mobile phase (Peak 2, Rt=0.679 min) was concentrated under reduced pressure to afford a yellow solid. The yellow solid was purified by reverse phase column (0.1% FA condition). The eluent was concentrated under reduced pressure to remove MeCN and lyophilized to afford: (R)-4-cyano-N-((4-((1r,3R)-3-(3-methoxyphenyl)cyclobutyl)pyridin-2-yl)methyl)-4-methylisochromane-6-carboxamide (14.46 mg, 30.93 umol, 17.01% yield) as a white solid.

(R)-4-Cyano-N-((4-((1s,3S)-3-(3-methoxyphenyl)cyclobutyl)pyridin-2-yl)methyl)-4-methylisochromane-6-carboxamide LCMS (ESI) m/z: [M+H]+=468.3.

$^1$H NMR (400 MHz, MeOD-d4) δ=8.40 (d, J=5.2 Hz, 1H), 8.11 (d, J=1.6 Hz, 1H), 7.86-7.83 (m, 1H), 7.34 (s, 1H), 7.28-7.21 (m, 2H), 7.18-7.14 (m, 1H), 6.81-6.80 (m, 1H), 6.77-6.70 (m, 2H), 4.90 (d, J=3.6 Hz, 2H), 4.69 (s, 2H), 4.19 (d, J=11.2 Hz, 1H), 3.91 (d, J=11.2 Hz, 1H), 3.75 (s, 3H), 3.61-3.48 (m, 2H), 2.86-2.74 (m, 2H), 2.26-2.15 (m, 2H), 1.73 (s, 3H) ppm.

Chiral SFC: AD-3_5CM_MEOH(DEA)_5_40_3ML_AT35.M, Rt=0.493 min, ee %=100%.

(R)-4-Cyano-N-((4-((1r,3R)-3-(3-methoxyphenyl)cyclobutyl)pyridin-2-yl)methyl)-4-methylisochromane-6-carboxamide LCMS (ESI) m/z: $[M+H]^+$=468.3.

$^1$H NMR (400 MHz, MeOD-d4) δ=8.46 (d, J=5.2 Hz, 1H), 8.14 (d, J=1.2 Hz, 1H), 7.90-7.87 (m, 1H), 7.46 (s, 1H), 7.37 (d, J=5.2 Hz, 1H), 7.32-7.21 (m, 2H), 6.92 (d, J=7.6 Hz, 1H), 6.87 (s, 1H), 6.78-6.75 (m, 1H), 4.92-4.91 (m, 2H), 4.74 (s, 2H), 4.20 (d, J=11.2 Hz, 1H), 3.93 (d, J=11.6 Hz, 1H), 3.81 (s, 3H), 3.73-3.61 (m, 2H), 2.72-2.58 (m, 4H), 1.76 (s, 3H) ppm.

Chiral SFC: Cellucoat-IPA+ACN(DEA)-50-3 mL-35T, Rt=0.639 min, ee %=100%.

The following examples in Table 12 were prepared using standard chemical manipulations and procedures similar to those used for the preparation of Examples 13 and 14.

TABLE 12

Compounds of the Invention

| # | LCMS (m/z) | 1H NMR |
|---|---|---|
| 70 | 468.4 | $^1$H NMR (400 MHz, MeOD) δ = 8.30 (d, J = 5.2 Hz, 1H), 8.01 (d, J = 1.6 Hz, 1H), 7.77-7.74 (m, 1H), 7.24 (s, 1H), 7.16-7.12 (m, 2H), 7.03 (d, J = 8.0 Hz, 2H), 6.70 (d, J = 8.8 Hz, 2H), 4.81-4.79 (m, 2H), 4.58 (s, 2H), 4.09 (d, J = 11.6 Hz, 1H), 3.81 (d, J = 11.6 Hz, 1H), 3.64 (s, 3H), 3.41-3.35 (m, 2H), 2.68-2.62 (m, 2H), 2.10-2.05 (m, 2H), 1.61 (s, 3H) ppm |
| 72 | 468.4 | 1H NMR (400 MHz, MeOD) δ = 8.44 (d, J = 4.8 Hz, 1H), 8.12 (d, J = 1.6 Hz, 1H), 7.87-7.85 (m, 1H), 7.43 (s, 1H), 7.34 (d, J = 4.8 Hz, 1H), 7.26 (d, J = 8.0 Hz, 1H), 7.23 (d, J = 8.4 Hz, 2H), 6.87 (d, J = 8.4 Hz, 2H), 4.91-4.90 (m, 2H), 4.71 (s, 2H), 4.19 (d, J = 11.2 Hz, 1H), 3.92 (d, J = 11.2 Hz, 1H), 3.76 (s, 3H), 3.66-3.57 (m, 2H), 2.60-2.57 (m, 4H), 1.73 (s, 3H) ppm |

Example 15: (R)-4-Cyano-4-methyl-N-((4-(6-methyl-5-oxo-3,4,5,6-tetrahydro-2,6-naphthyridin-2(1H)-yl)pyridin-2-yl)methyl)isochromane-6-carboxamide

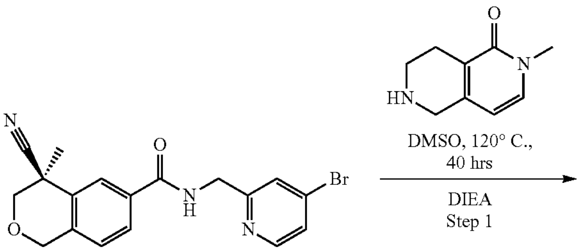

-continued

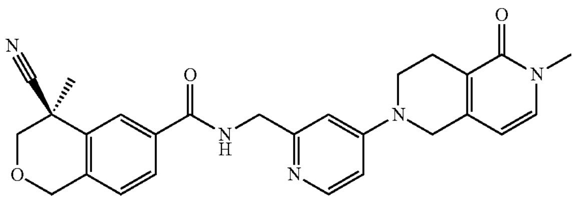

Step 1: (R)-4-cyano-4-methyl-N-((4-(6-methyl-5-oxo-3,4,5,6-tetrahydro-2,6-naphthyridin-2(1H)-yl)pyridin-2-yl)methyl)isochromane-6-carboxamide To a mixture of (4R)—N-[(4-bromo-2-pyridyl)methyl]-4-cyano-4-methyl-isochroman e-6-carboxamide (30 mg, 77.67 umol) in DMSO (1 mL) was added 2-methyl-5,6,7,8-tetrahydro-2,6-naphthyridin-1(2H)-one (43.22 mg, 155.34 umol, TEA salt) and DIEA (50.19 mg, 388.36 umol, 67.64 uL) at 30° C. The mixture was stirred at 120° C. for 40 hrs. The mixture was poured into $H_2O$ (10 mL) and extracted with EA (10 mL*2). The aqueous phase was purified by reverse phase column (0.1% FA condition). The eluent was concentrated under reduced pressure to remove MeCN and lyophilized to afford the title compound (10.33 mg, 20.04 umol, 25.8% yield, FA salt) as a yellow solid.

LCMS (ESI) m/z: $[M+H]^+$=470.2.

$^1$H NMR (400 MHz, MeOD) δ=8.65-8.41 (9, 1H), 8.18-8.09 (m, 2H), 7.87-7.84 (m, 1H), 7.50 (d, J=6.8 Hz, 1H), 7.27 (d, J=8.0 Hz, 1H), 7.04 (d, J=2.4 Hz, 1H), 6.98 (brd, J=6.4 Hz, 1H), 6.28 (d, J=7.2 Hz, 1H), 4.89 (d, J 2.6 Hz, 2H), 4.64 (m, 2H), 4.48 (m, 2H), 4.19 (d, J 11.6 Hz, 1H), 3.92 (d, J=11.6 Hz, 1H), 3.78-3.75 (m, 2H), 3.55 (s, 3H), 2.74-2.71 (m, 2H), 1.75 (s, 3H) ppm.

Chiral SFC: AD-3-MeOH+ACN(DEA)-50-3 mL-35T, Rt=0.893 m, ee %=100%.

The following examples in Table 13 were prepared using standard chemical manipulations and procedures similar to those used for the preparation of Example 15.

TABLE 13

Compounds of the Invention

| # | LCMS (m/z) | 1H NMR |
|---|---|---|
| 49 | 487.3 | 1H NMR (400 MHz, DMSO-d6) δ = 9.09-9.06 (m, 1H), 8.27 (s, 1H), 8.13-8.17 (m, 2H), 7.87-7.85 (m, 1H), 7.27 (d, J = 8.0 Hz, 1H), 6.86 (d, J = 2.4 Hz, 1H), 6.80-6.78 (m, 1H), 6.75-6.71 (m, 1H), 6.67-6.64 (m, 1H), 4.91-4.80 (m, 2H), 4.50-4.41 (m, 4H), 4.21 (d, J = 11.6 Hz, 1H), 3.86 (d, J = 11.6 Hz, 1H), 3.77 (s, 3H), 3.63-3.60 (m, 2H), 2.68-2.65 (m, 2H), 1.68 (s, 3H) ppm |
| 50 | 453.2 | 1HNMR (400 MHz, MeOD-d4) δ = 9.18-9.05 (m, 1H), 8.15 (s, 0.5H), 8.14 (d, J = 1.6 Hz, 1H), 8.10 (d, J = 6.0 Hz, 1H), 7.89-7.85 (m, 1H), 7.27 (d, J = 8.0 Hz, 1H), 7.15-7.07 (m, 4H), 6.80-6.72 (m, 2H), 4.93-4.78 (m, 2H), 4.54-4.41 (m, 2H), 4.21 (d, J = 11.6 Hz, 1H), 3.86 (d, J = 11.6 Hz, 1H), 3.68-3.61 (m, 4H), 2.93-2.85 (m, 4H), 1.69 (s, 3H) ppm |
| 51 | 487.3 | 1H NMR (400 MHz, DMSO-d6) δ = 9.09-9.06 (m, 1H), 8.27 (s, 1H), 8.13-8.17 (m, 2H), 7.87-7.85 (m, 1H), 7.27 (d, J = 8.0 Hz, 1H), 6.86 (d, J = 2.4 Hz, 1H), 6.80-6.78 (m, 1H), 6.75-6.71 (m, 1H), 6.67-6.64 (m, 1H), 4.91-4.80 (m, 2H), 4.50-4.41 (m, 4H), 4.21 (d, J = 11.6 Hz, 1H), 3.86 (d, J = 11.6 Hz, 1H), 3.77 (s, 3H), 3.63-3.60 (m, 2H), 2.68-2.65 (m, 2H), 1.68 (s, 3H) ppm |
| 53 | 426.4 | 1H NMR (400 MHz, DMSO-d6) δ = 9.17-9.14 (m, 1H), 8.64 (s, 1H), 8.52 (d, J = 4.8 Hz, 1H), 8.18-8.16 (m, 2H), 7.91-7.88 (m, 1H), 7.47 (d, J = 5.2 Hz, 1H), 7.29 (d, J = 8.0 Hz, 1H), 6.61 (d, J = 2.0 Hz, 1H), 6.56-6.54 (m, 1H), 4.92-4.81 (m, 2H), 4.70 (d, J = 4.8 Hz, 4H), 4.58-4.45 (m, 2H), 4.22 (d, J = 11.2 Hz, 1H), 3.88 (d, J = 11.6 Hz, 1H), 1.70 (s, 3H) ppm |
| 54 | 469.1 | 1HNMR (400 MHz, DMSO-d6) δ = 9.13-9.04 (m, 1H), 8.12 (s, 1H), 8.05 (d, J = 6.0 Hz, 1H), 7.91-7.83 (m, 1H), 7.54 (d, J = 7.2 Hz, 2H), 7.40-7.32 (m, 2H), 7.31-7.21 (m, 2H), 6.47-6.36 (m, 2H), 5.64-5.35 (m, 1H), 4.93-4.76 (m, 2H), 4.49-4.40 (m, 2H), 4.20 (d, J = 11.6 Hz, 1H), 3.84 (d, J = 11.6 Hz, 1H), 3.56-3.45 (m, 4H), 2.43-2.34 (m, 1H), 2.24-2.11 (m, 1H), 1.66 (s, 3H) ppm |
| 55 | 467.3 | 1H NMR (400 MHz, MeOD) δ = 8.10 (s, 1H), 8.02 (d, J = 7.2 Hz, 1H), 7.87-7.85 (m, 1H), 7.32-7.22 (m, 6H), 7.11-7.04 (m, 2H), 4.89 (d, J = 2.0 Hz, 2H), 4.65 (s, 2H), 4.33-4.25 (m, 1H), 4.24-4.13 (m, 2H), 3.93-3.91 (m, 1H), 3.30-3.23 (m, 2H), 2.89-2.72 (m, 1H), 2.09-2.06 (m, 1H), 2.02-1.86 (m, 2H), 1.71 (d, J = 5.2 Hz, 4H) ppm |
| 56 | 469.1 | 1HNMR (400 MHz, DMSO-d6) δ = 13.34-13.30 (m, 1H), 9.27-9.25 (m, 1H), 8.23-8.18 (m, 1H), 8.12 (d, J = 1.2 Hz, 1H), 7.88-7.86 (m, 1H), 7.31-7.20 (m, 4H), 6.91-6.85 (m, 2H), 4.92-4.78 (m, 4H), 4.64-4.62 (m, 2H), 4.21 (d, J = 11.6 Hz, 1H), 3.87-3.85(m, 3H), 3.80 (s, 3H), 2.87-2.84 (m, 2H), 1.68 (s, 3H) ppm |
| 57 | 445.3 | 1H NMR (400 MHz, DMSO-d6) δ = 9.27-9.24 (m, 1H), 8.24-8.06 (m, 2H), 7.90-7.88 (m, 1H), 7.30 (d, J = 8.0 Hz, 1H), 7.13 (br s, 1H), 7.08-6.99 (m, 1H), 5.00-4.76 (m, 2H), 4.57 (br d, J = 5.6 Hz, 2H), 4.30-4.15 (m, 2H), 4.02 (br d, J = 13.2 Hz, 1H), 3.86 (d, J = 11.6 Hz, 1H), 3.07-3.05 (m, 1H), 2.74-2.70 (m, 1H), 1.78-1.54 (m, 7H), 1.31-1.19 (m, 3H), 1.18-1.05 (m, 2H), 1.04-0.88 (m, 2H) ppm |
| 58 | 483.1 | 1HNMR (400 MHz, DMSO-d6) δ = 9.29 (s, 1H), 8.21-8.06 (m, 2H), 7.89 (d, J = 8.0 Hz, 1H), 7.50-7.36 (m, 5H), 7.29 (d, J = 8.0 Hz, 1H), 6.92-6.70 (m, 2H), 4.96-4.78 (m, 2H), 4.59 (d, J = 5.6 Hz, 2H), 4.22 (d, J = 11.2 Hz, 1H), 4.07 (d, J = 12.8 Hz, 1H), 3.86 (d, J = 11.6 Hz, 1H), 3.65 (d, J = 12.0 Hz, 2H), 3.59-3.51 (m, 1H), 2.92 (s, 3H), 2.72-2.65 (m, 1H), 2.42-2.31 (m, 1H), 1.68 (s, 3H) ppm |
| 59 | 478.1 | 1H NMR (400 MHz, DMSO-d6) δ = 9.16-9.12 (m, 1H), 8.18-8.10 (m, 2H), 7.89-7.86 (m, 1H), 7.67 (d, J = 3.2 Hz, 1H), 7.59-7.53 (m, 2H), 7.26 (d, J = 8.0 Hz, 1H), 7.19-7.12 (m, 1H), 7.10-7.01 (m, 1H), 6.53 (d, J = 3.2 Hz, 1H), 6.46 (d, J = 2.0 Hz, 1H), 6.42-6.40 (m, 1H), 5.68-5.54 (m, 1H), 4.93-4.75 (m, 2H), 4.56-4.40 (m, 4H), 4.28-4.18 (m, 3H), 3.85 (d, J = 11.6 Hz, 1H), 1.68 (s, 3H) ppm |
| 63 | 489.2 | 1H NMR (400 MHz, DMSO-d6) δ = 9.09-9.06 (m, 1H), 8.21-8.08 (m, 2H), 7.87 (d, J = 8.0 Hz, 1H), 7.45 (s, 1H), 7.41-7.32 (m, 2H), 7.27 (d, J = 8.0 Hz, 1H), 7.14-6.84 (m, 2H), 6.83-6.77 (m, 1H), 4.98-4.76 (m, 2H), 4.57 (s, 2H), 4.54-4.42 (m, 2H), 4.21 (d, J = 11.2 Hz, 1H), 3.86 (d, J = 11.2 Hz, 1H), 3.63-3.60 (m, 2H), 2.95 (s, 2H), 1.68 (s, 3H) ppm. |
| 66 | 457.1 | 1H NMR (400 MHz, MeOD) δ = 8.10 (d, J = 2.0 Hz, 1H), 8.04 (d, J = 5.6 Hz, 1H), 7.84-7.82 (m, 1H), 7.24 (d, J = 8.0 Hz, 1H), 7.18-7.17(m, 4H), 6.98-6.95 (m, 1H), 4.87 (s, 2H), 4.72 (d, J = 2.4 Hz, 2H), 4.54 (s, 2H), 4.19 (d, J = 11.6 Hz, 1H), 3.91 (d, J = 11.2 Hz, 1H), 3.73-3.70 (m, 2H), 3.00-2.97 (m, 2H), 1.73 (s, 3H) ppm. |
| 67 | 489.2 | 1H NMR (400 MHz, DMSO-d6) δ = 9.11-9.08 (m, 1H), 8.25 (s, 1H), 8.18-8.10 (m, 2H), 7.88-7.86 (m, 1H), 7.39 (d, J = 9.6 Hz, 3H), 7.27 (d, J = 8.0 Hz, 1H), 7.14-6.84 (m, 2H), 6.81-6.78 (m, 1H), 4.94-4.78 (m, 2H), 4.58-4.41 (m, 4H), 4.21 (d, J = 11.2 Hz, 1H), 3.86 (d, J = 11.6 Hz, 1H), 3.63-3.60 (m, 2H), 2.96-2.94 (m, 2H), 1.68 (s, 3H) ppm. |
| 68 | 443.3 | 1H NMR (400 MHz, MeOD) δ = 8.29 (br s, 1H), 8.11 (d, J = 1.6 Hz, 1H), 7.98 (d, J = 6.0 Hz, 1H), 7.86-7.84 (m, 1H), 7.38-7.36 (m, 2H), 7.33-7.31 (m, 2H), 7.25 (d, J = 8.0 Hz, 1H), 6.79-6.75 (m, 1H), 4.98 (d, J = 3.2 Hz, 4H), 4.88 (s, 2H), 4.73 (d, J = 2.0 Hz, 2H), 4.19 (d, J = 11.6 Hz, 1H), 3.91 (d, J = 11.6 Hz, 1H), 1.73 (s, 3H) ppm. |
| 75 | 440.3 | 1H NMR (400 MHz, MeOD) δ = 8.85 (d, J = 3.2 Hz, 1H), 8.11 (d, J = 1.6 Hz, 1H), 7.87-7.84 (m, 1H), 7.29-7.18 (m, 5H), 6.99 (d, J = 2.8 Hz, 1H), 4.89 (d, J = 2.8 Hz, 2H), 4.73 (s, 2H), 4.61 (s, 2H), 4.18 (d, J = 11.2 Hz, 1H), 3.91 (d, J = 11.6 Hz, 1H), 3.73-3.69 (m, 2H), 3.02-2.98 (m, 2H), 1.74 (s, 3H) ppm |

Example 16: (4R)-4-Cyano-N-((4-(3-fluoro-3-phenylpyrrolidin-1-yl)pyridin-2-yl)methyl)-4-methylisochromane-6-carboxamide

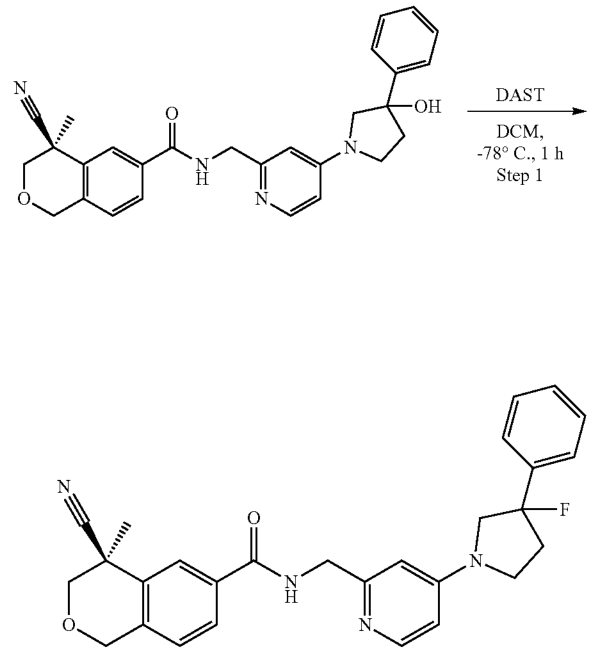

Step 1: (4R)-4-Cyano-N-((4-(3-fluoro-3-phenylpyrrolidin-1-yl)pyridin-2-yl)methyl)-4-methylisochromane-6-carboxamide To a solution of (4R)-4-cyano-N-((4-(3-hydroxy-3-phenylpyrrolidin-1-yl)pyridin-2-yl)methyl)-4-methylisochromane-6-carboxamide (20 mg, 42.69 umol) in DCM (0.5 mL) was added DAST (34.40 mg, 213.43 umol, 28.20 uL) at −78° C. The mixture was stirred at −78° C. for 1 hr then poured into water (30 mL) and extracted with EA (10 mL*3). The combined organic layers were washed with brine (10 mL), dried over $Na_2SO_4$, filtered and concentrated. The residue was purified by prep-HPLC (column: Phenomenex Gemini NX-C18 (75*30 mm*3 um); mobile phase: [water (10 mM $NH_4HCO_3$)-ACN]; B %: 38%-58%, 8 min). The product fraction was concentrated under vacuum to remove MeCN and lyophilized to give the title compound (3.55 mg, 7.27 umol, 17.04% yield) as a white solid.

LCMS (ESI) m/z: $[M+H]^+$=471.1.

$^1$HNMR (400 MHz, MeOD-$d_4$) δ=8.15-8.03 (m, 2H), 7.89-7.77 (m, 1H), 7.54 (d, J=7.6 Hz, 2H), 7.48-7.34 (m, 3H), 7.25 (d, J=8.4 Hz, 1H), 6.59 (s, 1H), 6.56-6.44 (m, 1H), 4.88 (br d, J=3.2 Hz, 3H), 4.17 (d, J=11.2 Hz, 1H), 3.96-3.79 (m, 3H), 3.78-3.58 (m, 3H), 2.74-2.47 (m, 2H), 1.72 (s, 3H) ppm.

Chiral SFC: IC-3-EtOH (DEA)-60-3 mL-35T.lcm; Rt=1.386 mins, Rt=1.826 mins.

Example 17: (R)-4-Cyano-N-((4-((3-cyanobenzyl)oxy)pyridin-2-yl)methyl)-4-methylisochromane-6-carboxamide

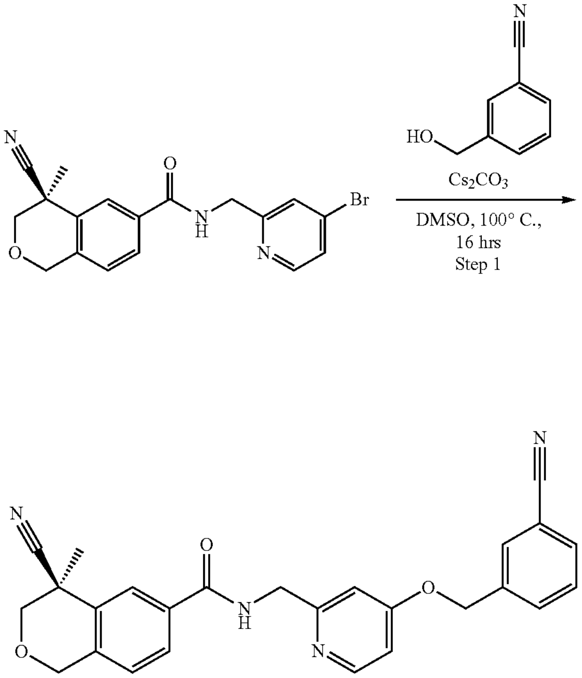

Step 1: (R)-4-Cyano-N-((4-((3-cyanobenzyl)oxy)pyridin-2-yl)methyl)-4-methylisochromane-6-carboxamide To a mixture of (R)—N-((4-bromopyridin-2-yl)methyl)-4-cyano-4-methylisochromane-6-carboxamide (100 mg, 258.91 umol) in DMSO (1 mL) was added $Cs_2CO_3$ (168.71 mg, 517.81 umol) and 3-(hydroxymethyl) benzonitrile (68.94 mg, 517.81 umol). The mixture was stirred at 100° C. for 16 hrs. Water (20 mL) was added and the mixture was extracted with EtOAc (20 mL*2). The combined organic phase was washed with brine (20 mL), dried over anhydrous $Na_2SO_4$, filtered and concentrated under vacuum. The residue was purified by prep. HPLC (FA condition) and the product fraction was concentrated under vacuum to remove MeCN followed by lyophilization to give the title compound (15.18 mg, 31.74 umol, 12.26% yield) as a white solid.

LCMS (ESI) m/z: $[M+H]^+$=439.1

$^1$H NMR (400 MHz, DMSO-d6) δ=9.18-9.15 (m, 1H), 8.36 (d, J=5.6 Hz, 1H), 8.12 (d, J=1.2 Hz, 1H), 7.90-7.86 (m, 2H), 7.81-7.76 (m, 2H), 7.59-7.55 (m, 1H), 7.27 (d, J=8.4 Hz, 1H), 6.97-6.95 (m, 2H), 5.23 (s, 2H), 4.91-4.80 (m, 2H), 4.54-4.52 (m, 2H), 4.21 (d, J=11.2 Hz, 1H), 3.85 (d, J=11.6 Hz, 1H), 1.68 (s, 3H) ppm.

Chiral SFC: Cellucoat-MeOH(DEA)-40-3 mL-35T.lcm, Rt=0.680 min, ee value=100%.

The following examples in Table 14 were prepared using standard chemical manipulations and procedures similar to those used for the preparation of Example 17.

TABLE 14

| Compounds of the Invention | | |
|---|---|---|
| # | LCMS (m/z) | 1H NMR |
| 64 | 439.1 | 1H NMR (400 MHz, MeOD) δ = 8.38-8.32 (m, 1 H), 8.12-8.08 (m, 1 H), 7.84-7.80 (m, 1 H), 7.69-7.63 (m, 2 H), 7.60-7.55 (m, 2 H), 7.30-7.25 (m, 1 H), 7.04-7.00 (m, 2 H), 5.35-5.29 (m, 2 H), 4.93-4.90 (m, 2 H), 4.66-4.63 (m, 2 H), 4.26-3.90 (m, 2 H), 1.75 (s, 3 H) ppm |

Example 18: (R)—N-((4-(Benzylthio)pyridin-2-yl)methyl)-4-cyano-4-methylisochromane-6-carboxamide

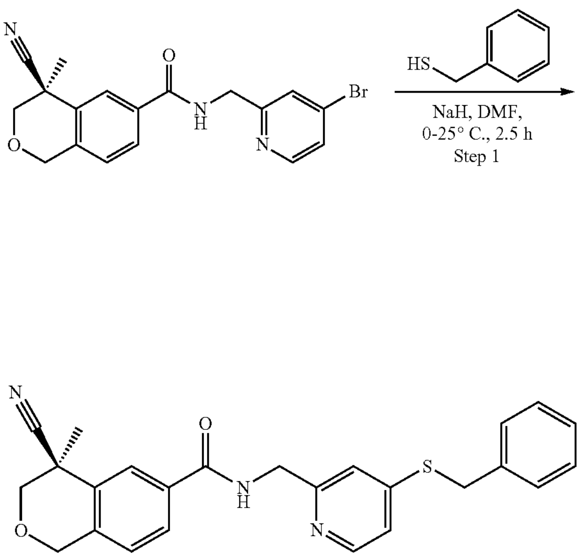

Step 1: (R)—N-((4-(Benzylthio)pyridin-2-yl)methyl)-4-cyano-4-methylisochromane-6-carboxamide To a solution of phenylmethanethiol (28.94 mg, 233.01 umol, 27.30 uL) in DMF (0.5 mL) was added NaH (8.70 mg, 217.48 umol, 60% purity) at 0° C. The reaction mixture stirred at 0° C. for 0.5 hr. (R)—N-((4-bromopyridin-2-yl)methyl)-4-cyano-4-methylisochromane-6-carboxamide (30 mg, 77.67 umol) was then added into the mixture. The reaction was stirred at 25° C. for 2 hrs. The mixture was poured into water (60 mL) and extracted with EA (30 mL*3). The combined organic layers were washed with brine (30 mL), dried over $Na_2SO_4$, filtered and concentrated. The crude product was purified by prep-TLC (PE/EA=0/1) and lyophilized to give the title compound (23.19 mg, 53.16 umol, 68.45% yield) as a white solid.

LCMS (ESI) m/z: $[M+H]^+$=430.0

$^1$HNMR (400 MHz, MeOD-$d_4$) δ=8.23 (d, J=5.6 Hz, 1H), 8.11 (d, J=1.6 Hz, 1H), 7.90-7.79 (m, 1H), 7.39-7.31 (m, 2H), 7.29-7.24 (m, 2H), 7.23-7.12 (m, 4H), 4.90 (d, J=4.0 Hz, 2H), 4.61 (s, 2H), 4.28 (s, 2H), 4.19 (d, J=11.6 Hz, 1H), 3.91 (d, J=11.2 Hz, 1H), 1.74 (s, 3H) ppm.

Chiral SFC: AD-3-MeOH+ACN (DEA)-60-3 mL-35T.lcm; Rt=0.585 mins, ee %=100%.

Example 19: (4R)-4-Cyano-N-((4-(1-(6-(difluoromethyl)pyridin-2-yl)pyrrolidin-3-yl)pyridin-2-yl)methyl)-4-methylisochromane-6-carboxamide

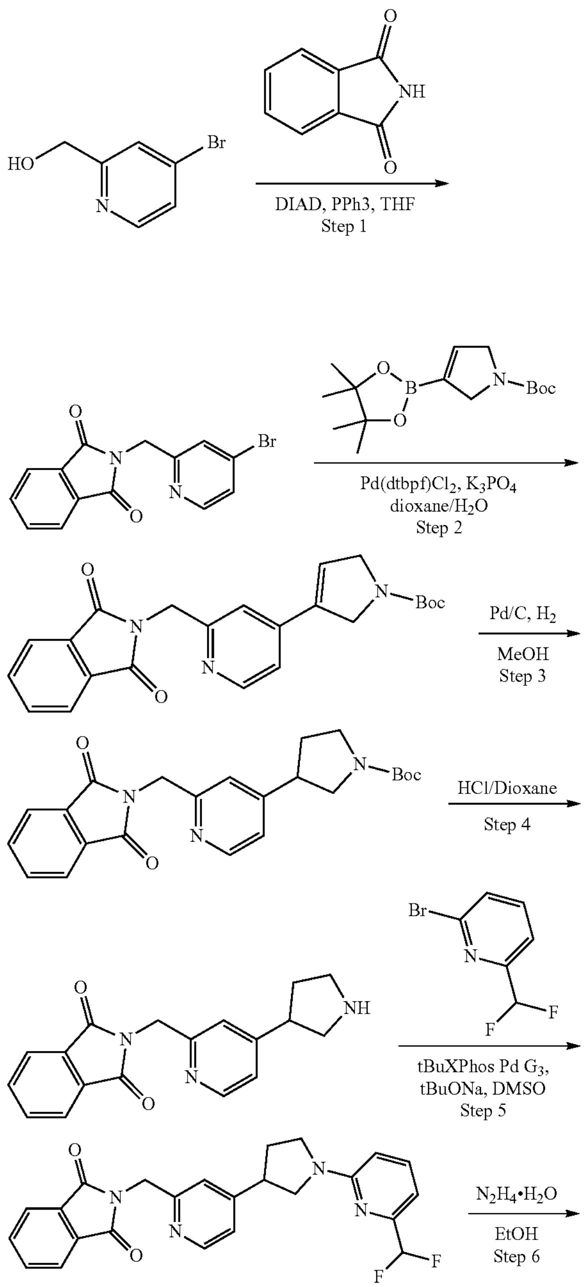

-continued

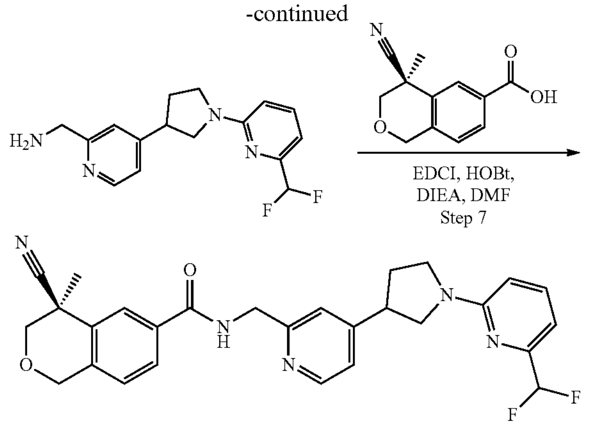

Step 1: 2-((4-Bromopyridin-2-yl)methyl)isoindoline-1,3-dione

To a solution of (4-bromopyridin-2-yl)methanol (20 g, 106.37 mmol), isoindoline-1,3-dione (23.48 g, 159.56 mmol) and $PPh_3$ (41.85 g, 159.56 mmol) in THF (400 mL) was added DIAD (32.26 g, 159.56 mmol) at 0° C. The resulting mixture was stirred at 30° C. for 2 hrs. The reaction mixture was poured into water (1000 mL) and EA (1000 mL), the solution was filtered and the filter cake was dried under vacuum to give the title compound (32 g, 100.90 mmol, 94.86% yield) as a white solid.

Step 2: tert-Butyl 3-(2-((1,3-dioxoisoindolin-2-yl)methyl)pyridin-4-yl)-2,5-dihydro-1H-pyrrole-1-carboxylate To a solution of 2-((4-bromopyridin-2-yl)methyl)isoindoline-1,3-dione (700 mg, 2.21 mmol) and tert-butyl 3-(4,4,5,5-tetramethyl-1,3,2-dioxaborolan-2-yl)-2,5-dihydro-1H-pyrrole-1-carboxylate (977.31 mg, 3.31 mmol) in dioxane (8 mL) and $H_2O$ (2 mL) was added [1,1'-bis(di-tert-butylphosphino)ferrocene]dichloropalladium(II) (143.86 mg, 220.72 umol) and $K_3PO_4$ (937.06 mg, 4.41 mmol) at 25° C. under $N_2$ atmosphere. The mixture was stirred for 2 hr at 60° C. Water (10 mL) was added and the mixture extracted with EA (20 mL*3). The combined organic layer was dried over $Na_2SO_4$, filtered and concentrated under vacuum. The residue was purified by column chromatography ($SiO_2$, Petroleum ether/Ethyl acetate=100/1 to 1/100) to give the title compound (890 mg, 2.20 mmol, 99.45% yield) as a yellow oil.

LCMS (ESI) m/z: $[M+H]^+$=406.0.

$^1$HNMR (400 MHz, MeOD-$d_4$) δ=8.43-8.37 (m, 1H), 7.93-7.88 (m, 2H), 7.86-7.81 (m, 2H), 7.46 (d, J=4.4 Hz, 1H), 7.36-7.33 (m, 1H), 6.66-6.58 (m, 1H), 4.99 (s, 2H), 4.55-4.43 (m, 2H), 4.36-4.27 (m, 2H), 1.51 (d, J=5.6 Hz, 9H) ppm.

Step 3: tert-Butyl 3-(2-((1,3-dioxoisoindolin-2-yl)methyl)pyridin-4-yl)pyrrolidine-1-carboxylate To a solution of tert-butyl 3-(2-((1,3-dioxoisoindolin-2-yl)methyl)pyridin-4-yl)-2,5-dihydro-1H-pyrrole-1-carboxylate (890 mg, 2.20 mmol) in MeOH (150 mL) was added Pd/C (100 mg, 220.35 umol, 10% purity) under $H_2$ atmosphere, then the mixture was stirred under hydrogen atmosphere (20 Psi) for 2 hrs at 25° C. The mixture was filtered and the filtrate was concentrated to give the title compound (890 mg, 2.18 mmol, 99.51% yield) as a yellow oil which was used directly in the next step.

LCMS (ESI) m/z: $[M+H]^+$=408.0.

Step 4: 2-((4-(Pyrrolidin-3-yl)pyridin-2-yl)methyl)isoindoline-1,3-dione hydrochloride To a solution of tert-butyl 3-(2-((1,3-dioxoisoindolin-2-yl)methyl)pyridin-4-yl)pyrrolidine-1-carboxylate (300 mg, 515.39 umol) in dioxane (3 mL) was added HCl/dioxane (4 M, 3.00 mL). The mixture was stirred at 25° C. for 0.5 hr and then concentrated to give the title compound (160 mg, 465.38 umol, 90.30% yield) as yellow oil which was used directly in the next step.

LCMS (ESI) m/z: $[M+H]^+$=308.0.

Step 5: 2-((4-(1-(6-(Difluoromethyl)pyridin-2-yl)pyrrolidin-3-yl)pyridin-2-yl)methyl)isoindoline-1,3-dione To a solution of 2-((4-(pyrrolidin-3-yl)pyridin-2-yl)methyl)isoindoline-1,3-dione hydrochloride (160 mg, 465.38 umol) and 2-bromo-6-(difluoromethyl) pyridine (387.20 mg, 1.86 mmol) in DMSO (2 mL) was added DIEA (601.45 mg, 4.65 mmol, 810.59 uL) at 25° C., then the mixture was stirred for 12 hrs at 140° C. Water (3 mL) was added and the mixture extracted with EA (5 mL*3). The combined organic layer was dried over $Na_2SO_4$, filtered and concentrated. The residue was purified by column chromatography ($SiO_2$, PE:EA=1:1, Rf=0.3) to give the title compound (200 mg, 460.37 umol, 98.92% yield) as a yellow solid.

LCMS (ESI) m/z: $[M+H]^+$=435.0.

Step 6: (4-(1-(6-(Difluoromethyl)pyridin-2-yl)pyrrolidin-3-yl)pyridin-2-yl)methanamine To a solution of 2-((4-(1-(6-(difluoromethyl)pyridin-2-yl)pyrrolidin-3-yl)pyridin-2-yl)methyl)isoindoline-1,3-dione (50 mg, 115.09 umol) in EtOH (0.5 mL) was added $N_2H_4{\cdot}H_2O$ (8.82 mg, 172.64 umol, 8.56 uL, 98% purity) at 25° C., then the mixture was stirred at 75° C. for 2 hrs. The mixture was filtered and the filtrate was concentrated to give the title compound (30 mg, 98.57 umol, 85.65% yield) as a yellow solid which was used directly in the next step.

LCMS (ESI) m/z: $[M+H]^+$=305.0.

Step 7: (4R)-4-Cyano-N-((4-(1-(6-(difluoromethyl)pyridin-2-yl)pyrrolidin-3-yl)pyridin-2-yl)methyl)-4-methylisochromane-6-carboxamide To a solution of (4-(1-(6-(difluoromethyl)pyridin-2-yl)pyrrolidin-3-yl)pyridin-2-yl)methanamine (20 mg, 65.72 umol), (R)-4-cyano-4-methylisochromane-6-carboxylic acid (14.27 mg, 65.72 umol) in DMF (0.2 mL) was added EDCI (25.20 mg, 131.43 umo), HOBt (17.76 mg, 131.43 umol) and DIEA (21.23 mg, 164.29 umol, 28.62 uL). The mixture was stirred at 25° C. for 1 hr. Water (3 mL) was added and the mixture extracted with EA (5 mL*3). The combined organic layer was dried over $Na_2SO_4$, filtered and concentrated. The crude product was purified by prep-HPLC (column: Phenomenex Synergi C18 150*25*10 um; mobile phase: [water (0.225% FA)-ACN]; B %: 33%-63%, 8.5 min) and lyophilized to give the title compound (8 mg, 15.77 umol, 24.00% yield) as a yellow solid.

LCMS (ESI) m/z: $[M+H]^+$=504.3.

$^1$HNMR (400 MHz, MeOD-$d_4$) δ=8.46 (d, J=5.2 Hz, 1H), 8.11 (d, J=1.6 Hz, 1H), 7.84-7.80 (m, 1H), 7.61-7.55 (m, 1H), 7.39 (d, J=5.6 Hz, 1H), 7.32 (d, J=5.2 Hz, 1H), 7.24 (d, J=8.0 Hz, 1H), 6.84-6.81 (m, 1H), 6.60-6.30 (m, 2H), 4.91 (d, J=4.0 Hz, 2H), 4.71 (s, 2H), 4.23-4.19 (m, 1H), 3.98-3.90 (m, 2H), 3.70-3.54 (m, 4H), 2.55-2.44 (m, 1H), 2.21-2.08 (m, 1H), 1.75 (d, J=1.6 Hz, 3H) ppm.

Chiral SFC: AD-3-MeOH+ACN (DEA)-40-3ML-35T.lcm; Rt=0.974 min/Rt=1.137 min.

The following examples in Table 15 were prepared using standard chemical manipulations and procedures similar to those used for the preparation of Example 19.

TABLE 15

| Compounds of the Invention | | |
|---|---|---|
| # | LCMS (m/z) | 1H NMR |
| 62 | 453.2 | 1HNMR (400 MHz, CDCl3) δ = 8.51 (d, J = 5.2 Hz, 1H), 8.02 (d, J = 1.6 Hz, 1H), 7.80-7.76 (m, 1H), 7.61-7.53 (m, 1H), 7.26 (d, J = 4.0 Hz, 2H), 7.17-7.12 (m, 2H), 6.76-6.71 (m, 1H), 6.62 (d, J = 8.0 Hz, 2H), 4.88 (s, 2H), 4.76 (d, J = 4.8 Hz, 2H), 4.14 (d, J = 11.2 Hz, 1H), 3.94 (d, J = 11.6 Hz, 1H), 3.77-3.72 (m, 1H), 3.58-3.51 (m, 2H), 3.50-3.39 (m, 2H), 2.53-2.42 (m, 1H), 2.18-2.11 (m, 1H), 1.77 (s, 3H) ppm |

Example 20: (R)-4-Cyano-N-((4-((3-((2-methoxyethyl)carbamoyl)phenyl)ethynyl)pyridin-2-yl)methyl)-4-methylisochromane-6-carboxamide

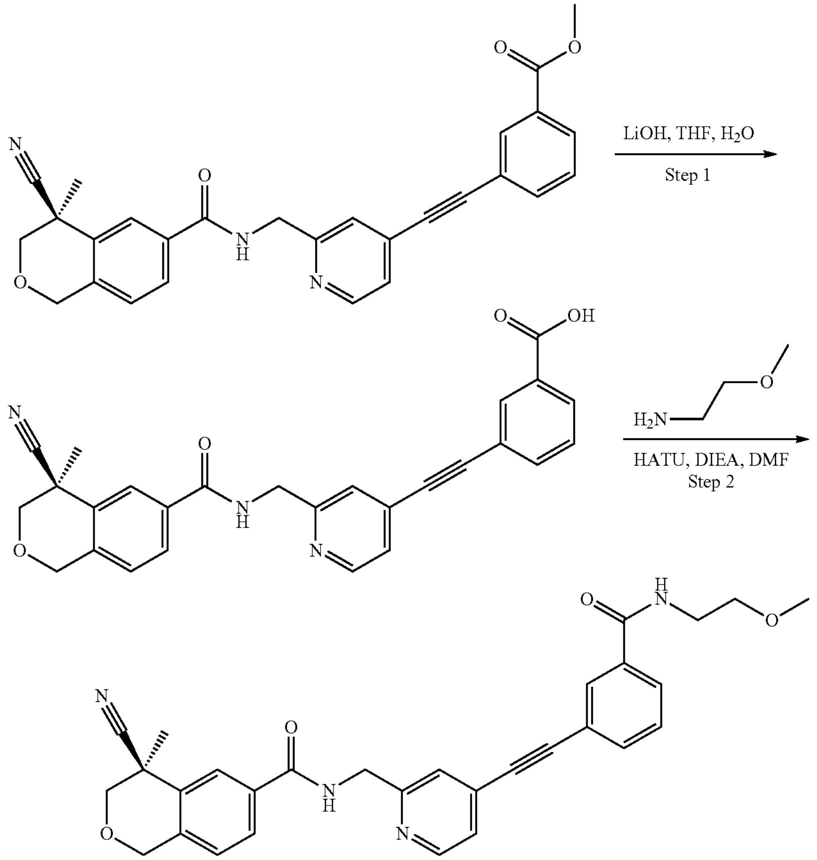

Step 1: (R)-3-((2-((4-Cyano-4-methylisochromane-6-carboxamido)methyl)pyridin-4-yl)ethynyl)benzoic acid A solution of methyl (R)-3-((2-((4-cyano-4-methylisochromane-6-carboxamido)methyl)pyridin-4-yl)ethynyl) benzoate (226.00 mg, 0.485 mmol, 1.00 equiv), LiOH·$H_2O$ (61.12 mg, 1.456 mmol, 3.00 equiv) and $H_2O$ (1.00 mL) in THF (5.00 mL) was stirred overnight at room temperature. The mixture was acidified to pH 5 with 2M HCl (aq.). The resulting mixture was diluted with water (30 mL) and extracted with EtOAc (3×40 mL). The combined organic layers were washed with brine (60 mL), dried over anhydrous $Na_2SO_4$. After filtration, the filtrate was concentrated under reduced pressure to afford the title compound (208 mg, 94.89%) as a light yellow solid.

LCMS (ESI) m/z: $[M+H]^+$=452.

$^1$H NMR (300 MHz, DMSO-$d_6$) δ 13.23 (s, 1H), 9.28 (t, J=5.9 Hz, 1H), 8.60 (dd, J=5.0, 0.9 Hz, 1H), 8.19-8.07 (m, 2H), 8.01 (dt, J=7.8, 1.5 Hz, 1H), 7.92 (dd, J=8.0, 1.7 Hz, 1H), 7.85 (dt, J=7.7, 1.5 Hz, 1H), 7.59 (t, J=7.8 Hz, 1H), 7.54-7.44 (m, 2H), 7.29 (d, J=8.1 Hz, 1H), 4.98-4.75 (m, 2H), 4.63 (d, J=5.8 Hz, 2H), 4.22 (d, J=11.5 Hz, 1H), 3.86 (d, J=11.5 Hz, 1H), 1.70 (s, 3H).

Step 2: (R)-4-Cyano-N-((4-((3-((2-methoxyethyl)carbamoyl)phenyl)ethynyl)pyridin-2-yl)methyl)-4-methylisochromane-6-carboxamide To a solution of (R)-3-((2-((4-cyano-4-methylisochromane-6-carboxamido)methyl)pyridin-4-yl)ethynyl)benzoic acid (20.00 mg, 0.044 mmol, 1.00 equiv) and 2-methoxyethan-1-amine (3.99 mg, 0.053 mmol, 1.2 equiv) in DMF (1.00 mL) was added HATU (25.27 mg, 0.066 mmol, 1.5 equiv) and DIEA (17.18 mg, 0.133 mmol, 3 equiv) at room temperature. The resulting mixture was stirred for 1 h at room temperature. The reaction solution was purified by reverse flash chromatography to afford the title compound (10 mg, 44.39%) as a white solid.

LCMS (ESI) m/z $[M+H]^+$=509.10.

$^1$H NMR (400 MHz, DMSO-d6) δ 9.30 (t, J=5.9 Hz, 1H), 8.63 (dd, J=22.5, 5.2 Hz, 2H), 8.16 (d, J=1.7 Hz, 1H), 8.07 (d, J=1.8 Hz, 1H), 7.92 (dq, J=8.0, 1.7 Hz, 2H), 7.75 (dt, J=7.7, 1.4 Hz, 1H), 7.55 (t, J=7.7 Hz, 1H), 7.46 (dd, J=6.9, 1.7 Hz, 2H), 7.29 (d, J=8.1 Hz, 1H), 4.96-4.78 (m, 2H), 4.63 (d, J=5.9 Hz, 2H), 4.22 (d, J=11.5 Hz, 1H), 3.86 (d, J=11.5 Hz, 1H), 3.45 (tt, J=9.6, 4.2 Hz, 4H), 3.26 (s, 3H), 1.69 (s, 3H).

The following examples in Table 16 were prepared using standard chemical manipulations and procedures similar to those used for the preparation of Example 20.

-continued

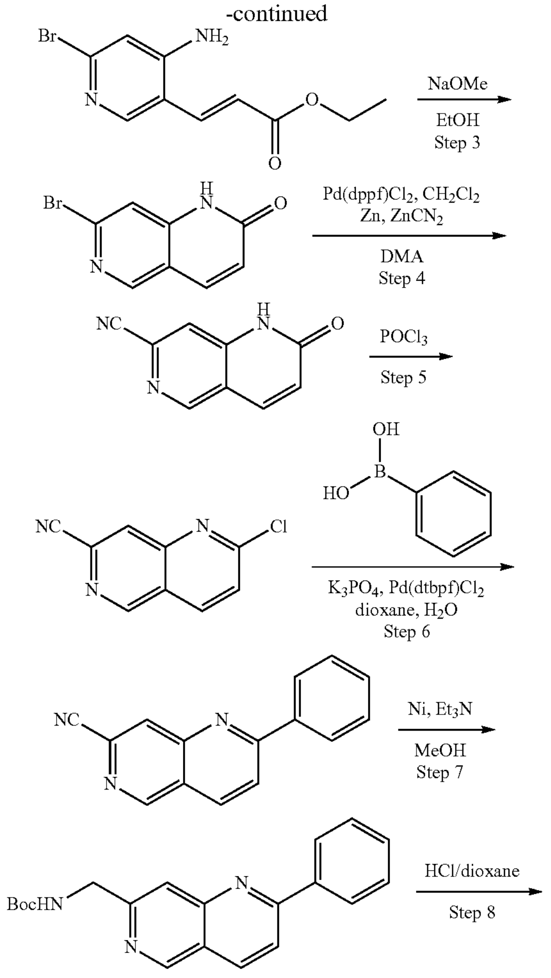

TABLE 16

| Compounds of the Invention | | |
|---|---|---|
| # | LCMS (m/z) | 1H NMR |
| 84 | 479.25 | 1H NMR (300 MHz, DMSO-d6) δ 9.29 (t, J = 5.9 Hz, 1H), 8.60 (dd, J = 5.0, 0.9 Hz, 1H), 8.15 (d, J = 1.8 Hz, 1H), 7.91 (dd, J = 8.1, 1.8 Hz, 1H), 7.72-7.58 (m, 2H), 7.57-7.42 (m, 4H), 7.29 (d, J = 8.0 Hz, 1H), 4.96-4.77 (m, 2H), 4.62 (d, J = 5.7 Hz, 2H), 4.22 (d, J = 11.5 Hz, 1H), 3.86 (d, J = 11.5 Hz, 1H), 2.94 (d, J = 26.3 Hz, 6H), 1.69 (s, 3H). |

Example 21. (R)-4-Cyano-4-methyl-N-((2-phenyl-1,6-naphthyridin-7-yl)methyl)chromane-6-carboxamide

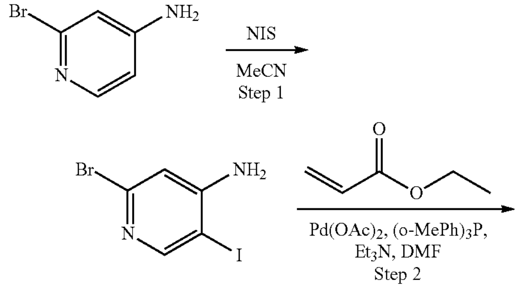

-continued

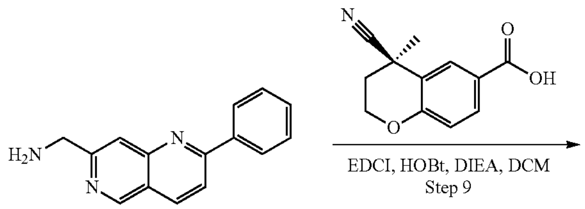

-continued

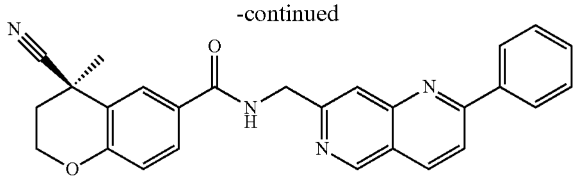

Step 1. 2-Bromo-5-iodo-pyridin-4-amine

NIS (93.6 g, 416 mmol) was added to a solution of 2-bromopyridin-4-amine (60 g, 347 mmol) in MeCN (1.5 L) at 80° C. The reaction mixture was stirred at 80° C. for 36 hrs. The reaction mixture was concentrated under reduced pressure to give a residue. The residue was diluted with saturated $Na_2SO_3$ (1.5 L) and extracted with EA (1.5 L×2). The combined organic layers were washed with brine (1 L), dried over $Na_2SO_4$, filtered, and concentrated under reduced pressure to give a residue. The residue was purified by column chromatography ($SiO_2$, PE/EA=20:3) and concentrated under reduced pressure affording the title compound (65 g, 217 mmol) as a light yellow solid.

$^1$H NMR (400 MHz, $CDCl_3$) δ=8.31 (s, 1H), 6.79 (s, 1H), 4.75 (br s, 2H) ppm.

Step 2. Ethyl-3-(4-amino-6-bromo-3-pyridyl)prop-2-enoate

Ethyl prop-2-enoate (45.1 mL, 415 mmol), $Et_3N$ (43.3 mL, 311 mmol), $Pd(OAc)_2$ (2.3 g, 10.4 mmol), and tris-o-tolylphosphane (6.3 g, 20.7 mmol) was added to a solution of 2-bromo-5-iodo-pyridin-4-amine (62 g, 207 mmol) in DMF (620 mL). The mixture was stirred at 100° C. for 3 hrs. The reaction mixture was diluted with water (4 L) and extracted with EA (2 L×2). The combined organic layers were washed with brine (2 L), dried over $Na_2SO_4$, filtered, and concentrated under reduced pressure to give a residue. The residue was purified by column chromatography ($SiO_2$, PE/EA=20:3) and concentrated under reduced pressure affording the title compound (50 g, 170 mmol) as a light yellow solid.

LCMS (ESI) m/z: [79BrM+H]+=271.1.

$^1$H NMR (400 MHz, DMSO-d6) δ=8.23 (s, 1H), 7.73 (d, J=16.0 Hz, 1H), 6.90-6.67 (m, 3H), 6.52 (d, J=16.0 Hz, 1H), 4.18 (d, J=7.2 Hz, 2H), 1.25 (d, J=7.2 Hz, 3H) ppm.

Step 3. 7-Bromo-1H-1,6-naphthyridin-2-one

NaSMe (24.2 mL, 380 mmol) was added to a solution of ethyl-3-(4-amino-6-bromo-3-pyridyl)prop-2-enoate (40 g, 148 mmol) in EtOH (200 mL). The reaction mixture was stirred at 60° C. for 2 hrs. The reaction mixture was diluted with water (400 mL) and then neutralized with 1N HCl to pH=7.0. The solid was filtered and the filter cake was washed with water (50 mL). The filter cake was concentrated under reduced pressure affording the title compound (22 g, 96.8 mmol) as an off-white solid.

LCMS (ESI) m/z: [79BrM+H]+=224.9.

$^1$H NMR (400 MHz, DMSO-d6) δ=12.08 (br s, 1H), 8.65 (s, 1H), 7.99 (d, J=9.6 Hz, 1H), 7.36 (s, 1H), 6.62 (d, J=9.6 Hz, 1H) ppm.

Step 4. 2-Oxo-1H-1,6-naphthyridine-7-carbonitrile

Zn (406.80 mg, 6.22 mmol) was added to a solution of 7-bromo-1H-1,6-naphthyridin-2-one (7 g, 31.1 mmol), $Zn(CN)_2$ (3.95 mL, 62.2 mmol), and $Pd(dppf)Cl_2$—$CH_2C_{12}$ (5.08 g, 6.22 mmol) in DMA (140 mL). The reaction mixture was degassed and purged with $N_2$ three times then the mixture was stirred at 120° C. for 2 hrs. The reaction mixture was diluted with water (200 mL) and extracted with DCM/isopropanol (v/v=3:1) (150 mL×2). The combined organic layers were filtered, washed with brine (200 mL), dried over $Na_2SO_4$, filtered, and concentrated under reduced pressure to give a residue. The residue was purified by column chromatography ($SiO_2$, PE/EA=1:1) and concentrated under reduced pressure affording the title compound (3 g, 17.5 mmol) as an off-white solid.

$^1$H NMR (400 MHz, DMSO-d6) δ=12.37 (br s, 1H), 8.97 (s, 1H), 8.09 (d, J=9.6 Hz, 1H), 7.67 (s, 1H), 6.77 (d, J=9.6 Hz, 1H) ppm.

Step 5. 2-Chloro-1,6-naphthyridine-7-carbonitrile

A mixture of 2-oxo-1H-1,6-naphthyridine-7-carbonitrile (3.0 g, 17.5 mmol) and $POCl_3$ (30 mL, 323 mmol) was stirred at 80° C. for 2 hrs. The reaction mixture was poured into $H_2O$ (2 L) and adjusted to pH=7 with $NaHCO_3$. The solution was extracted with EA (1.5 L×2), the combined organic layers were washed with brine (2 L), dried over $Na_2SO_4$, filtered, and concentrated under reduced pressure to afford the title compound (1.1 g, 5.76 mmol) as a brown solid.

LCMS (ESI) m/z: [M+H]+=190.1.

$^1$H NMR (400 MHz, DMSO-d6) δ=9.58 (d, J=0.8 Hz, 1H), 8.79 (d, J=0.8 Hz, 1H), 8.69 (s, 1H), 8.00 (d, J=8.8 Hz, 1H) ppm.

Step 6. 2-Phenyl-1,6-naphthyridine-7-carbonitrile

A mixture of 2-chloro-1,6-naphthyridine-7-carbonitrile (270 mg, 1.42 mmol), phenylboronic acid (208.4 mg, 1.71 mmol), $K_3PO_4$ (907 mg, 4.27 mmol), ditert-butyl(cyclopentyl)phosphane; dichloropalladium; iron (92.8 mg, 142 μmol), and $H_2O$ (0.3 mL) in dioxane (3 mL) was degassed and purged with $N_2$ three times. The mixture was stirred at 80° C. for 2 hrs. The reaction mixture was diluted with $H_2O$ (30 mL) and extracted with EA (30 mL×3). The combined organic layers were washed with brine (60 mL), dried over $Na_2SO_4$, filtered, and concentrated under reduced pressure to give a residue. The residue was purified by column chromatography ($SiO_2$, Petroleum ether/Ethyl acetate=30/1 to 3/1) to afford the title compound (248 mg, 1.07 mmol) as a white solid.

LCMS (ESI) m/z: [M+H]+=232.1

$^1$H NMR (400 MHz, DMSO-d6) δ=9.52 (s, 1H), 8.80 (d, J=8.8 Hz, 1H), 8.69 (s, 1H), 8.53 (d, J=8.8 Hz, 1H), 8.37-8.30 (m, 2H), 7.65-7.60 (m, 3H) ppm.

Step 7. tert-Butyl N-[(2-phenyl-1,6-naphthyridin-7-yl)methyl]carbamate $Boc_2O$ (340 mg, 1.56 mmol) and $Et_3N$ (0.29 mL, 2.08 mmol) were added to a solution of 2-phenyl-1,6-naphthyridine-7-carbonitrile (240 mg, 1.04 mmol) in MeOH (10 mL). Ni (305 mg, 5.19 mmol) was added and the reaction mixture was degassed and purged with $H_2$ three times. The reaction mixture was stirred at 25° C. for 16 hrs under $H_2$ atmosphere (15 psi). The suspension was filtered and the filter cake was washed with MeOH (2 mL×3), filtered, and concentrated under reduced pressure to give a residue. The residue was purified by column chromatography ($SiO_2$, Petroleum ether/

Ethyl acetate=10/1 to 1/1) affording the title compound (110 mg, 0.33 mmol) as a colorless oil.

LCMS (ESI) m/z: [M+H]+=336.2.

Step 8. (2-Phenyl-1,6-naphthyridin-7-yl)methanamine

A mixture of tert-butyl N-[(2-phenyl-1,6-naphthyridin-7-yl)methyl]carbamate (110 mg, 328 μmol) in HCl/dioxane (4N, 5 mL) was stirred at 25° C. for 1 hr. The reaction mixture was concentrated under vacuum affording the title compound (118 mg, crude, HCl) as an off-white solid.

LCMS (ESI) m/z: [M+H]+=236.2.

Step 9. (4R)-4-Cyano-4-methyl-N-[(2-phenyl-1,6-naphthyridin-7-yl)methyl]chromane-6-carboxamide EDCI (27.5 mg, 0.14 mmol), HOBt (19.4 mg, 0.14 mmol), and DIEA (0.058 mL, 0.33 mmol) were added to a solution of (4R)-4-cyano-4-methyl-chromane-6-carboxylic acid (28.8 mg, 0.13 mmol) in DCM (1 mL). (2-phenyl-1,6-naphthyridin-7-yl)methanamine (30 mg, 0.11 mmol, HCl salt) was added to the reaction mixture and stirred at 25° C. for 2 hrs. The reaction mixture was diluted with $H_2O$ (20 mL) and extracted with EA (15 mL×3). The combined organic layers were washed with brine (30 mL), dried over $Na_2SO_4$, filtered, and concentrated under reduced pressure to give a residue. The residue was purified by reversed phase flash chromatography. The eluent was concentrated under reduced pressure to remove MeCN and the residue was lyophilized affording the title compound (13.6 mg, 0.030 mmol) as an off-white solid.

LCMS (ESI) m/z: [M+H]+=435.1.

$^1$H NMR (400 MHz, $CD_3OD$) δ=9.34-9.25 (m, 1H), 8.60 (d, J=9.6 Hz, 1H), 8.22-8.14 (m, 4H), 7.95 (s, 1H), 7.88 (d, J=2.4, 1H), 7.59-7.52 (m, 3H), 6.97 (d, J=8.4 Hz, 1H), 4.91 (s, 3H), 4.41-4.36 (m, 2H), 2.52-2.44 (m, 1H), 2.27-2.18 (m, 1H), 1.85 (s, 3H) ppm.

The following examples in Table 17 were prepared using standard chemical manipulations and procedures similar to those used for the preparation of Example 21.

TABLE 17

Compounds of the Invention

| # | LCMS (m/z) | 1H NMR |
|---|---|---|
| 1 | 435.1 | 1H NMR (400 MHz, MeOD-d4) δ = 9.31 (s, 1H), 8.59 (d, J = 8.8 Hz, 1H), 8.22-8.14 (m, 4H), 7.99-7.90 (m, 2H), 7.59-7.52 (m, 3H), 7.29 (d, J = 8.0 Hz, 1H), 4.94-4.90 (m, 4H), 4.21 (d, J = 11.6 Hz, 1H), 3.92 (d, J = 11.6 Hz, 1H), 1.77 (s, 3H) ppm. |
| 2 | 428.2 | 1H NMR (400 MHz, DMSO-d6) δ = 9.47-9.34 (m, 2H), 8.66 (d, J = 8.8 Hz, 1H), 8.34-8.25 (m, 4H), 7.98 (d, J = 8.0 Hz, 1H), 7.79 (s, 1H), 7.64-7.51 (m, 3H), 7.35-7.25 (m, 1H), 4.96-4.69 (m, 4H), 4.08 (m, 1H), 3.92-3.78 (m, 1H), 1.80-1.64 (m, 3H) ppm. |
| 41 | 490.2 | 1H NMR (400 MHz, DMSO-d6) δ = 9.41-9.37 (m, 1H), 9.28 (s, 1H), 8.50 (br d, J = 8.4 Hz, 1H), 8.20-8.16 (m, 4H), 7.95 (d, J = 8.0 Hz, 1H), 7.73 (s, 1H), 7.31 (d, J = 8.0 Hz, 1H), 6.51 (d, J = 8.8 Hz, 2H), 4.94-4.77 (m, 6H), 4.23 (br d, J = 11.2 Hz, 2H), 3.96-3.91 (m, 4H), 1.70 (s, 3H) ppm. |
| 42 | 490.3 | 1H NMR (400 MHz, DMSO-d6) δ = 9.39-9.38 (m, 2H), 8.62 (d, J = 8.4 Hz, 1H), 8.23-8.19 (m, 2H), 7.93-7.92 (m, 1H), 7.80 (s, 1H), 7.56 (d, J = 8.0 Hz, 1H), 7.35-7.27 (m, 3H), 6.59-6.57 (m, 1H), 4.93-4.80 (m, 4H), 4.23 (d, J = 11.6 Hz, 1H), 3.90-3.85 (m, 6H), 2.33 (br s, 1H), 1.70 (s, 3H) ppm. |
| 5 | 426.1 | 1H NMR (400 MHz, MeOD-d4) δ = 9.31 (s, 1H), 8.59 (d, J = 8.8 Hz, 1H), 8.26-8.13 (m, 4H), 7.95 (s, 1H), 7.83 (d, J = 1.6 Hz, 1H), 7.59-7.52 (m, 3H), 7.19 (d, J = 8.0 Hz, 1H), 4.92 (s, 2H), 4.84 (d, J = 3.6 Hz, 2H), 3.82-3.73 (m, 2H), 1.56 (s, 3H) ppm. |
| 6 | 424.3 | 1H NMR (400 MHz, MeOD-d4) δ = 9.30 (s, 1H), 8.59 (d, J = 0.8 Hz, 1H), 8.21-8.14 (m, 3H), 7.95 (s, 1H), 7.82-7.77 (m, 2H), 7.58-7.51 (m, 3H), 7.33 (d J = 7.6 Hz, 1H), 4.90 (s, 2H), 3.60-3.53 (m, 2H), 3.02-2.91 (m, 2H), 2.29-2.27 (m, 1H), 1.90-1.86 (m, 1H), 1.33 (s, 3H) ppm. |
| 7 | 465.1 | 1H NMR (400 MHz, MeOD-d4) δ = 9.30 (s, 1H), 8.59-8.57 (m, 1H), 8.17-8.14 (m, 2H), 7.96 (s, 1H), 7.94-7.91 (m, 1H), 7.77-7.72 (m, 2H), 7.48-7.44 (m, 1H), 7.28 (d, J = 8.4 Hz, 1H), 7.11-7.09 (m, 1H), 4.92-4.90 (m, 4H), 4.20 (d, J = 11.6 Hz, 1H), 3.93-3.89 (m, 4H), 1.76 (s, 3H) ppm. |
| 3 | 449.2 | 1H NMR (400 MHz, DMSO-d6) δ = 9.39 (s, 1H), 9.10 (d, J = 8.0 Hz, 1H), 8.64 (d, J = 8.4 Hz, 1H), 8.30-8.27 (m, 3H), 8.18 (d, J = 1.6 Hz, 1H), 7.96-7.88 (m, 2H), 7.58-7.54 (m, 3H), 7.29 (d, J = 8.0 Hz, 1H), 5.44-5.39 (m, 1H), 4.92-4.81 (m, 2H), 4.22 (d, J = 11.6 Hz, 1H), 3.86 (d, J = 11.2 Hz, 1H), 1.72-1.63 (m, 6H) ppm. |
| 4 | 449.2 | 1H NMR (400 MHz, DMSO-d6) δ = 9.39 (s, 1H), 9.09 (d, J = 7.6 Hz, 1H), 8.64 (d, J = 8.4 Hz, 1H), 8.31-8.21 (m, 4H), 7.97-7.90 (m, 2H), 7.58-7.55 (m, 3H), 7.29 (d, J = 8.4 Hz, 1H), 5.45-5.41 (m, 1H), 4.92-4.81 (m, 2H), 4.22 (d, J = 11.6 Hz, 1H), 3.85 (d, J = 11.6 Hz, 1H), 1.69-1.65 (m, 6H) ppm. |
| 9 | 493.2 | 1H NMR (400 MHz, DMSO-d6) δ = 9.41-9.38 (m, 2H), 8.86-8.84 (m, 1H), 8.70 (d, J = 8.8 Hz, 1H), 8.55 (d, J = 8.0 Hz, 1H), 8.35 (d, J = 8.8 Hz, 1H), 8.20 (d, J = 1.2 Hz, 1H), 8.13-8.11 (m, 1H), 7.96-7.94 (m, 1H), 7.86 (s, 1H), 7.74-7.71 (m, 1H), 7.31 (d, J = 8.0 Hz, 1H), 4.93-4.81 (m, 4H), 4.22 (d, J = 11.6 Hz, 1H), 3.91-3.85 (m, 4H), 1.70 (s, 3H) ppm. |
| 10 | 399.2 | 1H NMR (400 MHz, MeOD-d4) δ = 9.17 (s, 1H), 8.34 (d, J = 8.4 Hz, 1H), 8.15 (s, 1H), 7.96-7.88 (m, 1H), 7.76 (s, 1H), 7.45 (d, J = 8.8 Hz, 1H), 7.28 (d, J = 8.0 Hz, 1H), 4.91 (d, J = 3.6 Hz, 2H), 4.87-4.86 (m, 2H), 4.20 (d, J = 11.6 Hz, 1H), 3.92 (d, J = 11.6 Hz, 1H), 2.35-2.26 (m, 1H), 1.76 (s, 3H), 1.21-1.17 (m, 4H) ppm. |
| 11 | 508.2 | 1H NMR (400 MHz, MeOD-d4) δ = 9.31 (s, 1H), 8.58 (d, J = 8.8 Hz, 1H), 8.18 (d, J = 1.6 Hz, 1H), 8.10 (d, J = 8.8 Hz, 1H), 7.97-7.90 (m, 2H), 7.29 (d, J = 8.4 Hz, 1H), 7.23-7.17 (m, 1H), 7.06-7.02 (m, 1H), 6.35-6.28 (m, 1H), 4.93-4.90 (m, 4H), 4.21 (d, J = 11.4 Hz, 1H), 4.01-3.89 (m, 5H), 2.46-2.36 (m, 2H), 1.77 (s, 3H) ppm. |
| 12 | 434.2 | 1H NMR (400 MHz, DMSO-d6) δ = 9.43 (s, 1H), 9.12-9.10 (m, 1H), 8.71 (d, J = 8.8 Hz, 1H), 8.41-8.29 (m, 3H), 8.06-7.93 (m, 2H), 7.82 (s, 1H), 7.62-7.60 (m, 3H), 6.80 (d, |

TABLE 17-continued

| Compounds of the Invention | | |
|---|---|---|
| # | LCMS (m/z) | 1H NMR |
| | | J = 8.4 Hz, 1H), 4.83 (d, J = 5.6 Hz, 2H), 3.92 (d, J = 9.6 Hz, 1H), 3.48 (d, J = 9.6 Hz, 1H), 2.90 (s, 3H), 1.77 (s, 3H) ppm. |
| 14 | 485.1 | 1H NMR (400 MHz, DMSO-d6) δ = 9.42 (s, 2H), 8.71 (d, J = 8.4 Hz, 1H), 8.52 (s, 1H), 8.47 (d, J = 7.6 Hz, 1H), 8.21 (d, J = 1.2 Hz, 1H), 7.98-7.95 (m, 1H), 7.85 (s, 1H), 7.80-7.67 (m, 2H), 7.35-7.01 (m, 2H), 5.03-4.73 (m, 4H), 4.24 (d, J = 11.6 Hz, 1H), 3.88 (d, J = 11.6 Hz, 1H), 1.71 (s, 3H) ppm. |
| 15 | 421 | 1H NMR (400 MHz, DMSO-d6) δ = 9.37 (s, 1H), 9.24 (t, J = 6.0 Hz, 1H), 8.66 (d, J = 8.8 Hz, 1H), 8.30-8.27 (m, 3H), 8.17 (d, J = 1.6 Hz, 1H), 8.00-7.97 (m, 1H), 7.79 (s, 1H), 7.59-7.54 (m, 3H), 7.08 (d, J = 8.4 Hz, 1H), 5.02 (d, J = 9.6 Hz, 1H), 4.79 (d, J = 6.0 Hz, 2H), 4.56 (d, J = 9.6 Hz, 1H), 1.78 (s, 3H) ppm. |
| 16 | 446.2 | 1H NMR (400 MHz, DMSO-d6) δ = 9.40-9.33 (m, 2H), 8.66 (d, J = 8.8 Hz, 1H), 8.33-8.27 (m, 3H), 7.99 (d, J = 8.4 Hz, 1H), 7.82 (d, J = 7.6 Hz, 2H), 7.60-7.54 (m, 4H), 7.44 (d, J = 6.8 Hz, 1H), 6.76-6.37 (m, 1H), 4.96 (s, 4H), 4.81 (d, J = 6.0 Hz, 2H) ppm |
| 17 | 483.2 | 1H NMR (400 MHz, DMSO-d6) δ = 9.31 (s, 1H), 8.59 (d, J = 8.8 Hz, 1H), 8.20-8.07 (m, 2H), 7.99-7.85 (m, 2H), 7.61 (d, J = 1.6 Hz, 1H), 7.55-7.51 (m, 1H), 7.28 (d, J = 8.0 Hz, 1H), 6.89-6.85 (m, 1H), 4.96-4.89 (m, 4H), 4.20 (d, J = 11.6 Hz, 1H), 3.94 (s, 1H), 3.91-3.90 (m, 3H), 1.76 (s, 3H) ppm |
| 18 | 436.2 | 1H NMR (400 MHz, MeOD-d4) δ = 9.34 (s, 1H), 8.76-8.71 (m, 1H), 8.68-8.60 (m, 3H), 8.18 (d, J = 1.6 Hz, 1H), 8.03-7.96 (m, 2H), 7.95-7.92 (m, 1H), 7.55-7.50 (m, 1H), 7.29 (d, J = 8.0 Hz, 1H), 4.95-4.90 (m, 4H), 4.21 (d, J = 11.6 Hz, 1H), 3.93 (d, J = 11.6 Hz, 1H), 1.77 (s, 3H) ppm |
| 20 | 439.1 | 1H NMR (400 MHz, DMSO-d6) δ = 9.40-9.37 (m, 1H), 9.25 (s, 1H), 8.55 (s, 1H), 8.50 (d, J = 8.4 Hz, 1H), 8.21 (s, 2H), 7.98-7.93 (m, 2H), 7.65 (s, 1H), 7.32 (d, J = 8.4 Hz, 1H), 4.94-4.84 (m, 2H), 4.78-4.77 (m, 2H), 4.25-4.22 (m, 1H), 3.92(s, 3H), 3.89-3.86 (m, 1H), 1.71 (s, 3H) ppm |
| 21 | 489.2 | 1H NMR (400 MHz, MeOD) δ = 9.29 (s, 1H), 8.64 (s, 1H), 8.57 (d, J = 8.8 Hz, 1H), 8.39-8.33 (m, 1H), 8.25 (d, J = 8.8 Hz, 1H), 8.20-8.14 (m, 2H), 7.98-7.92 (m, 2H), 7.71 (d, J = 8.8 Hz, 1H), 7.30 (d, J = 8.2 Hz, 1H), 4.93-4.91 (m, 4H), 4.21 (d, J = 11.4 Hz, 1H), 4.12 (s, 3H), 3.93 (d, J = 11.6 Hz, 1H), 1.77 (s, 3H) ppm |
| 22 | 435.2 | 1H NMR (400 MHz, DMSO-d6) δ = 9.38-9.35 (m, 1H), 9.01 (d, J = 2.0 Hz, 1H), 8.50 (d, J = 8.8 Hz, 1H), 8.38 (d, J = 8.8 Hz, 1H), 8.33-8.27 (m, 3H), 8.14 (d, J = 1.6 Hz, 1H), 7.92-7.90 (m, 1H), 7.61-7.50 (m, 3H), 7.29 (d, J = 8.0 Hz, 1H), 4.92-4.78(m, 4H), 4.21 (d, J = 11.6 Hz, 1H), 3.87-3.84 (m, 1H), 1.68 (s, 3H) ppm |
| 23 | 443.3 | 1H NMR (400 MHz, MeOD) δ = 9.37 (s, 1H), 8.57 (d, J = 8.6 Hz, 1H), 8.18 (d, J = 1.6 Hz, 1H), 7.98 (s, 1H), 7.94-7.92 (m, 1H), 7.73 (d, J = 8.6 Hz, 1H), 7.31 (d, J = 8.2 Hz, 1H), 4.96-4.91 (m, 4H), 4.22 (d, J = 11.4 Hz, 1H), 4.11-4.09(m, 2H), 3.95 (d, J = 11.4 Hz, 1H), 3.64-3.63 (m, 2H), 3.31-3.23 (m, 1H), 2.11-1.87 (m, 4H), 1.78 (s, 3H)ppm |
| 24 | 465.1 | 1H NMR (400 MHz, DMSO-d6) δ = 9.40-9.35 (m, 2H), 8.59 (d, J = 8.4 Hz, 1H), 8.30-8.19 (m, 4H), 7.96-7.93 (m, 1H), 7.7 (s, 1H), 7.31 (d, J = 8.4, 1H), 7.11-7.09 (m, 2H), 4.93-4.79 (m, 4H), 4.23 (m, J = 11.6, 1H), 3.86(d, J = 11.2, 4H), 1.70 (s, 3H) ppm |
| 25 | 440.1 | 1H NMR (400 MHz, DMSO-d6) δ = 9.38 (s, 1H), 9.27-9.26(m, 1H), 8.65 (d, J = 8.4 Hz, 1H), 8.34-8.25 (m, 3H), 7.98(s, 1H), 7.81-7.76 (m, 2H), 7.56-7.54(m, 3H), 7.16 (d, J = 8.0 Hz, 1H), 4.88-4.86 (m, 1H), 4.80-4.74(m, 4H), 3.96-3.93 (m, 1H), 3.59-3.57 (m, 1H), 3.42 (s, 2H), 1.19 (s, 3H) ppm |
| 26 | 489.3 | 1H NMR (400 MHz, DMSO-d6) δ = 9.43-9.40 (m, 2H), 8.70 (d, J = 8.4 Hz, 1H), 8.58 (s, 1H), 8.45 (d, J = 8.8 Hz, 1H), 8.21 (d, J = 1.2 Hz, 1H), 8.13-8.11 (m, 2H), 7.97-7.95 (m, 1H), 7.90 (d, J = 8.4 Hz, 1H), 7.84 (s, 1H), 7.32 (d, J = 8.0 Hz, 1H), 4.93-4.81 (m, 4H), 4.23 (d, J = 11.6 Hz, 1H), 4.16 (s, 3H), 3.87 (d, J = 11.6 Hz, 1H), 1.70 (s, 3H) ppm |
| 27 | 465.4 | 1H NMR (400 MHz, MeOD) δ = 9.30 (s, 1H), 8.50 (br d, J = 8.8 Hz, 1H), 8.16 (d, J = 1.6 Hz, 1H), 8.05 (d, J = 8.4 Hz, 1H), 7.93-7.90 (m, 2H), 7.71-7.69 (m, 1H), 7.50-7.48 (m, 1H), 7.28(br d, J = 8.0 Hz, 1H), 7.19 (d, J = 8.4 Hz, 1H), 7.11-7.09 (m, 1H), 4.91 (s, 2H), 4.90 (br d, J = 3.6 Hz, 2H), 4.20 (d, J = 11.6 Hz, 1H), 3.92 (d, J = 11.6 Hz, 1H), 3.88 (s, 3H), 1.75 (s, 3H)ppm |
| 29 | 439.2 | 1H NMR (400 MHz, DMSO-d6) δ = 9.39-9.36 (m, 1H), 9.31 (s, 1H), 8.54 (d, J = 8.8 Hz, 1H), 8.23-8.17 (m, 2H), 7.96-7.93(m, 1H), 7.85 (d, J = 2.4 Hz, 1H), 7.75-7.71 (m, 1H), 7.31 (d, J = 8.4 Hz, 1H), 7.01 (d, J = 2.4 Hz, 1H), 4.94-4.83 (m, 2H), 4.82-4.77 (m, 2H), 4.23 (d, J = 11.6 Hz, 1H), 3.97 (s, 3H), 3.87 (d, J = 11.6 Hz, 1H), 1.70 (s, 3H) ppm |
| 30 | 436.2 | 1H NMR (400 MHz, MeOD-d4) δ = 9.41-9.34 (m, 2H), 8.71-8.63 (m, 3H), 8.24 (d, J = 8.8 Hz, 1H), 8.17 (d, J = 1.6 Hz, 1H), 7.99 (s, 1H), 7.95-7.91 (m, 1H), 7.67-7.59 (m, 1H), 7.29 (d, J = 8.0 Hz, 1H), 4.93 (s, 2H), 4.91 (d, J = 3.6 Hz, 2H), 4.20 (d, J = 11.6 Hz, 1H), 3.93 (d, J = 11.6 Hz, 1H), 1.77 (s, 3H) ppm |
| 32 | 434.2 | 1H NMR (400 MHz, DMSO-d6) δ = 9.31 (s, 1H), 9.00-8.98 (m, 1H), 8.62 (d, J = 8.8 Hz, 1H), 8.21-8.19 (m, 3H), 7.88 (br s, 1H), 7.71 (s, 1H), 7.65 (br d, J = 8.4 Hz, 1H), 7.54-7.53 (m, 3H), 6.60 (d, J = 8.4 Hz, 1H), 4.72 (br d, J = 5.2 Hz, 2H), 3.33-3.30 (m, 2H), 2.19-2.14 (m, 1H), 1.97-1.93 (m, 1H), 1.68 (s, 3H) ppm |
| 37 | 500.3 | 1H NMR (400 MHz, DMSO-d6) δ = 9.38-9.35 (m, 1H), 9.32 (s, 1H), 8.51 (d, J = 8.4 Hz, 1H), 8.19 (d, J = 1.6 Hz, 1H), 7.95-7.92 (m, 1H), 7.69 (s, 1H), 7.63 (d, J = 8.4 Hz, 1H), 7.30 (d, J = 8.0 Hz, 1H), 4.92-4.81 (m, 2H), 4.78 (d, J = 5.6 Hz, 2H), 4.23-4.14 (m, 2H), 4.03-3.96 (m, 1H), 3.86 (d, J = 11.6 Hz, 1H), 3.58 (s, 3H), 3.21-2.99 (m, 2H), 2.91-2.81 (m, 1H), 2.07-2.02 (m, 1H), 1.84-1.72 (m, 2H), 1.69 (s, 3H), 1.57-1.46 (m, 1H) ppm |

TABLE 17-continued

| Compounds of the Invention | | |
|---|---|---|
| # | LCMS (m/z) | 1H NMR |
| 38 | 436.1 | 1H NMR (400 MHz, DMSO-d6) δ = 9.65-9.49 (m, 1H), 9.39 (s, 1H), 9.08 (d, J = 2.0 Hz, 1H), 8.69-8.62 (m, 1H), 8.57 (d, J = 2.0 Hz, 1H), 8.36-8.24 (m, 3H), 7.87 (s, 1H), 7.61-7.52 (m, 3H), 4.94-4.80 (m, 4H), 4.29 (d, J = 11.6 Hz, 1H), 3.93 (d, J = 11.6 Hz, 1H), 1.72 (s, 3H) ppm |
| 28 | 460.3 | 1H NMR (400 MHz, $CDCl_3$): δ = 9.33 (s, 1H), 8.53 (s, 1H), 8.47 (d, J = 8.1 Hz, 2H), 8.04 (d, J = 6.8 Hz, 2H), 7.84 (t, J = 7.8 Hz, 2H), 7.69 (t, J = 7.9 Hz, 1H), 7.15 (d, J = 7.8 Hz, 1H), 5.04 (s, 1H), 4.88 (s, 2H), 4.14 (d, J = 11.3 Hz, 1H), 3.94 (d, J = 11.4 Hz, 1H), 1.26 (s, 3H) ppm |

Example 22. (4R)-4-cyano-4-methyl-N-[[2-(1-piperidyl)-1,6-naphthyridin-7-yl]methyl]isochromane-6-carboxamide

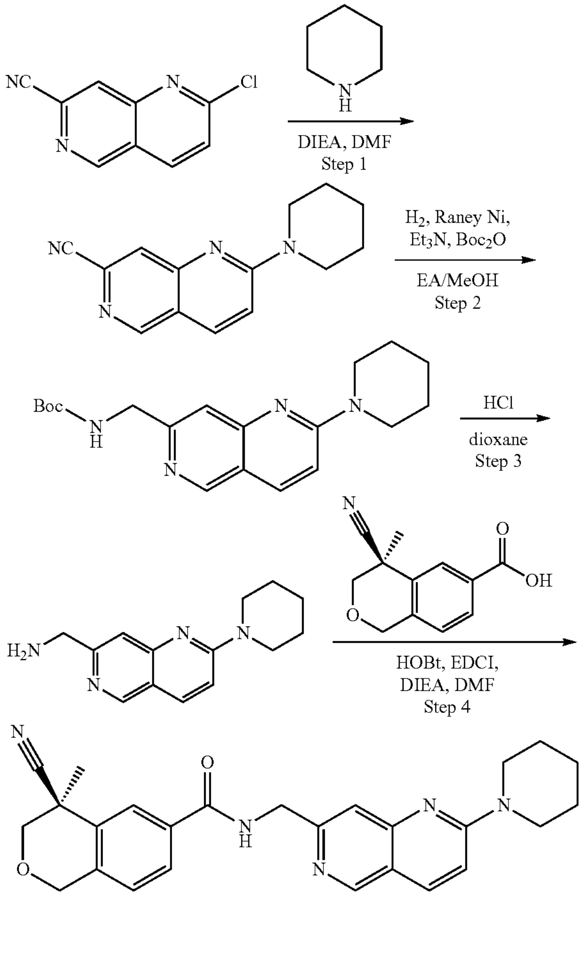

Step 1. 2-(1-Piperidyl)-1,6-naphthyridine-7-carbonitrile

DIEA (0.37 mL, 2.11 mmol) and piperidine (0.31 mL, 3.16 mmol) were added to a mixture of 2-chloro-1,6-naphthyridine-7-carbonitrile (200 mg, 1.05 mmol) in DMSO (2 mL) at 20° C. The mixture was heated and stirred at 100° C. for 2 hr. The mixture was poured into $H_2O$ (20 mL) and filtered. The filter cake was washed with MTBE (20 mL). The filter cake was dried under reduced pressure affording the title compound (170 mg, 0.62 mmol) as a yellow solid.

LCMS (ESI) m/z: [M+H]+=239.7.

Step 2. tert-Butyl N-[[2-(1-piperidyl)-1,6-naphthyridin-7-yl]methyl]carbamate

A mixture of 2-(1-piperidyl)-1,6-naphthyridine-7-carbonitrile (170 mg, 0.71 mmol), $Et_3N$ (0.20 mL, 1.43 mmol), $Boc_2O$ (234 mg, 1.07 mmol), and Raney-Ni (61.1 mg) in MeOH (20 mL) and EA (20 mL) was stirred at 20° C. for 16 hr under a $H_2$ atmosphere (15 psi). The reaction mixture was vented to nitrogen and then filtered. The filtrate was concentrated under reduced pressure. The crude residue was purified by silica gel chromatography (Petroleum Ether/EA=5/1) affording the title compound (165 mg, 0.48 mmol) as a white solid.

LCMS (ESI) m/z: [M+H]+=343.4.

$^1$H NMR (400 MHz, $CD_3OD$) δ=8.72 (s, 1H), 8.02 (d, J=9.6 Hz, 1H), 7.36 (s, 1H), 7.21 (d, J=9.6 Hz, 1H), 4.40 (s, 2H), 3.87-3.79 (m, 4H), 1.81-1.73 (m, 2H), 1.72-1.63 (m, 4H), 1.49 (s, 9H) ppm.

Step 3. [2-(1-Piperidyl)-1,6-naphthyridin-7-yl]methanamine

A mixture of tert-butyl N-[[2-(1-piperidyl)-1,6-naphthyridin-7-yl]methyl]carbamate (165 mg, 0.48 mmol) in HCl/dioxane (4N, 2 mL) was stirred at 20° C. for 2 hrs. The mixture was concentrated under reduced pressure affording the title compound (135 mg, 0.56 mmol, HCl salt) as a white solid.

LCMS (ESI) m/z: [M+H]+=243.0.

Step 4. (4R)-4-Cyano-4-methyl-N-[[2-(1-piperidyl)-1,6-naphthyridin-7-yl]methyl]isochromane-6-carboxamide DIEA (0.047 mL, 0.27 mmol) was added to a mixture of [2-(1-Piperidyl)-1,6-naphthyridin-7-yl]methanamine (25 mg, 0.090 mmol, HCl salt), (4R)-4-cyano-4-methylisochromane-6-carboxylic acid (21.4 mg, 0.099 mmol), EDCI (25.8 mg, 0.3 mmol), and HOBt (18.2 mg, 0.13 mmol) in DMF (0.5 mL). The mixture was stirred at 20° C. for 16 hrs. The mixture was poured into $H_2O$ (10 mL) and filtered. The filter cake was purified by prep-HPLC (column: Waters Xbridge 150*25 mm*5 m; mobile phase: [water (10 mM $NH_4$—$HCO_3$)-ACN]; B %: 28%-58%, 9 min) affording the title compound (20.2 mg, 0.046 mmol) as a white solid.

LCMS (ESI) m/z: [M+H]+=442.4.

$^1$H NMR (400 MHz, $CD_3OD$) δ=8.77 (s, 1H), 8.15 (d, J=1.6 Hz, 1H), 8.04 (d, J=9.2 Hz, 1H), 7.92-7.88 (m, 1H), 7.41 (s, 1H), 7.27 (d, J=8.0 Hz, 1H), 7.22 (d, J=9.6 Hz, 1H), 4.90 (d, J=4.0 Hz, 2H), 4.76 (s, 2H), 4.20 (d, J=11.2 Hz, 1H), 3.91 (d, J=11.2 Hz, 1H), 3.86-3.77 (m, 4H), 1.79-1.70 (m, 5H), 1.69-1.60 (m, 4H) ppm.

Example 23. (R)-4-cyano-4-methyl-N-((2-phenyl-1,6-naphthyridin-7-yl)methyl)chromane-6-carboxamide

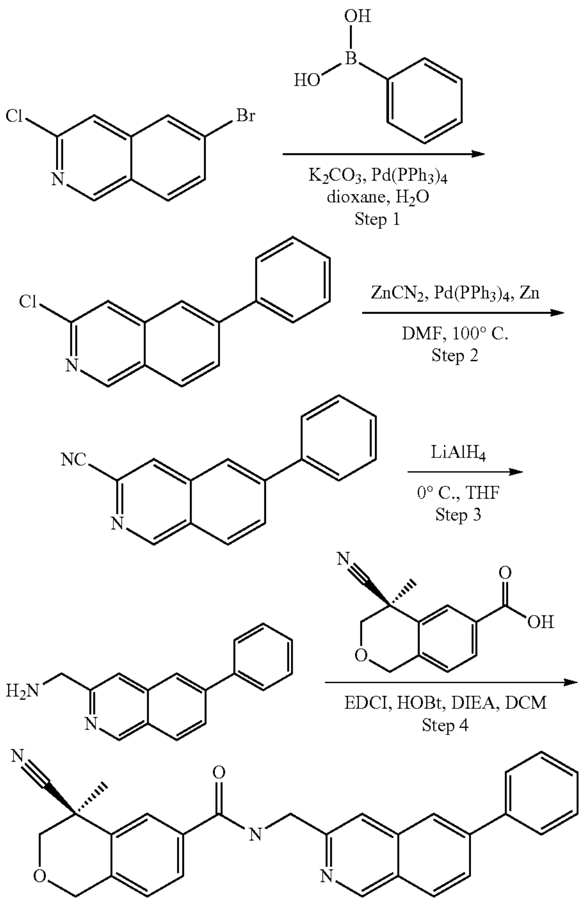

Step 1. 3-chloro-6-phenylisoquinoline 6-bromo-3-chloroisoquinoline (0.500 g, 2.06 mmol), $Pd(PPh_3)_4$ (0.476 g, 0.412 mmol), phenylboronic acid (0.500 g, 2.06 mmol), and zinc (6.3 mg, 0.096 mmol) were added to a 40 mL vial and it was purged with nitrogen. 10 mL of a 1:1 mixture of DME/water was added to the vial and the reaction mixture was heated to 80° C. and stirred under nitrogen atmosphere for 3 h at 80° C. After cooling down to rt, the reaction mixture was extracted with DCM (3×20 mL). The combined organic layers were dried over sodium sulfate, filtered, and concentrated under reduced pressure to give a residue. The residue was purified by column chromatography ($SiO_2$, 0-60% EtOAc in heptane) and concentrated under reduced pressure affording the title compound (310 mg, 1.29 mmol) as a light yellow solid.

LCMS (ESI) m/z: [M+H]+=240.1.

$^1$H NMR (400 MHz, $CDCl_3$) δ=9.09 (d, J=1.1 Hz, 1H), 8.05 (d, J=8.5 Hz, 1H), 7.93 (s, 1H), 7.86 (dd, J=8.5, 1.7 Hz, 1H), 7.77 (s, 1H), 7.74-7.67 (m, 2H), 7.57-7.49 (m, 2H), 7.49-7.41 (m, 1H) ppm.

Step 2. 6-phenylisoquinoline-3-carbonitrile 3-chloro-6-phenylisoquinoline (0.23 g, 0.9595 mmol), potassium carbonate (0.263 g, 1.91 mmol), $Pd(PPh_3)_4$ (0.221 g, 0.1919 mmol), and $Zn(CN)_2$ (0.167 g, 1.43 mmol) were added to a 20 mL vial and it was purged with nitrogen. DMF (4.8 mL) was added and the mixture was heated to 100° C. and stirred at for 3 hrs. After cooling down to rt, the reaction was quenched by the addition of water and the crude mixture was extracted with DCM (3×20 mL). The combined organic layers were dried over sodium sulfate, filtered, and concentrated under reduced pressure to give a residue. The residue was purified by column chromatography ($SiO_2$, 0-70% EtOAc in heptane) and concentrated under reduced pressure affording the title compound (140 mg, 0.608 mmol, 64% yield) as a light yellow solid.

LCMS (ESI) m/z: [M+H]+=231.2.

$^1$H NMR (500 MHz, $CDCl_3$) δ=9.30 (t, J=0.9 Hz, 1H), 8.20 (d, J=1.0 Hz, 1H), 8.17-8.11 (m, 1H), 8.10-8.03 (m, 2H), 7.75-7.69 (m, 2H), 7.58-7.51 (m, 2H), 7.51-7.45 (m, 1H) ppm.

Step 3. (6-phenylisoquinolin-3-yl)methanamine

A solution $LiAlH_4$ in THE (1.0 M, 0.22 mL, 0.22 mmol) was added dropwise to a solution of 6-phenylisoquinoline-3-carbonitrile (0.050 g, 0.217 mmol) in THE (1 mL) at 0° C. The reaction mixture was allowed to stir for 2 h at which point it had warmed to rt. The reaction was quenched by addition of 1 mL of water followed by 0.5 mL of a 6N NaOH aqueous solution. The reaction mixture was extracted with 10% MeOH in DCM solution (3×5 mL). The combined organic layers were dried over sodium sulfate, filtered, and concentrated under reduced pressure to give the crude amine (51.2 mg) as a brown solid.

LCMS (ESI) m/z: [79BrM+H]+=224.9.

$^1$H NMR (500 MHz, $CDCl_3$) δ=9.25 (s, 1H), 8.09-7.91 (m, 1H), 7.88-7.79 (m, 1H), 7.72 (d, J=7.8 Hz, 2H), 7.56-7.39 (m, 4H), 3.75 (s, 2H) ppm.

Step 4. (R)-4-cyano-4-methyl-N-((6-phenylisoquinolin-3-yl)methyl)isochromane-6-carboxamide EDCI (49.0 mg, 0.256 mmol), HOBt (34.5 mg, 0.256 mmol), and DIEA (66.1 mg, 0.512 mmol, 89 L) were added to a solution of (4R)-4-cyano-4-methyl-chromane-6-carboxylic acid (46.3 mg, 0.2133 mmol) in DCM (1 mL). 1-(6-phenylisoquinolin-3-yl)methanamine (50.0 mg, 0.2133 mmol) was added to the reaction mixture and stirred at 25° C. for 2 hrs. The reaction mixture was diluted with $H_2O$ (5 mL) and extracted with EA (5 mL×3). The combined organic layers were dried over $Na_2SO_4$, filtered, and concentrated under reduced pressure to give a residue. The residue was purified by reversed phase flash (0.1% FA condition). The eluent was concentrated under reduced pressure to remove MeCN and the residue was lyophilized affording the title compound (39.4 mg, 0.0909 mmol) as an off-white solid.

LCMS (ESI) m/z: [M+H]+=434.3.

$^1$H NMR (400 MHz, DMSO-d6) δ=8.56 (d, J=4.0 Hz, 2H), 7.51 (d, J=1.6 Hz, 1H), 7.47-7.41 (m, 2H), 7.21 (ddd, J=13.1, 8.3, 1.8 Hz, 2H), 7.10 (dd, J=8.3, 1.3 Hz, 2H), 7.04 (s, 1H), 6.77 (dd, J=8.3, 6.8 Hz, 2H), 6.71-6.65 (m, 1H), 6.54 (d, J=8.1 Hz, 1H), 4.01 (d, J=5.8 Hz, 2H), 3.46 (d, J=11.4 Hz, 1H), 3.11 (d, J=11.5 Hz, 1H), 2.75 (s, 1H), 0.94 (s, 3H) ppm.

Example 24. (R)-4-cyano-4-methyl-N-((6-phenyl-5,6,7,8-tetrahydro-2,6-naphthyridin-3-yl)methyl)isochromane-6-carboxamide

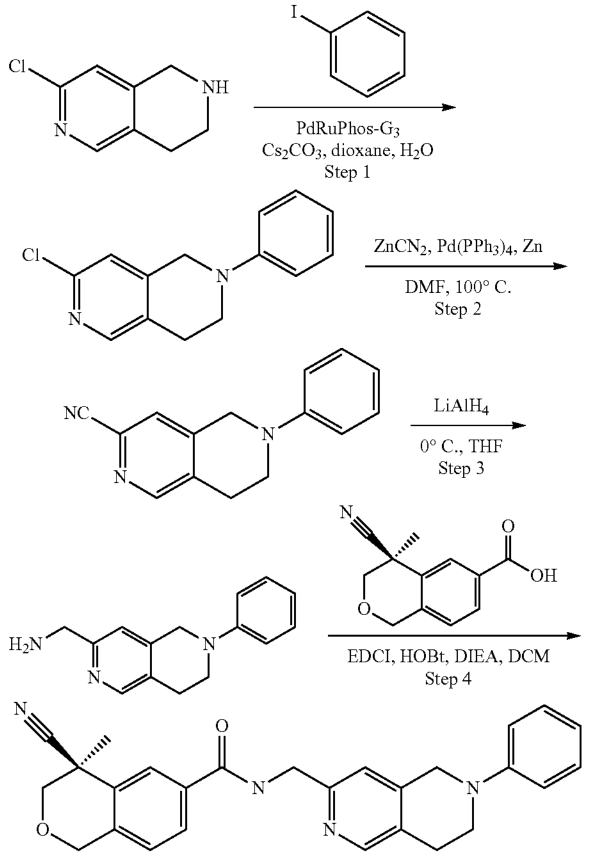

Step 1. 7-chloro-2-phenyl-1,2,3,4-tetrahydro-2,6-naphthyridine 7-chloro-1,2,3,4-tetrahydro-2,6-naphthyridine hydrochloride (0.300 g, 1.46 mmol), iodobenzene (0.455 g, 2.19 mmol), Pd-RuPhos G3 (0.183 g, 0.219 mmol), and cesium carbonate (0.951 g, 2.92 mmol) were added to a 20 mL vial. The vial was purged with nitrogen before a 5:1 mixture of dioxane/water (7.3 mL) was added and the reaction mixture heated to 80° C. and stirred at this temperature for 3 h. After cooling to rt, 5 mL of water was added. The reaction mixture was extracted with 10% MeOH in DCM solution (3×5 mL). The combined organic layers were dried over sodium sulfate, filtered, and concentrated under reduced pressure to give a residue. The residue was purified by column chromatography ($SiO_2$, 0-100% EtOAc in heptane) and concentrated under reduced pressure affording the title compound (80.0 mg, 0.327 mmol) as a white solid.

LCMS (ESI) m/z: [M+H]+=245.1.

$^1$H NMR (400 MHz, $CDCl_3$) δ=8.20 (s, 1H), 7.35-7.28 (m, 1H), 7.28 (d, J=0.8 Hz, 1H), 7.26 (s, 2H), 7.14 (s, 1H), 7.00-6.93 (m, 2H), 6.89 (td, J=7.3, 1.1 Hz, 1H), 4.36 (s, 2H), 3.58 (t, J=5.8 Hz, 2H), 2.95 (t, J=5.8 Hz, 2H) ppm.

Step 2. 6-phenyl-5,6,7,8-tetrahydro-2,6-naphthyridine-3-carbonitrile 7-chloro-2-phenyl-1,2,3,4-tetrahydro-2,6-naphthyridine (0.026 g, 0.106 mmol), $Pd(PPh_3)_4$ (0.0245 g, 0.0212 mmol), zinc (1.0 mg, 0.0159 mmol), and $Zn(CN)_2$ (18.7 mg, 0.159 mmol) were added to a 1 mL vial and it was purged with nitrogen. DMF (4.8 mL) was added and the mixture was heated to 100° C. and stirred at for 3 hrs. After cooling down to rt, the reaction was quenched by the addition of water and the crude mixture was extracted with DCM (3×5 mL). The combined organic layers were dried over sodium sulfate, filtered, and concentrated under reduced pressure to give a residue. The residue was purified by column chromatography ($SiO_2$, 0-70% EtOAc in heptane) and concentrated under reduced pressure affording the title compound (15.1 mg, 0.0642 mmol) as a light yellow solid.

LCMS (ESI) m/z: [M+H]+=236.1.

$^1$H NMR (400 MHz, $CDCl_3$) δ=8.54 (s, 1H), 7.50 (s, 1H), 7.37 (dd, J=8.7, 7.3 Hz, 2H), 7.13 (d, J=8.1 Hz, 2H), 7.03 (t, J=7.4 Hz, 1H), 4.45 (s, 2H), 3.65 (t, J=5.8 Hz, 2H), 3.15 (t, J=5.8 Hz, 2H) ppm.

Step 3. (6-phenyl-5,6,7,8-tetrahydro-2,6-naphthyridin-3-yl)methanamine

To 6-phenyl-5,6,7,8-tetrahydro-2,6-naphthyridine-3-carbonitrile (0.015 g, 0.0642 mmol) in THE (0.5 mL) at 0° C. was added a solution $LiAlH_4$ in THE (1.0 M, 0.22 mL, 0.22 mmol) dropwise. The reaction mixture was allowed to stir for 2 h at which point it had warmed to rt. The reaction was quenched by addition of 1 mL of water followed by 0.5 mL of a 6N NaOH aqueous solution. The reaction mixture was extracted with 10% MeOH in DCM solution (3×5 mL). The combined organic layers were dried over sodium sulfate, filtered, and concentrated under reduced pressure to give the crude amine (15.0 mg) as a brown solid.

LCMS (ESI) m/z: [M+H]+=240.1.

$^1$H NMR (400 MHz, $CDCl_3$) δ=8.55-8.28 (m, 1H), 7.26 (s, 2H), 7.07-6.76 (m, 4H) ppm, 4.40 (dd, J=23.8, 6.7 Hz, 2H), 4.03-3.34 (m, 4H), 3.08-2.88 (m, 2H).

Step 4. (R)-4-cyano-4-methyl-N-((6-phenyl-5,6,7,8-tetrahydro-2,6-naphthyridin-3-yl)methyl)isochromane-6-carboxamide DIEA (19.4 mg, 0.150 mmol, 26 μL) was added to a vial containing 1-(6-phenyl-5,6,7,8-tetrahydro-2,6-naphthyridin-3-yl)methanamine (15.0 mg, 0.0627 mmol), EDCI (14.5 mg, 0.0752 mmol), HOBt (10.4 mg, 0.0752 mmol), and (4R)-4-cyano-4-methyl-chromane-6-carboxylic acid (13.6 mg, 0.0627 mmol) in DCM (0.5 mL). The reaction mixture stirred at 25° C. for 2 hrs. The reaction mixture was concentrated under reduced pressure to give a residue. The residue was purified by reversed phase flash chromatography affording the title compound (6.2 mg, 0.0141 mmol) as an off-white solid.

LCMS (ESI) m/z: [M+H]+=439.2.

$^1$H NMR (400 MHz, $CDCl_3$) δ=8.38 (s, 1H), 8.28 (s, 1H), 8.09-8.00 (m, 2H), 7.81 (dd, J=8.0, 1.7 Hz, 1H), 7.35-7.27 (m, 3H), 7.13 (dd, J=15.5, 8.1 Hz, 2H), 7.02-6.95 (m, 2H), 6.89 (t, J=7.3 Hz, 1H), 4.87 (d, J=15.6 Hz, 4H), 4.75 (dd, J=5.5, 3.1 Hz, 2H), 4.42 (s, 2H), 4.14 (dd, J=11.3, 6.4 Hz, 2H), 3.93 (dd, J=14.3, 11.3 Hz, 2H), 3.59 (t, J=5.7 Hz, 2H), 3.50 (s, 2H), 3.00 (t, J=5.7 Hz, 2H), 1.78 (s, 3H) ppm.

Example 25. (4R)-4-cyano-4-methyl-N-[(2-phenylthiazolo[5,4-c]pyridin-6-yl)methyl]isochromane-6-carboxamide

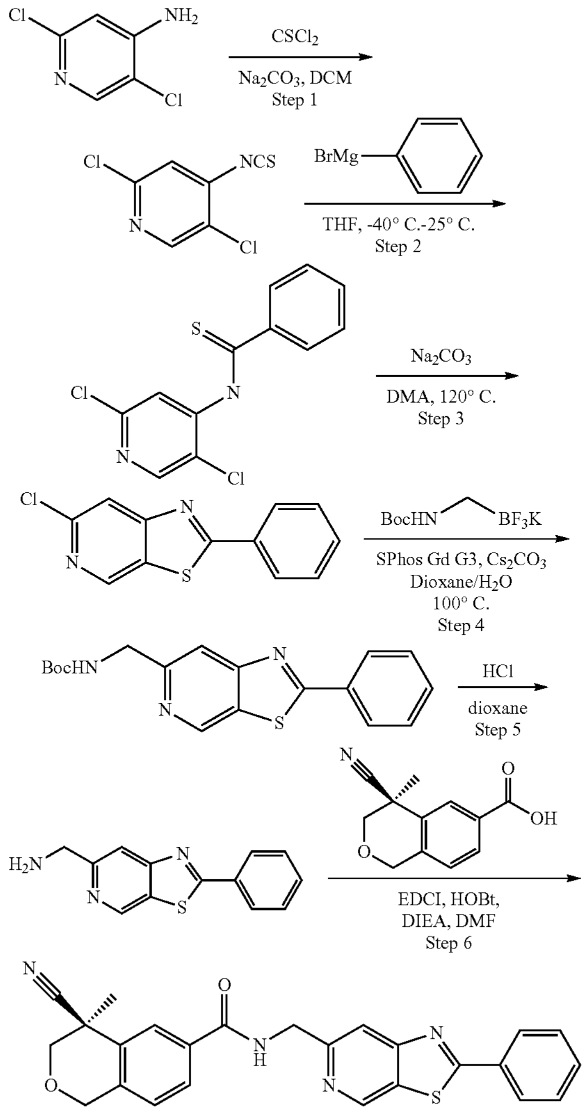

Step 1. 2,5-Dichloro-4-isothiocyanato-pyridine

Thiocarbonyl dichloride (0.94 mL, 12.3 mmol) was added to a solution of 2,5-dichloropyridin-4-amine (1 g, 6.13 mmol) and $Na_2CO_3$ (2.60 g, 24.5 mmol) in DCM (15 mL) at 25° C. The mixture was stirred for 15 hrs. The mixture was filtered and concentrated in vacuo. The crude residue was purified by column chromatography ($SiO_2$, Petroleum Ether/EA=10/1 to 5/1) affording the title compound (750 mg, 3.66 mmol) as a brown solid.

$^1$H NMR (400 MHz, DMSO-d6) δ=8.63 (s, 1H), 7.85-7.76 (m, 1H) ppm.

Step 2. N-(2,5-Dichloro-4-pyridyl)benzenecarbothioamide

Phenylmagnesium bromide (3 M, 1.6 mL) was added slowly to a mixture of 2,5-Dichloro-4-isothiocyanato-pyridine (650 mg, 3.17 mmol) in THE (8 mL) at −40° C. After the addition, the mixture was stirred at −40° C. for 30 min. The reaction mixture was then warmed to 25° C. and stirred for 2 hrs. The mixture was quenched via the addition of water (5 mL) and extracted with EA (5 mL). The organic layer was washed with brine (10 mL), dried over $Na_2SO_4$, filtered, and concentrated in vacuo. The crude residue was purified by column chromatography ($SiO_2$, Petroleum Ether/EA=10/1 to 5/1) affording the title compound (650 mg, 2.30 mmol) as a white solid.

$^1$H NMR (400 MHz, $CD_3OD$) δ=8.55-8.51 (m, 1H), 8.08-8.03 (m, 1H), 7.97-7.90 (m, 2H), 7.60-7.53 (m, 1H), 7.50-7.43 (m, 2H) ppm.

Step 3. 6-Chloro-2-phenyl-thiazolo[5,4-c]pyridine $Na_2CO_3$ (412 mg, 3.88 mmol) was added to a mixture of N-(2,5-Dichloro-4-pyridyl)benzenecarbothioamide (550 mg, 1.94 mmol) in DMA (8 mL) at 25° C. The mixture was warmed and stirred at 120° C. for 3 hrs. The mixture was quenched with water (20 mL) and extracted with EA (15 mL×3). The combined organic layer was washed with brine (20 mL), dried over $Na_2SO_4$, filtered, and concentrated in vacuo. The crude residue was purified by column chromatography ($SiO_2$, Petroleum Ether/EA=10/1 to 5/1) affording the title compound (250 mg, 1.01 mmol) as a yellow solid.

LCMS (ESI) m/z: [M+H]+=247.0.

$^1$H NMR (400 MHz, DMSO-d6) δ=9.25 (d, J=0.4 Hz, 1H), 8.21-8.16 (m, 3H), 7.70-7.59 (m, 3H) ppm.

Step 4. tert-Butyl N-[(2-phenylthiazolo[5,4-c]pyridin-6-yl)methyl]carbamate

SPhos Pd G3 (25.3 mg, 0.032 mmol) and $Cs_2CO_3$ (211 mg, 0.65 mmol) were added to a mixture of 6-chloro-2-phenyl-thiazolo[5,4-c]pyridine (80 mg, 0.32 mmol) and potassium; 2-(tertbutoxycarbonylamino) ethyl-trifluoro-boranuide (122 mg, 0.49 mmol) in dioxane (3 mL) and $H_2O$ (0.5 mL) at 20° C. The mixture was warmed and stirred at 100° C. for 15 hrs. The mixture was filtered and the filtrate was concentrated in vacuo. The crude residue was purified by column chromatography ($SiO_2$, Petroleum Ether/EA=5/1 to 3/1) affording the title compound (60 mg, 0.18 mmol) as a white solid.

LCMS (ESI) m/z: [M+H]+=342.1.

$^1$H NMR (400 MHz, $CDCl_3$) δ=9.13 (s, 1H), 8.15-8.13 (m, 2H), 7.94 (s, 1H), 7.62-7.49 (m, 4H), 5.50 (s, 1H), 4.62 (d, J=5.2 Hz, 2H), 1.49 (s, 9H) ppm.

Step 5. (2-Phenylthiazolo[5,4-c]pyridin-6-yl)methanamine

A mixture of tert-Butyl N-[(2-phenylthiazolo[5,4-c]pyridin-6-yl)methyl]carbamate (60 mg, 0.18 mmol) in HCl/dioxane (4N, 2 mL) was stirred at 25° C. for 2 hrs. The mixture was concentrated in vacuo affording the title compound (30 mg, 0.11 mmol, HCl salt) as a white solid.

LCMS (ESI) m/z: [M+H]+=242.1

Step 6. (4R)-4-Cyano-4-methyl-N-[(2-phenylthiazolo[5,4-c]pyridin-6-yl)methyl]isochromane-6-carboxamide EDCI (20.7 mg, 0.11 mmol), HOBt (14.6 mg, 0.11 mmol), and DIPEA (0.047 mL, 0.27 mmol) were added to a mixture of (2-phenylthiazolo[5,4-c]pyridin-6-yl)methanamine (15 mg, 0.054 mmol, HCl salt), and (4R)-4-cyano-4-methylisochromane-6-carboxylic acid (11.7 mg, 0.054 mmol) in DMF (1 mL) at 20° C. The mixture was stirred for 15 hrs. The mixture was quenched via the addition of water (5 mL) and then extracted with EA (3 mL×3). The combined organic layer was washed with brine (10 mL), dried over $Na_2SO_4$, filtered, and concentrated in vacuo. The crude product was purified by pre-HPLC (column: Phenomenex Synergi C18 150*25*10 m; mobile phase: [water (0.225% FA)-ACN]; B %: 39%-69%, 10 min) affording the title compound (20.8 mg, 0.047 mmol) as gray oil.

LCMS (ESI) m/z: [M+H]+=441.1.

$^1$H NMR (400 MHz, DMSO-d6) δ=9.41-9.30 (m, 2H), 8.21-8.13 (m, 3H), 7.96-7.90 (m, 2H), 7.68-7.57 (m, 3H), 7.29 (d, J=8.0 Hz, 1H), 4.94-4.80 (m, 2H), 4.75 (d, J=5.6 Hz, 2H), 4.22 (d, J=11.6 Hz, 1H), 3.86 (d, J=11.6 Hz, 1H), 1.70 (s, 3H) ppm.

The following examples in Table 18 were prepared using standard chemical manipulations and procedures similar to those used for the preparation of Example 25.

TABLE 18

| Compounds of the Invention | | |
|---|---|---|
| # | LCMS (m/z) | 1H NMR |
| 31 | 446.1 | 1H NMR (400 MHz, DMSO-d6) δ = 9.35 (s, 1H), 9.20-9.18(m, 1H), 8.20-8.13 (m, 2H), 7.93 (d, J = 20.0 Hz, 2H), 7.76(d, J = 8.0 Hz, 1H), 7.68-7.57 (m, 3H), 7.14 (d, J = 8.0 Hz, 1H), 4.89-4.87 (m, 1H), 4.78-4.70 (m, 4H), 3.94 (d, J = 11.2 Hz, 1H), 3.59-3.54 (m, 1H), 3.41 (s, 2H), 1.18 (s, 3H) ppm |
| 33 | 427.1 | 1H NMR (400 MHz, DMSO-d6) δ = 9.35 (d, J = 0.8 Hz, 1H), 9.18-9.15 (m, 1H), 8.22-8.12 (m, 3H), 8.01-7.89 (m, 2H), 7.69-7.57 (m, 3H), 7.06 (d, J = 8.4 Hz, 1H), 5.01 (d, J = 9.6 Hz, 1H), 4.73 (d, J = 6.0 Hz, 2H), 4.55 (d, J = 9.6 Hz, 1H), 1.78 (s, 3H) ppm |
| 34 | 441.1 | 1H NMR (400 MHz, DMSO-d6) δ = 9.35 (s, 1H), 9.21-9.19 (m, 1H), 8.20-8.12 (m, 3H), 7.91 (s, 1H), 7.88-7.86 (m, 1H), 7.67-7.58 (m, 3H), 6.96 (d, J = 8.4 Hz, 1H), 4.73 (br d, J = 6.0 Hz, 2H), 4.40-4.24 (m, 2H), 2.44-2.41 (m, 1H), 2.23-2.18 (m, 1H), 1.80 (s, 3H) ppm |
| 35 | 432.2 | 1H NMR (400 MHz, DMSO-d6) δ = 9.35 (d, J = 0.4 Hz, 1H), 9.24-9.21 (m, 1H), 8.18-8.15 (m, 3H), 7.88 (s, 1H), 7.80-7.77 (m, 1H), 7.67-7.58 (m, 3H), 7.14 (d, J = 8.0 Hz, 1H), 5.29 (s, 1H), 4.79-4.67 (m, 4H), 3.70-3.67 (m, 1H), 3.61-3.58 (m, 1H), 1.43 (s, 3H) ppm |
| 36 | 440.2 | 1H NMR (400 MHz, DMSO + D2O) δ = 9.30 (d, J = 3.2 Hz, 1H), 8.92-8.991 (m, 1H), 8.15-8.13 (m, 2H), 7.89-7.83 (m, 1H), 7.84 (s, 1H), 7.64-7.59 (m, 4H), 6.59 (d, J = 8.8 Hz, 1H), 4.74-4.62 (m, 2H), 3.34-3.31 (m, 2H), 2.21-2.15 (m, 1H), 1.99-1.94 (m, 1H), 1.70 (s, 3H) ppm |

-continued

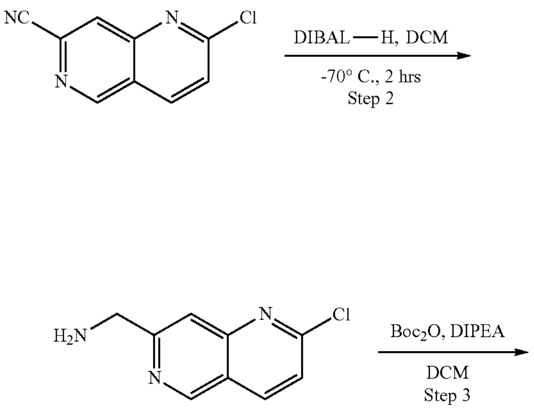

Example 26: (R)-4-Cyano-N-((2-(4-cyclobutyl-2-methoxyphenyl)-1,6-naphthyridin-7-yl)methyl)-4-methylisochromane-6-carboxamide

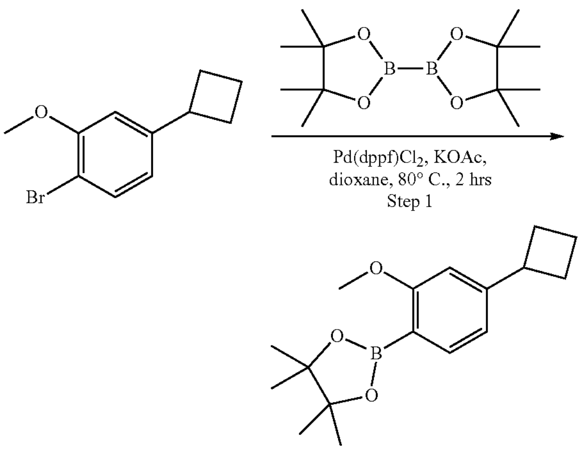

-continued

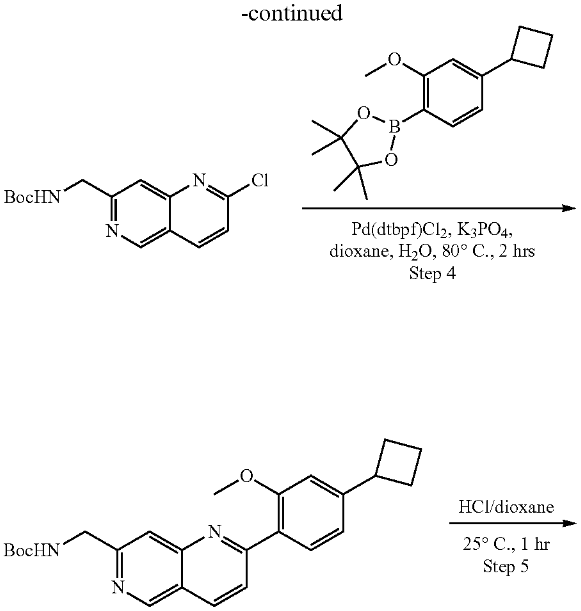

-continued

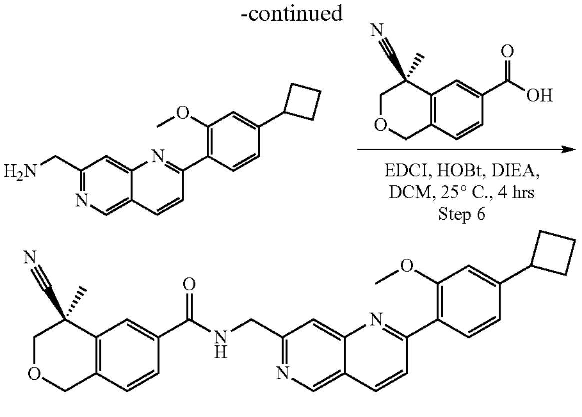

Step 1: 2-(4-Cyclobutyl-2-methoxyphenyl)-4,4,5,5-tetramethyl-1,3,2-dioxaborolane To a mixture 1-bromo-4-cyclobutyl-2-methoxybenzene (88.46 mg, 348.37 umol), 4,4,4',4',5,5,5',5'-octamethyl-2,2'-bi(1,3,2-dioxaborolane) (88.46 mg, 348.37 umol) and KOAc (85.47 mg, 870.92 umol) in dioxane (2 mL) was added [1,1-bis(di-tert-butylphosphino)ferrocene]dichloropalladium(II) (23.71 mg, 29.03 umol) under $N_2$. The mixture was stirred at 80° C. for 2 hrs. The mixture was diluted with EA (20 mL) and filtered. The filtrate was concentrated under vacuum to give the title compound (83 mg, crude) as black oil.

LCMS (ESI) m/z=$[M+H]^+$=289.1.

Step 2: (2-Chloro-1,6-naphthyridin-7-yl)methanamine

To a solution of 2-chloro-1,6-naphthyridine-7-carbonitrile (25 g, 131.86 mmol) in DCM (1000 mL) was added DIBAL-H (1 M, 329.64 mL, 2.5 eq) dropwise at −70° C. under $N_2$. The reaction mixture was stirred at −70° C. for 2 h. The reaction mixture was quenched with water (500 mL) and sat. potassium sodium tartrate (1500 mL) and stirred for an additional 30 min. The mixture was extracted with DCM:MeOH=10:1 (6000 mL*3). The combined organic layers were dried over $Na_2SO_4$, filtered and concentrated under reduced pressure to give the title compound (51 g, crude) as a brown solid, which was used directly in the next step.

LCMS (ESI) m/z: $[^{35}ClM+H]^+$=194.2

Step 3: tert-Butyl ((2-chloro-1,6-naphthyridin-7-yl)methyl)carbamate

To a solution of (2-chloro-1,6-naphthyridin-7-yl)methanamine (51 g, 263.39 mmol) in DCM (1500 mL) was added $(Boc)_2O$ (172.45 g, 790.16 mmol) and DIEA (102.12 g, 790.16 mmol). The mixture was stirred at 25° C. for 16 hr. The reaction mixture was diluted with water (1500 mL) and then filtered. The filtrate was extracted with DCM (1000 mL*3). The combined organic layers were washed with brine (1500 mL), dried over $Na_2SO_4$, filtered and concentrated under reduced pressure. The residue was purified by column chromatography ($SiO_2$, Petroleum ether/Ethyl acetate=10/1 to 2/1 to 1/3) to give the title compound (21 g, 64.34 mmol, 24.43% yield) as a light yellow solid.

LCMS (ESI) m/z: [M+H]+=293.9.

$^1H$ NMR (400 MHz, DMSO-$d_6$) δ=9.37 (s, 1H), 8.62 (d, J=8.4 Hz, 1H), 7.71 (d, J=8.4 Hz, 1H), 7.58-7.53 (m, 2H), 4.39 (d, J=6.4 Hz, 2H), 4.20-4.25 (m, 2H), 1.41 (s, 9H) ppm Step 4: tert-Butyl ((2-(4-cyclobutyl-2-methoxyphenyl)-1,6-naphthyridin-7-yl)methyl)carbamate A mixture of tert-butyl ((2-chloro-1,6-naphthyridin-7-yl)methyl)carbamate (45 mg, 153.19 umol), 2-(4-cyclobutyl-2-methoxyphenyl)-4,4,5,5-tetramethyl-1,3,2-dioxaborolane (79.47 mg, 275.75 umol), [1,1-bis(di-tert-butylphosphino)ferrocene]dichloropalladium(II) (9.98 mg, 15.32 umol) and $K_3PO_4$ (97.55 mg, 459.58 umol) in $H_2O$ (0.4 mL) and dioxane (2 mL) was degassed and purged with $N_2$ for 3 times. The mixture was then stirred at 80° C. for 2 hrs under $N_2$ atmosphere. The mixture was concentrated under vacuum and the residue purified by column chromatography ($SiO_2$, Petroleum ether/Ethyl acetate=20/1 to 0/1), to give the title compound (55 mg, 120.62 umol, 78.73% yield) as a yellow solid.

LCMS (ESI) m/z=$[M+H]^+$=420.3

Step 5: (2-(4-Cyclobutyl-2-methoxyphenyl)-1,6-naphthyridin-7-yl)methanamine hydrochloride A mixture of tert-butyl ((2-(4-cyclobutyl-2-methoxyphenyl)-1,6-naphthyridin-7-yl)methyl)carbamate (55 mg, 131.10 umol) in HCl/dioxane (4 M, 4 mL) was stirred at 25° C. for 1 hr under $N_2$ atmosphere. The mixture was concentrated under vacuum to give the title compound (46 mg, crude) as a yellow solid.

LCMS (ESI) m/z=$[M+H]^+$=320.3

Step 6: (R)-4-Cyano-N-((2-(4-cyclobutyl-2-methoxyphenyl)-1,6-naphthyridin-7-yl)methyl)-4-methylisochromane-6-carboxamide To a mixture of (2-(4-cyclobutyl-2-methoxyphenyl)-1,6-naphthyridin-7-yl)methanamine hydrochloride (46 mg, 129.26 umol), EDCI (37.17 mg, 193.90 umol), (R)-4-cyano-4-methylisochromane-6-carboxylic acid (33.69 mg, 155.12 umol) and DIEA (83.53 mg, 646.32 umol) in DCM (1 mL) was added EDCI (37.17 mg, 193.90 umol) and HOBt (26.20 mg, 193.90 umol). The mixture was stirred at 25° C. for 4 hrs under $N_2$ atmosphere. The mixture was concentrated under vacuum and the residue was purified by reversed phase HPLC (0.1% FA condition). The product fraction was concentrated under vacuum to remove MeCN, then lyophilized to give the title compound (27.13 mg, 52.31 umol, 40.47% yield) as a yellow solid.

LCMS (ESI) m/z=$[M+H]^+$=519.3.

$^1H$ NMR (400 MHz, DMSO-$d_6$) δ=9.39-9.36 (m, 1H), 9.34 (s, 1H), 8.51 (d, J=8.4 Hz, 1H), 8.19 (d, J=1.6 Hz, 1H), 8.06 (d, J=8.4 Hz, 1H), 7.95-7.93 (m, 1H), 7.77-7.75 (m, 2H), 7.30 (d, J=8.0 Hz, 1H), 7.02 (s, 1H), 6.97 (d, J=8.0 Hz, 1H), 4.92-4.79 (m, 4H), 4.22 (d, J=11.2 Hz, 1H), 3.84-3.84 (m, 4H), 3.62-3.57 (m, 1H), 2.34-2.31 (m, 2H), 2.21-2.12 (m, 2H), 2.03-1.964 (m, 1H), 1.87-1.83 (m, 1H), 1.69 (s, 3H) ppm Example 27: (R)-4-Cyano-N-((2-(7-fluoro-1,2-dimethyl-1H-indol-4-yl)-1,6-naphthyridin-7-yl)methyl)-4-methylisochromane-6-carboxamide

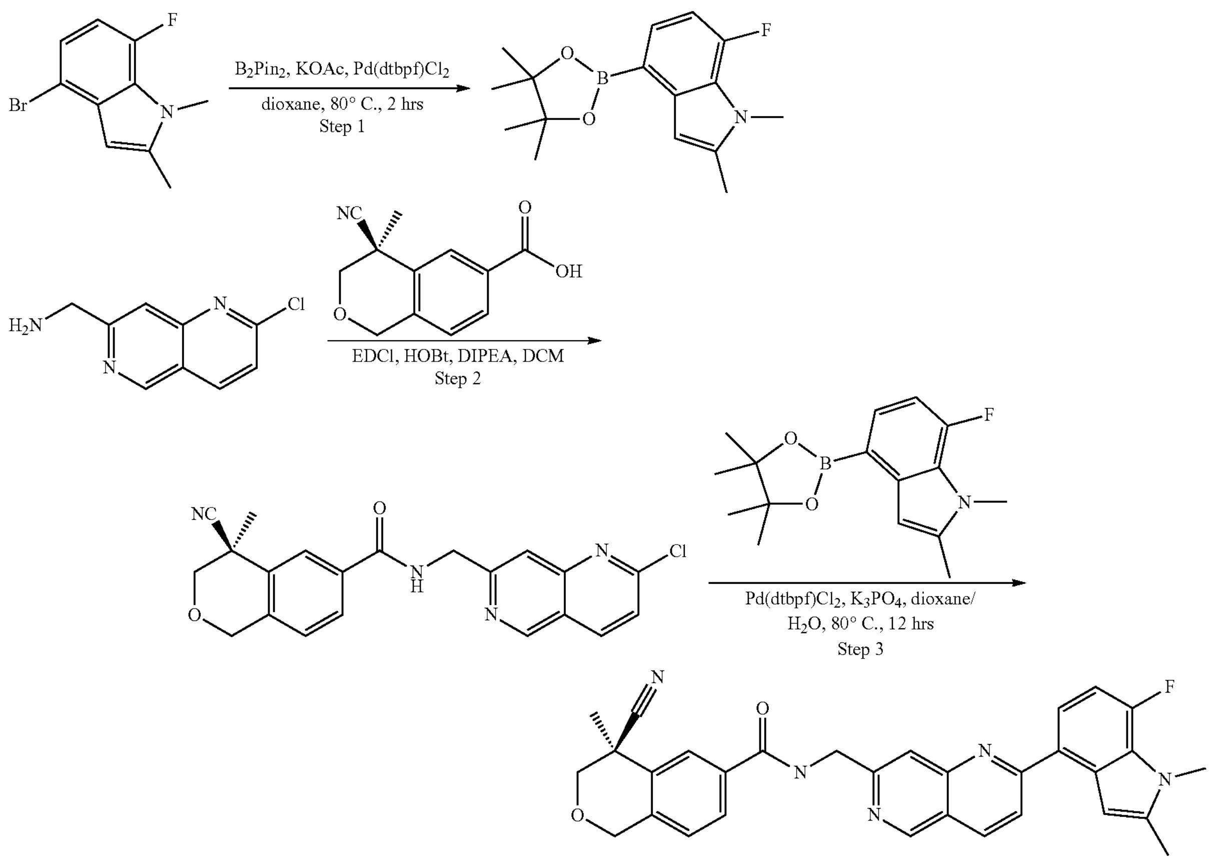

Step 1: 7-Fluoro-1,2-dimethyl-4-(4,4,5,5-tetramethyl-1,3,2-dioxaborolan-2-yl)-1H-indole To a solution of 4-bromo-7-fluoro-1,2-dimethyl-1H-indole (60 mg, 247.84 umol) and 4,4,4',4',5,5,5',5'-octamethyl-2,2'-bi(1,3,2-dioxaborolane) (69.23 mg, 272.63 umol) in dioxane (1 mL) was added KOAc (72.97 mg, 743.53 umol) and [1,1-bis(di-tert-butylphosphino)ferrocene]dichloropalladium(II) (16.15 mg, 24.78 umol). The mixture was stirred at 80° C. for 2 hrs under $N_2$. The mixture was diluted with EA (10 mL) and filtered. The filtrate was concentrated to afford the title compound (70 mg, crude) as brown oil which was used directly in the next step.

Step 2: (R)—N-((2-Chloro-1,6-naphthyridin-7-yl)methyl)-4-cyano-4-methylisochromane-6-carboxamide To a dry 4 mL vial containing 1-(2-chloro-1,6-naphthyridin-7-yl)methanamine (0.040 g, 0.207 mmol, 1 equiv.) was added (R)-4-cyano-4-methylisochromane-6-carboxylic acid (0.045 g, 0.207 mmol, 1 equiv.), EDCI (0.048 g, 0.248 mmol, 1.2 equiv.), DIEA (0.087 mL, 0.496 mmol, 2.4 equiv.), HOBt (0.034 g, 0.248 mmol, 1.2 equiv.) and DCM (1.4 mL, 0.15 M). The reaction mixture was stirred at rt overnight and directly loaded onto silica gel for purification (5% MeOH in DCM as the eluent) to give (4R)—N-[(2-chloro-1,6-naphthyridin-7-yl)methyl]-4-cyano-4-methyl-3,4-dihydro-1H-2-benzopyran-6-carboxamide (68.4 mg, 0.207 mmol, 84% yield) as an off-white solid.

LCMS (m/z) 393.17 [M+H]

Step 3: (R)-4-Cyano-N-((2-(7-fluoro-1,2-dimethyl-1H-indol-4-yl)-1,6-naphthyridin-7-yl)methyl)-4-methylisochromane-6-carboxamide To a solution of (R)—N-((2-chloro-1,6-naphthyridin-7-yl)methyl)-4-cyano-4-methylisochromane-6-carboxamide (40 mg, 101.82 umol) and 7-fluoro-1,2-dimethyl-4-(4,4,5,5-tetramethyl-1,3,2-dioxaborolan-2-yl)-1H-indole (58.88 mg, 203.65 umol) in dioxane/$H_2O$=4/1 (1 mL) was added $K_3PO_4$ (64.84 mg, 305.47 umol) and [1,1-bis(di-tert-butylphosphino)ferrocene]dichloropalladium(II) (6.64 mg, 10.18 umol). The mixture was stirred at 80° C. for 12 hrs under $N_2$. The mixture was diluted with sat. $NaHCO_3$ (10 mL) and extracted with DCM (10 mL*2). The combined organic layers were dried over anhydrous $Na_2SO_4$, filtered and concentrated. The residue was purified by reversed phase prep-HPLC (0.1% FA condition). The product fraction was concentrated to remove ACN and lyophilized to afford the title compound (12.07 mg, 22.87 umol, 22.46% yield) as a yellow solid.

LCMS (ESI) m/z: $[M+H]^+$=520.2

$^1H$ NMR (400 MHz, DMSO-d6) δ=9.40-9.35 (m, 2H), 8.60 (d, J=8.8 Hz, 1H), 8.20-8.16 (m, 2H), 7.95-7.93 (m,

1H), 7.84 (s, 1H), 7.69-7.68 (m, 1H), 7.30 (d, J=8.0 Hz, 1H), 7.08-7.01 (m, 2H), 4.92-4.81 (m, 4H), 4.23 (d, J=11.2 Hz, 1H), 3.89-3.84 (m, 4H), 2.44 (s, 3H), 1.70-1.68 (m, 3H) ppm.

Chiral SFC: Cellucoat-MeOH(DEA)-40-3 mL-35T.lcm, Rt=1.380; ee %=100%.

Example 28: (R)-4-Cyano-N-((2-(imidazo[1,2-b]pyridazin-3-yl)-1,6-naphthyridin-7-yl)methyl)-4-methylisochromane-6-carboxamide

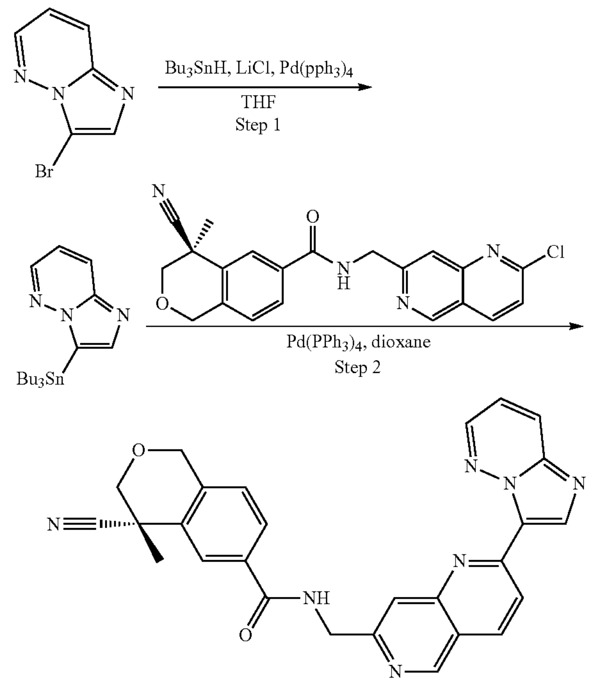

Step 1: 3-(Tributylstannyl)imidazo[1,2-b]pyridazine

To a solution of 3-bromoimidazo[1,2-b]pyridazine (200 mg, 1.01 mmol) and $Bu_3SnH$ (411.56 mg, 1.41 mmol, 374.14 uL) in THE (2 mL) was added LiCl (64.22 mg, 1.51 mmol, 31.02 uL) and $Pd(PPh_3)_4$ (116.71 mg, 101.00 umol) at 25° C. The mixture was stirred at 80° C. for 2 hr under $N_2$. Water (5 mL) was added and the products extracted into EA (10 mL*3). The organic layer was concentrated and the residue was purified by column chromatography ($SiO_2$, PE:EA=5:1, Rf=0.5) and concentrated to give the title compound (100 mg, 245.00 umol, 24.26% yield) as a colorless oil.

LCMS (ESI) m/z: [M+H]+=410.0.

Step 2: (R)-4-Cyano-N-((2-(imidazo[1,2-b]pyridazin-3-yl)-1,6-naphthyridin-7-yl)methyl)-4-methylisochromane-6-carboxamide To a solution of 3-(tributylstannyl)imidazo[1,2-b]pyridazine (37.41 mg, 91.64 umol) in dioxane (0.5 mL) was added (R)—N-((2-chloro-1,6-naphthyridin-7-yl)methyl)-4-cyano-4-methylisochromane-6-carboxamide (30 mg, 76.37 umol) and $Pd(PPh_3)_4$ (4.41 mg, 3.82 umol) at 2500 under $N_2$. The mixture was heated to 10000 and stirred for 2 hrs. The mixture was quenched with saturated aqueous KF (5 mL), then extracted with EA (10 mL*3). The organic layer was concentrated and the residue purified by prep-HPLC (FA method) to give the title compound (12 mg, 20.89 umol, 27.35% yield) as a light yellow solid.

LCMS (ESI) m/z: [M+H]+=476.3.

$^1$HNMR (400 MHz, MeOD-$d_4$) δ=9.34-9.28 (n, 1H), 8.96 (d, J=8.8 Hz, 1H), 8.75-8.62 (m, 3H), 8.54-8.44 (in, H), 8.23-8.17 (m, 2H), 7.97-7.91 (m, 2H), 7.47-7.43 (m, 1H), 7.30 (d, J=8.4 Hz, 1H), 4.93-4.91 (m, 4H), 4.21 (d, J=1.6 Hz, 1H), 3.93 (d, J=11.6 Hz, 1H), 1.77 (s, 3H) ppm.

Chiral SFC: Cellucoat-MeOH+ACN(DEA)-40-3 mL-35T.lcm; Rt=1.034 min, ee %=100%.

The following examples in Table 19 were prepared using standard chemical manipulations and procedures similar to those used for the preparation of Examples 21, 26, 27 and 28.

TABLE 19

Compounds of the Invention

| # | LCMS (m/z) | 1H NMR |
|---|---|---|
| 128 | 577.3 | 1H NMR (400 MHz, DMSO-d6) δ = 9.46-9.37 (m, 2H), 8.72-8.70 (m, 2H), 8.43 (d, J = 8.0 Hz, 1H), 8.21 (s, 2H), 7.99-7.88 (m, 2H), 7.84 (s, 1H), 7.46 (d, J = 7.6 Hz, 1H), 7.31 (d, J = 8.4 Hz, 1H), 4.96-4.80 (m, 4H), 4.23 (d, J = 11.6 Hz, 1H), 3.87 (d, J = 11.6 Hz, 1H), 3.49-3.46 (m, 2H), 3.26 (s, 3H), 3.05-3.02 (m, 2H), 2.84-2.74 (m, 1H), 2.56-2.53 (m, 2H), 2.16-2.15 (m, 2H), 1.94-1.84 (m, 4H), 1.71 (s, 3H) ppm |
| 130 | 495.05 | 1H NMR (300 MHz, DMSO-d6) δ 9.49 (s, 1H), 9.38-9.22 (m, 2H), 8.82 (d, J = 9.0 Hz, 2H), 8.65 (d, J = 8.7 Hz, 1H), 8.14 (d, J = 1.8 Hz, 1H), 7.88 (dd, J = 8.1, 1.7 Hz, 1H), 7.27 (d, J = 8.1 Hz, 1H), 5.05-4.73 (m, 4H), 4.21 (d, J = 11.5 Hz, 1H), 3.85 (d, J = 11.5 Hz, 1H), 2.45-2.32 (m, 1H), 1.68 (s, 3H), 1.28-1.08 (m, 4H). |
| 131 | 533.3 | 1H NMR (400 MHz, MeOD) δ = 9.34 (s, 1H), 8.76 (d, J = 8.4 Hz, 1H), 8.62 (d, J = 8.0 Hz, 1H), 8.55-8.47 (m, 3H), 8.18 (d, J = 1.6 Hz, 1H), 7.98 (s, 1H), 7.96-7.90 (m, 2H), 7.46 (d, J = 7.6 Hz, 1H), 7.30 (d, J = 8.0 Hz, 1H), 4.94-4.91 (m, 4H), 4.21 (d, J = 11.6 Hz, 1H), 3.93 (d, J = 11.6 Hz, 1H), 3.49 (d, J = 12.0 Hz, 2H), 3.16-3.06 (m, 1H), 3.02-2.90 (m, 2H), 2.79 (s, 3H), 2.27-2.19 (m, 4H), 1.77 (s, 3H) ppm |

TABLE 19-continued

| Compounds of the Invention | | |
|---|---|---|
| # | LCMS (m/z) | 1H NMR |
| 132 | 578.3 | 1H NMR (400 MHz, DMSO + D2O) δ = 9.44-9.42 (m, 1H), 9.35 (s, 1H), 8.69-8.53 (m, 2H), 8.26 (s, 1H), 8.15 (d, J = 1.6 Hz, 1H), 7.92-7.90 (m, 1H), 7.85 (d, J = 7.2 Hz, 1H), 7.78 (s, 1H), 7.73-7.69 (m, 1H), 7.30 (d, J = 8.0 Hz, 1H), 6.97 (d, J = 8.4 Hz, 1H), 4.95-4.70 (m, 4H), 4.20 (d, J = 11.6 Hz, 1H), 3.84-3.81 (m, 1H), 3.64-3.57 (m, 4H), 3.49-3.46 (m, 2H), 3.23 (s, 3H), 2.59-2.53 (m, 6H), 1.67 (s, 3H) ppm |
| 133 | 546.2 | 1H NMR (400 MHz, DMSO-d6) δ = 9.43-9.33 (m, 2H), 8.60 (d, J = 8.4 Hz, 1H), 8.41 (s, 1H), 8.24-8.18 (m, 2H), 7.95-7.93 (m, 1H), 7.85 (s, 1H), 7.72 (d, J = 7.2 Hz, 1H), 7.60 (d, J = 8.0 Hz, 1H), 7.30 (d, J = 8.0 Hz, 1H), 7.23-7.21 (m, 1H), 6.95 (s, 1H), 4.94-4.78 (m, 4H), 4.38-4.35 (m, 2H), 4.22 (d, J = 11.2 Hz, 1H), 3.86 (d, J = 11.6 Hz, 1H), 3.63-3.61 (m, 2H), 3.20 (s, 3H), 2.47 (s, 3H), 1.70 (s, 3H) ppm |
| 134 | 516.3 | 1H NMR (400 MHz, DMSO-d6) δ = 9.43-9.34 (m, 2H), 8.60 (d, J = 8.8 Hz, 1H), 8.44-8.39 (m, 1H), 8.26-8.17 (m, 2H), 7.94 (d, J = 1.6 Hz, 1H), 7.83 (s, 1H), 7.74 (d, J = 7.2 Hz, 1H), 7.59 (d, J = 8.4 Hz, 1H), 7.36-7.18 (m, 2H), 6.99 (s, 1H), 4.94-4.80 (m, 4H), 4.29-4.17 (m, 1H), 3.86 (d, J = 11.6 Hz, 1H), 3.74 (s, 3H), 2.85-2.79 (m, 2H), 1.69 (s, 3H), 1.30-1.27 (m, 3H) ppm |
| 135 | 528.3 | 1H NMR (400 MHz, DMSO-d6) δ = 9.47-9.29 (m, 2H), 8.59 (d, J = 8.8 Hz, 1H), 8.26-8.16 (m, 2H), 7.96 (d, J = 1.6 Hz, 1H), 7.84 (s, 1H), 7.74 (d, J = 7.2 Hz, 1H), 7.58 (d, J = 8.0 Hz, 1H), 7.35-7.20 (m, 2H), 6.83 (s, 1H), 4.94-4.80 (m, 4H), 4.22 (d, J = 11.2 Hz, 1H), 3.90-3.84 (m, 4H), 2.13-2.01 (m, 1H), 1.70 (s, 3H), 1.06-0.96 (m, 2H), 0.76-0.66 (m, 2H) ppm |
| 136 | 545.2 | 1H NMR (400 MHz, DMSO-d6) δ = 9.37-9.31 (m, 1H), 9.31-9.25 (m, 1H), 8.89 (s, 1H), 8.53 (d, J = 8.4 Hz, 1H), 8.16 (s, 1H), 7.99-7.90 (m, 2H), 7.69 (s, 1H), 7.35-7.25 (m, 1H), 6.69-6.35 (m, 1H), 5.62-5.59 (m, 1H), 4.98-4.93 (m, 4H), 4.92-4.81 (m, 2H), 4.87 (d, J = 6.0 Hz, 2H), 4.22 (d, J = 11.6 Hz, 1H), 3.87-3.85 (m, 1H), 3.80-3.66 (m, 2H), 1.69 (s, 3H) ppm |
| 137 | 507.3 | 1H NMR (400 MHz, DMSO-d6) δ = 9.51 (s, 1H), 9.44-9.41 (m, 1H), 9.05 (d, J = 5.2 Hz, 1H), 8.82 (d, J = 8.8 Hz, 1H), 8.71 (d, J = 8.4 Hz, 1H), 8.43 (d, J = 5.2 Hz, 1H), 8.21 (d, J = 1.6 Hz, 1H), 7.97-7.95 (m, 1H), 7.90 (s, 1H), 7.32 (d, J = 8.0 Hz, 1H), 5.13 (d, J = 5.6 Hz, 2H), 4.95-4.81 (m, 4H), 4.61 (d, J = 5.6 Hz, 2H), 4.23 (d, J = 11.6 Hz, 1H), 3.87 (d, J = 11.6 Hz, 1H), 1.80 (s, 3H), 1.71 (s, 3H) ppm |
| 138 | 506.2 | 1H NMR (400 MHz, DMSO-d6) δ = 9.46-9.32 (m, 2H), 8.62 (d, J = 8.8 Hz, 1H), 8.19 (d, J = 1.6 Hz, 1H), 7.96-7.94 (m, 2H), 7.80 (s, 1H), 7.65 (d, J = 2.0 Hz, 1H), 7.56-7.45 (m, 2H), 7.41-7.24 (m, 2H), 4.96-4.77 (m, 4H), 4.22 (d, J = 11.6 Hz, 1H), 3.86 (d, J = 11.6 Hz, 1H), 3.81 (s, 3H), 1.69 (s, 3H) ppm |
| 139 | 538.2 | 1H NMR (400 MHz, DMSO-d6) δ = 9.45-9.35 (m, 2H), 8.66 (d, J = 8.8 Hz, 1H), 8.47-8.39 (m, 1H), 8.26 (d, J = 8.8 Hz, 1H), 8.19 (d, J = 1.2 Hz, 1H), 7.98-7.85 (m, 3H), 7.79 (d, J = 8.4 Hz, 1H), 7.63 (s, 1H), 7.57-7.40 (m, 2H), 7.29 (d, J = 7.6 Hz, 1H), 4.95-4.79 (m, 4H), 4.22 (d, J = 11.2 Hz, 1H), 3.92 (s, 3H), 3.86 (d, J = 11.6 Hz, 1H), 1.70 (s, 3H) ppm |
| 140 | 531.2 | 1H NMR (400 MHz, DMSO-d6) δ = 9.49-9.34 (m, 1H), 9.25 (s, 1H), 8.56-8.46 (m, 2H), 8.42 (br s, 1H), 8.20 (s, 1H), 8.02 (d, J = 8.8 Hz, 1H), 7.95 (d, J = 8.4 Hz, 1H), 7.61 (s, 1H), 7.32 (d, J = 8.4 Hz, 1H), 4.98-4.82 (m, 2H), 4.77 (br d, J = 6.0 Hz, 2H), 4.53-4.39 (m, 1H), 4.23 (d, J = 11.6 Hz, 1H), 4.00 (s, 3H), 3.87 (d, J = 11.2 Hz, 1H), 2.62-2.56 (m, 1H), 2.34-2.22 (m, 1H), 1.70 (s, 3H) ppm |
| 141 | 532.2 | 1H NMR (400 MHz, DMSO-d6) δ = 9.45-9.30 (m, 2H), 8.63 (d, J = 8.8 Hz, 1H), 8.29-8.15 (m, 2H), 7.94 (d, J = 7.2 Hz, 1H), 7.78 (d, J = 7.6 Hz, 1H), 7.66 (d, J = 8.0 Hz, 1H), 7.39-7.25 (m, 2H), 7.23 (s, 1H), 4.97-4.71 (m, 4H), 4.65 (s, 2H), 4.29-4.16 (m, 1H), 3.86 (d, J = 11.2 Hz, 1H), 3.83-3.76 (m, 3H), 3.29 (s, 3H), 1.70 (s, 3H) ppm |
| 144 | 479.20 | $^1$H NMR (400 MHz, DMSO-$d_6$) δ 9.44-9.38 (m, 2H), 8.56 (d, J = 8.7 Hz, 1H), 8.19 (d, J = 1.8 Hz, 1H), 8.12 (d, J = 8.2 Hz, 1H), 7.99-7.90 (m, 1H), 7.82 (s, 1H), 7.75 (d, J = 7.8 Hz, 1H), 7.30 (d, J = 8.1 Hz, 1H), 7.06 (d, J = 1.5 Hz, 1H), 6.96-6.90 (m, 1H), 4.95-4.79 (m, 4H), 4.22 (d, J = 11.4 Hz, 1H), 3.91-3.83 (m, 4H), 2.39 (s, 3H), 1.70 (s, 3H). |
| 145 | 531.2 | 1H NMR (400 MHz, DMSO-d6) δ = 9.38-9.30 (m, 2H), 8.98 (s, 1H), 8.59 (d, J = 8.8 Hz, 1H), 8.18 (d, J = 1.6 Hz, 1H), 8.00-8.00 (m, 1H), 7.96-7.69 (m, 3H), 7.30 (d, J = 8.0 Hz, 1H), 5.73-5.66 (m, 1H), 5.01-4.94 (m, 4H), 4.92-4.85 (m, 2H), 4.81-4.78 (m, 2H), 4.22 (d, J = 11.2 Hz, 1H), 3.87 (d, J = 11.6 Hz, 1H), 1.69 (s, 3H)ppm |
| 146 | 520.2 | 1H NMR (400 MHz, DMSO-d6) δ = 9.37-9.34 (m, 1H), 9.24 (s, 1H), 8.39 (d, J = 8.8 Hz, 1H), 8.19 (d, J = 1.6 Hz, 1H), 8.10 (d, J = 8.8 Hz, 1H), 7.95-7.93 (m, 1H), 7.85 (d, J = 8.4 Hz, 1H), 7.68 (s, 1H), 7.30 (d, J = 8.0 Hz, 1H), 6.12-6.07 (m, 2H), 4.92-4.81 (m, 2H), 4.77 (br d, J = 6.0 Hz, 2H), 4.22 (d, J = 11.6 Hz, 1H), 3.94-3.90 (m, 4H), 3.87-3.84 (m, 4H), 2.38-2.33 (m, 2H), 1.69 (s, 3H) ppm |
| 147 | 538.2 | 1H NMR (400 MHz, DMSO-d6) δ = 9.46-9.39 (m, 2H), 8.64-8.62 (m, 1H), 8.25-8.20 (m, 2H), 7.95 (d, J = 8.0 Hz, 1H), 7.85 (s, 1H), 7.81-7.79 |

TABLE 19-continued

Compounds of the Invention

| # | LCMS (m/z) | 1H NMR |
| --- | --- | --- |
| | | (m, 2H), 7.53-7.52 (m, 1H), 7.35-7.27 (m, 3H), 6.53-6.26 (m, 1H), 4.92-4.74 (m, 6H), 4.23 (d, J = 11.2 Hz, 1H), 3.87 (d, J = 11.2 Hz, 1H), 1.70 (s, 3H) ppm |
| 148 | 521.2 | 1H NMR (400 MHz, DMSO-d6) δ = 9.39-9.35 (m, 2H), 8.51 (d, J = 8.8 Hz, 1H), 8.19 (d, J = 1.6 Hz, 1H), 8.07 (d, J = 8.4 Hz, 1H), 7.99-7.93 (m, 1H), 7.76-7.74 (m, 2H), 7.30 (d, J = 8.0 Hz, 1H), 7.15-7.11 (m, 2H), 4.92-4.79(m, 4H), 4.22 (d, J = 11.6 Hz, 1H), 3.89-3.84 (m, 4H), 1.69 (s, 3H), 1.34 (s, 9H) ppm |
| 149 | 504.2 | 1H NMR (400 MHz, DMSO-d6) δ = 9.45-9.31 (m, 2H), 8.59-8.57 (m, 1H), 8.17 (d, J = 1.6 Hz, 1H), 7.93-7.91 (m, 1H), 7.78-7.69 (m, 2H), 7.29 (d, J = 8.0 Hz, 1H), 7.14-7.12 (m, 1H), 6.75-6.62 (m, 2H), 4.92-4.84 (m, 2H), 4.80-4.79 (m, 2H), 4.21 (d, J = 11.6 Hz, 1H), 3.86 (d, J = 11.6 Hz, 1H), 3.24-3.18 (m, 2H), 2.89 (s, 3H), 2.65-2.62 (m, 2H), 1.81-1.75 (m, 2H), 1.69 (s, 3H) ppm |
| 150 | 503.2 | 1H NMR (400 MHz, DMSO-d6) δ = 9.44 (s, 1H), 9.40 (s, 1H), 8.71 (d, J = 8.4 Hz, 1H), 8.36-8.31 (m, 2H), 8.20 (d, J = 1.6 Hz, 1H), 7.96-7.91 (m, 2H), 7.76 (d, J = 4.8 Hz, 1H), 7.30 (d, J = 8.0 Hz, 1H), 6.99 (d, J = 0.8 Hz, 1H), 4.94-4.81 (m, 4H), 4.22 (d, J = 11.6 Hz, 1H), 3.87 (d, J = 11.2 Hz, 1H), 3.80 (s, 3H), 2.52 (s, 3H), 1.70 (s, 3H) ppm |
| 151 | 489.2 | 1H NMR (400 MHz, DMSO-d6) δ = 9.50-9.32 (m, 2H), 9.19 (s, 1H), 8.64 (d, J = 8.8 Hz, 1H), 8.41 (d, J = 8.8 Hz, 1H), 8.21 (d, J = 1.6 Hz, 1H), 8.07-7.98 (m, 2H), 7.95-7.93 (m, 1H), 7.82 (d, J = 8.4 Hz, 1H), 7.45-7.41 (m, 1H), 7.30 (d, J = 8.4 Hz, 1H), 4.92-4.78 (m, 4H), 4.25-4.17 (m, 4H), 3.87 (d, J = 11.6 Hz, 1H), 1.71 (s, 3H) ppm |
| 152 | 519.2 | 1H NMR (400 MHz, DMSO-d6) δ = 9.45-9.36 (m, 2H), 8.85 (s, 1H), 8.68 (d, J = 8.4 Hz, 1H), 8.41-8.36 (m, 1H), 8.20 (d, J = 1.2 Hz, 1H), 8.00-7.93 (m, 3H), 7.88 (d, J = 8.4 Hz, 1H), 7.58-7.53 (m, 1H), 7.31 (d, J = 8.0 Hz, 1H), 4.94-4.81 (m, 5H), 4.53-4.50 (m, 2H), 4.23 (d, J = 11.2 Hz, 1H), 3.89-3.81 (m, 3H), 1.70 (s, 3H) ppm |
| 153 | 479.25 | $^1$H NMR (400 MHz, Methanol-$d_4$) δ 9.30 (d, J = 0.8 Hz, 1H), 8.48 (dd, J = 8.7, 0.9 Hz, 1H), 8.16 (d, J = 1.8 Hz, 1H), 8.04 (d, J = 8.6 Hz, 1H), 7.95-7.89 (m, 2H), 7.57-7.50 (m, 1H), 7.33-7.23 (m, 2H), 7.06 (d, J = 8.4 Hz, 1H), 4.93-4.88 (m, 4H), 4.19 (d, J = 11.4 Hz, 1H), 3.91 (d, J = 11.4 Hz, 1H), 3.85 (s, 3H), 2.34 (s, 3H), 1.75 (s, 3H). |
| 154 | 547.1 | 1H NMR (400 MHz, DMSO-d6) δ = 9.41-9.38 (m, 1H), 9.29 (s, 1H), 8.70 (s, 1H), 8.59 (d, J = 8.8 Hz, 1H), 8.19 (d, J = 1.6 Hz, 1H), 7.95-7.91 (m, 2H), 7.75-7.38 (m, 2H), 7.31 (d, J = 8.0 Hz, 1H), 5.60-5.53 (m, 1H), 4.93-4.86 (m, 6H), 4.82-4.77 (m, 2H), 4.23 (d, J = 11.2 Hz, 1H), 3.86 (d, J = 11.2 Hz, 1H), 1.70 (s, 3H) ppm |
| 155 | 550.2 | 1H NMR (400 MHz, DMSO-d6) δ = 9.37-9.34 (m, 1H), 9.27 (s, 1H), 8.43 (d, J = 8.4 Hz, 1H), 8.19 (d, J = 1.2 Hz, 1H), 8.12 (d, J = 8.4 Hz, 1H), 7.95-7.93 (m, 1H), 7.87 (d, J = 8.4 Hz, 1H), 7.71 (s, 1H), 7.30 (d, J = 8.0 Hz, 1H), 6.67-6.65 (m, 2H), 4.92-4.77 (m, 4H), 4.22 (d, J = 11.6 Hz, 1H), 3.89-3.84 (m, 4H), 3.77-3.74 (m, 4H), 3.28-3.25 (m, 4H), 1.70 (s, 3H) ppm |
| 156 | 499.1 | 1H NMR (400 MHz, METHANOL-d4) δ = 9.44-9.35 (m, 2H), 8.56 (d, J = 8.4 Hz, 1H), 8.19 (s, 1H), 8.05 (d, J = 8.8 Hz, 1H), 7.95-7.93 (m, 1H), 7.86-7.76 (m, 2H), 7.36-7.27 (m, 2H), 7.17-7.15 (m, 1H), 4.96-4.76 (m, 4H), 4.22 (d, J = 11.6 Hz, 1H), 3.90 (s, 3H), 3.86 (d, J = 11.6 Hz, 1 H), 1.69 (s, 3H) ppm |
| 157 | 515.2 | 1H NMR (400 MHz, DMSO-d6) δ = 9.40 (s, 2H), 8.58 (d, J = 8.4 Hz, 1H), 8.19 (d, J = 1.2 Hz, 1H), 8.07 (d, J = 8.8 Hz, 1H), 7.99-7.86 (m, 2H), 7.80 (s, 1H), 7.39 (s, 1H), 7.30 (d, J = 8.0 Hz, 2H), 7.25-6.93 (m, 1H), 4.96-4.76 (m, 4H), 4.22 (d, J = 11.6 Hz, 1H), 3.91 (s, 3H), 3.86 (d, J = 11.2 Hz, 1H), 1.69 (s, 3H) ppm |
| 158 | 493.2 | 1H NMR (400 MHz, DMSO-d6) δ = 9.51 (s, 1H), 9.48-9.39 (m, 1H), 9.04 (d, J = 5.2 Hz, 1H), 8.87-8.78 (m, 1H), 8.73 (d, J = 8.4 Hz, 1H), 8.45 (d, J = 5.2 Hz, 1H), 8.20 (d, J = 1.6 Hz, 1H), 7.97-7.94 (m, 1H), 7.90 (s, 1H), 7.32 (d, J = 8.0 Hz, 1H), 5.03-4.82 (m, 8H), 4.73-4.52 (m, 1H), 4.23 (d, J = 11.2 Hz, 1H), 3.87 (d, J = 11.2 Hz, 1H), 1.71 (s, 3H) ppm |
| 159 | 518.1 | 1H NMR (400 MHz, DMSO-d6) δ = 9.42-9.35 (m, 2H), 8.62 (d, J = 8.4 Hz, 1H), 8.28-8.17 (m, 2H), 7.95-7.93 (m, 1H), 7.84 (s, 1H), 7.77 (d, J = 7.2 Hz, 1H), 7.69 (d, J = 8.0 Hz, 1H), 7.52 (d, J = 3.2 Hz, 1H), 7.35-7.26 (m, 2H), 7.18 (d, J = 2.8 Hz, 1H), 4.94-4.81 (m, 5H), 4.31-4.28 (m, 2H), 4.22 (d, J = 11.6 Hz, 1H), 3.87 (d, J = 11.2 Hz, 1H), 3.77-3.71 (m, 2H), 1.70 (s, 3H) ppm |
| 160 | 501.15 | $^1$H NMR (300 MHz, DMSO-$d_6$) δ 9.49-9.38 (m, 2H), 8.88-8.72 (m, 2H), 8.55 (dd, J = 7.9, 1.0 Hz, 1H), 8.30 (s, 1H), 8.10-7.95 (m, 2H), 7.85 (s, 1H), 7.81-7.73 (m, 1H), 7.32 (d, J = 8.1 Hz, 1H), 6.69 (s, 1H), 5.16-5.04 (m, 2H), 4.94-4.68 (m, 6H), 4.09 (t, J = 13.0 Hz, 1H), 3.86 (dd, J = 25.2, 12.5 Hz, 1H), 1.71 (d, J = 20.7 Hz, 3H). |
| 162 | 489.2 | 1H NMR (400 MHz, DMSO-d6) δ = 9.40-9.35 (m, 2H), 8.61 (d, J = 8.8 Hz, 1H), 8.51-8.47 (m, 1H), 8.22-8.19 (m, 2H), 7.96-7.93(m, 1H), 7.75 (s, 1H), 7.50-7.23 (m, 3H), 4.93-4.76 (m, 4H), 4.26-4.16 (m, 1H), 4.04 (s, 3H), 3.87 (d, J = 11.2 Hz, 1H), 1.70 (s, 3H) ppm |

TABLE 19-continued

| Compounds of the Invention | | |
|---|---|---|
| # | LCMS (m/z) | 1H NMR |
| 163 | 532.3 | 1H NMR (400 MHz, DMSO-d6) δ = 9.45-9.41 (m, 2H), 8.73 (d, J = 8.6 Hz, 1H), 8.71-8.57(m, 2H), 8.20 (d, J = 1.2 Hz, 1H), 8.01-7.99 (m, 1H), 7.96-7.94 (m, 1H), 7.84 (s, 1H), 7.70-7.68 (m, 1H), 7.32 (d, J = 8.4 Hz, 1H), 4.93-4.82 (m, 4H), 4.24 (d, J = 11.2 Hz, 1H), 3.88 (d, J = 11.6 Hz, 1H), 3.37 (s, 3H), 1.70 (s, 3H), 1.53 (s, 6H) ppm |
| 164 | 475.3 | 1HNMR (400 MHz, DMSO-d6) δ = 9.48-9.33 (m, 2H), 8.79-8.78 (m, 1H), 8.66 (d, J = 8.8 Hz, 1H), 8.39 (d, J = 8.8 Hz, 1H), 8.21 (d, J = 1.6 Hz, 1H), 7.97-7.95 (m, 1H), 7.86-7.71 (m, 2H), 7.40 (s, 1H), 7.35-7.24 (m, 2H), 7.02-6.98 (m, 1H), 4.96-4.76 (m, 4H), 4.23 (d, J = 11.6 Hz, 1H), 3.87 (d, J = 11.6 Hz, 1H), 1.71 (s, 3H), ppm |
| 165 | 543.2 | 1H NMR (400 MHz, DMSO-d6) δ = 9.46-9.42 (m, 2H), 8.85-8.83 (m, 1H), 8.78-8.76 (m, 1H), 8.51 (d, J = 8.0 Hz, 1H), 8.46 (s, 1H), 8.30 (d, J = 8.0 Hz, 1H), 8.22 (d, J = 1.6 Hz, 1H), 7.99-7.95 (m, 2H), 7.87 (s, 1H), 7.32 (d, J = 8.0 Hz, 1H), 6.69 (d, J = 9.6 Hz, 1H), 4.94-4.83 (m, 4H), 4.23 (d, J = 11.6 Hz, 1H), 3.88 (d, J = 11.6 Hz, 1H), 3.15-3.08 (m, 1H), 1.71 (s, 3H), 1.40-1.35 (m, 2H), 0.92-0.88 (m, 2H) ppm |
| 167 | 453.20 | $^{1}$H NMR (300 MHz, DMSO-$d_6$) δ 9.35-9.15 (m, 2H), 8.82-8.64 (m, 1H), 8.48-8.30 (m, 3H), 8.20-8.09 (m, 1H), 7.94-7.81 (m, 1H), 7.72-7.57 (m, 3H), 7.27 (d, J = 8.1 Hz, 1H), 5.02-4.69 (m, 4H), 4.22 (d, J = 11.5 Hz, 1H), 3.85 (d, J = 11.5 Hz, 1H), 1.68 (s, 3H). |
| 168 | 499.20 | $^{1}$H NMR (400 MHz, DMSO-d6) δ 9.45-9.38 (m, 2H), 8.70 (d, J = 8.6 Hz, 1H), 8.62 (d, J = 8.6 Hz, 1H), 8.36 (d, J = 7.7 Hz, 1H), 8.28 (d, J = 1.8 Hz, 1H), 7.98 (dt, J = 8.0, 1.7 Hz, 1H), 7.89 (t, J = 7.8 Hz, 1H), 7.82 (s, 1H), 7.67 (d, J = 7.9 Hz, 1H), 7.31 (d, J = 8.1 Hz, 1H), 4.94-4.69 (m, 5H), 4.08 (t, J = 13.0 Hz, 1H), 3.95-3.78 (m, 3H), 1.70 (d, J = 20.7 Hz, 3H), 1.29 (q, J = 3.7 Hz, 2H), 1.00 (q, J = 3.7 Hz, 2H). |
| 169 | 535.20 | $^{1}$H NMR (400 MHz, DMSO-d6) δ 9.43 (t, J = 1.4 Hz, 2H), 8.83-8.65 (m, 2H), 8.52 (dd, J = 7.9, 1.0 Hz, 1H), 8.29 (d, J = 1.9 Hz, 1H), 8.09-7.97 (m, 2H), 7.88-7.78 (m, 2H), 7.32 (d, J = 8.1 Hz, 1H), 6.47 (s, 1H), 4.92-4.69 (m, 4H), 4.09 (t, J = 13.0 Hz, 1H), 3.85 (dd, J = 25.2, 12.5 Hz, 1H), 3.42 (d, J = 13.5 Hz, 2H), 2.98-2.80 (m, 2H), 1.70 (d, J = 20.7 Hz, 3H). |
| 170 | 518.2 | 1H NMR (400 MHz, DMSO-d6) δ = 9.45-9.41 (m, 2H), 8.73 (d, J = 8.8 Hz, 1H), 8.61 (d, J = 8.8 Hz, 1H), 8.57 (d, J = 8.0 Hz, 1H), 8.40 (br s, 1H), 8.20 (d, J = 1.6 Hz, 1H), 8.00-7.94 (m, 2H), 7.84 (s, 1H), 7.63-7.62 (m, 1H), 7.32 (d, J = 8.0 Hz, 1H), 5.65 (br s, 1H), 4.93-4.82 (m, 4H), 4.24 (d, J = 11.6 Hz, 1H), 3.88 (d, J = 11.6 Hz, 1H), 1.70 (s, 3H), 1.52 (s, 6H) ppm |
| 171 | 506.2 | 1H NMR (400 MHz, DMSO-d6) δ = 9.40-9.38 (m, 2H), 8.66 (d, J = 8.4 Hz, 1H), 8.28 (d, J = 8.4 Hz, 1H), 8.19 (d, J = 1.6 Hz, 1H), 7.94-7.92 (m, 1H), 7.86 (s, 1H), 7.67-7.64 (m, 1H), 7.55-7.53 (m, 1H), 7.49 (d, J = 3.2 Hz, 1H), 7.30 (d, J = 8.0 Hz, 1H), 7.18 (d, J = 2.4 Hz, 1H), 4.92-4.81 (m, 4H), 4.23-4.20 (d, J = 11.6 Hz, 1H), 3.87 (d, J = 11.6 Hz, 1H), 3.83 (s, 3H), 1.69(s, 3H) ppm |
| 172 | 502.4 | 1H NMR (400 MHz, DMSO) δ = 9.44-9.34 (m, 2H), 8.65-8.57 (m, 1H), 8.31-8.27 (m, 1H), 8.26-8.16 (m, 2H), 7.98-7.91 (m, 1H), 7.85 (s, 1H), 7.73 (d, J = 6.8 Hz, 1H), 7.62-7.54 (m, 1H), 7.34-7.20 (m, 2H), 7.01-6.95 (m, 1H), 4.93-4.85 (m, 2H), 4.82 (br d, J = 5.4 Hz, 2H), 4.22 (d, J = 11.2 Hz, 1H), 3.86 (d, J = 11.2 Hz, 1H), 3.76-3.73 (m, 3H), 2.47-2.45 (m, 3H), 1.72-1.69 (m, 3H) ppm |
| 173 | 514.2 | 1H NMR (400 MHz, DMSO-d6) δ = 9.41-9.38 (m, 2H), 8.62 (d, J = 8.8 Hz, 1H), 8.24 (d, J = 8.4 Hz, 1H), 8.20 (d, J = 1.2 Hz, 1H), 7.95-7.93 (m, 1H), 7.83-7.80 (m, 2H), 7.76 (d, J = 8.0 Hz, 1H), 7.48 (d, J = 3.6 Hz, 1H), 7.37-7.33 (m, 1H), 7.30 (d, J = 8.0 Hz, 1H), 7.16 (d, J = 3.2 Hz, 1H), 4.92-4.81 (m, 4H), 4.23 (d, J = 11.6 Hz, 1H), 3.87 (d, J = 11.2 Hz, 1H), 3.54-3.49 (m, 1H), 1.70 (s, 3H), 1.12-1.08 (m, 2H), 0.99-0.96 (m, 2H) ppm |
| 174 | 516.3 | 1H NMR (400 MHz, DMSO-d6) δ = 9.42-9.38 (m, 2H), 8.62 (d, J = 8.4 Hz, 1H), 8.41 (d, J = 2.0 Hz, 1H), 8.24-8.20 (m, 2H), 7.95 (d, J = 6.4 Hz, 1H), 7.83 (s, 1H), 7.77-7.71 (m, 2H), 7.65 (d, J = 3.2 Hz, 1H), 7.33-7.29 (m, 2H), 7.21 (d, J = 2.8 Hz, 1H), 4.93-4.81 (m, 5H), 4.23 (d, J = 11.2 Hz, 1H), 3.86 (d, J = 11.2 Hz, 1H), 1.70 (s, 3H), 1.49 (d, J = 6.8 Hz, 6H) ppm |
| 175 | 521.3 | 1H NMR (400 MHz, MeOD) δ = 9.35-9.31 (m, 1H), 8.56-8.48 (m, 1H), 8.22-8.16 (m, 1H), 8.14-8.06 (m, 1H), 8.00-7.91 (m, 2H), 7.81-7.76 (m, 1H), 7.34-7.28 (m, 1H), 7.27-7.19 (m, 2H), 5.19-5.13 (m, 2H), 4.98-4.95 (m, 2H), 4.94-4.93 (m, 2H), 4.86-4.83 (m, 3H), 4.44-4.33 (m, 1H), 4.26-4.18 (m, 1H), 3.95 (s, 3H), 3.94-3.89 (m, 1H), 1.77 (s, 3H) ppm |
| 176 | 475.20 | $^{1}$H NMR (400 MHz, DMSO-d6) δ 9.59 (t, J = 5.9 Hz, 1H), 9.46 (s, 2H), 9.10 (t, J = 1.7 Hz, 1H), 8.79 (s, 1H), 8.75 (d, J = 8.7, 0.8 Hz, 1H), 8.62 (t, J = 1.8 Hz, 1H), 8.56 (d, J = 8.6 Hz, 1H), 7.93 (s, 1H), 4.94-4.78 (m, 2H), 2.41-2.30 (m, 1H), 1.71 (d, J = 20.9 Hz, 3H), 1.23-1.10 (m, 4H). |
| 177 | 502.2 | 1H NMR (400 MHz, DMSO-d6) δ = 9.47-9.35 (m, 2H), 8.61 (d, J = 8.4 Hz, 1H), 8.42 (br s, 1H), 8.17 (s, 1H), 7.92 (br d, J = 7.4 Hz, 1H), 7.86-7.76 (m, 2H), 7.54 (d, J = 8.0 Hz, 1H), 7.32-7.22 (m, 2H), 7.19-7.11 (m, 2H), 4.93-4.76 (m, 4H), 4.21 (d, J = 11.2 Hz, 1H), 3.85 (br d, J = 11.6 Hz, 1H), 3.78 (s, 3H), 1.82 (s, 3H), 1.68 (s, 3H) ppm |

TABLE 19-continued

| Compounds of the Invention | | |
|---|---|---|
| # | LCMS (m/z) | 1H NMR |
| 178 | 502.3 | 1H NMR (400 MHz, DMSO-d6) δ = 9.47-9.32 (m, 2H), 8.62 (d, J = 8.8 Hz, 1H), 8.24 (d, J = 8.7 Hz, 1H), 8.20 (d, J = 1.2 Hz, 1H), 7.95 (d, J = 8.0 Hz, 1H), 7.84 (s, 1H), 7.78 (d, J = 7.6 Hz, 1H), 7.69 (d, J = 8.4 Hz, 1H), 7.55 (d, J = 3.2 Hz, 1H), 7.36-7.26 (m, 2H), 7.19 (d, J = 3.2 Hz, 1H), 4.98-4.76 (m, 4H), 4.36-4.16 (m, 3H), 3.87 (d, J = 11.2 Hz, 1H), 1.70 (s, 3H), 1.41-1.37 (m, 3H) ppm |
| 179 | 488.3 | 1H NMR (400 MHz, DMSO-d6) δ = 9.46-9.32 (m, 2H), 8.62 (d, J = 8.8 Hz, 1H), 8.25 (d, J = 8.8 Hz, 1H), 8.20 (d, J = 1.2 Hz, 1H), 7.95 (d, J = 1.6 Hz, 1H), 7.85 (s, 1H), 7.80 (d, J = 7.2 Hz, 1H), 7.65 (d, J = 8.4 Hz, 1H), 7.48 (d, J = 3.2 Hz, 1H), 7.38-7.27 (m, 2H), 7.20 (d, J = 2.8 Hz, 1H), 4.96-4.76 (m, 4H), 4.23 (d, J = 11.6 Hz, 1H), 3.90-3.83 (m, 4H), 1.70 (s, 3H) ppm |
| 180 | 517.3 | 1H NMR (400 MHz, DMSO-d6) δ = 9.57-9.36 (m, 2H), 8.89-8.73 (m, 2H), 8.53 (d, J = 8.0 Hz, 1H), 8.48-8.43 (m, 1H), 8.41-8.33 (m, 1H), 8.22 (s, 1H), 8.10-8.01 (m, 1H), 8.00-7.94 (m, 1H), 7.88 (s, 1H), 7.32 (d, J = 8.4 Hz, 1H), 6.79 (d, J = 9.6 Hz, 1H), 4.98-4.77 (m, 4H), 4.23 (d, J = 11.6 Hz, 1H), 3.89-3.83 (m, 4H), 1.71 (s, 3H) ppm |
| 181 | 477.2 | 1H NMR (400 MHz, DMSO-d6) δ = 9.55-9.52 (m, 1H), 9.36 (s, 1H), 9.16 (s, 1H), 9.08 (d, J = 2.0 Hz, 1H), 8.72 (s, 1H), 8.65 (s, 1H), 8.55 (d, J = 2.0 Hz, 1H), 8.36-8.33 (m, 1H), 8.25 (d, J = 8.8 Hz, 1H), 7.89 (s, 1H), 4.91-4.85 (m, 2H), 4.80(d, J = 6 Hz, 2H), 4.29 (d, J = 11.6 Hz, 1H), 3.93 (d, J = 11.6 Hz, 1H), 2.31-2.27 (m, 1H), 1.71 (s, 3H), 1.16-1.10 (m, 4H) ppm. |
| 182 | 489.2 | 1H NMR (400 MHz, DMSO) δ = 9.45-9.34 (m, 2H), 8.87-8.82 (m, 1H), 8.72-8.64 (m, 1H), 8.39 (d, J = 8.8 Hz, 1H), 8.20 (d, J = 1.6 Hz, 1H), 8.02 (d, J = 7.6 Hz, 1H), 7.97-7.93 (m, 2H), 7.91-7.81 (m, 1H), 7.63-7.53 (m, 1H), 7.34-7.26 (m, 1H), 4.95-4.80 (m, 4H), 4.27 (s, 1H), 4.15-4.11 (m, 3H), 3.87 (d, J = 11.6 Hz, 1H), 1.73-1.67 (m, 3H) ppm |
| 184 | 505.3 | 1H NMR (400 MHz, DMSO-d6) δ = 9.38-9.35 (m, 1H), 9.33 (s, 1H), 8.60 (d, J = 8.8 Hz, 1H), 8.42 (s, 1H), 8.18 (d, J = 1.2 Hz, 1H), 8.00-7.68 (m, 4H), 7.30 (d, J = 8.0 Hz, 1H), 4.92-4.78 (m, 4H), 4.22 (d, J = 11.6 Hz, 1H), 4.15 (s, 3H), 3.87 (d, J = 11.6 Hz, 1H), 1.69 (s, 3H) ppm |
| 185 | 527.3 | 1H NMR (400 MHz, DMSO-d6) δ = 9.39-9.36 (m, 1H), 9.21 (s, 1H), 8.46-8.45 (m, 2H), 8.43 (s, 1H), 8.19 (d, J = 1.6 Hz, 1H), 8.00 (d, J = 8.8 Hz, 1H), 7.95-7.92 (m, 1H), 7.57 (s, 1H), 7.31 (d, J = 8.0 Hz, 1H), 5.49-5.29 (m, 1H), 5.05-4.98 (m, 1H), 4.92-4.81 (m, 2H), 4.75 (br d, J = 4.8 Hz, 2H), 4.22 (d, J = 11.2 Hz, 1H), 4.00 (s, 3H), 3.86 (d, J = 11.2 Hz, 1H), 2.86-2.75 (m, 2H), 2.73-2.68 (m, 2H), 1.69 (s, 3H) ppm |
| 186 | 521.2 | 1H NMR (400 MHz, DMSO-d6) δ = 9.36-9.33 (m, 1H), 9.25 (s, 1H), 8.66 (s, 1H), 8.50 (d, J = 8.4 Hz, 1H), 8.17 (d, J = 1.6 Hz, 1H), 8.00 (d, J = 8.8 Hz, 1H), 7.92-7.90 (m, 1H), 7.68 (s, 1H), 7.29 (d, J = 8.0 Hz, 1H), 5.55-5.48 (m, 1H), 4.95-4.85 (m, 6H), 4.81-4.75 (m, 2H), 4.22 (d, J = 11.6 Hz, 1H), 3.86 (d, J = 11.2 Hz, 1H), 3.00-2.92 (m, 1H), 1.69 (s, 3H), 0.97-0.89 (m, 4H) ppm |
| 187 | 495.4 | 1H NMR (400 MHz, DMSO-d6) δ = 9.40-9.31 (m, 1H), 9.26 (s, 1H), 8.49 (d, J = 8.8 Hz, 1H), 8.35 (s, 1H), 8.17 (d, J = 1.6 Hz, 1H), 7.99 (d, J = 8.8 Hz, 1H), 7.92 (d, J = 8.0 Hz, 1H), 7.69 (s, 1H), 7.30 (d, J = 8.4 Hz, 1H), 5.81-5.63 (m, 1H), 5.08-4.69 (m, 8H), 4.31-4.12 (m, 1H), 3.86 (d, J = 11.6 Hz, 1H), 2.74-2.67 (m, 3H), 1.69 (s, 3H) ppm |
| 188 | 495.4 | 1H NMR (400 MHz, DMSO-d6) δ = 9.39-9.36 (m, 1H), 9.26 (s, 1H), 8.71 (s, 1H), 8.50 (d, J = 8.8 Hz, 1H), 8.18 (d, J = 1.6 Hz, 1H), 7.93 (d, J = 9.2 Hz, 2H), 7.70 (s, 1H), 7.31 (d, J = 8.4 Hz, 1H), 5.65-5.47 (m, 1H), 4.93 (d, J = 7.2 Hz, 4H), 4.90-4.72 (m, 4H), 4.23 (d, J = 11.6 Hz, 1H), 3.87 (d, J = 11.6 Hz, 1H), 2.64 (s, 3H), 1.70 (s, 3H) ppm |
| 189 | 478.20 | $^{1}$H NMR (300 MHz, DMSO-d6) δ 9.79 (t, J = 5.7 Hz, 1H), 9.14 (d, J = 2.0 Hz, 1H), 9.08 (dd, J = 8.9, 1.0 Hz, 1H), 8.96 (d, J = 9.0 Hz, 1H), 8.63 (d, J = 2.0 Hz, 1H), 8.45 (d, J = 7.4 Hz, 1H), 8.34 (s, 1H), 7.98 (t, J = 7.8 Hz, 1H), 7.61 (d, J = 7.6 Hz, 1H), 5.23 (d, J = 5.7 Hz, 2H), 5.01-4.84 (m, 2H), 4.36 (d, J = 11.5 Hz, 1H), 4.00 (d, J = 11.6 Hz, 1H), 2.36-2.28 (m, 1H), 1.79 (s, 3H), 1.24-1.05 (m, 4H). |
| 192 | 499.2 | 1H NMR (400 MHz, DMSO-d6) δ = 9.57-9.54 (m, 1H), 9.31 (s, 1H), 9.09 (s, 1H), 8.84 (s, 1H), 8.62-8.57 (m, 2H), 8.07 (d, J = 8.8 Hz, 1H), 7.83-7.53 (m, 2H), 4.86-4.73 (m, 4H), 4.15-4.06 (m, 4H), 3.96-3.86 (m, 1H), 1.71 (d, J = 20.8 Hz, 3H) ppm |
| 193 | 505.2 | 1H NMR (400 MHz, DMSO-d6) δ = 9.42-9.38 (m, 1H), 9.31 (s, 1H), 8.85 (s, 1H), 8.58 (d, J = 8.8 Hz, 1H), 8.20 (d, J = 1.6 Hz, 1H), 8.06 (d, J = 8.8 Hz, 1H), 7.96-7.94 (m, 1H), 7.81-7.52 (m, 2H), 7.31 (d, J = 8.4 Hz, 1H), 4.93-4.77(m, 4H), 4.23 (d, J = 11.2 Hz, 1H), 4.08-4.05 (m, 3H), 3.88-3.85 (m, 1H), 1.70 (s, 3H) ppm |
| 194 | 541.2 | 1H NMR (400 MHz, DMSO-d6) δ = 9.40-9.38 (m, 2H), 8.68 (d, J = 8.8 Hz, 1H), 8.33 (d, J = 8.8 Hz, 1H), 8.28 (d, J = 8.0 Hz, 1H), 8.20 (d, J = 1.2 Hz, 1H), 8.10 (s, 1H), 7.96-7.93 (m, 1H), 7.83 (s, 1H), 7.63-7.59 (m, 1H), 7.40 (d, J = 7.6 Hz, 1H), 7.31 (d, J = 8.0 Hz, 1H), 6.70-6.42 (m, 1H), 4.99-4.86 (m, 6H), 4.82 (br d, J = 4.4 Hz, 2H), 4.23 (d, J = 11.6 Hz, 1H), 3.87 (d, J = 11.2 Hz, 1H), 1.70 (s, 3H) ppm |

TABLE 19-continued

| Compounds of the Invention | | |
|---|---|---|
| # | LCMS (m/z) | 1H NMR |
| 195 | 469.3 | 1H NMR (400 MHz, MeOD-d4) δ = 9.18 (s, 1H), 8.49 (d, J = 9.2 Hz, 1H), 8.21-8.13 (m, 2H), 7.91-7.89 (m, 1H), 7.76 (s, 1H), 7.28 (d, J = 8.0 Hz, 1H), 5.84 (s, 1H), 4.91-4.90 (m, 4H), 4.20 (d, J = 11.6 Hz, 1H), 3.98-3.89 (m, 4H), 2.79 (s, 3H), 1.76 (s, 3H) ppm |
| 196 | 517 | 1H NMR (400 MHz, DMSO-d6) δ = 9.55-9.35 (m, 2H), 8.94-8.70 (m, 3H), 8.30 (d, J = 8.4 Hz, 1H), 8.22 (s, 1H), 7.98-7.95 (m, 1H), 7.87 (s, 1H), 7.69 (d, J = 7.2 Hz, 1H), 7.32 (d, J = 8.0 Hz, 1H), 6.71 (d, J = 7.2 Hz, 1H), 4.94-4.84 (m, 4H), 4.23 (d, J = 11.2 Hz, 1H), 3.87 (d, J = 11.2 Hz, 1H), 3.59 (s, 3H), 1.71 (s, 3H) ppm |
| 197 | 525.3 | 1H NMR (400 MHz, DMSO-d6) δ = 9.40-9.37 (m, 1H), 9.22 (s, 1H), 8.47 (d, J = 8.0 Hz, 1H), 8.41 (s, 1H), 8.21 (d, J = 1.6 Hz, 1H), 8.02 (d, J = 8.8 Hz, 1H), 7.97-7.94 (m, 1H), 7.60 (s, 1H), 7.32 (d, J = 8.0 Hz, 1H), 4.96-4.82 (m, 3H), 4.76 (br d, J = 5.6 Hz, 2H), 4.24 (d, J = 11.6 Hz, 1H), 4.02-3.96 (m, 4H), 3.94 (d, J = 5.2 Hz, 2H), 3.88 (d, J = 11.6 Hz, 1H), 3.82-3.77 (m, 1H), 2.39-2.33 (m, 2H), 1.70 (s, 3H) ppm |
| 198 | 477.15 | $^1$H NMR (300 MHz, Chloroform-d) δ 9.12 (s, 1H), 8.92 (d, J = 8.3 Hz, 1H), 8.58-8.27 (m, 3H), 8.22-7.93 (m, 3H), 7.56 (t, J = 7.7 Hz, 1H), 7.45-7.38 (m, 1H), 5.37 (s, 2H), 4.92 (s, 2H), 4.25 (d, J = 11.3 Hz, 1H), 4.05 (d, J = 11.0 Hz, 1H), 2.14 (s, 1H), 1.35 (s, 3H), 1.16 (d, J = 7.9 Hz, 2H), 1.01-0.85 (m, 2H). |
| 199 | 476.15 | $^1$H NMR (300 MHz, DMSO-$d_6$) δ 9.59-9.21 (m, 2H), 8.93 (d, J = 5.1 Hz, 1H), 8.25 (s, 1H), 8.14-7.85 (m, 3H), 7.30 (d, J = 8.1 Hz, 1H), 5.02-4.57 (m, 4H), 4.08 (t, J = 13.0 Hz, 1H), 3.84 (dd, J = 25.2, 12.5 Hz, 1H), 2.42-2.20 (m, 1H), 1.69 (d, J = 20.7 Hz, 3H), 1.35-1.01 (m, 4H). |
| 200 | 509.2 | 1H NMR (400 MHz, DMSO-d6) δ = 9.42-9.38 (m, 1H), 9.21 (s, 1H), 8.47-8.42 (m, 2H), 8.40 (br s, 1H), 8.20 (d, J = 1.2 Hz, 1H), 8.01 (d, J = 8.8 Hz, 1H), 7.96-7.94 (m, 1H), 7.58 (s, 1H), 7.33-7.30 (m, 1H), 4.93-4.82 (m, 2H), 4.76-4.71 (m, 3H), 4.23 (d, J = 11.2 Hz, 1H), 4.02-3.98 (m, 3H), 3.87 (d, J = 11.6 Hz, 1H), 2.46-2.42 (m, 2H), 2.36-2.33 (m, 2H), 1.79-1.67 (m, 5H) ppm |
| 201 | 504.2 | 1H NMR (400 MHz, DMSO) δ = 9.43-9.34 (m, 1H), 9.23 (s, 1H), 8.55-8.43 (m, 2H), 8.27 (s, 1H), 8.06-7.93 (m, 2H), 7.57 (s, 1H), 7.31 (d, J = 8.0 Hz, 1H), 5.56-5.44 (m, 1H), 4.95-4.83 (m, 5H), 4.80-4.70 (m, 3H), 4.13-4.04 (m, 4H), 3.90-3.82 (m, 1H), 1.76-1.61 (m, 3H) ppm |
| 202 | 519.3 | 1H NMR (400 MHz, DMSO-d6) δ = 9.40-9.37 (m, 1H), 9.24 (s, 1H), 8.55-8.42 (m, 2H), 8.20 (d, J = 1.2 Hz, 1H), 8.05-7.92 (m, 2H), 7.60 (s, 1H), 7.31 (d, J = 8.0 Hz, 1H), 6.61-6.17 (m, 1H), 4.95-4.81 (m, 2H), 4.76 (d, J = 5.6 Hz, 2H), 4.56-4.54 (m, 2H), 4.23 (d, J = 11.6 Hz, 1H), 4.00 (s, 3H), 3.86 (d, J = 11.6 Hz, 1H), 1.70 (s, 3H) ppm |
| 203 | 513.3 | 1H NMR (400 MHz, DMSO-d6) δ = 9.37 (s, 1H), 9.21 (s, 1H), 8.46 (d, J = 8.8 Hz, 1H), 8.35 (s, 1H), 8.20 (s, 1H), 8.00 (d, J = 8.8 Hz, 1H), 7.95 (br d, J = 7.2 Hz, 1H), 7.59 (s, 1H), 7.31 (d, J = 8.0 Hz, 1H), 4.93-4.82 (m, 2H), 4.75 (d, J = 5.6 Hz, 2H), 4.24-4.16 (m, 3H), 3.98 (s, 3H), 3.86 (d, J = 11.6 Hz, 1H), 3.69-3.67 (m, 2H), 3.24 (s, 3H), 1.70 (s, 3H) ppm |
| 204 | 495.3 | 1H NMR (400 MHz, MeOD-d4) δ = 9.40 (s, 1H), 8.94 (d, J = 5.2 Hz, 1H), 8.70 (s, 2H), 8.50 (d, J = 5.2 Hz, 1H), 8.18 (d, J = 1.6 Hz, 1H), 8.02 (s, 1H), 7.97-7.90 (m, 1H), 7.30 (d, J = 8.0 Hz, 1H), 4.94 (s, 2H), 4.92 (d, J = 3.6 Hz, 2H), 4.21 (d, J = 11.2 Hz, 1H), 3.93 (d, J = 11.6 Hz, 1H), 1.77 (s, 3H), 1.68 (s, 2H), 1.66-1.61 (m, 2H) ppm |
| 205 | 501.29 | $^1$H NMR (300 MHz, DMSO-$d_6$) δ 9.49 (d, J = 4.0 Hz, 2H), 8.79 (s, 2H), 8.51 (d, J = 7.7 Hz, 1H), 8.36 (s, 1H), 8.04 (t, J = 8.0 Hz, 2H), 7.95-7.80 (m, 2H), 7.39 (d, J = 8.0 Hz, 1H), 5.25 (s, 1H), 5.05-4.67 (m, 4H), 4.16 (t, J = 13.0 Hz, 1H), 3.92 (dd, J = 25.1, 12.5 Hz, 1H), 1.97 (dt, J = 33.8, 6.6 Hz, 2H), 1.78 (d, J = 20.7 Hz, 3H), 1.62 (s, 3H), 0.81 (t, J = 7.3 Hz, 3H). |
| 206 | 477.25 | $^1$H NMR (400 MHz, DMSO-$d_6$) δ 9.66 (s, 1H), 9.35 (t, 1H), 9.25 (s, 1H), 8.70 (s, 1H), 8.65 (s, 1H), 8.45 (d, J = 8.5 Hz, 1H), 8.29 (d, J = 8.6 Hz, 1H), 8.19 (s, 1H), 7.92 (d, J = 8.0 Hz, 1H), 7.30 (d, J = 8.1 Hz, 1H), 4.99-4.79 (m, 4H), 4.23 (d, J = 11.5 Hz, 1H), 3.87 (d, J = 11.5 Hz, 1H), 2.38-2.27 (m, 1H), 1.71 (s, 3H), 1.18-1.08 (m, 4H). |
| 208 | 477.3 | 1H NMR (400 MHz, DMSO-d6) δ = 9.57 (s, 1H), 9.42 (s, 1H), 9.08 (d, J = 2.0 Hz, 1H), 8.71-8.66 (m, 1H), 8.64-8.60 (m, 1H), 8.57 (d, J = 2.0 Hz, 1H), 8.34 (d, J = 8.0 Hz, 1H), 7.91-7.82 (m, 2H), 7.47 (d, J = 8.0 Hz, 1H), 4.93-4.80 (m, 4H), 4.29 (d, J = 11.6 Hz, 1H), 3.93 (d, J = 11.6 Hz, 1H), 2.24 (s, 1H), 1.72 (s, 3H), 1.10-1.08 (m, 2H), 1.06-1.03 (m, 2H) ppm |
| 210 | 492.2 | 1H NMR (400 MHz, DMSO-d6) δ = 9.58-9.55 (m, 1H), 9.40 (s, 1H), 9.08 (d, J = 2.0 Hz, 1H), 8.71-8.54 (m, 3H), 7.93-7.84 (m, 2H), 7.73-7.69 (m, 1H), 6.53 (d, J = 8.0 Hz, 1H), 4.94-4.81 (m, 4H), 4.30 (d, J = 11.6 Hz, 1H), 4.09-4.05 (m, 4H), 3.93 (d, J = 11.6 Hz, 1H), 2.43-2.35 (m, 2H), 1.73 (s, 3H) ppm |
| 211 | 473.15 | 1H NMR (300 MHz, Chloroform-d) δ 9.70 (s, 1H), 9.39 (s, 1H), 9.12 (dd, J = 2.2, 1.2 Hz, 1H), 8.73-8.67 (m, 2H), 8.60-8.46 (m, 2H), 8.13 (s, 1H), 7.63 (t, J = 4.8 Hz, 1H), 5.11 (d, J = 4.9 Hz, 2H), 4.18 (t, J = 11.4 Hz, 1H), 4.00 (dd, J = 15.8, 12.1 Hz, 1H), 2.35-2.21 (m, 1H), 1.85 (d, J = 21.0 Hz, 3H), 1.40-1.30 (m, 2H), 1.30-1.20 (m, 2H). |

TABLE 19-continued

Compounds of the Invention

| # | LCMS (m/z) | 1H NMR |
|---|---|---|
| 212 | 473.15 | $^1$H NMR (400 MHz, Chloroform-d) δ 9.43 (s, 1H), 8.96-8.64 (m, 3H), 8.54 (d, J = 8.8 Hz, 1H), 8.43 (s, 1H), 8.17 (d, J = 1.8 Hz, 1H), 8.04-7.81 (m, 2H), 7.51 (d, J = 7.8 Hz, 1H), 7.13 (d, J = 8.1 Hz, 1H), 5.09-4.73 (m, 5H), 4.08 (t, J = 11.9 Hz, 1H), 3.82 (dd, J = 19.0, 12.1 Hz, 1H), 1.73 (d, J = 20.8 Hz, 3H), 1.62 (d, J = 6.5 Hz, 3H). |
| 213 | 473.15 | $^1$H NMR (400 MHz, Chloroform-d) δ 9.44 (s, 1H), 9.05-8.90 (m, 2H), 8.68 (d, J = 7.8 Hz, 1H), 8.60-8.42 (m, 2H), 8.18 (s, 1H), 8.02-7.82 (m, 2H), 7.52 (d, J = 7.7 Hz, 1H), 7.13 (d, J = 8.1 Hz, 1H), 5.13-4.98 (m, 3H), 4.91-4.71 (m, 2H), 4.08 (t, J = 12.0 Hz, 1H), 3.82 (dd, J = 19.2, 12.1 Hz, 1H), 1.78-1.58 (m, 6H). |
| 217 | 513 | 1H NMR (400 MHz, MeOD) δ = 9.33-9.25 (m, 1H), 8.85-8.78 (m, 1H), 8.70-8.53 (m, 2H), 8.44-8.33 (m, 1H), 8.10-8.06 (m, 1H), 7.93-7.87 (m, 1H), 7.85-7.80 (m, 1H), 7.27-7.13 (m, 1H), 4.84 (s, 2H), 4.83-4.80 (m, 2H), 4.15-4.06 (m, 1H), 3.87-3.75 (m, 1H), 3.19-3.12 (m, 1H), 2.54-2.35 (m, 1H), 2.07-1.84 (m, 1H), 1.66 (s, 3H) ppm |
| 218 | 513 | 1H NMR (400 MHz, MeOD) δ = 9.35-9.25 (m, 1H), 8.87-8.78 (m, 1H), 8.69-8.56 (m, 2H), 8.46-8.32 (m, 1H), 8.14-8.04 (m, 1H), 7.94-7.89 (m, 1H), 7.86-7.81 (m, 1H), 7.23-7.17 (m, 1H), 4.84 (s, 2H), 4.81 (d, J = 3.2 Hz, 2H), 4.15-4.07 (m, 1H), 3.87-3.81 (m, 1H), 3.20-3.12 (m, 1H), 2.53-2.37 (m, 1H), 2.08-1.90 (m, 1H), 1.66 (s, 3H) ppm |
| 221 | 478.3 | 1H NMR (400 MHz, DMSO-d6) δ = 9.67-9.54 (m, 1H), 9.46 (s, 2H), 9.08 (d, J = 2.0 Hz, 1H), 8.84-8.70 (m, 2H), 8.60-8.50 (m, 2H), 7.93 (s, 1H), 4.96-4.76 (m, 4H), 4.29 (d, J = 11.6 Hz, 1H), 3.93 (d, J = 11.6 Hz, 1H), 2.38-2.28 (m, 1H), 1.72 (s, 3H), 1.20-1.02 (m, 4H) ppm |
| 222 | 473.15 | $^1$H NMR (300 MHz, Chloroform-d) δ 9.63 (s, 1H), 9.37-9.29 (m, 1H), 9.07-9.03 (m, 1H), 8.65 (t, J = 4.3 Hz, 2H), 8.47-8.42 (m, 2H), 8.10 (s, 1H), 7.72-7.63 (m, 1H), 5.01 (dd, J = 24.4, 4.0 Hz, 2H), 4.88 (m, 2H), 2.27-2.17 (m, 1H), 1.84-1.75 (m, 3H), 1.28-1.23 (m, 2H), 1.22-1.15 (m, 2H). |
| 223 | 480.20 | $^1$H NMR (400 MHz, DMSO-$d_6$) δ 9.54 (t, J = 5.7 Hz, 1H), 9.00-8.89 (m, 2H), 8.21-8.13 (m, 2H), 7.99-7.92 (m, 1H), 7.89-7.82 (m, 1H), 7.78-7.70 (m, 1H), 7.30 (d, J = 8.1 Hz, 1H), 6.88 (d, J = 8.4 Hz, 1H), 5.12 (d, J = 5.7 Hz, 2H), 4.95-4.78 (m, 2H), 4.22 (d, J = 11.5 Hz, 1H), 3.86 (d, J = 11.5 Hz, 1H), 3.17 (s, 6H), 1.70 (s, 3H). |
| 224 | 509.3 | 1H NMR (400 MHz, MeOD) δ = 9.29 (s, 1H), 9.16-9.15 (m, 1H), 8.71 (d, J = 8.8 Hz, 1H), 8.62 (s, 1H), 8.57-8.55 (m, 1H), 7.97 (s, 1H), 7.82 (d, J = 7.2 Hz, 1H), 7.67-7.65 (m, 1H), 6.79 (d, J = 8.4 Hz, 1H), 6.56-6.27 (m, 1H), 4.93 (s, 2H), 4.89-4.88 (m, 2H), 4.40-4.33(m, 1H), 4.16-4.11 (m, 1H), 3.19 (s, 6H) ppm |
| 225 | 495.5 | 1H NMR (400 MHz, MeOD) δ = 9.15 (s, 1H), 8.44-8.36 (m, 1H), 8.29-8.25 (m, 1H), 8.21-8.11 (m, 2H), 7.97-7.90 (m, 1H), 7.81-7.75 (m, 1H), 7.34-7.25 (m, 1H), 4.92 (br d, J = 3.6 Hz, 4H), 4.24-4.18 (m, 1H), 4.05 (s, 3H), 3.96-3.92 (m, 1H), 3.64-3.57 (m, 1H), 1.81-1.73 (m, 3H), 1.15-1.07 (m, 2H), 1.05-1.00 (m, 2H) ppm |
| 226 | 526.20 | $^1$H NMR (300 MHz, Chloroform-d) δ 9.28 (d, J = 2.5 Hz, 1H), 8.79-8.72 (m, 1H), 8.38 (d, J = 8.7 Hz, 1H), 8.08-7.90 (m, 3H), 7.76-7.65 (m, 2H), 7.63-7.55 (m, 1H), 6.73-6.68 (m, 1H), 6.38-5.95 (m, 1H), 5.04-4.82 (m, 4H), 4.37 (t, J = 11.7 Hz, 1H), 4.02 (t, J = 11.4 Hz, 1H), 3.32-3.11 (m, 6H). |
| 227 | 509.3 | 1H NMR (400 MHz, MeOH) δ = 9.28 (s, 1H), 9.15-9.14 (m, 1H), 8.70-8.67 (m, 1H), 8.62 (s, 1H), 8.56-8.54 (m, 1H), 7.96 (s, 1H), 7.81 (d, J = 7.6 Hz, 1H), 7.69-7.65 (m, 1H), 6.78 (d, J = 8.4 Hz, 1H), 6.56-6.27 (m, 1H), 4.92 (s, 2H), 4.91-4.89 (m, 2H), 4.40-4.33 (m, 1H), 4.16-4.10 (m, 1H), 3.18 (s, 6H) ppm |
| 228 | 507.3 | 1H NMR (400 MHz, MeOH) δ = 9.46 (s, 1H), 9.34 (s, 1H), 9.15-9.14 (m, 1H), 8.64-8.58 (m, 4H), 8.01 (s, 1H), 6.55-6.26 (m, 1H), 4.94 (s, 2H), 4.88 (br s, 2H), 4.40-4.33 (m, 1H), 4.16-4.10 (m, 1H), 2.33-2.28 (m, 1H), 1.23-1.21 (m, 2H), 1.19-1.17 (m, 2H) ppm |
| 229 | 507.3 | 1H NMR (400 MHz, MeOD) δ = 9.47 (s, 1H), 9.34 (s, 1H), 9.15-9.14 (m, 1H), 8.65-8.58 (m, 4H), 8.02 (s, 1H), 6.55-6.26 (m, 1H), 4.94 (s, 2H), 4.89 (br s, 2H), 4.40-4.33 (m, 1H), 4.16-4.13 (m, 1H), 2.32-2.27 (m, 1H), 1.23-1.17 (m, 4H) ppm |
| 231 | 440.3 | 1H NMR (400 MHz, DMSO-d6) δ = 9.45 (s, 1H), 9.42-9.39 (m, 1H), 8.77-8.75 (m, 1H), 8.19-8.17 (m, 2H), 7.96-7.93 (m, 1H), 7.81 (s, 1H), 7.31-7.29 (m, 2H), 4.93-4.81 (m, 4H), 4.23 (d, J = 11.6 Hz, 1H), 3.87 (d, J = 11.6 Hz, 1H), 2.35 (s, 3H), 1.70 (s, 3H) ppm |
| 232 | 501.3 | 1H NMR (400 MHz, DMSO-d6) δ = 9.53 (s, 1H), 9.46-9.43 (m, 1H), 9.18 (d, J = 5.2 Hz, 1H), 8.85 (d, J = 8.4 Hz, 1H), 8.74-8.66 (m, 2H), 8.21 (d, J = 1.2 Hz, 1H), 8.00-7.87 (m, 2H), 7.32 (d, J = 8.0 Hz, 1H), 4.97-4.80 (m, 4H), 4.23 (d, J = 11.2 Hz, 1H), 3.87 (d, J = 11.6 Hz, 1H), 2.21-2.11 (m, 3H), 1.71 (s, 3H) ppm |

TABLE 19-continued

Compounds of the Invention

| # | LCMS (m/z) | 1H NMR |
|---|---|---|
| 233 | 486.4 | 1H NMR (400 MHz, MeOD) δ = 9.32 (s, 1H), 8.64-8.53 (m, 2H), 8.41-8.35 (m, 1H), 8.24 (s, 1H), 7.98-7.88 (m, 2H), 7.28 (d, J = 7.6 Hz, 1H), 7.16-7.06 (m, 1H), 4.95-4.90 (m, 3H), 4.83-4.76 (m, 1H), 4.28-4.20 (m, 1H), 4.12-4.03 (m, 1H), 3.94-3.83 (m, 1H), 1.80-1.66 (m, 3H), 1.34-1.29 (m, 2H), 1.19-1.11 (m, 2H) ppm |
| 235 | 515.3 | 1H NMR (400 MHz, DMSO-d6) δ = 9.45 (d, J = 0.8 Hz, 1H), 9.40-9.32 (m, 1H), 8.17 (d, J = 1.6 Hz, 1H), 8.07 (d, J = 5.2 Hz, 1H), 8.02 (s, 1H), 7.93-7.91 (m, 1H), 7.48-7.40 (m, 1H), 7.29 (d, J = 8.0 Hz, 1H), 4.95-4.74 (m, 4H), 4.26-4.14 (m, 5H), 3.86 (d, J = 11.6 Hz, 1H), 2.44-2.35 (m, 2H), 1.69 (s, 3H) ppm |
| 236 | 511.1 | 1H NMR (400 MHz, MeOD) δ = 9.16 (s, 1H), 8.45-8.39 (m, 1H), 8.34 (s, 1H), 8.20-8.13 (m, 2H), 7.95-7.90 (m, 1H), 7.77 (s, 1H), 7.29 (d, J = 8.0 Hz, 1H), 5.52-5.43 (m, 1H), 5.14-5.08 (m, 2H), 5.05-4.98 (m, 2H), 4.92 (d, J = 3.6 Hz, 2H), 4.60 (s, 2H), 4.23-4.19 (m, 1H), 4.13 (s, 3H), 3.95-3.90 (m, 1H), 1.77 (s, 3H) ppm |
| 237 | 524.30 | $^1$H NMR (300 MHz, Chloroform-d) δ 9.64 (s, 1H), 9.34 (s, 1H), 8.69-8.63 (m, 2H), 8.45 (d, J = 8.4 Hz, 1H), 8.11 (s, 1H), 7.95 (s, 1H), 7.77-7.66 (m, 2H), 6.19 (td, J = 54.0, 8.9 Hz, 1H), 5.09-5.03 (d, J = 5.2 Hz, 2H), 4.93-4.88 (m, 2H), 4.45-4.31 (t, J = 11.5 Hz, 1H), 4.11-3.96 (t, J = 13.0 Hz, 1H), 2.29-2.18 (m, 1H), 1.28-1.18 (m, 4H). |
| 238 | 473.30 | $^1$H NMR (400 MHz, DMSO-$d_6$) δ 9.53 (t, J = 5.8 Hz, 1H), 9.00-8.95 (m, 1H), 8.91 (d, J = 9.0 Hz, 1H), 8.30-8.24 (m, 1H), 8.15 (d, J = 1.0 Hz, 1H), 8.00-7.93 (m, 1H), 7.86 (d, J = 7.3 Hz, 1H), 7.77-7.68 (m, 1H), 7.30 (d, J = 8.1 Hz, 1H), 6.90-6.85 (m, 1H), 5.20-5.05 (m, 2H), 4.90-4.80 (m, 1H), 4.78-4.67 (m, 1H), 4.07 (t, J = 13.0 Hz, 1H), 3.91-3.76 (m, 1H), 3.17 (s, 6H), 1.69 (d, J = 20.7 Hz, 3H). |
| 239 | 513.20 | $^1$H NMR (300 MHz, DMSO-d6) δ 9.62 (t, J = 5.8 Hz, 1H), 9.11 (dd, J = 9.0, 1.0 Hz, 1H), 8.98 (d, J = 9.0 Hz, 1H), 8.58 (d, J = 8.3 Hz, 1H), 8.45 (d, J = 7.5 Hz, 1H), 8.34 (d, J = 2.0 Hz, 1H), 8.27 (s, 1H), 8.13 (t, J = 8.0 Hz, 1H), 8.04 (dd, J = 7.9, 1.8 Hz, 1H), 7.38 (d, J = 8.2 Hz, 1H), 5.28-5.14 (m, 2H), 5.00-4.74 (m, 2H), 4.32 (t, J = 7.1 Hz, 2H), 4.15 (t, J = 13.0 Hz, 1H), 3.91 (dd, J = 25.1, 12.5 Hz, 1H), 2.73 (t, J = 8.0 Hz, 2H), 2.21 (p, J = 7.7 Hz, 2H), 1.76 (d, J = 20.7 Hz, 3H). |
| 240 | 470.15 | $^1$H NMR (400 MHz, Chloroform-d) δ 8.96 (d, J = 9.0 Hz, 1H), 8.84 (dd, J = 9.1, 1.0 Hz, 1H), 8.42 (dd, J = 7.8, 1.0 Hz, 1H), 8.21 (s, 1H), 8.12 (s, 1H), 7.83 (dt, J = 8.1, 1.6 Hz, 1H), 7.75 (t, J = 7.8 Hz, 1H), 7.57 (d, J = 5.8 Hz, 1H), 7.32 (dd, J = 7.8, 1.0 Hz, 1H), 7.14 (d, J = 8.1 Hz, 1H), 5.26 (d, J = 5.5 Hz, 2H), 4.93-4.75 (m, 2H), 4.07 (t, J = 11.7 Hz, 1H), 3.86 (dd, J = 17.1, 12.0 Hz, 1H), 2.15 (tt, J = 8.1, 4.8 Hz, 1H), 1.74 (d, J = 20.8 Hz, 3H), 1.26-1.16 (m, 2H), 1.09 (dt, J = 8.2, 3.2 Hz, 2H). |
| 241 | 506.80 | $^1$H NMR (300 MHz, DMSO-$d_6$) δ 9.46-9.42 (m, 3H), 8.92 (t, J = 1.9 Hz, 1H), 8.79-8.74 (m, 2H), 8.59-8.54 (m, 2H), 7.91 (s, 1H), 7.25-6.65 (m, 1H), 4.83 (d, J = 5.3 Hz, 2H), 4.58-4.54 (m, 1H), 4.41-4.35 (m, 1H), 2.37 (dd, J = 12.3, 6.0 Hz, 1H), 1.17 (d, J = 5.4 Hz, 4H). |
| 243 | 506.80 | $^1$H NMR (300 MHz, DMSO-$d_6$) δ 9.47-9.42 (m, 3H), 8.92 (t, J = 1.9 Hz, 1H), 8.83-8.74 (m, 2H), 8.59-8.55 (m, 2H), 7.93 (s, 1H), 7.24-6.65 (m, 1H), 4.84 (d, J = 5.3 Hz, 2H), 4.58-4.52 (m, 1H), 4.42-4.38 (m, 1H), 2.37 (dd, J = 12.3, 6.0 Hz, 1H), 1.17 (d, J = 5.4 Hz, 4H). |
| 244 | 492.10 | $^1$H NMR (300 MHz, DMSO-$d_6$) δ 9.59 (s, 1H), 9.49 (m, 1H), 9.14 (s, 1H), 8.88-8.48 (m, 2H), 8.12 (m, 1H), 7.54 (d, J = 4.9 Hz, 1H), 5.13-4.71 (m, 4H), 4.36-4.08 (m, 5H), 3.98 (dd, J = 25.3, 12.7 Hz, 1H), 2.45 (t, J = 7.4 Hz, 2H), 1.78 (d, J = 20.9 Hz, 3H). |
| 245 | 491.10 | $^1$H NMR (300 MHz, DMSO-$d_6$) δ 9.50-9.25 (m, 2H), 8.61 (d, J = 4.9 Hz, 1H), 8.24 (m, 1H), 7.95 (d, J = 12.5 Hz, 2H), 7.46 (d, J = 4.9 Hz, 1H), 7.29 (d, J = 8.1 Hz, 1H), 4.99-4.58 (m, 4H), 4.26-4.04 (m, 5H), 3.84 (dd, J = 25.2, 12.5 Hz, 1H), 2.39 (q, J = 7.4 Hz, 2H), 1.69 (d, J = 20.7 Hz, 3H). |
| 246 | 505.3 | 1H NMR (400 MHz, MeOD) δ = 9.47-9.46 (m, 1H), 9.34 (s, 1H), 9.05 (d, J = 2.0 Hz, 1H), 8.64-8.58 (m, 4H), 8.00 (s, 1H), 6.25-5.97 (m, 1H), 4.94 (s, 2H), 4.86 (br s, 2H), 4.28 (d, J = 12.0 Hz, 1H), 3.77 (br d, J = 1.2 Hz, 1H), 2.33-2.28 (m, 1H), 1.23-1.20(m, 2H), 1.18-1.17 (m, 2H) ppm |
| 248 | 472.3 | 1H NMR (400 MHz, MeOD) δ = 9.40-9.37 (m, 2H), 8.65 (s, 2H), 8.27 (s, 1H), 7.98 (d, J = 8.0 Hz, 1H), 7.83-7.79 (m, 2H), 7.68-7.66 (m, 1H), 7.30 (d, J = 8.0 Hz, 1H), 6.82 (d, J = 8.4 Hz, 1H), 4.88-4.75 (m, 4H), 4.11-4.04 (m, 1H), 3.89-3.79 (m, 1H), 3.15 (s, 6H), 1.72-1.67 (m, 3H) ppm |
| 249 | 515.4 | 1H NMR (400 MHz, DMSO-d6) δ = 9.42-9.37 (m, 2H), 8.70-8.69 (m, 2H), 8.49-8.47 (m, 1H), 8.28 (s, 1H), 8.03-8.01 (m, 2H), 7.88-7.83 (m, 2H), 7.31 (d, J = 8.4 Hz, 1H), 5.77 (s, 1H), 4.85-4.76 (m, 4H), 4.12-4.07 (m, 4H), 3.89-3.86 (m, 2H), 2.67-2.66 (m, 1H), 2.16-2.11 (m, 1H), 1.72-1.67 (m, 3H) ppm |
| 251 | 461.2 | 1H NMR (400 MHz, DMSO-d6) δ = 9.30-9.27 (m, 1H), 9.16 (s, 1H), 8.25 (s, 1H), 8.21 (s, 1H), 8.07-8.03 (m, 2H), 7.96-7.94 (m, 1H), 7.89-7.86 (m, 1H), 7.58 (s, 1H), 7.29 (d, J = 8.0 Hz, 1H), 4.84-4.83 (m, 1H), 4.75-4.70 (m, 3H), 4.12-4.01 (m, 1H), 3.94 (s, 3H), 3.88-3.79 (m, 1H), 3.74 (s, 3H), 1.68 (d, J = 20.4 Hz, 1H) ppm |

TABLE 19-continued

Compounds of the Invention

| # | LCMS (m/z) | 1H NMR |
|---|---|---|
| 252 | 469.20 | $^1$H NMR (300 MHz, Methanol-$d_4$) δ 9.49 (s, 1H), 9.37 (s, 1H), 9.11 (s, 1H), 8.74 (dd, J = 7.8, 2.5 Hz, 4H), 8.13 (s, 1H), 5.04 (s, 2H), 3.13-3.00 (m, 2H), 2.53-2.03 (m, 5H), 1.88 (d, J = 21.1 Hz, 3H), 1.35-1.24 (m, 4H). |
| 253 | 478.10 | $^1$H NMR (300 MHz, Methanol-$d_4$) δ 9.48 (s, 1H), 9.37 (s, 1H), 8.77 (d, J = 2.3 Hz, 1H), 8.71-8.58 (m, 3H), 8.56 (d, J = 2.3 Hz, 1H), 8.04 (s, 1H), 4.93 (s, 2H), 4.58 (dd, J = 6.5, 4.1 Hz, 2H), 2.60-2.46 (m, 1H), 2.38-2.21 (m, 2H), 1.87 (s, 3H), 1.29-1.12 (m, 4H). |
| 254 | 480.10 | $^1$H NMR (300 MHz, Methanol-$d_4$) δ 9.12 (d, J = 9.1 Hz, 1H), 9.03 (dd, J = 9.1, 1.0 Hz, 1H), 8.95-8.88 (m, 1H), 8.41-8.36 (m, 1H), 8.35-8.23 (m, 2H), 8.06-7.92 (m, 2H), 7.36 (d, J = 8.0 Hz, 1H), 6.97 (t, J = 55.2 Hz, 1H), 5.31 (s, 2H), 4.93-4.82 (m, 2H), 4.16 (t, J = 12.3 Hz, 1H), 3.97 (dd, J = 20.0, 12.2 Hz, 1H), 1.81 (d, J = 20.6 Hz, 3H). |
| 255 | 470.85 | $^1$H NMR (300 MHz, DMSO-d6) δ 9.56 (t, J = 5.8 Hz, 1H), 9.49 (s, 1H), 9.06 (dd, J = 8.9, 1.0 Hz, 1H), 8.84-8.79 (m, 2H), 8.27-8.24 (m, 2H), 7.96 (dt, J = 8.0, 1.7 Hz, 1H), 7.31 (d, J = 8.1 Hz, 1H), 5.16-5.14 (m, 2H), 4.90-4.70 (m, 2H), 4.08 (t, J = 13.0 Hz, 1H), 3.84 (dd, J = 25.1, 12.5 Hz, 1H), 2.42-2.34 (m, 1H), 1.69 (d, J = 20.7 Hz, 3H), 1.22-1.13 (m, 4H). |
| 257 | 485.2 | 1HNMR (400 MHz, DMSO-d6) δ = 9.35-9.32 (m, 2H), 8.46 (s, 1H), 8.25 (s, 1H), 8.17 (d, J = 8.8 Hz, 1H), 8.04-8.01 (m, 2H), 7.97-7.94 (m, 1H), 7.76-7.73 (m, 2H), 7.29 (d, J = 8.0 Hz, 1H), 4.87-4.70 (m, 4H), 4.19-4.13 (m, 1H), 410-4.03 (m, 1H), 3.87-3.78 (m, 1H), 1.75 (d, J = 20.8 Hz, 1H) ppm |
| 259 | 515.2 | 1H NMR (400 MHz, DMSO-d6) δ = 9.48 (s, 1H), 9.43-9.41 (m, 1H), 8.77-8.75 (m, 1H), 8.66 (d, J = 8.4 Hz, 1H), 8.61 (d, J = 5.2 Hz, 1H), 8.37-8.32 (m, 1H), 8.28 (s, 1H), 7.98-7.97 (m, 1H), 7.85 (s, 1H), 7.74 (d, J = 4.8 Hz, 1H), 7.32 (d, J = 8.4 Hz, 1H), 4.85-4.82 (m, 4H), 4.08 (s, 1H), 3.89-3.83 (m, 5H), 3.74-3.71 (m, 4H), 1.72-1.67 (m, 3H) ppm |
| 260 | 486.2 | 1H NMR (400 MHz, DMSO-d6) δ = 9.47-9.39 (m, 3H), 8.89-8.82 (m, 2H), 8.76 (d, J = 8.8 Hz, 1H), 8.44 (d, J = 8.8 Hz, 1H), 8.28 (s, 1H), 8.20-8.18 (m, 1H), 7.99-7.96 (m, 1H), 7.86 (s, 1H), 7.31 (d, J = 8.0 Hz, 1H), 4.89-4.72 (m, 4H), 4.11-4.05 (m, 1H), 3.89-3.80 (m, 1H), 2.87 (d, J = 4.8 Hz, 3H), 1.72-1.67 (m, 3H) ppm |
| 261 | 469.3 | 1H NMR (400 MHz, MeOD-d4) δ = 9.29-9.23 (m, 2H), 8.49 (d, J = 1.6 Hz, 1H), 8.16 (d, J = 1.6 Hz, 1H), 8.13 (s, 1H), 7.92-7.89 (m, 1H), 7.77 (s, 1H), 7.28 (d, J = 8.0 Hz, 1H), 4.91-4.86 (m, 4H), 4.20 (d, J = 11.2 Hz, 1H), 4.05 (s, 3H), 3.93 (d, J = 11.6 Hz, 1H), 3.83 (s, 3H), 1.76 (s, 3H) ppm |
| 262 | 491.2 | 1H NMR (400 MHz, MeOD) δ = 9.23 (s, 1H), 8.50 (s, 1H), 8.38-8.30 (m, 1H), 8.17-8.11 (m, 2H), 7.92-7.90 (m, 1H), 7.88-7.82 (m, 3H), 7.74-7.71 (m, 1H), 7.27 (d, J = 8.0 Hz, 1H), 4.93-4.87 (m, 4H), 4.19 (d, J = 11.6 Hz, 1H), 3.92 (d, J = 11.6 Hz, 1H), 1.75 (s, 3H), 1.53-1.48 (m, 2H), 1.25-1.21 (m, 2H) ppm |
| 263 | 537 | 1H NMR (400 MHz, DMSO-d6) δ = 9.44-9.41 (m, 1H), 9.31 (s, 1H), 8.58 (s, 1H), 8.34 (d, J = 10 Hz, 1H), 8.17 (d, J = 10 Hz, 1H), 8.14 (s, 1H), 7.96-7.93 (m, 1H), 7.83 (s, 1H), 7.66-7.64 (m, 1H), 7.42 (d, J = 7.6 Hz, 1H), 6.75-6.60 (m, 1H), 6.42 (d, J = 8.4 Hz, 1H), 5.0 (d, J = 16 Hz, 1H), 4.84 (d, J = 16 Hz, 1H), 4.77-4.76 (m, 2H), 4.27-4.15 (m, 2H), 4.06-4.03 (m, 4H), 2.40-2.33 (m, 2H) ppm |
| 264 | 439.3 | 1H NMR (400 MHz, DMSO-d6) δ = 13.19-12.78 (m, 1H), 9.44-9.26 (m, 2H), 8.58-8.45 (m, 1H), 8.28-8.13 (m, 2H), 7.96-7.94 (m, 1H), 7.72 (s, 1H), 7.31 (d, J = 8.0 Hz, 1H), 6.84-6.72 (m, 1H), 4.94-4.82 (m, 2H), 4.79 (d, J = 6.0 Hz, 2H), 4.23 (d, J = 11.2 Hz, 1H), 3.87 (d, J = 11.2 Hz, 1H), 2.30 (s, 3H), 1.70 (s, 3H) ppm |
| 265 | 528.4 | 1H NMR (400 MHz, DMSO-d6) δ = 9.35-9.34 (m, 2H), 8.66-8.58 (m, 2H), 8.37-8.35 (m, 1H), 8.27-8.21 (m, 2H), 7.94 (d, J = 4.0 Hz, 2H), 7.82-7.79 (m, 1H), 7.30 (d, J = 8.0 Hz, 1H), 4.85-4.75 (m, 4H), 4.15-4.04 (m, 2H), 3.89-3.83 (m, 1H), 3.68-3.65 (m, 3H), 3.52-3.50 (m, 1H), 3.30 (s, 3H), 2.13-2.10 (m, 2H), 1.72-1.67 (m, 3H) ppm |
| 266 | 528.4 | 1H NMR (400 MHz, DMSO-d6) δ = 9.36-9.34 (m, 2H), 8.68 (s, 1H), 8.58 (s, 1H), 8.37-8.34 (m, 1H), 8.27-8.21 (m, 2H), 8.02-7.96 (m, 2H), 7.82 (s, 1H), 7.30 (d, J = 8.0 Hz, 1H), 4.85-4.75 (m, 4H), 4.15-4.08 (m, 2H), 3.89-3.83 (m, 1H), 3.68-3.65 (m, 3H), 3.54-3.50 (m, 1H), 3.30 (s, 3H), 2.14-2.08 (m, 2H), 1.72-1.67 (m, 3H) ppm |
| 267 | 542.2 | 1H NMR (400 MHz, DMSO-d6) δ = 9.48 (s, 1H), 9.42-9.39 (m, 1H), 8.77 (d, J = 8.4 Hz, 1H), 8.68 (d, J = 8.8 Hz, 1H), 8.64 (d, J = 4.8 Hz, 1H), 8.27 (s, 1H), 7.98-7.96 (m, 1H), 7.85 (s, 1H), 7.78 (d, J = 5.2 Hz, 1H), 7.31 (d, J = 8.0 Hz, 1H), 4.88-4.81(m, 3H), 4.76-4.71 (m, 1H), 4.38-4.28 (m, 2H), 4.14-4.04 (m, 3H), 3.89-3.79 (m, 1H), 3.49-3.46 (m, 2H), 2.91 (s, 3H), 1.72-1.63 (m, 3H) ppm |
| 268 | 486.2 | 1H NMR (400 MHz, DMSO-d6) δ = 9.43-9.39 (m, 2H), 8.69-8.63 (m, 2H), 8.53-8.42 (m, 1H), 8.27 (s, 1H), 8.19 (d, J = 4.4 Hz, 1H), 8.07 (d, J = 4 Hz, 1H), 7.97-7.95 (m, 1H), 7.78 (s, 1H), 7.30 (d, J = 8.0 Hz, 1H), 4.88-4.70 (m, 4H), 4.23-4.19(m, 1H), 4.18-4.04 (m, 1H), 3.88-3.79 (m, 1H), 1.68 (d, J = 20.4 Hz, 1H), 1.10-1.00 (m, 4H) ppm |

TABLE 19-continued

| Compounds of the Invention | | |
|---|---|---|
| # | LCMS (m/z) | 1H NMR |
| 269 | 502.2 | 1H NMR (400 MHz, DMSO-d6) δ = 9.44-9.41 (m, 1H), 9.33 (s, 1H), 8.63-8.57 (m, 2H), 8.32-8.29 (m, 1H), 8.22-8.20 (m, 1H), 8.15 (s, 1H), 7.88 (s, 1H), 7.82-7.77 (m, 2H), 4.94 (d, J = 16.8 Hz, 1H), 4.78-4.71 (m, 3H), 4.16-4.04 (m, 5H), 3.89-3.80 (m, 1H), 2.45-2.38 (m, 2H), 1.72-1.66 (m, 3H) ppm |
| 270 | 509.2 | 1H NMR (400 MHz, DMSO-d6) δ = 9.44-9.41 (m, 1H), 9.33 (s, 1H), 8.63-8.60 (m, 2H), 8.32-8.29 (m, 1H), 8.22-8.20 (m, 1H), 8.03 (d, J = 1.2 Hz, 1H), 7.88-7.83 (m, 2H), 7.78-7.76 (m, 1H), 4.97-4.83 (m, 2H), 4.77 (d, J = 5.6 Hz, 2H), 4.23 (d, J = 11.6 Hz, 1H), 4.16-4.12 (m, 4H), 3.87 (d, J = 11.2 Hz, 1H), 2.45-2.40 (m, 2H), 1.70 (s, 3H) ppm |
| 271 | 485.3 | 1H NMR (400 MHz, DMSO-d6) δ = 9.40 (s, 2H), 8.66 (d, J = 0.8 Hz, 1H), 8.55 (d, J = 8.4 Hz, 1H), 8.35 (d, J = 1.2 Hz, 1H), 8.28 (s, 1H), 7.95 (s, 2H), 7.89-7.79 (m, 2H), 7.35-7.28 (m, 1H), 6.29 (s, 1H), 4.92-4.69 (m, 4H), 4.14-4.03 (m, 1H), 3.91-3.77 (m, 1H), 1.70 (d, J = 20.8 Hz, 3H), 1.42-1.41 (m, 2H), 1.19-1.18 (m, 2H) ppm |
| 272 | 508.2 | 1H NMR (400 MHz, DMSO-d6) δ = 9.36-9.32 (m, 2H), 8.24-8.17 (m, 2H), 7.99-7.92 (m, 2H), 7.82-7.80 (m, 1H), 7.29 (d, J = 8.0 Hz, 1H), 6.90 (d, J = 8.0 Hz, 1H), 4.88-4.76 (m, 4H), 4.22 (d, J = 11.6 Hz, 1H), 4.14-4.10 (m, 4H), 3.87-3.84 (d, J = 11.6 Hz, 1H), 2.37-2.32 (m, 1H), 1.68 (s, 3H) ppm |
| 273 | 520.1 | 1H NMR (400 MHz, MeOD) δ = 9.30 (s, 1H), 8.67-8.54 (m, 2H), 8.27-8.23 (m, 1H), 8.09-8.08 (m, 1H), 7.96-7.91 (m, 2H), 7.76-7.73 (m, 1H), 7.27 (d, J = 8.4 Hz, 1H), 6.89-6.87 (m, 1H), 4.92 (s, 2H), 4.91-4.89 (m, 1H), 4.81-4.80 (m, 1H), 4.15-4.02 (m, 1H), 3.96-3.81 (m, 1H), 3.50 (s, 6H), 1.73 (d, J = 20.4 Hz, 3H) ppm |
| 274 | 475.20 | $^1$H NMR (300 MHz, DMSO-$d_6$) δ 9.31 (t, J = 5.9 Hz, 1H), 9.20 (d, J = 0.9 Hz, 1H), 8.44 (s, 1H), 8.17 (d, J = 1.7 Hz, 1H), 8.01-7.86 (m, 1H), 7.75 (d, J = 0.9 Hz, 1H), 7.29 (d, J = 8.1 Hz, 1H), 5.00-4.78 (m, 2H), 4.71 (d, J = 5.8 Hz, 2H), 4.23 (d, J = 11.5 Hz, 1H), 4.03 (s, 3H), 3.85 (d, J = 21.7 Hz, 4H), 1.70 (s, 3H). |
| 275 | 463.20 | $^1$H-NMR (300 MHz, DMSO-$d_6$) δ 9.50 (t, J = 5.8 Hz, 1H), 8.75 (dd, J = 9.1, 1.0 Hz, 1H), 8.44 (s, 1H), 8.29-8.20 (m, 2H), 7.95 (dt, J = 8.1, 1.7 Hz, 1H), 7.84 (s, 1H), 7.30 (d, J = 8.2 Hz, 1H), 5.05 (dd, J = 5.9, 2.8 Hz, 2H), 4.86 (dd, J = 15.6, 2.5 Hz, 1H), 4.73 (dd, J = 15.7, 4.4 Hz, 1H), 4.08 (t, J = 13.0 Hz, 1H), 4.00 (s, 3H), 3.93-3.80 (m, 1H), 3.79 (s, 3H), 1.69 (d, J = 20.7 Hz, 3H). LCMS (ESI) m/z $[M + H]^+$ = 271. |
| 276 | 485.90 | $^1$H NMR (400 MHz, Methanol-$d_4$) δ 8.97 (s, 1H), 8.94-8.83 (m, 2H), 8.28 (s, 2H), 7.91 (d, J = 5.2 Hz, 2H), 7.27 (d, J = 8.1 Hz, 1H), 5.21 (s, 2H), 4.84 (m, 2H), 4.26 (t, J = 7.5 Hz, 4H), 4.07 (t, J = 12.2 Hz, 1H), 3.94-3.81 (m, 1H), 2.54 (p, J = 7.5 Hz, 2H), 1.75 (s, 3H). |
| 277 | 429.20 | $^1$H NMR (400 MHz, DMSO-$d_6$) δ 9.53 (t, J = 5.8 Hz, 1H), 8.95 (dd, J = 9.0, 1.0 Hz, 1H), 8.58 (d, J = 9.1 Hz, 1H), 8.41-8.33 (m, 2H), 8.30-8.22 (m, 1H), 8.14 (s, 1H), 8.00-7.92 (m, 1H), 7.64-7.56 (m, 3H), 7.30 (d, J = 8.1 Hz, 1H), 5.17-5.09 (m, 2H), 4.90-4.82 (m, 1H), 4.78-4.68 (m, 1H), 4.07 (t, J = 13.0 Hz, 1H), 3.92-3.75 (m, 1H), 1.69 (d, J = 20.7 Hz, 3H). |
| 278 | 650.30 | $^1$H NMR (300 MHz, DMSO-$d_6$) δ9.53-9.43 (m, 2H), 8.80-8.66 (m, 2H), 8.31-8.25 (m, 1H), 8.08-7.95 (m, 2H), 7.92-7.78 (m, 2H), 7.39 (d, J = 8.1 Hz, 1H), 7.12 (d, J = 8.4 Hz, 1H), 5.05-4.85 (m, 4H), 4.31 (d, J = 11.5 Hz, 1H), 3.95 (d, J = 11.5 Hz, 1H), 3.79-3.68 (m, 10H), 3.63-3.45 (m, 4H), 3.30 (s, 3H), 2.72 (t, J = 6.6 Hz, 2H), 1.78 (s, 3H). |
| 280 | 494.1 | 1H NMR (400 MHz, METHANOL-d4) δ = 9.45 (s, 1H), 9.31-9.20 (m, 1H), 8.68 (d, J = 0.8 Hz, 1H), 8.36 (d, J = 4.8 Hz, 1H), 8.16 (d, J = 1.6 Hz, 1H), 7.96 (s, 1H), 7.93-7.87 (m, 1H), 7.51-7.40 (m, 1H), 7.28 (d, J = 8.0 Hz, 1H), 4.93-4.90 (m, 4H), 4.20 (d, J = 11.6 Hz, 1H), 3.92 (d, J = 11.2 Hz, 1H), 2.58-2.37 (m, 1H), 1.76 (s, 3H), 1.16-1.08 (m, 4H) ppm |
| 284 | 534.3 | 1H NMR (400 MHz, DMSO-d6) δ = 9.48 (s, 1H), 9.44-9.41 (m, 1H), 8.80-8.75 (m, 1H), 8.73-8.68 (m, 1H), 8.65 (d, J = 5.2 Hz, 1H), 8.21 (d, J = 1.6 Hz, 1H), 7.98-7.95 (m, 1H), 7.88 (s, 1H), 7.79 (d, J = 4.8 Hz, 1H), 7.32 (d, J = 8.0 Hz, 1H), 4.97-4.82 (m, 4H), 4.76 (br s, 2H), 4.24 (d, J = 11.6 Hz, 1H), 4.16-4.04 (m, 1H), 4.00-3.67 (m, 4H), 3.22-3.13 (m, 1H), 1.93 (d, J = 8.8 Hz, 1H), 1.71 (s, 3H) ppm |
| 285 | 518.3 | 1H NMR (400 MHz, DMSO-d6) δ = 9.47 (s, 1H), 9.43-9.40 (m, 1H), 8.81-8.72 (m, 1H), 8.65 (d, J = 8.8 Hz, 1H), 8.54 (d, J = 4.8 Hz, 1H), 8.20 (d, J = 1.6 Hz, 1H), 7.96-7.93 (m 1H), 7.86 (s, 1H), 7.67 (d, J = 4.8 Hz, 1H), 7.31 (d, J = 8.0 Hz, 1H), 5.12-4.96 (m, 1H), 4.95-4.79 (m, 4H), 4.23 (d, J = 11.6 Hz, 1H), 3.87 (d, J = 11.6 Hz, 1H), 3.58 (br s, 2H), 3.03-2.95 (m, 1H), 2.05 (br s, 2H), 1.70 (s, 3H), 1.47-1.38 (m, 2H) ppm |
| 287 | 645.00 | $^1$H NMR (300 MHz, DMSO-$d_6$) δ 9.42 (d, J = 5.1 Hz, 2H), 8.73-8.58 (m, 2H), 8.20 (d, J = 1.7 Hz, 1H), 8.01-7.88 (m, 2H), 7.85-7.70 (m, 2H), 7.31 (d, J = 8.1 Hz, 1H), 7.04 (d, J = 8.5 Hz, 1H), 4.96-4.73 (m, 4H), 4.23 (d, J = 11.5 Hz, 1H), 3.87 (d, J = 11.5 Hz, 1H), 3.66 (d, J = 17.0 Hz, 8H), 2.84 (d, J = 11.0 Hz, 2H), 2.62 (t, J = 7.3 Hz, 1H), 2.21 (s, 3H), 2.01 (s, 2H), 1.71 (s, 3H), 1.65 (dd, J = 8.1, 3.3 Hz, 4H). |
| 288 | 606.40 | $^1$H NMR (300 MHz, DMSO-$d_6$) δ 9.41 (s, 2H), 8.77-8.54 (m, 2H), 8.20 (s, 1H), 8.01-7.88 (m, 2H), 7.84-7.71 (m, 2H), 7.31 (d, J = 8.1 Hz, 1H), 7.04 (d, J = 8.5 Hz, 1H), 4.85 (dd, J = 19.0, 6.6 Hz, 4H), 4.23 (d, J = 11.5 |

TABLE 19-continued

| Compounds of the Invention | | |
|---|---|---|
| # | LCMS (m/z) | 1H NMR |
| | | Hz, 1H), 3.87 (d, J = 11.6 Hz, 1H), 3.78-3.51 (m, 10H), 3.24 (s, 3H), 2.64 (t, J = 6.5 Hz, 2H), 1.71 (s, 3H). |
| 289 | 445.15 | $^{1}$H NMR (300 MHz, DMSO-$d_6$) δ 9.32 (t, J = 5.9 Hz, 1H), 9.24 (d, J = 0.9 Hz, 1H), 8.63 (s, 1H), 8.24-8.11 (m, 2H), 7.92 (d, 1H), 7.84-7.78 (m, 1H), 7.30 (d, J = 8.1 Hz, 1H), 5.00-4.62 (m, 4H), 4.23 (d, J = 11.5 Hz, 1H), 3.94 (s, 3H), 3.91 (d, 1H), 1.70 (s, 3H). |
| 290 | 435.20 | $^{1}$H NMR (300 MHz, Methanol-$d_4$) δ 9.27-9.20 (m, 1H), 9.11-9.02 (m, 1H), 8.64-8.57 (m, 1H), 8.26-8.13 (m, 2H), 8.06-8.00 (m, 1H), 7.69-7.53 (m, 3H), 4.93-4.90 (m, 2H), 4.88-4.83 (m, 2H), 4.20-4.07 (m, 1H), 4.02-3.89 (m, 1H), 1.77 (d, J = 20.7 Hz, 3H). |
| 291 | 524.3 | 1H NMR (400 MHz, DMSO-d6) δ = 9.47-9.37 (m, 2H), 8.93 (s, 1H), 8.75-8.70 (m, 1H), 8.59 (d, J = 8.4 Hz, 1H), 8.22-8.17 (m, 2H), 7.97-7.94 (m, 1H), 7.86 (s, 1H), 7.31 (d, J = 8.0 Hz, 1H), 5.63-5.43 (m, 1H), 4.96-4.77 (m, 4H), 4.23 (d, J = 11.6 Hz, 1H), 4.00-3.57 (m, 5H), 2.36-2.15 (m, 2H), 1.71 (s, 3H) ppm |
| 292 | 570.4 | 1H NMR (400 MHz, DMSO-d6) δ = 9.46 (s, 1H), 9.41-9.38 (m, 1H), 8.75 (d, J = 8.0 Hz, 1H), 8.63 (d, J = 8.4 Hz, 1H), 8.58 (d, J = 4.8 Hz, 1H), 8.26 (s, 1H), 7.97-7.95 (m, 1H), 7.84 (s, 1H), 7.70 (d, J = 4.8 Hz, 1H), 7.30 (d, J = 8.4 Hz, 1H), 4.88-4.70 (m, 4H), 4.58-4.55 (m, 2H), 4.51-4.48 (m, 2H), 4.10-4.04 (m, 1H), 3.89 (br d, J = 5.6 Hz, 4H), 3.85-3.79 (m, 1H), 3.48-3.42 (m, 1H), 2.38-2.36 (m, 4H), 1.71-1.66 (m, 3H) ppm |
| 293 | 460.3 | 1H NMR (400 MHz, METHANOL-d4) δ = 9.36 (s, 1H), 8.60 (s, 2H), 8.23-8.21 (m, 2H), 8.08 (d, J = 4.0 Hz, 1H), 7.93-7.91 (m, 2H), 7.27 (d, J = 7.6 Hz, 1H), 4.92 (s, 2H), 4.90 (br d, J = 2.8 Hz, 1H), 4.81 (br d, J = 3.6 Hz, 1H), 4.10-4.04 (m, 1H), 3.92-3.84 (m, 4H), 1.75-1.70 (m, 3H) ppm |
| 294 | 509.3 | 1H NMR (400 MHz, METHANOL-d4) δ = 9.43 (s, 1H), 9.18 (s, 1H), 8.61 (s, 1H), 8.16 (d, J = 0.8 Hz, 1H), 8.00-7.88 (m, 3H), 7.27 (d, J = 8.0 Hz, 1H), 6.91-6.88 (m, 1H), 4.93-4.89 (m, 4H), 4.29-4.17 (m, 5H), 3.92 (d, J = 11.6 Hz, 1H), 2.50-2.39 (m, 2H), 1.75 (s, 3H) ppm |
| 295 | 484.30 | 1H NMR (400 MHz, MeOD) δ = 9.30 (s, 1H), 8.64-8.62 (m, 1H), 8.57-8.55 (m, 1H), 8.25 (s, 1H), 7.95-7.93 (m, 2H), 7.85 (d, J = 7.2 Hz, 1H), 7.70-7.66 (m, 1H), 7.29 (d, J = 8.0 Hz, 1H), 6.52-6.50 (m, 1H), 4.92 (s, 2H), 4.82-4.77 (m, 2H), 4.15-4.05 (m, 5H), 3.93-3.88 (m, 1H), 2.48-2.41 (m, 2H), 1.76-1.71 (m, 3H) ppm |
| 296 | 503.1 | 1H NMR (400 MHz, DMSO-d6) δ = 9.57-9.54 (m, 1H), 9.47 (s, 1H), 9.08-9.07 (m, 1H), 8.72 (d, J = 8.0 Hz, 1H), 8.61 (s, 1H), 8.07-7.99 (m, 2H), 7.88 (s, 1H), 7.16-7.14 (m, 1H), 4.91-4.71 (m, 4H), 4.21-4.06 (m, 5H), 3.97-3.84 (m, 1H), 2.39-2.33 (m, 2H), 1.79-1.64 (m, 3H) ppm |
| 297 | 469.2 | 1H NMR (400 MHz, DMSO-d6) δ = 9.37-9.33 (m, 2H), 8.61-8.59 (m, 1H), 8.17 (d, J = 1.6 Hz, 1H), 8.09 (d, J = 8.8 Hz, 1H), 7.93-7.91 (m, 1H), 7.78 (s, 1H), 7.55 (s, 1H), 7.30 (d, J = 8.0 Hz, 1H), 4.92-4.78 (m, 4H), 4.23-4.20 (m, 4H), 3.89-3.87 (m, 4H), 1.69 (s, 3H) ppm |
| 299 | 501.4 | 1H NMR (400 MHz, MeOD) δ = 9.91 (s, 1H), 9.39 (s, 1H), 9.05 (s, 1H), 8.70 (d, J = 0.8 Hz, 2H), 8.18 (d, J = 1.6 Hz, 1H), 8.05 (s, 1H), 7.92 (d, J = 1.6 Hz, 1H), 7.30 (d, J = 8.0 Hz, 1H), 4.97-4.94 (m, 2H), 4.92 (d, J = 3.6 Hz, 2H), 4.21 (d, J = 11.2 Hz, 1H), 3.93 (d, J = 11.2 Hz, 1H), 2.22-2.12 (m, 3H), 1.77 (s, 3H) ppm |
| 300 | 433.90 | $^{1}$H NMR (300 MHz, Methanol-$d_4$) δ 9.29 (s, 1H), 8.35-8.22 (m, 3H), 8.10-7.97 (m, 2H), 7.74-7.61 (m, 3H), 7.41-7.27 (m, 1H), 5.01-4.97 (m, 1H), 4.94-4.90 (m, 2H), 4.90-4.82 (m, 1H), 4.24-4.08 (m, 1H), 4.06-3.88 (m, 1H), 1.82 (d, J = 20.5 Hz, 3H). |
| 301 | 471.00 | $^{1}$H NMR (400 MHz, DMSO-$d_6$) δ 9.59 (t, J = 5.9 Hz, 1H), 9.47 (d, J = 4.1 Hz, 2H), 9.10 (t, J = 1.8 Hz, 1H), 8.82-8.73 (m, 2H), 8.63 (t, J = 1.8 Hz, 1H), 8.56 (d, J = 8.6 Hz, 1H), 7.94 (s, 1H), 4.93-4.72 (m, 4H), 4.13 (t, J = 12.9 Hz, 1H), 3.91 (dd, J = 25.3, 12.6 Hz, 1H), 2.36 (dt, J = 8.5, 5.6 Hz, 1H), 1.72 (d, J = 20.9 Hz, 3H), 1.19-1.12 (m, 4H). |
| 302 | 529.3 | 1H NMR (400 MHz, CDCl3) δ = 9.41 (s, 1H), 8.83 (d, J = 8.6 Hz, 1H), 8.68 (d, J = 7.5 Hz, 1H), 8.56 (d, J = 8.6 Hz, 1H), 8.30 (s, 2H), 8.21 (s, 1H), 8.03 (t, J = 7.8 Hz, 1H), 7.95-7.85 (m, 1H), 7.63 (d, J = 7.7 Hz, 1H), 7.14 (d, J = 8.2 Hz, 1H), 5.07 (br d, J = 5.5 Hz, 2H), 4.94-4.70 (m, 2H), 4.20-3.93 (m, 6H), 3.84 (br dd, J = 12.1, 19.0 Hz, 1H), 2.37-2.22 (m, 2H), 1.80-1.71 (m, 3H), 1.67 (br d, J = 12.8 Hz, 2H) ppm |
| 305 | 457.4 | 1H NMR (400 MHz, CHLOROFORM-d) δ = 9.25 (s, 1H), 8.38-8.36 (m, 1H), 8.28 (s, 1H), 8.12-8.10 (m, 2H), 7.91 (s, 1H), 7.84 (d, J = 8.0 Hz, 1H), 7.16 (d, J = 8.4 Hz, 1H), 4.99 (d, J = 5.2 Hz, 2H), 4.91-4.76 (m, 2H), 4.12-4.03 (m, 4H), 3.90-3.80 (m, 1H), 1.78-1.73 (m, 3H) ppm |
| 306 | 524.5 | 1H NMR (400 MHz, DMSO-d6) δ = 9.47 (s, 1H), 9.43-9.39 (m, 1H), 8.79-8.74 (m, 1H), 8.67 (d, J = 8.4 Hz, 1H), 8.59 (d, J = 5.2 Hz, 1H), 8.20 (d, J = 1.6 Hz, 1H), 7.96-7.94 (m, 1H), 7.87 (s, 1H), 7.72 (d, J = 5.2 Hz, 1H), 7.31 (d, J = 8.4 Hz, 1H), 5.60-5.39 (m, 1H), 4.94-4.81 (m, 4H), 4.23 (d, J = 11.6 Hz, 1H), 4.01-3.59 (m, 5H), 2.33-2.15 (m, 2H), 1.70 (s, 3H) ppm |
| 307 | 555.2 | 1H NMR (400 MHz, DMSO-d6) δ = 9.47 (s, 1H), 9.42-9.39 (m, 1H), 8.75 (d, J = 8.8 Hz, 1H), 8.64 (d, J = 8.8 Hz, 1H), 8.58 (d, J = 5.2 Hz, 1H), 8.28 (s, 1H), 7.97 (d, J = 8.0 Hz, 1H), 7.85 (s, 1H), 7.69 (d, J = 5.2 Hz, 1H), |

TABLE 19-continued

Compounds of the Invention

| # | LCMS (m/z) | 1H NMR |
|---|---|---|
| | | 7.31 (d, J = 8.0 Hz, 1H), 5.22-5.03 (m, 2H), 4.92-4.70 (m, 4H), 4.11-4.04 (m, 1H), 3.97-3.78 (m, 3H), 3.35 (s, 1H), 3.25-3.20 (m, 1H), 2.98-2.88 (m, 1H), 2.82-2.76 (m, 1H), 2.02-1.93 (m, 1H), 1.90-1.80 (m, 1H), 1.77-1.63 (m, 4H), 1.40-1.31 (m, 1H) ppm |
| 308 | 555.2 | 1H NMR (400 MHz, DMSO-d6) δ = 9.47 (s, 1H), 9.41-7.38 (m, 1H), 8.75 (d, J = 8.8 Hz, 1H), 8.64 (d, J = 8.8 Hz, 1H), 8.58 (d, J = 4.8 Hz, 1H), 8.27 (s, 1H), 7.97 (d, J = 8.0 Hz, 1H), 7.85 (s, 1H), 7.69 (d, J = 4.8 Hz, 1H), 7.31 (d, J = 8.0 Hz, 1H), 5.24-5.01 (m, 2H), 4.93-4.69 (m, 4H), 4.11-4.04 (m, 1H), 4.00-3.76 (m, 3H), 3.37-3.34 (m, 1H), 3.25-3.20 (m, 1H), 2.97-2.88 (m, 1H), 2.82-2.76 (m, 1H), 1.98-1.96 (m, 1H), 1.92-1.80 (m, 1H), 1.75-1.65 (m, 4H), 1.36-1.32 (m, 1H) ppm |
| 309 | 526.4 | 1H NMR (400 MHz, MeOD) δ = 9.40 (s, 1H), 9.12 (d, J = 7.6 Hz, 1H), 8.86 (d, J = 8.8 Hz, 1H), 8.71 (d, J = 8.8 Hz, 1H), 8.48-8.38 (m, 2H), 8.19 (d, J = 1.6 Hz, 1H), 8.04 (s, 1H), 7.95-7.92 (m, 1H), 7.49-7.14 (m, 2H), 4.92 (d, J = 3.6 Hz, 2H), 4.58 (s, 2H), 4.21 (d, J = 11.2 Hz, 1H), 3.94 (d, J = 11.2 Hz, 1H), 1.75 (s, 3H) ppm |
| 310 | 534.5 | 1H NMR (400 MHz, DMSO-d6) δ = 9.47 (s, 1H), 9.43-9.39 (m, 1H), 8.79-8.72 (m, 1H), 8.65 (br s, 1H), 8.57 (d, J = 5.2 Hz, 1H), 8.20 (d, J = 1.6 Hz, 1H), 7.96-7.94 (m, 1H), 7.87 (s, 1H), 7.71 (d, J = 4.8 Hz, 1H), 7.31 (d, J = 8.0 Hz, 1H), 5.32-4.96 (m, 1H), 4.95-4.69 (m, 5H), 4.23 (d, J = 11.2 Hz, 1H), 3.87 (br d, J = 11.2 Hz, 2H), 3.78-3.44 (m, 3H), 2.02-1.96 (m, 1H), 1.95-1.87 (m, 1H), 1.70 (s, 3H) ppm |
| 311 | 524.5 | 1H NMR (400 MHz, DMSO-d6) δ = 9.46-9.36 (m, 2H), 8.93 (s, 1H), 8.72 (d, J = 8.8 Hz, 1H), 8.59 (d, J = 8.4 Hz, 1H), 8.24-8.13 (m, 2H), 7.97-7.94 (m, 1H), 7.86 (s, 1H), 7.31 (d, J = 8.4 Hz, 1H), 5.64-5.44 (m, 1H), 4.96-4.76 (m, 4H), 4.23 (d, J = 11.2 Hz, 1H), 4.03-3.69 (m, 4H), 3.64-3.59 (m, 1H), 2.34-2.12 (m, 2H), 1.71 (s, 3H) ppm |
| 316 | 580.25 | $^1$H NMR (400 MHz, DMSO-$d_6$) δ 9.51-9.34 (m, 2H), 8.83-8.65 (m, 3H), 8.44 (dt, J = 8.0, 1.4 Hz, 1H), 8.35 (d, J = 8.7 Hz, 1H), 8.21 (d, J = 1.8 Hz, 1H), 8.07-7.91 (m, 2H), 7.85 (s, 1H), 7.66 (t, J = 7.8 Hz, 1H), 7.32 (d, J = 8.1 Hz, 1H), 4.99-4.75 (m, 4H), 4.23 (d, J = 11.4 Hz, 1H), 3.87 (d, J = 11.5 Hz, 1H), 3.65-3.50 (m, 4H), 3.51-3.41 (m, 4H), 3.23 (s, 3H), 1.71 (s, 3H). |
| 317 | 575.35 | $^1$H NMR (400 MHz, DMSO-$d_6$) δ 9.42 (d, J = 3.2 Hz, 2H), 8.77-8.64 (m, 2H), 8.55-8.40 (m, 2H), 8.35 (d, J = 8.7 Hz, 1H), 8.21 (d, J = 1.7 Hz, 1H), 8.07-7.92 (m, 2H), 7.85 (s, 1H), 7.65 (t, J = 7.8 Hz, 1H), 7.32 (d, J = 8.1 Hz, 1H), 5.02-4.72 (m, 4H), 4.23 (d, J = 11.4 Hz, 1H), 3.95-3.72 (m, 2H), 2.83 (d, J = 11.1 Hz, 2H), 2.21 (s, 3H), 2.04 (q, J = 11.9, 8.9 Hz, 2H), 1.87-1.76 (m, 2H), 1.71 (s, 3H), 1.63 (qd, J = 12.1, 3.9 Hz, 2H). |
| 318 | 510 | 1H NMR (400 MHz, CHLOROFORM-d) δ ppm 1.71-1.81 (m, 3 H) 3.88 (dd, J = 17.31, 12.02 Hz, 1 H) 4.09 (t, J = 11.69 Hz, 1 H) 4.67 (td, J = 13.06, 4.52 Hz, 2 H) 4.75-4.94 (m, 2 H) 5.01 (d, J = 5.29 Hz, 2 H) 6.11-6.52 (m, 1 H) 7.11-7.20 (m, 2 H) 7.27 (s, 8 H) 7.36 (br s, 1 H) 7.84 (d, J = 8.16 Hz, 1 H) 7.98 (s, 1 H) 8.11 (s, 1 H) 8.39 (s, 2 H) 8.65 (d, J = 9.92 Hz, 1 H) 9.30 (s, 1 H) ppm. |
| 319 | 515.2 | 1H NMR (400 MHz, CDCl3) δ = 9.27-9.33 (m, 1H), 9.18-9.23 (m, 1H), 8.55 (d, J = 8.4 Hz, 1H), 8.40 (d, J = 8.4 Hz, 1H), 8.26-8.31 (m, 1H), 8.12 (s, 1H), 8.02-8.07 (m, 1H), 7.83-7.89 (m, 1H), 7.34-7.38 (m, 1H), 7.19 (s, 1H), 4.99-5.05 (m, 2H), 4.76-4.93 (m, 2H), 4.06-4.14 (m, 1H), 3.89-3.95 (m, 4H), 3.82-3.89 (m, 1H), 3.69-3.75 (m, 4H), 1.83 (s, 3H) ppm |
| 320 | 534.1 | 1HNMR (400 MHz, DMSO-d6) δ = 9.70-9.63 (m, 1H), 9.61-9.54 (m, 1H), 8.79-8.71 (m, 1H), 8.27-8.22 (m, 1H), 8.22-8.19 (m, 1H), 8.11-8.02 (m, 1H), 7.99-7.90 (m, 1H), 7.65-7.50 (m, 1H), 7.36-7.25 (m, 1H), 7.11-7.00 (m, 1H), 4.95-4.79 (m, 5H), 4.42-4.34 (m, 2H), 4.26-4.18 (m, 1H), 3.97-3.90 (m, 2H), 3.86 (d, J = 11.6 Hz, 1H), 2.28 (s, 3H), 1.70 (s, 3H) ppm. |
| 321 | 518.4 | 1H NMR (400 MHz, DMSO-d6) δ = 9.46 (s, 1H), 9.42-9.39 (m, 1H), 8.75 (d, J = 8.4 Hz, 1H), 8.63 (d, J = 8.4 Hz, 1H), 8.53 (d, J = 4.8 Hz, 1H), 8.20 (d, J = 1.6 Hz, 1H), 7.96-7.93 (m, 1H), 7.86 (s, 1H), 7.68 (d, J = 5.2 Hz, 1H), 7.31 (d, J = 8.4 Hz, 1H), 4.95-4.80 (m, 4H), 4.23 (d, J = 11.6 Hz, 1H), 3.87 (d, J = 11.2 Hz, 3H), 3.57 (br d, J = 3.2 Hz, 2H), 1.70 (s, 5H), 0.8-0.75 (m, 1H), 0.22-0.19 (m, 1H) ppm. |
| 322 | 536.4 | 1H NMR (400 MHz, DMSO-d6) δ = 9.53-9.36 (m, 2H), 8.76 (d, J = 8.4 Hz, 1H), 8.66 (d, J = 8.8 Hz, 1H), 8.60 (d, J = 4.8 Hz, 1H), 8.20 (s, 1H), 7.95 (d, J = 7.6 Hz, 1H), 7.87 (s, 1H), 7.73 (d, J = 4.8 Hz, 1H), 7.31 (d, J = 8.0 Hz, 1H), 4.96-4.78 (m, 4H), 4.70-4.52 (m, 2H), 4.23 (d, J = 11.6 Hz, 1H), 3.95 (d, J = 11.2 Hz, 1H), 3.87 (d, J = 11.2 Hz, 1H), 3.62-3.51 (m, 2H), 3.09-3.01 (m, 1H), 2.76-2.67 (m, 1H), 1.70 (s, 3H), 1.20 (d, J = 6.4 Hz, 3H) ppm |
| 323 | 536.2 | 1H NMR (400 MHz, METHANOL-d4) δ = 9.32 (s, 1H), 8.62 (d, J = 8.8 Hz, 1H), 8.31 (d, J = 8.4 Hz, 2H), 8.22 (d, J = 8.4 Hz, 1H), 8.18 (d, J = 1.6 Hz, 1H), 8.06-7.97 (m, 3H), 7.94-7.92 (m, 1H), 7.29 (d, J = 8.0 Hz, 1H), 4.90-4.90 (m, 4H), 4.21 (d, J = 11.6 Hz, 1H), 3.93 (d, J = 11.2 Hz, 1H), 3.59 (s, 4H), 3.39 (s, 3H), 1.76 (s, 3H) ppm |

TABLE 19-continued

| Compounds of the Invention | | |
|---|---|---|
| # | LCMS (m/z) | 1H NMR |
| 324 | 492.2 | 1H NMR (400 MHz, METHANOL-d4) δ = 9.33 (s, 1H), 8.62 (d, J = 8.8 Hz, 1H), 8.32-8.29 (m, 2H), 8.22 (d, J = 8.4 Hz, 1H), 8.18 (d, J = 1.6 Hz, 1H), 7.99-7.97 (m, 3H), 7.94-7.92 (m, 1H), 7.29 (d, J = 8.0 Hz, 1H), 4.92-4.91 (m, 4H), 4.21 (d, J = 11.2 Hz, 1H), 3.93 (d, J = 11.6 Hz, 1H), 2.95 (s, 3H), 1.76 (s, 3H) ppm |
| 325 | 470.2 | 1H NMR (400 MHz, DMSO-d6) δ = 9.43 (s, 2H), 9.42 (br s, 1H), 8.77 (s, 1H), 8.74(d, J = 8.4 Hz, 1H), 8.54 (d, J = 8.4 Hz, 1H), 8.27 (s, 1H), 7.98-7.96 (m, 1H), 7.85 (s, 1H), 7.31 (d, J = 8.0 Hz, 1H), 4.88-4.81 (m, 3H), 4.75-4.74(m, 1H), 4.11-4.04 (m, 1H), 3.88-3.79 (m, 1H), 2.35-2.32 (m, 1H), 1.71-1.66 (m, 3H), 1.15-1.13 (m, 4H) ppm. |
| 329 | 469.2 | 1H NMR (400 MHz, MeOD) δ = 8.31-8.30 (m, 1H), 8.21-8.19 (m, 2H), 8.15 (d, J = 1.6 Hz, 1H), 8.06 (d, J = 5.2 Hz, 2H), 7.90-7.89 (m, 1H), 7.28 (d, J = 8.0 Hz, 1H), 5.09 (s, 2H), 4.90 (s, 2H), 4.20 (d, J = 11.2 Hz, 1H), 4.03 (s, 3H), 3.93 (d, J = 11.6 Hz, 1H), 3.82-3.81 (m, 3H), 1.75 (s, 3H) ppm. |
| 333 | 480.2 | 1H NMR (400 MHz, DMSO-d6) δ = 9.46-9.43 (m, 1H), 9.20 (s, 1H), 8.46 (d, J = 0.4, 1H), 8.35 (s, 1H), 8.16 (s, 1H), 8.00-7.96(m, 1H), 7.79 (d, J = 10.4 Hz, 1H), 7.57 (s, 1H), 4.95 (d, J = 16.8 Hz, 1H), 4.77-4.71 (m, 3H), 4.16-4.04 (m, 1H), 3.97 (s, 3H), 3.90-3.78 (m, 1H), 3.76 (s, 3H), 1.75-1.61 (m, 3H) ppm. |
| 334 | 463.2 | 1H NMR (400 MHz, DMSO-d6) δ = 9.54-9.52 (m, 1H), 9.21 (s, 1H), 9.09-9.08 (m, 1H), 8.62 (s, 1H), 8.46-8.42 (m, 1H), 8.35 (s, 1H), 8.00 (d, J = 8.8 Hz, 1H), 7.60 (s, 1H), 4.86-4.74 (m, 4H), 4.16-4.09 (m, 1H), 3.98 (s, 3H), 3.93-3.83(m, 1H), 3.78 (s, 3H), 1.71 (d, J = 21.2, 3H) ppm |
| 335 | 492.2 | 1H NMR (400 MHz, DMSO-d6) δ = 9.49-9.46 (m, 1H), 8.99 (d, J = 1.6 Hz, 1H), 8.81-8.78 (m, 1H), 8.55 (d, J = 9.2 Hz, 1H), 8.36 (d, J = 5.6 Hz, 1H), 8.31 (s, 1H), 8.17 (d, J = 1.6 Hz, 1H), 7.94-7.92 (m, 1H), 7.30 (d, J = 8.0 Hz, 1H), 6.41 (d, J = 6.0 Hz, 1H), 5.06 (d, J = 5.6 Hz, 2H), 4.92-4.81 (m, 2H), 4.23-4.14 (m, 5H), 3.87 (d, J = 11.6 Hz, 1H), 2.45-2.40 (m, 2H), 1.69 (s, 3H) ppm. |
| 336 | 492.2 | 1H NMR (400 MHz, DMSO-d6) δ = 9.52-9.49 (m, 1H), 8.84 (s, 1H), 8.59-8.58 (m, 2H), 8.51 (d, J = 5.2 Hz, 1H), 8.23 (s, 1H), 8.18 (d, J = 1.6 Hz, 1H), 7.95-7.92 (m, 1H), 7.42 (d, J = 5.2 Hz, 1H), 7.30 (d, J = 8.0 Hz, 1H), 5.09 (d, J = 6.0 Hz, 2H), 4.92-4.81 (m, 2H), 4.23 (d, J = 11.6 Hz, 1H), 4.16-4.12 (m, 4H), 3.87 (d, J = 11.2 Hz, 1H), 2.37-2.33(m, 2H), 1.68(s, 3H) ppm. |
| 337 | 477.2 | 1H NMR (400 MHz, DMSO-d6) δ = 9.72 (d, J = 2.4 Hz, 1H), 9.46 (s, 1H), 9.42-9.40 (m, 1H), 9.21 (d, J = 1.2 Hz, 1H), 8.82 (d, J = 5.2 Hz, 1H), 8.19 (d, J = 1.2 Hz, 1H), 8.07 (d, J = 5.2 Hz, 1H), 7.97-7.94 (m, 2H), 7.31 (d, J = 8.0 Hz, 1H), 4.97 93-4.81 (m, 4H), 4.24 (d, J = 11.6 Hz, 1H), 3.88 (d, J = 11.6 Hz, 1H), 2.34-2.30 (m, 1H), 1.69 (s, 3H), 1.15-1.12 (m, 4H) ppm. |
| 338 | 462.2 | 1HNMR (400 MHz, DMSO-d6) δ = 9.33-9.30 (m, 1H), 9.26-9.20 (m, 2H), 8.43-8.35 (m, 2H), 8.25 (s, 1H), 7.96(d, J = 8.0 Hz, 1H), 7.71 (s, 1H), 7.29 (d, J = 8.0 Hz, 1H), 4.88-4.82 (m, 1H), 4.76-4.70 (m, 3H), 4.10-4.04 (m, 1H), 3.96 (s, 3H), 3.88-3.80 (m, 1H), 3.77 (s, 3H), 1.71-1.61 (m, 3H) ppm. |
| 339 | 536.3 | 1H NMR (400 MHz, DMSO-d6) δ = 9.47 (s, 1H), 9.44-9.40 (m, 1H), 8.79-8.74 (m, 1H), 8.67 (d, J = 8.8 Hz, 1H), 8.57 (d, J = 4.8 Hz, 1H), 8.49 (s, 1H), 8.21 (d, J = 1.2 Hz, 1H), 7.97-7.95 (m, 1H), 7.87 (s, 1H), 7.68 (d, J = 5.2 Hz, 1H), 7.32 (d, J = 8.4 Hz, 1H), 4.96-4.81 (m, 4H), 4.24 (d, J = 11.6 Hz, 1H), 4.12 (br s, 1H), 3.90-3.51 (m, 5H), 3.30 (s, 3H), 2.16-2.07 (m, 2H), 1.71 (s, 3H) ppm |
| 340 | 534.3 | 1H NMR (400 MHz, DMSO-d6) δ = 9.47 (s, 1H), 9.43-9.39 (m, 1H), 8.78-8.73 (m, 1H), 8.70-8.60 (m, 1H), 8.57 (d, J = 5.2 Hz, 1H), 8.20 (d, J = 1.6 Hz, 1H), 7.97-7.94 (m, 1H), 7.87 (s, 1H), 7.71 (d, J = 5.2 Hz, 1H), 7.31 (d, J = 8.0 Hz, 1H), 4.95-4.70 (m, 6H), 4.23 (d, J = 11.2 Hz, 1H), 3.90-3.84 (m, 2H), 3.77-3.49 (m, 3H), 2.00-1.89 (m, 2H), 1.70 (s, 3H) ppm |
| 341 | 524.2 | 1H NMR (400 MHz, DMSO-d6) δ = 9.47 (s, 1H), 9.43-9.39 (m, 1H), 8.80-8.74 (m, 1H), 8.67 (d, J = 8.4 Hz, 1H), 8.59 (d, J = 4.8 Hz, 1H), 8.20 (d, J = 1.6 Hz, 1H), 7.97-7.87 (m, 1H), 7.87 (s, 1H), 7.72 (d, J = 4.8 Hz, 1H), 7.31 (d, J = 8.4 Hz, 1H), 5.60-5.39 (m, 1H), 4.95-4.80 (m, 4H), 4.23 (d, J = 11.2 Hz, 1H), 4.09-3.54 (m, 5H), 2.32-2.12 (m, 2H), 1.71 (s, 3H) ppm |
| 342 | 477.2 | 1H NMR (400 MHz, DMSO-d6) δ = 9.67 (d, J = 2.0 Hz, 1H), 9.44 (s, 1H), 9.42-9.41 (m, 1H), 9.22 (s, 1H), 9.13 (d, J = 1.6 Hz, 1H), 8.71 (s, 1H), 8.20 (d, J = 1.6 Hz, 1H), 7.97-7.95 (m, 1H), 7.92 (s, 1H), 7.32 (d, J = 8.0 Hz, 1H), 4.93-4.81 (m, 4H), 4.24 (d, J = 11.6 Hz, 1H), 3.88 (d, J = 11.6 Hz, 1H), 2.34-2.31 (m, 1H), 1.70 (s, 3H), 1.19-1.12 (m, 4H) ppm. |
| 343 | 462.2 | 1H NMR (400 MHz, DMSO-d6) δ = 9.39-9.36 (m, 1H), 9.20 (s, 1H), 8.46-8.44 (m, 2H), 8.36 (s, 1H), 8.28 (s, 1H), 8.00-7.96 (m, 2H), 7.55 (s, 1H), 7.31 (d, J = 8.4 Hz, 1H), 4.88-4.84 (m, 1H), 4.76-4.71 (m, 3H), 4.11-4.04 (m, 1H), 3.97 (s, 3H), 3.69-3.79 (m, 1H), 3.75 (s, 3H), 168 (d, J = 12.4, 3H) ppm. |

TABLE 19-continued

| Compounds of the Invention | | |
|---|---|---|
| # | LCMS (m/z) | 1H NMR |
| 344 | 473.1 | 1H NMR (400 MHz, DMSO-d6) δ = 9.42 (s, 1H), 9.37-9.34 (m, 1H), 9.09 (s, 1H), 8.58 (s, 1H), 8.18 (d, J = 1.2 Hz, 1H), 8.00 (s, 1H), 7.95-7.92 (m, 1H), 7.30 (d, J = 8.4 Hz, 1H), 4.94-4.80 (m, 2H), 4.77 (d, J = 6.0 Hz, 2H), 4.22 (d, J = 11.6 Hz, 1H), 4.07 (s, 3H), 3.86 (d, J = 11.6 Hz, 1H), 1.70 (s, 3H) ppm |
| 345 | 491.2 | 1H NMR (400 MHz, MeOD) δ = 9.21 (s, 1H), 8.42 (d, J = 8.8 Hz, 1H), 8.24 (s, 1H), 7.96-7.92(m, 2H), 7.86-7.85 (m, 1H), 7.28 (d, J = 8.0 Hz, 1H), 7.10 (d, J = 1.6 Hz, 1H), 4.88 (s, 3H), 4.81-4.76(m, 1H), 4.61-4.50 (m, 2H), 4.10-4.04 (m, 1H), 3.92-3.84 (m, 1H), 3.73 (s, 3H), 3.66-3.63(m, 2H), 2.47-2.46 (m, 2H), 1.76-1.70 (m, 3H) ppm. |
| 346 | 490 | 1H NMR (400 MHz, DMSO-d6) δ = 9.63 (s, 1H), 9.42 (s, 2H), 8.73 (s, 2H), 8.21 (d, J = 1.6 Hz, 1H), 8.09 (d, J = 3.2 Hz, 1H), 8.01-7.93 (m, 1H), 7.88 (s, 1H), 7.31 (d, J = 8.0 Hz, 1H), 6.76 (d, J = 3.2 Hz, 1H), 4.97-4.81 (m, 4H), 4.23 (d, J = 11.6 Hz, 1H), 3.97 (s, 3H), 3.87 (d, J = 11.6 Hz, 1H), 1.71 (s, 3H) ppm. |
| 347 | 484.2 | 1H NMR (400 MHz, MeOH) δ = 9.63 (s, 1H), 9.36 (s, 1H), 8.85 (s, 1H), 8.23 (s, 1H), 7.93-7.91 (m, 2H), 7.66-7.63(m, 1H), 7.36 (d, J = 7.6 Hz, 1H), 7.27 (d, J = 8.0 Hz, 1H), 6.45(d, J = 8.4 Hz, 1H), 4.90 (s, 3H), 4.80 (d, J = 3.2 Hz, 1H), 4.14-4.03 (m, 5H), 3.91-3.86 (m, 1H), 2.46-2.42 (m, 2H), 1.75-1.69 (m, 3H) ppm. |
| 348 | 498.1 | 1H NMR (400 MHz, DMSO-d6) δ = 9.41 (s, 1H), 9.36-9.33 (m, 1H), 8.61 (d, J = 4.8 Hz, 1H), 8.17 (d, J = 1.6 Hz, 1H), 7.98 (s, 1H), 7.93-7.90 (m, 1H), 7.46 (d, J = 4.8 Hz, 1H), 7.29 (d, J = 8.0 Hz, 1H), 4.93-4.80 (m, 2H), 4.76 (d, J = 6.0 Hz, 2H), 4.22 (d, J = 11.2 Hz, 1H), 4.17-4.13 (m, 4H), 3.86 (d, J = 11.6 Hz, 1H), 2.41-2.34 (m, 2H), 1.69 (s, 3H) ppm |
| 349 | 467.1 | 1H NMR (400 MHz, MeOD-d4) δ = 8.90 (s, 1H), 8.77 (s, 1H), 8.66 (d, J = 8.8 Hz, 1H), 8.56 (d, J = 8.8 Hz, 1H), 8.28-8.26 (m, 2H), 8.15 (s, 1H), 7.90 (d, J = 8.0 Hz, 1H), 7.27 (d, J = 8.0 Hz, 1H), 5.17 (s, 2H), 4.92-4.81 (m, 2H), 4.20 (d, J = 11.2 Hz, 1H), 4.13 (s, 3H), 3.92 (d, J = 11.2 Hz, 1H), 1.74 (s, 3H) ppm |
| 351 | 491 | 1H NMR (400 MHz, MeOD-d4) δ = 8.61-8.60 (m, 2H), 8.50-8.49 (m, 1H), 8.25 (s, 1H), 8.17 (s, 1H), 7.91 (d, J = 8.0 Hz, 1H), 7.68-7.64 (m, 1H), 7.38 (d, J = 7.6 Hz, 1H), 7.30-7.28 (m, 1H), 7.65 (d, J = 8.4 Hz, 1H), 5.17 (s, 2H), 4.92-4.81 (m, 2H), 4.20 (d, J = 11.2 Hz, 1H), 4.16-4.12 (m, 4H), 3.92 (d, J = 11.2 Hz, 1H), 2.49-2.42 (m, 2H), 1.76 (s, 3H) ppm |
| 352 | 539.1 | 1H NMR (400 MHz, DMSO-d6) δ = 9.49-9.46(m, 1H), 9.42 (s, 1H), 8.93 (s, 1H), 8.73 (d, J = 8.4 Hz, 1H), 8.52 (d, J = 8.8 Hz, 1H), 8.14(s, 1H), 8.01 (s, 1H), 7.96 (d, J = 10.4 Hz, 1H), 7.87 (s, 1H), 6.88-6.59 (m, 1H), 5.00-4.96 (m, 1H), 4.86-4.82(m, 3H), 4.30-4.20 (m, 1H), 4.18-4.16 (m, 4H), 4.12 (s, 1H), 2.46-2.43 (m, 2H) ppm. |
| 353 | 498.2 | 1H NMR (400 MHz, DMSO-d6) δ = 9.44-9.29 (m, 2H), 8.68 (s, 1H), 8.17 (d, J = 1.2 Hz, 1H), 8.08 (s, 1H), 7.98-7.90 (m, 2H), 7.29 (d, J = 8.4 Hz, 1H), 4.95-4.80 (m, 2H), 4.75 (d, J = 6.0 Hz, 2H), 4.26-4.12 (m, 5H), 3.86 (d, J = 11.6 Hz, 1H), 2.46-2.40 (m, 2H), 1.70 (s, 3H) ppm |
| 354 | 472 | 1H NMR (400 MHz, DMSO-d6) δ = 9.38 (s, 1H), 9.36-9.33 (m, 1H), 8.82-8.79 (m, 1H), 8.47-8.45 (m, 1H), 8.40 (s, 1H), 8.17 (d, J = 1.2 Hz, 1H), 7.96-7.90 (m, 2H), 7.33-7.25 (m, 2H), 4.93-4.81 (m, 2H), 4.76 (br d, J = 6.0 Hz, 2H), 4.22 (d, J = 11.6 Hz, 1H), 4.18 (s, 3H), 3.86 (d, J = 11.6 Hz, 1H), 1.70 (s, 3H) ppm |
| 355 | 487 | 1H NMR (400 MHz, DMSO-d6) δ = 9.90 (s, 1H), 9.50 (s, 1H), 9.45-9.42 (m, 1H), 9.14 (s, 1H), 8.82 (d, J = 8.4 Hz, 1H), 8.59 (d, J = 8.4 Hz, 1H), 8.20 (d, J = 1.2 Hz, 1H), 8.02-7.89 (m, 2H), 7.44-7.11 (m, 2H), 4.96-4.78 (m, 4H), 4.23 (d, J = 11.2 Hz, 1H), 3.87 (d, J = 11.6 Hz, 1H), 1.71 (s, 3H) ppm |
| 356 | 492 | 1H NMR (400 MHz, MeOD-d4) δ = 8.68 (s, 1H), 8.62-8.61 (m, 1H), 8.55-8.52 (m, 2H), 8.27 (s, 1H), 8.17 (s, 1H), 7.93-7.92 (m, 1H), 7.83 (s, 1H), 7.29 (d, J = 8.0 Hz, 1H), 5.18 (s, 2H), 4.92-4.81 (m, 2H), 4.27-4.19 (m, 5H), 3.92 (d, J = 11.2 Hz, 1H), 2.58-2.50 (m, 2H), 1.77 (s, 3H) ppm |
| 357 | 466 | 1H NMR (400 MHz, MeOD-d4) δ = 8.48-8.46 (m, 2H), 8.25-8.16 (m, 5H), 7.92-7.90 (m, 2H), 7.29-7.27 (m, 1H), 7.15-7.13 (m, 1H), 5.17 (s, 2H), 4.92-4.81 (m, 2H), 4.20 (d, J = 11.2 Hz, 1H), 4.00 (s, 3H), 3.92 (d, J = 11.2 Hz, 1H), 1.76 (s, 3H) ppm |
| 358 | 487 | 1H NMR (400 MHz, MeOD) δ = 9.32 (s, 1H), 9.02 (d, J = 5.2 Hz, 1H), 8.71-8.63 (m, 3H), 8.07 (d, J = 1.6 Hz, 1H), 7.93 (s, 1H), 7.84-7.82 (m, 1H), 7.21 (d, J = 8.4 Hz, 1H), 6.91-6.64 (m, 1H), 4.85 (s, 2H), 4.82 (d, J = 3.2 Hz, 2H), 4.12 (d, J = 11.6 Hz, 1H), 3.84 (d, J = 11.6 Hz, 1H), 1.67 (s, 3H) ppm |
| 359 | 505.2 | 1H NMR (400 MHz, MeOD) δ = 9.36 (s, 1H), 8.88 (d, J = 8.8 Hz, 1H), 8.69 (d, J = 8.4 Hz, 1H), 8.58 (d, J = 8.0 Hz, 1H), 8.52 (br s, 1H), 8.18 (d, J = 1.6 Hz, 1H), 8.00-7.91 (m, 3H), 7.45 (d, J = 6.8 Hz, 1H), 7.30 (d, J = 8.0 Hz, 1H), 4.93 (s, 2H), 4.91 (d, J = 3.2 Hz, 2H), 4.42-4.37(m, 4H), 4.29-4.26 (m, 1H), 4.22 (d, J = 11.2 Hz, 1H), 3.94 (d, J = 11.6 Hz, 1H), 2.98 (s, 3H), 1.76 (s, 3H) ppm. |
| 360 | 479.2 | 1H NMR (400 MHz, MeOD) δ = 9.27 (s, 1H), 8.68 (d, J = 8.4 Hz, 1H), 8.55 (d, J = 8.8 Hz, 1H), 8.17(d, J = 1.6 Hz, 1H), 7.94-7.91 (m, 2H), 7.81 (d, J = |

TABLE 19-continued

Compounds of the Invention

| # | LCMS (m/z) | 1H NMR |
| --- | --- | --- |
| | | 7.2 Hz, 1H), 7.67-7.65 (m, 1H), 7.29 (d, J = 8.0 Hz, 1H), 6.77 (d, J = 8.4 Hz, 1H), 4.91-4.90 (m, 4H), 4.21 (d, J = 11.2 Hz, 1H), 3.93 (d, J = 11.6 Hz, 1H), 3.18 (s, 6H), 1.76 (s, 3H) ppm. |
| 361 | 505.1 | 1H NMR (400 MHz, MeOD) δ = 9.31 (s, 1H), 8.72 (d, J = 8.8 Hz, 1H), 8.58 (d, J = 8.4 Hz, 1H), 8.20 (d, J = 1.6 Hz, 1H), 8.01-7.93 (m, 2H), 7.80 (d, J = 7.2 Hz, 1H), 7.67-7.64 (m, 1H), 7.31 (d, J = 8.0 Hz, 1H), 6.62 (d, J = 8.4 Hz, 1H), 4.95-4.92 (m, 4H), 4.23 (d, J = 11.2 Hz, 1H), 3.95 (d, J = 11.2 Hz, 1H), 3.61-3.57 (m, 4H), 2.17-2.05 (m, 4H), 1.79 (s, 3H) ppm |
| 362 | 536.3 | 1H NMR (400 MHz, METHANOL-d4) δ = 9.48 (d, J = 0.8 Hz, 1H), 9.43-9.40 (m, 1H), 8.77-8.75 (m, 1H), 8.66 (d, J = 8.8 Hz, 1H), 8.61 (d, J = 4.8 Hz, 1H), 8.20 (d, J = 1.6 Hz, 1H), 7.96-7.94 (m, 1H), 7.87 (s, 1H), 7.73 (d, J = 5.2 Hz, 1H), 7.32 (d, J = 8.0 Hz, 1H), 4.93-4.82 (m, 4H), 4.67-4.58 (m, 2H), 4.23 (d, J = 11.6 Hz, 1H), 3.97-3.94 (m, 1H), 3.88 (d, J = 11.2 Hz, 1H), 3.61-3.52 (m, 2H), 3.09-3.02 (m, 1H), 2.76-2.70 (m, 1H), 1.70 (s, 3H), 1.21 (d, J = 6.4 Hz, 3H) ppm |
| 363 | 536.2 | 1H NMR (400 MHz, DMSO-d6) δ = 9.47 (s, 1H), 9.45-9.35 (m, 1H), 8.76 (d, J = 8.8 Hz, 1H), 8.68-8.56 (m, 2H), 8.20 (d, J = 1.2 Hz, 1H), 8.02-7.92 (m, 1H), 7.87 (s, 1H), 7.73 (d, J = 4.8 Hz, 1H), 7.31 (d, J = 8.0 Hz, 1H), 4.96-4.74 (m, 5H), 4.44 (br d, J = 12.0 Hz, 1H), 4.23 (d, J = 11.6 Hz, 1H), 4.05-3.92 (m, 1H), 3.87 (d, J = 11.6 Hz, 1H), 3.81-3.73 (m, 1H), 3.69-3.61 (m, 1H), 3.56-3.43 (m, 1H), 3.28-3.20 (m, 1H), 1.70 (s, 3H), 1.25 (d, J = 6.4 Hz, 3H) ppm. |
| 364 | 457.2 | 1H NMR (400 MHz, DMSO-d6) δ 9.41 (t, J = 6.0 Hz, 1H), 9.33 (s, 1H), 8.62-8.51 (m, 2H), 8.24 (d, J = 1.8 Hz, 1H), 7.99 (dd, J = 8.1, 1.8 Hz, 1H), 7.85 (d, J = 8.6 Hz, 1H), 7.69 (s, 1H), 7.35 (d, J = 8.1 Hz, 1H), 4.95 (d, J = 16.0 Hz, 1H), 4.88 (d, J = 16.1 Hz, 1H), 4.82 (d, J = 5.8 Hz, 2H), 4.27 (d, J = 11.4 Hz, 1H), 3.91 (d, J = 11.5 Hz, 1H), 3.85 (s, 3H), 1.74 (s, 3H). |
| 365 | 491.3 | 1H NMR (400 MHz, DMSO-d6) δ 9.39 (d, J = 11.6 Hz, 2H), 8.74 (s, 1H), 8.51 (d, J = 5.2 Hz, 1H), 8.39 (dd, J = 8.5, 1.7 Hz, 1H), 8.27 (d, J = 8.7 Hz, 1H), 8.23 (d, J = 1.7 Hz, 1H), 7.99 (dd, J = 8.1, 1.7 Hz, 1H), 7.89 (s, 1H), 7.45 (d, J = 5.2 Hz, 1H), 7.34 (d, J = 8.1 Hz, 1H), 4.99-4.79 (m, 4H), 4.26 (d, J = 11.4 Hz, 1H), 4.18 (t, J = 7.5 Hz, 4H), 3.91 (d, J = 11.6 Hz, 1H), 2.40 (d, J = 7.6 Hz, 1H), 1.74 (s, 3H). |
| 366 | 535.4 | 1H NMR (400 MHz, DMSO-d6) δ 9.37 (d, J = 5.0 Hz, 2H), 8.71 (s, 1H), 8.61 (s, 1H), 8.40 (dd, J = 8.7, 1.6 Hz, 1H), 8.29-8.20 (m, 2H), 8.06 (s, 1H), 7.99 (dd, J = 8.0, 1.8 Hz, 1H), 7.87 (s, 1H), 7.34 (d, J = 8.1 Hz, 1H), 4.95 (d, J = 16.0 Hz, 1H), 4.88 (d, J = 15.9 Hz, 1H), 4.82 (d, J = 5.8 Hz, 2H), 4.35 (d, J = 4.3 Hz, 0H), 4.26 (d, J = 11.4 Hz, 1H), 4.18 (s, 1H), 3.91 (d, J = 11.5 Hz, 1H), 3.73 (d, J = 11.6 Hz, 2H), 3.68 (dd, J = 11.7, 4.3 Hz, 1H), 3.57 (q, J = 8.8 Hz, 1H), 2.15 (td, J = 8.7, 8.3, 4.3 Hz, 2H), 1.74 (s, 3H). |
| 367 | 468.2 | 1H NMR (400 MHz, DMSO-d6) δ 9.31 (t, J = 5.9 Hz, 1H), 9.21 (s, 1H), 8.27-8.19 (m, 2H), 8.14-8.05 (m, 2H), 7.97 (dd, J = 8.0, 1.7 Hz, 1H), 7.92 (dd, J = 8.6, 1.7 Hz, 1H), 7.64 (s, 1H), 7.33 (d, J = 8.1 Hz, 1H), 4.95 (d, J = 16.0 Hz, 1H), 4.88 (d, J = 16.0 Hz, 1H), 4.84-4.73 (m, 2H), 4.26 (d, J = 11.5 Hz, 1H), 3.99 (s, 3H), 3.91 (d, J = 11.6 Hz, 1H), 3.79 (s, 3H), 1.74 (s, 3H). |
| 368 | 483.3 | 1H NMR (500 MHz, DMSO-d6) δ 9.35 (s, 1H), 8.61 (s, 1H), 8.44 (s, 1H), 8.37 (dd, J = 8.7, 1.7 Hz, 1H), 8.30 (s, 1H), 8.21 (d, J = 8.6 Hz, 1H), 8.00 (d, J = 8.2 Hz, 1H), 7.83 (s, 1H), 7.68 (t, J = 7.8 Hz, 1H), 7.45 (d, J = 7.4 Hz, 1H), 7.33 (d, J = 8.0 Hz, 1H), 6.44 (d, J = 8.2 Hz, 1H), 4.90 (d, J = 15.9 Hz, 1H), 4.85-4.74 (m, 3H), 4.16-4.05 (m, 5H), 3.88 (dd, J = 25.2, 12.5 Hz, 1H), 2.44-2.36 (m, 2H), 1.73 (d, J = 20.7 Hz, 3H). |
| 369 | 490.3 | 1H NMR (500 MHz, DMSO-d6) δ 9.42-9.33 (m, 2H), 8.61 (s, 1H), 8.42-8.34 (m, 3H), 8.26-8.18 (m, 3H), 7.98 (dd, J = 8.1, 1.7 Hz, 1H), 7.84 (s, 1H), 7.72-7.65 (m, 1H), 7.45 (d, J = 7.5 Hz, 1H), 7.34 (d, J = 8.1 Hz, 1H), 6.64 (s, 1H), 6.44 (d, J = 8.3 Hz, 1H), 4.91 (q, J = 15.9 Hz, 3H), 4.80 (d, J = 6.0 Hz, 2H), 4.26 (d, J = 11.5 Hz, 1H), 4.08 (td, J = 7.4, 4.3 Hz, 5H), 3.91 (d, J = 11.5 Hz, 1H), 1.74 (s, 3H). |
| 370 | 484.3 | 1H NMR (400 MHz, DMSO-d6) δ 9.36 (d, J = 6.3 Hz, 2H), 8.69-8.62 (m, 2H), 8.38-8.22 (m, 3H), 8.01 (dd, J = 8.0, 1.9 Hz, 1H), 7.94 (d, J = 7.7 Hz, 1H), 7.84 (d, J = 6.4 Hz, 1H), 7.33 (d, J = 8.1 Hz, 1H), 4.94-4.72 (m, 4H), 4.18 (dt, J = 12.2, 7.4 Hz, 4H), 4.10 (d, J = 13.0 Hz, 1H), 3.88 (dd, J = 24.9, 12.5 Hz, 1H), 2.45 (ddq, J = 11.3, 7.4, 3.7 Hz, 2H), 1.73 (d, J = 20.7 Hz, 3H) |
| 371 | 491.3 | 1H NMR (400 MHz, DMSO-d6) δ 9.37 (s, 2H), 8.70-8.62 (m, 2H), 8.35 (dd, J = 8.6, 1.6 Hz, 1H), 8.29-8.20 (m, 2H), 8.02-7.90 (m, 2H), 7.86 (s, 1H), 7.34 (d, J = 8.1 Hz, 1H), 4.95 (d, J = 16.0 Hz, 1H), 4.88 (d, J = 15.9 Hz, 1H), 4.81 (d, J = 5.8 Hz, 2H), 4.26 (d, J = 11.5 Hz, 1H), 4.18 (dt, J = 12.5, 7.5 Hz, 5H), 3.91 (d, J = 11.5 Hz, 1H), 2.52-2.39 (m, 3H), 1.74 (s, 3H), 1.08 (d, J = 6.1 Hz, 2H). |
| 372 | 492.2 | 1H NMR (400 MHz, DMSO-d6) δ = 9.83 (d, J = 1.6 Hz, 1H), 9.43 (s, 1H), 9.39-9.33 (m, 1H), 9.19 (s, 1H), 8.35 (d, J = 6.0 Hz, 1H), 8.18 (s, 1H), 8.01 (s, 1H), 7.94 (d, J = 8.0 Hz, 1H), 7.29 (d, J = 8.0 Hz, 1H), 6.42 (d, J = |

TABLE 19-continued

Compounds of the Invention

| # | LCMS (m/z) | 1H NMR |
|---|---|---|
| | | 6.0 Hz, 1H), 4.95-4.84 (m, 2H), 4.80 (d, J = 5.6 Hz, 2H), 4.25-4.12 (m, 5H), 3.86 (d, J = 11.6 Hz, 1H), 2.45-2.39 (m, 2H), 1.69 (s, 3H) ppm. |
| 373 | 521.1 | 1H NMR (400 MHz, DMSO-d6) δ = 9.48-9.36 (m, 2H), 8.72-8.58 (m, 2H), 8.21 (s, 1H), 8.04-7.90 (m, 2H), 7.85-7.73 (m, 2H), 7.32 (d, J = 8.0 Hz, 1H), 7.03 (d, J = 8.4 Hz, 1H), 5.00-4.78 (m, 4H), 4.24 (d, J = 11.6 Hz, 1H), 3.88 (d, J = 11.6 Hz, 1H), 3.82-3.71 (m, 4H), 3.65-3.55 (m, 4H), 1.71 (s, 3H) ppm |
| 374 | 510 | 1H NMR (400 MHz, CDCl3) δ = 9.28 (s, 1H), 9.20 (s, 1H), 8.57 (d, J = 8.4 Hz, 1H), 8.40 (d, J = 8.4 Hz, 1H), 8.04-8.03 (m, 2H), 7.96 (s, 1H), 7.83-7.81 (m, 1H), 7.48-7.44 (m, 1H), 7.16 (d, J = 8.0 Hz, 1H), 5.62-5.47 (m, 1H), 5.00 (d, J = 5.2 Hz, 2H), 4.99-4.88 (m, 2H), 4.53-4.48 (m, 2H), 4.37-4.31 (m, 2H), 4.15 (d, J = 11.2 Hz, 1H), 3.96 (d, J = 11.2 Hz, 1H), 1.77 (s, 3H) ppm |
| 375 | 539.5 | 1H NMR (400 MHz, DMSO-d6) δ = 9.50-9.47 (m, 1H), 9.42 (s, 1H), 8.93 (s, 1H), 8.73 (d, J = 8.8 Hz, 1H), 8.52 (d, J = 8.8 Hz, 1H), 8.14 (s, 1H), 8.01 (s, 1H), 7.96 (d, J = 10.4 Hz, 1H), 7.87 (s, 1H), 6.88-6.59 (m, 1H), 5.00-4.96 (m, 1H), 4.86-4.82 (m, 3H), 4.30-4.22 (m, 1H), 4.19-4.16 (m, 4H), 4.16-4.10 (m, 1H), 2.46-2.42 (m, 2H) ppm. |
| 376 | 536.5 | 1H NMR (400 MHz, DMSO-d6) δ = 9.49 (s, 1H), 9.44-9.41 (m, 1H), 8.77 (d, J = 8.8 Hz, 1H), 8.68-8.60 (m, 2H), 8.20 (d, J = 1.6 Hz, 1H), 7.96-7.93 (m, 1H), 7.89 (s, 1H), 7.72 (d, J = 5.2 Hz, 1H), 7.31 (d, J = 8.0 Hz, 1H), 4.94-4.85 (m, 2H), 4.83 (d, J = 6.0 Hz, 2H), 4.78-4.78 (m, 1H), 4.44 (d, J = 12.4 Hz, 1H), 4.22 (d, J = 11.2 Hz, 1H), 3.98-3.95 (m, 1H), 3.88 (s, 1H), 3.75 (s, 1H), 3.66-3.62 (m, 1H), 3.55-3.43 (m, 1H), 3.29-3.21 (m, 1H), 1.70 (s, 3H), 1.25 (d, J = 6.8 Hz, 3H) ppm. |
| 377 | 492.1 | 1H NMR (400 MHz, DMSO-d6) δ = 9.67 (d, J = 2.4 Hz, 1H), 9.45-9.39 (m, 2H), 9.12 (s, 1H), 8.53-8.51(m, 1H), 8.19 (d, J = 1.6 Hz, 1H), 7.96-7.93 (m, 2H), 7.46 (d, J = 4.8 Hz, 1H), 7.31-7.29 (m, 1H), 4.89-4.80 (m, 4H), 4.24-4.20 (m, 1H), 4.17-4.13 (m, 4H), 3.87 (d, J = 11.6 Hz, 1H), 2.37-2.35 (m, 2H), 1.69 (s, 3H) ppm |
| 378 | 519.1 | 1H NMR (400 MHz, MeOD-d4) δ = 9.68 (s, 1H), 8.96-8.81 (m, 2H), 8.61-8.46 (m, 2H), 8.35 (s, 1H), 8.17 (d, J = 1.6 Hz, 1H), 8.09-7.98 (m, 1H), 7.97-7.88 (m, 1H), 7.31 (d, J = 8.0 Hz, 1H), 5.02 (s, 2H), 4.91 (d, J = 2.4 Hz, 2H), 4.37-4.29 (m, 2H), 4.20 (d, J = 11.2 Hz, 1H), 3.94 (d, J = 11.6 Hz, 1H), 2.78-2.69 (m, 2H), 2.30-2.19 (m, 2H), 1.76 (s, 3H) ppm. |
| 379 | 536.3 | 1H NMR (400 MHz, METHANOL-d4) δ = 9.39 (s, 1H), 8.75-8.73 (m, 1H), 8.68-8.66 (m, 1H), 8.52 (d, J = 5.2 Hz, 1H), 8.20 (d, J = 1.6 Hz, 1H), 8.01 (s, 1H), 7.96-7.93 (m, 1H), 7.77 (d, J = 4.8 Hz, 1H), 7.32 (d, J = 8.0 Hz, 1H), 4.95 (s, 2H), 4.94 (d, J = 3.6 Hz, 2H), 4.24-4.18 (m, 2H), 3.95 (d, J = 11.6 Hz, 1H), 3.91-3.65 (m, 4H), 3.42 (s, 3H), 2.30-2.11 (m, 2H), 1.78 (s, 3H) ppm |
| 380 | 506.2 | 1H NMR (400 MHz, MeOD) δ = 9.36 (s, 1H), 8.75-8.67 (m, 1H), 8.67-8.61 (m, 1H), 8.48 (d, J = 5.2 Hz, 1H), 8.18 (d, J = 1.6 Hz, 1H), 7.99 (s, 1H), 7.96-7.90 (m, 1H), 7.71 (d, J = 5.2 Hz, 1H), 7.30 (d, J = 8.2 Hz, 1H), 4.94 (s, 2H), 4.92 (d, J = 3.6 Hz, 2H), 4.21 (d, J = 11.6 Hz, 1H), 3.93 (d, J = 11.6 Hz, 1H), 3.68 (br s, 4H), 2.13-2.01 (m, 4H), 1.77 (s, 3H) ppm |
| 381 | 521.3 | 1H NMR (400 MHz, DMSO-d6) δ = 9.31-9.28 (m, 1H), 8.91 (s, 1H), 8.20-8.17 (m, 2H), 7.95-7.92 (m, 1H), 7.54 (d, J = 7.2 Hz, 1H), 7.38 (d, J = 9.2 Hz, 1H), 7.33-7.27 (m, 2H), 6.17 (d, J = 6.8 Hz, 1H), 4.94-4.80 (m, 2H), 4.71 (s, 2H), 4.69-4.61 (m, 2H), 4.23 (d, J = 11.6 Hz, 1H), 3.98-3.94 (m, 2H), 3.87 (d, J = 11.6 Hz, 1H), 3.40 (s, 3H), 2.54 (br s, 2H), 1.70 (s, 3H) ppm |
| 384 | 491.2 | 1H NMR (400 MHz, DMSO-d6) δ = 9.67 (d, J = 2.0 Hz, 1H), 9.39-9.37 (m, 2H), 8.96 (d, J = 1.6 Hz, 1H), 8.19 (d, J = 1.6 Hz, 1H), 7.96-7.93 (m, 1H), 7.89 (s, 1H), 7.70-7.66 (m, 1H), 7.47 (d, J = 7.6 Hz, 1H), 7.30 (d, J = 8.0 Hz, 1H), 6.46 (d, J = 8.0 Hz, 1H), 4.93-4.79 (m, 4H), 4.22 (d, J = 11.2 Hz, 1H), 4.07-4.03 (m, 4H), 3.86 (d, J = 11.6 Hz, 1H), 2.38-2.34(m, 2H), 1.69 (s, 3H) ppm. |
| 385 | 492.2 | 1H NMR (400 MHz, DMSO-d6) δ = 9.65 (d, J = 2 Hz, 1H), 9.42-9.38 (m, 2H), 9.04 (d, J = 1.6 Hz, 1H), 8.66 (s, 1H), 8.19 (d, J = 1.6 Hz, 1H), 7.98-7.94 (m, 2H), 7.90 (s, 1H), 7.30 (d, J = 8.0 Hz, 1H), 4.93-4.80 (m, 4H), 4.24-4.14 (m, 5H), 3.86 (d, J = 11.6 Hz, 1H), 2.44-2.41 (m, 2H), 1.69 (s, 3H) ppm |
| 386 | 467.1 | 1H NMR (400 MHz, DMSO-d6) δ = 9.74 (d, J = 3, 1H), 9.46-9.41 (m, 2H), 9.18 (d, J = 2, 1H), 9.08 (s, 1H), 8.41(s, 1H), 8.19 (d, J = 1.6, 1H), 7.97-7.91 (m, 2H), 7.30 (d, J = 8, 1H), 4.93-4.81 (m, 4H), 4.23(d, J = 11.6, 1H), 4.08 (s, 3H), 3.86(d, J = 11.6, 1H), 1.69(s, 3H) ppm. |
| 387 | 507.2 | 1H NMR (400 MHz, DMSO-d6) δ = 9.48-9.38 (m, 2H), 8.73 (d, J = 8.8 Hz, 1H), 8.61 (d, J = 8.8 Hz, 1H), 8.47 (d, J = 7.2 Hz, 1H), 8.21 (d, J = 1.6 Hz, 1H), 8.08-8.04 (m, 1H), 7.97-7.94 (m, 1H), 7.86 (s, 1H), 7.71 (d, J = 8.0 Hz, 1H), 7.32 (d, J = 8.0 Hz, 1H), 4.95-4.86 (m, 2H), 4.83 (d, J = 4.8 Hz, 2H), 4.23 (d, J = 11.2 Hz, 1H), 3.87 (d, J = 11.2 Hz, 1H), 3.43 (s, 3H), 2.17 (s, 3H), 1.71 (s, 3H) ppm. |
| 388 | 466.4 | 1H NMR (400 MHz, MeOD) δ = 9.38 (s, 1H), 9.20 (d, J = 2.0 Hz, 1H), 8.52 (d, J = 1.6 Hz, 1H), 8.29-8.24 (m, 1H), 8.16 (d, J = 1.6 Hz, 1H), 7.95- |

TABLE 19-continued

| Compounds of the Invention | | |
|---|---|---|
| # | LCMS (m/z) | 1H NMR |
| | | 7.88 (m, 3H), 7.27 (d, J = 8.0 Hz, 1H), 7.17-7.11 (m, 1H), 4.92-4.89 (m, 4H), 4.19 (d, J = 11.6 Hz, 1H), 4.00 (s, 3H), 3.92 (d, J = 11.6 Hz, 1H), 1.78-1.71 (m, 3H) ppm |
| 389 | 508.2 | 1H NMR (400 MHz, DMSO-d6) δ = 9.45-9.31 (m, 2H), 8.65-8.63(m, 1H), 8.51-8.45 (m, 2H), 8.20 (d, J = 1.6 Hz, 1H), 7.96-7.94 (m, 1H), 7.78 (s, 1H), 7.31 (d, J = 8.4 Hz, 1H), 4.99-4.73 (m, 4H), 4.52-4.43 (m, 2H), 4.23 (d, J = 11.6 Hz, 1H), 3.87 (d, J = 11.6 Hz, 1H), 3.63-3.54 (m, 2H), 3.21 (s, 3H), 1.70 (s, 3H) ppm. |
| 390 | 503.2 | 1H NMR (400 MHz, METHANOL-d4) δ = 9.37 (s, 1H), 8.72-8.62 (m, 2H), 8.46 (d, J = 8.8 Hz, 1H), 8.17 (d, J = 1.6 Hz, 1H), 8.04-7.72 (m, 3H), 7.30 (d, J = 8.4 Hz, 1H), 7.17 (d, J = 9.6 Hz, 1H), 4.94-4.91 (m, 4H), 4.21 (d, J = 11.6 Hz, 1H), 3.93 (d, J = 11.6 Hz, 1H), 1.77 (s, 3H) ppm. |
| 391 | 505.2 | 1H NMR (400 MHz, DMSO-d6) δ = 9.43-9.40 (m, 2H), 8.74 (d, J = 8.8 Hz, 1H), 8.63 (d, J = 8.8 Hz, 1H), 8.33 (d, J = 7.6 Hz, 1H), 8.20 (d, J = 1.2 Hz, 1H), 8.03-7.99 (m, 1H), 7.97-7.94 (m, 1H), 7.84 (s, 1H), 7.75-7.73 (m, 1H), 7.31 (d, J = 8.0 Hz, 1H), 4.93-4.81 (m, 4H), 4.23 (d, J = 11.6 Hz, 1H), 3.89-3.84 (m, 3H), 3.17-3.15 (m, 2H), 1.71 (s, 3H) ppm. |
| 392 | 504.1 | 1H NMR (400 MHz, DMSO-d6) δ = 9.45-9.37 (m, 2H), 8.68 (d, J = 8.8 Hz, 1H), 8.32 (s, 1H), 8.27 (d, J = 8.8 Hz, 1H), 8.20 (d, J = 1.2 Hz, 1H), 8.18 (s, 1H), 8.01-7.94 (m, 2H), 7.83 (s, 1H), 7.58-7.54 (m, 2H), 7.32-7.29 (m, 1H), 4.93-4.81 (m, 4H), 4.23 (d, J = 11.6 Hz, 1H), 3.88-3.85 (m, 1H), 3.75-3.73 (m, 2H), 3.12-3.10 (m, 2H), 1.70 (s, 3H) ppm. |
| 393 | 504.1 | 1H NMR (400 MHz, DMSO-d6) δ = 9.45-9.37 (m, 2H), 8.68 (d, J = 8.8 Hz, 1H), 8.32 (s, 1H), 8.27 (d, J = 8.8 Hz, 1H), 8.20 (d, J = 1.2 Hz, 1H), 8.18 (s, 1H), 8.01-7.94 (m, 2H), 7.83 (s, 1H), 7.58-7.54 (m, 2H), 7.32-7.29 (m, 1H), 4.93-4.81 (m, 4H), 4.23 (d, J = 11.6 Hz, 1H), 3.88-3.85 (m, 1H), 3.75-3.73 (m, 2H), 3.12-3.10 (m, 2H), 1.70 (s, 3H) ppm. |
| 394 | 536.3 | 1H NMR (EW18644-416-P1A, 400 MHz, METHANOL-d4) δ = 9.34 (s, 1H), 8.93 (s, 1H), 8.64-8.57 (m, 2H), 8.18 (d, J = 1.6 Hz, 1H), 7.98 (s, 1H), 7.96-7.86 (m, 2H), 7.30 (d, J = 8.4 Hz, 1H), 4.93 (s, 2H), 4.92 (d, J = 3.6 Hz, 2H), 4.32-4.25 (m, 2H), 4.21 (d, J = 11.6 Hz, 1H), 4.01-3.97 (m, 2H), 3.93 (d, J = 11.6 Hz, 1H), 3.65 (d, J = 6.4 Hz, 2H), 3.41 (s, 3H), 3.15-3.08 (m, 1H), 1.77 (s, 3H) ppm |
| 395 | 486.1 | 1H NMR (400 MHz, DMSO-d6)δ = 9.59-9.56 (m, 1H), 9.43 (s, 1H), 9.10 (s, 1H), 8.94 (s, 1H), 8.72 (d, J = 8.4 Hz, 1H), 8.62 (s, 1H), 8.52 (d, J = 8.8 Hz, 1H), 8.01 (s, 1H), 7.90 (s, 1H), 4.94-4.69 (m, 4H), 4.22-4.08 (m, 5H), 4.01-3.81 (m, 1H), 2.49-2.40 (m, 2H), 1.72 (d, J = 20.4 Hz, 3H) ppm |
| 396 | 506.3 | 1H NMR (400 MHz, DMSO-d6) δ = 9.45-9.37 (m, 2H), 8.68 (d, J = 8.4 Hz, 1H), 8.39-8.17 (m, 4H), 7.96-7.94 (m, 1H), 7.82 (s, 1H), 7.64-7.49 (m, 2H), 7.31 (d, J = 8.0 Hz, 1H), 4.95-4.77 (m, 4H), 4.23 (d, J = 11.6 Hz, 1H), 3.87 (d, J = 11.6 Hz, 1H), 3.22 (s, 3H), 2.00-1.73 (m, 3H), 1.70 (s, 3H) ppm. |
| 397 | 521.3 | 1H NMR (400 MHz, METHANOL-d4) δ = 9.41 (s, 1H), 8.93 (d, J = 5.2 Hz, 1H), 8.82-8.80 (m, 1H), 8.73-8.71 (m, 1H), 8.47 (d, J = 5.2 Hz, 1H), 8.20 (d, J = 2.0 Hz, 1H), 8.02 (s, 1H), 7.96-7.93 (m, 1H), 7.32 (d, J = 8.4 Hz, 1H), 4.96 (s, 2H), 4.93 (d, J = 3.6 Hz, 2H), 4.23 (d, J = 11.6 Hz, 1H), 4.14-4.10 (m, 2H), 3.95 (d, J = 11.2 Hz, 1H), 3.70-3.63 (m, 2H), 3.30-3.26 (m, 1H), 2.16-2.05 (m, 4H), 1.78 (s, 3H) ppm |
| 398 | 503.2 | 1H NMR (400 MHz, DMSO-d6) δ = 9.50-9.47 (m, 1H), 9.42 (s, 1H), 8.92 (s, 1H), 8.72 (d, J = 8.4 Hz, 1H), 8.51 (d, J = 8.4 Hz, 1H), 8.16 (s, 1H), 8.00 (s, 1H), 7.85 (s, 1H), 7.80 (d, J = 10.4 Hz, 1H), 4.96 (d, J = 16.0 Hz, 1H), 4.83-4.80 (m, 2H), 4.76-4.75 (m, 1H), 4.18-4.15 (m, 4H), 4.08-4.05 (m, 1H), 3.89-3.83 (m, 1H), 2.47-2.39 (m, 2H), 1.72-1.67 (m, 3H) ppm. |
| 399 | 510.3 | 1H NMR (400 MHz, DMSO-d6) δ = 9.50-9.47 (m, 1H), 9.41 (s, 1H), 8.92 (s, 1H), 8.71 (d, J = 8.4 Hz, 1H), 8.51 (d, J = 8.4 Hz, 1H), 8.09 (s, 1H), 7.99 (s, 1H), 7.86 (s, 1H), 7.79 (d, J = 10.4 Hz, 1H), 4.98-4.85 (m, 2H), 4.83 (d, J = 5.6 Hz, 2H), 4.25(d, J = 11.6 Hz, 1H), 4.18-4.16 (m, 4H), 3.89 (d, J = 11.6 Hz, 1H), 2.45-2.41 (m, 2H), 1.71 (s, 3H) ppm. |
| 400 | 453.2 | 1H NMR (400 MHz, DMSO-d6) δ = 9.50-9.48 (m, 1H), 9.39 (s, 1H), 8.67 (d, J = 8.0 Hz, 1H), 8.33-8.29 (m, 3H), 8.11 (s, 1H), 7.83 (s, 1H), 7.80-7.78 (m, 1H), 7.60-7.56 (m, 3H), 4.99-4.84 (m, 2H), 4.82 (br d, J = 5.6 Hz, 2H), 4.25 (d, J = 11.6 Hz, 1H), 3.89 (d, J = 11.6 Hz, 1H), 1.72 (s, 3H) ppm |
| 401 | 485.3 | 1H NMR (400 MHz, DMSO-d6) δ = 9.48-9.34 (m, 2H), 8.92 (s, 1H), 8.71 (d, J = 8.8 Hz, 1H), 8.50 (d, J = 8.8 Hz, 1H), 8.27 (s, 1H), 8.07-7.92 (m, 2H), 7.84 (s, 1H), 7.30 (d, J = 8.0 Hz, 1H), 4.93-4.69 (m, 4H), 4.19-4.15 (m, 4H), 4.11-4.04 (m, 1H), 3.92-3.78 (m, 1H), 2.46-2.40 (m, 2H), 1.78-1.59 (m, 3H) ppm |
| 403 | 534.4 | 1H NMR (400 MHz, CHLOROFORM-d) δ = 9.32 (s, 1H), 8.67 (d, J = 8.4 Hz, 1H), 8.56 (d, J = 5.2 Hz, 1H), 8.44 (d, J = 8.8 Hz, 1H), 8.03-8.02 (m, 2H), 7.86 (d, J = 5.2 Hz, 1H), 7.81-7.80 (m, 1H), 7.39-7.38 (m, 1H), 7.16 (d, J = 8.0 Hz, 1H), 5.01 (d, J = 5.2 Hz, 2H), 4.91 (s, 4H), 4.88 (s, 2H), 4.42 (s, 4H), 4.16 (d, J = 11.2 Hz, 1H), 3.97 (d, J = 11.2 Hz, 1H), 1.77 (s, 3H) ppm |

TABLE 19-continued

Compounds of the Invention

| # | LCMS (m/z) | 1H NMR |
|---|---|---|
| 404 | 528.5 | 1H NMR (400 MHz, CDCl3-d) δ = 9.31 (s, 2H), 8.57 (d, J = 8.4 Hz, 1H), 8.42 (d, J = 8.4 Hz, 1H), 8.04-8.03 (m, 3H), 7.84-7.81 (m, 1H), 7.41-7.40 (m, 1H), 7.17 (d, J = 8.0 Hz, 1H), 5.02 (d, J = 5.2 Hz, 2H), 4.89 (s, 2H), 4.60-4.54 (m, 4H), 4.16 (d, J = 11.2 Hz, 1H), 3.97 (d, J = 11.2 Hz, 1H), 1.78 (s, 3H) ppm |
| 405 | 481.3 | 1H NMR (400 MHz, MeOD-d4) δ = 9.14 (s, 1H), 8.39 (d, J = 8.4 Hz, 1H), 8.17 (d, J = 1.6 Hz, 1H), 8.13 (s, 1H), 8.00 (d, J = 8.8 Hz, 1H), 7.94-7.92 (m, 1H), 7.81 (s, 1H), 7.29 (d, J = 8.4 Hz, 1H), 4.92 (d, J = 3.6 Hz, 2H), 4.59-4.55 (m, 4H), 4.247-4.19 (m, 3H), 3.93 (d, J = 11.2 Hz, 1H), 2.38-2.35 (m, 2H), 1.77 (s, 3H) ppm |
| 406 | 477.3 | 1H NMR (400 MHz, CDCl3) δ = 9.61 (s, 1H), 9.33-9.30 (m, 1H), 8.62-8.59 (m, 2H), 8.42-8.40 (m, 1H), 8.04-8.03 (m, 2H), 7.84-7.81 (m, 1H), 7.42-7.41 (m, 1H), 7.16 (d, J = 8.0 Hz, 1H), 5.02 (d, J = 5.2 Hz, 2H), 4.89 (s, 2H), 4.16 (d, J = 11.6 Hz, 1H), 3.97 (d, J = 11.6 Hz, 1H), 2.22-2.19 (m, 1H), 1.78 (s, 3H), 1.25-1.23 (m, 2H), 1.18-1.16 (m, 2H) ppm |
| 407 | 480.2 | 1H NMR (400 MHz, MeOD-d4) δ = 9.33 (s, 1H), 8.90 (s, 1H), 8.64 (d, J = 1.6 Hz, 2H), 8.18-8.17 (m, 2H), 7.98 (s, 1H), 7.94-7.92 (m, 1H), 7.30 (d, J = 8.0 Hz, 1H), 4.93 (s, 2H), 4.92 (d, J = 3.6 Hz, 2H), 4.22 (d, J = 11.6 Hz, 1H), 3.94 (d, J = 11.6 Hz, 1H), 3.26 (s, 6H), 1.76 (s, 3H) ppm |
| 408 | 451.3 | 1H NMR (400 MHz, CDCl3) δ = 9.67 (s, 1H), 9.32 (s, 1H), 8.69 (d, J = 8.8 Hz, 1H), 8.59 (s, 1H), 8.45-8.43 (m, 1H), 8.07 (s, 1H), 8.04 (s, 1H), 7.84-7.81 (m, 1H), 7.44-7.43 (m, 1H), 7.16 (d, J = 8.0 Hz, 1H), 5.02 (d, J = 5.2 Hz, 2H), 4.89 (s, 2H), 4.16 (d, J = 11.2 Hz, 1H), 3.96 (d, J = 11.6 Hz, 1H), 2.70 (s, 3H), 1.78 (s, 3H) ppm |
| 409 | 522.4 | 1H NMR (400 MHz, MeOD-d4) δ = 9.33 (s, 1H), 8.95 (s, 1H), 8.63-8.58 (m, 2H), 8.17 (s, 1H), 7.98 (s, 1H), 7.94-7.91 (m, 2H), 7.30 (d, J = 8.4 Hz, 1H), 4.93 (s, 2H), 4.92 (d, J = 3.6 Hz, 2H), 4.49-4.45 (m, 1H), 4.43-4.40 (m, 2H), 4.22 (d, J = 11.2 Hz, 1H), 4.07-4.03 (m, 2H), 3.94 (d, J = 11.6 Hz, 1H), 3.38 (s, 3H), 1.76 (s, 3H) ppm |
| 410 | 494.2 | 1H NMR (400 MHz, METHANOL-d4)δ = 9.24 (s, 1H), 8.70 (d, J = 8.4 Hz, 1H), 8.53 (d, J = 8.4 Hz, 1H), 8.39 (d, J = 7.6 Hz, 1H), 8.08 (s, 1H), 7.93-7.80 (m, 3H), 7.69 (d, J = 7.6 Hz, 1H), 7.20 (d, J = 7.6 Hz, 1H), 5.05 (s, 1H), 4.84-4.81 (m, 4H), 4.12 (d, J = 11.6 Hz, 1H), 3.83 (d, J = 11.2 Hz, 1H), 1.67 (s, 3H), 1.56 (s, 6H) ppm |
| 412 | 509.3 | 1H NMR (400 MHz, DMSO-d6) δ = 9.46 (s, 1H), 9.42-9.39 (m, 1H), 8.72 (d, J = 8.4 Hz, 1H), 8.47 (br s, 1H), 8.18 (s, 1H), 8.04-8.00 (m, 2H), 7.95-7.93 (m, 1H), 7.83 (s, 1H), 7.30 (d, J = 8.0 Hz, 1H), 7.16-7.14 (m, 1H), 4.92-4.81 (m, 4H), 4.22 (d, J = 11.6 Hz, 1H), 4.16-4.13 (m, 4H), 3.86 (d, J = 11.6 Hz, 1H), 2.37-2.33 (m, 2H), 1.69 (s, 3H) ppm |
| 413 | 429.1 | 1H NMR (400 MHz, MeOD-d4) δ = 9.31 (s, 1H), 9.09-9.04 (m, 1H), 8.63-8.56 (m, 2H), 8.23-8.14 (m, 3H), 7.98 (s, 1H), 7.59-7.52 (m, 3H), 4.94 (s, 2H), 4.85 (br s, 1H), 4.83 (d, J = 3.6 Hz, 1H), 4.17-4.06 (m, 1H), 4.00-3.87 (m, 1H), 1.87-1.63 (m, 3H) ppm. |
| 414 | 492.3 | 1H NMR (400 MHz, DMSO-d6) δ = 9.40-9.36 (m, 1H), 9.33 (s, 1H), 9.18 (d, J = 1.6 Hz, 1H), 8.59 (d, J = 8.8 Hz, 1H), 8.42 (d, J = 8.8 Hz, 1H), 8.19 (s, 1H), 7.97-7.93 (m, 2H), 7.78 (s, 1H), 7.31 (d, J = 8.4 Hz, 1H), 4.92-4.78 (m, 4H), 4.23-4.16 (m, 5H), 3.87 (d, J = 11.6 Hz, 1H), 2.46-2.41 (m, 2H), 1.70 (s, 3H) ppm |
| 415 | 506.6 | 1H NMR (400 MHz, MeOD-d4) δ = 9.33 (s, 1H), 8.87 (s, 1H), 8.66-8.63 (m, 2H), 8.18-8.17 (m, 1H), 8.00-7.98 (m, 2H), 7.94-7.92 (m, 1H), 7.30 (d, J = 8.0 Hz, 1H), 4.93 (s, 2H), 4.92 (d, J = 3.6 Hz, 2H), 4.22 (d, J = 11.6 Hz, 1H), 3.94 (d, J = 11.6 Hz, 1H), 3.66-3.61 (m, 4H), 2.12-2.09 (m, 4H), 1.76 (s, 3H) ppm |
| 416 | 522.2 | 1HNMR (400 MHz, METHANOL-d4) δ = 9.37 (s, 1H), 8.70-8.63 (m, 2H), 8.55 (d, J = 5.2 Hz, 1H), 8.18 (d, J = 1.6 Hz, 1H), 7.99 (s, 1H), 7.94-7.91 (m, 1H), 7.78 (d, J = 5.2 Hz, 1H), 7.29 (d, J = 8.4 Hz, 1H), 4.96-4.90 (m, 4H), 4.21 (d, J = 11.2 Hz, 1H), 3.94 (d, J = 2.8 Hz, 1H), 3.92 (d, J = 4.4 Hz, 4H), 3.83-3.78 (m, 4H), 1.77 (s, 3H) ppm |
| 417 | 477.4 | 1H NMR (400 MHz, METHANOL-d4) δ = 9.39 (s, 1H), 8.78 (d, J = 7.2 Hz, 1H), 8.74-8.66 (m, 2H), 8.35 (d, J = 7.2 Hz, 1H), 8.18 (d, J = 1.6 Hz, 1H), 8.00 (s, 1H), 7.94-7.92 (m, 1H), 7.30 (d, J = 8.0 Hz, 1H), 4.94 (s, 2H), 4.92 (d, J = 3.6 Hz, 2H), 4.21 (d, J = 11.6 Hz, 1H), 3.93 (s, 1H), 2.43-2.32 (m, 1H), 1.77 (s, 3H), 1.29-1.23 (m, 2H), 1.21-1.13 (m, 2H) ppm. |
| 418 | 521.2 | 1H NMR (400 MHz, DMSO-d6) δ = 9.42-9.36 (m, 2H), 8.68 (d, J = 8.8 Hz, 1H), 8.37-8.31 (m, 2H), 8.31-8.27 (m, 1H), 8.20 (d, J = 1.2 Hz, 1H), 7.96-7.94 (m, 1H), 7.85 (s, 1H), 7.68-7.60 (m, 2H), 7.31 (d, J = 8.0 Hz, 1H), 4.94-4.79 (m, 8H), 4.23 (d, J = 11.6 Hz, 1H), 3.87 (d, J = 11.6 Hz, 1H), 3.07 (s, 3H), 1.70 (s, 3H) ppm. |
| 419 | 522.2 | 1H NMR (400 MHz, METHANOL-d4) δ = 9.35 (s, 1H), 8.86 (d, J = 8.4 Hz, 1H), 8.68-8.61 (m, 2H), 8.18 (d, J = 1.6 Hz, 1H), 8.06-8.05 (m, 1H), 8.00 (s, 1H), 7.94-7.93 (m, 1H), 7.65-7.63 (m, 1H), 7.30 (d, J = 8.0 Hz, 1H), 5.22 (d, J = 7.2 Hz, 2H), 4.97-4.94 (m, 4H), 4.92 (d, J = 4.0 Hz, 2H), 4.21 (d, J = 11.2 Hz, 1H), 3.93 (d, J = 11.6 Hz, 1H), 3.29 (s, 3H), 1.77 (s, 3H) ppm |

TABLE 19-continued

Compounds of the Invention

| # | LCMS (m/z) | 1H NMR |
|---|---|---|
| 420 | 491.3 | 1H NMR (400 MHz, METHANOL-d4) δ = 9.40 (s, 1H), 8.89 (d, J = 5.2 Hz, 1H), 8.82 (d, J = 8.8 Hz, 1H), 8.71 (d, J = 8.4 Hz, 1H), 8.43 (d, J = 5.2 Hz, 1H), 8.18 (d, J = 1.2 Hz, 1H), 8.02 (s, 1H), 7.93-7.92 (m, 1H), 7.30 (d, J = 8.4 Hz, 1H), 4.94 (s, 2H), 4.92 (d, J = 3.2 Hz, 2H), 4.21 (d, J = 11.2 Hz, 1H), 3.96-3.90 (m, 2H), 2.65-2.53 (m, 2H), 2.52-2.41 (m, 2H), 2.25-2.12 (m, 1H), 2.09-1.98 (m, 1H), 1.77 (s, 3H) ppm |
| 421 | 504.3 | 1H NMR (400 MHz, DMSO-d6) δ = 9.45-9.37 (m, 2H), 8.66 (d, J = 8.4 Hz, 1H), 8.30 (d, J = 8.4 Hz, 1H), 8.21 (s, 2H), 8.14 (d, J = 7.2 Hz, 1H), 7.96 (d, J = 8.0 Hz, 1H), 7.83 (s, 1H), 7.60-7.50 (m, 2H), 7.32 (d, J = 8.0 Hz, 1H), 4.98-4.76 (m, 4H), 4.23 (d, J = 11.6 Hz, 1H), 3.88 (d, J = 11.2 Hz, 1H), 3.78-3.65 (m, 3H), 3.21-3.18 (m, 2H), 2.31 (s, 3H), 1.71 (s, 3H) ppm |
| 422 | 536.3 | $^{1}$H NMR (400 MHz, METHANOL-d4) δ = 9.37 (s, 1H), 8.76-8.62 (m, 2H), 8.50 (d, J = 5.0 Hz, 1H), 8.18 (s, 1H), 7.99 (s, 1H), 7.93 (dd, J = 1.7, 8.1 Hz, 1H), 7.74 (d, J = 5.1 Hz, 1H), 7.30 (d, J = 8.0 Hz, 1H), 4.95-4.91 (m, 4H), 4.27-4.12 (m, 2H), 3.90-3.62 (m, 4H), 3.93 (d, J = 11.3 Hz, 1H), 3.40 (s, 3H), 2.27-2.11 (m, 2H), 1.77 (s, 3H) ppm |
| 423 | 467.1 | $^{1}$H NMR (400 MHz, DMSO-d6) δ = 9.46 (s, 1H), 9.42 (br t, J = 5.7 Hz, 1H), 9.30 (s, 1H), 8.78 (d, J = 8.7 Hz, 1H), 8.61 (d, J = 8.8 Hz, 1H), 8.49 (s, 1H), 8.20 (s, 1H), 7.96 (d, J = 8.4 Hz, 1H), 7.88 (s, 1H), 7.31 (d, J = 8.3 Hz, 1H), 4.94-4.81 (m, 4H), 4.23 (d, J = 11.4 Hz, 1H), 4.10 (s, 3H), 3.87 (d, J = 11.6 Hz, 1H), 1.71 (s, 3H) ppm |
| 424 | 480.2 | $^{1}$H NMR (400 MHz, DMSO-d6) δ = 9.47 (s, 1H), 9.41 (br t, J = 5.7 Hz, 1H), 8.76 (d, J = 8.6 Hz, 1H), 8.69-8.63 (m, 1H), 8.56 (d, J = 4.9 Hz, 1H), 8.20 (s, 1H), 7.98-7.93 (m, 1H), 7.86 (s, 1H), 7.66 (d, J = 4.9 Hz, 1H), 7.31 (d, J = 8.2 Hz, 1H), 4.94-4.81 (m, 4H), 4.23 (d, J = 11.6 Hz, 1H), 3.87 (d, J = 11.6 Hz, 1H), 3.25 (s, 6H), 1.70 (s, 3H) ppm |
| 427 | 505.2 | $^{1}$H NMR (400 MHz, DMSO-d6) δ = 9.50-9.40 (m, 2H), 8.80-8.68 (m, 3H), 8.28-8.19 (m, 2H), 7.97 (d, J = 8.0 Hz, 1H), 7.87 (s, 1H), 7.32 (d, J = 8.0 Hz, 1H), 4.97-4.77 (m, 4H), 4.71-4.61 (m, 2H), 4.23 (d, J = 11.2 Hz, 1H), 3.87 (d, J = 11.6 Hz, 1H), 3.15 (s, 3H), 1.71 (s, 3H) ppm |
| 428 | 446.3 | $^{1}$H NMR (400 MHz, MeOD) δ = 9.30 (s, 1H), 8.59 (d, J = 8.8 Hz, 1H), 8.23-8.14 (m, 3H), 8.09 (s, 1H), 7.95 (s, 1H), 7.69 (brd, J = 10.6 Hz, 1H), 7.60-7.51 (m, 3H), 4.97-4.88 (m, 4H), 4.10-3.99 (m, 1H), 3.94-3.81 (m, 1H), 1.82-1.64 (m, 3H) ppm |
| 429 | 485.2 | $^{1}$H NMR (400 MHz, DMSO-d6) δ = 9.46 (s, 1H), 9.41-7.38 (m, 1H), 8.75 (d, J = 8.8 Hz, 1H), 8.61-8.53 (m, 2H), 8.27 (s, 1H), 7.97 (d, J = 8.0 Hz, 1H), 7.85 (s, 1H), 7.71-7.70 (m, 1H), 7.31 (d, J = 8.0 Hz, 1H), 4.90-4.70 (m, 4H), 4.18-4.14 (m, 4H), 4.11-4.04 (m, 1H), 3.91-3.79 (m, 1H), 2.42-2.35 (m, 2H), 1.74-1.65 (m, 3H) ppm |
| 430 | 522.2 | $^{1}$H NMR (400 MHz, METHANOL-d4) δ = 9.37 (s, 1H), 8.65 (s, 2H), 8.50 (d, J = 5.2 Hz, 1H), 8.17 (d, J = 1.6 Hz, 1H), 7.98 (s, 1H), 7.96-7.90 (m, 1H), 7.80 (d, J = 5.2 Hz, 1H), 7.29 (d, J = 8.0 Hz, 1H), 4.96-4.89 (m, 4H), 4.48-4.36 (m, 3H), 4.21 (d, J = 11.6 Hz, 1H), 4.06 (br d, J = 6.8 Hz, 2H), 3.93 (d, J = 11.2 Hz, 1H), 3.38 (s, 3H), 1.77 (s, 3H) ppm |
| 431 | 495.2 | 1H NMR (400 MHz, DMSO-d6) δ = 9.40-9.37 (m, 2H), 8.52 (d, J = 8.8 Hz, 1H), 8.25 (d, J = 8.8 Hz, 1H), 8.19 (d, J = 1.6 Hz, 1H), 7.95-7.93 (m, 1H), 7.85-7.83 (m, 1H), 7.78-7.76 (m, 1H), 7.49-7.44 (m, 1H), 7.30 (d, J = 8.0 Hz, 1H), 7.22 (d, J = 8.4 Hz, 1H), 7.11-7.07 (m, 1H), 4.92-4.79 (m, 5H), 4.23-4.13 (m, 3H), 3.86 (d, J = 11.6 Hz, 1H), 3.74-3.71 (m, 2H), 1.69 (s, 3H) ppm |
| 432 | 484.2 | 1H NMR (400 MHz, MeOD) δ = 9.40 (s, 1H), 8.68 (d, J = 8.4 Hz, 1H), 8.17 (d, J = 1.6 Hz, 1H), 8.12-8.04 (m, 2H), 7.99 (s, 1H), 7.95-7.88 (m, 1H), 7.55-7.51 (m, 1H), 7.29 (d, J = 8.4 Hz, 1H), 4.94 (s, 2H), 4.91 (d, J = 4.0 Hz, 2H), 4.20 (d, J = 11.6 Hz, 1H), 4.07 (s, 3H), 3.92 (d, J = 11.6 Hz, 1H), 1.76 (s, 3H) ppm |
| 434 | 534.3 | 1H NMR (400 MHz, DMSO-d6) δ = 9.45-9.37 (m, 2H), 8.97 (s, 1H), 8.71 (d, J = 8.8 Hz, 1H), 8.52-8.41 (m, 2H), 8.20 (s, 1H), 7.97 (d, J = 8.4 Hz, 1H), 7.87 (s, 1H), 7.74-7.65 (m, 1H), 7.31 (d, J = 8.4 Hz, 1H), 6.73 (d, J = 7.6 Hz, 1H), 4.93-4.80 (m, 4H), 4.23 (d, J = 11.6 Hz, 1H), 3.87 (d, J = 11.6 Hz, 1H), 3.57 (s, 3H), 1.71 (s, 3H) ppm |
| 435 | 522.5 | 1H NMR (400 MHz, MeOD-d4) δ = 9.33 (s, 1H), 8.99 (s, 1H), 8.61-8.56 (m, 2H), 8.32 (s, 1H), 8.18 (d, J = 1.6 Hz, 1H), 7.98 (s, 1H), 7.96-7.91 (m, 1H), 7.30 (d, J = 8.0 Hz, 1H), 4.93-4.90 (m, 4H), 4.22 (d, J = 11.6 Hz, 1H), 3.94 (d, J = 11.6 Hz, 1H), 3.87-3.85 (m, 4H), 3.75-3.72 (m, 4H), 1.76 (s, 3H) ppm |
| 437 | 491.3 | 1H NMR (400 MHz, DMSO-d6) δ = 9.49-9.38 (m, 2H), 8.72 (d, J = 8.4 Hz, 1H), 8.31 (d, J = 8.4 Hz, 1H), 8.26-8.18 (m, 2H), 7.96 (d, J = 8.0 Hz, 1H), 7.86 (s, 1H), 7.44 (d, J = 5.2 Hz, 1H), 7.31 (d, J = 8.4 Hz, 1H), 7.14 (s, 1H), 4.97-4.80 (m, 4H), 4.23 (d, J = 11.6 Hz, 1H), 4.06-4.02 (m, 4H), 3.88 (d, J = 11.6 Hz, 1H), 2.38-2.32 (m, 2H), 1.71 (s, 3H) ppm |

TABLE 19-continued

Compounds of the Invention

| # | LCMS (m/z) | 1H NMR |
|---|---|---|
| 438 | 442.3 | 1H NMR (400 MHz, DMSO-d6) δ = 9.46 (s, 1H), 9.38-9.36 (m, 1H), 8.91-8.80 (m, 2H), 8.18 (s, 1H), 8.14-8.07 (m, 2H), 8.02 (s, 1H), 7.94 (d, J = 8.0 Hz, 1H), 7.30 (d, J = 8.0 Hz, 1H), 4.94-4.82 (m, 2H), 4.78 (d, J = 6.0 Hz, 2H), 4.23 (d, J = 11.2 Hz, 1H), 3.87 (d, J = 11.6 Hz, 1H), 1.70 (s, 3H) ppm |
| 439 | 442.1 | 1H NMR (400 MHz, DMSO-d6) δ = 9.53-9.24 (m, 3H), 8.83-8.81 (m, 1H), 8.54-8.52 (m, 1H), 8.18 (s, 1H), 7.99 (s, 1H), 7.95-7.93 (m, 1H), 7.67-7.64 (m, 1H), 7.30 (d, J = 8.0 Hz, 1H), 4.95-4.81 (m, 2H), 4.77 (d, J = 6.0 Hz, 2H), 4.23 (d, J = 11.6 Hz, 1H), 3.87 (d, J = 11.6 Hz, 1H), 1.71 (s, 3H) ppm |
| 440 | 442.1 | 1H NMR (400 MHz, DMSO-d6) δ = 9.39 (s, 1H), 9.38-9.35 (m, 1H), 8.79-8.78 (m, 1H), 8.38 (d, J = 8.0 Hz, 1H), 8.18 (s, 1H), 8.11-8.07 (m, 1H), 7.98 (s, 1H), 7.95-7.93 (m, 1H), 7.70-7.66 (m, 1H), 7.30 (d, J = 8.0 Hz, 1H), 4.95-4.81 (m, 2H), 4.77 (d, J = 6.0 Hz, 2H), 4.23 (d, J = 11.6 Hz, 1H), 3.87 (d, J = 11.6 Hz, 1H), 1.71 (s, 3H) ppm |
| 441 | 491.3 | 1H NMR (400 MHz, DMSO-d6) δ = 9.46-9.35 (m, 2H), 8.76 (d, J = 2.0 Hz, 1H), 8.68 (d, J = 8.8 Hz, 1H), 8.32 (d, J = 8.4 Hz, 1H), 8.20 (d, J = 1.2 Hz, 1H), 7.99-7.92 (m, 2H), 7.84 (s, 1H), 7.58-7.57 (m, 1H), 7.31 (d, J = 8.4 Hz, 1H), 4.98-4.77(m, 4H), 4.23 (d, J = 11.6 Hz, 1H), 3.99-3.98 (m, 4H), 3.88 (d, J = 11.6 Hz, 1H), 2.41-2.39 (m, 2H), 1.71 (s, 3H) ppm. |
| 442 | 522.4 | 1HNMR (400 MHz, METHANOL-d4) δ = 9.34 (s, 1H), 8.62-8.55 (m, 2H), 8.17 (d, J = 1.6 Hz, 1H), 7.98 (s, 1H), 7.93-7.91 (m, 1H), 7.29 (d, J = 8.0 Hz, 1H), 7.13 (s, 1H), 4.92 (d, J = 3.6 Hz, 4H), 4.24-4.19 (m, 5H), 3.96-3.91 (m, 4H), 2.45-2.37 (m, 2H), 1.76 (s, 3H) ppm. |
| 443 | 523.3 | 1H NMR (400 MHz, DMSO-d6) δ = 9.51 (s, 1H), 9.43 (m, 1H), 8.83 (d, J = 8.6 Hz, 1H), 8.50 (d, J = 8.6 Hz, 1H), 8.20 (d, J = 1.6 Hz, 1H), 7.96 (m, 1H), 7.91-7.82 (m, 2H), 7.32 (d, J = 8.4 Hz, 1H), 7.06 (d, J = 7.6 Hz, 1H), 4.98-4.78 (m, 4H), 4.23 (d, J = 11.4 Hz, 1H), 3.87 (d, J = 11.4 Hz, 1H), 3.59 (s, 3H), 1.71 (s, 3H) ppm |
| 444 | 451.3 | 1HNMR (400 MHz, METHANOL-d4) δ = 9.40 (s, 1H), 8.86 (d, J = 5.6 Hz, 1H), 8.79-8.67 (m, 2H), 8.44 (d, J = 5.2 Hz, 1H), 8.18 (s, 1H), 8.01 (s, 1H), 7.95-7.92 (m, 1H), 7.30 (d, J = 8.0 Hz, 1H), 4.94 (s, 2H), 4.92 (d, J = 3.6 Hz, 2H), 4.21 (d, J = 11.6 Hz, 1H), 3.93 (d, J = 11.6 Hz, 1H), 2.83 (s, 3H), 1.77 (s, 3H) ppm |
| 445 | 548.5 | 1H NMR (400 MHz, DMSO-d6) δ = 9.45-9.35 (m, 2H), 8.69 (d, J = 8.6 Hz, 1H), 8.51-8.48 (m, 1H), 8.43 (d, J = 8.0 Hz, 1H), 8.35 (d, J = 8.8 Hz, 1H), 8.20 (d, J = 1.4 Hz, 1H), 7.96 (m, 1H), 7.84 (s, 1H), 7.78 (d, J = 7.6 Hz, 1H), 7.68-7.60 (m, 1H), 7.31 (d, J = 8.4 Hz, 1H), 4.98-4.76 (m, 4H), 4.48 (m, 1H), 4.33-4.12 (m, 4H), 3.87 (m, 2H), 3.22 (s, 3H), 1.70 (s, 3H) ppm |
| 446 | 484.3 | 1H NMR (400 MHz, DMSO-d6) δ = 9.50 (s, 1H), 9.42 (t, J = 6.0 Hz, 1H), 8.77 (d, J = 8.7 Hz, 1H), 8.39 (d, J = 2.5 Hz, 1H), 8.22-8.18 (m, 1H), 8.09 (dd, J = 1.8, 8.5 Hz, 1H), 7.95 (dd, J = 1.6, 8.1 Hz, 1H), 7.87 (s, 1H), 7.38 (d, J = 5.1 Hz, 1H), 7.31 (d, J = 8.2 Hz, 1H), 4.95-4.79 (m, 4H), 4.23 (d, J = 11.5 Hz, 1H), 3.91 (s, 3H), 3.87 (d, J = 11.5 Hz, 1H), 1.71 (s, 3H) ppm |
| 447 | 476.4 | 1H NMR (400 MHz, METHANOL-d4) δ = 9.38 (s, 1H), 9.04 (d, J = 7.6 Hz, 1H), 8.81 (d, J = 8.8 Hz, 1H), 8.69 (d, J = 8.8 Hz, 1H), 8.28 (d, J = 7.2 Hz, 1H), 8.24 (d, J = 2.4 Hz, 1H), 8.19 (s, 1H), 8.02 (s, 1H), 7.93-7.92 (m, 1H), 7.31 (d, J = 8.0 Hz, 1H), 6.89-6.88 (m, 1H), 4.94 (s, 2H), 4.92 (d, J = 3.6 Hz, 2H), 4.22 (d, J = 11.6 Hz, 1H), 3.95 (d, J = 11.2 Hz, 1H), 1.77 (s, 3H) ppm |
| 448 | 517 | 1H NMR (400 MHz, MeOD-d4) δ = 9.36 (s, 1H), 9.16 (s, 1H), 8.80-8.78 (m, 1H), 8.69-8.67 (m, 1H), 8.42 (s, 1H), 8.35 (d, J = 8.4 Hz, 1H), 8.18 (d, J = 1.6 Hz, 1H), 8.07 (d, J = 8.4 Hz, 1H), 8.00 (s, 1H), 7.95-7.93 (m, 1H), 7.31 (d, J = 8.4 Hz, 1H), 4.94 (s, 2H), 4.92 (d, J = 3.6 Hz, 2H), 4.22 (d, J = 11.6 Hz, 1H), 3.94 (d, J = 11.2 Hz, 1H), 3.87 (s, 3H), 1.77 (s, 3H) ppm |
| 449 | 520.2 | 1H NMR (400 MHz, METHANOL-d4) δ = 9.32 (br s, 1H), 8.63-8.55 (m, 2H), 8.42 (dd, J = 2.2, 11.0 Hz, 1H), 8.22-8.13 (m, 2H), 8.10-7.76 (m, 3H), 7.31 (d, J = 8.2 Hz, 1H), 4.93 (s, 4H), 4.22 (d, J = 11.4 Hz, 1H), 3.95 (d, J = 11.4 Hz, 1H), 1.78 (s, 3H) ppm |
| 450 | 493 | 1H NMR (400 MHz, DMSO-d6) δ = 9.53-9.47 (m, 1 H), 9.46-9.38 (m, 1 H), 8.97-8.73 (m, 4 H), 8.53-8.36 (m, 2 H), 8.25-8.15 (m, 1 H), 8.01-7.95 (m, 1 H), 7.94-7.88 (m, 1 H), 7.40-7.23 (m, 1 H), 5.00-4.72 (m, 4 H), 4.30-4.16 (m, 1 H), 3.94-3.83(m, 1 H), 2.95-2.80 (m, 3 H), 1.80-1.59 (m, 3 H) ppm |
| 451 | 436.2 | 1H NMR (400 MHz, METHANOL-d4) δ = 9.40 (s, 1H), 8.78-8.74 (m, 2H), 8.71 (d, J = 8.4 Hz, 1H), 8.33-8.26 (m, 3H), 8.20 (d, J = 1.6 Hz, 1H), 8.02 (s, 1H), 7.96-7.94 (m, 1H), 7.31 (d, J = 8.0 Hz, 1H), 4.96 (s, 2H), 4.93 (d, J = 3.6 Hz, 2H), 4.23 (d, J = 11.6 Hz, 1H), 3.95 (d, J = 11.6 Hz, 1H), 1.79 (s, 3H) ppm |

TABLE 19-continued

| Compounds of the Invention | | |
|---|---|---|
| # | LCMS (m/z) | 1H NMR |
| 452 | 516.2 | 1H NMR (400 MHz, DMSO-d6) δ = 9.41 (s, 2H), 9.12 (s, 1H), 8.69 (d, J = 8.8 Hz, 1H), 8.64-8.62 (m, 1H), 8.40 (d, J = 8.8 Hz, 1H), 8.21 (s, 1H), 7.98 (d, J = 8.0 Hz, 1H), 7.89-7.81 (m, 2H), 7.59 (d, J = 7.2 Hz, 1H), 7.32 (d, J = 8.0 Hz, 1H), 6.72 (d, J = 7.2 Hz, 1H), 4.96-4.78 (m, 4H), 4.24 (d, J = 11.6 Hz, 1H), 3.88 (d, J = 11.6 Hz, 1H), 3.56 (s, 3H), 1.72 (s, 3H) ppm |
| 454 | 469.1 | 1H NMR (400 MHz, DMSO-d6) δ = 9.39 (t, J = 5.2 Hz, 1H), 9.21 (s, 1H), 8.46 (d, J = 8.8 Hz, 1H), 8.37 (s, 1H), 8.20 (d, J = 1.6 Hz, 1H), 8.02-7.93 (m, 2H), 7.57 (s, 1H), 7.31 (d, J = 8.2 Hz, 1H), 4.95-4.81 (m, 2H), 4.76 (br d, J = 5.9 Hz, 2H), 4.23 (d, J = 11.4 Hz, 1H), 3.98 (s, 3H), 3.87 (d, J = 11.4 Hz, 1H), 3.76 (s, 3H), 1.70 (s, 3H) ppm |
| 456 | 491.3 | 1HNMR (400 MHz, DMSO-d6) δ = 9.40-9.34 (m, 1H), 9.28 (s, 1H), 9.00 (d, J = 2.0 Hz, 1H), 8.52 (d, J = 8.4 Hz, 1H), 8.42-8.40(m, 1H), 8.21-8.15 (m, 2H), 7.95-7.93(m, 1H), 7.71 (s, 1H), 7.31 (d, J = 8.0 Hz, 1H), 6.46 (d, J = 9.2 Hz, 1H), 4.94-4.81 (m, 2H), 4.80-4.75 (m, 2H), 4.23 (d, J = 11.2 Hz, 1H), 4.07-4.03 (m, 4H), 3.87 (d, J = 11.6 Hz, 1H), 2.39-2.35 (m, 2H), 1.70 (s, 3H) ppm |
| 459 | 475.2 | 1HNMR (400 MHz, DMSO-d6) δ = 9.45-9.39 (m, 2H), 8.80 (d, J = 7.2 Hz, 1H), 8.73-8.68 (m, 2H), 8.43 (d, J = 8.4 Hz, 1H), 8.21 (s, 1H), 8.09 (d, J = 2.0 Hz, 1H), 7.97-7.95(m, 1H), 7.87-7.82 (m, 2H), 7.32 (d, J = 7.6 Hz, 1H), 6.84 (s, 1H), 4.95-4.85 (m, 2H), 4.82 (d, J = 4.4 Hz, 2H), 4.23 (d, J = 11.2 Hz, 1H), 3.87 (d, J = 11.2 Hz, 1H), 1.71 (s, 3H) ppm |
| 460 | 509.9 | 1H NMR (400 MHz, DMSO-d6) δ = 9.46 (s, 1H), 9.45-9.42 (m, 1H), 8.71 (d, J = 8.4 Hz, 1H), 8.43 (d, J = 4.4 Hz, 1H), 8.20 (d, J = 1.6 Hz, 1H), 8.11-8.01 (m, 2H), 7.96-7.94 (m, 1H), 7.83 (s, 1H), 7.78-7.71 (m, 1H), 7.45-7.41 (m, 1H), 7.31 (d, J = 8.0 Hz, 1H), 4.97-4.79 (m, 4H), 4.23 (d, J = 11.6 Hz, 1H), 3.87 (d, J = 11.6 Hz, 1H), 2.81 (d, J = 4.8 Hz, 3H), 1.70 (s, 3H) ppm. |
| 462 | 469.3 | 1H NMR (400 MHz, DMSO-d6) δ = 9.37-9.36 (m, 1H), 9.25 (s, 1H), 8.50 (d, J = 8.8 Hz, 1H), 8.19 (d, J = 1.2 Hz, 1H), 8.09 (s, 1H), 7.94-7.91 (m, 2H), 7.69 (s, 1H), 7.30 (d, J = 8.0 Hz, 1H), 4.88-4.76 (m, 4H), 4.22 (d, J = 11.6 Hz, 1H), 4.06 (s, 3H), 3.87 (d, J = 11.2 Hz, 1H), 3.72 (s, 3H), 1.69 (s, 3H) ppm |
| 464 | 507.5 | 1H NMR (400 MHz, MeOD) δ = 9.35 (s, 1H), 8.76-8.72 (m, 1H), 8.72-8.68 (m, 1H), 8.67-8.62 (m, 1H), 8.18 (d, J = 2.0 Hz, 1H), 8.14-8.09 (m, 1H), 8.00 (s, 1H), 7.95-7.92 (m, 1H), 7.74 (d, J = 7.2 Hz, 1H), 7.30 (d, J = 8.4 Hz, 1H), 4.94 (s, 2H), 4.92 (d, J = 3.6 Hz, 2H), 4.21 (d, J = 11.6 Hz, 1H), 3.93 (d, J = 11.6 Hz, 1H), 3.19 (d, J = 10.4 Hz, 6H), 1.77 (s, 3H) ppm |
| 465 | 534.6 | 1H NMR (400 MHz, MeOD) δ = 9.30 (s, 1H), 8.69-8.63 (m, 1H), 8.60-8.55 (m, 1H), 8.18 (d, J = 1.6 Hz, 1H), 8.00-7.90 (m, 3H), 7.76-7.71 (m, 1H), 7.29 (d, J = 8.0 Hz, 1H), 6.98 (d, J = 8.4 Hz, 1H), 4.93-4.89 (m, 4H), 4.21 (d, J = 11.2 Hz, 1H), 3.93 (d, J = 11.6 Hz, 1H), 3.75 (br s, 4H), 2.72-2.68 (m, 4H), 2.44 (s, 3H), 1.77 (s, 3H) ppm |
| 466 | 493.2 | 1H NMR (400 MHz, MeOD) δ = 9.37 (s, 1H), 8.98 (d, J = 8.8 Hz, 1H), 8.82 (d, J = 7.6 Hz, 1H), 8.68 (d, J = 8.0 Hz, 1H), 8.26-8.21 (m, 1H), 8.20-8.13 (m, 2H), 8.01 (s, 1H), 7.95-7.92 (m, 1H), 7.30 (d, J = 8.0 Hz, 1H), 4.94 (s, 2H), 4.92 (br d, J = 4.0 Hz, 2H), 4.21 (d, J = 11.2 Hz, 1H), 3.93 (d, J = 11.2 Hz, 1H), 3.06 (s, 3H), 1.77 (s, 3H) ppm |
| 467 | 510.2 | 1H NMR (400 MHz, DMSO-d6) δ = 9.44-9.39 (m, 2H), 8.68 (d, J = 8.4 Hz, 1H), 8.53-8.51 (m, 1H), 8.45-8.43 (m, 2H), 8.33 (d, J = 8.4 Hz, 1H), 8.20 (d, J = 1.6 Hz, 1H), 7.96-7.94 (m, 1H), 7.82 (s, 1H), 7.48-7.47 (m, 1H), 7.31 (d, J = 8.0 Hz, 1H), 4.93-4.80 (m, 4H), 4.23 (d, J = 11.2 Hz, 1H), 3.87 (d, J = 11.6 Hz, 1H), 2.81 (d, J = 4.8 Hz, 3H), 1.70 (s, 3H) ppm. |
| 468 | 536.3 | 1H NMR (400 MHz, MeOD-d4) δ = 9.32 (s, 1H), 8.67-8.66 (m, 1H), 8.62 (d, J = 8.4 Hz, 1H), 8.41-8.34 (m, 1H), 8.23 (d, J = 8.74 Hz, 1H), 8.18 (d, J = 1.6 Hz, 1H), 8.02-7.91 (m, 3H), 7.65 (t, J = 8.0 Hz, 1H), 7.29 (d, J = 8.0 Hz, 1H), 4.92-4.87 (m, 4H), 4.21 (d, J = 11.6 Hz, 1H), 3.93 (d, J = 11.2 Hz, 1H), 3.60 (s, 4H), 3.38 (s, 3H), 1.76 (s, 3H) ppm. |
| 469 | 486.2 | 1H NMR (400 MHz, DMSO-d6) δ = 9.46-9.42 (m, 2H), 8.77-8.74 (m, 2H), 8.65 (d, J = 8.8 Hz, 1H), 8.50-8.44 (m, 1H), 8.24-8.20 (m, 2H), 7.97-7.50 (m, 1H), 7.88 (d, J = 5.6 Hz, 2H), 7.31 (d, J = 8.8 Hz, 1H), 7.26-6.98 (m, 1H), 4.93-4.82(m, 4H), 4.23(d, J = 11.6 Hz, 1H), 3.93-3.80(m, 1H), 1.70 (s, 3H) ppm. |
| 470 | 429.2 | 1H NMR (400 MHz, DMSO-d6) δ = 9.43-9.38 (m, 2H), 9.28 (d, J = 1.6 Hz, 1H), 8.67 (d, J = 8.8 Hz, 1H), 8.64-8.61 (m, 1H), 8.32 (d, J = 8.4 Hz, 1H), 8.20 (d, J = 1.2 Hz, 1H), 7.96-7.94 (m, 1H), 7.87 (d, J = 8.4 Hz, 1H), 7.81 (s, 1H), 7.31 (d, J = 8.0 Hz, 1H), 6.30 (s, 1H), 4.94-4.85 (m, 2H), 4.81 (d, J = 6.0 Hz, 2H), 4.23 (d, J = 11.2 Hz, 1H), 3.87 (d, J = 11.2 Hz, 1H), 1.70 (s, 3H), 1.34-1.29 (m, 2H), 1.20-1.14 (m, 2H) ppm. |
| 472 | 480.3 | 1HNMR (400 MHz, MeOD-d4) δ = 9.22-9.14 (m, 1H), 9.13-9.07 (m, 2H), 8.49-8.41 (m, 1H), 8.17 (s, 1H), 8.05-7.97 (m, 1H), 7.92 (d, J = 8.0 Hz, 1H), 7.86-7.81 (m, 1H), 7.27 (d, J = 8.0 Hz, 1H), 4.90 (d, J = 3.2 Hz, 2H), 4.89-4.88 (m, 2H), 4.20 (d, J = 11.2 Hz, 1H), 3.92 (d, J = 11.6 Hz, 1H), 3.27-3.24 (m, 6H), 1.75 (s, 3H) ppm |
| 474 | 533 | 1HNMR (400 MHz, METHANOL-d4) δ = 9.40 (s, 1H), 8.64 (d, J = 8.8 Hz, 1H), 8.23 (d, J = 8.8 Hz, 1H), 8.18 (s, 1H), 8.05-8.01 (m, 1H), 7.95-7.89 |

TABLE 19-continued

Compounds of the Invention

| # | LCMS (m/z) | 1H NMR |
|---|---|---|
| | | (m, 2H), 7.74 (d, J = 7.6 Hz, 1H), 7.53-7.45 (m, 1H), 7.33-7.21 (m, 2H), 4.95 (s, 2H), 4.91 (d, J = 2.8 Hz, 2H), 4.21 (d, J = 11.6 Hz, 1H), 3.99 (d, J = 12.8 Hz, 2H), 3.95-3.89 (m, 1H), 3.64 (d, J = 11.2 Hz, 2H), 3.30 (s, 2H), 3.22-3.07 (m, 2H), 2.98 (s, 3H), 1.80-1.73 (m, 3H) ppm |
| 475 | 534.2 | 1H NMR (400 MHz, MeOD-d4) δ = 9.25 (s, 1H), 8.53 (d, J = 8.4 Hz, 1H), 8.44-8.20 (m, 1H), 8.17 (s, 1H), 8.11-8.08 (m, 1H), 8.01-7.95 (m, 1H), 7.93-7.90 (m, 2H), 7.29 (d, J = 8.0 Hz, 1H), 7.06 (d, J = 8.4 Hz, 1H), 4.91-4.90 (m, 4H), 4.39-4.37 (m, 2H), 4.21 (d, J = 11.2 Hz, 1H), 4.00-3.99 (m, 2H), 3.93 (d, J = 11.6 Hz, 1H), 2.38 (s, 3H), 1.76 (s, 3H) ppm |
| 476 | 504.1 | 1H NMR (400 MHz, MeOD-d4) δ = 9.31 (s, 1H), 8.59 (d, J = 8.4 Hz, 1H), 8.20-8.18 (m, 2H), 7.96-7.84 (m, 3H), 7.84 (s, 1H), 7.47 (d, J = 8.0 Hz, 1H), 7.30 (d, J = 8.0 Hz, 1H), 4.92-4.90 (m, 4H), 4.21 (d, J = 11.6 Hz, 1H), 3.93 (d, J = 11.6 Hz, 1H), 3.65 (s, 2H), 3.32 (s, 3H), 1.77 (s, 3H) ppm. |
| 477 | 502.3 | 1H NMR (400 MHz, DMSO-d6) δ = 9.58 (s, 1H), 9.44-9.40 (m, 1H), 9.32 (s, 1H), 8.73-8.69 (m, 2H), 8.65-8.61 (m, 2H), 8.21 (d, J = 1.6 Hz, 1H), 8.13 (d, J = 8.4 Hz, 1H), 8.01-7.94 (m, 3H), 7.73 (s, 1H), 7.33 (d, J = 8.0 Hz, 1H), 4.96-4.78 (m, 4H), 4.24 (d, J = 11.6 Hz, 1H), 3.88 (d, J = 11.6 Hz, 1H), 1.71 (s, 3H) ppm |
| 478 | 486.2 | 1H NMR (400 MHz, DMSO-d6) δ = 9.55 (d, J = 1.2 Hz, 1H), 9.45 (s, 1H), 9.43-9.38 (m, 1H), 8.86-8.83 (m, 1H), 8.76 (d, J = 8.4 Hz, 1H), 8.42 (d, J = 8.4 Hz, 1H), 8.20 (d, J = 1.2 Hz, 1H), 7.97-7.94 (m, 1H), 7.91-7.85 (m, 2H), 7.31 (d, J = 8.0 Hz, 1H), 7.24-6.91 (m, 1H), 4.95-4.80 (m, 4H), 4.23 (d, J = 11.6 Hz, 1H), 3.87 (d, J = 11.6 Hz, 1H), 1.70 (s, 3H) ppm |
| 479 | 507.2 | 1H NMR (400 MHz, DMSO-d6) δ = 9.46-9.35 (m, 2H), 8.67 (d, J = 8.8 Hz, 1H), 8.50 (s, 1H), 8.31 (d, J = 8.8 Hz, 1H), 8.25-8.17 (m, 2H), 7.96-7.94 (m, 1H), 7.87-7.76 (m, 2H), 7.62-7.58 (m, 1H), 7.31 (d, J = 8.0 Hz, 1H), 6.74-6.18 (m, 1H), 4.94-4.76 (m, 8H), 4.23 (d, J = 11.6 Hz, 1H), 3.87 (d, J = 11.6 Hz, 1H), 1.70 (s, 3H) ppm. |
| 480 | 519.2 | 1H NMR (400 MHz, DMSO-d6) δ = 9.42-9.39 (m, 1H), 9.36 (s, 1H), 8.52 (d, J = 8.8 Hz, 1H), 8.20 (d, J = 1.6 Hz, 1H), 8.13 (s, 1H), 8.05-8.01 (m, 2H), 7.96-7.94 (m, 1H), 7.78 (s, 1H), 7.33-7.27 (m, 2H), 4.93-4.85 (m, 2H), 4.81 (d, J = 5.6 Hz, 2H), 4.22 (d, J = 11.6 Hz, 1H), 4.05 (s, 3H), 3.95 (s, 3H), 3.86 (d, J = 11.6 Hz, 1H), 1.70 (s, 3H) ppm. |
| 481 | 483.1 | 1H NMR (400 MHz, DMSO-d6) δ = 9.43-9.34 (m, 2H), 8.54 (d, J = 8.4 Hz, 1H), 8.19 (d, J = 1.2 Hz, 1H), 8.05 (d, J = 8.4 Hz, 1H), 7.95-7.93 (m, 1H), 7.86-7.77 (m, 1H), 7.77 (s, 1H), 7.30 (d, J = 8.0 Hz, 1H), 7.14-7.11 (m, 1H), 6.93-6.92 (m, 1H), 4.94-4.76 (m, 4H), 4.22 (d, J = 11.6 Hz, 1H), 3.88-3.84 (m, 4H), 1.70 (s, 3H) ppm. |
| 482 | 466.2 | 1H NMR (400 MHz, DMSO-d6) δ = 9.46-9.36 (m, 2H), 9.05 (d, J = 1.6 Hz, 1H), 8.71 (d, J = 8.8 Hz, 1H), 8.45 (d, J = 2.8 Hz, 1H), 8.43 (br s, 1H), 8.38 (d, J = 8.4 Hz, 1H), 8.20-8.15 (m, 2H), 7.97-7.92 (m, 1H), 7.85 (s, 1H), 7.30 (d, J = 8.4 Hz, 1H), 4.95-4.77 (m, 4H), 4.26-4.19 (m, 1H), 3.94 (s, 3H), 3.86 (d, J = 11.6 Hz, 1H), 1.70 (s, 3H) ppm |
| 483 | 492.2 | 1H NMR (400 MHz, DMSO-d6) δ = 9.46-9.35 (m, 2H), 8.73-8.68 (m, 2H), 8.66-8.60 (m, 1H), 8.43 (d, J = 8.0 Hz, 1H), 8.37 (br s, 1H), 8.34 (d, J = 8.8 Hz, 1H), 8.20 (d, J = 1.2 Hz, 1H), 8.02-7.93 (m, 2H), 7.84 (s, 1H), 7.69-7.61 (m, 1H), 7.31 (d, J = 8.0 Hz, 1H), 4.96-4.75 (m, 4H), 4.23 (d, J = 11.2 Hz, 1H), 3.87 (d, J = 11.2 Hz, 1H), 2.83 (d, J = 4.4 Hz, 3H), 1.71 (s, 3H) ppm |
| 484 | 518.2 | 1HNMR (400 MHz, DMSO-d6) δ = 9.41-9.36 (m, 2H), 8.69 (d, J = 8.0 Hz, 1H), 8.50 (s, 1H), 8.43-8.39 (m, 1H), 8.34 (d, J = 8.4 Hz, 1H), 8.21 (d, J = 1.2 Hz, 1H), 7.96-7.94 (m, 1H), 7.84 (s, 1H), 7.76 (d, J = 7.6 Hz, 1H), 7.65-7.62 (m, 1H), 7.31 (d, J = 7.6 Hz, 1H), 4.93-4.81 (m, 4H), 4.36-4.32 (m, 2H), 4.24-4.16 (m, 1H), 4.10-4.06 (m, 2H), 3.86 (d, J = 11.6 Hz, 1H), 2.29-2.26 (m, 2H), 1.70 (s, 3H) ppm. |
| 485 | 504.2 | 1H NMR (400 MHz, DMSO-d6) δ = 9.51-9.29 (m, 2H), 8.68 (d, J = 8.4 Hz, 1H), 8.59-8.50 (m, 2H), 8.41 (d, J = 8.8 Hz, 1H), 8.20 (s, 1H), 7.97-7.95 (m, 1H), 7.85 (s, 1H), 7.77 (d, J = 8.4 Hz, 1H), 7.31 (d, J = 8.0 Hz, 1H), 4.98-4.77 (m, 4H), 4.56 (s, 2H), 4.24 (s, 1H), 3.87 (d, J = 7.2 Hz, 1H), 3.12 (s, 3H), 1.71 (s, 3H) ppm. |
| 487 | 509.2 | 1H NMR (400 MHz, DMSO-d6) δ = 9.57-9.54 (m, 1H), 9.42-9.37 (m, 1H), 9.07 (d, J = 2.0 Hz, 1H), 8.65 (d, J = 8.8 Hz, 1H), 8.56 (d, J = 2.0 Hz, 1H), 8.26 (d, J = 8.8 Hz, 1H), 7.87 (s, 1H), 7.37-7.30 (m, 1H), 7.12-7.11 (m, 1H), 6.39-6.35 (m, 1H), 4.93-4.80 (m, 4H), 4.29 (d, J = 11.6 Hz, 1H), 3.95-3.89 (m, 5H), 2.52 (s, 1H), 2.38-2.34 (m, 1H), 1.72 (s, 3H) ppm. |
| 488 | 466.1 | 1H NMR (400 MHz, DMSO-d6) δ = 9.46-9.32 (m, 2H), 8.61 (d, J = 8.8 Hz, 1H), 8.39-8.25 (m, 2H), 8.23-8.12 (m, 2H), 7.94(d, J = 8.0 Hz, 1H), 7.79 (s, 1H), 7.30 (d, J = 8.0 Hz, 1H), 7.19 (d, J = 2.0 Hz, 1H), 4.98-4.73 (m, 4H), 4.22 (d, J = 11.6 Hz, 1H), 3.98 (s, 3H), 3.86 (d, J = 11.6 Hz, 1H), 1.69 (s, 3H) ppm. |

TABLE 19-continued

Compounds of the Invention

| # | LCMS (m/z) | 1H NMR |
|---|---|---|
| 489 | 466.3 | 1H NMR (400 MHz, DMSO-d6) δ = 9.40-9.38 (m, 2H), 8.79 (s, 1H), 8.61-8.56 (m, 2H), 8.18 (d, J = 1.2 Hz, 1H), 8.06 (d, J = 8.4 Hz, 1H), 7.95-7.93 (m, 1H), 7.82 (s, 1H), 7.30-7.27 (m, 2H), 4.92-4.80 (m, 4H), 4.22 (d, J = 11.6 Hz, 1H), 3.94 (s, 3H), 3.86 (d, J = 11.6 Hz, 1H), 1.69 (s, 3H) ppm. |
| 490 | 506.2 | 1H NMR (400 MHz, DMSO-d6) δ = 9.41-9.38 (m, 2H), 8.68 (d, J = 8.8 Hz, 1H), 8.41 (br s, 1H), 8.37-8.30 (m, 3H), 8.20 (d, J = 1.2 Hz, 1H), 7.96-7.94 (m, 1H), 7.82 (s, 1H), 7.64-7.60 (m, 1H), 7.57-7.55 (m, 1H), 7.31 (d, J = 8.0 Hz, 1H), 4.93-4.80 (m, 4H), 4.23 (d, J = 11.2 Hz, 1H), 3.87 (d, J = 11.2 Hz, 1H), 3.02-2.94 (m, 6H), 1.70 (s, 3H) ppm |
| 491 | 519.2 | 1H NMR (400 MHz, DMSO-d6) δ = 9.46-9.35 (m, 2H), 8.65 (d, J = 8.0 Hz, 1H), 8.22-8.14 (m, 2H), 8.12 (s, 1H), 7.98-7.91 (m, 1H), 7.83 (s, 1H), 7.65-7.59 (m, 1H), 7.56-7.50 (m, 1H), 7.30 (d, J = 8.4 Hz, 1H), 4.95-4.77 (m, 4H), 4.27 (s, 3H), 4.22 (d, J = 11.2 Hz, 1H), 3.86 (d, J = 11.6 Hz, 1H), 3.59 (s, 3H), 1.70 (s, 3H) ppm. |
| 492 | 466.2 | 1HNMR (400 MHz, DMSO-d6) δ = 9.45-9.37 (m, 2H), 8.76-8.64 (m, 2H), 8.25-8.18 (m, 2H), 7.97-7.94 (m, 1H), 7.93-7.88 (m, 1H), 7.83 (s, 1H), 7.31 (d, J = 8.0 Hz, 1H), 7.01 (d, J = 8.0 Hz, 1H), 4.95-4.84 (m, 2H), 4.82 (d, J = 5.6 Hz, 2H), 4.23 (d, J = 11.6 Hz, 1H), 4.04 (s, 3H), 3.87 (d, J = 11.6 Hz, 1H), 1.71 (s, 3H) ppm |
| 493 | 475.2 | 1HNMR (400 MHz, DMSO-d6) δ = 9.38-9.35 (m, 1H), 9.24 (s, 1H), 8.97 (s, 1H), 8.88-8.83 (m, 2H), 8.50 (d, J = 8.4 Hz, 1H), 8.23-8.18 (m, 2H), 7.96-7.93 (m, 1H), 7.80 (s, 1H), 7.60-7.53 (m, 1H), 7.31 (d, J = 8.0 Hz, 1H), 7.17-7.11 (m, 1H), 4.95-4.83 (m, 2H), 4.83-4.74 (m, 2H), 4.23 (d, J = 11.5 Hz, 1H), 3.88 (d, J = 11.2 Hz, 1H), 1.71 (s, 3H) ppm |
| 494 | 435.2 | 1H NMR (400 MHz, METHANOL-d4) δ = 8.51 (d, J = 8.8 Hz, 1H), 8.25-8.21 (m, 3H), 8.15 (d, J = 2.0 Hz, 1H), 7.91-7.88 (m, 1H), 7.84-7.81 (m, 2H), 7.53-7.51 (m, 2H), 7.49-7.45 (m, 1H), 7.27 (d, J = 8.0 Hz, 1H), 5.15 (s, 2H), 4.89 (d, J = 3.6 Hz, 2H), 4.20 (d, J = 11.2 Hz, 1H), 3.92 (d, J = 11.6 Hz, 1H), 1.74 (s, 3H) ppm |
| 495 | 504.2 | 1H NMR (400 MHz, DMSO-d6) δ = 9.44-9.41 (m, 2H), 8.72 (d, J = 8.4 Hz, 1H), 8.52 (s, 1H), 8.44 (s, 1H), 8.41-8.39 (m, 1H), 8.37 (d, J = 8.8 Hz, 1H), 8.22 (d, J = 1.2 Hz, 1H), 7.98-7.96 (m, 1H), 7.83-7.81 (m, 2H), 7.33 (d, J = 8.0 Hz, 1H), 4.94-4.82 (m, 4H), 4.57 (s, 2H), 4.24 (d, J = 11.6 Hz, 1H), 3.88 (d, J = 11.2 Hz, 1H), 3.12 (s, 3H), 1.71 (s, 3H) ppm |
| 496 | 491.2 | 1H NMR (400 MHz, DMSO-d6) δ = 9.50-9.31 (m, 2H), 8.74-8.54 (m, 2H), 8.21 (s, 1H), 7.98-7.95 (m, 1H), 7.88 (d, J = 7.2 Hz, 1H), 7.82 (s, 1H), 7.72-7.70 (m, 1H), 7.32 (d, J = 8.0 Hz, 1H), 6.54 (d, J = 8.0 Hz, 1H), 4.95-4.80 (m, 4H), 4.24 (d, J = 11.6 Hz, 1H), 4.09-4.05 (m, 4H), 3.88 (d, J = 11.6 Hz, 1H), 2.43-2.33 (m, 2H), 1.71 (s, 3H) ppm |
| 497 | 492.2 | 1HNMR (400 MHz, DMSO-d6) δ = 9.40-9.37 (m, 1H), 9.25 (s, 1H), 8.63 (s, 1H), 8.51 (d, J = 8.4 Hz, 1H), 8.26-8.20 (m, 2H), 8.00-7.94 (m, 2H), 7.66 (s, 1H), 7.32 (d, J = 8.0 Hz, 1H), 5.11-5.07 (m, 1H), 4.94-4.77 (m, 2H), 4.78 (br d, J = 5.2 Hz, 2H), 4.24 (d, J = 11.6 Hz, 1H), 4.02-3.96 (m, 3H), 3.89-3.83 (m, 2H), 2.44-2.35 (m, 2H), 1.71 (s, 3H) ppm. |
| 498 | 504.1 | 1H NMR (400 MHz, DMSO-d6) δ = 9.40-9.37 (m, 1H), 9.32 (s, 1H), 8.59 (d, J = 8.4 Hz, 1H), 8.28-8.24 (m, 3H), 8.20 (d, J = 1.2 Hz, 1H), 7.97-7.94 (m, 1H), 7.74 (s, 1H), 7.32 (d, J = 8.4 Hz, 1H), 7.15 (d, J = 8.4 Hz, 1H), 4.93-4.89 (m, 2H), 4.80 (d, J = 6.0 Hz, 2H), 4.24 (d, J = 11.6 Hz, 1H), 3.87 (d, J = 11.6 Hz, 1H), 3.66 (s, 2H), 3.18 (s, 3H), 1.70 (s, 3H) ppm. |
| 499 | 502.4 | 1H NMR (400 MHz, MeOD) δ = 9.23 (s, 1H), 9.18 (s, 1H), 9.14 (d, J = 1.6 Hz, 1H), 8.56 (d, J = 4.4 Hz, 1H), 8.53-8.51 (m, 2H), 8.33 (d, J = 8.0 Hz, 1H), 8.18 (s, 1H), 8.06 (d, J = 8.4 Hz, 1H), 7.95-7.93 (m, 1H), 7.86 (s, 1H), 7.61-7.60 (m, 1H), 7.31 (d, J = 8.0 Hz, 1H), 4.92-4.90 (m, 4H), 4.22 (d, J = 11.2 Hz, 1H), 3.95 (d, J = 11.6 Hz, 1H), 1.77 (s, 3H). ppm |
| 500 | 486.1 | 1HNMR (400 MHz, MeOD-d4) δ = 9.31 (s, 1H), 9.05 (d, J = 2.0 Hz, 1H), 8.65-8.57 (m, 1H), 8.55 (d, J = 2.0 Hz, 1H), 8.41 (s, 1H), 8.34 (d, J = 7.2 Hz, 1H), 8.20 (d, J = 8.4 Hz, 1H), 8.00 (s, 1H), 7.75-7.63 (m, 2H), 6.89 (s, 1H), 4.95-4.89 (m, 4H), 4.26 (d, J = 11.6 Hz, 1H), 3.97 (d, J = 11.6 Hz, 1H), 1.78 (s, 3H) ppm. |
| 501 | 453.1 | 1HNMR (400 MHz, MeOD-d4) δ = 9.30 (s, 1H), 8.55 (s, 1H), 8.18 (s, 1H), 8.04-7.88 (m, 3H), 7.30 (d, J = 8.4 Hz, 1H), 6.82 (s, 1H), 4.93 (s, 4H), 4.30 (s, 3H), 4.22 (d, J = 11.6 Hz, 1H), 3.94 (d, J = 10.8 Hz, 1H), 2.32 (s, 3H), 1.78 (s, 3H) ppm |
| 504 | 475.1 | 1H NMR (400 MHz, DMSO-d6) δ = 9.42-9.39 (m, 1H), 9.32 (s, 1H), 9.13 (s, 1H), 8.61 (d, J = 8.4 Hz, 1H), 8.56 (s, 1H), 8.21 (d, J = 1.2 Hz, 1H), 8.14-7.90 (m, 3H), 7.75-7.72 (m, 1H), 7.32 (d, J = 8.0 Hz, 1H), 4.94-4.83 (m, 2H), 4.80 (br d, J = 5.6 Hz, 2H), 4.24 (d, J = 11.6 Hz, 1H), 3.88 (d, J = 11.2 Hz, 1H), 1.71 (s, 3H) ppm |
| 506 | 492.3 | 1H NMR (400 MHz, MeOD-d4) δ = 9.36 (s, 1H), 8.64 (s, 2H), 8.47 (d, J = 5.2 Hz, 1H), 8.17 (d, J = 1.2 Hz, 1H), 7.98 (s, 1H), 7.93-7.91 (m, 1H), 7.76 (d, J = 4.8 Hz, 1H), 7.29 (d, J = 8.4 Hz, 1H), 4.93-4.90 (m, 4H), 4.27-4.19 (m, 5H), 3.93 (d, J = 11.6 Hz, 1H), 2.47-2.43 (m, 2H), 1.77 (s, 3H) ppm |
| 507 | 466.3 | 1H NMR (400 MHz, MeOD) δ = 9.37 (s, 1 H), 8.60 (d, J = 8.8 Hz, 1 H), 8.52 (s, 1 H), 8.36 (d, J = 4.8 Hz, 1 H), 8.16-8.13 (m, 2 H), 7.96 (s, 1H), |

TABLE 19-continued

| Compounds of the Invention | | |
|---|---|---|
| # | LCMS (m/z) | 1H NMR |
| | | 7.91-7.86 (m, 1 H), 7.83 (d, J = 4.8 Hz, 1 H), 7.29 (d, J = 8.0 Hz, 1 H), 4.95-4.93 (m, 2 H), 4.91 (d, J = 3.6 Hz, 2 H), 4.21 (d, J = 11.6 Hz, 1 H), 4.03 (s, 3H), 3.93 (d, J = 11.2 Hz, 1 H), 1.75 (s, 3H) ppm. |
| 508 | 435.1 | 1HNMR (400 MHz, DMSO-d6) δ = 9.60 (s, 1H), 9.52 (s, 1H), 9.45-9.38 (m, 1H), 8.50 (s, 1H), 8.26 (d, J = 7.2 Hz, 2H), 8.21 (s, 1H), 8.00-7.93 (m, 1H), 7.80 (s, 1H), 7.58-7.44 (m, 3H), 7.32 (d, J = 8.0 Hz, 1H), 4.96-4.83 (m, 2H), 4.80 (d, J = 5.6 Hz, 2H), 4.24 (d, J = 11.6 Hz, 1H), 3.88 (d, J = 11.6 Hz, 1H), 1.71 (s, 3H) ppm |
| 509 | 453.1 | 1HNMR (400 MHz, MeOD-d4) δ = 9.18 (s, 1H), 8.42 (d, J = 8.8 Hz, 1H), 8.27 (s, 1H), 8.16 (d, J = 1.6 Hz, 1H), 7.92-7.90 (m, 1H), 7.86-7.80 (m, 2H), 7.29 (d, J = 8.4 Hz, 1H), 4.91 (d, J = 3.6 Hz, 2H), 4.89 (s, 2H), 4.20 (d, J = 11.6 Hz, 1H), 3.93 (d, J = 11.2 Hz, 1H), 3.90 (s, 3H), 2.62 (s, 3H), 1.76 (s, 3H) ppm |
| 510 | 466.2 | 1H NMR (400 MHz, MeOD) δ = 9.68-9.61 (m, 1H), 9.10-8.99 (m, 1H), 8.96-8.81 (m, 2H), 8.35-8.21 (m, 2H), 8.18 (d, J = 2.0 Hz, 1H), 7.96-7.93 (m, 1H), 7.32 (d, J = 8.0 Hz, 1H), 6.85-6.77 (m, 1H), 5.02 (s, 2H), 4.93 (d, J = 2.8 Hz, 2H), 4.22 (d, J = 11.6 Hz, 1H), 3.96 (d, J = 11.6 Hz, 1H), 3.81 (s, 3H), 1.81-1.75 (m, 3H) ppm |
| 511 | 435.1 | 1HNMR (400 MHz, DMSO-d6) δ = 9.45-9.39 (m, 2H), 9.39 (d, J = 2.4 Hz, 1H), 8.76 (d, J = 2.4 Hz, 1H), 8.20 (d, J = 1.6 Hz, 1H), 7.98-7.92 (m, 3H), 7.87 (s, 1H), 7.61-7.55 (m, 2H), 7.53-7.48 (m, 1H), 7.31 (d, J = 8.0 Hz, 1H), 4.95-4.85 (m, 2H), 4.81 (d, J = 6.0 Hz, 2H), 4.23 (d, J = 11.6 Hz, 1H), 3.89-3.86 (m, 1H), 1.70 (s, 3H) ppm |
| 512 | 466.2 | 1HNMR (400 MHz, MeOD-d4) δ = 9.36 (s, 1H), 8.65 (d, J = 8.8 Hz, 1H), 8.30 (d, J = 5.6 Hz, 1H), 8.23-8.13 (m, 2H), 7.99 (s, 1H), 7.94-7.91 (m, 1H), 7.77-7.71 (m, 1H), 7.58 (s, 1H), 7.29 (d, J = 8.0 Hz, 1H), 4.96-4.90 (m, 4H), 4.20 (d, J = 11.6 Hz, 1H), 3.99 (s, 3H), 3.93 (d, J = 11.6 Hz, 1H), 1.76 (s, 3H) ppm |
| 513 | 481.1 | 1H NMR (400 MHz, MeOD-d4) δ = 9.20 (s, 1H), 8.58 (s, 1H), 8.47-8.45 (m, 1H), 8.36 (s, 1H), 8.18 (d, J = 1.6 Hz, 1H), 7.95-7.91 (m, 2H), 7.83 (s, 1H), 7.29 (d, J = 8.4 Hz, 1H), 5.68-5.61 (m, 1H), 5.09 (s, 2H), 5.08 (s, 2H), 4.92 (d, J = 3.6 Hz, 2H), 4.89 (s, 2H), 4.21 (d, J = 11.6 Hz, 1H), 3.93 (d, J = 11.6 Hz, 1H), 1.77 (s, 3H) ppm. |
| 515 | 501.2 | 1H NMR (400 MHz, DMSO-d6) δ = 9.47 (s, 1H), 9.39-9.38 (m, 1H), 8.71 (d, J = 5.6 Hz, 1H), 8.17 (d, J = 1.6 Hz, 1H), 7.93-7.92 (m, 1H), 7.83 (d, J = 8.8 Hz, 1H), 7.80 (s, 1H), 7.36-7.35 (m, 1H), 7.30-7.17 (m, 2H), 4.96-4.73 (m, 4H), 4.21 (d, J = 3.6 Hz, 1H), 3.91-3.81 (m, 4H), 1.68 (s, 3H) ppm. |
| 516 | 483.2 | 1H NMR (400 MHz, DMSO-d6) δ = 9.46-9.38 (m, 2H), 8.65 (s, 1H), 8.19 (d, J = 1.6 Hz, 1H), 8.01 (d, J = 8.4 Hz, 1H), 7.95 (d, J = 1.6, 1H), 7.82 (s, 1H), 7.61 (d, J = 7.6 Hz, 1H), 7.32-7.29 (m, 1H), 7.34-7.22 (m, 2H), 4.94-4.80 (m, 4H), 4.23 (d, J = 11.6 Hz, 1H), 3.87 (d, J = 11.6 Hz, 1H), 3.82 (d, J = 1.6 Hz, 3H), 1.70 (s, 3H) ppm. |
| 517 | 483.2 | 1H NMR (400 MHz, DMSO-d6) δ = 9.43-9.33 (m, 2H), 8.57 (d, J = 8.2 Hz, 1H), 8.18 (d, J = 1.6 Hz, 1H), 8.09 (d, J = 8.4 Hz, 1H), 7.93 (d, J = 1.6, 1H), 7.79 (s, 1H), 7.60 (d, J = 2.0 Hz, 1H), 7.38-7.27 (m, 2H), 7.26-7.21 (m, 1H), 4.93-4.76 (m, 4H), 4.21 (d, J = 11.6 Hz, 1H), 3.88-3.83 (m, 4H), 1.69 (s, 3H) ppm. |
| 518 | 471.2 | 1HNMR (400 MHz, DMSO-d6) δ = 9.42-9.39 (m, 2H), 8.72 (d, J = 8.8 Hz, 1H), 8.44 (s, 1H), 8.36 (d, J = 8.8 Hz, 1H), 8.19 (d, J = 1.3 Hz, 1H), 8.06-8.02 (m, 2H), 7.96-7.94 (m, 1H), 7.84 (s, 1H), 7.48-7.42 (m, 1H), 7.31 (d, J = 8.0 Hz, 1H), 4.93-4.81 (m, 4H), 4.23 (d, J = 11.2 Hz, 1H), 3.87 (d, J = 11.6 Hz, 1H), 1.70 (s, 3H) ppm |
| 519 | 485.2 | 1HNMR (400 MHz, DMSO-d6) δ = 9.43-9.31 (m, 2H), 8.69-8.61 (m, 2H), 8.21-8.10(m, 2H), 7.96-7.94 (m, 1H), 7.78-7.76 (m, 1H), 7.66 (s, 1H), 7.31 (d, J = 8.0 Hz, 1H), 4.93-4.78 (m, 4H), 4.24-4.19 (m, 1H), 3.87 (d, J = 11.6 Hz, 1H), 2.11 (s, 3H), 1.70 (s, 3H) ppm. |
| 520 | 437.1 | 1H NMR (400 MHz, DMSO-d6) δ = 9.74 (d, J = 1.2 Hz, 1H), 9.47 (s, 1H), 9.44-9.41 (m, 1H), 8.85-8.76 (m, 3H), 8.60 (d, J = 8.8 Hz, 1H), 8.20 (d, J = 1.2 Hz, 1H), 7.96-7.94 (m, 1H), 7.90 (s, 1H), 7.31 (d, J = 8.0 Hz, 1H), 4.93-4.83 (m, 4H), 4.23 (d, J = 11.6 Hz, 1H), 3.87 (br d, J = 11.6 Hz, 1H), 1.70 (s, 3H) ppm |
| 521 | 485.2 | 1HNMR (400 MHz, DMSO-d6) δ = 9.46 (s, 1H), 9.42-9.36 (m, 1H), 8.72 (d, J = 8.8 Hz, 1H), 8.17 (d, J = 1.6 Hz, 1H), 7.98-7.91 (m, 2H), 7.86-7.77 (m, 3H), 7.75-7.66 (m, 2H), 7.61 (s, 0.3H), 7.47 (s, 0.5H), 7.33 (s, 0.2H), 7.29 (d, J = 8.0 Hz, 1H), 4.94-4.75 (m, 4H), 4.21 (d, J = 11.6 Hz, 1H), 3.86 (d, J = 11.6 Hz, 1H), 1.69 (s, 3H) ppm |
| 522 | 435.2 | 1H NMR (400 MHz, DMSO-d6) δ = 9.61 (s, 1H), 9.34-9.31 (m, 1H), 8.27-8.16 (m, 3H), 8.08 (d, J = 1.6 Hz, 1H), 7.95-7.86 (m, 3H), 7.58-7.51 (m, 2H), 7.50-7.45 (m, 1H), 7.29 (d, J = 8.4 Hz, 1H), 4.97-4.77 (m, 4H), 4.23 (d, J = 11.2 Hz, 1H), 3.87 (d, J = 11.2 Hz, 1H), 1.70 (s, 3H) ppm. |

TABLE 19-continued

| Compounds of the Invention | | |
|---|---|---|
| # | LCMS (m/z) | 1H NMR |
| 525 | 464.2 | 1HNMR (400 MHz, DMSO-d6) δ = 9.53-9.30 (m, 2H), 8.66 (d, J = 8.4 Hz, 1H), 8.39-8.21 (m, 4H), 8.09 (d, J = 8.0 Hz, 1H), 7.81 (s, 1H), 7.66-7.51 (m, 3H), 7.43 (d, J = 8.0 Hz, 1H), 6.98-6.55 (m, 1H), 5.01-4.74 (m, 4H), 4.36-4.09 (m, 2H) ppm |

Example 29: (R)-4-Cyano-N-((2-(3-(dimethylamino)-2-oxopyridin-1(2H)-yl)-1,6-naphthyridin-7-yl)methyl)-4-methylisochromane-6-carboxamide

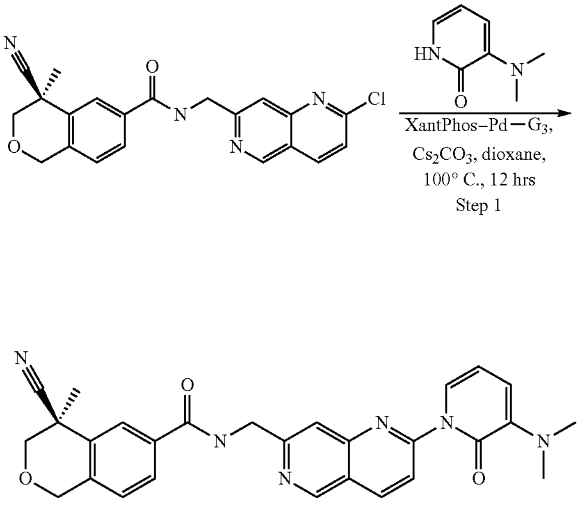

Step 1: (R)-4-Cyano-N-((2-(3-(dimethylamino)-2-oxopyridin-1(2H)-yl)-1,6-naphthyridin-7-yl)methyl)-4-methylisochromane-6-carboxamide To a solution of (R)—N-((2-chloro-1,6-naphthyridin-7-yl)methyl)-4-cyano-4-methylisochromane-6-carboxamide (30 mg, 76.37 umol) and 3-(dimethylamino)pyridin-2(1H)-one (21.10 mg, 152.73 umol) in dioxane (1 mL) was added $Cs_2CO_3$ (74.65 mg, 229.10 umol) and XantPhos Pd G3 (7.24 mg, 7.64 umol). The mixture was stirred at 100° C. for 12 hrs under $N_2$. The mixture was diluted with $H_2O$ (10 mL) and extracted with EA (10 mL*2). The combined organic layers were dried over anhydrous $Na_2SO_4$, filtered and concentrated. The residue was purified by reverse phase prep-HPLC (0.1% FA condition) to give the title compound (12.66 mg, 22.61 umol, 29.61% yield, FA salt) as a yellow solid.

LCMS (ESI) m/z: $[M+H]^+$=495.4.

$^1$H NMR (400 MHz, MeOD) δ=9.39 (s, 1H), 8.65 (d, J=8.8 Hz, 1H), 8.15 (d, J=1.6 Hz, 1H), 7.99 (d, J=8.8 Hz, 1H), 7.91-7.89 (m, 2H), 7.60-7.58 (m, 1H), 7.28 (d, J=8.0 Hz, 1H), 6.93-6.91 (m, 1H), 6.46-6.43 (m, 1H), 4.92 (s, 2H), 4.90 (d, J=4.0 Hz, 2H), 4.21 (d, J=11.6 Hz, 1H), 3.93 (d, J=11.6 Hz, 1H), 2.85 (s, 6H), 1.75 (s, 3H) ppm.

Chiral SFC: Cellucoat-MeOH+ACN(DEA)-40-3 mL-35T.lcm, Rt=0.908 min, ee value=100%.

The following examples in Table 20 were prepared using standard chemical manipulations and procedures similar to those used for the preparation of Examples 29.

TABLE 20

| Compounds of the Invention | | |
|---|---|---|
| # | LCMS (m/z) | 1H NMR |
| 142 | 498.4 | 1H NMR (400 MHz, DMSO-d6) δ = 9.48-9.45 (m, 1H), 8.75 (d, J = 4.4 Hz, 1H), 8.50 (d, J = 9.6 Hz, 1H), 8.30-8.27 (m, 1H), 8.18-8.13 (m, 2H), 8.05 (s, 1H), 7.95-7.92 (m, 1H), 7.30 (d, J = 8.0 Hz, 1H), 5.01 (d, J = 5.6 Hz, 2H), 4.94-4.80 (m, 2H), 4.22 (d, J = 11.6 Hz, 1H), 4.02-3.98 (m, 4H), 3.86 (d, J = 11.6 Hz, 1H), 2.42-2.34 (m, 2H), 1.69 (s, 3H) ppm |
| 219 | 530.5 | 1H NMR (400 MHz, METHANOL-d4) δ = 8.29 (d, J = 9.6 Hz, 1H), 8.14 (d, J = 1.6 Hz, 1H), 7.94-7.87 (m, 3H), 7.68 (s, 1H), 7.27 (d, J = 8.0 Hz, 1H), 7.21 (d, J = 2.4 Hz, 1H), 7.06-6.76 (m, 1H), 5.04 (s, 2H), 4.90 (s, 2H), 4.84 (s, 2H), 4.37-4.35 (m, 2H), 4.20 (d, J = 11.6 Hz, 1H), 4.11 (t, J = 5.6 Hz, 2H), 3.92 (d, J = 11.6 Hz, 1H), 1.75 (s, 3H) ppm |
| 220 | 530.4 | 1H NMR (400 MHz, DMSO-d6) δ = 9.36-9.33 (m, 1H), 9.14 (s, 1H), 9.08 (d, J = 2.8 Hz, 1H), 8.19 (d, J = 1.6 Hz, 1H), 7.96-7.94 (m, 1H), 7.71 (s, 1H), 7.66 (d, J = 2.4 Hz, 1H), 7.57 (s, 1H), 7.30 (d, J = 8.0 Hz, 1H), 7.25-6.92 (m, 1H), 4.94-4.81 (m, 2H), 4.79 (s, 2H), 4.72 (d, J = 6.0 Hz, 2H), 4.32-4.30 (m, 2H), 4.23 (d, J = 11.2 Hz, 1H), 4.12-4.05 (m, 2H), 3.86 (d, J = 11.6 Hz, 1H), 1.69 (s, 3H)ppm |
| 279 | 512 | 1H NMR (400 MHz, DMSO-d6) δ = 9.36-9.33 (m, 1H), 9.22 (s, 1H), 8.55 (d, J = 9.2 Hz, 1H), 8.25 (s, 1H), 7.96-7.94 (m, 1H), 7.52-7.47 (m, 2H), 7.30 (d, J = 8.0 Hz, 1H), 4.87-4.73 (m, 4H), 4.12-4.07 (m, 3H), 3.88-3.82 (m, 1H), 3.61-3.57 (m, 2H), 2.45-2.43 (m, 1H), 1.71-1.66 (m, 3H), 0.77-0.75 (m, 4H) ppm |

TABLE 20-continued

Compounds of the Invention

| # | LCMS (m/z) | 1H NMR |
|---|---|---|
| 282 | 492.2 | 1H NMR (400 MHz, MeOH) δ = 9.43-9.36 (m, 1H), 8.69-8.61 (m, 1H), 8.17-8.13 (m, 1H), 8.05-7.99 (m, 1H), 7.94-7.87 (m, 2H), 7.87-7.81 (m, 1H), 7.31-7.24 (m, 1H), 7.24-7.19 (m, 1H), 6.49-6.38 (m, 1H), 4.94-4.92 (m, 2H), 4.91-4.89 (m, 2H), 4.23-3.87 (m, 2H), 2.13-2.02 (m, 1H), 1.79-1.73 (m, 3H), 1.02-0.89 (m, 2H), 0.74-0.66 (m, 2H) ppm |
| 283 | 507 | 1H NMR (400 MHz, MeOD) δ = 9.40 (s, 1H), 8.65 (d, J = 8.4 Hz, 1H), 8.17 (d, J = 1.2 Hz, 1H), 7.98 (d, J = 8.4 Hz, 1 H), 7.95-7.89 (m, 2H), 7.43-7.41 (m, 1H), 7.29 (d, J = 8.0 Hz, 1H), 6.46-6.38 (m, 2H), 4.95-4.93 (m, 2H), 4.93-4.91 (m, 2H), 4.22 (d, J = 11.2 Hz, 1H), 4.03-4.01 (m, 4H), 3.94 (d, J = 11.2 Hz, 1H), 2.36-2.32 (m, 2H), 1.77 (s, 3H) ppm |
| 303 | 490.1 | 1HNMR (400 MHz, MeOD-d4) δ = 9.20-9.13 (m, 1H), 8.98 (s, 1H), 8.32-8.27 (m, 1H), 8.07-8.02 (m, 1H), 8.01-7.95 (m, 1H), 7.85-7.78 (m, 2H), 7.73-7.65 (m, 1H), 7.64-7.59 (m, 1H), 7.58-7.43 (m, 2H), 7.18-7.12 (m, 1H), 5.30-5.23 (m, 2H), 4.95 (d, J = 5.1 Hz, 2H), 4.91-4.85 (m, 2H), 4.20-4.10 (m, 1H), 4.01-3.91 (m, 1H), 1.81-1.75 (m, 3H) ppm |
| 312 | 483.2 | 1H NMR (400 MHz, DMSO-d6) δ = 9.41-9.29 (m, 1H), 9.14 (s, 1H), 8.61-8.55 (m, 1H), 8.43-8.36 (m, 1H), 8.22-8.16 (m, 1H), 7.98-7.89 (m, 1H), 7.50 (s, 1H), 7.34-7.27 (m, 1H), 4.94-4.80 (m, 2H), 4.77-4.66 (m, 2H), 4.27-4.18 (m, 1H), 4.04-3.98 (m, 2H), 3.90-3.83 (m, 1H), 3.47-3.43 (m, 2H), 2.66-2.60 (m, 1H), 1.70(s, 3H), 0.72-0.69 (m, 4H) ppm |
| 313 | 497.3 | 1H NMR (400 MHz, DMSO-d6) δ = 9.36-9.33 (m, 1H), 9.15-9.13 (m, 1H), 8.56 (d, J = 9.2 Hz, 1H), 8.38 (d, J = 9.2 Hz, 1H), 8.19 (d, J = 1.2 Hz, 1H), 7.95-7.92 (m, 1H), 7.49 (s, 1H), 7.31 (d, J = 8.0 Hz, 1H), 4.93-4.86 (m, 2H), 4.73 (br d, J = 4.4 Hz, 2H), 4.47-4.42 (m, 1H), 4.23 (d, J = 11.6 Hz, 1H), 4.09-4.05 (m, 2H), 3.87 (d, J = 11.6 Hz, 1H), 3.61-3.57 (m, 2H), 2.28-2.23 (m, 2H), 2.04-1.99 (m, 2H), 1.70-1.64 (m, 5H) ppm |
| 315 | 497.2 | 1H NMR (400 MHz, CD3OD) δ = 9.13 (s, 1H), 8.37-8.26 (m, 1H), 8.18 (s, 1H), 8.14-8.07 (m, 1H), 7.96-7.87 (m, 1H), 7.72 (s, 1H), 7.36-7.18 (m, 1H), 4.95-4.92 (m, 2H), 4.86-4.85 (m, 2H), 4.25-4.18 (m, 1H), 4.13-4.05 (m, 2H), 3.97-3.90 (m, 1H), 3.49-3.44 (m, 2H), 2.81-2.68 (m, 1H), 2.14-2.05 (m, 2H), 1.79-1.74 (m, 3H), 0.88-0.81 (m, 2H), 0.79-0.70 (m, 2H) ppm |
| 350 | 511.1 | 1H NMR (400 MHz, MeOD-d4) δ = 9.13 (s, 1H), 8.28 (d, J = 10.2 Hz, 1H), 8.17 (s, 1H), 8.03 (d, J = 10.2 Hz, 1H), 7.92 (d, J = 8.0 Hz, 1H), 7.71 (s, 1H), 7.30 (d, J = 7.6 Hz, 1H), 4.97-4.81 (m, 4H), 4.81-4.80 (m, 1H), 4.22 (d, J = 11.2 Hz, 1H), 4.11-4.08 (m, 2H), 3.94 (d, J = 11.2 Hz, 1H), 3.52-3.49 (m, 2H), 2.29-2.17 (m, 2H), 2.14-2.11 (m, 4H), 1.77-1.73 (m, 5H) ppm |
| 471 | 442.3 | 1H NMR (400 MHz, DMSO-d6) δ = 9.39-9.33 (m, 1H), 9.23 (s, 1H), 8.62 (d, J = 8.8 Hz, 1H), 8.51 (d, J = 9.2 Hz, 1H), 8.18 (s, 1H), 7.94-7.91 (m, 1H), 7.58 (s, 1H), 7.30 (d, J = 8.0 Hz, 1H), 4.92-4.75 (m, 4H), 4.22 (d, J = 11.6 Hz, 1H), 4.12-4.08 (m, 2H), 3.86 (d, J = 11.2 Hz, 1H), 2.67-2.63 (m, 2H), 2.08-2.04 (m, 2H), 1.69 (s, 3H) ppm |

Example 30: (R)-4-Cyano-4-methyl-N-((2-(6-methyl-5-oxo-3,4,5,6-tetrahydro-2,6-naphthyridin-2(1H)-yl)-1,6-naphthyridin-7-yl)methyl)isochromane-6-carboxamide

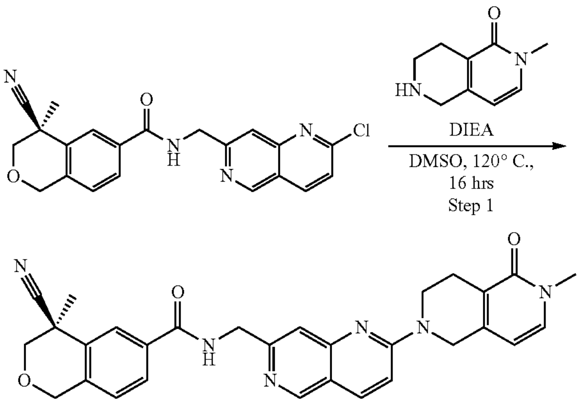

Step 1: (R)-4-Cyano-4-methyl-N-((2-(6-methyl-5-oxo-3,4,5,6-tetrahydro-2,6-naphthyridin-2(1H)-yl)-1,6-naphthyridin-7-yl)methyl)isochromane-6-carboxamide To a mixture of 2-methyl-5,6,7,8-tetrahydro-2,6-naphthyridin-1(2H)-one (30 mg, 107.83 umol, TFA salt) in DMSO (1 mL) was added (R)—N-((2-chloro-1,6-naphthyridin-7-yl)methyl)-4-cyano-4-methylisochromane-6-carboxamide (28.24 mg, 71.88 umol) and DIEA (46.45 mg, 359.42 umol, 62.60 uL).

The mixture was stirred at 120° C. for 16 hrs. The mixture was poured into $H_2O$ (15 mL) and extracted with EA/MeOH=10/1 (15 mL*3). The combined organic layers were washed with brine (10 mL), dried over anhydrous $Na_2SO_4$, filtered and concentrated under reduced pressure. The residue was purified by prep-TLC (DCM/MeOH=10/1, Rf=0.3) to afford a yellow solid. The yellow solid was further purified by reverse phase column (0.1% FA condition). The product fraction was concentrated under reduced pressure to remove MeCN and lyophilized to give the title compound (8.23 mg, 15.81 umol, 22.0% yield) as a white solid.

LCMS (ESI) m/z: $[M+H]^+$=521.3.

$^1$H NMR (400 MHz, DMSO-d6) δ=9.31-9.28 (m, 1H), 8.91 (s, 1H), 8.20-8.17 (m, 2H), 7.95-7.92 (m, 1H), 7.54 (d, J=7.2 Hz, 1H), 7.38 (d, J=9.2 Hz, 1H), 7.33-7.27 (m, 2H), 6.17 (d, J=6.8 Hz, 1H), 4.94-4.80 (m, 2H), 4.71 (5, 2H), 4.69-4.61 (d, 2H), 4.23 (d, J=11.6 Hz, 1H), 3.98-3.94 (i, 2H), 3.87 (d, J=11.6 Hz, 1H), 3.40 (m, 3H), 2.54 (brs, 2H), 1.70 (d, 3H) ppm.

Chiral SFC: Cellucoat-MeOH+ACN(DEA)-40-3 mL-35T, Rt=1.153 min, ee %=100%.

The following examples in Table 21 were prepared using standard chemical manipulations and procedures similar to those used for the preparation of Examples 30.

TABLE 21

Compounds of the Invention

| # | LCMS (m/z) | 1H NMR |
|---|---|---|
| 382 | 530.3 | 1H NMR (400 MHz, DMSO-d6) δ = 9.32-9.29 (m, 1H), 8.98 (s, 1H), 8.36-8.35 (m, 1H), 8.28 (d, J = 9.6 Hz, 1H), 8.18 (d, J = 1.2 Hz, 1H), 7.94-7.92 (m, 1H), 7.69 (s, 1H), 7.47 (d, J = 9.2 Hz, 1H), 7.36 (s, 1H), 7.30 (d, J = 8.0 Hz, 1H), 7.25-6.97 (m, 1H), 5.10 (s, 2H), 4.92-4.81 (m, 2H), 4.69 (br d, J = 5.2 Hz, 2H), 4.29-4.21 (m, 5H), 3.87 (d, J = 11.6 Hz, 1H), 1.69 (s, 3H) ppm |
| 383 | 492.2 | 1H NMR (400 MHz, DMSO-d6) δ = 9.31 (s, 1H), 8.64-8.57 (m, 2H), 8.49 (brs, 1H), 8.40 (d, J = 7.6 Hz, 1H), 8.18 (d, J = 1.6 Hz, 1H), 7.97-7.86 (m, 4H), 7.29 (d, J = 8.0 Hz, 1H), 4.92 (brd, J = 5.6 Hz, 5H), 4.21 (d, J = 11.2 Hz, 1H), 3.93 (d, J = 11.6 Hz, 1H), 1.76 (s, 3H), 1.54-1.51 (m, 2H), 1.27-1.24 (m, 2H) ppm |
| 425 | 498.5 | 1H NMR (400 MHz, MeOD) δ = 9.15 (s, 1H), 8.52 (d, J = 4.4 Hz, 1H), 8.48 (d, J = 8.8 Hz, 1H), 8.16 (d, J = 1.6 Hz, 1H), 8.08 (d, J = 8.8 Hz, 1H), 7.93-7.90 (m, 1H), 7.72 (s, 1H), 7.29 (d, J = 8.0 Hz, 1H), 4.91 (d, J = 3.2 Hz, 2H), 4.86 (br s, 2H), 4.20 (d, J = 11.2 Hz, 1H), 4.11-4.07 (m, 4H), 3.93 (d, J = 11.6 Hz, 1H), 2.50-2.43 (m, 2H), 1.76 (s, 3H) ppm |
| 426 | 480.5 | 1H NMR (400 MHz, MeOD) δ = 9.16 (s, 1H), 8.57 (d, J = 2.8 Hz, 1H), 8.50 (d, J = 9.2 Hz, 1H), 8.16 (d, J = 1.6 Hz, 1H), 8.09 (d, J = 8.8 Hz, 1H), 7.93-7.90 (m, 1H), 7.73 (s, 1H), 7.29 (d, J = 8.0 Hz, 1H), 5.99 (d, J = 3.2 Hz, 1H), 4.91 (d, J = 3.6 Hz, 2H), 4.87 (brs, 2H), 4.20 (d, J = 11.6 Hz, 1H), 4.03-3.99 (m, 4H), 3.93 (d, J = 11.2 Hz, 1H), 2.47-2.39 (m, 2H), 1.76 (s, 3H) ppm |
| 453 | 494.3 | 1HNMR (400 MHz, METHANOL-d4) δ = 8.83 (d, J = 2.8 Hz, 1H), 8.19-8.08 (m, 2H), 7.93-7.90 (m, 1H), 7.46 (s, 1H), 7.36-7.25 (m, 3H), 4.91 (d, J = 3.6 Hz, 2H), 4.82-4.74 (m, 4H), 4.23-4.13 (m, 3H), 3.93 (d, J = 11.6 Hz, 1H), 3.73 (d, J = 1.6 Hz, 3H), 2.86 (s, 2H), 1.76 (s, 3H) ppm |
| 455 | 494.3 | 1HNMR (400 MHz, METHANOL-d4) δ = 8.83 (s, 1H), 8.18-8.07 (m, 2H), 7.91 (d, J = 8.0 Hz, 1H), 7.46 (s, 1H), 7.34-7.28 (m, 2H), 4.91 (d, J = 3.6 Hz, 2H), 4.81-4.77 (m, 4H), 4.24-4.12 (m, 3H), 3.93 (d, J = 11.6 Hz, 1H), 3.83-3.72 (m, 3H), 2.86-2.81 (m, 2H), 1.76 (s, 3H) ppm |
| 457 | 494.5 | 1H NMR (400 MHz, MeOD) δ = 8.85 (s, 1H), 8.35-8.33 (m, 1H), 8.16-8.13 (m, 2H), 7.91-7.89 (m, 1H), 7.49 (s, 1H), 7.38-7.35(m, 1H), 7.28-7.26 (m, 2H), 4.96 (s, 2H), 4.90 (d, J = 3.2 Hz, 2H), 4.78 (s, 2H), 4.21 (d, J = 11.2 Hz, 1H), 4.03-4.01 (m, 2H), 3.93 (d, J = 11.2 Hz, 1H), 3.79-3.78 (m, 3H), 2.71 (brs, 2H), 1.76 (s, 3H) ppm. |
| 458 | 494.5 | 1H NMR (400 MHz, MeOD) δ = 8.82-8.81 (m, 1H), 8.27 (s, 1H), 8.15 (s, 1H), 8.13-8.08 (m, 1H), 7.91-7.89 (m, 1H), 7.45 (s, 1H), 7.33 (s, 1H), 7.30-7.26 (m, 2H), 4.89 (s, 2H), 4.77 (s, 2H), 4.21-4.17 (m, 1H), 4.05 (s, 2H), 3.93-3.89 (m, 1H), 3.82 (s, 3H), 2.72 (s, 2H), 1.75 (d, J = 1.2 Hz, 3H) ppm. |
| 461 | 480.2 | 1H NMR (400 MHz, MeOD-d4) δ = 8.85 (s, 1H), 8.29 (s, 1H), 8.19-8.12 (m, 2H), 7.93-7.91 (m, 1H), 7.51 (s, 1H), 7.34-7.26 (m, 2H), 7.01 (d, J = 9.2 Hz, 1H), 4.91 (d, J = 3.2 Hz, 2H), 4.83-4.75 (m, 4H), 4.74-4.64 (m, 2H), 4.21 (d, J = 11.6 Hz, 1H), 3.93 (d, J = 11.6 Hz, 1H), 3.85 (s, 3H), 1.77 (s, 3H) ppm. |
| 473 | 425.3 | 1HNMR (400 MHz, DMSO-d6) δ = 9.44-9.41 (m, 1H), 9.38 (s, 1H), 8.86 (d, J = 2.4 Hz, 1H), 8.75 (d, J = 8.8 Hz, 1H), 8.28 (d, J = 8.8 Hz, 1H), 8.21 (s, 1H), 8.15-8.13 (m, 1H), 7.98-7.93 (m, 2H), 7.73 (s, 1H), 7.32 (d, J = 8.0 Hz, 1H), 6.68-6.67(m, 1H), 4.95-4.84 (m, 2H), 4.83-4.79 (m, 2H), 4.24 (d, J = 11.6 Hz, 1H), 3.88 (d, J = 11.6 Hz, 1H), 1.71 (s, 3H) ppm |
| 486 | 480.2 | 1H NMR (400 MHz, DMSO-d6) δ = 9.32-9.30 (m, 1H), 8.95 (s, 1H), 8.28-8.15 (m, 2H), 7.94-7.91 (m, 1H), 7.48-7.39 (m, 2H), 7.36-7.25 (m, 2H), 6.17 (d, J = 1.6 Hz, 1H), 5.01 (s, 2H), 4.94-4.80 (m, 2H), 4.67 (d, J = 3.2, 2H), 4.30-4.18 (m, 5H), 3.86 (d, J = 11.6 Hz, 1H), 1.69 (s, 3H) ppm. |
| 502 | 540.3 | 1H NMR (400 MHz, Chloroform-d) δ 8.71 (s, 1H), 8.13 (s, 1H), 7.92 (d, J = 8.6 Hz, 1H), 7.62 (s, 1H), 7.11 (d, J = 8.1 Hz, 1H), 6.93 (s, 1H), 5.35 (s, 1H), 4.90 (d, J = 5.7 Hz, 2H), 4.85 (d, J = 4.6 Hz, 2H), 4.21 (q, J = 7.2 Hz, 2H), 4.13 (d, J = 11.3 Hz, 1H), 3.87 (d, J = 11.3 Hz, 1H), 3.68 (s, 2H), 2.15-1.15 (m, 14H) |
| 503 | 439 | 1H NMR (400 MHz, MeOD) δ = 9.23 (s, 1H), 8.69 (d, J = 2.4 Hz, 1H), 8.59 (d, J = 8.8 Hz, 1H), 8.24 (d, J = 8.8 Hz, 1H), 8.17 (d, J = 1.6 Hz, 1H), 7.95-7.90 (m, 1H), 7.80 (s, 1H), 7.29 (d, J = 8.2 Hz, 1H), 6.42 (d, J = 2.8 Hz, 1H), 4.91 (br d, J = 3.8 Hz, 4H), 4.20 (d, J = 11.6 Hz, 1H), 3.93 (d, J = 11.2 Hz, 1H), 2.37 (s, 3H), 1.76 (s, 3H) ppm |
| 505 | 439.2 | 1HNMR (400 MHz, DMSO-d6) δ = 9.43-9.31 (m, 2H), 8.69-8.61 (m, 2H), 8.21-8.10(m, 2H), 7.96-7.94 (m, 1H), 7.78-7.76 (m, 1H), 7.66 (s, 1H), |

TABLE 21-continued

Compounds of the Invention

| # | LCMS (m/z) | 1H NMR |
|---|---|---|
| | | 7.31 (d, J = 8.0 Hz, 1H), 4.93-4.78 (m, 4H), 4.24-4.19 (m, 1H), 3.87 (d, J = 11.6 Hz, 1H), 2.11 (s, 3H), 1.70 (s, 3H) ppm. |
| 514 | 428.3 | 1H NMR (400 MHz, DMSO-d6) δ = 9.30-9.27 (m, 1H), 8.85 (s, 1H), 8.19 (s, 1H), 8.09 (d, J = 9.2 Hz, 1H), 7.95-7.93 (m, 1H), 7.30 (d, J = 8.0 Hz, 1H), 7.24 (s, 1H), 6.92 (d, J = 9.2 Hz, 1H), 4.95-4.79 (m, 2H), 4.66-4.64 (m, 2H), 4.23 (d, J = 11.6 Hz, 1H), 3.86 (d, J = 11.6 Hz, 1H), 3.11-3.09 (m, 1H), 2.56-2.52 (m, 2H), 1.96 (br s, 4H), 1.90-1.76 (m, 1H), 1.70 (s, 3H) ppm |

Example 31: (R)—N-((2-(6-(Azetidin-1-yl)pyridin-2-yl)-2H-pyrazolo[4,3-c]pyridin-6-yl)methyl)-4-cyano-4-methylisochromane-6-carboxamide

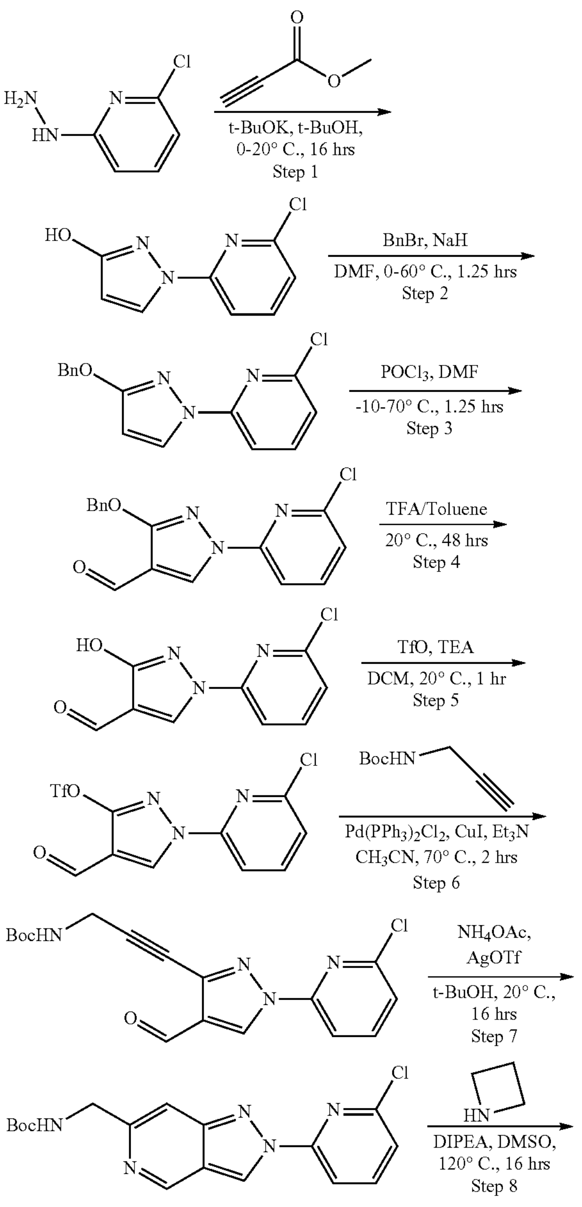

-continued

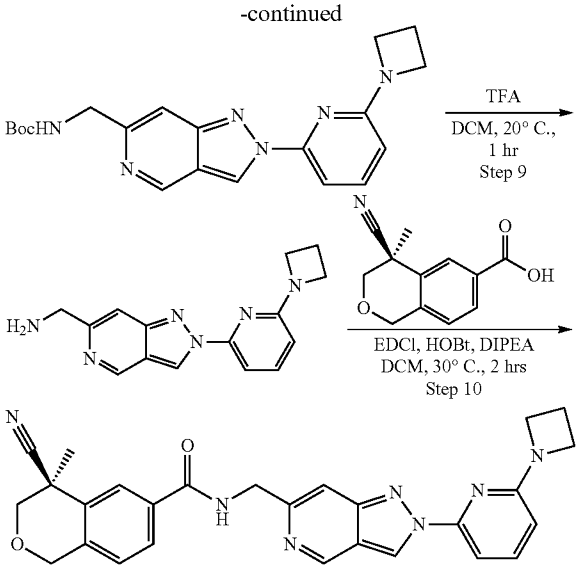

Step 1: 1-(6-Chloropyridin-2-yl)-1H-pyrazol-3-ol

Methyl prop-2-ynoate (1.29 g, 15.32 mmol, 1.28 mL) was added dropwise to a solution of (6-chloro-2-pyridyl)hydrazine (2 g, 13.93 mmol) in t-BuOH (10 mL) at 20° C. t-BuOK (3.13 g, 27.86 mmol) was then added at 0° C. before stirring at 20° C. for 16 hrs. The reaction was quenched by adding water (100 mL) and the mixture was adjusted to pH 9 with 1N HCl solution, forming a yellow precipitate. The solid was collected by filtration, washed with water (20 mL) and dried to give the title compound (1.6 g, 8.18 mmol, 58.72% yield).

LCMS (ESI) m/z: $[M+H]^+$=196.1.

$^1$H NMR (400 MHz, $CDCl_3$) δ=8.38-8.36 (m, 1H), 7.83-7.71 (m, 1H), 7.57-7.48 (m, 1H), 7.21-7.11 (m, 1H), 6.06-5.89 (m, 1H), 4.71 (br s, 1H) ppm.

Step 2: 2-(3-(Benzyloxy)-1H-pyrazol-1-yl)-6-chloropyridine

NaH (173.21 mg, 4.33 mmol, 60% purity) was added portion wise to a solution of 1-(6-chloropyridin-2-yl)-1H-pyrazol-3-ol (0.77 g, 3.94 mmol) in DMF (10 mL) at 0° C. The mixture was stirred at 0° C. for 15 mins. (Bromomethyl) benzene (673.27 mg, 3.94 mmol, 467.55 uL) was added dropwise at 0° C. and the mixture was stirred at 60° C. for 1 hr. The reaction was quenched by pouring into water (50 mL), forming a yellow precipitate was formed. The solid was collected by filtration, washed with water (20 mL) and dried. The residue was purified by column chromatography ($SiO_2$, Petroleum ether/Ethyl acetate=3/1) to give the title compound (0.5 g, 1.75 mmol, 44.45% yield).

LCMS (ESI) m/z: $[M+H]^+$=286.1.

$^1$H NMR (400 MHz, $CDCl_3$) δ=8.38-8.36 (m, 1H), 7.76-7.67 (m, 2H), 7.55-7.46 (m, 2H), 7.44-7.34 (m, 4H), 7.14-7.05 (m, 1H), 6.00-5.97 (m, 1H), 5.32 (s, 2H) ppm.

Step 3: 3-(Benzyloxy)-1-(6-chloropyridin-2-yl)-1H-pyrazole-4-carbaldehyde $POCl_3$ (429.30 mg, 2.80 mmol, 260.18 uL) was added dropwise to a solution of DMF (204.64 mg, 2.80 mmol, 215.41 uL) at −10° C. and the mixture was stirred at 0° C. for 15 mins. 2-(3-(Benzyloxy)-1H-pyrazol-1-yl)-6-chloropyridine (0.2 g, 699.97 umol) was added portion wise at 0° C. The mixture was then stirred at 70° C. for 1 hr. The reaction was quenched by adding sat. $NaHCO_3$ (20 mL) and a yellow precipitate was formed. The solid was collected by filtration, washed with water (10 mL) and dried to give the title compound (0.21 g, 669.35 umol, 95.63% yield).

LCMS (ESI) m/z: $[M+H]^+$=314.1.

$^1$H NMR (400 MHz, $CDCl_3$) δ=9.92 (s, 1H), 8.91 (s, 1H), 7.84-7.74 (m, 2H), 7.57-7.49 (m, 2H), 7.45-7.36 (m, 3H), 7.26-7.24 (m, 1H), 5.46 (s, 2H) ppm.

Step 4: 1-(6-Chloropyridin-2-yl)-3-hydroxy-1H-pyrazole-4-carbaldehyde

TFA (3.39 g, 29.71 mmol, 2.20 mL) was added dropwise to a solution of 3-(benzyloxy)-1-(6-chloropyridin-2-yl)-1H-pyrazole-4-carbaldehyde (110 mg, 350.61 umol) in toluene (2.2 mL). The mixture was stirred at 20° C. for 48 hrs. The reaction mixture was concentrated under vacuum. The residue was triturated with MTBE (5 mL) to give the title compound (50 mg, crude) as yellow solid.

LCMS (ESI) m/z: $[M+H]^+$=224.0.

Step 5: 1-(6-Chloropyridin-2-yl)-4-formyl-1H-pyrazol-3-yl trifluoromethanesulfonate To a solution of 1-(6-chloropyridin-2-yl)-3-hydroxy-1H-pyrazole-4-carbaldehyde (40 mg, 178.88 umol) in DCM (3 mL) was added TEA (54.30 mg, 536.64 umol) and dropwise $Tf_2O$ (75.70 mg, 268.32 umol). The mixture was stirred at 20° C. for 1 hr. The reaction was quenched by adding water (50 mL) and the products were extracted with ethyl acetate (30 mL*3). The combined organic layers were washed with brine (30 mL), dried over $Na_2SO_4$, filtered and concentrated. The residue was purified by column chromatography ($SiO_2$, Petroleum ether/Ethyl acetate=1/1) to give the title compound (30 mg, crude) as a yellow oil.

Step 6: tert-Butyl (3-(1-(6-chloropyridin-2-yl)-4-formyl-1H-pyrazol-3-yl)prop-2-yn-1-yl)carbamate A mixture of tert-butyl prop-2-yn-1-ylcarbamate (13.74 mg, 88.56 umol), 1-(6-chloropyridin-2-yl)-4-formyl-1H-pyrazol-3-yl trifluoromethanesulfonate (30 mg, 84.35 umol), $Et_3N$ (85.35 mg, 843.46 umol), CuI (1.61 mg, 8.43 umol) and $Pd(PPh_3)_2Cl_2$ (5.92 mg, 8.43 umol) in $CH_3CN$ (2 mL) was de-gassed and purged with $N_2$. The mixture was stirred at 70° C. for 2 hours under $N_2$. The reaction mixture was quenched by adding (water 30 mL) and the products were extracted with ethyl acetate (30 mL*3). The combined organic phase was washed with brine (30 mL), dried over $Na_2SO_4$, filtered and concentrated under reduced pressure. The residue was purified by prep-TLC (SiO2, Petroleum ether/Ethyl acetate=1/1) to give the title compound (40 mg, crude) as a yellow oil.

LCMS (ESI) m/z: $[M+Na]^+$=383.1.

Step 7: tert-Butyl ((2-(6-chloropyridin-2-yl)-2H-pyrazolo[4,3-c]pyridin-6-yl)methyl)carbamate To a solution of tert-butyl (3-(1-(6-chloropyridin-2-yl)-4-formyl-1H-pyrazol-3-yl)prop-2-yn-1-yl)carbamate (40 mg, 110.87 umol) in t-BuOH (2 mL) was added $NH_4OAc$ (12.82 mg, 166.30 umol) and AgOTf (5.70 mg, 22.17 umol) under $N_2$. The mixture was stirred at 20° C. for 16 hrs. The reaction was quenched by addition of $NaHCO_3$ (0.2 g), and the mixture was stirred at 20° C. for 30 mins. The resulting mixture was filtered and the solid was washed with ethyl acetate (30 mL*3). The combined organic phase was dried over $Na_2SO_4$, filtered and concentrated under reduced pressure. The residue was purified by column chromatography ($SiO_2$, Petroleum ether/Ethyl acetate=0/1) to give the title compound (35 mg, crude) as a yellow solid.

LCMS (ESI) m/z: $[M+H]^+$=360.1.

$^1$H NMR (400 MHz, $CDCl_3$) δ=9.27 (s, 1H), 9.24-9.14 (m, 1H), 8.28-8.18 (m, 1H), 7.97-7.84 (m, 1H), 7.53 (s, 1H), 7.45-7.36 (m, 1H), 5.48-5.29 (m, 1H), 4.58-4.48 (m, 2H), 1.48 (s, 9H) ppm.

Step 8: tert-Butyl ((2-(6-(azetidin-1-yl)pyridin-2-yl)-2H-pyrazolo[4,3-c]pyridin-6-yl)methyl)carbamate Azetidine (15.23 mg, 266.81 umol) and DIEA (114.94 mg, 889.36 umol) were added dropwise to a solution of tert-butyl ((2-(6-chloropyridin-2-yl)-2H-pyrazolo[4,3-c]pyridin-6-yl)methyl)carbamate (32 mg, 88.94 umol) in DMSO (2 mL). The mixture was stirred at 120° C. for 16 hrs. The reaction mixture was cooled to 20° C. and poured into water (20 mL). The products were extracted with ethyl acetate (20 mL*3). The combined organic phases were washed with water (20 mL), dried over $Na_2SO_4$, filtered and concentrated to give the title compound (22 mg, crude) as a yellow oil.

LCMS (ESI) m/z: $[M+H]^+$=381.2.

Step 9: (2-(6-(Azetidin-1-yl)pyridin-2-yl)-2H-pyrazolo[4,3-c]pyridin-6-yl)methanamine TFA (410.67 mg, 3.60 mmol, 266.67 uL) was added to a solution of tert-butyl ((2-(6-(azetidin-1-yl)pyridin-2-yl)-2H-pyrazolo[4,3-c]pyridin-6-yl)methyl)carbamate (20 mg, 52.57 umol) in DCM (2 mL). The mixture was stirred at 20° C. for 1 hr. The solvent was evaporated by a flow of $N_2$ gas to give the title compound (12 mg, crude) as a yellow oil, which was used in the next step without further purification.

LCMS (ESI) m/z: $[M+H]^+$=281.2.

Step 10: (R)—N-((2-(6-(Azetidin-1-yl)pyridin-2-yl)-2H-pyrazolo[4,3-c]pyridin-6-yl)methyl)-4-cyano-4-methylisochromane-6-carboxamide To a solution of (2-(6-(azetidin-1-yl)pyridin-2-yl)-2H-pyrazolo[4,3-c]pyridin-6-yl)methanamine (12 mg, 42.81 umol) in DCM (2 mL) was added (R)-4-cyano-4-methylisochromane-6-carboxylic acid (11.16 mg, 51.37 umol), DIEA (27.66 mg, 214.04 umol), HOBt (6.94 mg, 51.37 umol) and EDCI (9.85 mg, 51.37 umol). Water (30 mL) was added and the products were extracted with ethyl acetate (30 mL*3). The combined organic phase was washed with brine (10 ml*3), dried over $Na_2SO_4$, filtered and concentrated under reduced pressure. The residue was purified by prep-HPLC (0.1% $NH_3 \cdot H_2O$ condition) to give the title compound (4.44 mg, 9.26 umol, 21.63% yield) as a yellow solid.

LCMS (ESI) m/z: $[M+H]^+$=480.2.

$^1$H NMR (400 MHz, DMSO-$d_6$) δ=9.38 (s, 1H), 9.30-9.22 (m, 2H), 8.21-8.15 (m, 1H), 7.95-7.90 (m, 1H), 7.80-7.73 (m, 1H), 7.46 (s, 1H), 7.43-7.37 (m, 1H), 7.32-7.26 (m, 1H), 6.51-6.43 (m, 1H), 4.93-4.81 (m, 2H), 4.72-4.65 (m, 2H), 4.27-4.21 (m, 1H), 4.11-4.07 (m, 4H), 3.90-3.84 (m, 1H), 2.42-2.38 (m, 2H), 1.70 (s, 3H) ppm.

The following examples in Table 22 were prepared using standard chemical manipulations and procedures similar to those used for the preparation of Example 31.

TABLE 22

| Compounds of the Invention | | |
|---|---|---|
| # | LCMS (m/z) | 1H NMR |
| 524 | 424.1 | 1HNMR (400 MHz, DMSO-d6) δ = 9.39 (s, 1H), 9.29-9.22 (m, 2H), 8.18 (d, J = 1.6 Hz, 1H), 8.10 (d, J = 7.6 Hz, 2H), 7.95-7.91 (m, 1H), 7.65-7.59 (m, 2H), 7.53-7.47 (m, 2H), 7.29 (d, J = 8.0 Hz, 1H), 4.95-4.80 (m, 2H), 4.69 (d, J = 5.6 Hz, 2H), 4.22 (d, J = 11.4 Hz, 1H), 3.86 (d, J = 11.6 Hz, 1H), 1.70 (s, 3H) ppm |

Example 32: (R)-4-Cyano-N-((6-(2-methoxyphenyl)-5,6,7,8-tetrahydro-2,6-naphthyridin-3-yl)methyl)-4-methylisochromane-6-carboxamide

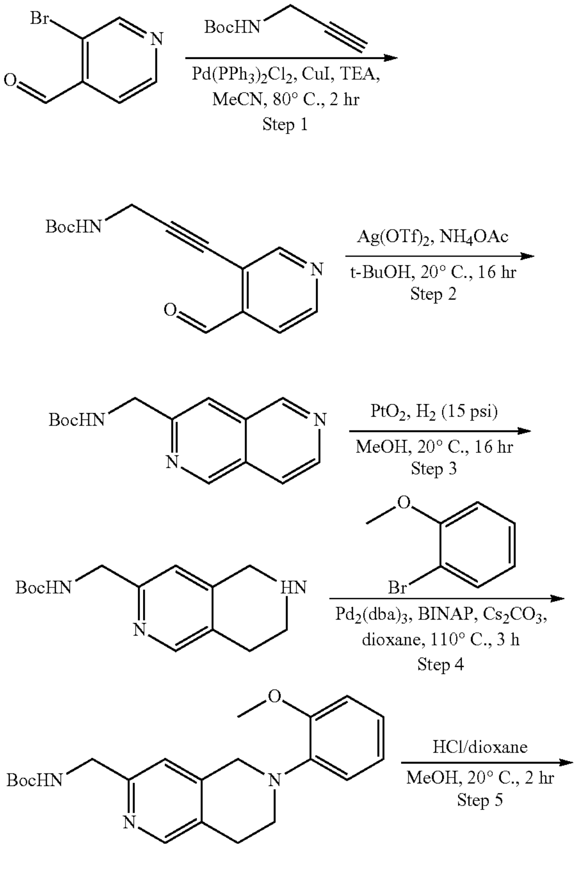

-continued

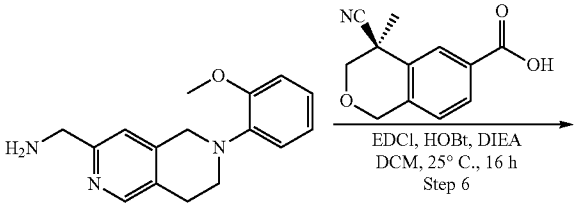

-continued

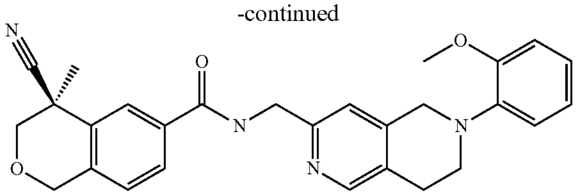

Step 1: tert-Butyl (3-(4-formylpyridin-3-yl)prop-2-yn-1-yl)carbamate

A mixture of 3-bromopyridine-4-carbaldehyde (15 g, 80.64 mmol), tert-butyl prop-2-yn-1-ylcarbamate (13.14 g, 84.67 mmol), $Et_3N$ (81.60 g, 806.43 mmol, 112.25 mL), CuI (1.54 g, 8.06 mmol) and $Pd(PPh_3)_2Cl_2$ (5.66 g, 8.06 mmol) in $CH_3CN$ (120 mL) was stirred at 80° C. for 2 hrs under $N_2$. The reaction mixture was quenched by addition of water (300 mL) and extracted with ethyl acetate (300 mL*3). The combined organic phase was washed with brine (300 mL), dried over $Na_2SO_4$, filtered and concentrated under reduced pressure. The residue was purified by column chromatography ($SiO_2$, Petroleum ether/Ethyl acetate=1/1) to give the title compound (18 g, 69.15 mmol, 85.75% yield) as a brown oil.

LCMS (ESI) m/z: $[M+H]^+$=261.1.

$^1$HNMR (400 MHz, $CDCl_3$) δ=10.48 (s, 1H), 8.66 (s, 1H), 8.78-8.68 (m, 1H), 7.78-7.62 (m, 1H), 4.88 (br s, 1H), 4.32-4.18 (m, 2H), 1.46 (s, 9H) ppm.

Step 2: tert-Butyl ((2,6-naphthyridin-3-yl)methyl)carbamate

To a solution of tert-butyl (3-(4-formylpyridin-3-yl)prop-2-yn-1-yl)carbamate (17 g, 65.31 mmol) in t-BuOH (60 mL) was added $NH_4OAc$ (7.55 g, 97.97 mmol) and AgOTf (3.36 g, 13.06 mmol). The mixture was stirred at 20° C. for 16 hrs. The reaction mixture was quenched by addition of $NaHCO_3$ (22 g), and the reaction mixture was stirred at 20° C. for 30 mins. The mixture was filtered and the filter cake was washed with ethyl acetate (30 mL*3). The combined organic phases were concentrated under reduced pressure and the residue was purified by column chromatography ($SiO_2$, Petroleum ether/Ethyl acetate=0/1) to give the title compound (8.5 g, 32.39 mmol, 49.59% yield) as a yellow oil.

LCMS (ESI) m/z: $[M+H]^+$=260.1.

$^1$HNMR (400 MHz, $CDCl_3$) δ=9.36-9.25 (m, 2H), 8.75-8.61 (m, 1H), 7.82-7.71 (m, 1H), 5.46 (br s, 1H), 4.64-4.62 (m, 2H), 1.46 (s, 9H) ppm.

Step 3: tert-Butyl ((5,6,7,8-tetrahydro-2,6-naphthyridin-3-yl)methyl)carbamate

A mixture of tert-butyl ((2,6-naphthyridin-3-yl)methyl) carbamate (8 g, 30.85 mmol) and $PtO_2$ (700.59 mg, 3.09 mmol) in MeOH (80 mL) was degassed and purged with $H_2$ 3 times. The mixture was stirred at 20° C. for 16 hrs under $H_2$ atmosphere (15 psi). The reaction was filtered and the filter cake was washed with MeOH (50 mL*2). The filtrate was concentrated under vacuum and the residue was purified by column chromatography ($SiO_2$, DCM:MeOH=10/1) to give crude product (5 g) as a black oil. The crude product was purified by reversed-phase HPLC (0.1% FA condition). The desired fraction was adjusted to pH 9 with sat. $NaHCO_3$ and extracted with DCM (200 mL*3). The combined organic phases were dried over $Na_2SO_4$, filtered and concentrated to give the title compound (3.8 g, 14.43 mmol, 46.77% yield) as a yellow oil.

LCMS (ESI) m/z: $[M+H]^+$=264.2.

$^1$HNMR (400 MHz, $CDCl_3$) δ=8.26 (s, 1H), 6.92 (s, 1H), 5.46 (br s, 1H), 4.37-4.35 (m, 2H), 3.98 (s, 2H), 3.17-3.13 (m, 2H), 2.79-2.75 (m, 2H), 1.46 (s, 9H) ppm.

Step 4: tert-Butyl ((6-(2-methoxyphenyl)-5,6,7,8-tetrahydro-2,6-naphthyridin-3-yl)methyl)carbamate A mixture of tert-butyl ((5,6,7,8-tetrahydro-2,6-naphthyridin-3-yl)methyl)carbamate (100 mg, 379.75 umol), 1-bromo-2-methoxy-benzene (213.08 mg, 1.14 mmol, 142.05 uL), BINAP (47.29 mg, 75.95 umol), $Pd_2(dba)_3$ (34.77 mg, 37.97 umol) and $Cs_2CO_3$ (371.18 mg, 1.14 mmol) in dioxane (3 mL) was degassed and purged with $N_2$ 3 times. The mixture was stirred at 110° C. for 3 hrs under $N_2$ atmosphere. The mixture was poured into water (40 mL) and extracted with EA (20 mL*3). The combined organic layers were washed with brine (20 mL), dried over $Na_2SO_4$, filtered and concentrated under vacuum. The residue was purified by reversed-phase HPLC (0.1% FA condition) to give the title compound (80 mg, 155.90 umol, 41.06% yield) as a yellow solid.

LCMS (ESI) m/z: $[M+H]^+$=370.1

Step 5: (6-(2-methoxyphenyl)-5,6,7,8-tetrahydro-2,6-naphthyridin-3-yl)methanamine hydrochloride To a solution of tert-butyl ((6-(2-methoxyphenyl)-5,6,7,8-tetrahydro-2,6-naphthyridin-3-yl)methyl)carbamate (35 mg, 94.73 umol) in MeOH (0.5 mL) was added HCl/dioxane (4 M, 0.5 mL). The mixture was stirred at 20° C. for 2 hrs. The solvent was removed under vacuum to give the title compound (30 mg, crude) as a yellow oil.

LCMS (ESI) m/z: $[M+H]^+$=270.2.

Step 6: (R)-4-Cyano-N-((6-(2-methoxyphenyl)-5,6,7,8-tetrahydro-2,6-naphthyridin-3-yl)methyl)-4-methylisochromane-6-carboxamide To a solution of (6-(2-methoxyphenyl)-5,6,7,8-tetrahydro-2,6-naphthyridin-3-yl)methanamine hydrochloride (30 mg, 98.10 umol) and ((R)-4-cyano-4-methylisochromane-6-carboxylic acid (27.70 mg, 127.53 umol) in DCM (1 mL) was added EDCI (28.21 mg, 147.15 umol), DIEA (63.40 mg, 490.51 umol, 85.44 uL) and HOBt (19.88 mg, 147.15 umol). The mixture was stirred at 25° C. for 16 hrs. The mixture was poured into water (30 mL) and extracted with EA (20 mL*3). The combined organic layers were washed with brine (20 mL, dried over $Na_2SO_4$, filtered and concentrated. The residue was purified by prep-HPLC (column: Phenomenex Gemini-NX C18 75*30 mm*3 um; mobile phase: [water (10 mM $NH_4HCO_3$)-ACN]; B %: 26%-56%, 8 min) to give the title compound (15.64 mg, 31.70 umol, 32.31% yield) as an off-white solid.

LCMS (ESI) m/z: [M+H]+=469.3

$^1$H NMR (400 MHz, METHANOL-$d_4$) δ=8.31 (s, 1H), 8.11 (d, J=1.6 Hz, 1H), 7.90-7.81 (m, 1H), 7.29-7.20 (m, 2H), 7.08-6.96 (m, 3H), 6.94-6.86 (m, 1H), 4.89 (d, J=3.2 Hz, 2H), 4.67 (m, 2H), 4.23 (s, 2H), 4.19 (d, J=11.6 Hz, 1H), 3.91 (d, J=11.6 Hz, 1H), 3.87 (m, 3H), 3.42-3.35 (m, 2H), 3.03-2.94 (m, 2H), 1.74 (s, 3H) ppm.

The following examples in Table 23 were prepared using standard chemical manipulations and procedures similar to those used for the preparation of Example 32.

TABLE 23

| Compounds of the Invention | | |
|---|---|---|
| # | LCMS (m/z) | 1H NMR |
| 209 | 495.4 | 1H NMR (400 MHz, DMSO-d6) δ = 9.25-9.13 (m, 1H), 8.39-8.31 (m, 1H), 8.17-8.08 (m, 2H), 7.79 (s, 2H), 7.36-7.21 (m, 2H), 5.55-5.42 (m, 1H), 4.94-4.81 (m, 2H), 4.61-4.47 (m, 2H), 4.38-4.27 (m, 1H), 4.26-4.17 (m, 1H), 3.95-3.77 (m, 2H), 2.95-2.82 (m, 2H), 2.08-1.93 (m, 1H), 1.69 (s, 3H), 1.47-1.35 (m, 3H), 1.01-0.82 (m, 3H) ppm |
| 230 | 497.5 | 1H NMR (400 MHz, MeOD) δ = 8.31 (s, 1H), 8.16-8.09 (m, 1H), 7.88-7.84 (m, 1H), 7.54 (d, J = 9.6 Hz, 1H), 7.30-7.23 (m, 2H), 6.91 (d, J = 9.6 Hz, 1H), 4.90 (br s, 2H), 4.67 (s, 2H), 4.55-4.50 (m, 2H), 4.19 (d, J = 11.6 Hz, 1H), 4.08-4.00 (m, 1H), 3.96-3.88 (m, 1H), 3.73-3.65 (m, 2H), 2.99-2.91 (m, 2H), 1.76-1.74 (m, 3H), 1.14-1.10 (m, 2H), 0.96-0.88 (m, 2H) ppm |
| 234 | 496.5 | 1H NMR (400 MHz, MeOD) δ = 8.11 (d, J = 2.0 Hz, 1H), 7.87-7.85 (m, 1H), 7.60 (s, 1H), 7.36-7.32 (m, 1H), 7.26 (d, J = 8.0 Hz, 1H), 6.18 (d, J = 8.0 Hz, 1H), 5.72 (d, J = 7.6 Hz, 1H), 4.90 |

TABLE 23-continued

| Compounds of the Invention | | |
|---|---|---|
| # | LCMS (m/z) | 1H NMR |
| | | (br s, 2H), 4.85-4.85 (m, 2H), 4.76 (s, 2H), 4.19 (d, J = 11.6 Hz, 1H), 3.99-3.96 (m, 2H), 3.95-3.89 (m, 5H), 3.22-3.19 (m, 2H), 2.34-2.26 (m, 2H), 1.74 (s, 3H) ppm |
| 247 | 497.3 | 1H NMR (400 MHz, MeOD) δ = 8.11 (d, J = 1.6 Hz, 1H), 7.8-7.85 (m, 1H), 7.62 (s, 1H), 7.49 (s, 1H), 7.26 (d, J = 8.4 Hz, 1H), 7.03 (s, 1H), 4.89 (d, J = 3.6 Hz, 2H), 4.86-4.86 (m, 2H), 4.81 (s, 2H), 4.19 (d, J = 11.6 Hz, 1H), 4.07-3.99 (m, 6H), 3.91 (d, J = 11.6 Hz, 1H), 3.26-3.23 (m, 2H), 2.46-2.36 (m, 2H), 1.74 (s, 3H) ppm |
| 258 | 513.4 | 1H NMR (400 MHz, CHLOROFORM-d) δ = 8.38 (s, 1H), 8.01 (d, J = 1.6 Hz, 1H), 7.80-7.72 (m, 2H), 7.59-7.52 (m, 1H), 7.17-7.12 (m, 2H), 6.26-6.23 (m, 1H), 4.87 (s, 2H), 4.73 (d, J = 4.8 Hz, 2H), 4.43 (s, 2H), 4.22-4.11 (m, 5H), 3.94 (d, J = 11.2 Hz, 1H), 3.61-3.58 (m, 2H), 2.99-2.97 (m, 2H), 2.45-2.33 (m, 2H), 1.77 (s, 3H) ppm |
| 286 | 440.1 | 1HNMR (400 MHz, DMSO-d6) δ = 9.27-9.14 (m, 1H), 8.37-8.31 (m, 1H), 8.16-8.11 (m, 2H), 7.93-7.88 (m, 1H), 7.59-7.51 (m, 1H), 7.31-7.26 (m, 1H), 7.22 (s, 1H), 6.96-6.87 (m, 1H), 6.67-6.60 (m, 1H), 4.93-4.81 (m, 2H), 4.68 (s, 2H), 4.60-4.51 (m, 2H), 4.27-4.19 (m, 1H), 3.89-3.83 (m, 3H), 2.89-2.84 (m, 2H), 1.69 (s, 3H)ppm |
| 298 | 496.3 | 1HNMR (400 MHz, DMSO-d6) δ = 8.54-8.46 (m, 1H), 8.34 (s, 1H), 8.14-8.13 (m, 1H), 7.91-7.86 (m, 1H), 7.49-7.44 (m, 1H), 7.32 (s, 1H), 7.29-7.27 (m, 1H), 7.02 (s, 1H), 4.91 (br s, 2H), 4.75-4.72 (m, 2H), 4.60 (s, 2H), 4.26-4.17 (m, 2H), 4.08 (s, 4H), 3.96-3.90 (m, 3H), 2.98-2.94 (m, 2H), 2.47-2.39 (m, 2H), 1.77 (s, 3H) ppm |
| 304 | 490.5 | 1H NMR (400 MHz, CHLOROFORM-d) δ = 8.40 (s, 1H), 8.03 (d, J = 1.6 Hz, 1H), 7.80-7.78 (m, 1H), 7.66-7.62 (m, 2H), 7.14 (d, J = 8.4 Hz, 1H), 6.96 (d, J = 7.6 Hz, 1H), 6.78 (d, J = 8.4 Hz, 1H), 6.62-6.34 (m, 1H), 4.87 (s, 2H), 4.76-4.74 (m, 4H), 4.14 (d, J = 11.2 Hz, 1H), 3.95-3.91 (m, 3H), 2.99-2.96 (m, 2H), 1.76 (s, 3H) ppm |
| 314 | 526.3 | 1H NMR (400 MHz, DMSO-d6) δ = 9.28-9.17 (m, 1H), 8.34 (s, 1H), 8.14 (m, 1H), 7.95-7.86 (m, 1H), 7.66 (s, 1H), 7.53 (s, 1H), 7.31-7.26 (m, 1H), 7.22 (s, 1H), 4.92-4.81 (m, 2H), 4.66(s, 2H), 4.61-4.50(m, 2H), 4.25-4.19 (m, 1H), 3.89-3.80 (m, 3H), 3.71-3.65 (m, 4H), 3.46-3.42 (m, 4H), 2.91-2.82 (m, 2H), 1.66 (s, 3H) ppm |
| 326 | 484.2 | 1H NMR (400 MHz, DMSO-d6) δ = 9.22-9.19 (m, 1H), 8.34 (s, 1H), 8.17-8.12 (m, 2H), 7.92-7.85 (m, 2H), 7.27 (d, J = 8.4 Hz, 1H), 7.21 (s, 1H), 6.12(d, J = 6.0 Hz, 1H), 4.94-4.78 (m, 2H), 4.71 (s, 2H), 4.61-4.48 (m, 2H), 4.21 (d, J = 11.6 Hz, 1H), 3.90-3.79 (m, 3H), 3.05 (s, 6H), 2.85-2.82 (m, 2H), 1.68 (s, 3H) ppm. |
| 327 | 481.2 | 1H NMR (400 MHz, MeOD) δ = 8.35 (s, 1H), 8.32 (br s, 1H), 8.12 (d, J = 1.6 Hz, 1H), 8.04 (d, J = 6.8 Hz, 1H), 7.87-7.85 (m, 1H), 7.32 (s, 1H), 7.27 (d, J = 8.0 Hz, 1H), 6.72 (d, J = 6.4 Hz, 1H), 4.89 (d, J = 3.2 Hz, 2H), 4.83 (s, 2H), 4.67(s, 2H), 4.20 (d, J = 11.6 Hz, 1H), 3.98-3.96 (m, 2H), 3.92 (d, J = 11.6 Hz, 1H), 2.97-2.94 (m, 2H), 2.04-2.01 (m, 1H), 1.74 (s, 3H), 1.14-1.12 (m, 2H), 1.06-1.04(m, 2H) ppm. |
| 328 | 481.2 | 1H NMR (400 MHz, MeOD) δ = 8.32 (s, 1H), 8.12 (d, J = 1.6 Hz, 1H), 7.96 (s, 1H), 7.88-7.85 (m, 1H), 7.74 (s, 1H), 7.31(s, 1H), 7.27 (d, J = 8.0 Hz, 1H), 4.89 (d, J = 3.6 Hz, 2H), 4.73 (s, 2H), 4.67 (s, 2H), 4.20 (d, J = 11.6 Hz, 1H), 3.92-3.89 (m, 3H), 2.96-2.93 (m, 2H), 2.02-1.97 (m, 1H), 1.74 (s, 3H), 1.01-0.95 (m, 4H) ppm. |
| 330 | 526.2 | 1H NMR (400 MHz, DMSO-d6) δ = 9.22-9.19 (m, 1H), 8.34 (s, 1H), 8.14 (d, J = 1.2 Hz, 1H), 7.94-7.87 (m, 2H), 7.28 (d, J = 8.4 Hz, 1H), 7.21 (s, 1H), 6.21 (d, J = 6.0 Hz, 1H), 4.91-4.80 (m, 2H), 4.70 (s, 2H), 4.60-4.52 (m, 2H), 4.21 (d, J = 11.2 Hz, 1H), 3.93-3.75 (m, 3H), 3.62 (s, 8H), 2.85-2.82 (m, 2H), 1.68 (s, 3H) ppm. |
| 331 | 510.2 | 1H NMR (400 MHz, DMSO-d6) δ = 9.34-9.12 (m, 1H), 8.40-8.27 (m, 1H), 8.14 (d, J = 1.2 Hz, 1H), 7.95-7.82 (m, 2H), 7.36-7.14 (m, 2H), 6.20-6.07 (m, 1H), 4.93-4.78 (m, 2H), 4.71 (s, 2H), 4.62-4.47 (m, 2H), 4.27-4.15 (m, 1H), 3.84-3.83 (m, 3H), 3.50-3.43 (m, 4H), 2.83-2.82 (m, 2H), 1.92-1.82 (m, 4H), 1.68 (s, 3H) ppm. |
| 332 | 496.2 | 1HNMR (400 MHz, DMSO-d6) δ = 9.32-9.11 (m, 1H), 8.41-8.30 (m, 2H), 8.14 (s, 1H), 7.94-7.85 (m, 2H), 7.32-7.25 (m, 1H), 7.19 (s, 1H), 6.22-6.15 (m, 1H), 4.96-4.87 (m, 2H), 4.69 (s, 2H), 4.59-4.50 (m, 2H), 4.27-4.17 (m, 1H), 3.97-3.90 (m, 4H), 3.88 (s, 1H), 2.87-2.80 (m, 2H), 2.24-2.19 (m, 2H), 1.69 (s, 3H) ppm |

TABLE 23-continued

| Compounds of the Invention | | |
| --- | --- | --- |
| # | LCMS (m/z) | 1H NMR |
| 402 | 495.5 | 1H NMR (400 MHz, CHLOROFORM-d) δ = 8.35 (s, 1H), 8.01 (d, J = 1.6 Hz, 1H), 7.79-7.76 (m, 1H), 7.57-7.36(m, 1H), 7.35-7.31 (m, 1H), 7.18 (s, 1H), 7.13 (d, J = 8.0 Hz, 1H), 6.01 (d, J = 8.0 Hz, 1H), 5.68 (d, J = 7.6 Hz, 1H), 4.87 (s, 2H), 4.72 (d, J = 4.8 Hz, 2H), 4.69 (s, 2H), 4.14 (d, J = 11.6 Hz, 1H), 3.99-3.95 (m, 4H), 3.94 (d, J = 11.2 Hz, 1H), 3.87-3.84 (m, 2H), 2.96-2.89 (m, 2H), 2.38-2.31 (m, 2H), 1.76 (s, 3H) ppm. |

Example 33: (R)-4-cyano-4-methyl-N-((6-phenylthiazolo[5,4-c]pyridazin-3-yl)methyl)isochromane-6-carboxamide

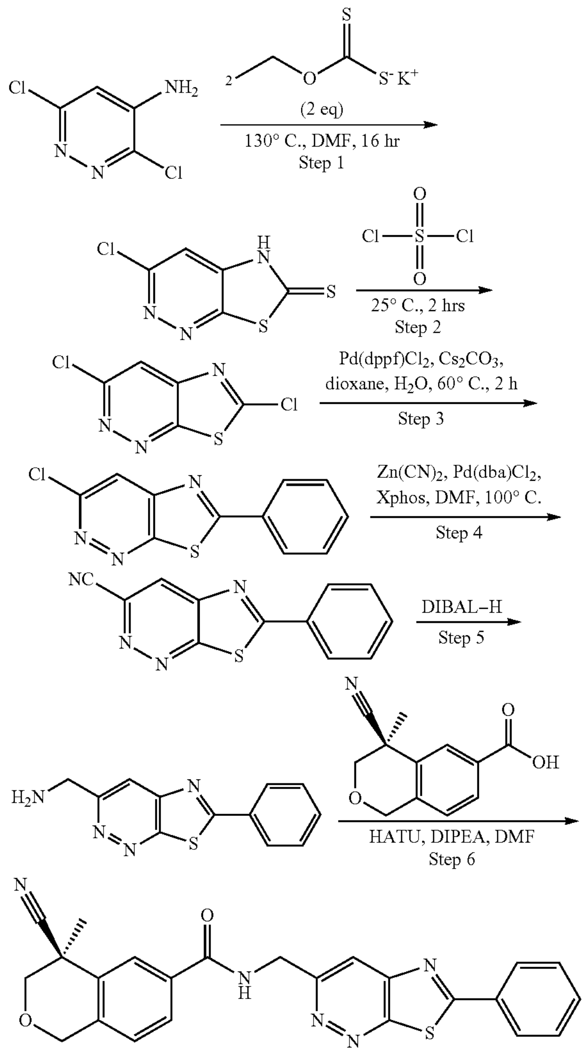

Step 1: 3-Chlorothiazolo[5,4-c]pyridazine-6(5H)-thione

A mixture of 3,6-dichloropyridazin-4-amine (5.00 g, 30.490 mmol, 1.00 equiv) and potassium ethyl xanthogenate (14.78 g, 121.957 mmol, 4.00 equiv) in DMF (10 mL) was stirred at 130° C. for 12 h. The resulting mixture was diluted with water (500 mL) and extracted with EtOAc (500 mL×3). The combined organic layers were washed with brine (100 mL×1), dried over anhydrous $Na_2SO_4$, filtered and concentrated under reduced pressure to give the title compound (4.8 g, 79.67%) as a white solid that was used directly without further purification.

LCMS (ESI) m/z $[M+H]^+$=204.

Step 2: 3,6-Dichlorothiazolo[5,4-c]pyridazine

A mixture of 3-chlorothiazolo[5,4-c]pyridazine-6(5H)-thione (2.00 g, 9.820 mmol, 1.00 equiv) in sulfonyl chloride (3.00 mL) was stirred for 2 h at 0 degrees C. under nitrogen atmosphere. The residue was neutralized to pH 9 with saturated aq. $Na_2CO_3$. The resulting mixture was extracted with $CH_2Cl_2$ (1 L×3) and concentrated under reduced pressure. The residue was purified by silica gel column chromatography, elution gradient 0 to 100% EtOAc in petroleum ether. Pure fractions were evaporated to dryness to afford intermediate 3 (1.3 g, 61.68%) as a white solid which was used directly without further purification.

LCMS (ESI) m/z [M+H]+=206.

Step 3: 3-Chloro-6-phenylthiazolo[5,4-c]pyridazine

To a stirred mixture of 3,6-dichlorothiazolo[5,4-c]pyridazine (800.00 mg, 3.883 mmol, 1.00 equiv) and $Cs_2CO_3$ (2530.15 mg, 7.765 mmol, 2.00 equiv) in dioxane (4.00 mL) and $H_2O$ (1.00 mL) was added Pd(dppf)$Cl_2$ (284.10 mg, 0.388 mmol, 0.10 equiv). The resulting mixture was stirred for 2.5 h at room temperature. The resulting mixture was diluted with water (30.0 mL) and extracted with EtOAc (30.0 mL×3). The combined organic layers were washed with brine (25.0 mL×1), dried over anhydrous $Na_2SO_4$, filtered and concentrated under reduced pressure. The residue was purified by prep-HPLC to give the title compound (320 mg, 29.95%) as a white solid.

LCMS (ESI) m/z $[M+H]^+$=248.

Step 4: 6-Phenylthiazolo[5,4-c]pyridazine-3-carbonitrile

To a stirred mixture of 3-chloro-6-phenylthiazolo[5,4-c]pyridazine (310.00 mg, 1.252 mmol, 1.00 equiv) and $Zn(CN)_2$ (293.97 mg, 2.503 mmol, 2.00 equiv) in DMF (4.00 mL) were added $Pd_2(dba)_3$ (229.21 mg, 0.250 mmol, 0.20 equiv) and XPhos (238.65 mg, 0.501 mmol, 0.40 equiv). The reaction mixture was stirred at 40° C. under nitrogen atmosphere for 2 h. The resulting mixture was diluted with water (30.0 mL) and extracted with EtOAc (30.0 mL×3). The combined organic layers were washed with brine (25.0 mL×1), dried over anhydrous $Na_2SO_4$, filtered and concentrated under reduced pressure. The residue was purified by silica gel column chromatography, elution gradient 0 to 100% EtOAc in petroleum ether to give the title compound (150 mg, 48.29%) as a yellow solid.

LCMS (ESI) m/z $[M+H]^+$=239.

Step 5: (6-Phenylthiazolo[5,4-c]pyridazin-3-yl) methanamine

To a stirred mixture of 6-phenylthiazolo[5,4-c]pyridazine-3-carbonitrile (130.00 mg, 0.546 mmol, 1.00 equiv) in DCM (4.00 mL) was added DIBAL-H (77.59 mg, 0.546 mmol, 1.00 equiv) dropwise at 0° C. The mixture was stirred for 30 min. The resulting mixture was diluted with water (30.0 mL) and extracted with EtOAc (30.0 mL×3). The combined organic layers were washed with brine (25.0 mL×1), dried over anhydrous $Na_2SO_4$, filtered and concentrated under reduced pressure. The residue was purified by silica gel column chromatography, elution gradient 0 to 100% EtOAc in petroleum ether, to give the title compound (40 mg, 29.05%) as an off-white solid.

LCMS (ESI) m/z $[M+H]^+$=243.

Step 6: (R)-4-Cyano-4-methyl-N-((6-phenylthiazolo [5,4-c]pyridazin-3-yl)methyl)isochromane-6-carboxamide To a stirred mixture of (R)-4-cyano-4-methylisochromane-6-carboxylic acid (16.14 mg, 0.025 mmol, 1.00 equiv) and (6-phenylthiazolo[5,4-c]pyridazin-3-yl)methanamine (18 mg, 0.025 mmol, 1.00 equiv) in DMF (1.50 mL) were added HATU (22.55 mg, 0.021 mmol, 1.00 equiv) and DIEA (24.00 mg, 0.062 mmol, 3.00 equiv). The resulting mixture was stirred for 1 h at room temperature. Without any additional work-up, the mixture was purified by prep-HPLC (Column: Xselect CSH F-Phenyl OBD column, 19*250, Sum; Mobile Phase A: Water (0.05% FA), Mobile Phase B: ACN; Flow rate: 25 mL/min; Gradient: 27 B to 55 B in 10 min, 55 B to B in min, B to B in min, B to B in min, B to B in min; 254/220 nm; $RT_1$:8.4; $RT_2$; Injection Volume: mL; Number of Runs;) to give the title compound (6.0 mg, 31.71%) as a white solid.

LCMS (ESI) m/z $[M+H]^+$=443.05.

$^1H$ NMR (300 MHz, Methanol-$d_4$) δ 8.32-8.24 (m, 2H), 8.22 (s, 1H), 8.16 (d, J=1.8 Hz, 1H), 7.91 (dd, J=8.1, 1.8 Hz, 1H), 7.66 (dt, J=14.7, 7.1 Hz, 3H), 7.30 (d, J=8.2 Hz, 1H), 5.09 (s, 2H), 4.92 (s, 2H), 4.22 (d, J=11.4 Hz, 1H), 3.94 (d, J=11.4 Hz, 1H), 1.77 (s, 3H).

Example 34: (S)—N-((2-(6-Cyclopropylpyrazin-2-yl)pyrido[3,4-b]pyrazin-7-yl)methyl)-4-fluoro-4-methylisochromane-6-carboxamide

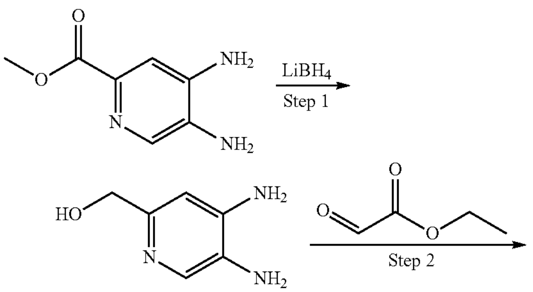

-continued

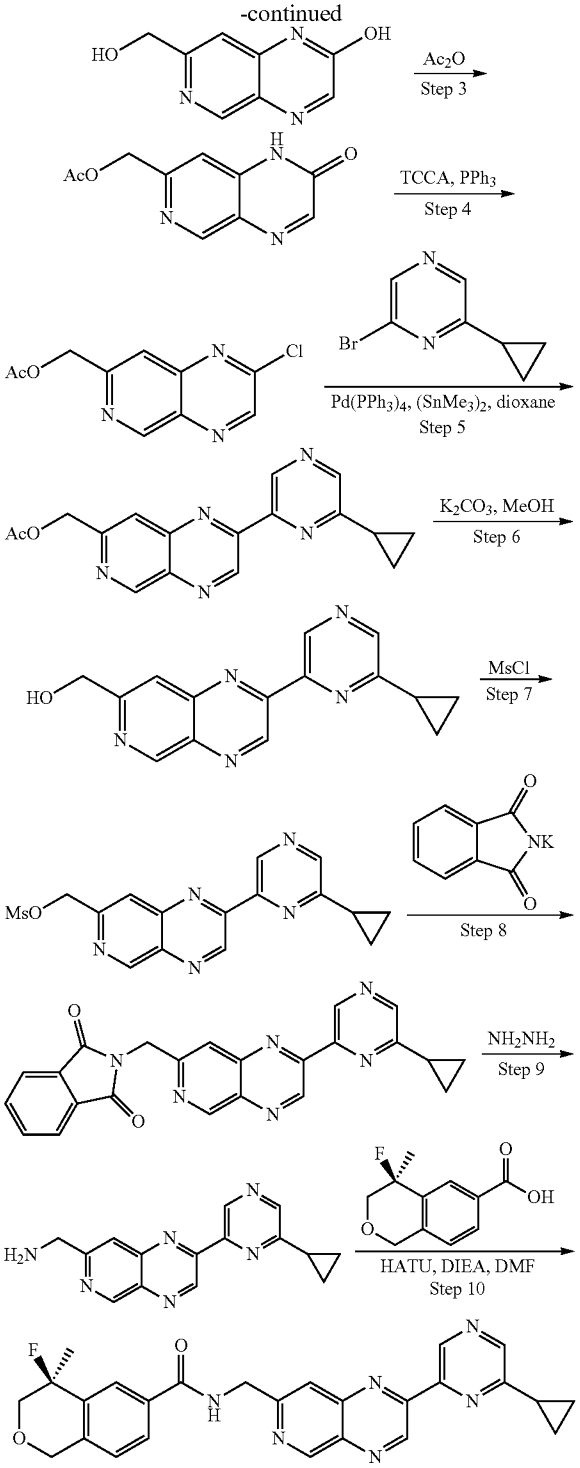

Step 1: (4,5-Diaminopyridin-2-yl)methanol

To a stirred mixture of methyl 4,5-diaminopyridine-2-carboxylate (8.00 g, 47.856 mmol, 1.00 equiv) in THF (80 mL) was added LiBH4 (2M in THF, 119.64 mL, 239.280 mmol, 5.00 equiv) dropwise at 0° C. The resulting mixture was stirred for 13 h at room temperature. The mixture was quenched with sat. aq. $NaHCO_3$ (500 mL) and concentrated under vacuum to give a crude product. The crude product was purified by aluminum oxide column chromatography, eluted with DCM/MeOH from 20/1 to 2/1 to give the title compound (6 g, 90.10%) as an off-white solid.

LCMS (ESI) m/z: [M+H]+=140.

Step 2: 7-(Hydroxymethyl)pyrido[3,4-b]pyrazin-2-ol

To a solution of (4,5-diaminopyridin-2-yl)methanol (5.00 g, 35.930 mmol, 1.00 equiv) in n-BuOH (500.00 mL) was added ethyl glyoxylate (7.70 g, 37.727 mmol, 1.05 equiv, 50%). The resulting mixture was stirred for 8 h at 100° C. The reaction was cooled and filtered, and the filtrate was concentrated to give the title compound (3.1 g, 48.70%) as a yellow solid that was used directly without further purification.

LCMS (ESI) m/z: [M+H]+=178.

Step 3: (2-Oxo-1,2-dihydropyrido[3,4-b]pyrazin-7-yl)methyl acetate

To a solution of 7-(hydroxymethyl)pyrido[3,4-b]pyrazin-2-ol (3.10 g, 17.498 mmol, 1.00 equiv) and DMAP (1068.85 mg, 8.749 mmol, 0.50 equiv) in DCM (50 mL) were added TEA (2.66 g, 26.287 mmol, 1.50 equiv) and Ac2O (5.36 g, 52.503 mmol, 3.00 equiv). The resulting mixture was stirred for 2 h at room temperature. The resulting mixture was concentrated and the residue was purified by silica gel column chromatography eluted with DCM/MeOH=50/1 to give the title compound (3.1 g, 80.82%) as a yellow solid.

LCMS (ESI) m/z: [M+H]+=220.

Step 4: (2-Chloropyrido[3,4-b]pyrazin-7-yl)methyl acetate

To a solution of $PPh_3$ (5.80 g, 22.112 mmol, 4.8 equiv) in toluene (100.00 mL) was added trichloroisocyanuric acid (1.71 g, 7.371 mmol, 1.60 equiv). The resulting mixture was stirred for 24 h at room temperature. To the above mixture, (2-oxo-1,2-dihydropyrido[3,4-b]pyrazin-7-yl)methyl acetate (1.53 g, 6.97 mmol, 1.00 equiv) was added. The resulting mixture was stirred for an additional 5 h at 110° C. The mixture was concentrated and the residue was purified by silica gel column chromatograph eluting with PE/EA from 50/1 to 8/1 to give the title compound (610 mg, 55.72%) as an off-white solid.

LCMS (ESI) m/z: [M+H]+=238.

Step 5: (2-(6-Cyclopropylpyrazin-2-yl)pyrido[3,4-b]pyrazin-7-yl)methyl acetate

To a stirred solution of (2-chloropyrido[3,4-b]pyrazin-7-yl)methyl acetate (250.00 mg, 1.052 mmol, 1.00 equiv) and $Sn_2Me_6$ (413.60 mg, 1.262 mmol, 1.20 equiv) in dioxane (2.00 mL) was added $Pd(PPh_3)_4$ (121.57 mg, 0.105 mmol, 0.10 equiv) at room temperature under nitrogen atmosphere. The resulting mixture was stirred at 100° C. for 2 h under nitrogen atmosphere. To the above mixture was added additional (2-chloropyrido[3,4-b]pyrazin-7-yl)methyl acetate (250.00 mg, 1.052 mmol, 1.00 equiv) at room temperature and the resulting mixture was stirred overnight at 100° C. The solvent was removed under reduced pressure and the residue was purified by silica gel column chromatography, eluting with PE/EtOAc (12:1) to give the title compound (298 mg, crude) as a light yellow solid.

(LCMS (ESI) m/z [M+H]+=321.

Step 6: (2-(6-Cyclopropylpyrazin-2-yl)pyrido[3,4-b]pyrazin-7-yl)methanol

To a stirred solution of (2-(6-cyclopropylpyrazin-2-yl)pyrido[3,4-b]pyrazin-7-yl)methyl acetate (285.00 mg, 0.887 mmol, 1.00 equiv) in MeOH (5.00 mL) was added $K_2CO_3$ (245.15 mg, 1.774 mmol, 2.00 equiv). The resulting mixture was stirred at 60° C. for 2 h. The solid was filtered off and the filtrate was concentrated under vacuum to give the title compound (48 mg, 30.32%) as a light yellow solid that was used directly without further purification.

(LCMS (ESI) m/z [M+H]+=280.

Step 7: (2-(6-Cyclopropylpyrazin-2-yl)pyrido[3,4-b]pyrazin-7-yl)methyl methanesulfonate To a stirred solution (2-(6-cyclopropylpyrazin-2-yl)pyrido[3,4-b]pyrazin-7-yl)methanol (270.00 mg, 0.967 mmol, 1.00 equiv) and TEA (195.64 mg, 1.934 mmol, 2.00 equiv) in DCM (5.00 mL) was added MsCl (166.10 mg, 1.451 mmol, 1.50 equiv) at room temperature. The resulting mixture was stirred for 2 h at room temperature. The resulting mixture was concentrated under vacuum. The residue was purified by silica gel column chromatography, eluting with PE/EtOAc (1:1) to give the title compound (115 mg, 33.29%) as a light yellow solid.

(LCMS (ESI) m/z $[M+H]^+$=358.

Step 8: 2-((2-(6-Cyclopropylpyrazin-2-yl)pyrido[3,4-b]pyrazin-7-yl)methyl)isoindoline-1,3-dione To a stirred solution of (2-(6-cyclopropylpyrazin-2-yl)pyrido[3,4-b]pyrazin-7-yl)methyl methanesulfonate (105.00 mg, 0.294 mmol, 1.00 equiv) in DMF (2.00 mL) was added potassium 1,3-dioxoisoindolin-2-ide (108.84 mg, 0.588 mmol, 2.00 equiv) at room temperature. The resulting mixture was stirred for 2 h at room temperature. The reaction was quenched with water (10 mL) and the precipitated solids were collected by filtration and washed with $H_2O$ (3×10 mL). The resulting solid was dried under vacuum to give the title compound (69 mg, 57.50%) as a light yellow solid.

(LCMS (ESI) m/z $[M+H]^+$=409.

Step 9: (2-(6-Cyclopropylpyrazin-2-yl)pyrido[3,4-b]pyrazin-7-yl)methanamine

To a stirred solution of 2-((2-(6-cyclopropylpyrazin-2-yl)pyrido[3,4-b]pyrazin-7-yl)methyl)isoindoline-1,3-dione (60.00 mg, 0.147 mmol, 1.00 equiv) in EtOH (5.00 mL) was added hydrazine hydrate (0.50 mL) at room temperature. The resulting mixture was stirred for 2 h at 80° C. under nitrogen atmosphere. The resulting mixture was concentrated under vacuum to the title compound (72 mg, crude) as a light yellow solid that was used directly without further purification.

(LCMS (ESI) m/z $[M+H]^+$=279.

Step 10: (S)—N-((2-(6-Cyclopropylpyrazin-2-yl)pyrido[3,4-b]pyrazin-7-yl)methyl)-4-fluoro-4-methylisochromane-6-carboxamide To a stirred solution of (S)-4-fluoro-4-methylisochromane-6-carboxylic acid (20.00 mg, 0.095 mmol, 1.00 equiv) and HATU (43.41 mg, 0.114 mmol, 1.20 equiv) in DMF (2.00 mL) were added DIEA (36.89 mg, 0.285 mmol, 3.00 fequiv) and (2-(6-cyclopropylpyrazin-2-yl)pyrido[3,4-b]pyrazin-7-yl)methanamine (29.13 mg, 0.105 mmol, 1.10 equiv) at room temperature. The resulting mixture was stirred for 2 h at room temperature. Without any additional work-up, the mixture was purified by prep-HPLC to give the title compound (20 mg, 44.68%) as a light yellow solid.

LCMS (ESI) m/z: [M+H]+=471.20.

1H NMR (400 MHz, DMSO-d6) δ 9.84 (s, 1H), 9.55 (s, 1H), 9.46 (t, J=5.8 Hz, 1H), 9.40 (s, 1H), 8.85 (s, 1H), 8.28 (d, J=1.8 Hz, 1H), 8.02-7.90 (m, 2H), 7.31 (d, J=8.0 Hz, 1H), 4.95-4.81 (m, 3H), 4.79-4.69 (m, 1H), 4.08 (t, J=13.0 Hz, 1H), 3.85 (dd, J=25.1, 12.5 Hz, 1H), 2.43-2.31 (m, 1H), 1.70 (d, J=20.7 Hz, 3H), 1.29-1.09 (m, 4H).

The following examples in Table 24 were prepared using standard chemical manipulations and procedures similar to those used for the preparation of Example 34.

TABLE 24

| Compounds of the Invention | | |
|---|---|---|
| # | LCMS (m/z) | 1H NMR |
| 143 | 513.20 | $^1$H NMR (300 MHz, Methanol-$d_4$) δ 9.97 (s, 1H), 9.47 (d, J = 0.8 Hz, 1H), 8.55 (dd, J = 8.4, 0.8 Hz, 1H), 8.39 (dd, J = 7.6, 0.9 Hz, 1H), 8.29-8.24 (m, 1H), 8.06-7.90 (m, 3H), 7.30 (d, J = 8.1 Hz, 1H), 4.97 (s, 2H), 4.86-4.76 (m, 2H), 4.37-4.29 (m, 2H), 4.10 (t, J = 12.3 Hz, 1H), 3.98-3.83 (m, 1H), 2.79-2.69 (m, 2H), 2.32-2.18 (m, 2H), 1.75 (d, 3H). |
| 161 | 463.10 | $^1$H NMR (400 MHz, DMSO-$d_6$) δ 9.42 (t, J = 5.9 Hz, 1H), 9.31 (d, J = 1.2 Hz, 2H), 8.49 (s, 1H), 8.28 (d, J = 1.7 Hz, 1H), 7.97 (dt, J = 8.0, 1.7 Hz, 1H), 7.63 (d, J = 0.9 Hz, 1H), 7.31 (d, J = 8.0 Hz, 1H), 4.87 (dd, J = 15.9, 2.5 Hz, 1H), 4.85-4.69 (m, 3H), 4.08 (t, J = 13.0 Hz, 1H), 4.00 (s, 3H), 3.85 (dd, J = 25.3, 12.5 Hz, 1H), 3.79 (s, 3H), 1.70 (d, J = 20.7 Hz, 3H). |
| 183 | 487.05 | $^1$H NMR (300 MHz, DMSO-$d_6$) δ 9.88 (s, 1H), 9.66-9.56 (m, 2H), 9.13-9.06 (m, 1H), 8.62 (d, J = 4.9 Hz, 2H), 8.04-7.98 (m, 1H), 7.66 (d, J = 5.0 Hz, 1H), 4.95-4.71 (m, 4H), 4.26-4.08 (m, 5H), 3.92 (dd, J = 25.3, 12.7 Hz, 1H), 2.46-2.31 (m, 2H), 1.72 (d, J = 20.9 Hz, 3H). |
| 190 | 486.20 | $^1$H NMR (400 MHz, DMSO-$d_6$) δ 9.86 (s, 1H), 9.56 (s, 1H), 9.45 (t, J = 5.9 Hz, 1H), 8.60 (d, J = 4.9 Hz, 1H), 8.31-8.24 (m, 1H), 8.01-7.91 (m, 2H), 7.66 (d, J = 5.0 Hz, 1H), 7.31 (d, J = 8.1 Hz, 1H), 4.92-4.82 (m, 3H), 4.77-4.71 (m, 1H), 4.19 (t, J = 7.5 Hz, 4H), 4.08 (t, J = 13.0 Hz, 1H), 3.84 (dd, J = 25.2, 12.5 Hz, 1H), 2.44-2.32 (m, 2H), 1.69 (d, J = 20.7 Hz, 3H). |
| 207 | 503.25 | $^1$H NMR (300 MHz, DMSO-$d_6$) δ 9.57 (d, J = 0.8 Hz, 1H), 9.49-9.38 (m, 2H), 8.27 (s, 1H), 8.11-8.06 (m, 1H), 8.01-7.91 (m, 2H), 7.31 (d, J = 8.1 Hz, 1H), 7.25-7.17 (m, 1H), 4.92-4.81 (m, 3H), 4.78-4.68 (m, 1H), 4.23-4.17 (m, 3H), 4.10-4.02 (m, 1H), 3.85 (dd, J = 25.1, 12.6 Hz, 1H), 2.43-2.32 (m, 2H), 1.70 (d, J = 20.7 Hz, 3H). |
| 214 | 485.30 | $^1$H NMR (300 MHz, DMSO-$d_6$) δ 9.90 (s, 1H), 9.50 (s, 1H), 9.48-9.39 (m, 1H), 8.28 (s, 1H), 7.98 (d, J = 7.9 Hz, 1H), 7.93-7.64 (m, 3H), 7.31 (d, J = 8.2 Hz, 1H), 6.60 (d, J = 8.0 Hz, 1H), 4.97-4.62 (m, 4H), 4.21-3.96 (m, 5H), 3.85 (dd, J = 24.9, 12.6 Hz, 1H), 2.45-2.22 (m, 2H), 1.70 (d, J = 20.7 Hz, 3H). |
| 215 | 504.20 | $^1$H NMR (400 MHz, DMSO-$d_6$) δ 9.59 (d, J = 12.5 Hz, 2H), 9.40 (s, 1H), 9.08 (s, 1H), 8.61 (s, 1H), 8.12-7.97 (m, 2H), 7.20 (s, 1H), 4.97-4.71 (m, 4H), 4.27-4.12 (m, 5H), 3.91 (dd, J = 25.2, 12.6 Hz, 1H), 2.45-2.31 (m, 2H), 1.71 (d, J = 20.9 Hz, 3H). |
| 216 | 486.30 | $^1$H NMR (300 MHz, DMSO-$d_6$) δ 9.90 (s, 1H), 9.67-9.57 (m, 1H), 9.51 (s, 1H), 9.10 (d, J = 2.1 Hz, 1H), 8.63 (s, 1H), 7.96 (s, 1H), 7.90-7.67 (m, 2H), 6.61 (d, J = 8.0 Hz, 1H), 4.97-4.71 (m, 4H), 4.26-4.02 (m, 5H), 3.92 (dd, J = 25.3, 12.6 Hz, 1H), 2.45-2.26 (m, 2H), 1.72 (d, J = 20.9 Hz, 3H). |
| 256 | 459.05 | $^1$H NMR (300 MHz, DMSO-$d_6$) δ 9.54-9.39 (m, 3H), 8.28 (d, J = 1.8 Hz, 1H), 8.02-7.93 (m, 1H), 7.92-7.81 (m, 2H), 7.66-7.53 (m, 1H), 7.37-7.24 (m, 2H), 7.22-7.11 (m, 1H), 4.94-4.80 (m, 3H), 4.73 (dd, J = 15.8, 4.5 Hz, 1H), 4.08 (t, J = 13.0 Hz, 1H), 3.98-3.76 (m, 4H), 1.70 (d, J = 20.7 Hz, 3H). |
| 463 | 435.9 | 1H NMR (400 MHz, DMSO-$d_6$) δ = 9.71 (s, 1H), 9.49 (s, 1H), 9.47-9.41 (m, 1H), 8.43-8.34 (m, 2H), 8.20 (d, J = 1.6 Hz, 1H), 7.99-7.93 (m, 1H), 7.90 (s, 1H), 7.67-7.59 (m, 3H), 7.36-7.27 (m, 1H), 5.01-4.79 (m, 4H), 4.29-4.16 (m, 1H), 3.89-3.85 (m, 1H), 1.70 (s, 3H) ppm. |

Examples 35 and 36: (R)-4-Cyano-N-((2-(4-fluoro-3-methyl-1H-pyrazol-1-yl)-1,6-naphthyridin-7-yl)methyl)-4-methylisochromane-6-carboxamide and (R)-4-cyano-N-((2-(4-fluoro-1H-pyrazol-1-yl)-1,6-naphthyridin-7-yl)methyl)-4-methylisochromane-6-carboxamide

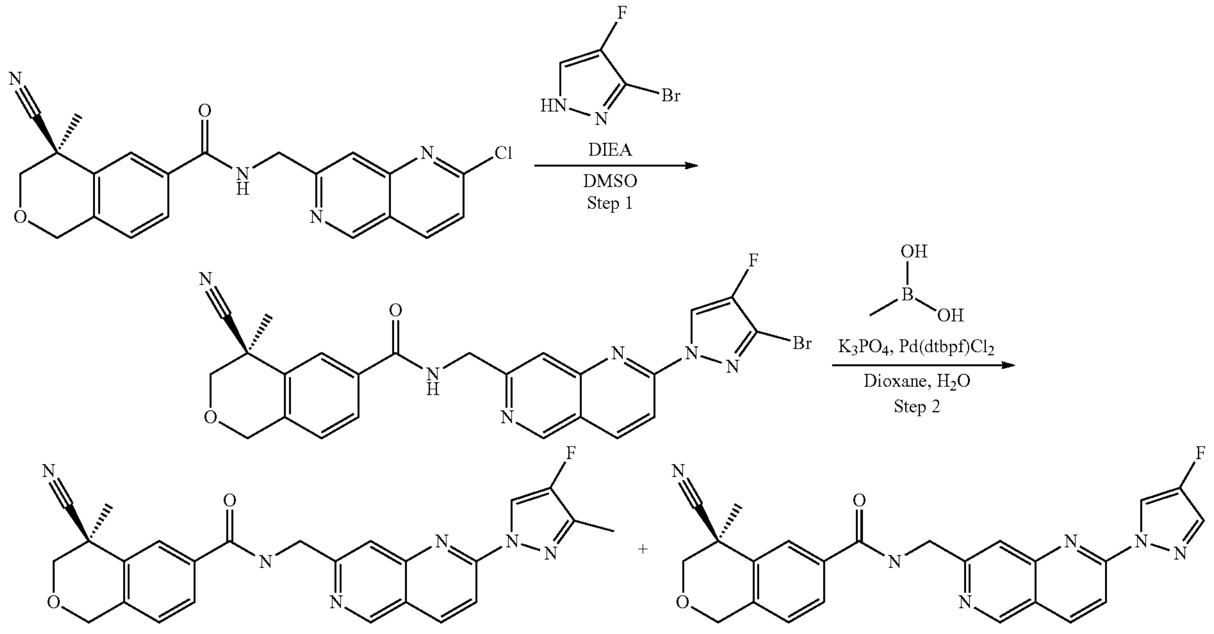

Step 1: (R)—N-((2-(3-Bromo-4-fluoro-1H-pyrazol-1-yl)-1,6-naphthyridin-7-yl)methyl)-4-cyano-4-methylisochromane-6-carboxamide A mixture of (R)—N-((2-chloro-1,6-naphthyridin-7-yl)methyl)-4-cyano-4-methylisochromane-6-carboxamide (30 mg, 76.37 umol), 3-bromo-4-fluoro-1H-pyrazole (62.99 mg, 381.85 umol) and DIEA (98.70 mg, 763.70 umol, 133.02 uL) in DMSO (0.5 mL) was stirred at 120° C. for 2 hrs. The reaction was poured into water (4 mL) and extracted with EA (4 mL*3). The combined organic layers were dried by $Na_2SO_4$, filtered and concentrated under reduced pressure. The residue was purified by prep-HPLC (FA condition) to give the title compound (30 mg, 56.38 umol, 73.83% yield,) as a white solid.

LCMS (ESI) m/z: [81 BrM+H]+=523.1.

1 HNMR (400 MHz, DMSO-d6) δ=9.45-9.42 (m, 1H), 9.41 (s, 1H), 9.08 (d, J=4.8 Hz, 1H), 8.78 (d, J=8.8 Hz, 1H), 8.23-8.16 (m, 2H), 7.97-7.94 (m, 1H), 7.71 (s, 1H), 7.32 (d, J=8.4 Hz, 1H), 4.95-4.83 (m, 2H), 4.81 (d, J=6.0 Hz, 2H), 4.24 (d, J=11.2 Hz, 1H), 3.88 (d, J=11.6 Hz, 1H), 1.71 (s, 3H) ppm.

Step 2: (R)-4-Cyano-N-((2-(4-fluoro-3-methyl-1H-pyrazol-1-yl)-1,6-naphthyridin-7-yl)methyl)-4-methylisochromane-6-carboxamide and (R)-4-cyano-N-((2-(4-fluoro-1H-pyrazol-1-yl)-1,6-naphthyridin-7-yl)methyl)-4-methylisochromane-6-carboxamide A mixture of (R)—N-((2-(3-bromo-4-fluoro-1H-pyrazol-1-yl)-1,6-naphthyridin-7-yl)methyl)-4-cyano-4-methylisochromane-6-carboxamide (30 mg, 57.54 umol), methylboronic acid (4.13 mg, 69.05 umol), $K_3PO_4$ (36.64 mg, 172.62 umol) and [1,1'-bis(di-tert-butylphosphino)ferrocene]dichloropalladium(II) (37.50 mg, 57.54 umol) in dioxane (1 mL) was degassed and purged with $N_2$ 3 times. The mixture was stirred at 60° C. for 2 hrs under $N_2$ atmosphere. The reaction was poured into 4 mL of $H_2O$ and extracted with EA (4 mL*3). The combined organic layers were dried over $Na_2SO_4$, filtered and concentrated under reduced pressure. The residue was purified by prep-HPLC (column: Phenomenex Luna C18 150*25 mm*10 um; mobile phase: [water (0.225% FA)-ACN]; B %: 38%-68%, 10 min) to give (R)-4-cyano-N-((2-(4-fluoro-3-methyl-1H-pyrazol-1-yl)-1,6-naphthyridin-7-yl)methyl)-4-methylisochromane-6-carboxamide (2.83 mg, 5.35 umol, 9.30% yield, FA salt) as a yellow solid and (R)-4-cyano-N-((2-(4-fluoro-1H-pyrazol-1-yl)-1,6-naphthyridin-7-yl)methyl)-4-methylisochromane-6-carboxamide (4.77 mg, 9.44 umol, 16.41% yield, FA salt) as a yellow solid.

(R)-4-cyano-N-((2-(4-fluoro-3-methyl-1H-pyrazol-1-yl)-1,6-naphthyridin-7-yl)methyl)-4-methylisochromane-6-carboxamide LCMS (ESI) m/z: [M+H]+=457.3.

1HNMR (400 MHz, METHANOL-d4) δ=9.23 (s, 1H), 8.65 (d, J=4.8 Hz, 1H), 8.58 (d, J=9.2 Hz, 1H), 8.24 (d, J=9.2 Hz, 1H), 8.17 (s, 1H), 7.93-7.90 (m, 1H), 7.80 (s, 1H), 7.29 (d, J=8.0 Hz, 1H), 4.91 (d, J=3.2 Hz, 2H), 4.89 (s, 2H), 4.21 (d, J=11.6 Hz, 1H), 3.93 (d, J=11.2 Hz, 1H), 2.34 (s, 3H), 1.77 (s, 3H) ppm.

(R)-4-cyano-N-((2-(4-fluoro-1H-pyrazol-1-yl)-1,6-naphthyridin-7-yl)methyl)-4-methylisochromane-6-carboxamide LCMS (ESI) m/z: [M+H]+=443.2.

1 HNMR (400 MHz, METHANOL-d4) 5=9.26 (s, 1H), 8.75 (d, J=4.8 Hz, 1H), 8.62 (d, J=8.8 Hz, 1H), 8.30 (d, J=8.8 Hz, 1H), 8.17 (s, 1H), 7.93-7.90 (m, 1H), 7.86-7.80 (m, 2H), 7.29 (d, J=8.0 Hz, 1H), 4.91 (d, J=3.6 Hz, 2H), 4.90 (s, 2H), 4.21 (d, J=11.2 Hz, 1H), 3.93 (d, J=11.2 Hz, 1H), 1.77 (s, 3H) ppm.

Example 37: Methyl 1-(7-(((R)-4-cyano-4-methylisochromane-6-carboxamido)methyl)-1,6-naphthyridin-2-yl)-3-azabicyclo[4.1.0]heptane-3-carboxylate

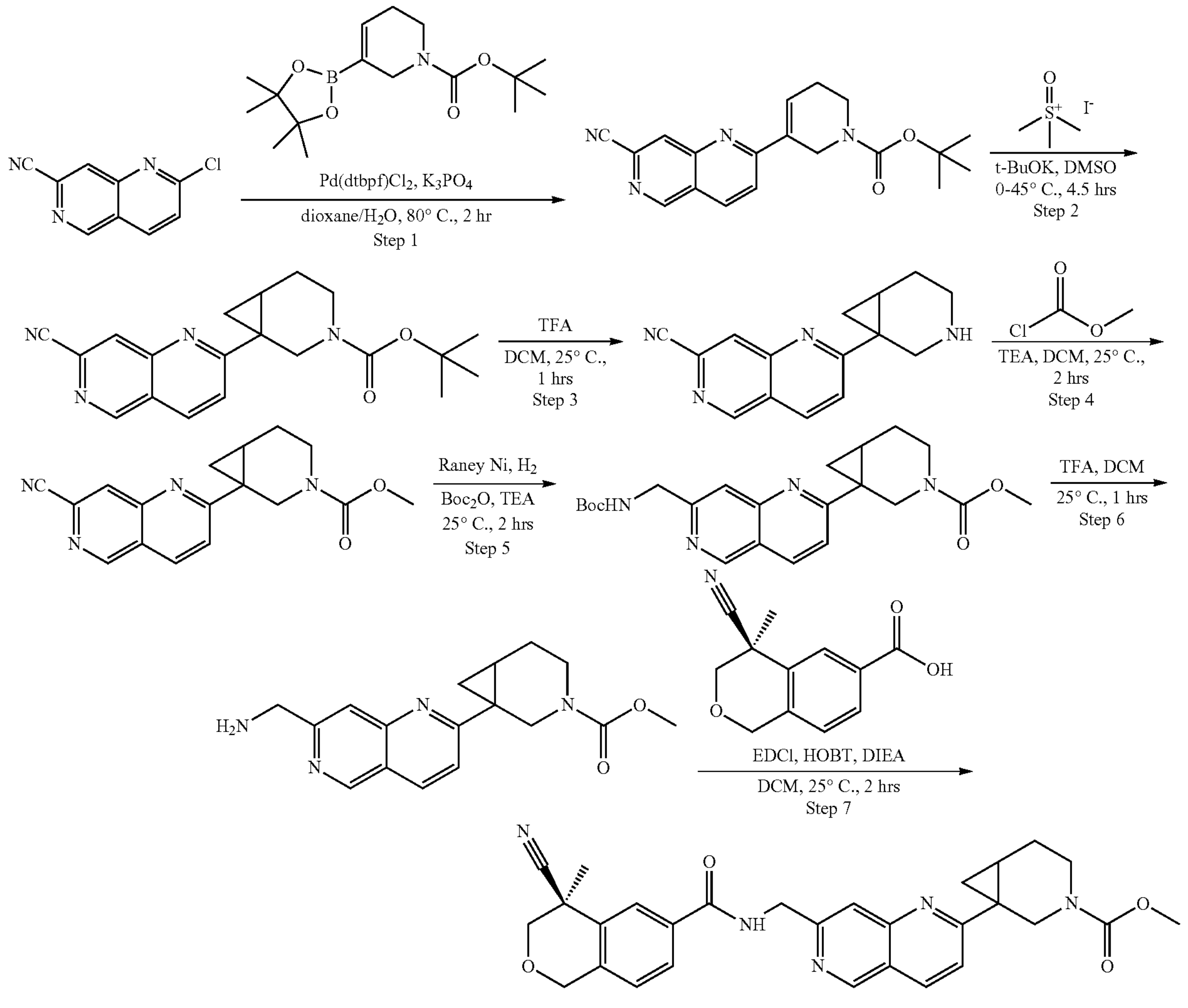

Step 1: tert-Butyl 5-(7-cyano-1,6-naphthyridin-2-yl)-3,6-dihydropyridine-1(2H)-carboxylate To a mixture of 2-chloro-1,6-naphthyridine-7-carbonitrile (400 mg, 2.11 mmol) and tert-butyl 5-(4,4,5,5-tetramethyl-1,3,2-dioxaborolan-2-yl)-3,6-dihydro-2H-pyridine-1-carboxylate (848.03 mg, 2.74 mmol) in dioxane (4 mL) and $H_2O$ (0.4 mL) was added [1,1'-bis(di-tert-butylphosphino)ferrocene]dichloropalladium(II) (137.50 mg, 210.97 umol) and $K_3PO_4$ (1.34 g, 6.33 mmol). The mixture was purged with $N_2$ for 1 min and the resulting mixture was stirred at 80° C. for 2 hrs. The reaction mixture was diluted with $H_2O$ (30 mL) and extracted with EA (40 mL*3). The combined organic layers were washed with brine (30 mL*2), dried over $Na_2SO_4$, filtered and concentrated under reduced pressure. The residue was slurried in MeOH (8 mL), and the precipitate was collected by filtration and dried. Further purification by column chromatography ($SiO_2$, PE:EtOAc=20:1-1:1) gave the title compound (460 mg, 1.37 mmol, 64.82% yield) as a yellow solid.

LCMS (ESI) m/z: [M+H]+=337.2.

Step 2: tert-Butyl 1-(7-cyano-1,6-naphthyridin-2-yl)-3-azabicyclo[4.1.0]heptane-3-carboxylate To a mixture of t-BuOK (70.05 mg, 624.28 umol) in DMSO (2 mL) was added trimethylsulfoxonium iodide (137.39 mg, 624.28 umol) at 0° C. and the mixture was stirred at 25° C. for 30 min. The mixture was then added to the solution of tert-butyl 5-(7-cyano-1,6-naphthyridin-2-yl)-3,6-dihydropyridine-1(2H)-carboxylate (210 mg, 624.28 umol) dissolved in DMSO (1 mL) and the resulting mixture was stirred at 45° C. for 4 hrs. The reaction mixture was diluted with $H_2O$ (30 mL) and extracted with EA (40 mL*3). The combined organic layers were washed with brine (30 mL*2), dried over $Na_2SO_4$, filtered and concentrated under reduced pressure. The residue was purified by column chromatography ($SiO_2$, PE:EtOAc=20:1-1:1) to give the title compound (80 mg, 215.17 umol, 34.47% yield) as a colorless oil.

LCMS (ESI) m/z: [M+H]+=351.2.

1H NMR (400 MHz, $CDCl_3$) δ=9.21 (s, 1H), 8.30-8.19 (m, 2H), 7.71-7.40 (m, 1H), 4.32-4.25 (m, 1H), 4.24-4.14

(m, 1H), 3.76-3.52 (m, 1H), 3.20-2.96 (m, 1H), 2.18- (m, 1H), 1.97-1.82 (m, 2H), 1.78-1.60 (m, 1H), 1.54-1.46 (m, 10H) ppm.

Step 3: 2-(3-Azabicyclo[4.1.0]heptan-1-yl)-1,6-naphthyridine-7-carbonitrile

To a mixture of tert-butyl 1-(7-cyano-1,6-naphthyridin-2-yl)-3-azabicyclo[4.1.0]heptane-3-carboxylate (120 mg, 342.45 umol) in DCM (2 mL) was added TFA (770.00 mg, 6.75 mmol, 0.5 mL) at 0° C. and the mixture was stirred at 25° C. for 1 hr. The reaction mixture was poured into sat. $NaHCO_3$ (20 mL) and extracted with EA (20 mL*3). The combined organic layers were washed with brine (30 mL), dried over $Na_2SO_4$, filtered and concentrated under reduced pressure to give the title compound (85 mg, crude) as a yellow solid.

Step 4: Methyl 1-(7-cyano-1,6-naphthyridin-2-yl)-3-azabicyclo[4.1.0]heptane-3-carboxylate To a mixture of 2-(3-azabicyclo[4.1.0]heptan-1-yl)-1,6-naphthyridine-7-carbonitrile (85 mg, 339.60 umol) and TEA (171.82 mg, 1.70 mmol, 236.34 uL) in DCM (1 mL) was added methyl chloroformate (96.27 mg, 1.02 mmol, 78.91 uL) dropwise at 0° C., and the mixture was stirred at 25° C. for 2 hrs. The reaction mixture was diluted with $H_2O$ (30 mL) and extracted with EA (40 mL*3). The combined organic layers were washed with brine (30 mL*2), dried over $Na_2SO_4$, filtered and concentrated under reduced pressure. The residue was purified by column chromatography ($SiO_2$, PE:EtOAc=20:1-1:1) to give the title compound (55 mg, 173.78 umol, 51.17% yield) as a colorless oil.

LCMS (ESI) m/z: [M+H]+=309.1.

1H NMR (400 MHz, DMSO-d6) δ=9.43 (d, J=0.8 Hz, 1H), 8.60 (d, J=8.8 Hz, 1H), 8.52 (s, 1H), 7.76-7.60 (m, 1H), 4.35-4.15 (m, 2H), 3.64 (s, 3H), 3.63-3.50 (m, 1H), 3.16-2.97 (m, 1H), 2.18-2.06 (m, 1H), 1.96-1.78 (m, 2H), 1.54-1.53 (m, 1H), 1.10-1.08 (m, 1H) ppm.

Step 5: Methyl 1-(7-(((tert-butoxycarbonyl)amino)methyl)-1,6-naphthyridin-2-yl)-3-azabicyclo[4.1.0]heptane-3-carboxylate To a mixture of methyl 1-(7-cyano-1,6-naphthyridin-2-yl)-3-azabicyclo[4.1.0]heptane-3-carboxylate (55 mg, 178.38 umol) in MeOH (10 mL) was added TEA (36.10 mg, 356.76 umol, 49.66 uL) and $Boc_2O$ (58.40 mg, 267.57 umol, 61.47 uL). The mixture was purged with $N_2$ and Raney-Ni (76.41 mg, 891.89 umol) was added. The mixture was then purged with $H_2$ 3 times and the resulting mixture was stirred at 25° C. under $H_2$ (15 psi) for 2 hrs. The reaction mixture was filtered and the filtrate was concentrated under vacuum. The residue was purified by column chromatography ($SiO_2$, PE:EtOAc=20:1-1:1) to give the title compound (35 mg, 84.27 umol, 47.24% yield) as a colorless oil.

LCMS (ESI) m/z: [M+H]+=413.2.

Step 6: Methyl 1-(7-(aminomethyl)-1,6-naphthyridin-2-yl)-3-azabicyclo[4.1.0]heptane-3-carboxylate To a solution of methyl 1-(7-(((tert-butoxycarbonyl)amino)methyl)-1,6-naphthyridin-2-yl)-3-azabicyclo[4.1.0]heptane-3-carboxylate (35 mg, 84.85 umol) in DCM (3 mL) was added TFA (1 mL) at 0° C. The mixture was stirred at 25° C. for 1 hr. The reaction mixture was poured into sat. $NaHCO_3$ (20 mL) and extracted with EA (20 mL*3). The combined organic layers were washed with brine (30 mL), dried over $Na_2SO_4$, filtered and concentrated under reduced pressure to give the title compound (28 mg, crude) as a yellow solid.

LCMS (ESI) m/z: [M+H]+=313.2.

Step 7: Methyl 1-(7-(((R)-4-cyano-4-methylisochromane-6-carboxamido)methyl)-1,6-naphthyridin-2-yl)-3-azabicyclo[4.1.0]heptane-3-carboxylate To a solution of (R)-4-cyano-4-methylisochromane-6-carboxylic acid (23.37 mg, 107.57 umol) in DCM (1 mL) was added EDCI (22.34 mg, 116.53 umol), HOBt (15.75 mg, 116.53 umol) and DIEA (34.76 mg, 268.92 umol, 46.84 uL). Methyl 1-(7-(aminomethyl)-1,6-naphthyridin-2-yl)-3-azabicyclo[4.1.0]heptane-3-carboxylate (28 mg, 89.64 umol) was then added and the mixture was stirred at 25° C. for 2 hrs. The reaction mixture was poured into $NaHCO_3$ (30 mL) and extracted with EA (20 mL*3). The combined organic layers were washed with brine (30 mL), dried over $Na_2SO_4$, filtered and concentrated. The residue was purified by prep-HPLC (0.1% FA condition) to give the title compound (5.30 mg, 10.36 umol, 11.56% yield) as a white solid.

LCMS (ESI) m/z: [M+H]+=512.2.

1H NMR (400 MHz, DMSO-d6) δ=9.41-9.32 (m, 1H), 9.28 (s, 1H), 8.45 (d, J=8.8 Hz, 1H), 8.19 (d, J=1.6 Hz, 1H), 7.94 (d, J=1.6, 1H), 7.64 (s, 1H), 7.51-7.39 (m, 1H), 7.31 (d, J=8.4 Hz, 1H), 4.94-4.81 (m, 2H), 4.77 (d, J=5.6 Hz, 2H), 4.33-4.19 (m, 2H), 4.18-4.07 (m, 1H), 3.87 (d, J=11.2 Hz, 1H), 3.61 (s, 3H), 3.52-3.43 (m, 1H), 3.13-2.97 (m, 1H), 2.14-2.04 (m, 1H), 1.88-1.76 (m, 2H), 1.70 (s, 3H), 1.53-1.43 (m, 1H), 1.04-0.96 (m, 1H) ppm.

Example 38. Assay for ATPase Catalytic Activity of BRM and BRG-1

The ATPase catalytic activity of BRM or BRG-1 was measured by an in vitro biochemical assay using ADP-Glo™ (Promega, V9102). The ADP-Glo™ kinase assay is performed in two steps once the reaction is complete. The first step is to deplete any unconsumed ATP in the reaction. The second step is to convert the reaction product ADP to ATP, which will be utilized by the luciferase to generate luminesce and be detected by a luminescence reader, such as Envision.

The assay reaction mixture (10 μL) contains 30 nM of BRM or BRG-1, 20 nM salmon sperm DNA (from Invitrogen, UltraPure™ Salmon Sperm DNA Solution, cat #15632011), and 400 μM of ATP in the ATPase assay buffer, which comprises of 20 mM Tris, pH 8, 20 mM $MgCl_2$, 50 mM NaCl, 0.1% Tween-20, and 1 mM fresh OTT (Pierce™ OTT (Dithiothreitol), cat #20290). The reaction is initiated by the addition of the 2.5 μL ATPase solution to 2.5 μL ATP/DNA solution on low volume white Proxiplate-384 plus plate (PerkinElmer, cat #6008280) and incubates at room temperature for 1 hour. Then following addition of 5 μL of ADP-Glo™ Reagent provided in the kit, the reaction incubates at room temperature for 40 minutes. Then 10 μL of Kinase Detection Reagent provided in the kit is added to convert ADP to ATP, and the reaction incubates at room temperature for 60 minutes. Finally, luminescence measurement is collected with a plate-reading luminometer, such as Envision.

BRM and BRG-1 were synthesized from high five insect cell lines with a purity of greater than 90%. $IC_{50}$ data for compounds 1-126 from the ATPase catalytic activity assay described herein are shown in Table 25 below.

TABLE 25

BRM and BRG-1 Inhibition Data for Compounds of the Invention

| Compound # | BRM ATPase: IC50 (uM) | BRM Max % Inhibition | BRG1 ATPase: IC50 (uM) | BRG1 Max % Inhibition |
|---|---|---|---|---|
| 1 | +++ | 90 | + | 56 |
| 2 | +++ | 96 | + | 65 |
| 3 | ++++ | 99 | + | 78 |
| 4 | +++ | 97 | + | 74 |
| 5 | + | 64 | + | 12 |
| 6 | +++ | 95 | + | 44 |
| 7 | + | 81 | + | 12 |
| 8 | + | 73 | + | 9 |
| 9 | +++ | 95 | + | 56 |
| 10 | + | 71 | + | 30 |
| 11 | + | 82 | + | 26 |
| 12 | + | 79 | + | 22 |
| 13 | + | 84 | + | 44 |
| 14 | ++ | 94 | + | 64 |
| 15 | ++ | 94 | + | 64 |
| 16 | +++ | 94 | + | 51 |
| 17 | +++ | 94 | + | 58 |
| 18 | ++++ | 93 | + | 87 |
| 19 | +++ | 97 | ++ | 89 |
| 20 | ++ | 83 | + | 41 |
| 21 | + | 78 | + | 31 |
| 22 | + | 70 | + | 31 |
| 23 | ++ | 85 | + | 35 |
| 24 | +++ | 94 | + | 65 |
| 25 | +++ | 94 | + | 68 |
| 26 | ++++ | 100 | +++ | 90 |
| 27 | +++ | 97 | + | 62 |
| 28 | ++++ | 98 | ++ | 86 |
| 29 | +++ | 98 | + | 69 |
| 30 | +++ | 92 | + | 35 |
| 31 | +++ | 96 | + | 73 |
| 32 | + | 89 | + | 55 |
| 33 | +++ | 98 | + | 78 |
| 34 | +++ | 94 | + | 53 |
| 35 | ++ | 91 | + | 47 |
| 36 | + | 64 | + | 44 |
| 37 | + | 76 | + | 21 |
| 38 | ++++ | 97 | + | 86 |
| 39 | + | 75 | + | 28 |
| 40 | +++ | 96 | + | 67 |
| 41 | ++ | 85 | + | 55 |
| 42 | +++ | 97 | ++ | 84 |
| 43 | + | 68 | + | 34 |
| 44 | +++ | 97 | + | 69 |
| 45 | ++++ | 96 | ++ | 79 |
| 46 | + | 78 | + | 29 |
| 47 | +++ | 90 | + | 47 |
| 48 | + | 67 | + | 11 |
| 49 | +++ | 84 | + | 26 |
| 50 | +++ | 90 | + | 53 |
| 51 | ++++ | 99 | +++ | 94 |
| 52 | +++ | 86 | + | 34 |
| 53 | +++ | 88 | + | 48 |
| 54 | +++ | 81 | + | 42 |
| 55 | +++ | 82 | + | 33 |
| 56 | ++++ | 98 | +++ | 92 |
| 57 | +++ | 85 | + | 37 |
| 58 | +++ | 92 | ++ | 50 |
| 59 | +++ | 93 | ++ | 56 |
| 60 | +++ | 93 | ++ | 75 |
| 61 | +++ | 85 | + | 25 |
| 62 | +++ | 90 | + | 42 |
| 63 | ++++ | 99 | ++ | 84 |
| 64 | +++ | 87 | + | 36 |
| 65 | +++ | 90 | + | 39 |
| 66 | +++ | 99 | ++ | 76 |
| 67 | +++ | 97 | ++ | 84 |
| 68 | ++++ | 98 | +++ | 91 |
| 69 | +++ | 90 | ++ | 50 |
| 70 | +++ | 94 | ++ | 55 |
| 71 | +++ | 89 | + | 42 |
| 72 | ++++ | 94 | +++ | 91 |
| 73 | +++ | 84 | + | 44 |
| 74 | ++++ | 98 | +++ | 87 |
| 75 | +++ | 97 | ++ | 54 |
| 76 | +++ | 98 | + | 91 |
| 77 | +++ | 99 | ++ | 102 |
| 78 | ++++ | 96 | ++ | 79 |
| 79 | +++ | 96 | ++ | 74 |
| 80 | +++ | 83 | + | 29 |
| 81 | ++++ | 98 | +++ | 90 |
| 82 | +++ | 88 | + | 38 |
| 83 | ++++ | 101 | ++++ | 99 |
| 84 | +++ | 89 | ++ | 53 |
| 85 | ++++ | 98 | + | 77 |
| 86 | +++ | 96 | + | 62 |
| 87 | ++ | 88 | + | 87 |
| 88 | +++ | 96 | + | 73 |
| 89 | + | 76 | + | 15 |
| 90 | + | 82 | + | 24 |
| 91 | ++++ | 97 | ++ | 85 |
| 92 | +++ | 95 | + | 64 |
| 93 | ++++ | 99 | +++ | 93 |
| 94 | + | 83 | + | 45 |
| 95 | ++++ | 99 | +++ | 93 |
| 96 | + | 84 | + | 20 |
| 97 | +++ | 93 | + | 47 |
| 98 | ++++ | 97 | + | 81 |
| 99 | + | 63 | + | 22 |
| 100 | ++ | 83 | + | 25 |
| 101 | ++++ | 98 | ++ | 78 |
| 102 | +++ | 93 | + | 56 |
| 103 | +++ | 94 | + | 71 |
| 104 | ++ | 84 | + | 33 |
| 105 | ++++ | 98 | ++ | 87 |
| 106 | + | 80 | + | 32 |
| 107 | + | 71 | + | 16 |
| 108 | ++++ | 99 | ++ | 91 |
| 109 | + | 75 | + | 11 |
| 110 | ++++ | 99 | ++ | 86 |
| 111 | ++++ | 101 | +++ | 93 |
| 112 | +++ | 94 | + | 55 |
| 113 | + | 79 | + | 32 |
| 114 | ++ | 86 | + | 42 |
| 115 | + | 84 | + | 19 |
| 116 | + | 76 | + | 22 |
| 117 | + | 74 | + | 27 |
| 118 | + | 89 | + | 40 |
| 119 | + | 81 | + | 18 |
| 120 | + | 8 | + | 0 |
| 121 | + | 81 | + | 44 |
| 122 | +++ | 94 | + | 62 |
| 123 | +++ | 96 | + | 74 |
| 124 | ++++ | 97 | + | 98 |
| 125 | +++ | 98 | ++ | 86 |
| 126 | +++ | 95 | + | 51 |
| 127 | ++++ | 96 | ++ | 74 |
| 128 | +++ | 82 | + | 39 |
| 129 | ++++ | 100 | ++++ | 98 |
| 130 | ++++ | 97 | +++ | 90 |
| 131 | +++ | 83 | + | 25 |
| 132 | +++ | 97 | ++ | 71 |
| 133 | ++++ | 102 | ++++ | 98 |
| 134 | ++++ | 101 | ++++ | 97 |
| 135 | ++++ | 103 | ++++ | 98 |
| 136 | +++ | 83 | + | 25 |
| 137 | +++ | 88 | + | 39 |
| 138 | ++++ | 101 | +++ | 94 |
| 139 | ++++ | 100 | +++ | 94 |
| 140 | +++ | 94 | ++ | 48 |
| 141 | ++++ | 100 | +++ | 96 |
| 142 | ++++ | 98 | +++ | 88 |
| 143 | ++++ | 103 | +++ | 89 |
| 144 | ++++ | 102 | +++ | 95 |
| 145 | +++ | 94 | ++ | 65 |
| 146 | +++ | 98 | +++ | 80 |
| 147 | ++++ | 101 | +++ | 90 |
| 148 | +++ | 90 | + | 32 |

TABLE 25-continued

BRM and BRG-1 Inhibition Data for Compounds of the Invention

| Compound # | BRM ATPase: IC50 (uM) | BRM Max % Inhibition | BRG1 ATPase: IC50 (uM) | BRG1 Max % Inhibition |
|---|---|---|---|---|
| 149 | +++ | 95 | ++ | 67 |
| 150 | ++++ | 99 | ++++ | 97 |
| 151 | +++ | 93 | ++ | 56 |
| 152 | +++ | 96 | ++ | 85 |
| 153 | +++ | 87 | + | 37 |
| 154 | ++++ | 101 | +++ | 95 |
| 155 | +++ | 96 | ++ | 67 |
| 156 | ++++ | 99 | +++ | 97 |
| 157 | ++++ | 99 | +++ | 96 |
| 158 | +++ | 96 | ++ | 75 |
| 159 | ++++ | 99 | +++ | 95 |
| 160 | +++ | 93 | ++ | 62 |
| 161 | +++ | 94 | ++ | 53 |
| 162 | +++ | 91 | ++ | 59 |
| 163 | ++++ | 98 | +++ | 87 |
| 164 | +++ | 92 | ++ | 68 |
| 165 | ++++ | 97 | +++ | 80 |
| 166 | +++ | 91 | + | 40 |
| 167 | +++ | 93 | ++ | 69 |
| 168 | ++++ | 99 | +++ | 93 |
| 169 | ++++ | 98 | +++ | 91 |
| 170 | +++ | 96 | ++ | 80 |
| 171 | ++++ | 98 | +++ | 92 |
| 172 | ++++ | 99 | ++++ | 97 |
| 173 | ++++ | 98 | +++ | 94 |
| 174 | ++++ | 98 | +++ | 95 |
| 175 | ++++ | 97 | +++ | 86 |
| 176 | ++++ | 98 | ++ | 83 |
| 177 | +++ | 94 | ++ | 66 |
| 178 | ++++ | 99 | +++ | 96 |
| 179 | ++++ | 99 | +++ | 96 |
| 180 | ++++ | 100 | +++ | 99 |
| 181 | ++++ | 100 | +++ | 97 |
| 182 | ++++ | 99 | +++ | 95 |
| 183 | ++++ | 98 | +++ | 82 |
| 184 | +++ | 94 | ++ | 67 |
| 185 | ++++ | 99 | +++ | 87 |
| 186 | ++++ | 97 | ++ | 66 |
| 187 | +++ | 88 | + | 42 |
| 188 | +++ | 93 | + | 41 |
| 189 | ++++ | 99 | +++ | 93 |
| 190 | ++++ | 98 | +++ | 89 |
| 191 | ++++ | 97 | ++ | 76 |
| 192 | +++ | 94 | ++ | 60 |
| 193 | ++++ | 99 | ++ | 86 |
| 194 | +++ | 93 | ++ | 60 |
| 195 | +++ | 84 | + | 47 |
| 196 | +++ | 86 | + | 59 |
| 197 | +++ | 89 | + | 59 |
| 198 | +++ | 94 | ++ | 76 |
| 199 | +++ | 85 | + | 14 |
| 200 | +++ | 97 | ++ | 71 |
| 201 | ++++ | 99 | ++ | 76 |
| 202 | ++++ | 94 | ++ | 67 |
| 203 | +++ | 84 | + | 26 |
| 204 | ++++ | 97 | ++ | 82 |
| 205 | +++ | 91 | ++ | 52 |
| 206 | ++++ | 99 | +++ | 85 |
| 207 | ++++ | 98 | +++ | 89 |
| 208 | ++++ | 98 | +++ | 92 |
| 209 | +++ | 89 | ++ | 51 |
| 210 | ++++ | 99 | +++ | 96 |
| 211 | +++ | 97 | ++ | 82 |
| 212 | +++ | 89 | + | 39 |
| 213 | +++ | 97 | ++ | 63 |
| 214 | ++++ | 99 | +++ | 93 |
| 215 | ++++ | 97 | +++ | 90 |
| 216 | ++++ | 98 | +++ | 90 |
| 217 | ++++ | 98 | ++ | 79 |
| 218 | ++++ | 99 | ++ | 79 |
| 219 | +++ | 94 | ++ | 57 |
| 220 | +++ | 92 | + | 47 |
| 221 | ++++ | 99 | +++ | 88 |
| 222 | ++++ | 98 | ++ | 83 |

TABLE 25-continued

BRM and BRG-1 Inhibition Data for Compounds of the Invention

| Compound # | BRM ATPase: IC50 (uM) | BRM Max % Inhibition | BRG1 ATPase: IC50 (uM) | BRG1 Max % Inhibition |
|---|---|---|---|---|
| 223 | ++++ | 101 | ++++ | 101 |
| 224 | ++++ | 101 | ++++ | 100 |
| 225 | +++ | 92 | ++ | 72 |
| 226 | +++ | 98 | +++ | 85 |
| 227 | ++++ | 99 | +++ | 94 |
| 228 | ++++ | 100 | +++ | 98 |
| 229 | ++++ | 100 | +++ | 90 |
| 230 | +++ | 97 | ++ | 62 |
| 231 | +++ | 91 | + | 46 |
| 232 | ++++ | 98 | +++ | 85 |
| 233 | +++ | 98 | ++ | 74 |
| 234 | +++ | 96 | ++ | 49 |
| 235 | ++++ | 99 | +++ | 72 |
| 236 | ++++ | 100 | +++ | 90 |
| 237 | ++++ | 100 | +++ | 92 |
| 238 | ++++ | 100 | ++++ | 96 |
| 239 | ++++ | 101 | +++ | 93 |
| 240 | ++++ | 101 | +++ | 89 |
| 241 | +++ | 97 | ++ | 63 |
| 242 | +++ | 94 | ++ | 51 |
| 243 | +++ | 81 | + | 9 |
| 244 | +++ | 88 | + | 25 |
| 245 | +++ | 96 | ++ | 75 |
| 246 | +++ | 88 | + | 23 |
| 247 | +++ | 93 | + | 65 |
| 248 | ++++ | 98 | +++ | 100 |
| 249 | +++ | 97 | ++ | 71 |
| 250 | +++ | 87 | + | 25 |
| 251 | ++++ | 100 | +++ | 91 |
| 252 | +++ | 87 | + | 33 |
| 253 | +++ | 92 | ++ | 57 |
| 254 | ++++ | 99 | ++ | 77 |
| 255 | ++++ | 100 | +++ | 90 |
| 256 | ++++ | 98 | ++ | 76 |
| 257 | +++ | 92 | ++ | 65 |
| 258 | +++ | 96 | +++ | 75 |
| 259 | ++++ | 99 | +++ | 88 |
| 260 | +++ | 83 | + | 42 |
| 261 | +++ | 94 | ++ | 61 |
| 262 | ++++ | 102 | ++++ | 99 |
| 263 | ++++ | 101 | +++ | 98 |
| 264 | +++ | 98 | ++ | 72 |
| 265 | ++++ | 104 | ++++ | 99 |
| 266 | ++++ | 103 | +++ | 96 |
| 267 | ++++ | 103 | +++ | 88 |
| 268 | +++ | 97 | ++ | 67 |
| 269 | ++++ | 104 | +++ | 97 |
| 270 | ++++ | 104 | ++++ | 98 |
| 271 | ++++ | 104 | +++ | 95 |
| 272 | ++++ | 104 | +++ | 95 |
| 273 | +++ | 98 | ++ | 64 |
| 274 | +++ | 93 | ++ | 45 |
| 275 | ++++ | 96 | ++ | 77 |
| 276 | ++++ | 98 | +++ | 95 |
| 277 | +++ | 96 | ++ | 69 |
| 278 | ++++ | 101 | +++ | 96 |
| 279 | +++ | 83 | ++ | 67 |
| 280 | +++ | 96 | +++ | 82 |
| 281 | +++ | 92 | + | 48 |
| 282 | +++ | 87 | + | 45 |
| 283 | +++ | 96 | ++ | 63 |
| 284 | ++++ | 99 | +++ | 93 |
| 285 | ++++ | 98 | +++ | 92 |
| 286 | +++ | 85 | + | 43 |
| 287 | ++++ | 99 | ++ | 99 |
| 288 | ++++ | 101 | +++ | 98 |
| 289 | +++ | 90 | + | 41 |
| 290 | +++ | 94 | ++ | 53 |
| 291 | ++++ | 100 | ++++ | 97 |
| 292 | ++++ | 99 | +++ | 94 |
| 293 | +++ | 88 | + | 33 |
| 294 | ++++ | 100 | +++ | 86 |
| 295 | ++++ | 100 | +++ | 93 |
| 296 | ++++ | 100 | +++ | 88 |

TABLE 25-continued

BRM and BRG-1 Inhibition Data for Compounds of the Invention

| Compound # | BRM ATPase: IC50 (uM) | BRM Max % Inhibition | BRG1 ATPase: IC50 (uM) | BRG1 Max % Inhibition |
|---|---|---|---|---|
| 297 | +++ | 96 | ++ | 66 |
| 298 | ++++ | 99 | +++ | 82 |
| 299 | ++++ | 99 | ++ | 78 |
| 300 | +++ | 99 | ++ | 63 |
| 301 | ++++ | 96 | +++ | 86 |
| 302 | +++ | 93 | ++ | 58 |
| 303 | +++ | 96 | +++ | 87 |
| 304 | +++ | 86 | + | 38 |
| 305 | +++ | 87 | + | 40 |
| 306 | ++++ | 99 | +++ | 94 |
| 307 | ++++ | 98 | +++ | 97 |
| 308 | ++++ | 99 | ++++ | 96 |
| 309 | ++++ | 97 | +++ | 82 |
| 310 | ++++ | 97 | +++ | 84 |
| 311 | ++++ | 99 | +++ | 95 |
| 312 | +++ | 83 | + | 46 |
| 313 | +++ | 92 | ++ | 72 |
| 314 | ++++ | 96 | +++ | 83 |
| 315 | +++ | 81 | + | 33 |
| 316 | +++ | 98 | + | 92 |
| 317 | +++ | 100 | + | 96 |
| 318 | +++ | 107 | ++ | 55 |
| 319 | ++++ | 104 | +++ | 92 |
| 320 | +++ | 107 | ++ | 80 |
| 321 | ++++ | 105 | +++ | 95 |
| 322 | ++++ | 106 | ++++ | 97 |
| 323 | +++ | 108 | ++ | 76 |
| 324 | +++ | 105 | ++ | 81 |
| 325 | ++++ | 101 | +++ | 90 |
| 326 | +++ | 97 | ++ | 70 |
| 327 | +++ | 89 | + | 48 |
| 328 | ++++ | 99 | ++ | 81 |
| 329 | ++++ | 100 | +++ | 86 |
| 330 | +++ | 93 | ++ | 64 |
| 331 | +++ | 97 | ++ | 73 |
| 332 | +++ | 96 | ++ | 67 |
| 333 | ++++ | 100 | ++ | 79 |
| 334 | +++ | 96 | ++ | 61 |
| 335 | ++++ | 101 | +++ | 84 |
| 336 | ++++ | 99 | +++ | 92 |
| 337 | +++ | 99 | ++ | 63 |
| 338 | +++ | 97 | ++ | 56 |
| 339 | ++++ | 100 | +++ | 95 |
| 340 | ++++ | 99 | +++ | 91 |
| 341 | ++++ | 100 | +++ | 93 |
| 342 | ++++ | 97 | ++ | 80 |
| 343 | ++++ | 101 | ++ | 78 |
| 344 | +++ | 94 | ++ | 57 |
| 345 | +++ | 81 | + | 25 |
| 346 | ++++ | 102 | ++++ | 94 |
| 347 | ++++ | 100 | +++ | 79 |
| 348 | ++++ | 99 | ++ | 72 |
| 349 | ++++ | 100 | +++ | 87 |
| 350 | +++ | 96 | + | 54 |
| 351 | ++++ | 101 | +++ | 95 |
| 352 | ++++ | 99 | +++ | 89 |
| 353 | ++++ | 93 | +++ | 82 |
| 354 | +++ | 79 | + | 39 |
| 355 | +++ | 93 | ++ | 74 |
| 356 | ++++ | 97 | +++ | 95 |
| 357 | ++++ | 97 | +++ | 87 |
| 358 | +++ | 92 | ++ | 67 |
| 359 | +++ | 89 | + | 39 |
| 360 | ++++ | 99 | + | 99 |
| 361 | ++++ | 98 | + | 98 |
| 362 | ++++ | 99 | + | 98 |
| 363 | ++++ | 98 | +++ | 94 |
| 364 | +++ | 90 | ++ | 62 |
| 365 | ++++ | 99 | +++ | 98 |
| 366 | ++++ | 99 | ++++ | 99 |
| 367 | ++++ | 102 | +++ | 93 |
| 368 | ++++ | 103 | +++ | 96 |
| 369 | ++++ | 104 | ++++ | 95 |
| 370 | ++++ | 103 | +++ | 96 |
| 371 | ++++ | 104 | ++++ | 97 |
| 372 | +++ | 93 | + | 47 |
| 373 | ++++ | 103 | ++++ | 100 |
| 374 | ++++ | 101 | +++ | 94 |
| 375 | ++++ | 100 | ++++ | 101 |
| 376 | +++ | 98 | ++ | 79 |
| 377 | ++++ | 98 | ++ | 89 |
| 378 | ++++ | 100 | +++ | 99 |
| 379 | ++++ | 100 | +++ | 94 |
| 380 | ++++ | 101 | ++++ | 98 |
| 381 | ++++ | 101 | ++++ | 98 |
| 382 | +++ | 98 | ++ | 77 |
| 383 | ++++ | 98 | ++ | 79 |
| 384 | ++++ | 101 | ++++ | 100 |
| 385 | ++++ | 98 | +++ | 91 |
| 386 | ++++ | 98 | +++ | 94 |
| 387 | +++ | 97 | ++ | 73 |
| 388 | +++ | 97 | ++ | 71 |
| 389 | +++ | 93 | ++ | 56 |
| 390 | ++++ | 100 | ++++ | 97 |
| 391 | ++++ | 96 | ++ | 81 |
| 392 | ++++ | 100 | +++ | 95 |
| 393 | ++++ | 99 | ++++ | 96 |
| 394 | ++++ | 101 | +++ | 93 |
| 395 | +++ | 92 | ++ | 62 |
| 396 | +++ | 74 | + | 32 |
| 397 | +++ | 93 | ++ | 66 |
| 398 | ++++ | 98 | +++ | 91 |
| 399 | ++++ | 100 | +++ | 98 |
| 400 | +++ | 96 | ++ | 68 |
| 401 | ++++ | 97 | +++ | 91 |
| 402 | ++++ | 96 | ++ | 74 |
| 403 | ++++ | 99 | +++ | 91 |
| 404 | +++ | 93 | +++ | 78 |
| 405 | +++ | 85 | ++ | 55 |
| 406 | ++++ | 100 | +++ | 93 |
| 407 | ++++ | 99 | +++ | 97 |
| 408 | +++ | 91 | ++ | 65 |
| 409 | ++++ | 96 | +++ | 95 |
| 410 | +++ | 93 | ++ | 75 |
| 411 | +++ | 91 | ++ | 50 |
| 412 | ++++ | 99 | +++ | 98 |
| 413 | +++ | 92 | ++ | 51 |
| 414 | +++ | 91 | ++ | 67 |
| 415 | ++++ | 99 | ++++ | 95 |
| 416 | ++++ | 99 | +++ | 95 |
| 417 | ++++ | 97 | +++ | 91 |
| 418 | +++ | 90 | + | 51 |
| 419 | +++ | 93 | ++ | 64 |
| 420 | ++++ | 98 | +++ | 89 |
| 421 | +++ | 84 | + | 37 |
| 422 | ++++ | 99 | ++++ | 97 |
| 423 | ++++ | 98 | +++ | 89 |
| 424 | ++++ | 99 | ++++ | 96 |
| 425 | ++++ | 98 | +++ | 93 |
| 426 | +++ | 97 | ++ | 78 |
| 427 | ++++ | 99 | +++ | 87 |
| 428 | +++ | 97 | ++ | 65 |
| 429 | ++++ | 99 | +++ | 93 |
| 430 | ++++ | 100 | +++ | 92 |
| 431 | +++ | 86 | ++ | 53 |
| 432 | ++++ | 98 | +++ | 88 |
| 433 | +++ | 96 | ++ | 59 |
| 434 | ++++ | 100 | ++++ | 92 |
| 435 | ++++ | 100 | +++ | 93 |
| 436 | ++++ | 100 | +++ | 85 |
| 437 | ++++ | 99 | +++ | 87 |
| 438 | +++ | 84 | + | 28 |
| 439 | +++ | 88 | + | 36 |
| 440 | +++ | 88 | + | 40 |
| 441 | +++ | 97 | ++ | 80 |
| 442 | ++++ | 96 | ++ | 75 |
| 443 | +++ | 96 | +++ | 82 |
| 444 | +++ | 93 | ++ | 67 |

TABLE 25-continued

BRM and BRG-1 Inhibition Data for Compounds of the Invention

| Compound # | BRM ATPase: IC50 (uM) | BRM Max % Inhibition | BRG1 ATPase: IC50 (uM) | BRG1 Max % Inhibition |
|---|---|---|---|---|
| 445 | +++ | 96 | ++ | 72 |
| 446 | +++ | 87 | + | 44 |
| 447 | +++ | 95 | ++ | 84 |
| 448 | ++++ | 97 | +++ | 93 |
| 449 | +++ | 92 | + | 50 |
| 450 | +++ | 96 | ++ | 73 |
| 451 | +++ | 93 | ++ | 58 |
| 452 | ++++ | 97 | +++ | 98 |
| 453 | +++ | 91 | ++ | 61 |
| 454 | ++++ | 97 | +++ | 88 |
| 455 | +++ | 94 | ++ | 75 |
| 456 | +++ | 95 | ++ | 80 |
| 457 | +++ | 95 | ++ | 61 |
| 458 | +++ | 95 | ++ | 74 |
| 459 | ++++ | 97 | +++ | 86 |
| 460 | +++ | 98 | ++ | 75 |
| 461 | +++ | 93 | ++ | 65 |
| 462 | +++ | 93 | ++ | 71 |
| 463 | ++++ | 98 | ++ | 82 |
| 464 | +++ | 88 | + | 48 |
| 465 | ++++ | 99 | +++ | 89 |
| 466 | ++++ | 99 | ++ | 79 |
| 467 | ++++ | 99 | +++ | 86 |
| 468 | ++++ | 100 | ++ | 80 |
| 469 | ++++ | 98 | +++ | 85 |
| 470 | +++ | 97 | ++ | 82 |
| 471 | +++ | 96 | + | 63 |
| 472 | +++ | 86 | + | 51 |
| 473 | +++ | 96 | + | 72 |
| 474 | +++ | 93 | + | 53 |
| 475 | ++++ | 99 | +++ | 98 |
| 476 | +++ | 94 | ++ | 63 |
| 477 | +++ | 88 | + | 49 |
| 478 | +++ | 95 | ++ | 63 |
| 479 | +++ | 96 | ++ | 72 |
| 480 | +++ | 93 | ++ | 73 |
| 481 | ++++ | 98 | +++ | 95 |
| 482 | +++ | 90 | ++ | 55 |
| 483 | +++ | 93 | ++ | 72 |
| 484 | +++ | 96 | ++ | 77 |
| 485 | +++ | 93 | ++ | 82 |
| 486 | +++ | 95 | + | 70 |
| 487 | ++++ | 100 | +++ | 95 |
| 488 | ++++ | 101 | +++ | 91 |
| 489 | +++ | 97 | ++ | 76 |
| 490 | +++ | 93 | + | 40 |
| 491 | +++ | 98 | ++ | 76 |
| 492 | ++++ | 99 | +++ | 91 |
| 493 | +++ | 96 | ++ | 68 |
| 494 | ++++ | 99 | +++ | 90 |
| 495 | ++++ | 99 | +++ | 88 |
| 496 | ++++ | 100 | ++++ | 92 |
| 497 | ++++ | 100 | ++++ | 97 |
| 498 | +++ | 98 | +++ | 83 |
| 499 | +++ | 85 | + | 29 |
| 500 | ++++ | 95 | ++ | 83 |
| 501 | +++ | 85 | + | 47 |
| 502 | +++ | 89 | ++ | 70 |
| 503 | +++ | 94 | + | 72 |
| 504 | +++ | 84 | + | 44 |
| 505 | +++ | 96 | ++ | 72 |
| 506 | ++++ | 97 | +++ | 96 |
| 507 | ++++ | 97 | +++ | 77 |
| 508 | +++ | 90 | + | 46 |
| 509 | +++ | 93 | ++ | 54 |
| 510 | +++ | 89 | + | 64 |
| 511 | ++++ | 96 | ++ | 79 |
| 512 | ++++ | 97 | ++ | 80 |
| 513 | +++ | 87 | + | 36 |
| 514 | +++ | 95 | + | 59 |
| 515 | +++ | 90 | ++ | 68 |
| 516 | +++ | 96 | ++ | 77 |
| 517 | ++++ | 98 | +++ | 88 |
| 518 | +++ | 96 | ++ | 72 |
| 519 | ++++ | 96 | +++ | 90 |
| 520 | +++ | 88 | ++ | 53 |
| 521 | +++ | 85 | + | 34 |
| 522 | +++ | 97 | ++ | 83 |
| 523 | +++ | 90 | ++ | 58 |
| 524 | +++ | 95 | + | 50 |
| 525 | +++ | 97 | ++ | 69 |
| 526 | +++ | 90.7 | ++ | 61.2 |

"+" indicates inhibitory effect of >1 μM; "++" indicates inhibitory effect of 0.5-1 μM; "+++" indicates inhibitory effect of 0.1-0.5 μM, "++++" indicates inhibitory effect of <0.1 μM

Example 39. Synthesis of Compound A

BRG1/BRM Inhibitor compound A has the structure:

Compound A

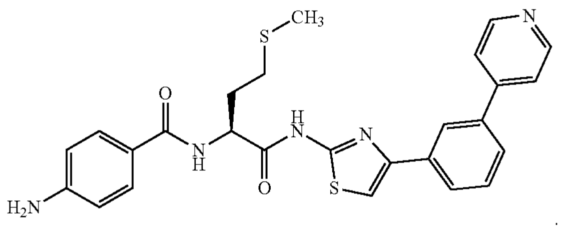

Compound A was synthesized as shown in Scheme 1 below.

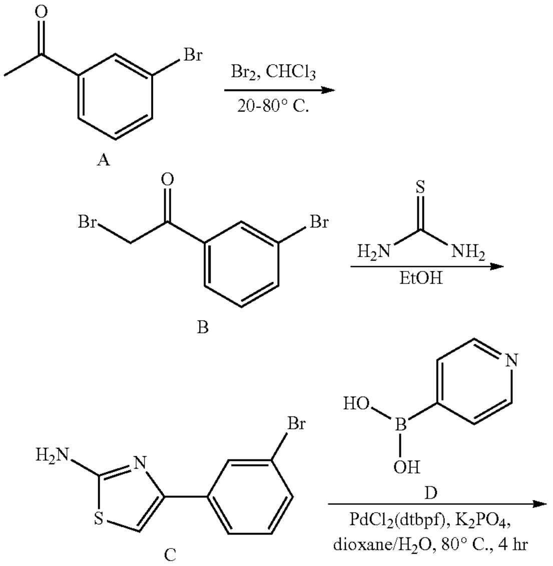

-continued

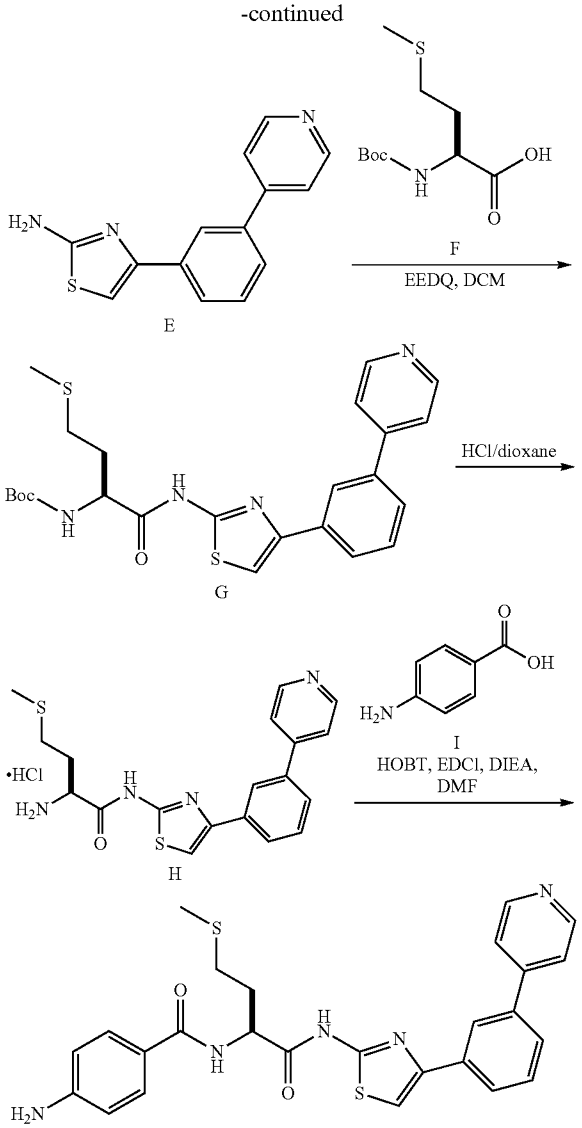

The ATPase catalytic activity of BRM or BRG-1 in the presence of Compound A was measured by the in vitro biochemical assay using ADP-Glo™ (Promega, V9102) described above. Compound A was found to have an $IC_{50}$ of 10.4 nM against BRM and 19.3 nM against BRG1 in the assay.

Example 40. Effects of BRG1/BRM ATPase Inhibition on the Growth of Uveal Melanoma and Hematological Cancer Cell Lines Procedure: Uveal melanoma cell lines (92-1, MP41, MP38, MP46), prostate cancer cell lines (LNCAP), lung cancer cell lines (NCI-H1299), and immortalized embryonic kidney lines (HEK293T) were plated into 96 well plates with growth media (see Table 5). BRG1/BRM ATPase inhibitor, Compound A, was dissolved in DMSO and added to the cells in a concentration gradient from 0 to 10 micromolar at the time of plating. Cells were incubated at 37 degrees Celsius for 3 days. After three days of treatment, the media was removed from the cells and 30 microliters of TrypLE (Gibco) was added to cells for 10 minutes. Cells were detached from the plates and resuspended with the addition of 170 microliters of growth media. Cells from two DMSO-treated control wells were counted, and the initial number of cells plated at the start of the experiment, were re-plated into fresh-compound containing plates for an additional four days at 37 degrees Celsius. At day 7, cells were harvested as described above. On day 3 and day 7, relative cell growth was measured by the addition of Cell-titer glo (Promega) and luminescence was measured on an Envision plate reader (Perkin Elmer). The concentration of compound at which each cell line's growth was inhibited by 50% ($GI_{50}$), was calculated using Graphpad Prism, and is plotted below. For multiple myeloma cell lines (OPM2, MM1S, LP1), ALL cell lines (TALL1, JURKAT, RS411), DLBCL cell lines (SUDHL6, SUDHL4, DB, WSUDLCL2, PFEIFFER), AML cell lines (OCIAML5), MDS cell lines (SKM1), ovarian cancer cell lines (OV7, TYKNU), esophageal cancer cell lines (KYSE150), rhabdoid tumor lines (RD, G402, G401, HS729, A204), liver cancer cell lines (HLF, HLE, PLCRPF5), and lung cancer cell lines (SW1573, NCIH2444), the above methods were performed with the following modifications: Cells were plated in 96 well plates, and the next day, BRG1/BRM ATPase inhibitor, Compound A, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 26 lists the tested cell lines and growth media used.

TABLE 26

Cell Lines and Growth Media

| Cell Line | Source | Growth Media |
|---|---|---|
| 92-1 | SIGMA | RPMI1640 + 20% FBS |
| A204 | ATCC | McCoy's 5A + 10% FBS |
| DB | ATCC | RPMI1640 + 10% FBS |
| G401 | ATCC | McCoy's 5A + 10% FBS |
| G402 | ATCC | McCoy's 5A + 10% FBS |
| HEK293T | ATCC | DMEM + 10% FBS |
| HLE | JCRB | DMEM + 10% FBS |
| HLF | JCRB | DMEM + 10% FBS |
| HS729 | ATCC | DMEM + 10% FBS |
| JURKAT | ATCC | RPMI1640 + 10% FBS |
| KYSE150 | DSMZ | RPMI1640/Ham's F12 + 10% FBS |
| LNCAP | ATCC | RPMI1640 + 10% FBS |
| LP1 | DSMZ | IMDM + 20% FBS |
| MM1S | ATCC | RPMI1640 + 10% FBS |
| MP38 | ATCC | RPMI1640 + 20% FBS |
| MP41 | ATCC | RPMI1640 + 20% FBS |
| MP46 | ATCC | RPMI1640 + 20% FBS |
| NCIH1299 | ATCC | RPMI1640 + 10% FBS |
| NCIH2444 | ATCC | RPMI1640 + 20% FBS |
| OCIAML5 | DSMZ | alpha-MEM + 20% FBS + 10 ng/ml GM-CSF |
| OPM2 | DSMZ | RPMI1640 + 10% FBS |
| OV7 | ECACC | DMEM/Ham's F12 (1:1) + 2 mM Glutamine + 10% FBS + 0.5 ug/ml hydrocortisone + 10 ug/ml insulin |
| PFEIFFER | ATCC | RPMI1640 + 10% FBS |
| PLCPRF5 | ATCC | EMEM + 10% FBS |
| RD | ATCC | DMEM + 10% FBS |
| RS411 | ATCC | RPMI1640 + 10% FBS |
| SKM1 | JCRB | RPMI1640 + 10% FBS |
| SUDHL4 | DSMZ | RPMI1640 + 10% FBS |
| SUDHL6 | ATCC | RPMI1640 + 20% FBS |
| SW1573 | ATCC | DMEM + 10% FBS |
| TALL1 | JCRB | RPMI1640 + 10% FBS |
| TYKNU | JCRB | EMEM + 20% FBS |
| WSUDLCL2 | DSMZ | RPMI1640 + 10% FBS |

Results: As shown in FIG. 1, the uveal melanoma and hematologic cancer cell lines were more sensitive to BRG1/

BRM inhibition than the other tested cell lines. Inhibition of the uveal melanoma and hematologic cancer cell lines was maintained through day 7.

Example 41. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 26). BAF ATPase inhibitors (Compound A), PKC inhibitor (LXS196; MedChemExpress), or MEK inhibitor (Selumetinib; Selleck Chemicals) were dissolved in DMSO and added to the cells in a concentration gradient from 0 to 10 micromolar at the time of plating. Cells were incubated at 37 degrees Celsius for 3 days. After three days of treatment, cell growth was measured with Cell-titer glow (Promega), and luminescence was read on an Envision plate reader (Perkin Elmer).

Figure 2A:
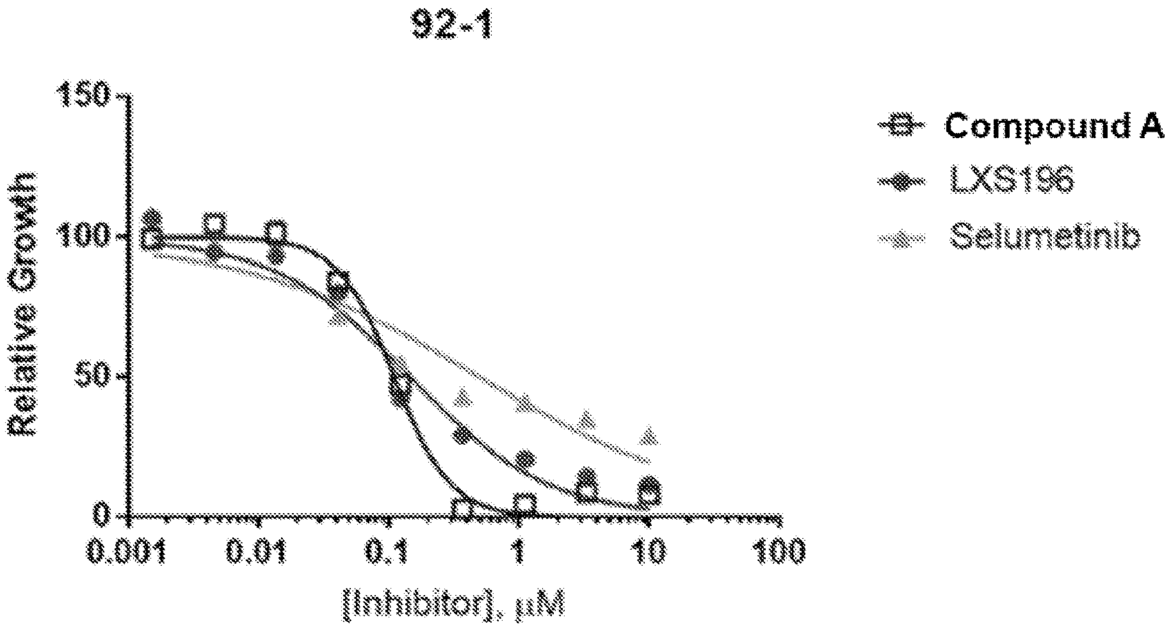
FIG. 2A is a graph illustrating inhibition of cell proliferation of uveal melanoma cell line 92-1 by a BRG1/BRM inhibitor (Compound A), a MEK inhibitor (Selumetinib), and a PKC inhibitor (LXS196).
Figure 2B:
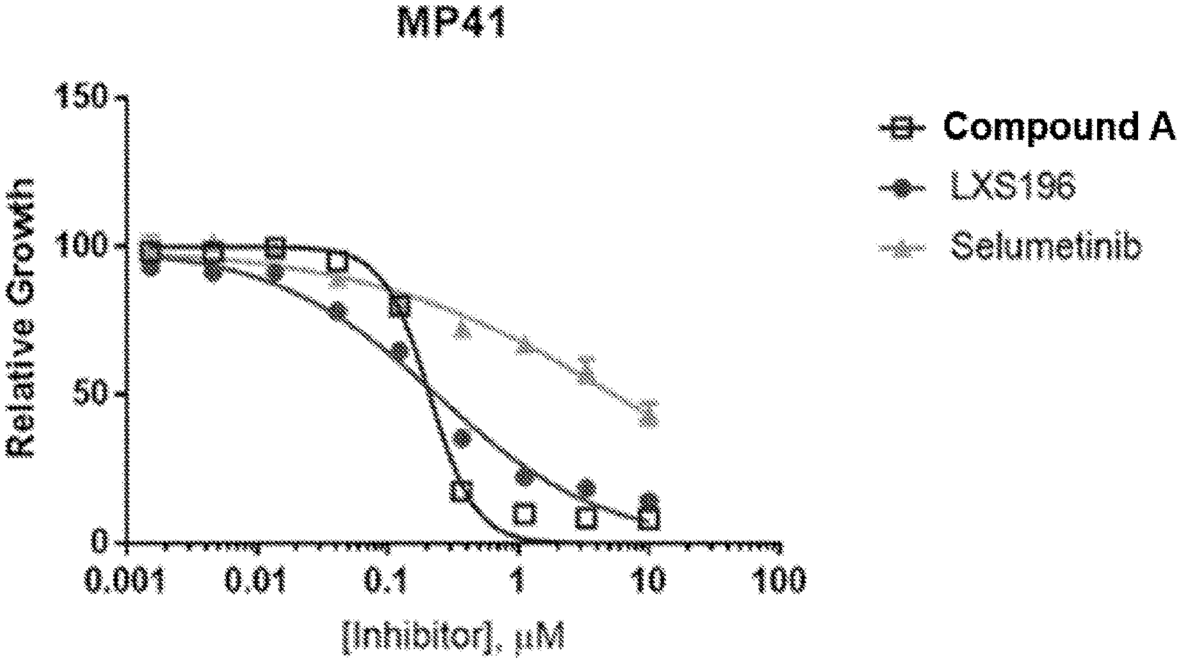
FIG. 2B is a graph illustrating inhibition of cell proliferation of uveal melanoma cell line MP41 by a BRG1/BRM inhibitor (Compound A), a MEK inhibitor (Selumetinib), and a PKC inhibitor (LXS196).

Results: As shown in FIG. 2A and FIG. 2B, Compound A showed comparable growth inhibition of uveal melanoma cells as the clinical PKC and MEK inhibitors. Further, compound A was found to result in a faster onset of inhibition than the clinical PKC and MEK inhibitors.

Example 42. Synthesis of Compound B

BRG1/BRM Inhibitor Compound B has the structure:

Compound B

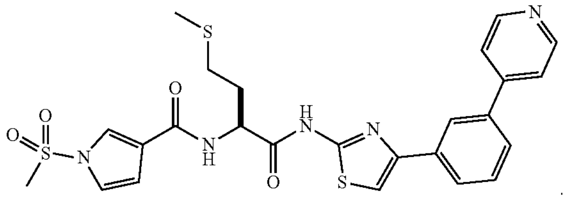

Compound B was synthesized as shown in Scheme 2 below.

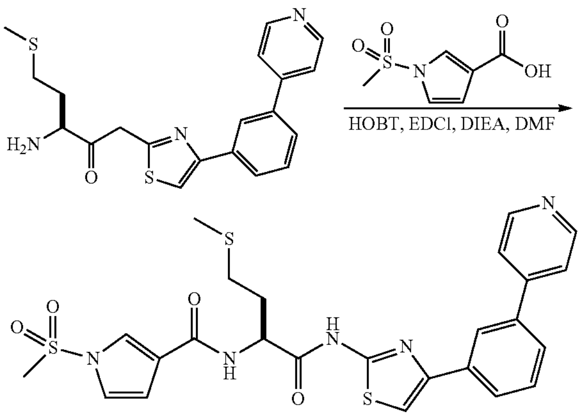

Compound B

Step 1: Preparation of (S)-1-(methylsulfonyl)-N-(4-(methylthio)-1-oxo-1-((4-(3-(pyridin-4-yl)phenyl)thiazol-2-yl)amino)butan-2-yl)-1H-pyrrole-3-carboxamide (Compound B)

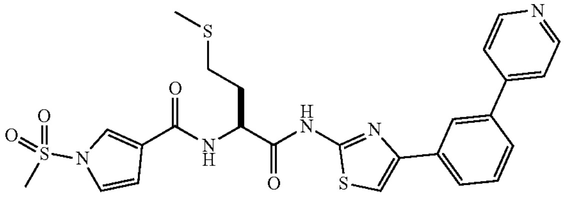 [SMILES: CSCC[C@H](NC(=O)c1ccn(S(C)(=O)=O)c1)C(=O)Nc1nc(-c2cccc(-c3ccncc3)c2)cs1]

To a mixture of (2S)-2-amino-4-methylsulfanyl-N-[4-[3-(4-pyridyl)phenyl]thiazol-2-yl]butanamide (2 g, 4.75 mmol, HCl salt) and 1-methylsulfonylpyrrole-3-carboxylic acid (898.81 mg, 4.75 mmol) in DMF (20 mL) was added EDCI (1.37 g, 7.13 mmol), HOBt (962.92 mg, 7.13 mmol), and DIEA (2.46 g, 19.00 mmol, 3.31 mL) and the mixture was stirred at 25° C. for 3 hours. The mixture was poured into $H_2O$ (100 mL) and the precipitate was collected by filtration. The solid was triturated in MeOH (20 mL) and the precipitate was collected by filtration. The solid was dissolved in DMSO (10 mL) and then the mixture was poured into MeOH (50 mL) and the formed precipitate was collected by filtration and lyophilized to give Compound B (2.05 g, 3.66 mmol, 77.01% yield) as a white solid. LCMS (ESI) m/z $[M+H]^+$=555.9. $^1H$ NMR (400 MHz, DMSO) δ 12.49 (s, 1H), 8.68-8.66 (m, 2H), 8.46 (d, J=7.2 Hz, 1H), 8.31-8.30 (m, 1H), 8.02-8.00 (m, 1H), 7.94-7.96 (m, 1H), 7.83 (s, 1H), 7.73-7.74 (m, 3H), 7.61-7.57 (m, 1H), 7.31-7.29 (m, 1H), 6.79-6.77 (m, 1H), 4.74-4.69 (m, 1H), 3.57 (s, 3H), 2.67-2.53 (m, 2H), 2.13-2.01 (m, 5H). SFC: AS-3-MeOH (DEA)-40-3 mL-35T.lcm, t=0.932 min, ee %=100%.

Example 43. Effects of BRG1/BRM ATPase Inhibition on the Growth of Uveal Melanoma, Hematological Cancer, Prostate Cancer, Breast Cancer, and Ewing's Sarcoma Cell Lines Procedure: All cell lines described above in Example 28 were also tested as described above with Compound B. In addition, the following cell lines were also tested as follows. Briefly, for Ewing's sarcoma cell lines (CADOES1, RDES, SKES1), retinoblastoma cell lines (WERIRB1), ALL cell lines (REH), AML cell lines (KASUMI1), prostate cancer cell lines (PC3, DU145, 22RV1), melanoma cell lines (SH4, SKMEL28, WM115, COL0829, SKMEL3, A375), breast cancer cell lines (MDAMB415, CAMA1, MCF7, BT474, HCC1419, DU4475, BT549), B-ALL cell lines (SUPB15), CML cell lines (K562, MEGO1), Burkitt's lymphoma cell lines (RAMOS2G64C10, DAUDI), mantle cell lymphoma cell lines (JEKO1, REC1), bladder cancer cell lines (HT1197), and lung cancer cell lines (SBC5), the above methods were performed with the following modifications: Cells were plated in 96 well plates, and the next day, BRG1/BRM ATPase inhibitor, Compound B, was dissolved in DMSO and added to the cells in a concentration gradient from 0 to 10 micromolar. At the time of cell splitting on days 3 and 7, cells were split into new 96 well plates, and fresh compound was added four hours after re-plating.

Table 27 lists the tested cell lines and growth media used.

TABLE 27

| Cell Lines And Growth Media | | |
|---|---|---|
| Cell Line | Source | Growth Media |
| 22RV1 | ATCC | RPMI1640 + 10% FBS |
| A375 | ATCC | DMEM + 10% FBS |
| BT474 | ATCC | Hybricare medium + 1.5 g/L sodium bicarbonate + 10% FBS |
| BT549 | ATCC | RPMI1640 + 0.023 IU/ml insulin + 10% FBS |
| CADOES1 | DSMZ | RPMI1640 + 10% FBS |
| CAMA1 | ATCC | EMEM + 10% FBS |
| COLO829 | ATCC | RPMI1640 + 10% FBS |
| DAUDI | ATCC | RPMI1640 + 10% FBS |
| DU145 | ATCC | EMEM + 10% FBS |
| DU4475 | ATCC | RPMI1640 + 10% FBS |
| HCC1419 | ATCC | RPMI1640 + 10% FBS |
| HT1197 | ATCC | EMEM + 10% FBS |
| JEKO1 | ATCC | RPMI1640 + 20% FBS |
| K562 | ATCC | IMDM + 10% FBS |
| KSUMI1 | ATCC | RPMI1640 + 10% FBS |
| MCF7 | ATCC | EMEM + 0.01 mg/ml bovine insulin + 10% FBS |
| MDAMB415 | ATCC | Leibovitz's L-15 + 2 mM L-glutamine + 10 mcg/ml insulin + 10 mcg/ml glutathione + 15% FBS |
| MEG01 | ATCC | RPMI1640 + 10% FBS |
| PC3 | ATCC | F-12K + 10% FBS |
| RAMOS2G64C10 | ATCC | RPMI1640 + 10% FBS |
| RDES | ATCC | RPMI1640 + 15% FBS |
| REC1 | ATCC | RPMI1640 + 10% FBS |
| REH | ATCC | RPMI1640 + 10% FBS |
| SBC5 | JCRB | EMEM + 10% FBS |
| SH4 | ATCC | DMEM + 10% FBS |
| SKES1 | ATCC | McCoy's 5A + 15% FBS |
| SKMEL28 | ATCC | EMEM + 10% FBS |
| SKMEL3 | ATCC | McCoy's 5A + 15% FBS |
| SUPB15 | ATCC | IMDM + 4 mM L-glutamine + 1.5 g/L sodium bicarbonate + 0.05 mM 2-mercaptoethanol + 20% FBS |
| WERIRB1 | ATCC | RPMI1640 + 10% FBS |
| WM115 | ATCC | EMEM + 10% FBS |

Figure 3:
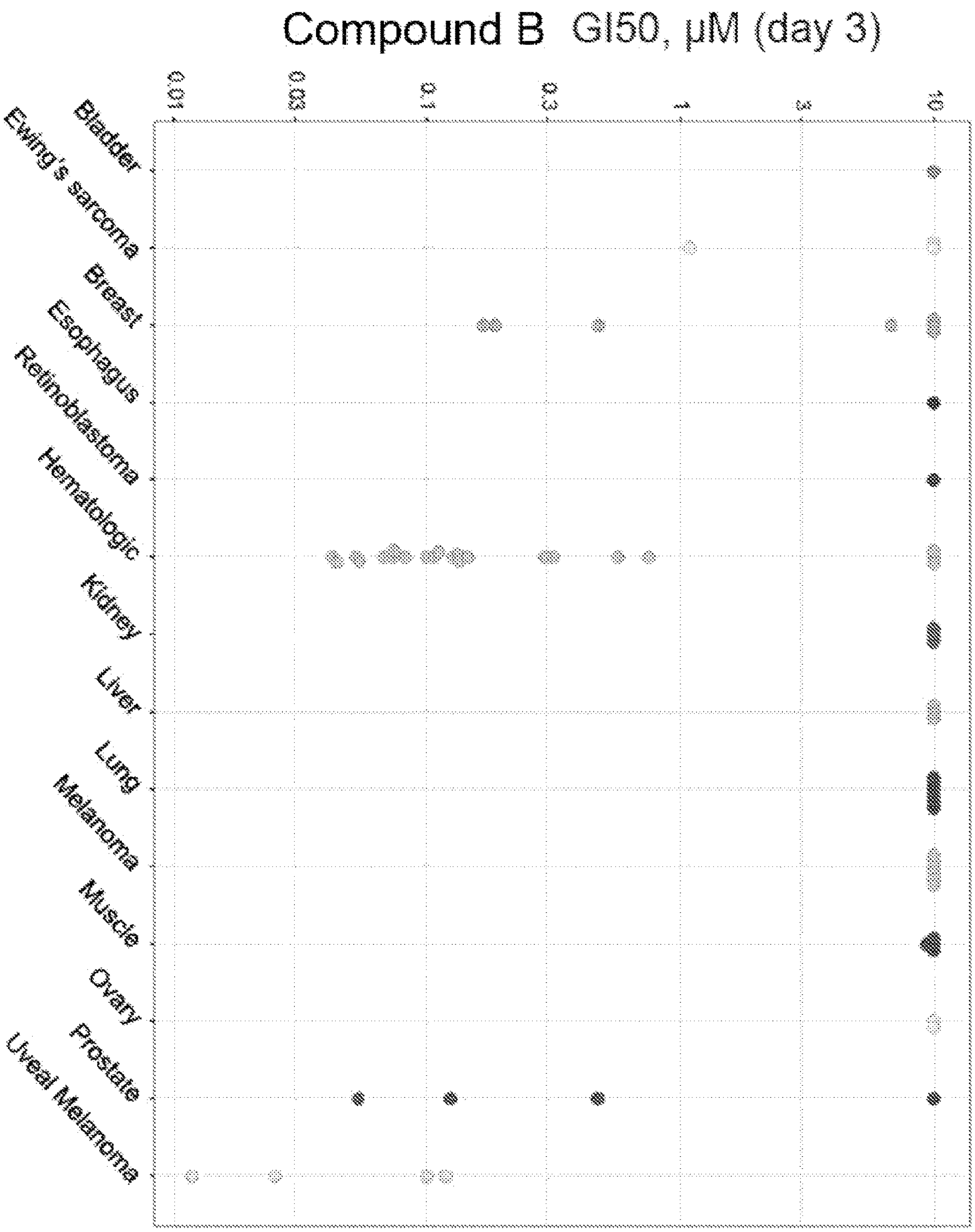
FIG. 3 is a graph illustrating inhibition of cell proliferation of several cancer cell lines by a BRG1/BRM inhibitor (Compound B).

Results: As shown in FIG. 3, the uveal melanoma, hematologic cancer, prostate cancer, breast cancer, and Ewing's sarcoma cell lines were more sensitive to BRG1/BRM inhibition than the other tested cell lines. Inhibition of the uveal melanoma, hematologic cancer, prostate cancer, breast cancer, and Ewing's sarcoma cell lines was maintained through day 7.

Example 44. Effects of BRG1/BRM ATPase Inhibition on the Growth of Cancer Cell Lines Procedure: A pooled cell viability assay was performed using PRISM (Profiling Relative Inhibition Simultaneously in Mixtures) as previously described ("High-throughput identification of genotype-specific cancer vulnerabilities in mixtures of barcoded tumor cell lines", Yu et al, Nature Biotechnology 34, 419-423, 2016), with the following modifications. Cell lines were obtained from the Cancer Cell Line Encyclopedia (CCLE) collection and adapted to RPMI-1640 medium without phenol red, supplemented with 10% heat-inactivated fetal bovine serum (FBS), in order to apply a unique infection and pooling protocol to such a big compendium of cell lines. A lentiviral spin-infection protocol was executed to introduce a 24 nucleotide-barcode in each cell line, with an estimated multiplicity of infection (MOI) of 1 for all cell lines, using blasticidin as selection marker. Over 750 PRISM cancer cell lines stably barcoded were then pooled together according to doubling time in pools of 25. For the screen execution, instead of plating a pool of 25 cell lines in each well as previously described (Yu et al.), all the adherent or all the suspension cell line pools were plated together using T25 flasks (100,000 cells/flask) or 6-well plates (50,000 cells/well), respectively. Cells were treated with either DMSO or compound in a 8-point 3-fold dose response in triplicate, starting from a top concentration of 10 μM. As control for assay robustness, cells were treated in parallel with two previously validated compounds, the pan-Raf inhibitor AZ-628, and the proteasome inhibitor bortezomib, using a top concentration of 2.5 μM and 0.039 μM, respectively.

Figure 4:
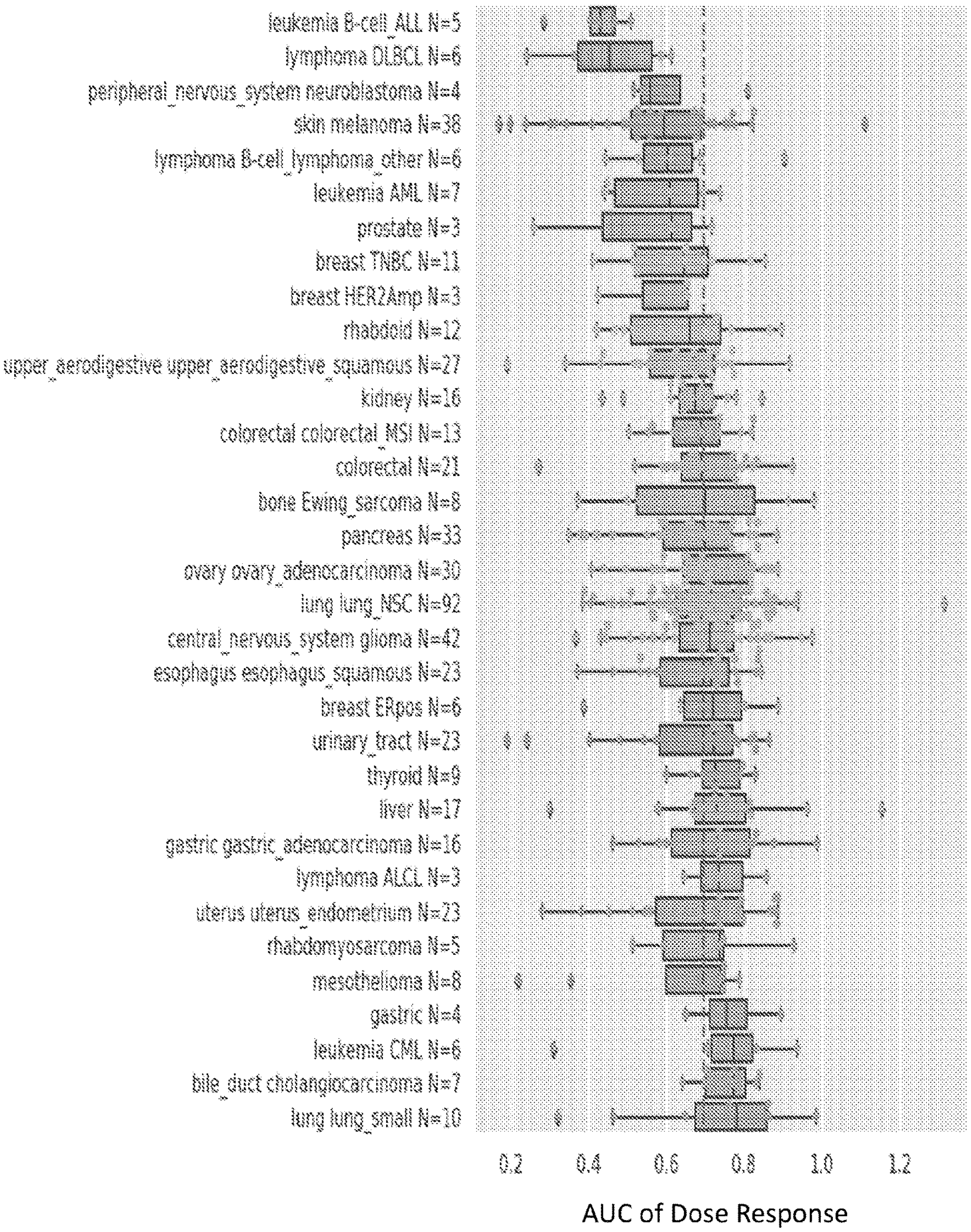
FIG. 4 is a graph illustrating the area under the curves (AUCs) calculated from dose-response curves for cancer cell lines treated with a BRG1/BRM inhibitor.

Following 3 days of treatment with compounds, cells were lysed, genomic DNA was extracted, barcodes were amplified by PCR and detected with Next-Generation Sequencing. Cell viability was determined by comparing the counts of cell-line specific barcodes in treated samples to those in the DMSO-control and Day 0 control. Dose-response curves were fit for each cell line and corresponding area under the curves (AUCs) were calculated and compared to the median AUC of all cell lines (FIG. 4). Cell lines with AUCs less than the median were considered most sensitive.

Example 45. Effects of BRG1/BRM ATPase Inhibitors on the Growth of Uveal Melanoma Cell Lines Procedure: Uveal melanoma cell lines (92-1, MP41, MP38, MP46) and Non-small cell lung cancer cells (NCIH1299) were plated into 96 well plates with growth media (see Table 27). BRG1/BRM ATPase inhibitor, compound 67, was dissolved in DMSO and added to the cells in a concentration gradient from 0 to 10 micromolar at the time of plating. Cells were incubated at 37° C. for 3 days. After three days of treatment, cell growth was measured with Cell-titer glow (Promega), and luminescence was read on an Envision plate reader (Perkin Elmer).

Figure 5:
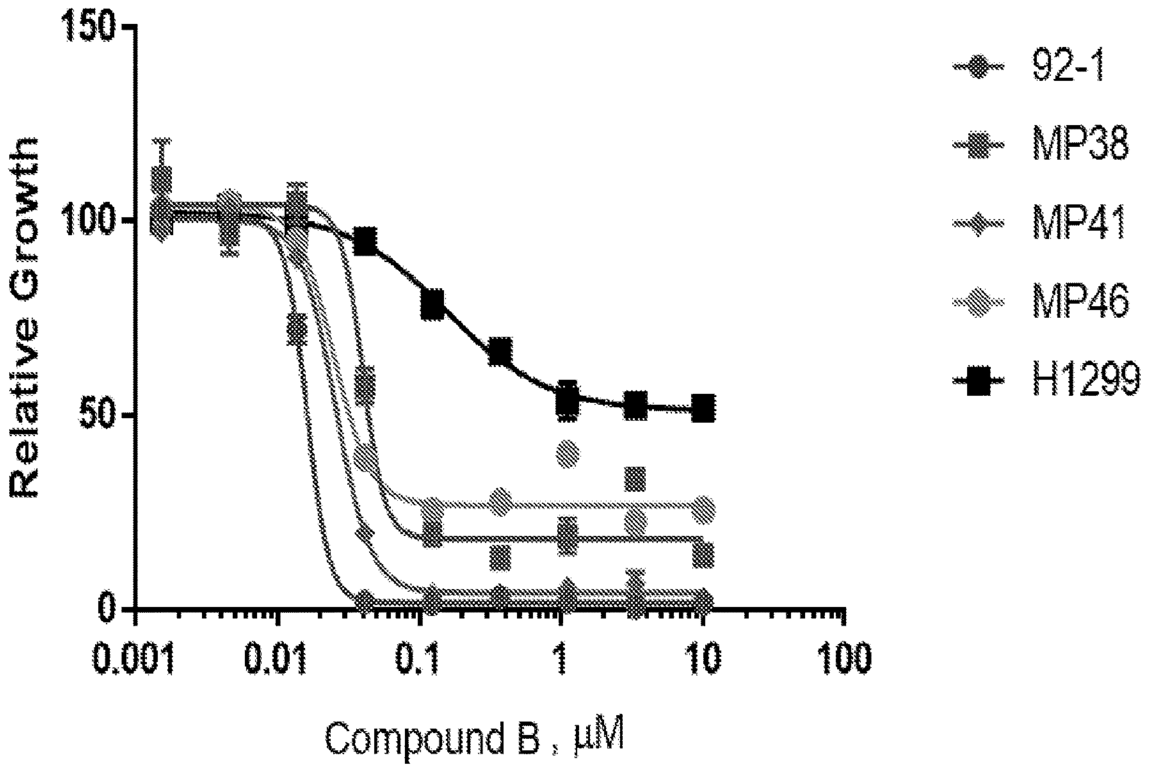
FIG. 5 is a graph illustrating inhibition of cell proliferation of uveal melanoma and non-small cell lung cancer cell lines by a BRG1/BRM inhibitor (Compound B).

Results: As shown in FIG. 5, Compound B resulted in potent growth inhibition in the uveal melanoma cell lines.

Example 46. Comparison of BRG1/BRM Inhibitors to Clinical PKC and MEK Inhibitors in Uveal Melanoma Cell Lines Procedure: Uveal melanoma cell lines, 92-1 or MP41, were plated in 96 well plates in the presence of growth media (see Table 27). BAF ATPase inhibitor (Compound B), PKC inhibitor (LXS196; MedChemExpress), and MEK inhibitor (Selumetinib; Selleck Chemicals) were dissolved in DMSO and added to the cells in a concentration gradient from 0 to 10 micromolar at the time of plating. Cells were incubated at 37° C. for 3 days. After three days of treatment, cell growth was measured with Cell-titer glow (Promega), and luminescence was read on an Envision plate reader (Perkin Elmer).

Figure 6A:
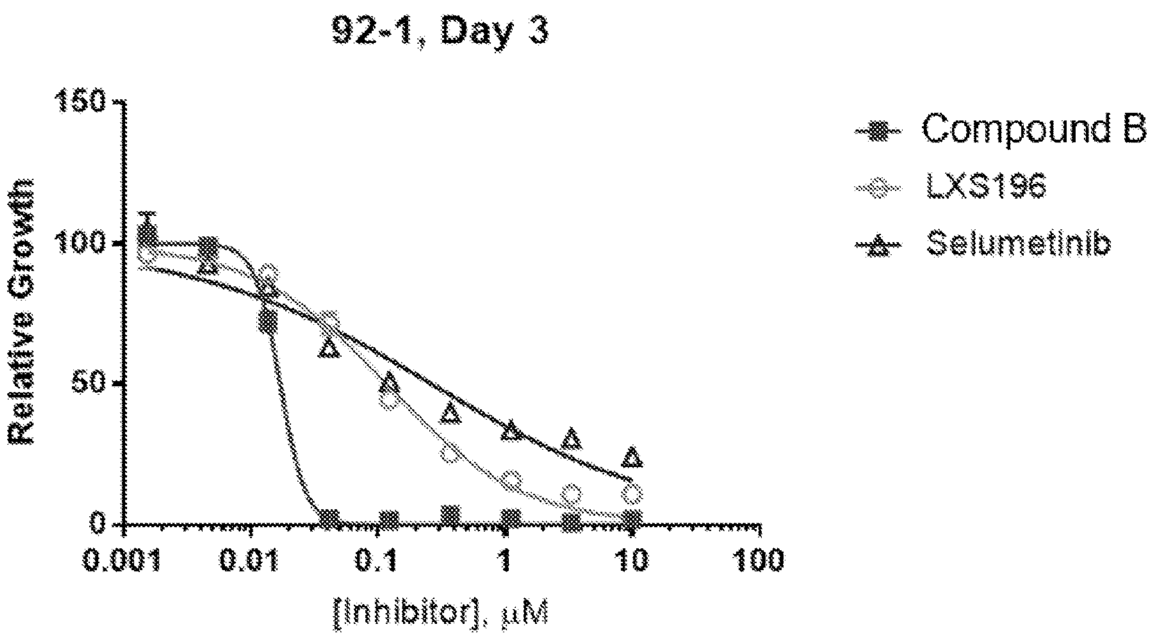
FIG. 6A is a graph illustrating inhibition of cell proliferation of uveal melanoma cell line 92-1 by a BRG1/BRM inhibitor (Compound B), a MEK inhibitor (Selumetinib), and a PKC inhibitor (LXS196).
Figure 6B:
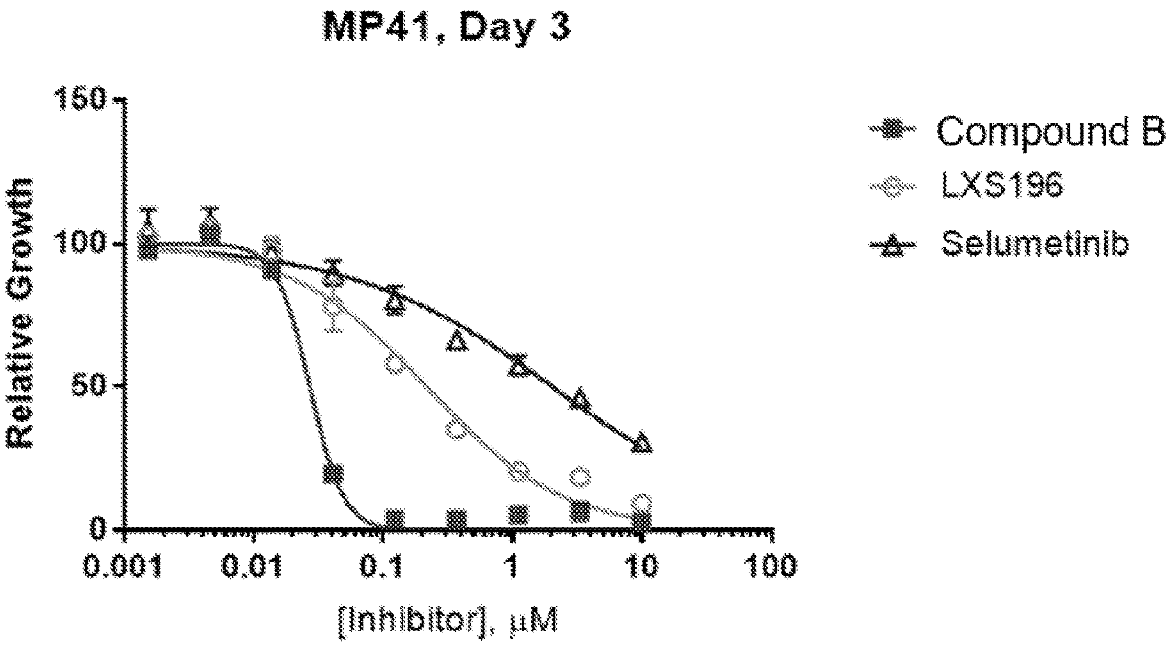
FIG. 6B is a graph illustrating inhibition of cell proliferation of uveal melanoma cell line MP41 by a BRG1/BRM inhibitor (Compound B), a MEK inhibitor (Selumetinib), and a PKC inhibitor (LXS196).

Results: As shown in FIG. 6A and FIG. 6B, compound B showed more potent effects on growth inhibition of uveal melanoma cells as compared to the clinical PKC and MEK inhibitors. Further, Compound B was found to result in a faster onset of growth inhibition than the clinical PKC and MEK inhibitors.

Example 47. BRG1/BRM ATPase Inhibitors are Effective at Inhibiting the Growth of PKC Inhibitor-Resistant Cells Procedure: MP41 uveal melanoma cells were made resistant to the PKC inhibitor (LXS196; MedChemExpress), by long-term culture in growth media (see Table 27) containing increasing concentrations of the compound, up to 1 micromolar. After 3 months, sensitivity of the parental MP41 cells and the PKC inhibitor (PKCi)-resistant cells to the PKC inhibitor (LXS196) or the BRG1/BRM ATPase inhibitor (Compound B) was tested in a 7-day growth inhibition assay as described above in Example 9.

Figure 7A:
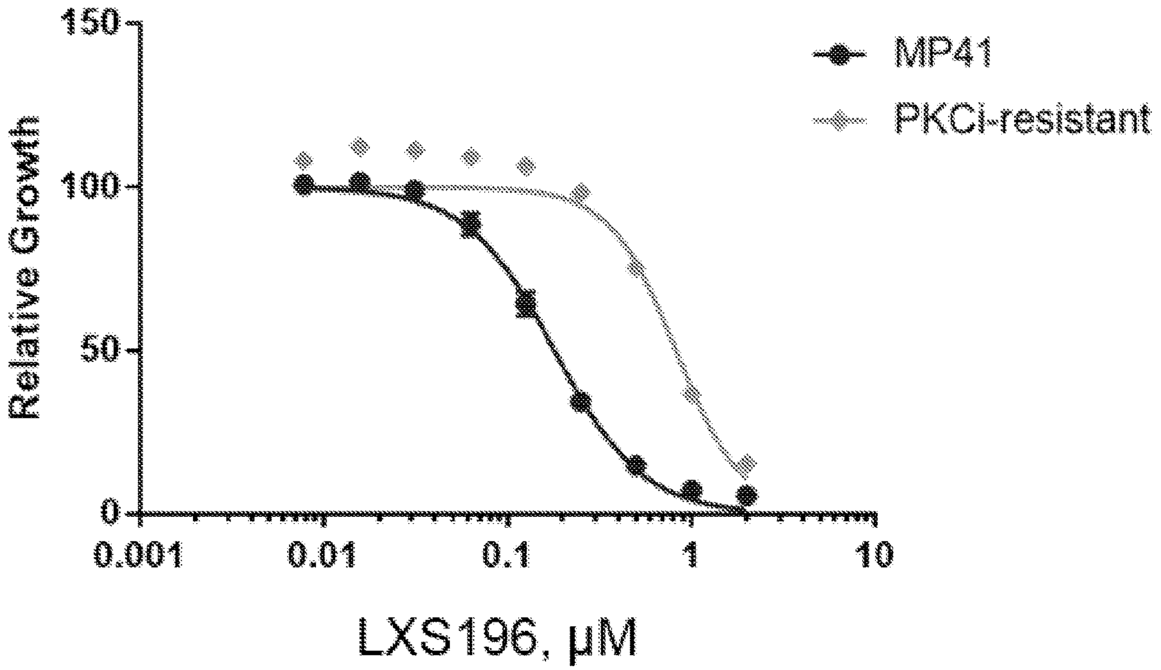
FIG. 7A is a graph illustrating inhibition of cell proliferation of parental and PKC-inhibitor refractory uveal melanoma cell lines by a PKC inhibitor (LXS196).
Figure 7B:
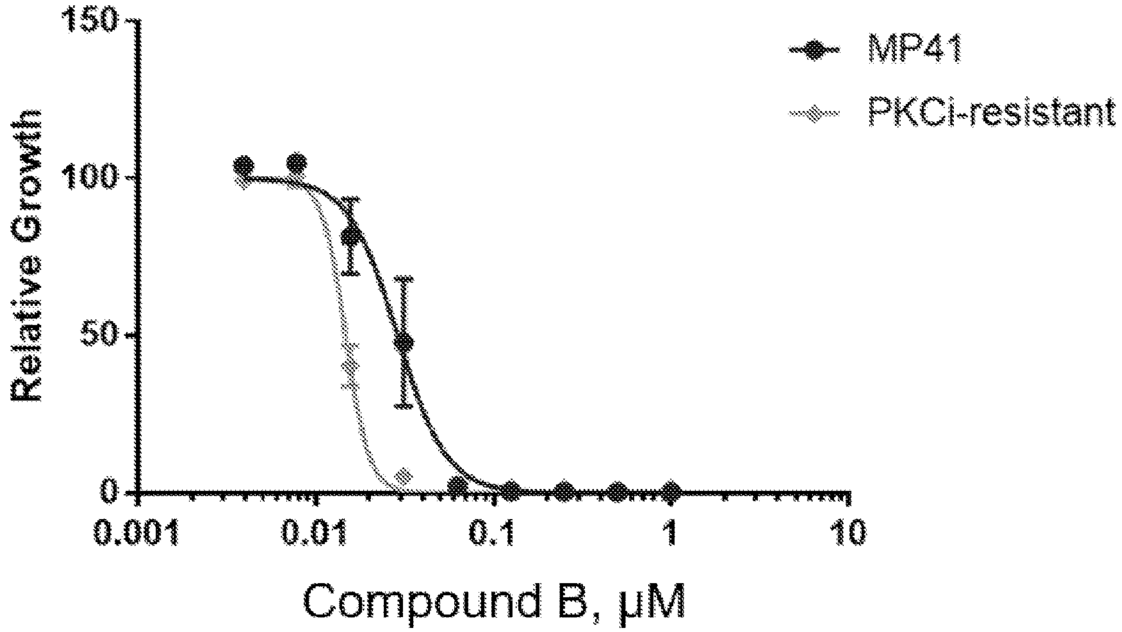
FIG. 7B is a graph illustrating inhibition of cell proliferation of parental and PKC-inhibitor refractory uveal melanoma cell lines by a BRG1/BRM inhibitor (Compound B).

Results: While the PKCi-resistant cells could tolerate growth at higher concentrations of LXS196 than could the parental MP41 cell line (FIG. 7A), the BRG1/BRM ATPase inhibitor (Compound B) still resulted in strong growth inhibition of both the PKCi-resistant and parental cell lines (FIG. 7B). The PKCi-resistant cells were more sensitive to Compound B than were the parental MP41 cells (FIG. 7B).

Example 48. Synthesis of Compound C

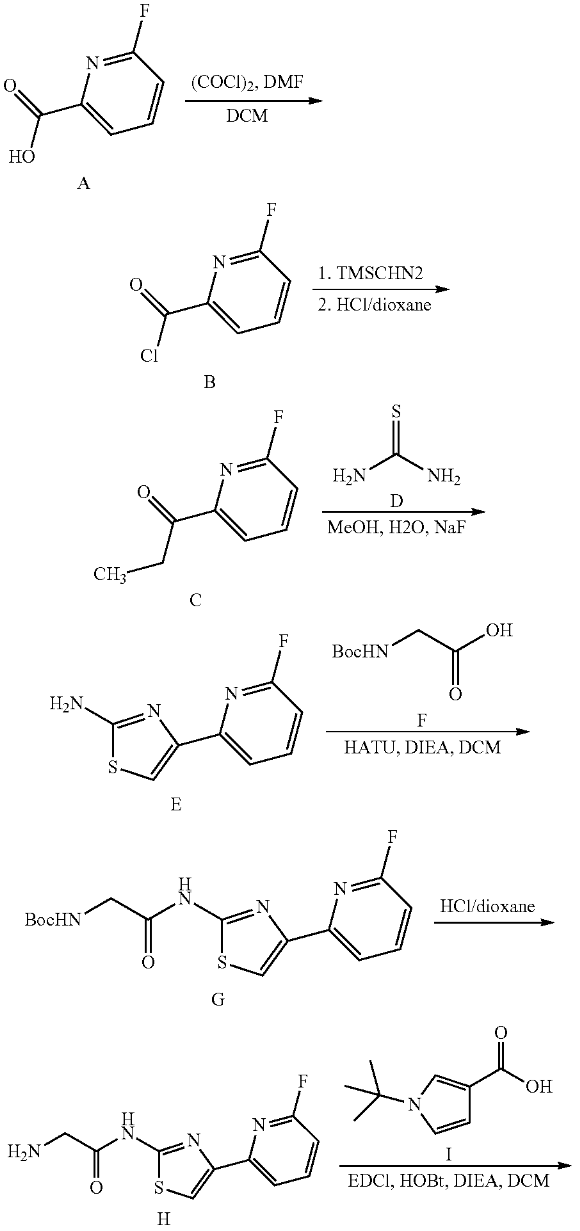

-continued

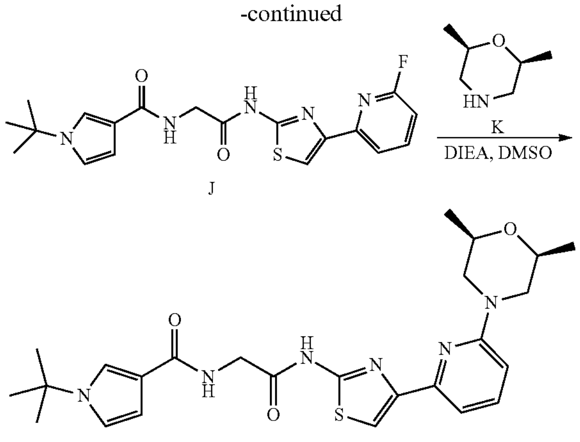

Compound C

Step 1: Preparation of 6-fluoropyridine-2-carbonyl chloride (Intermediate B)

B

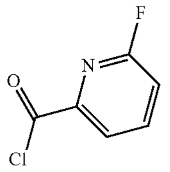

To a cooled (0° C.) solution of 6-fluoropyridine-2-carboxylic acid (50.00 g, 354.36 mmol) in dichloromethane (500 mL) and N,N-dimethylformamide (0.26 mL, 3.54 mmol) was added oxalyl chloride (155.10 ml, 1.77 mol). After complete addition of oxalyl chloride, the reaction mixture was warmed to room temperature and stirred for an additional 0.5 h. The mixture was concentrated under vacuum to give Intermediate B (56.50 g) as a white solid, which was used to next step without further purification.

Step 2: Preparation of 2-chloro-1-(6-fluoro-2-pyridyl)ethenone (Intermediate C)

C

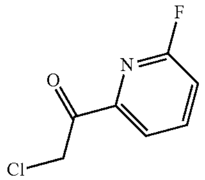

To a cooled (0°) mixture of Intermediate B (56.00 g, 351.00 mmol) in 1,4-dioxane (800 mL) was added in a dropwise manner a solution of 2 M trimethylsilyl diazomethane in hexanes (351 mL). The resulting reaction mixture was stirred at 25° C. for 10 h. The reaction mixture was subsequently quenched with a solution of 4 M HCl in 1,4-dioxane (500 mL). After stirring for 2 h, the reaction solution was concentrated under vacuum to give an oil. The residue was diluted with saturated aqueous $NaHCO_3$ (500 mL) and extracted with ethyl acetate (200 mL×3). The combined organic layers were washed with brine (300 mL×2), dried over $Na_2SO_4$, filtered, and concentrated under reduced pressure to give Intermediate C (35.50 g) as a white solid, which was used to next step directly. LCMS (ESI) m/z: $[M+H]^+$=173.8.

Step 3: Preparation of 4-(6-fluoro-2-pyridyl)thiazol-2-amine (Intermediate E)

E

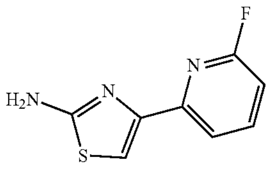

To a solution of Intermediate C (35.50 g, 204.53 mmol) and thiourea (14.01 g, 184.07 mmol) in a mixture of MeOH (250 mL) and $H_2O$ (250 mL) at room temperature was added NaF (3.56 g, 84.82 mmol). After stirring for 0.5 h, the reaction mixture was partially concentrated under vacuum to remove MeOH, and the resulting solution was acidified to pH ~3 with aqueous 2 M HCl. After 15 min, the solution was extracted with ethyl acetate (200 mL×3), the organic layers were discarded and the aqueous phase was alkalized with $NaHCO_3$ (500 mL) and stirred for 30 min, then extracted with ethyl acetate (325 mL*3), the combined organic layers were washed with brine (225 mL*3), dried over $Na_2SO_4$, filtered, and concentrated under reduced pressure. The residue was triturated with petroleum ether (300 mL) and stirred at 25° C. for 10 min and filtered. The resultant solids were dried under vacuum to give Intermediate E (28.00 g, 143.43 mmol, 70.13% yield, 100% purity) as a white solid. LCMS (ESI) m/z: $[M+H]^+$=195.8; $^1$H NMR (400 MHz, DMSO-$d_6$) δ 8.00-7.96 (m, 1H), 7.72 (d, J=7.2 Hz, 1H), 7.24 (s, 1H), 7.16 (s, 2H), 7.02 (d, J=8.0 Hz, 1H).

Step 4: Preparation of tert-butyl N-[2-[[4-(6-fluoro-2-pyridyl)thiazol-2-yl]amino]-2-oxo-ethyl]carbamate (Intermediate G)

G

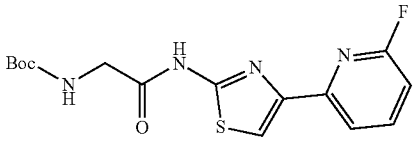

To a solution of N-Boc-glycine (5.92 g, 33.81 mmol), HATU (12.86 g, 33.81 mmol), and DIEA (15.89 g, 122.94 mmol, 21.41 mL) in dichloromethane (100 mL) was added Intermediate E (6.00 g, 30.74 mmol). After stirring for 2 h, the reaction mixture was concentrated and subsequently diluted with water (100 mL) and extracted with ethyl acetate (60 mL×4). The combined organic layers were washed with brine (100 mL×2), dried over $Na_2SO_4$, filtered, and concentrated under reduced pressure to give a residue. The residue was triturated with a 1:1 mixture of petroleum ether and MeOH (40 mL). After stirring at 25° C. for 20 min, the suspension was filtered, the filter cake was washed with MTBE (20 mL) and dried in vacuo to give Intermediate G (7.7 g, 21.63 mmol, 70.4% yield, 99.0% purity) as a white solid. LCMS (ESI) m/z: $[M+H]^+$=353.1.

Step 5: Preparation of 2-((4-(6-fluoropyridin-2-yl)thiazol-2-yl)amino)-2-oxoethan-1-aminium chloride (Intermediate H)

H

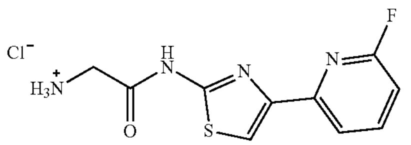

A solution of Intermediate G (5.40 g, 15.32 mmol) in 4 M HCl in 1,4-dioxane (35 mL) was stirred at 25° C. for 1.5 h. The mixture was concentrated under vacuum to give Intermediate H (4.42 g) as a white solid, which was used to next step directly without further purification. LCMS (ESI) m/z: $[M+H]^+$=252.9.

Step 6: Preparation of 1-tert-butyl-N-[2-[[4-(6-fluoro-2-pyridyl)thiazol-2-yl]amino]-2-oxo-ethyl]pyrrole-3-carboxamide (Intermediate J)

J

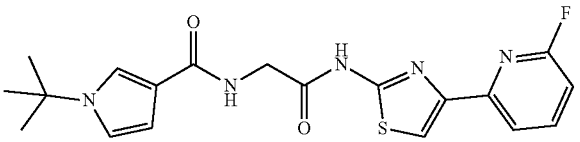

To a solution of Intermediate H (3.00 g, 10.39 mmol), 1-tert-butylpyrrole-3-carboxylic acid (1.74 g, 10.39 mmol), and DIEA (6.71 g, 51.95 mmol, 9.05 mL) in dichloromethane (40 mL) was sequentially added HOBt (1.68 g, 12.47 mmol) and EDCI (2.39 g, 12.47 mmol). After stirring for 4 h, the mixture was concentrated under vacuum. The residue was diluted with water (250 mL) and extracted with ethyl acetate (200 mL×3). The combined organic layers were washed with brine (300 mL×3), dried over $Na_2SO_4$, filtered, and concentrated under reduced pressure. The resulting solids were triturated with a 1:1 mixture of MTBE/ethyl acetate (400 mL) and after 30 min, the suspension was filtered. The solids were washed with MTBE (85 mL×3) and then dried under vacuum to give Intermediate J (3.10 g, 7.64 mmol, 73.6% yield, 99.0% purity) as a white solid.

LCMS (ESI) m/z: $[M+H]^+$=402.3.

$^1$H NMR (400 MHz, DMSO-$d_6$) δ 12.40 (s, 1H), 8.18-8.15 (m, 1H), 8.09-8.08 (m, 1H), 7.87-7.83 (m, 2H), 7.52 (s, 1H), 7.11 (d, J=8.0 Hz, 1H), 6.97 (m, 1H), 6.47 (s, 1H), 4.10 (d, J=5.6 Hz, 2H), 1.49 (s, 9H).

Step 7: Preparation of 1-(tert-butyl)-N-(2-((4-(6-(cis-2,6-dimethylmorpholino)pyridin-2-yl)thiazol-2-yl)amino)-2-oxoethyl)-1H-pyrrole-3-carboxamide (Compound C)

Compound C

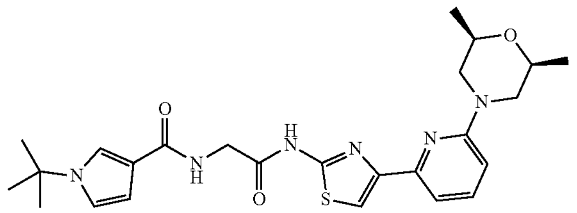

To a solution of Intermediate J (0.100 g, 0.249 mmol) in DMSO (1 mL) was added DIEA (0.130 mL, 0.747 mmol) and cis-2,6-dimethylmorpholine (0.057 g, 0.498 mmol) and the mixture was stirred at 120° C. After 12 h, the solution was cooled to room temperature and reaction mixture was diluted with MeOH (3 mL). The residue was purified by prep-HPLC (0.1% TFA; column: Luna C18 150*25 5 u; mobile phase: [water (0.075% TFA)-ACN]; B %: 30%-60%, 2 min). The appropriate fractions were collected and lyophilized to give Compound C (0.079 g, 0.129 mmol, 51.94% yield, 100% purity) as a white solid.

LCMS (ESI) m/z: $[M+H]^+$=497.5.

$^1H$ NMR (400 MHz, DMSO-$d_6$) δ 12.27 (s, 1H), 8.17-8.14 (m, 1H), 7.75 (s, 1H), 7.63-7.59 (m, 1H), 7.51 (s, 1H), 7.25 (d, J=7.2 Hz, 1H), 6.96 (s, 1H), 6.79 (d, J=8.8 Hz, 1H), 6.47 (s, 1H), 4.24 (d, J=12.4 Hz, 2H), 4.08 (d, J=5.6 Hz, 2H), 3.64-3.61 (m, 2H), 2.44-2.38 (m, 2H), 1.49 (s, 9H), 1.18 (d, J=5.6 Hz, 6H).

Example 49. BRG1/BRM ATPase Inhibitors Cause Uveal Melanoma Tumor Growth Inhibition in Vivo Procedure: Nude mice (Envigo) were engrafted subcutaneously in the axillary region with $5\times10^6$ 92-1 uveal melanoma cells in 50% Matrigel. Tumors were grown to a mean of ~200 $mm^3$, at which point mice were grouped and dosing was initiated. Mice were dosed once daily by oral gavage with vehicle (20% 2-Hydroxypropyl-β-Cyclodextrin) or increasing doses of Compound C. Tumor volumes and body weights were measured over the course of 3 weeks, and doses were adjusted by body weight to achieve the proper dose in terms of mg/kg. At this time, animals were sacrificed, and tumors were dissected and imaged.

Figure 8A:
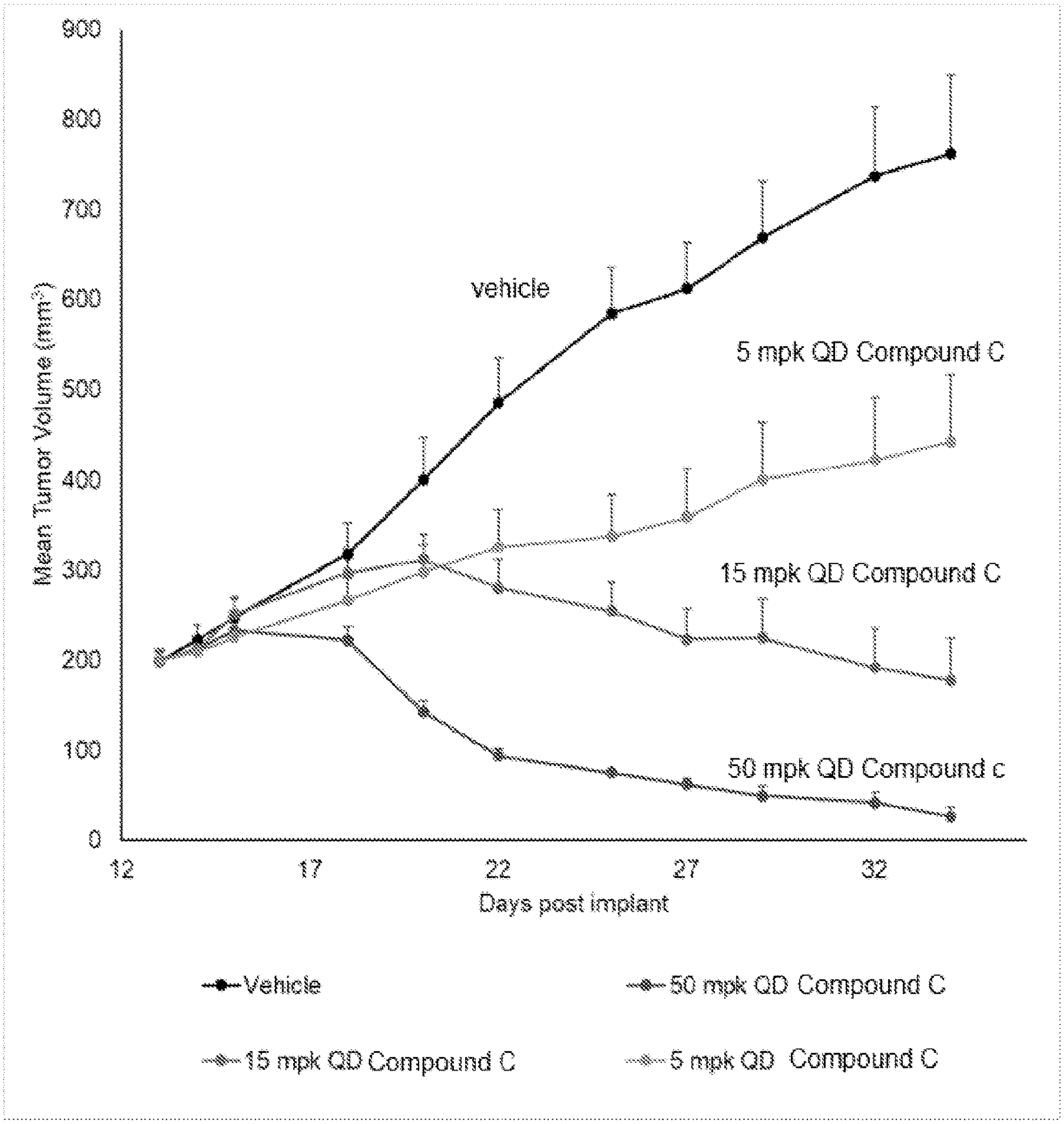
FIG. 8A is a graph illustrating inhibition of tumor growth in mice engrafted with uveal melanoma cell lines by a BRG1/BRM inhibitor (Compound C).
Figure 8B:
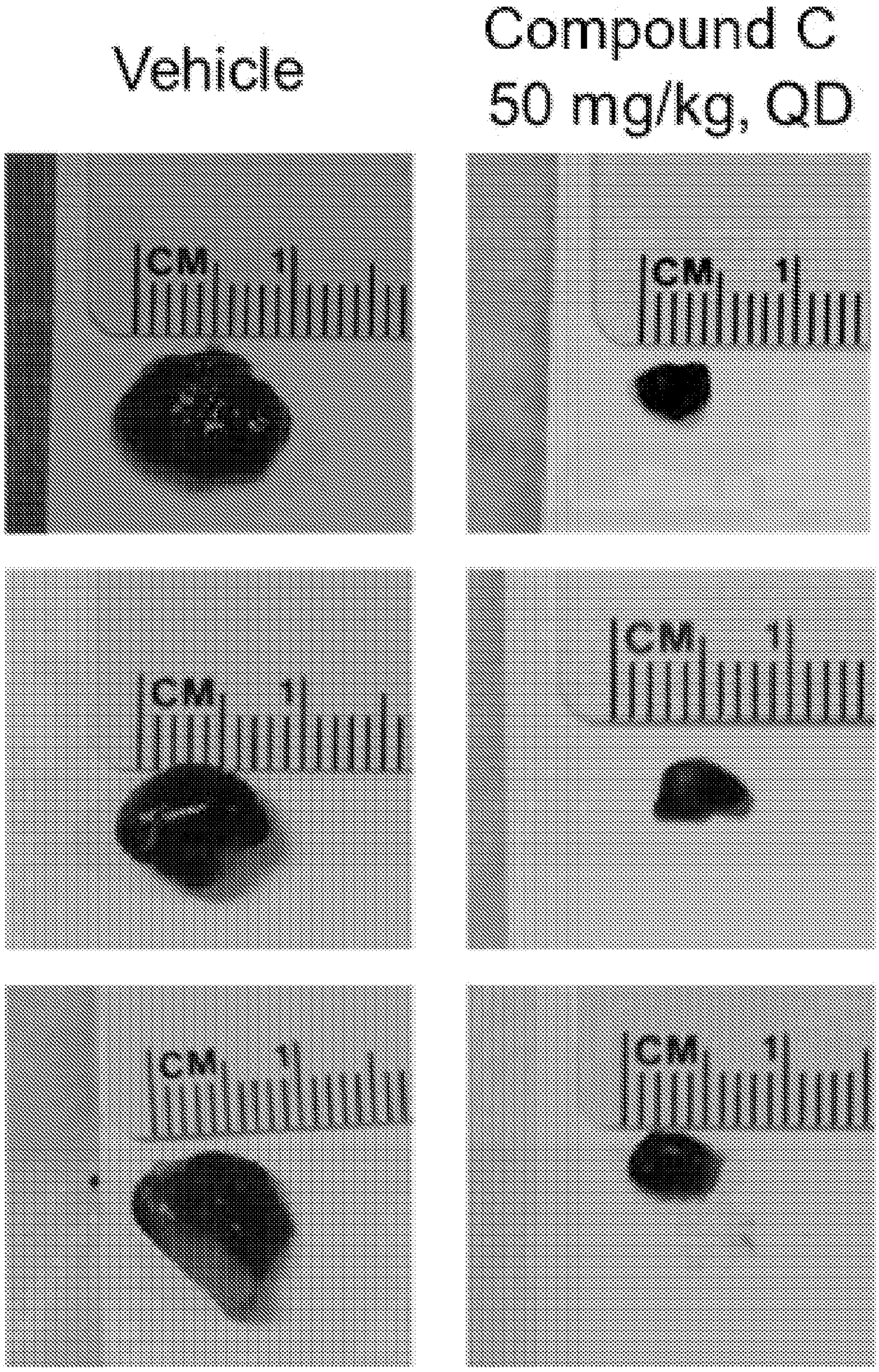
FIG. 8B is an illustration of the size of tumors from mice engrafted with uveal melanoma cell lines and dosed with a BRG1/BRM inhibitor (Compound C).
Figure 8C:
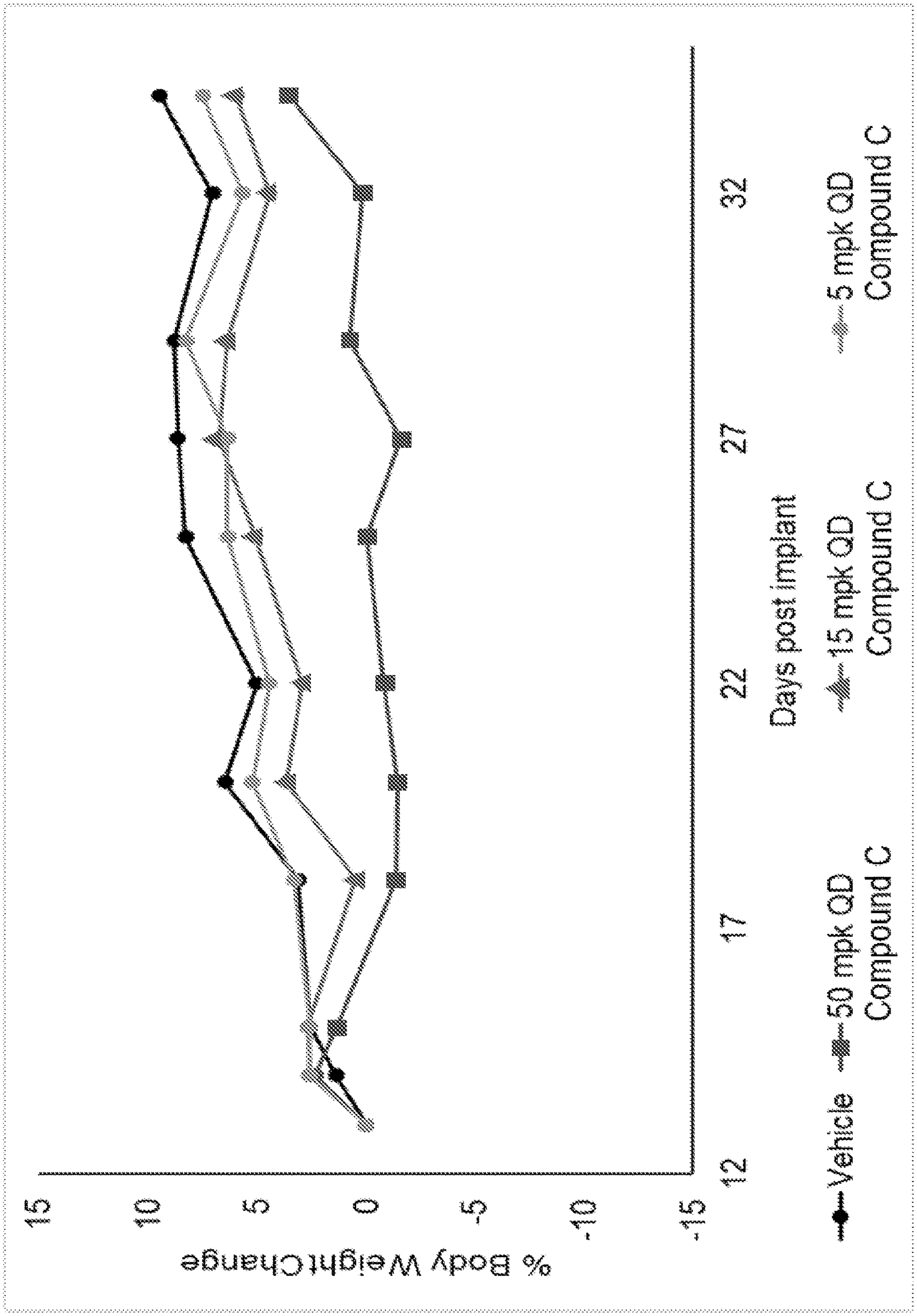
FIG. 8C is a graph illustrating body weight change of mice engrafted with uveal melanoma cell lines and dosed with a BRG1/BRM inhibitor (Compound C).

Results: Treatment with Compound C led to tumor growth inhibition in a dose-dependent manner with tumor regression observed at the highest (50 mg/kg) dose. (FIG. 8A and FIG. 8B). All treatments were well tolerated with no body weight loss observed (FIG. 8C).

OTHER EMBODIMENTS

While the invention has been described in connection with specific embodiments thereof, it will be understood that invention is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the claims.

Other embodiments are in the claims.

The invention claimed is:

1. A compound having the structure:

Formula I

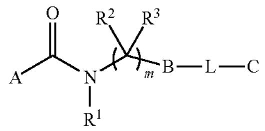

wherein

A is

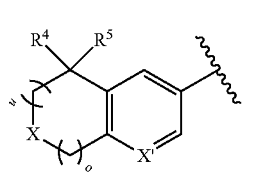

or

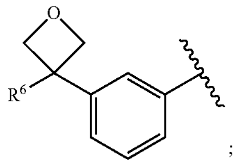

;

m is 0, 1, 2, or 3;

n is 1 or 2;

o is 0 or 1;

X is O, $CH_2$, or $NR^7$;

X' is N, CH, or $CR^X$, wherein $R^X$ is a halogen;

B is an optionally substituted 6-membered monocyclic heteroarylene or an optionally substituted 9- or 10-membered bicyclic heteroarylene;

L is a covalent bond, optionally substituted $C_1$-$C_3$ alkylene, $C_2$ alkynylene, optionally substituted $C_2$ alkenylene, optionally substituted $C_2$-$C_3$ heteroalkylene, optionally substituted $C_3$-$C_5$ cycloalkylene, or optionally substituted 4- to 10-membered heterocyclylene;

C is optionally substituted 3- to 10-membered cycloalkyl; optionally substituted 6- to 10-membered aryl; optionally substituted 5- to 10-membered heteroaryl; or optionally substituted 5- to 10-membered heterocyclyl;

$R^1$ and $R^7$ are, independently, hydrogen or optionally substituted $C_1$-$C_6$ alkyl;

each $R^2$ and $R^3$ is independently, hydrogen, optionally substituted $C_1$-$C_6$ alkyl; or optionally substituted $C_1$-$C_6$ heteroalkyl;

$R^4$ is cyano, fluoro, hydroxy, or —$CH_2OH$;

$R^5$ is $C_1$-$C_3$ alkyl optionally substituted with one, two, three, four, five, six, or seven fluoro groups; and $R^6$ is $C_1$-$C_3$ alkyl optionally substituted with one, two, three, four, five, six, or seven fluoro groups, or a pharmaceutically acceptable salt thereof.

2. The compound of claim 1, wherein $R^1$ is hydrogen.

3. The compound of claim 1, wherein m is 1.

4. The compound of claim 1, wherein $R^3$ is hydrogen.

5. The compound of claim 1, wherein $R^2$ is hydrogen.

6. The compound of claim 1, wherein $R^2$ is optionally substituted $C_1$-$C_6$ alkyl.

7. The compound of claim 1, wherein $R^2$ is optionally substituted $C_1$-$C_6$ heteroalkyl.

8. The compound of claim 1, wherein A is

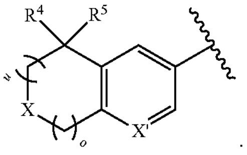

.

9. The compound of claim 8, wherein A is

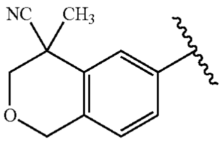
,
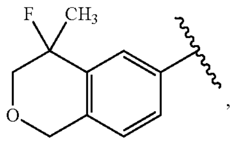
,
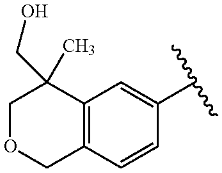
,
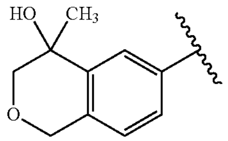
,
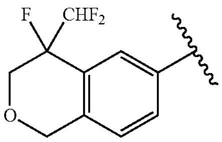
,
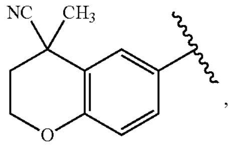
,
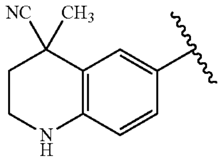
,
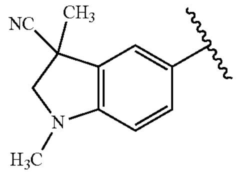
,
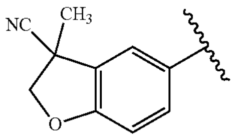
,
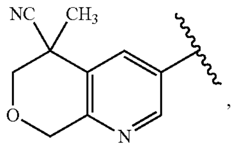
,
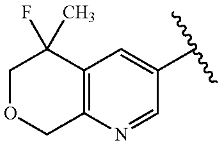
,
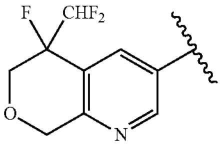
,
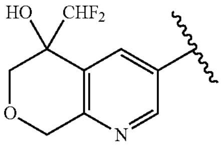
,
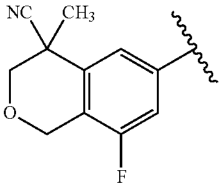
,
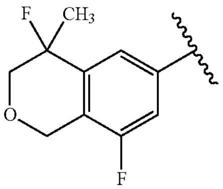
,
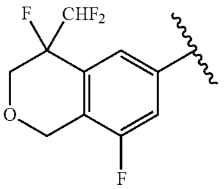
, -continued

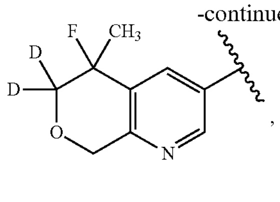
,
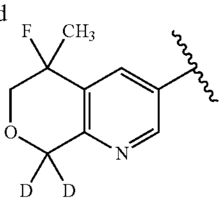
,
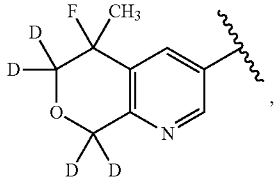
, or
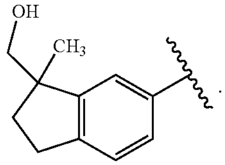 [SMILES: *c1ccc2c(c1)C(C)(CO)CC2]
.

10. The compound of claim 1, wherein C is optionally substituted 3- to 10-membered cycloalkyl.

11. The compound of claim 1, wherein C is optionally substituted 6- to 10-membered aryl.

12. The compound of claim 11, wherein C is phenyl, 3-difluoromethyl-phenyl, 4-difluoromethylphenyl, 2-methoxy-phenyl, 3-methoxy-phenyl, 4-methoxy-phenyl, 3,5-difluorophenyl, 3-difluoromethylphenyl, 2-methoxy-5-methyl-phenyl, 2-methoxy-4-chloro-phenyl, 3-cyano-phenyl, 3-fluoro-5-methoxy-phenyl, 3-fluoro-5-azetidinyl-phenyl, 3-azetidyl-phenyl, 4-azetidyl-2-methoxy-phenyl, 4-morpholin-4-yl-2-methoxy-phenyl, 4-tert-butyl-2-methoxy-phenyl, 4-azetidyl-phenyl, 2-methoxy-4-oxetan-3-yl-phenyl, 2-azetidin-2-one-1-yl-phenyl, 3-(3-difluoromethyloxetan-3-yl)-phenyl, 3-(3-methoxyoxetan-3-yl)-phenyl, 3-(N-methyl-N-acetamido)-phenyl, 3-cyclopropylphenyl, 3-(N-methylazetidin-3-yl)-phenyl, 3-(N-methyl-N'-piperazinyl)-phenyl, 3-fluoro-5-azetidyl-phenyl, 3-methyl ester-phenyl,

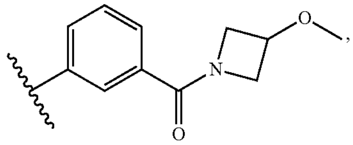
,
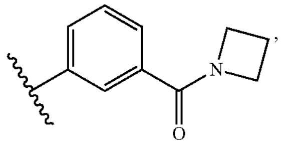
,
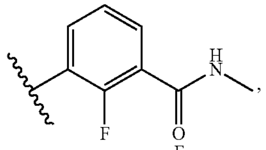
,
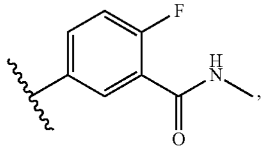
,

-continued
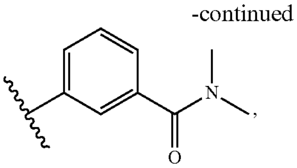
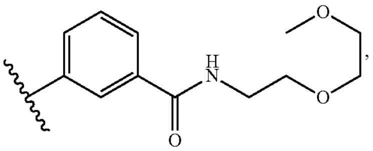
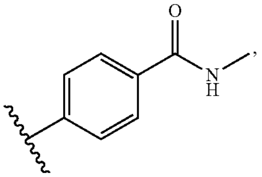
or
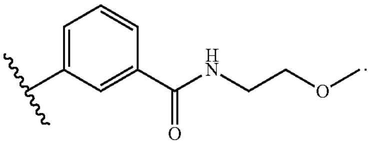
13. The compound of claim 1, wherein C is optionally substituted 5- to 10-membered heteroaryl.
14. The compound of claim 13, wherein C is
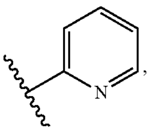
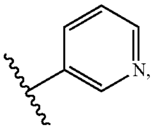
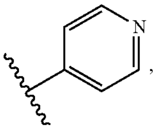
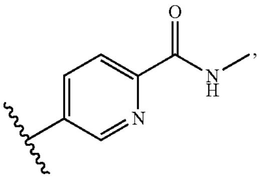
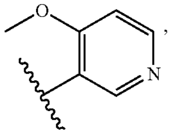
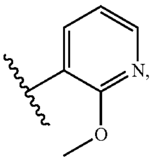
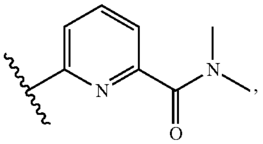
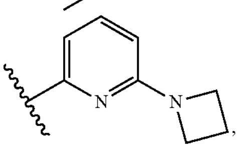
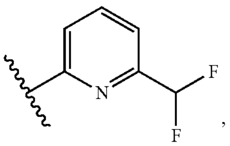
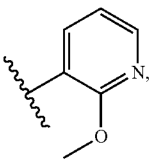
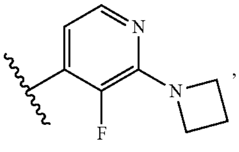
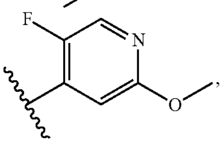
-continued
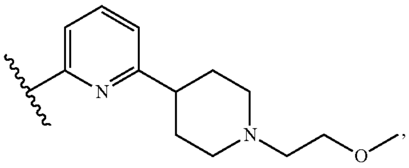
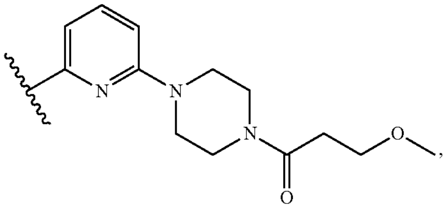
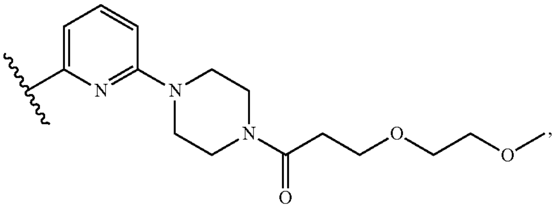
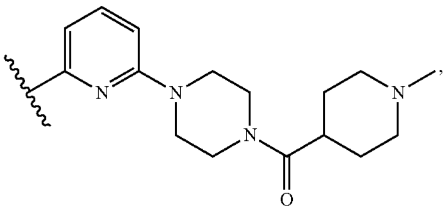
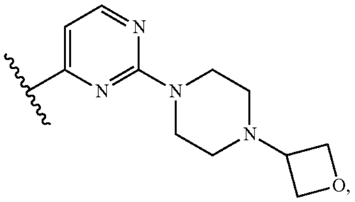
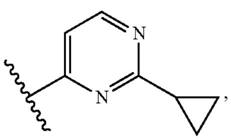
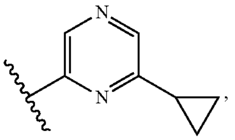
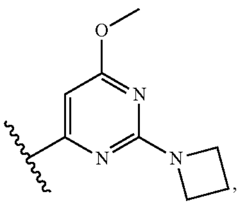
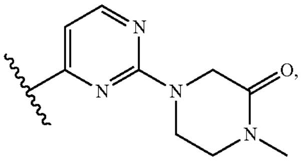
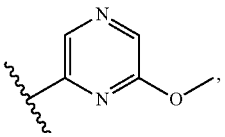
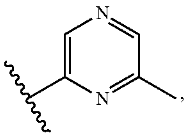

-continued
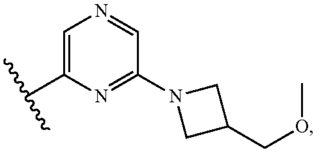
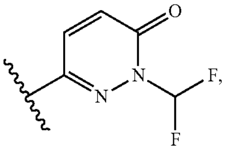
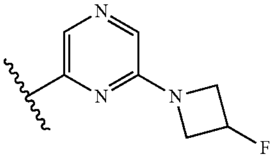
,
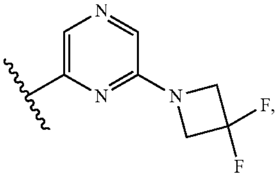
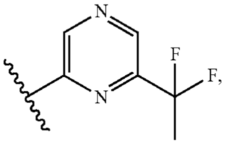
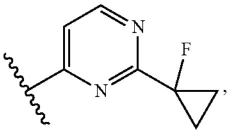
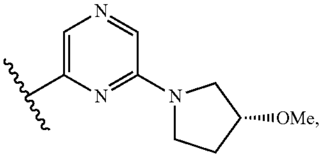
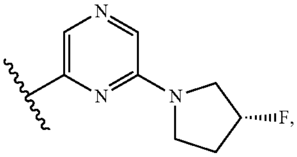
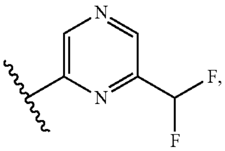
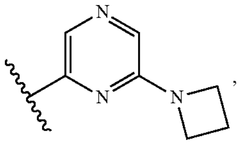
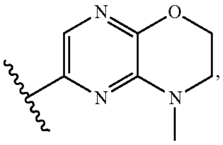
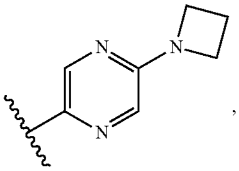
,
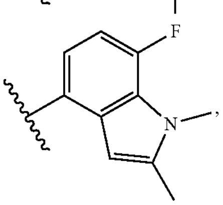
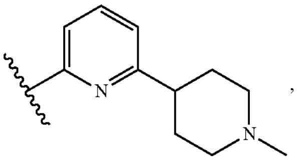
,
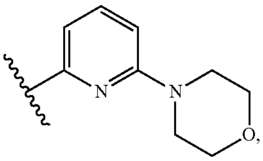
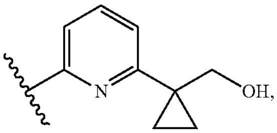
-continued
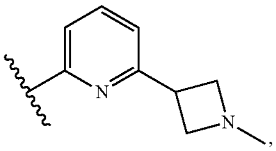
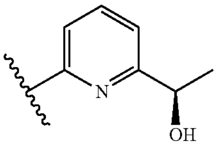
,
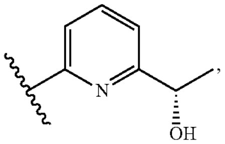
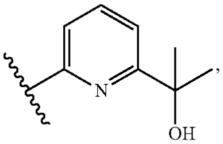
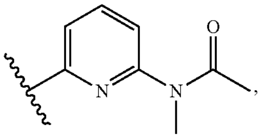
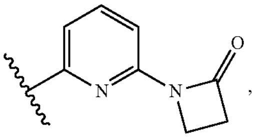
,
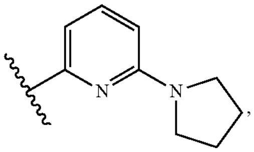
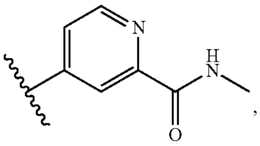
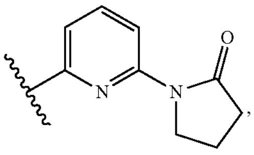
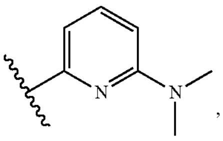
,
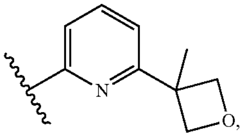
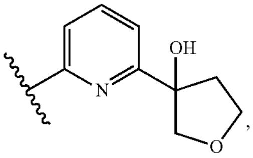
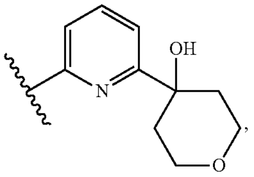
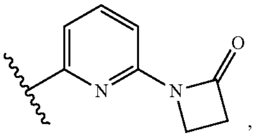
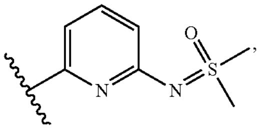
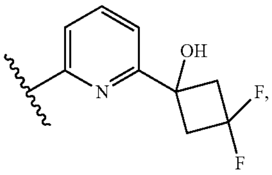
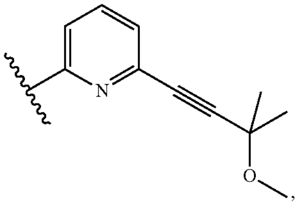

-continued
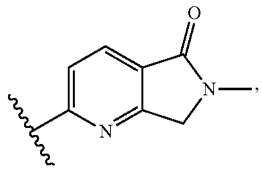
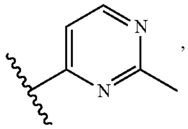
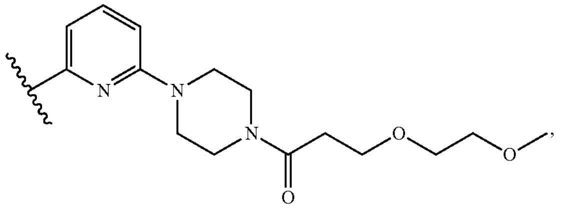
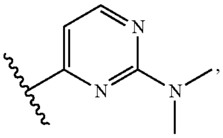
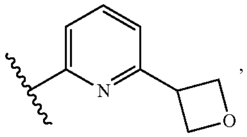
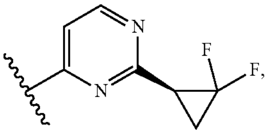
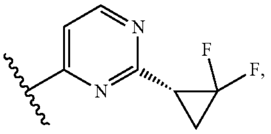
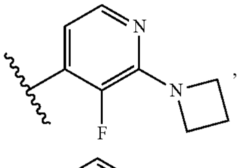
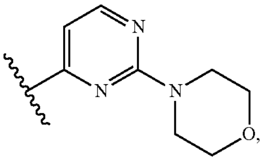
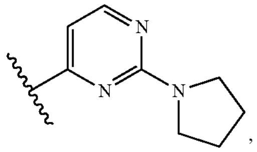
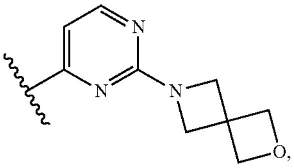
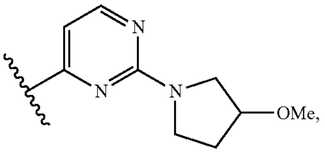
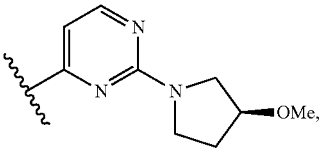
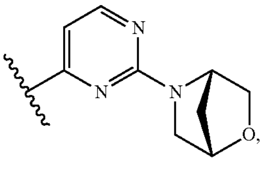
-continued
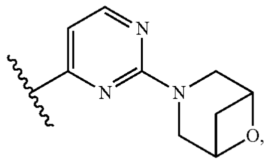
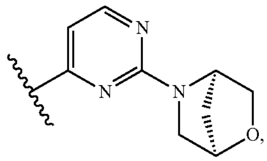
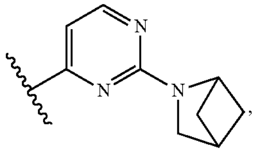
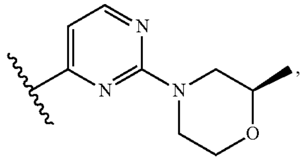
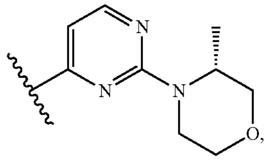
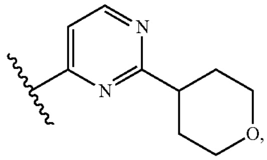
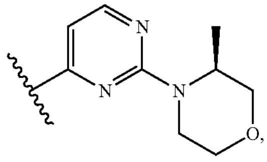
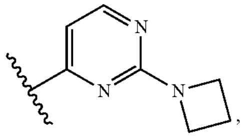
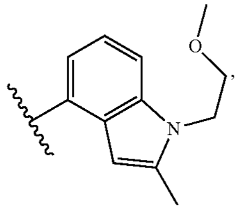
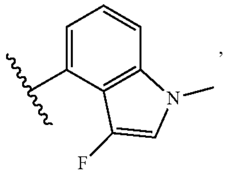
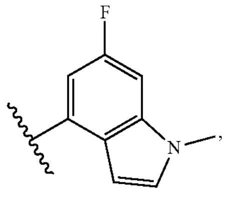
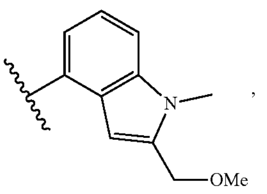
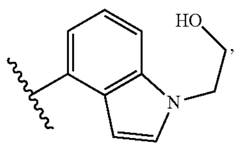
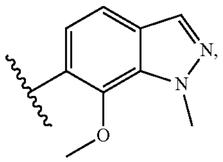

-continued
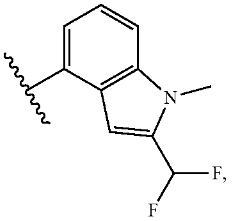
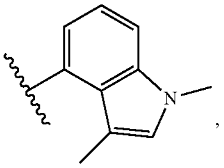
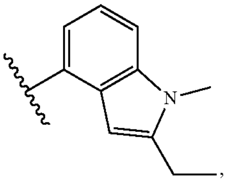
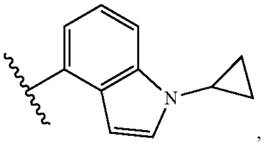
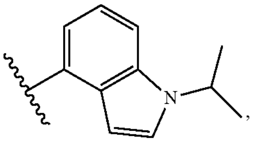
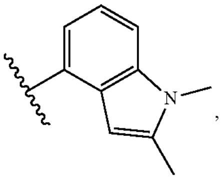
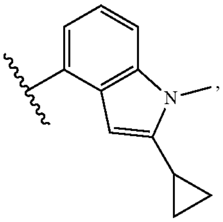
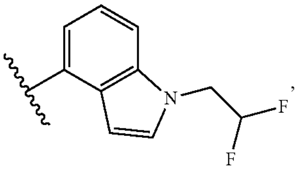
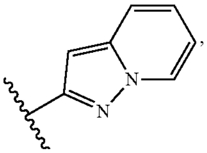
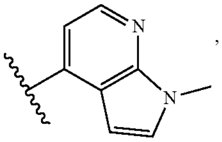
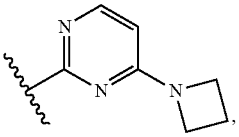
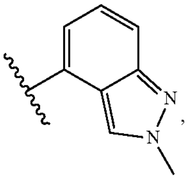
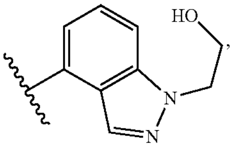
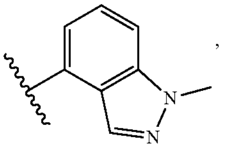
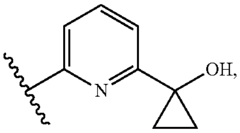
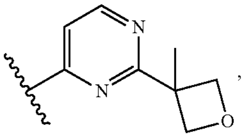
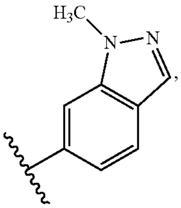
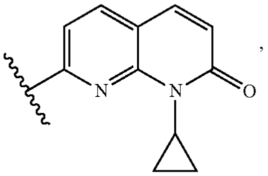
-continued
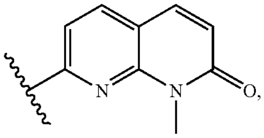
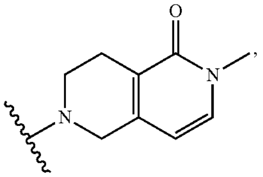
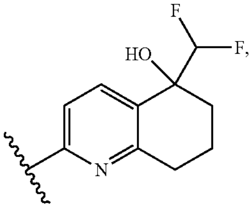
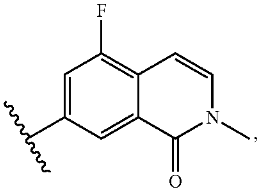
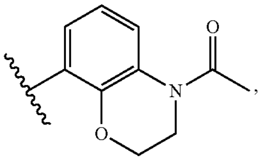
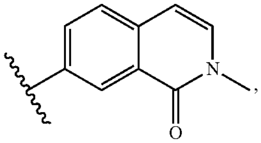
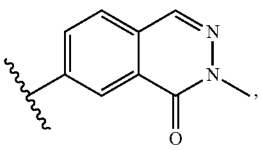
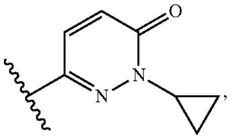
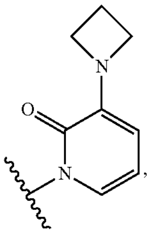
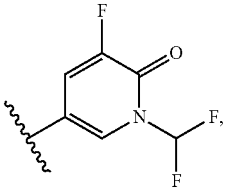
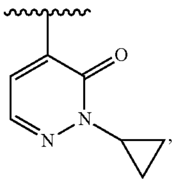
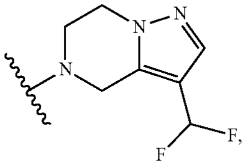
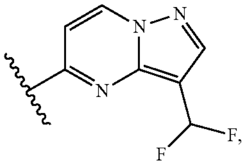
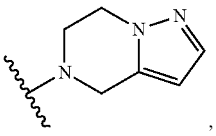

-continued
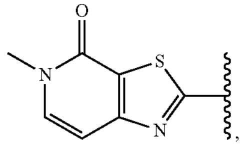, 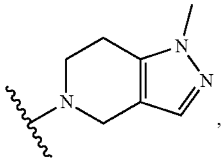,
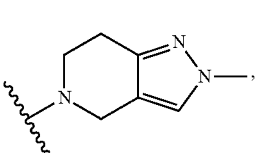, 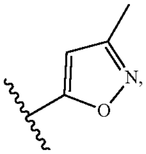
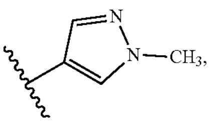 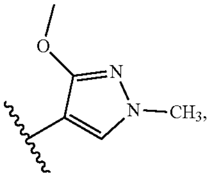
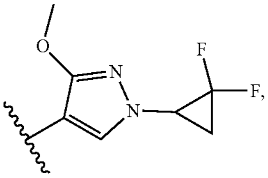 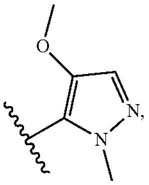
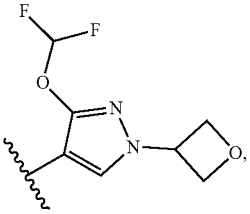 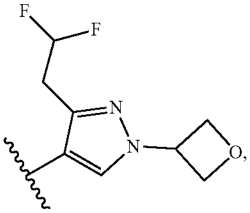
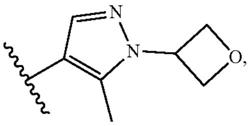 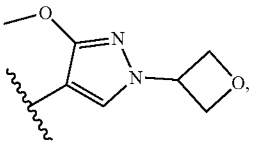
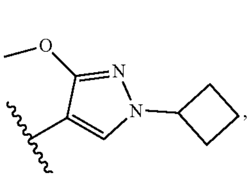, 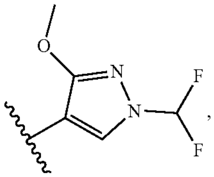,
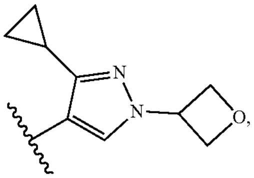
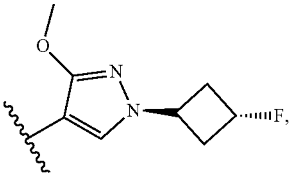
-continued
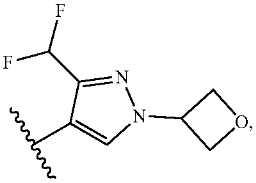 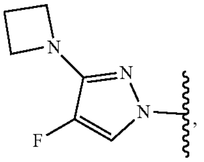
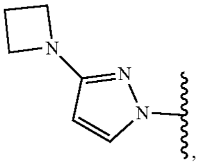, 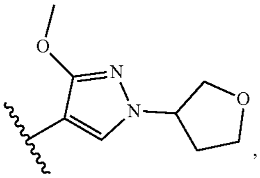,
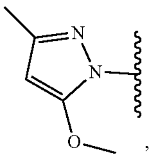, 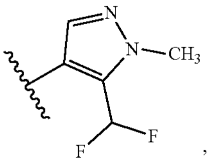,
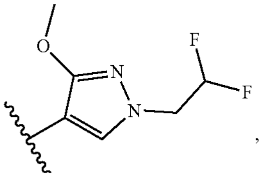,
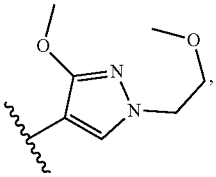 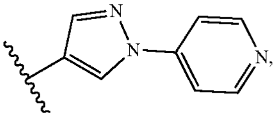
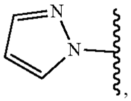, 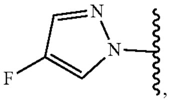, 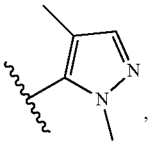,
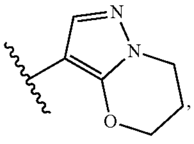 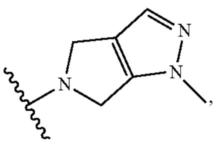
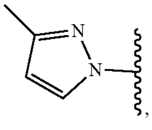, 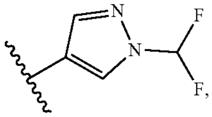
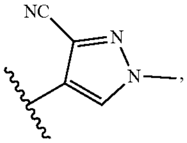 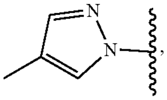 or
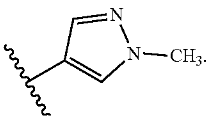

15. The compound of claim 13, wherein C is

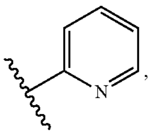
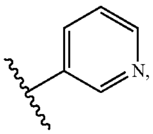
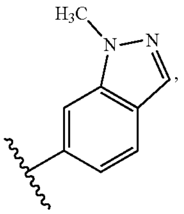
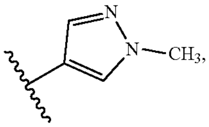
or
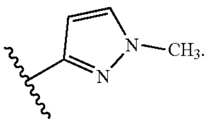

16. The compound of claim 1, wherein C is optionally substituted 5- to 10-membered heterocyclyl.

17. The compound of claim 16, wherein C is

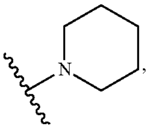
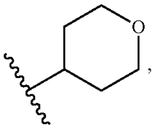
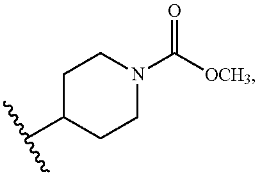
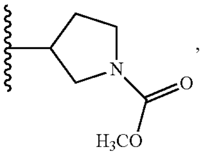
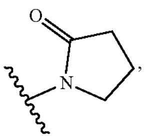
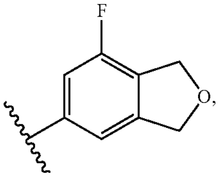
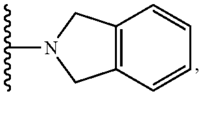
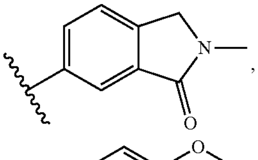
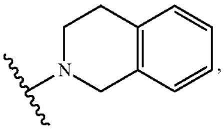
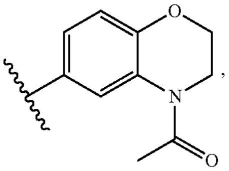
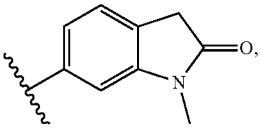
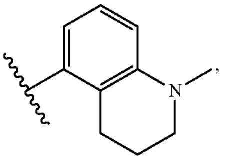

-continued

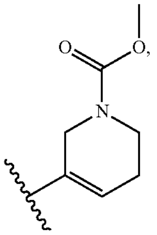
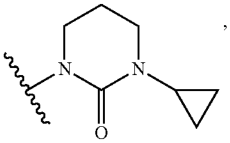
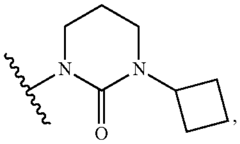
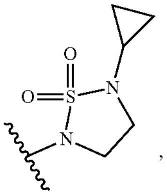
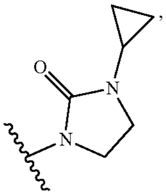
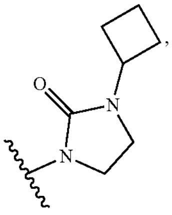
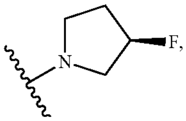
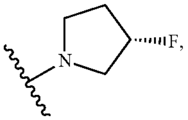
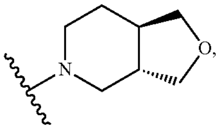
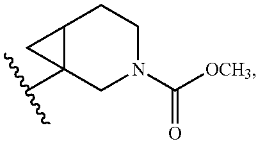
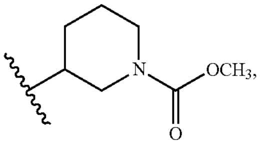

or N-pyrrolidinyl.

18. The compound of claim 16, wherein C is

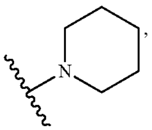
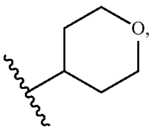
or
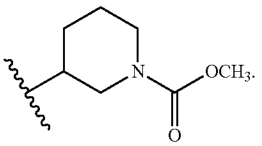

19. The compound of claim 1, wherein B is an optionally substituted 6-membered monocyclic heteroarylene.

20. The compound of claim 19, wherein B has the structure:

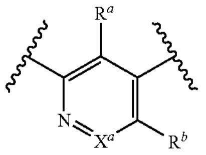

wherein $R^a$ is hydrogen or fluoro;

$R^b$ is hydrogen, fluoro, or $C_1$-$C_3$ alkyl; and $X^a$ is N or CH.

21. The compound of claim 20, wherein B is

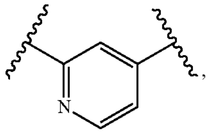
,
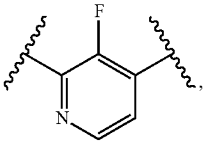
,
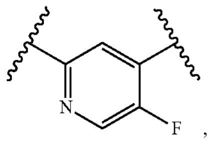
,
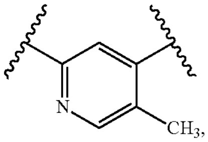
or
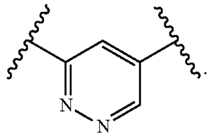
.

22. The compound of claim 1, wherein B has the structure:

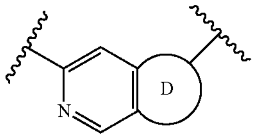

wherein D is an optionally substituted 5- or 6-membered heteroaryl or optionally substituted 5- or 6-membered heterocyclyl.

23. The compound of claim 1, wherein B is

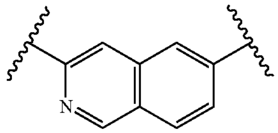
,
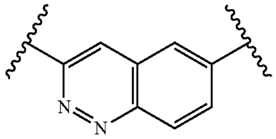
,
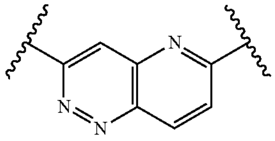
,

-continued

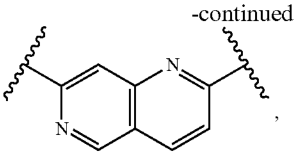
,
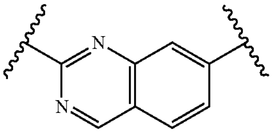
,
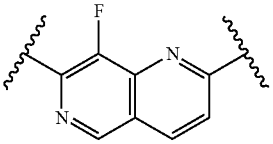
,
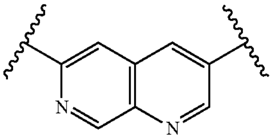
,
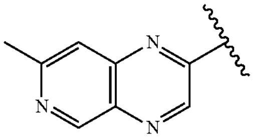
,
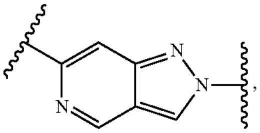
,
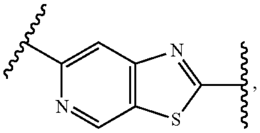
,
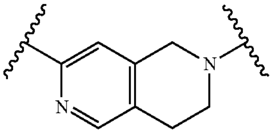
,
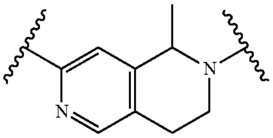
, or
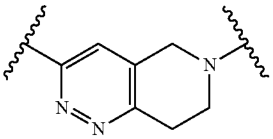
.

24. The compound of claim 1, wherein L is optionally substituted $C_1$-$C_3$ alkylene.

25. The compound of claim 1, wherein L is optionally substituted $C_2$ alkenylene.

26. The compound of claim 25, wherein L is

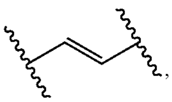
,
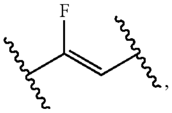
,

-continued

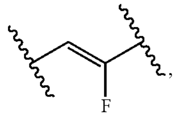

or

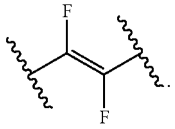

27. The compound of claim 1, wherein L is optionally substituted $C_2$-$C_3$ heteroalkylene.

28. The compound of claim 1, wherein L is optionally substituted $C_3$-$C_5$ cycloalkylene.

29. The compound of claim 28, wherein L is

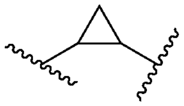

or

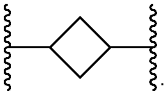

30. The compound of claim 1, wherein L is optionally substituted 4- to 10-membered heterocyclylene.

31. The compound of claim 30, wherein L is

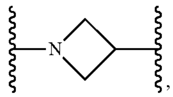

,

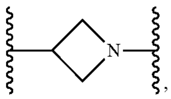

,

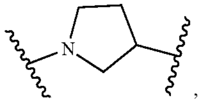

,

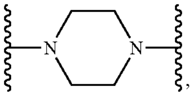

,

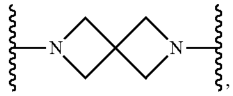

,

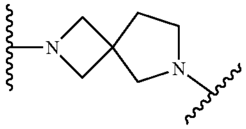

, or

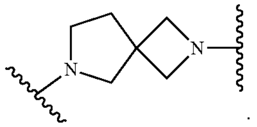

.

32. The compound of claim 1, wherein the compound is any one of the following compounds

| # | Compound |
|---|---|
| 1 | 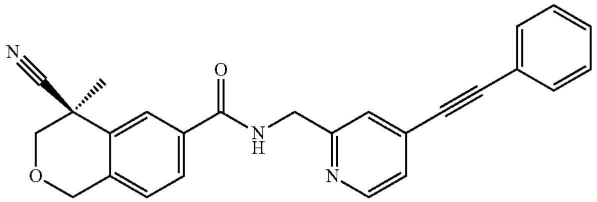 [SMILES: C[C@@]1(C#N)COCc2ccc(C(=O)NCc3cc(C#Cc4ccccc4)ccn3)cc21] |
| 2 | 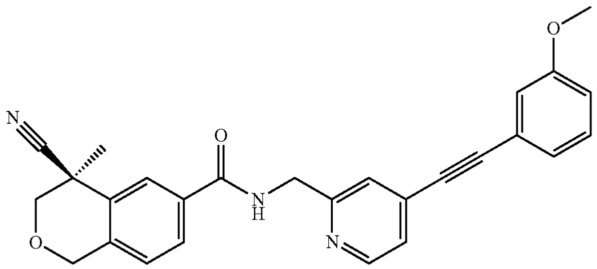 [SMILES: COc1cccc(C#Cc2ccnc(CNC(=O)c3ccc4c(c3)[C@](C)(C#N)COC4)c2)c1] |
| 3 | 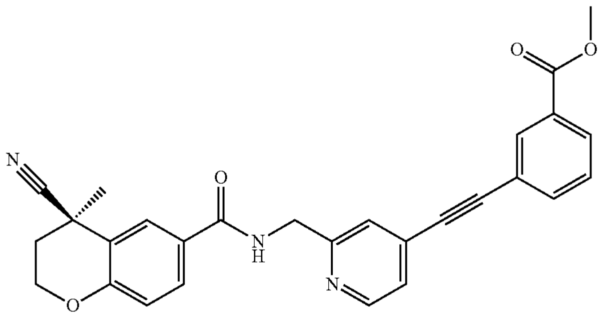 [SMILES: COC(=O)c1cccc(C#Cc2ccnc(CNC(=O)c3ccc4c(c3)[C@](C)(C#N)CCO4)c2)c1] |
| 4 | 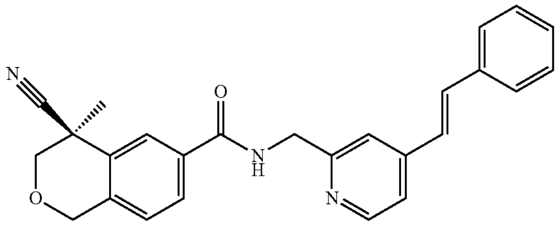 [SMILES: C[C@@]1(C#N)COCc2ccc(C(=O)NCc3cc(/C=C/c4ccccc4)ccn3)cc21] |

-continued
| # | Compound |
| --- | --- |
| 5 | 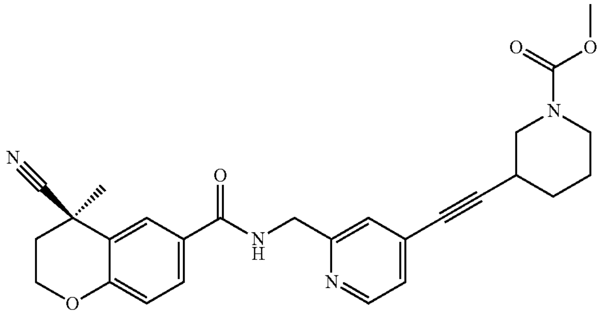 [SMILES: COC(=O)N1CCCC(C#Cc2ccnc(CNC(=O)c3ccc4c(c3)[C@](C)(C#N)CCO4)c2)C1] |
| 6 | 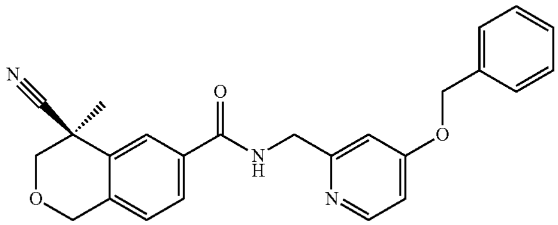 [SMILES: C[C@@]1(C#N)COCc2ccc(C(=O)NCc3cc(OCc4ccccc4)ccn3)cc21] |
| 7 | 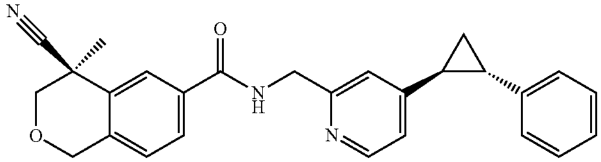 [SMILES: C[C@@]1(C#N)COCc2ccc(C(=O)NCc3cc([C@H]4C[C@@H]4c4ccccc4)ccn3)cc21] |
| 8 | 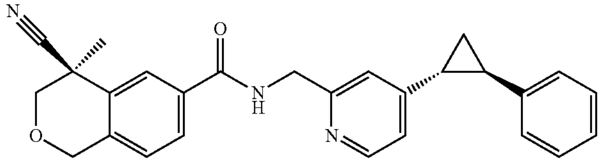 [SMILES: C[C@@]1(C#N)COCc2ccc(C(=O)NCc3cc([C@@H]4C[C@H]4c4ccccc4)ccn3)cc21] |
| 9 | 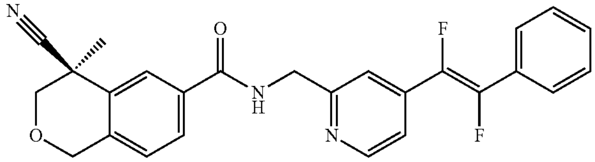 [SMILES: C[C@@]1(C#N)COCc2ccc(C(=O)NCc3cc(/C(F)=C(\F)c4ccccc4)ccn3)cc21] |
| 10 | 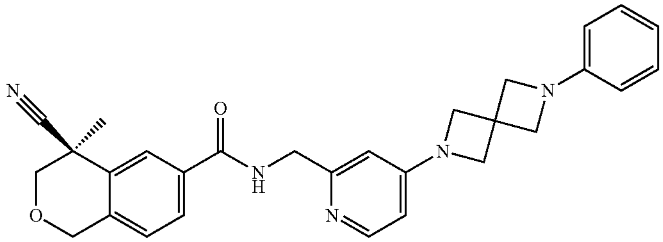 [SMILES: C[C@@]1(C#N)COCc2ccc(C(=O)NCc3cc(N4CC5(CN(c6ccccc6)C5)C4)ccn3)cc21] |
| 11 | 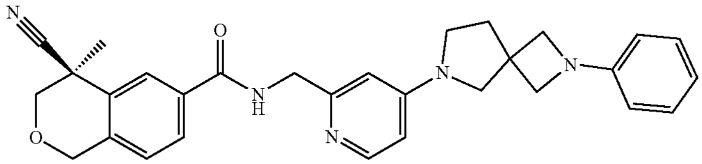 [SMILES: C[C@@]1(C#N)COCc2ccc(C(=O)NCc3cc(N4CCC5(C4)CN(c4ccccc4)C5)ccn3)cc21] |

-continued
| # | Compound |
|---|---|
| 12 | 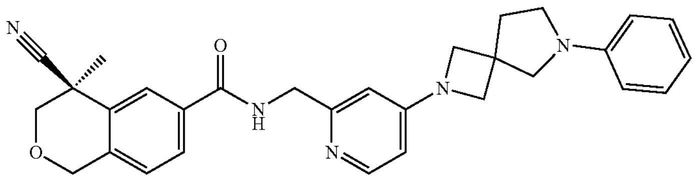 [SMILES: C[C@@]1(C#N)COCc2ccc(C(=O)NCc3cc(N4CC5(CCN(c6ccccc6)C5)C4)ccn3)cc21] |
| 13 | 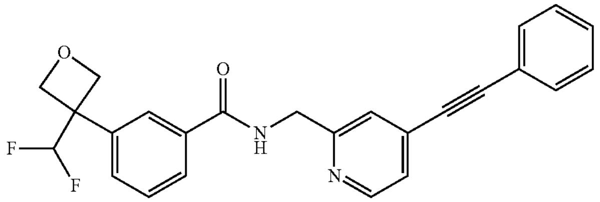 [SMILES: O=C(NCc1cc(C#Cc2ccccc2)ccn1)c1cccc(C2(C(F)F)COC2)c1] |
| 14 | 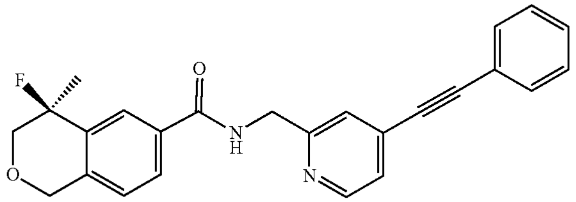 [SMILES: C[C@@]1(F)COCc2ccc(C(=O)NCc3cc(C#Cc4ccccc4)ccn3)cc21] |
| 15 | 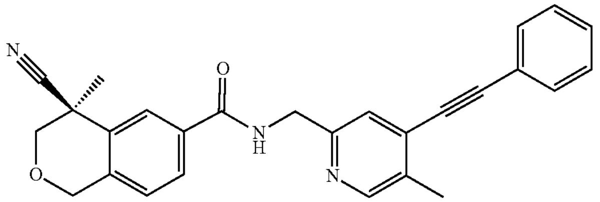 [SMILES: Cc1cnc(CNC(=O)c2ccc3c(c2)[C@](C)(C#N)COC3)cc1C#Cc1ccccc1] |
| 16 | 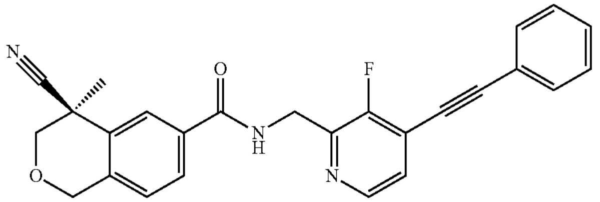 [SMILES: C[C@@]1(C#N)COCc2ccc(C(=O)NCc3nccc(C#Cc4ccccc4)c3F)cc21] |
| 17 | 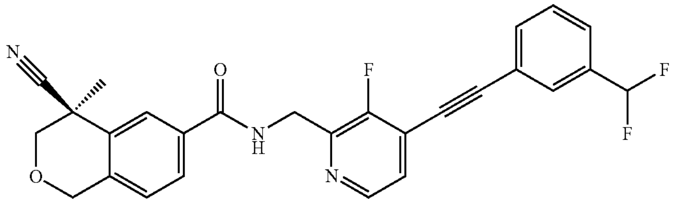 [SMILES: C[C@@]1(C#N)COCc2ccc(C(=O)NCc3nccc(C#Cc4cccc(C(F)F)c4)c3F)cc21] |
| 18 | 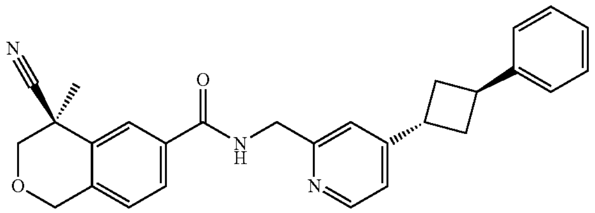 [SMILES: C[C@@]1(C#N)COCc2ccc(C(=O)NCc3cc([C@H]4C[C@H](c5ccccc5)C4)ccn3)cc21] |

-continued
| # | Compound |
|---|---|
| 19 | 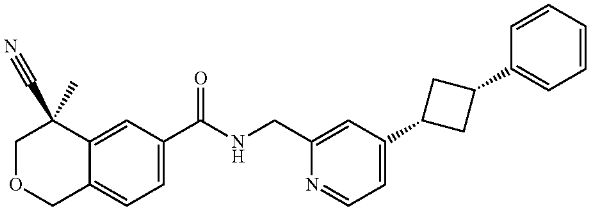 [SMILES: C[C@@]1(C#N)COCc2ccc(C(=O)NCc3cc([C@H]4C[C@@H](c5ccccc5)C4)ccn3)cc21] |
| 20 | 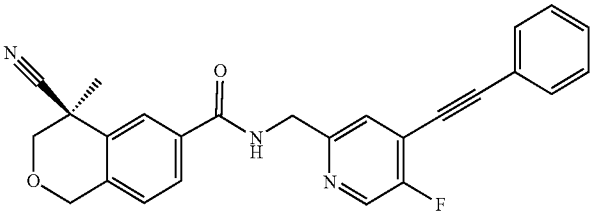 [SMILES: C[C@@]1(C#N)COCc2ccc(C(=O)NCc3cc(C#Cc4ccccc4)c(F)cn3)cc21] |
| 21 | 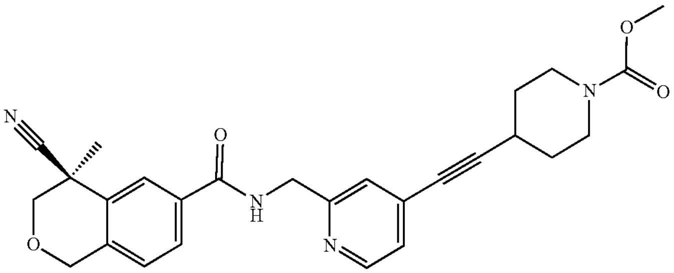 [SMILES: COC(=O)N1CCC(C#Cc2ccnc(CNC(=O)c3ccc4c(c3)[C@](C)(C#N)COC4)c2)CC1] |
| 22 | 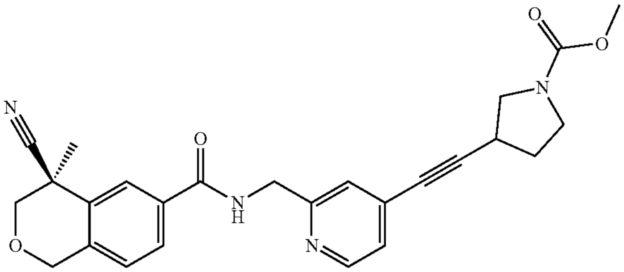 [SMILES: COC(=O)N1CCC(C#Cc2ccnc(CNC(=O)c3ccc4c(c3)[C@](C)(C#N)COC4)c2)C1] |
| 23 | 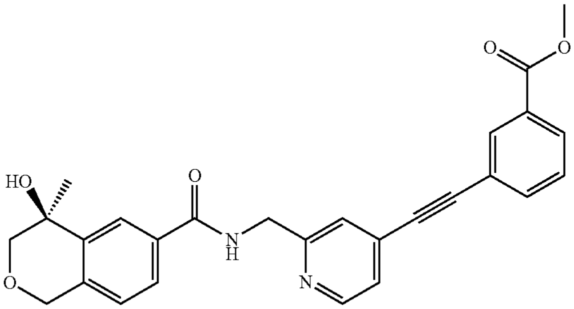 [SMILES: COC(=O)c1cccc(C#Cc2ccnc(CNC(=O)c3ccc4c(c3)[C@](C)(O)COC4)c2)c1] |

-continued
| # | Compound |
|---|---|
| 24 | 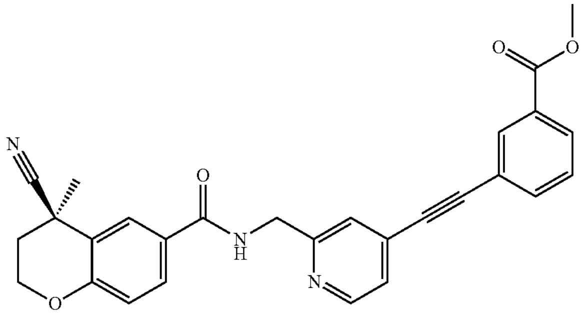 [SMILES: COC(=O)c1cccc(C#Cc2ccnc(CNC(=O)c3ccc4c(c3)[C@](C)(C#N)CCO4)c2)c1] |
| 25 | 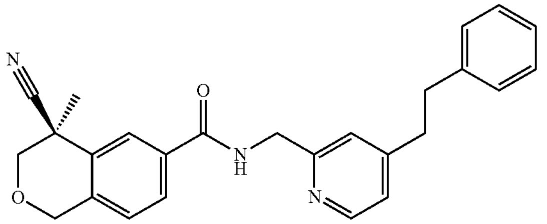 [SMILES: C[C@@]1(C#N)COCc2ccc(C(=O)NCc3cc(CCc4ccccc4)ccn3)cc21] |
| 26 | 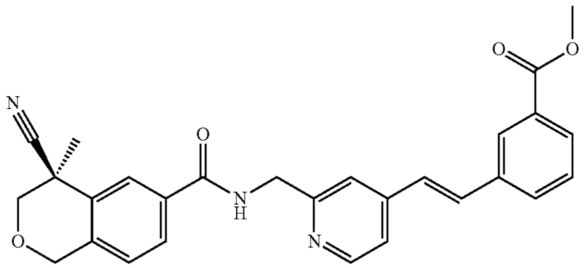 [SMILES: COC(=O)c1cccc(/C=C/c2ccnc(CNC(=O)c3ccc4c(c3)[C@](C)(C#N)COC4)c2)c1] |
| 27 | 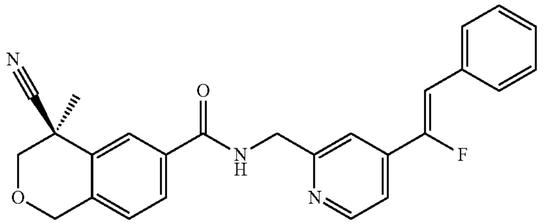 [SMILES: C[C@@]1(C#N)COCc2ccc(C(=O)NCc3cc(/C(F)=C/c4ccccc4)ccn3)cc21] |
| 28 | 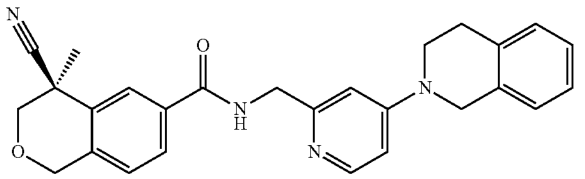 [SMILES: C[C@@]1(C#N)COCc2ccc(C(=O)NCc3cc(N4CCc5ccccc5C4)ccn3)cc21] |
| 29 | 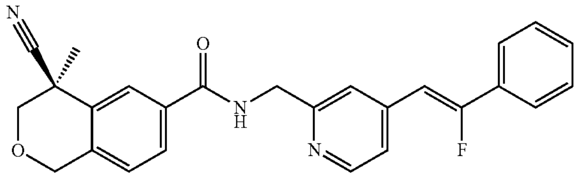 [SMILES: C[C@@]1(C#N)COCc2ccc(C(=O)NCc3cc(/C=C(\F)c4ccccc4)ccn3)cc21] |

-continued
| # | Compound |
|---|---|
| 30 | 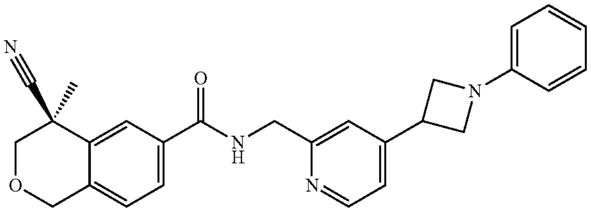 [SMILES: C[C@@]1(C#N)COCc2ccc(C(=O)NCc3cc(C4CN(c5ccccc5)C4)ccn3)cc21] |
| 31 | 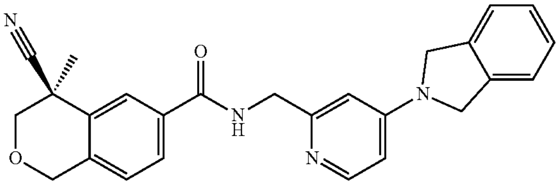 [SMILES: C[C@@]1(C#N)COCc2ccc(C(=O)NCc3cc(N4Cc5ccccc5C4)ccn3)cc21] |
| 32 | 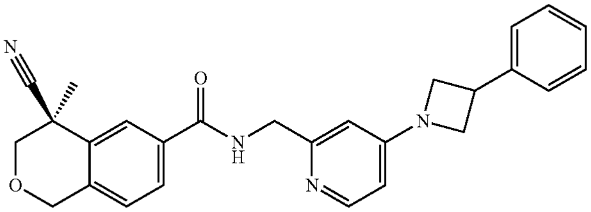 [SMILES: C[C@@]1(C#N)COCc2ccc(C(=O)NCc3cc(N4CC(c5ccccc5)C4)ccn3)cc21] |
| 33 | 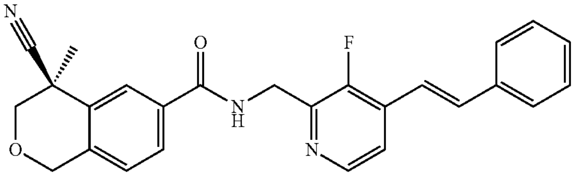 [SMILES: C[C@@]1(C#N)COCc2ccc(C(=O)NCc3nccc(/C=C/c4ccccc4)c3F)cc21] |
| 34 | 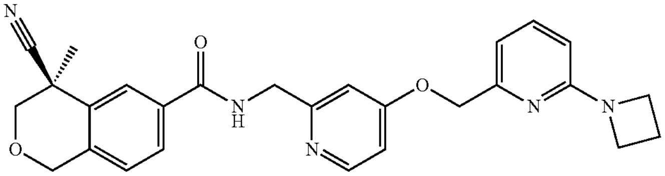 [SMILES: C[C@@]1(C#N)COCc2ccc(C(=O)NCc3cc(OCc4cccc(N5CCC5)n4)ccn3)cc21] |
| 35 | 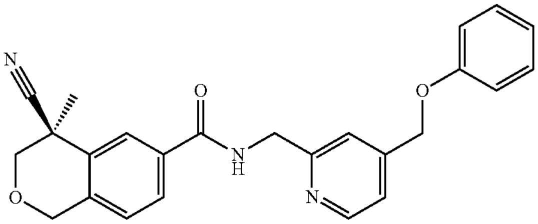 |
| 36 | 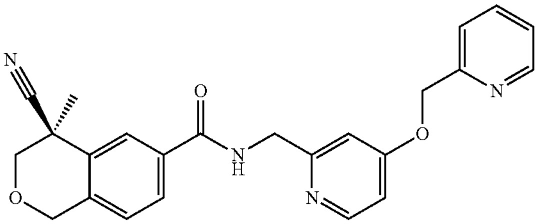 [SMILES: C[C@@]1(C#N)COCc2ccc(C(=O)NCc3cc(OCc4ccccn4)ccn3)cc21] |

-continued
| # | Compound |
|---|---|
| 37 | 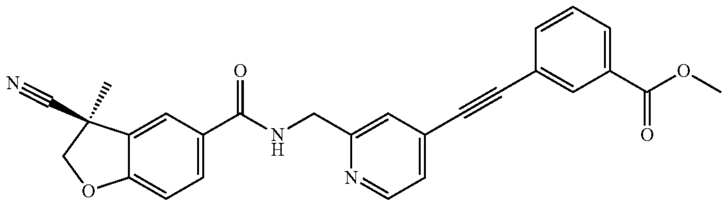 [SMILES: COC(=O)c1cccc(C#Cc2ccnc(CNC(=O)c3ccc4c(c3)[C@](C)(C#N)CO4)c2)c1] |
| 38 | 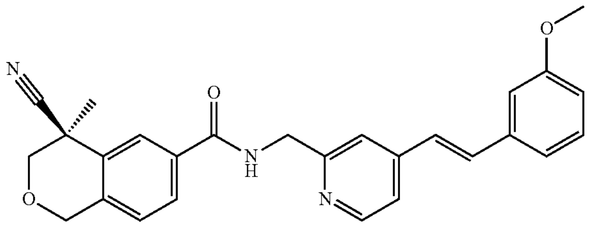 [SMILES: COc1cccc(/C=C/c2ccnc(CNC(=O)c3ccc4c(c3)[C@](C)(C#N)COC4)c2)c1] |
| 39 | 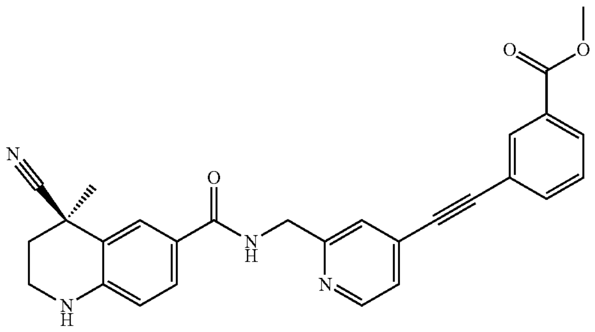 [SMILES: COC(=O)c1cccc(C#Cc2ccnc(CNC(=O)c3ccc4c(c3)[C@](C)(C#N)CCN4)c2)c1] |
| 40 | 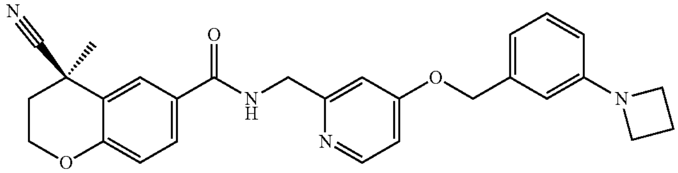 [SMILES: C[C@@]1(C#N)CCOc2ccc(C(=O)NCc3cc(OCc4cccc(N5CCC5)c4)ccn3)cc21] |
| 41 | 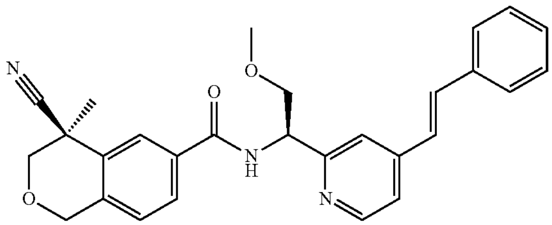 [SMILES: COC[C@H](NC(=O)c1ccc2c(c1)[C@](C)(C#N)COC2)c1cc(/C=C/c2ccccc2)ccn1] |
| 42 | 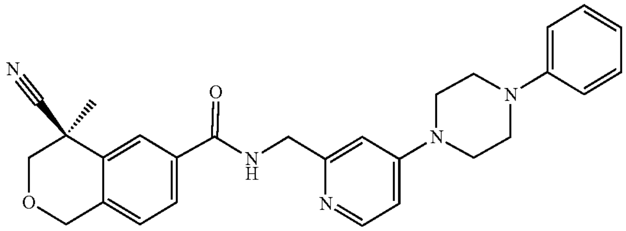 [SMILES: C[C@@]1(C#N)COCc2ccc(C(=O)NCc3cc(N4CCN(c5ccccc5)CC4)ccn3)cc21] |

-continued
| # | Compound |
|---|---|
| 43 | 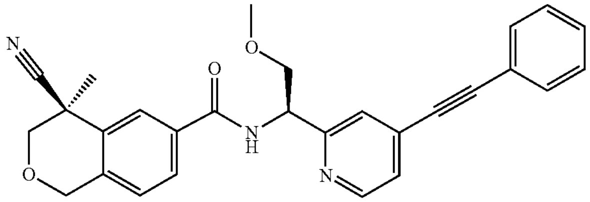 [SMILES: COC[C@H](NC(=O)c1ccc2c(c1)[C@](C)(C#N)COC2)c1cc(C#Cc2ccccc2)ccn1] |
| 44 | 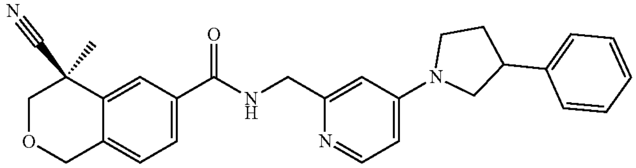 [SMILES: C[C@@]1(C#N)COCc2ccc(C(=O)NCc3cc(N4CCC(c5ccccc5)C4)ccn3)cc21] |
| 45 | 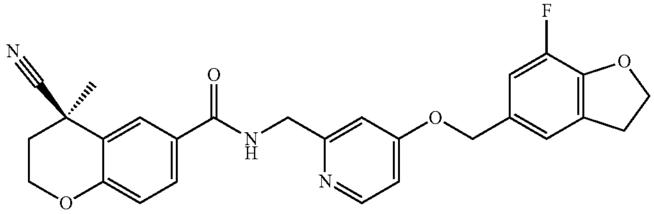 [SMILES: C[C@@]1(C#N)CCOc2ccc(C(=O)NCc3cc(OCc4cc(F)c5c(c4)CCO5)ccn3)cc21] |
| 46 | 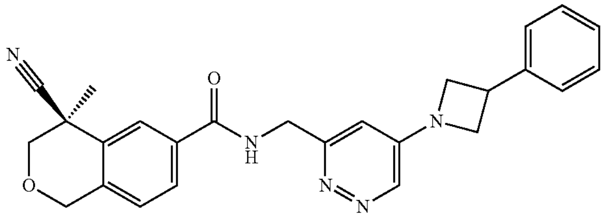 [SMILES: C[C@@]1(C#N)COCc2ccc(C(=O)NCc3cc(N4CC(c5ccccc5)C4)cnn3)cc21] |
| 47 | 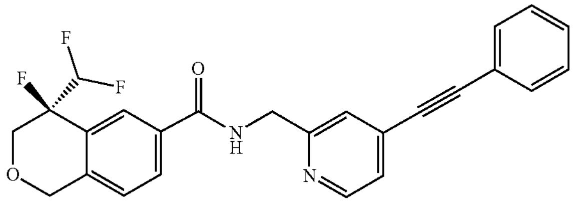 [SMILES: O=C(NCc1cc(C#Cc2ccccc2)ccn1)c1ccc2c(c1)[C@@](F)(C(F)F)COC2] |
| 48 | 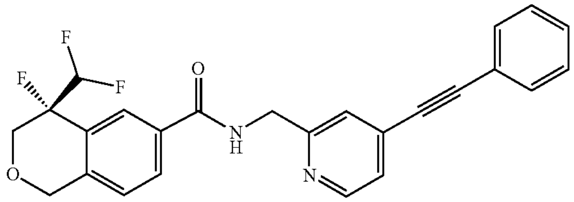 [SMILES: O=C(NCc1cc(C#Cc2ccccc2)ccn1)c1ccc2c(c1)[C@](F)(C(F)F)COC2] |
| 49 | 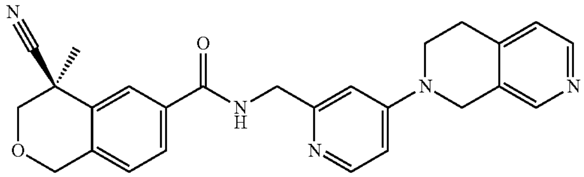 [SMILES: C[C@@]1(C#N)COCc2ccc(C(=O)NCc3cc(N4CCc5ccncc5C4)ccn3)cc21] |

-continued
| # | Compound |
|---|---|
| 50 | 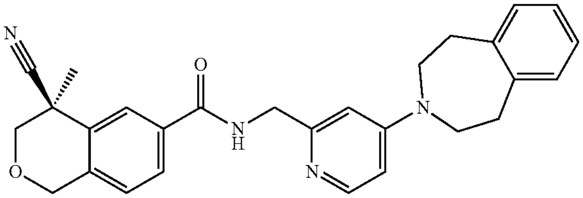 [SMILES: C[C@@]1(C#N)COCc2ccc(C(=O)NCc3cc(N4CCc5ccccc5CC4)ccn3)cc21] |
| 51 | 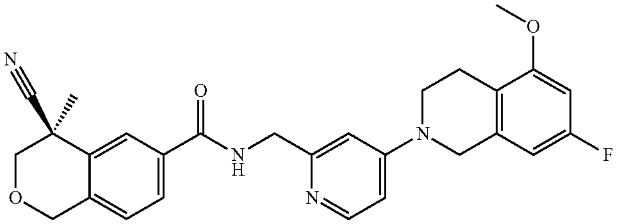 [SMILES: COc1cc(F)cc2c1CCN(c1ccnc(CNC(=O)c3ccc4c(c3)[C@](C)(C#N)COC4)c1)C2] |
| 52 | 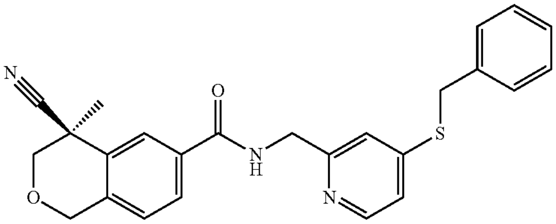 |
| 53 | 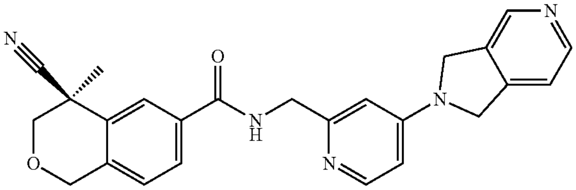 [SMILES: C[C@@]1(C#N)COCc2ccc(C(=O)NCc3cc(N4Cc5ccncc5C4)ccn3)cc21] |
| 54 | 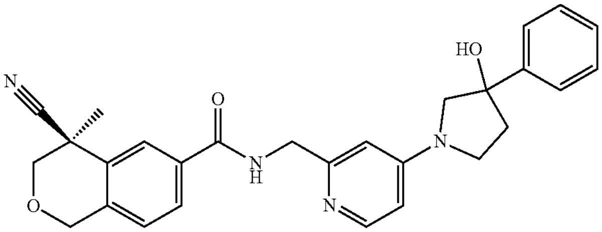 [SMILES: C[C@@]1(C#N)COCc2ccc(C(=O)NCc3cc(N4CCC(O)(c5ccccc5)C4)ccn3)cc21] |
| 55 | 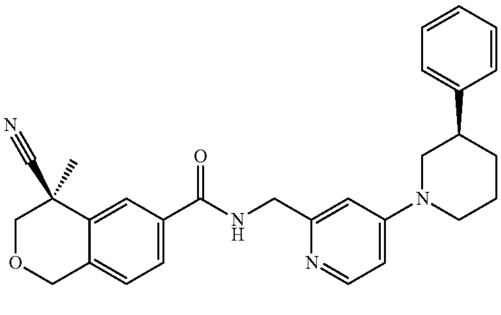 [SMILES: C[C@@]1(C#N)COCc2ccc(C(=O)NCc3cc(N4CCC[C@H](c5ccccc5)C4)ccn3)cc21] |

-continued
| # | Compound |
|---|---|
| 56 | 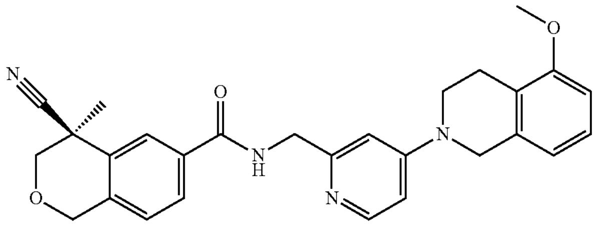 [SMILES: COc1cccc2c1CCN(c1ccnc(CNC(=O)c3ccc4c(c3)[C@](C)(C#N)COC4)c1)C2] |
| 57 | 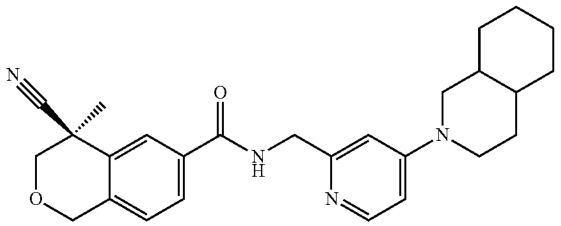 [SMILES: C[C@@]1(C#N)COCc2ccc(C(=O)NCc3cc(N4CCC5CCCCC5C4)ccn3)cc21] |
| 58 | 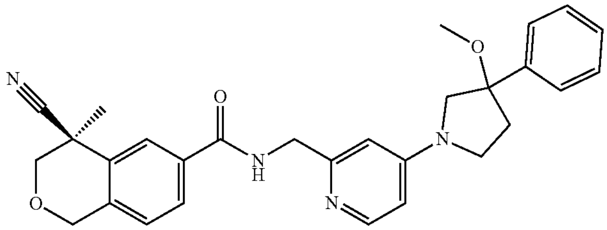 [SMILES: COC1(c2ccccc2)CCN(c2ccnc(CNC(=O)c3ccc4c(c3)[C@](C)(C#N)COC4)c2)C1] |
| 59 | 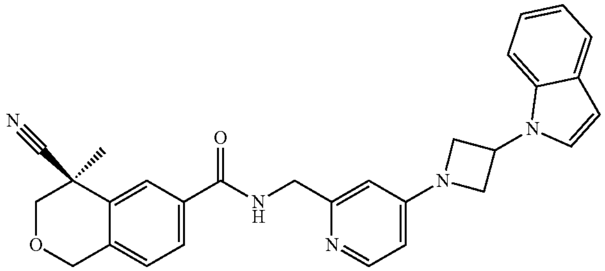 [SMILES: C[C@@]1(C#N)COCc2ccc(C(=O)NCc3cc(N4CC(n5ccc6ccccc65)C4)ccn3)cc21] |
| 60 | 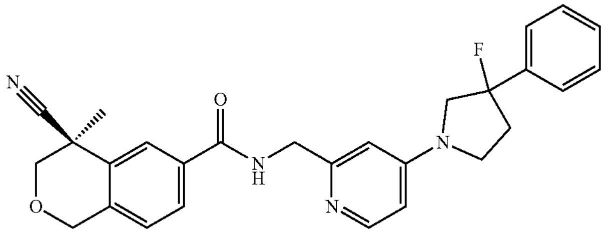 [SMILES: C[C@@]1(C#N)COCc2ccc(C(=O)NCc3cc(N4CCC(F)(c5ccccc5)C4)ccn3)cc21] |
| 61 | 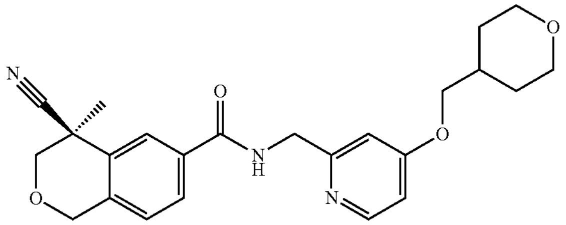 [SMILES: C[C@@]1(C#N)COCc2ccc(C(=O)NCc3cc(OCC4CCOCC4)ccn3)cc21] |

-continued
| # | Compound |
|---|---|
| 62 | 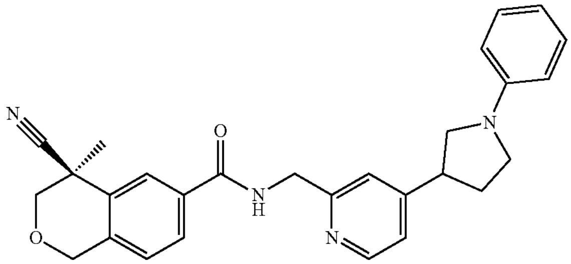 [SMILES: C[C@@]1(C#N)COCc2ccc(C(=O)NCc3cc(C4CCN(c5ccccc5)C4)ccn3)cc21] |
| 63 | 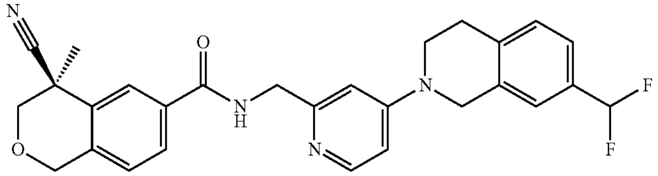 [SMILES: C[C@@]1(C#N)COCc2ccc(C(=O)NCc3cc(N4CCc5ccc(C(F)F)cc5C4)ccn3)cc21] |
| 64 | 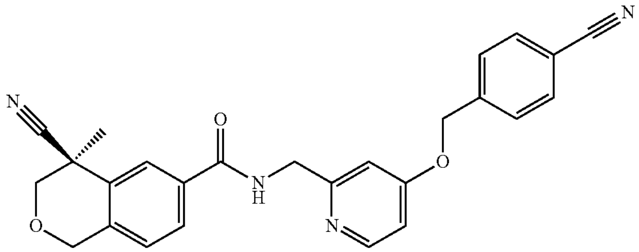 [SMILES: C[C@@]1(C#N)COCc2ccc(C(=O)NCc3cc(OCc4ccc(C#N)cc4)ccn3)cc21] |
| 65 | 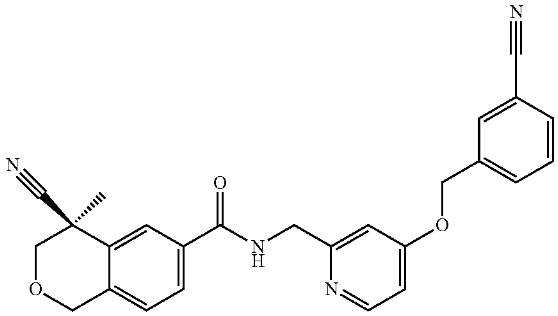 [SMILES: C[C@@]1(C#N)COCc2ccc(C(=O)NCc3cc(OCc4cccc(C#N)c4)ccn3)cc21] |
| 66 | 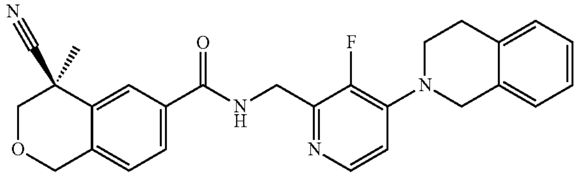 [SMILES: C[C@@]1(C#N)COCc2ccc(C(=O)NCc3nccc(N4CCc5ccccc5C4)c3F)cc21] |
| 67 | 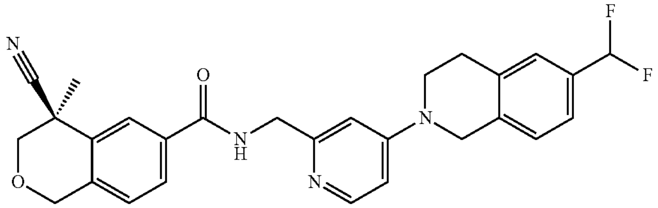 [SMILES: C[C@@]1(C#N)COCc2ccc(C(=O)NCc3cc(N4CCc5cc(C(F)F)ccc5C4)ccn3)cc21] |

-continued
| # | Compound |
|---|---|
| 68 | 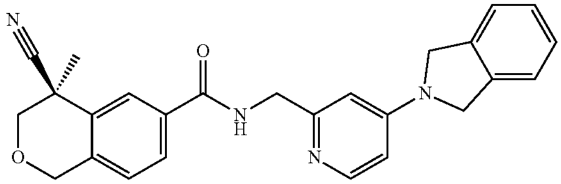 [SMILES: C[C@@]1(C#N)COCc2ccc(C(=O)NCc3cc(N4Cc5ccccc5C4)ccn3)cc21] |
| 69 | 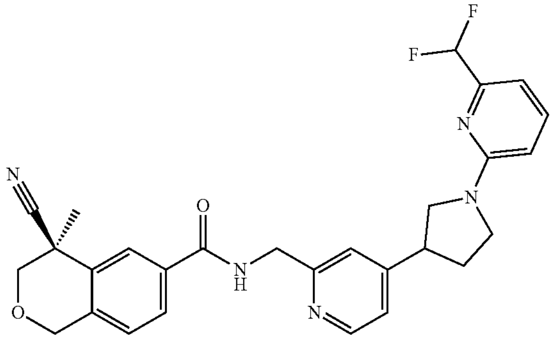 [SMILES: C[C@@]1(C#N)COCc2ccc(C(=O)NCc3cc(C4CCN(c5cccc(C(F)F)n5)C4)ccn3)cc21] |
| 70 | 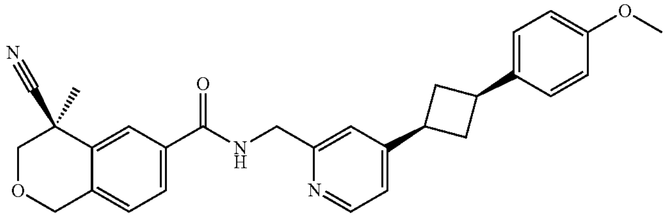 [SMILES: COc1ccc([C@H]2C[C@@H](c3ccnc(CNC(=O)c4ccc5c(c4)[C@](C)(C#N)COC5)c3)C2)cc1] |
| 71 | 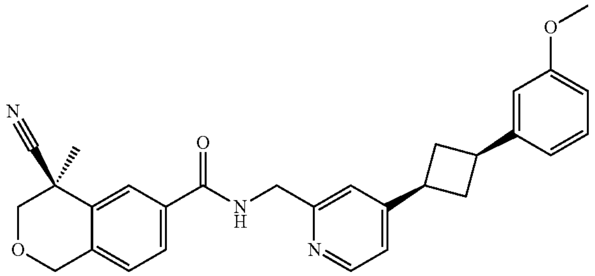 [SMILES: COc1cccc([C@H]2C[C@@H](c3ccnc(CNC(=O)c4ccc5c(c4)[C@](C)(C#N)COC5)c3)C2)c1] |
| 72 | 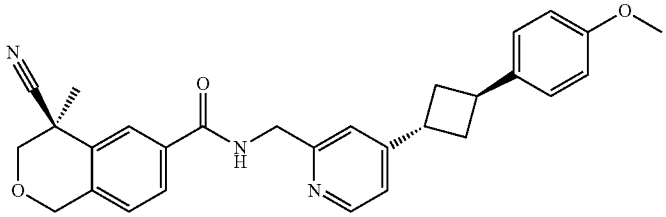 [SMILES: COc1ccc([C@H]2C[C@H](c3ccnc(CNC(=O)c4ccc5c(c4)[C@](C)(C#N)COC5)c3)C2)cc1] |
| 73 | 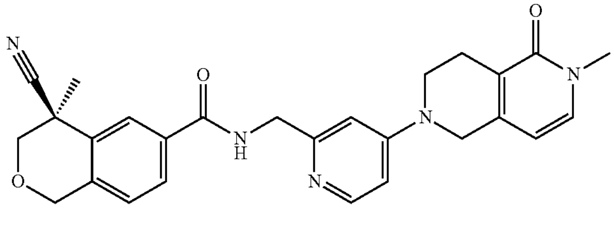 [SMILES: Cn1ccc2c(c1=O)CCN(c1ccnc(CNC(=O)c3ccc4c(c3)[C@](C)(C#N)COC4)c1)C2] |

-continued
| # | Compound |
|---|---|
| 74 | 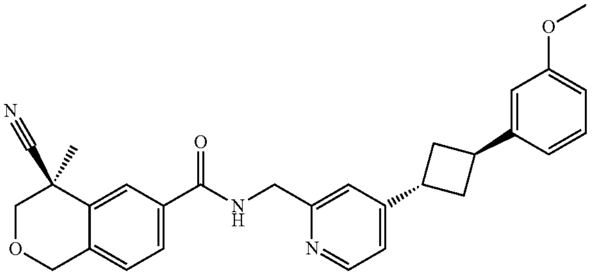 [SMILES: COc1cccc([C@H]2C[C@H](c3ccnc(CNC(=O)c4ccc5c(c4)[C@](C)(C#N)COC5)c3)C2)c1] |
| 75 | 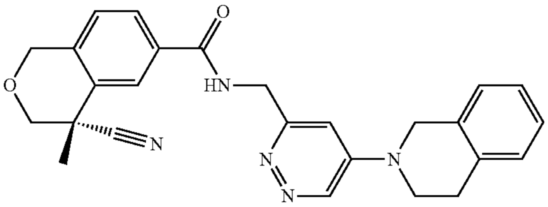 [SMILES: C[C@@]1(C#N)COCc2ccc(C(=O)NCc3cc(N4CCc5ccccc5C4)cnn3)cc21] |
| 76 | 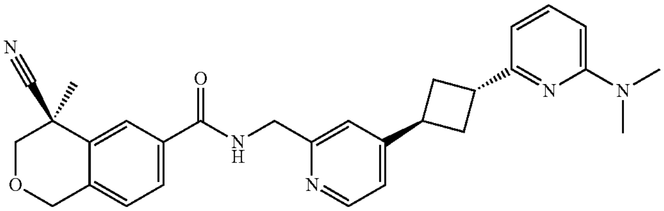 [SMILES: CN(C)c1cccc([C@H]2C[C@H](c3ccnc(CNC(=O)c4ccc5c(c4)[C@](C)(C#N)COC5)c3)C2)n1] |
| 77 | 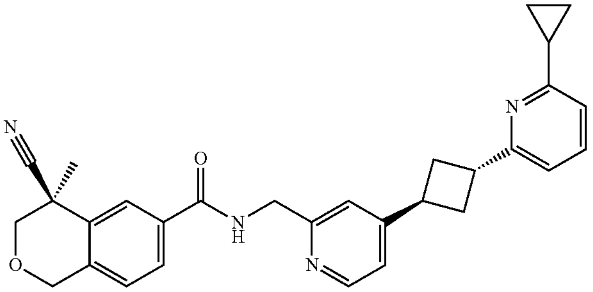 [SMILES: C[C@@]1(C#N)COCc2ccc(C(=O)NCc3cc([C@H]4C[C@H](c5cccc(C6CC6)n5)C4)ccn3)cc21] |
| 78 | 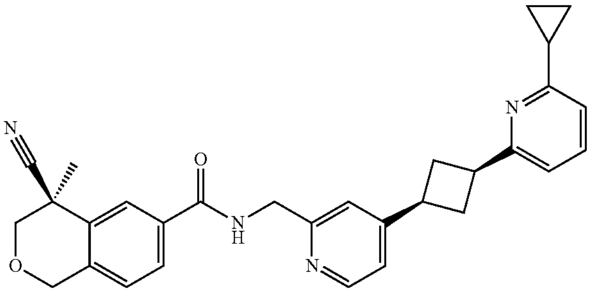 [SMILES: C[C@@]1(C#N)COCc2ccc(C(=O)NCc3cc([C@H]4C[C@@H](c5cccc(C6CC6)n5)C4)ccn3)cc21] |
| 79 | 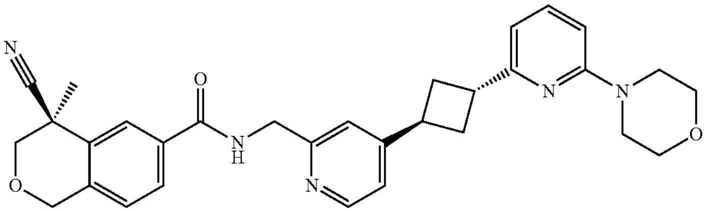 [SMILES: C[C@@]1(C#N)COCc2ccc(C(=O)NCc3cc([C@H]4C[C@H](c5cccc(N6CCOCC6)n5)C4)ccn3)cc21] |

-continued
| # | Compound |
|---|---|
| 80 | 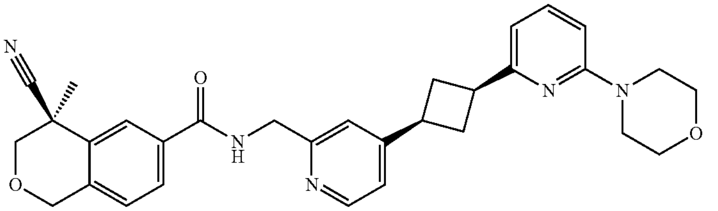 [SMILES: C[C@@]1(C#N)COCc2ccc(C(=O)NCc3cc([C@H]4C[C@@H](c5cccc(N6CCOCC6)n5)C4)ccn3)cc21] |
| 81 | 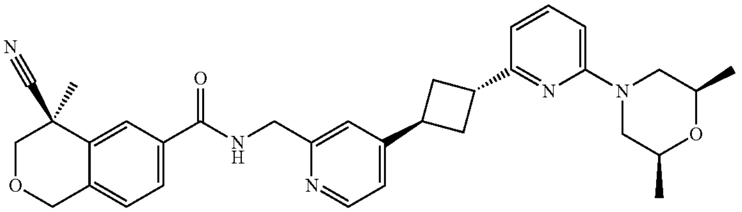 [SMILES: C[C@@H]1CN(c2cccc([C@H]3C[C@H](c4ccnc(CNC(=O)c5ccc6c(c5)[C@](C)(C#N)COC6)c4)C3)n2)C[C@H](C)O1] |
| 82 | 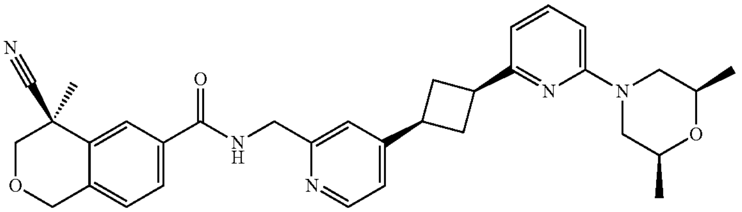 [SMILES: C[C@@H]1CN(c2cccc([C@H]3C[C@@H](c4ccnc(CNC(=O)c5ccc6c(c5)[C@](C)(C#N)COC6)c4)C3)n2)C[C@H](C)O1] |
| 83 | 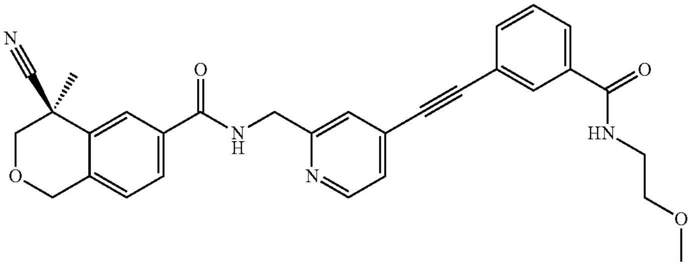 [SMILES: COCCNC(=O)c1cccc(C#Cc2ccnc(CNC(=O)c3ccc4c(c3)[C@](C)(C#N)COC4)c2)c1] |
| 84 | 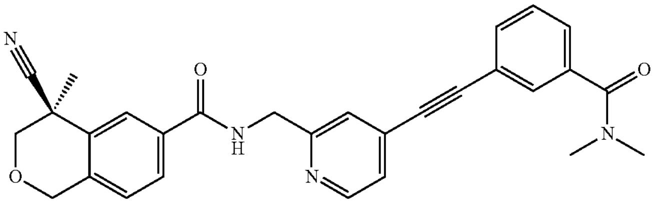 [SMILES: CN(C)C(=O)c1cccc(C#Cc2ccnc(CNC(=O)c3ccc4c(c3)[C@](C)(C#N)COC4)c2)c1] |
| 85 | 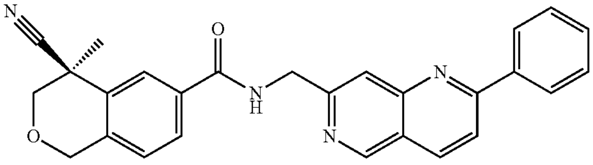 [SMILES: C[C@@]1(C#N)COCc2ccc(C(=O)NCc3cc4nc(-c5ccccc5)ccc4cn3)cc21] |
| 86 | 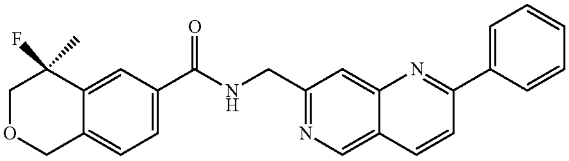 [SMILES: C[C@@]1(F)COCc2ccc(C(=O)NCc3cc4nc(-c5ccccc5)ccc4cn3)cc21] |

-continued
| # | Compound |
|---|---|
| 87 | 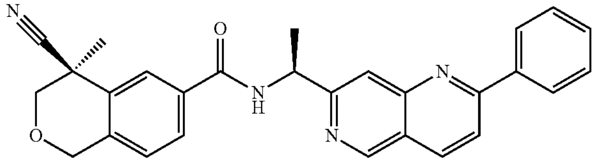 [SMILES: C[C@H](NC(=O)c1ccc2c(c1)[C@](C)(C#N)COC2)c1cc2nc(-c3ccccc3)ccc2cn1] |
| 88 | 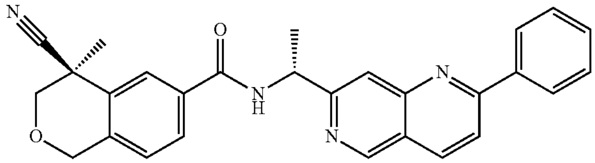 [SMILES: C[C@@H](NC(=O)c1ccc2c(c1)[C@](C)(C#N)COC2)c1cc2nc(-c3ccccc3)ccc2cn1] |
| 89 | 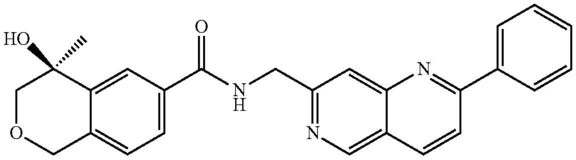 [SMILES: C[C@@]1(O)COCc2ccc(C(=O)NCc3cc4nc(-c5ccccc5)ccc4cn3)cc21] |
| 90 | 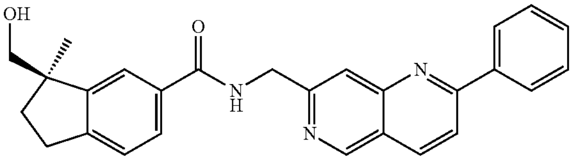 [SMILES: C[C@@]1(CO)CCc2ccc(C(=O)NCc3cc4nc(-c5ccccc5)ccc4cn3)cc21] |
| 91 | 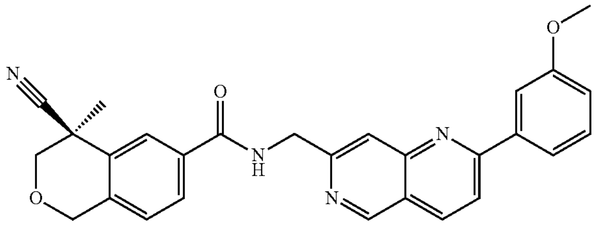 [SMILES: COc1cccc(-c2ccc3cnc(CNC(=O)c4ccc5c(c4)[C@](C)(C#N)COC5)cc3n2)c1] |
| 92 | 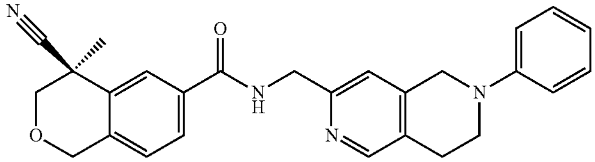 [SMILES: C[C@@]1(C#N)COCc2ccc(C(=O)NCc3cc4c(cn3)CCN(c3ccccc3)C4)cc21] |
| 93 | 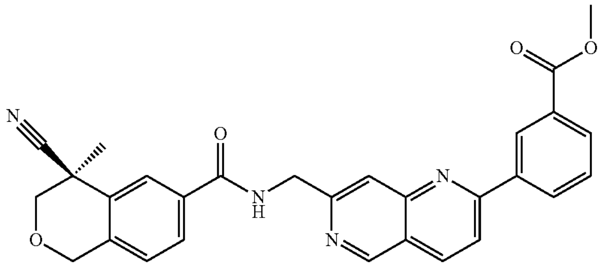 [SMILES: COC(=O)c1cccc(-c2ccc3cnc(CNC(=O)c4ccc5c(c4)[C@](C)(C#N)COC5)cc3n2)c1] |
| 94 | 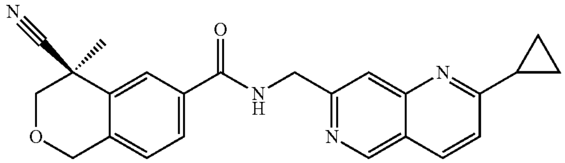 [SMILES: C[C@@]1(C#N)COCc2ccc(C(=O)NCc3cc4nc(C5CC5)ccc4cn3)cc21] |

-continued
| # | Compound |
|---|---|
| 95 | 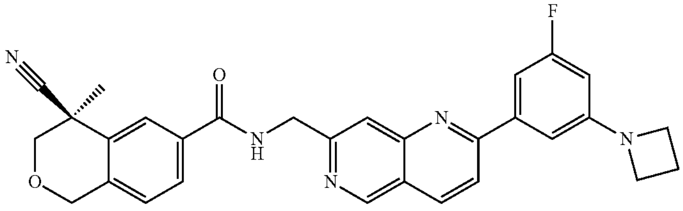 [SMILES: C[C@@]1(C#N)COCc2ccc(C(=O)NCc3cc4nc(-c5cc(F)cc(N6CCC6)c5)ccc4cn3)cc21] |
| 96 | 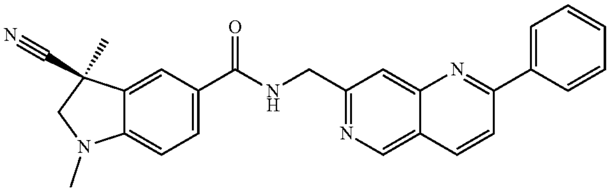 [SMILES: CN1C[C@@](C)(C#N)c2cc(C(=O)NCc3cc4nc(-c5ccccc5)ccc4cn3)ccc21] |
| 97 | 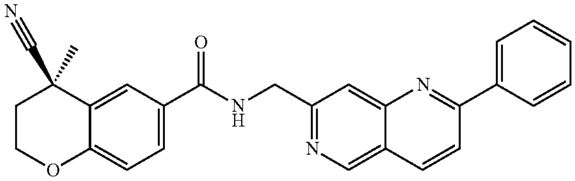 [SMILES: C[C@@]1(C#N)CCOc2ccc(C(=O)NCc3cc4nc(-c5ccccc5)ccc4cn3)cc21] |
| 98 | 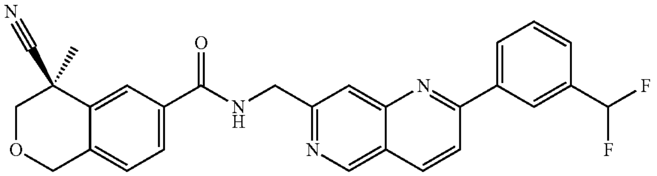 [SMILES: C[C@@]1(C#N)COCc2ccc(C(=O)NCc3cc4nc(-c5cccc(C(F)F)c5)ccc4cn3)cc21] |
| 99 | 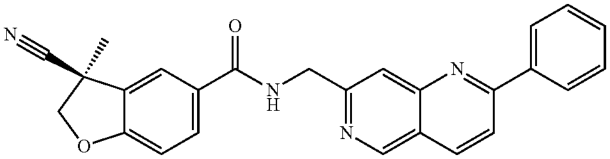 [SMILES: C[C@@]1(C#N)COc2ccc(C(=O)NCc3cc4nc(-c5ccccc5)ccc4cn3)cc21] |
| 100 | 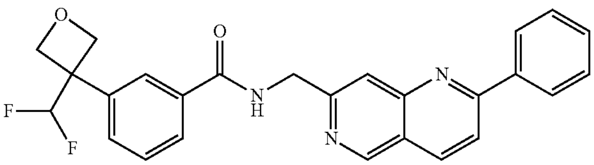 [SMILES: O=C(NCc1cc2nc(-c3ccccc3)ccc2cn1)c1cccc(C2(C(F)F)COC2)c1] |
| 101 | 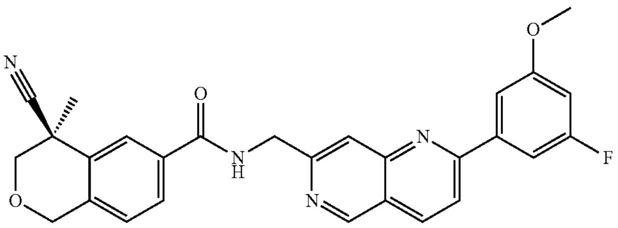 [SMILES: COc1cc(F)cc(-c2ccc3cnc(CNC(=O)c4ccc5c(c4)[C@](C)(C#N)COC5)cc3n2)c1] |
| 102 | 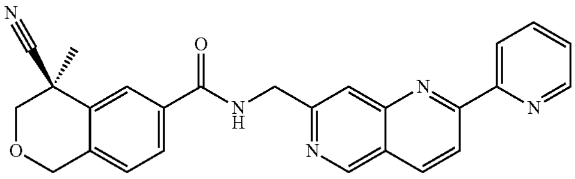 [SMILES: C[C@@]1(C#N)COCc2ccc(C(=O)NCc3cc4nc(-c5ccccn5)ccc4cn3)cc21] |

-continued
| # | Compound |
|---|---|
| 103 | 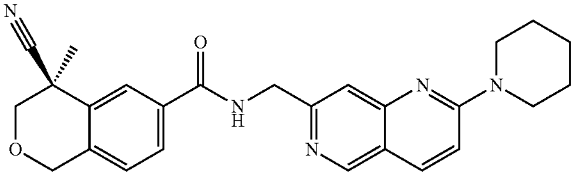 [SMILES: C[C@@]1(C#N)COCc2ccc(C(=O)NCc3cc4nc(N5CCCCC5)ccc4cn3)cc21] |
| 104 | 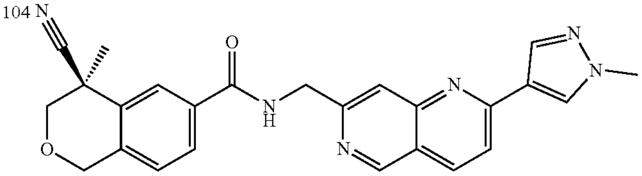 |
| 105 | 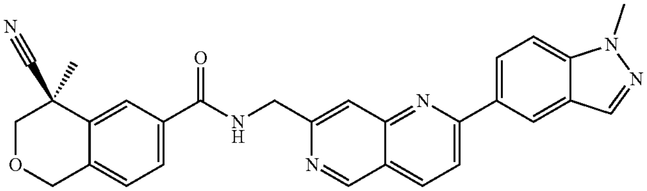 or |
| 106 | 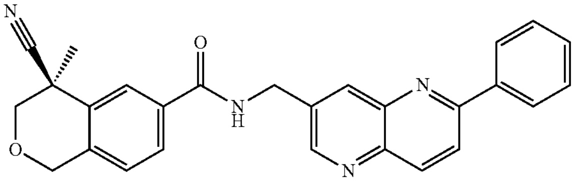 [SMILES: C[C@@]1(C#N)COCc2ccc(C(=O)NCc3cnc4ccc(-c5ccccc5)nc4c3)cc21] |
| 107 | 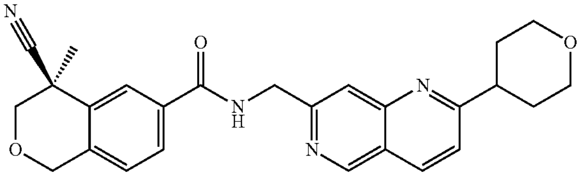 [SMILES: C[C@@]1(C#N)COCc2ccc(C(=O)NCc3cc4nc(C5CCOCC5)ccc4cn3)cc21] |
| 108 | 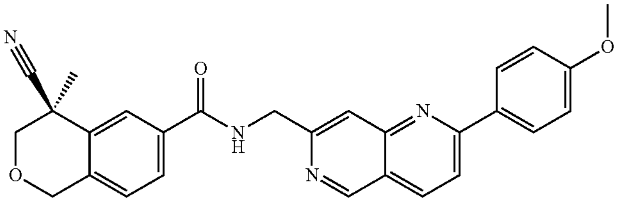 [SMILES: COc1ccc(-c2ccc3cnc(CNC(=O)c4ccc5c(c4)[C@](C)(C#N)COC5)cc3n2)cc1] |
| 109 | 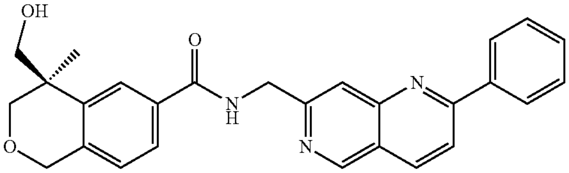 [SMILES: C[C@@]1(CO)COCc2ccc(C(=O)NCc3cc4nc(-c5ccccc5)ccc4cn3)cc21] |
| 110 | 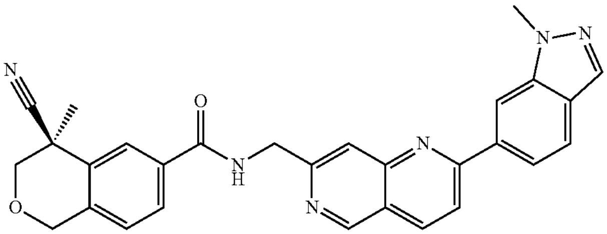 [SMILES: Cn1ncc2ccc(-c3ccc4cnc(CNC(=O)c5ccc6c(c5)[C@](C)(C#N)COC6)cc4n3)cc21] |

-continued
| # | Compound |
|---|---|
| 111 | 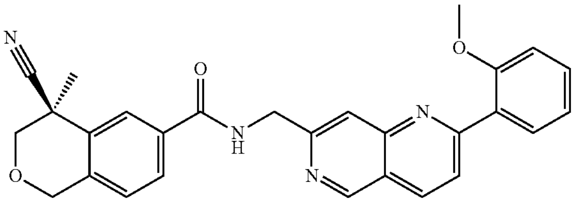 [SMILES: COc1ccccc1-c1ccc2cnc(CNC(=O)c3ccc4c(c3)[C@](C)(C#N)COC4)cc2n1] |
| 112 | 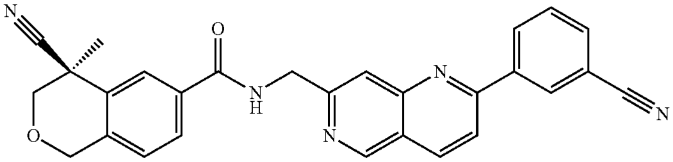 [SMILES: C[C@@]1(C#N)COCc2ccc(C(=O)NCc3cc4nc(-c5cccc(C#N)c5)ccc4cn3)cc21] |
| 113 | 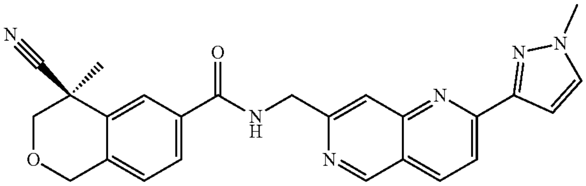 [SMILES: Cn1ccc(-c2ccc3cnc(CNC(=O)c4ccc5c(c4)[C@](C)(C#N)COC5)cc3n2)n1] |
| 114 | 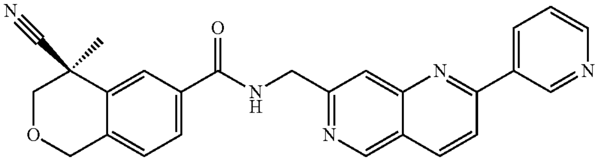 [SMILES: C[C@@]1(C#N)COCc2ccc(C(=O)NCc3cc4nc(-c5cccnc5)ccc4cn3)cc21] |
| 115 | 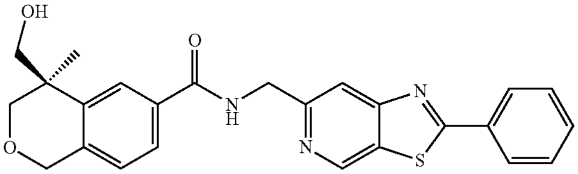 [SMILES: C[C@@]1(CO)COCc2ccc(C(=O)NCc3cc4nc(-c5ccccc5)sc4cn3)cc21] |
| 116 | 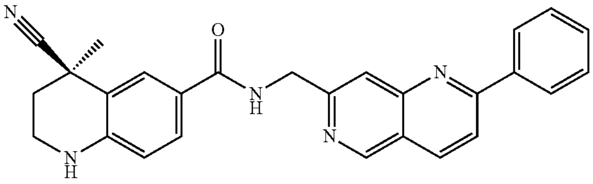 [SMILES: C[C@@]1(C#N)CCNc2ccc(C(=O)NCc3cc4nc(-c5ccccc5)ccc4cn3)cc21] |
| 117 | 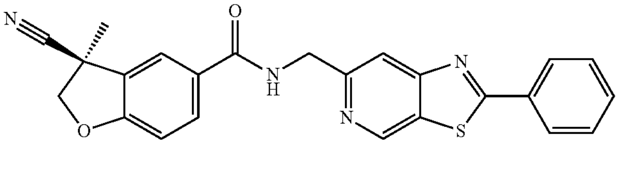 [SMILES: C[C@@]1(C#N)COc2ccc(C(=O)NCc3cc4nc(-c5ccccc5)sc4cn3)cc21] |
| 118 | 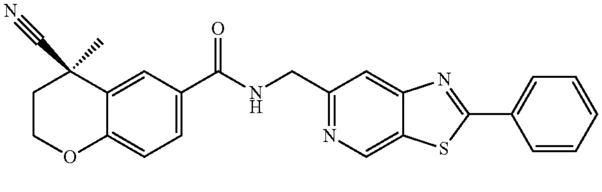 [SMILES: C[C@@]1(C#N)CCOc2ccc(C(=O)NCc3cc4nc(-c5ccccc5)sc4cn3)cc21] |

-continued
| # | Compound |
|---|---|
| 119 | 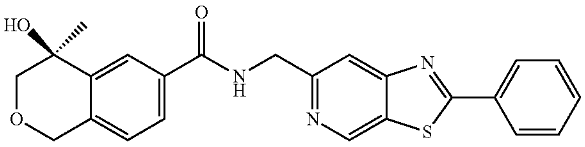 [SMILES: C[C@@]1(O)COCc2ccc(C(=O)NCc3cc4nc(-c5ccccc5)sc4cn3)cc21] |
| 120 | 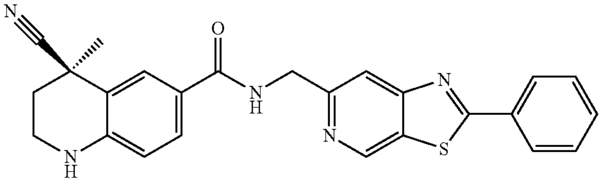 [SMILES: C[C@@]1(C#N)CCNc2ccc(C(=O)NCc3cc4nc(-c5ccccc5)sc4cn3)cc21] |
| 121 | 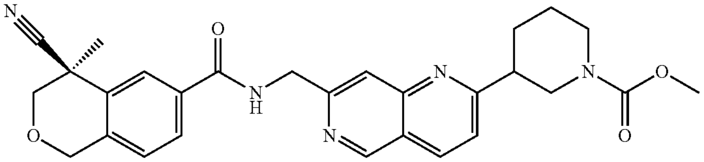 [SMILES: COC(=O)N1CCCC(c2ccc3cnc(CNC(=O)c4ccc5c(c4)[C@](C)(C#N)COC5)cc3n2)C1] |
| 122 | 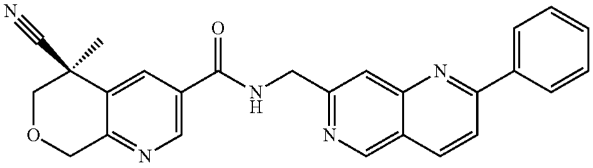 [SMILES: C[C@@]1(C#N)COCc2ncc(C(=O)NCc3cc4nc(-c5ccccc5)ccc4cn3)cc21] |
| 123 | 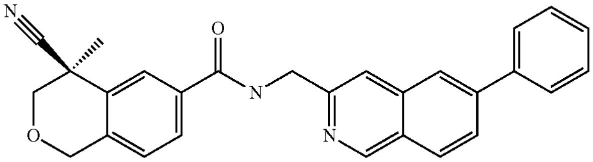 [SMILES: C[C@@]1(C#N)COCc2ccc(C(=O)NCc3cc4cc(-c5ccccc5)ccc4cn3)cc21] |
| 124 | 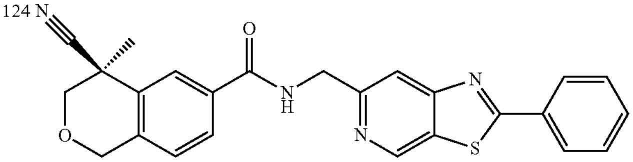 |
| 125 | 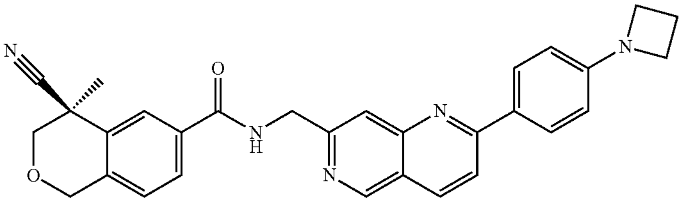 [SMILES: C[C@@]1(C#N)COCc2ccc(C(=O)NCc3cc4nc(-c5ccc(N6CCC6)cc5)ccc4cn3)cc21] |
| 126 | 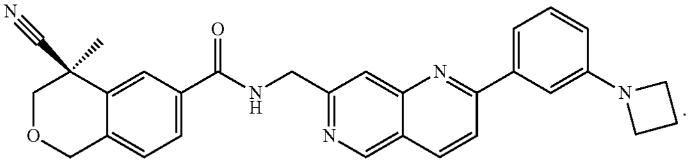 [SMILES: C[C@@]1(C#N)COCc2ccc(C(=O)NCc3cc4nc(-c5cccc(N6CCC6)c5)ccc4cn3)cc21] |

33. A pharmaceutical composition comprising a compound of claim 1 and a pharmaceutically acceptable excipient.

34. A method of treating cancer in a subject in need thereof, the method comprising administering to the subject an effective amount of a compound of claim 1.

35. The method of claim 34, wherein the cancer is non-small cell lung cancer, colorectal cancer, bladder cancer, cancer of unknown primary, glioma, breast cancer, melanoma, non-melanoma skin cancer, endometrial cancer, esophagogastric cancer, pancreatic cancer, hepatobiliary cancer, soft tissue sarcoma, ovarian cancer, head and neck cancer, renal cell carcinoma, bone cancer, non-Hodgkin lymphoma, small-cell lung cancer, prostate cancer, embryonal tumor, germ cell tumor, cervical cancer, thyroid cancer, salivary gland cancer, gastrointestinal neuroendocrine tumor, uterine sarcoma, gastrointestinal stromal tumor, CNS cancer, thymic tumor, Adrenocortical carcinoma, appendiceal cancer, small bowel cancer, or penile cancer.

36. The method of claim 35, wherein the cancer is non-small cell lung cancer, colorectal cancer, bladder cancer, cancer of unknown primary, glioma, breast cancer, melanoma, non-melanoma skin cancer, endometrial cancer, soft tissue sarcoma, or penile cancer.

37. The method of claim 36, wherein the cancer is non-small cell lung cancer.

38. The method of claim 36, wherein the cancer is soft tissue sarcoma.

39. A method of treating melanoma, prostate cancer, breast cancer, bone cancer, renal cell carcinoma, or a hematologic cancer in a subject in need thereof, the method comprising administering to the subject an effective amount of a compound of claim 1.

40. The method of claim 39, wherein the melanoma, prostate cancer, breast cancer, bone cancer, renal cell carcinoma, or hematologic cancer is metastatic.

* * * * *